US011034977B2

(12) United States Patent
Gao et al.

(10) Patent No.: US 11,034,977 B2
(45) Date of Patent: *Jun. 15, 2021

(54) METHOD OF DETECTING AND/OR IDENTIFYING ADENO-ASSOCIATED VIRUS (AAV) SEQUENCES AND ISOLATING NOVEL SEQUENCES IDENTIFIED THEREBY

(71) Applicant: The Trustees of the University of Pennsylvania, Philadelphia, PA (US)

(72) Inventors: Guangping Gao, Westborough, MA (US); James M. Wilson, Philadelphia, PA (US); Mauricio R. Alvira, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/698,412

(22) Filed: Nov. 27, 2019

(65) Prior Publication Data

US 2020/0087684 A1    Mar. 19, 2020

Related U.S. Application Data

(60) Continuation of application No. 15/584,674, filed on May 2, 2017, now Pat. No. 10,508,286, which is a
(Continued)

(51) Int. Cl.
*C12N 7/00* (2006.01)
*A61K 39/23* (2006.01)
(Continued)

(52) U.S. Cl.
CPC ............ *C12N 15/86* (2013.01); *A61K 38/177* (2013.01); *A61K 38/4846* (2013.01); *C07K 14/005* (2013.01); *C12N 7/00* (2013.01); *C12Q 1/701* (2013.01); *C12Y 304/21022* (2013.01); *A61K 48/00* (2013.01); *C12N 2750/14121* (2013.01); *C12N 2750/14122* (2013.01);
(Continued)

(58) Field of Classification Search
None
See application file for complete search history.

(56) References Cited

U.S. PATENT DOCUMENTS 5,412,073 A    5/1995  Kalsheker
5,449,616 A    9/1995  Campbell
(Continued)

FOREIGN PATENT DOCUMENTS

CA    2406745 A1    1/2006
EP    1310571 A2    5/2003
(Continued)

OTHER PUBLICATIONS

Afione SA et al., In vivo model of adeno-associated virus vector persistence and rescue, Journal of Virology, vol. 70(5):3235-3241, May 1996.
(Continued)

*Primary Examiner* — M Franco G Salvoza
(74) *Attorney, Agent, or Firm* — Howson & Howson LLP; Colleen M. Schaller

(57) ABSTRACT

Adeno-associated virus rh.20 sequences, vectors containing same, and methods of use are provided.

21 Claims, 112 Drawing Sheets

Specification includes a Sequence Listing.

Related U.S. Application Data continuation of application No. 14/956,934, filed on Dec. 2, 2015, now Pat. No. 10,041,090, which is a continuation of application No. 13/633,971, filed on Oct. 3, 2012, now Pat. No. 9,790,472, which is a division of application No. 12/962,793, filed on Dec. 8, 2010, now Pat. No. 8,524,446, which is a continuation of application No. 10/291,583, filed on Nov. 12, 2002, now abandoned.

(60) Provisional application No. 60/386,675, filed on Jun. 5, 2002, provisional application No. 60/377,066, filed on May 1, 2002, provisional application No. 60/341,117, filed on Dec. 17, 2001, provisional application No. 60/350,607, filed on Nov. 13, 2001.

(51) Int. Cl.
| | |
|---|---|
| *C12N 15/86* | (2006.01) |
| *C07K 14/005* | (2006.01) |
| *C12Q 1/70* | (2006.01) |
| *A61K 38/17* | (2006.01) |
| *A61K 38/48* | (2006.01) |
| *A61K 48/00* | (2006.01) |

(52) U.S. Cl.
CPC .............. *C12N 2750/14143* (2013.01); *C12N 2750/14151* (2013.01); *C12N 2750/14152* (2013.01); *C12N 2750/14162* (2013.01); *C12N 2750/14171* (2013.01); *C12N 2830/008* (2013.01); *C12N 2830/48* (2013.01); *C12N 2830/85* (2013.01); *C12N 2830/90* (2013.01); *C12Q 2600/158* (2013.01)

(56) References Cited

U.S. PATENT DOCUMENTS

| | | | |
|---|---|---|---|
| 5,871,982 | A | 2/1999 | Wilson et al. |
| 5,866,552 | A | 5/1999 | Chiorini et al. |
| 6,039,942 | A | 3/2000 | Lassen |
| 6,156,303 | A | 12/2000 | Russell |
| 6,251,677 | B1 | 6/2001 | Wilson et al. |
| 6,274,354 | B1 | 8/2001 | Wilson et al. |
| 6,312,957 | B1 | 11/2001 | Einerhand et al. |
| 6,365,394 | B1 | 4/2002 | Gao et al. |
| 6,376,237 | B1 | 4/2002 | Colosi |
| 6,387,368 | B1 | 5/2002 | Wilson et al. |
| 6,399,385 | B1 | 6/2002 | Croyle et al. |
| 6,428,988 | B1 | 8/2002 | Wilson et al. |
| 6,468,524 | B1 | 10/2002 | Chiorini et al. |
| 6,475,769 | B1 | 11/2002 | Wilson et al. |
| 6,482,634 | B1 | 11/2002 | Wilson et al. |
| 6,485,966 | B2 | 11/2002 | Gao et al. |
| 6,632,670 | B1 | 10/2003 | Wadsworth et al. |
| 6,759,237 | B1 | 7/2004 | Wilson et al. |
| 6,821,512 | B1 | 11/2004 | Gao et al. |
| 6,943,019 | B2 | 9/2005 | Wilson |
| 6,953,690 | B1 | 10/2005 | Gao et al. |
| 7,022,519 | B2 | 4/2006 | Gao |
| 7,056,502 | B2 | 6/2006 | Hildinger |
| 7,235,393 | B2 | 6/2007 | Gao |
| 7,238,526 | B2 | 7/2007 | Wilson |
| 7,282,199 | B2 | 10/2007 | Gao |
| 7,790,449 | B2 | 9/2010 | Gao |
| 9,102,949 | B2 | 8/2015 | Gao |
| 2001/0006955 | A1 | 7/2001 | Wilson et al. |
| 2002/0037867 | A1 | 3/2002 | Wilson et al. |
| 2002/0090717 | A1 | 7/2002 | Gao et al. |
| 2002/0159978 | A1 | 10/2002 | Allen |
| 2003/0040101 | A1 | 2/2003 | Wilson |
| 2003/0073232 | A1 | 4/2003 | Wilson |
| 2003/0119191 | A1 | 6/2003 | Gao |
| 2003/0138772 | A1 | 7/2003 | Gao et al. |
| 2004/0052764 | A1 | 3/2004 | Hildinger |
| 2005/0287122 | A1 | 12/2005 | Bartlett et al. |
| 2007/0036760 | A1 | 2/2007 | Wilson |
| 2008/0075737 | A1 | 3/2008 | Gao et al. |
| 2008/0075740 | A1 | 3/2008 | Gao |
| 2009/0054823 | A1 | 2/2009 | Bridges |
| 2009/0197338 | A1 | 8/2009 | Vandenberghe |
| 2009/0227030 | A1 | 9/2009 | Gao |
| 2009/0275107 | A1 | 11/2009 | Lock |
| 2009/0280103 | A1 | 11/2009 | Flueck |
| 2011/0053221 | A1 | 3/2011 | Chen |
| 2011/0070210 | A1 | 3/2011 | Andrijauskas |
| 2011/0151434 | A1 | 6/2011 | Gao |
| 2011/0301226 | A1 | 12/2011 | Mendell |
| 2013/0195801 | A1 | 8/2013 | Gao |
| 2015/0159173 | A1 | 6/2015 | Vandenberghe et al. |

FOREIGN PATENT DOCUMENTS

| | | |
|---|---|---|
| EP | 3085389 A1 | 10/2016 |
| WO | WO-1996/000587 A1 | 1/1996 |
| WO | WO-1996/013598 A2 | 5/1996 |
| WO | WO-1998/009657 A2 | 3/1998 |
| WO | WO-1998/010086 A1 | 3/1998 |
| WO | WO-1998/010088 A1 | 3/1998 |
| WO | WO-1998/011244 A1 | 3/1998 |
| WO | WO-1999/014354 A1 | 3/1999 |
| WO | WO-1999/015677 A1 | 4/1999 |
| WO | WO-1999/015685 A1 | 4/1999 |
| WO | WO-1999/047691 A1 | 9/1999 |
| WO | WO-1999/061601 A2 | 12/1999 |
| WO | WO-2000/028061 A2 | 5/2000 |
| WO | WO-2000/075353 A1 | 12/2000 |
| WO | WO-2001/014539 A2 | 3/2001 |
| WO | WO-2001/023001 A2 | 4/2001 |
| WO | WO-2001/023597 A3 | 4/2001 |
| WO | WO-2001/040455 A2 | 6/2001 |
| WO | WO-2001/068888 A2 | 9/2001 |
| WO | WO-2001/070276 A2 | 9/2001 |
| WO | WO-2001/083692 A2 | 11/2001 |
| WO | WO-2002/018659 A2 | 3/2002 |
| WO | WO-2003/042397 A2 | 5/2003 |
| WO | WO-2003/104392 A2 | 12/2003 |
| WO | WO 2004/112727 A2 | 12/2004 |
| WO | WO-2013/078316 A1 | 5/2013 |
| WO | WO-2013/123503 A1 | 8/2013 |

OTHER PUBLICATIONS

Alloca M et al., Novel adeno-associated virus serotypes efficiently transduce murine photoreceptors, Journal of Virology, 81(20):11372-80, Oct. 2007. (Epub Aug. 15, 2007).

Anissimov M, "How many species of bacteria are there", accessed Sep. 23, 2011 from http://www.wisegeek.org/how-many-species-of-bacteria-are-there.htm (last modified Nov. 19, 2015).

Bantel-Schaal U et al., Human adeno-associated virus type 5 is only distantly related to other known primate helper-dependent parvoviruses, Journal of Virology, vol. 73(2):939-947, Feb. 1999.

Bevan et al., Systemic Gene Delivery in Large Species for Targeting Spinal Cord, Brain, and Peripheral Tissues for Pediatric Disorders, Mol Ther. Nov. 2011;19(11):1971-80. doi: 10.1038/mt.2011.157. Epub Aug. 2, 2011.

Black A et al., Adeno-associated virus 8-mediated gene therapy for choroideremia: preclinical studies in in vitro and in vivo models, The Journal of Gene Medicine, vol. 16:122-130, Jun. 24, 2014.

Brown KE et al., Cloning and sequencing of the simian parvovirus genome, Virology, vol. 210:314-322, May 1995.

Calcedo R et al., Serologic Characterization of Human and Non-Human Primate AAVs, Abstract 102, Molecular Therapy, vol. 7(5): S41, May 2003.

Cearley CN et al., A single injection of an adeno-associated virus vector into nuclei with divergent connections results in widespread vector distribution in the brain and global correction of a neurogenetic disease, Neurobiology of Disease, vol. 27(37):9928-40, Sep. 12, 2007.

(56) References Cited

OTHER PUBLICATIONS

Cearley CN et al., Transduction characteristics of adeno-associated virus vectors expressing cap serotypes 7, 8, 9, and Rh10 in the mouse brain, Mol Ther. Mar. 2006;13(3):528-37. Epub Jan. 18, 2006.13(3):528-37. Mar. 2006. (Epub Jan. 18, 2006).

Charan RA et al., Adeno-associated Virus Serotype 8 (AAV8) Delivery of Recombinant A20 to Skeletal Muscle Reduces Pathological Activation of Nuclear Factor (NF)-kB in Muscle of mdx Mice, Molecular Medicine, vol. 18:1527-35, Feb. 2013. (Epub Nov. 6, 2012).

Chen et al., Epidemiology of hepatitis B virus infection in the Asia-Pacific region, J Gastroenterol Hepatol. May 2000;15 Suppl:E3-6.

Chicoine LG et al., Vascular Delivery of rAAVrh741MCK. GALGT2 to the Gastrocnemius Muscle of the Rhesus Macaque Stimulates the Expression of Dystrophin and Laminin $\alpha 2$ Surrogates, Molecular Therapy, vol. 22(4):713-24, Apr. 2014. (Epub Oct. 22, 2013).

Childers MK et al., Gene Therapy Prolongs Survival and Restores Function in Murine and Canine Models of Myotubular Myopathy, Sci Transl Med, vol. 6(220):1-31, Jan. 22, 2014.

Chiorini JA et al., Cloning and characterization of AAV5, Journal of Virology, vol. 73(2):1309-1319, Feb. 1999.

Chirmule et al., Immune responses to adenovirus and adeno-associated virus in humans, Gene Therapy, 6:1574-1583, Sep. 1999. Clinicaltrials.org, "AAV8 Vector Trials", Nov. 2017.

Dai X et al., Long-term retinal cone rescue using a capsid mutant AAV8 vector in a mouse model of CNGA3-achromatopsia, PLOS One, vol. 12(11):e0188032, Nov. 13, 2017.

Davidson BL et al., Recombinant adeno-associated virus type 2, 4, and 5 vectors: transduction of variant cell types and regions in the mammalian central nervous system, PNAS, vol. 97(7): 3428-3432, Mar. 28, 2000.

De BP et al. Induction of Persistent Passive Immunity Against Anthrax Toxin by an Adeno-Associated Virus Type rh10 Vector Expressing Anti-Protective Antigen Antibody [Abstract No. 611], Molecular Therapy, 13(Supp 1):S236, May 2006.

De BP et al., High levels of persistent expression of alpha1-antitrypsin mediated by the nonhuman primate serotype rh.10 adeno-associated virus despite preexisting immunity to common human adeno-associated viruses, Mol Ther., vol. 13(1):67-76, Jan. 2006. (Epub Nov. 2, 2005).

De BP et al., Therapeutic Levels For alpha1-Antitrypsin Following Intrapleural Administration of a Non-Human Primate Serotype rh10 AAV Vector Expressing alpha1-Antitrypsin, Abstract 338, 7$^{th}$ Annual Meeting of The American Society of Gene Therapy [Jun. 2-6, 2004] Minneapolis, Minnesota, p. 1, e-published May 2, 2004.

Durigon EL et al., Multiple primer pairs for polymerase chain reaction (PCR) amplification of human parvovirus B19 DNA, Journal of Virological Methods, vol. 44:155-65, Feb. 1993.

Ellis et al., Virology Journal, Mar. 2013, A survey of ex vivo/in vitro transduction efficiency of mammalian primary cells and cell lines with Nine natural adeno-associated virus (AAV1-9) and one engineered adeno-associated virus serotype, 10:74.

Faria et al., The early spread and epidemic ignition of HIV-1 in human populations, Science, Oct. 2014, 346(6205):56-61.

Fischer MD et al., Codon-Optimized RPGR Improves Stability and Efficacy of AAV8 Gene Therapy in Two Mouse Models of X-Linked Retinitis Pigmentosa, Molecular Therapy, vol. 25(8):1854-65, Aug. 2, 2017. (Epub May 24, 2017).

Forslund O et al., A broad range of human papillomavirus types detected with a general PCR method suitable for analysis of cutaneous tumors and normal skin, Journal of General Virology, vol. 80(9):2437-43, XP002229850, Sep. 1999.

Gao et al., Clades of Adeno Associated Viruses Are Widely Disseminated in Human Tissues, J. Virol, Jun. 2004, 78(12) :6381-8.

Gao et al., Origin of HIV-1 in the chimpanzee Pan troglodytes troglodytes, Nature, Feb. 1999, 397 :436-440.

Gao G et al., Adeno-Associated Viruses Undergo Substantial Evolution in Primates During Natural Infections, PNAS, vol. 100(10):6081-86, May 13, 2003. (Epub Apr. 25, 2003).

Gao G et al., Autoimmune Anemia in Macaques Following Erythropoietin Gene Therapy, Abstract 341, 7$^{th}$ Annual Meeting of The American Society of Gene Therapy [Jun. 2-6, 2004] Minneapolis, Minnesota, p. 1, (Epub May 2, 2004).

Gao G et al., Clades of Adeno-Associated Viruses are Widely Disseminated in human Tissues, Journal of Virology, vol. 78(12):6381-6388, Jun. 2004.

Gao G et al., Diversity of Latent AAV Genomes in Non-Human Primate and Human Tissues, Abstract 400, Molecular Therapy, vol. 7(5):S158, May 2003.

Gao G et al., Erythropoietin Gene Therapy Leads to Autoimmune Anemia in Macaques, Blood, vol. 103(9):3300-2, May 2004.

Gao GP et al., Biology of Adenovirus vectors with E1 and E4 deletions for liver-directed gene therapy, Journal of Virology, vol. 70(12):8934-8943, Dec. 1996.

Gao GP et al., Novel adeno-associated viruses from rhesus monkeys as vectors for human gene therapy, PNAS, vol. 99(18):11854-59, Sep. 2002. (Epub Aug. 21, 2002).

GenBank entry AF513851, Sep. 2002.

GenBank entry AF513852, Sep. 2002.

Giles et al., Deamidation of Amino Acids on the Surface of Adeno-Associated Virus Capsids Leads to Charge Heterogeneity and Altered Vector Function, Mol Ther, 26(12), Dec. 2018.

Gilkes JA et al., Mucopolysaccharidosis IIIB confers enhanced neonatal intracranial transduction by AAV8 but not by 5, 9 or rh10, Gene Therapy, vol. 23(3):263-271, Mar. 2016. (Epub Dec. 16, 2015).

Girod A et al. Genetic capsid modifications allow efficient retargeting of adeno-associated virus type 2. Nat Med. 5(9):1052-6. Sep. 1999.

Girod et al., The VP1 capsid protein of adeno-associated virus type 2 is carrying a phospholipase A2 domain required for virus infectivity, J. General Virol, 2002, 83:973-978.

Green SW et al., Rhesus and pig-tailed macaque parvoviruses: identification of two new members of the erythrovirus genus in monkeys, Virology, vol. 269:105-12, Mar. 30, 2000.

Grieger et al., Surface-Exposed Adeno-Associated Virus Vp1-NLS Capsid Fusion Protein Rescues Infectivity of Noninfectious Wild-Type Vp2/Vp3 and , Vp3-Only Capsids but Not That of Fivefold Pore Mutant Virions, J. Virol, 81(15):7833-7483, Aug. 2007.

Grosse et al., Relevance of Assembly-Activating Protein for Adeno-associated Virus Vector Production and Capsid Protein Stability in Mammalian and Insect Cells, J Virol 91:e01198-17, Aug. 2017.

Halbert et al., Repeat Transduction in the Mouse Lung by Using Adeno-Associated Virus Vectors with Different Serotypes, J. Virol, 74(3):1524-1532, Feb. 2000.

Hamilton et al., Adenoviral-Mediated Gene Transfer to Murine Small Intestine Is More Efficient in Neonates Than Adults, J Pediatr Surg. Feb. 1997;32(2):373-7.

Hernandez YJ et al., Latent Adeno-associated virus infection elicits humoral but no cell-mediated immune responses in a nonhuman primate model, Journal of Virology, vol. 73(10):8549-8558, Oct. 1999.

Herzog RW et al., Stable gene transfer and expression of human blood coagulation factor IX after intramuscular injection of recombinant adeno-associated virus, Proc. Natl. Acad. Sci. USA, vol. 94:5804-5809, May 27, 1997.

Hicks MJ et al., AAV-directed persistent expression of a gene encoding anti-nicotine antibody for smoking cessation, Science Translational Medicine, vol. 4(140):140ra87, Jun. 27, 2012.

Hu C et al., AAV-based neonatal gene therapy for hemophilia A: long-term correction and avoidance of immune responses in mice, vol. 19(12):1166-76. Dec. 2012. (Epub Jan. 12, 2012).

Hu C et al., RH10 provides superior transgene expression in mice when compared with natural AAV serotypes for neonatal gene therapy, vol. 12(9):766-78. doi: 10.1002/jgm.1496, Sep. 2010.

Kapturczak MH et al. Adeno-Associated Virus (AAV) as a Vehicle for Therapeutic Gene Delivery Improvements in Vector Design and Viral Production Enhance Potential to Prolong Graft Survival in

(56) References Cited

OTHER PUBLICATIONS

Pancreatic Islet Cell Transplantation for the Reversal of Type 1 Diabetes. Curr Mol Med. 1(2):245-58. May 2001.
Kawamura et al., Hiv-2 in West Africa in 1966, The Lancet, Feb. 1989, 385.
Kay MA et al. Therapeutic Serum Concentrations of Human Alpha-1-Antitrypsin After Adenoviral-Mediated Gene Transfer Into Mouse Hepatocytes, Hepatology, 21(3):815-9, Mar. 1995.
Kelkar S et al., A common mechanism for cytoplasmic dynein-dependent microtubule binding shared among adeno-associated virus and adenovirus serotypes, vol. 80(15):7781-5. Aug. 2006.
Kitajima K et al, Complete Prevention of Atherosclerosis in apoE-Deficient Mice by Hepatic Human ApoE Gene Transfer with Adeno-Associated Virus Serotype 7 and 8, Arterioscler Thromb Vasc Biol, vol. 26:1852-57, Jul. 20, 2006.
Klein RL et al., AAV8, 9, Rh10, Rh43 vector gene transfer in the rat brain: effects of serotype, promoter and purification method, vol. 16(1):89-96. Jan. 2008. (Epub Oct. 23, 2007).
Kobinger GP et al., Pseudotyping HIV Vector with the Spike Envelope Protein of SARS-CoV for Studying Viral Tropism, Immunology and Gene Therapy Applications, Abstract 368, 7$^{th}$ Annual Meeting of The American Society of Gene Therapy [Jun. 2-6, 2004] Minneapolis, Minnesota, p. 1, e-published May 2, 2004.
Lawlor PA et al., Efficient gene delivery and selective transduction of glial cells in the mammalian brain by AAV serotypes isolated from nonhuman primates, Mol Ther, vol. 17(10):1692-702. doi: 10.1038/mt.2009.170. Oct. 2009. (Epub Jul. 28, 2009).
Le Guenno, HIV1 and HIV2: two ancient viruses for a new disease? Transactions of the Royal Society of Tropical Medicine and Hygiene, 1989, 83, 847.
Lebherz C et al., Gene Therapy with Novel Adeno-Associated Virus Vectors Substantially Diminishes Atherosclerosis in a Murine Model of Familial Hypercholesterolemia, The Journal of Gene Medicine, vol. 6(6):663-672, Jun. 2004.
Lebherz C et al., Novel AAV serotypes for improved ocular gene transfer, J. Gene Med, vol. 10(4):375-82, Apr. 2008.
Li et al., 2015, Site-Directed Mutagenesis of Surface-Exposed Lysine Residues Leads to Improved Transduction by AAV2,But Not AAV8, Vectors in Murine Hepatocytes In Vivo, Hum Gene Ther Methods. Oct. 2015;26(6):211-20.
Limberis M et al., A Novel AAV Vector for the Treatment of Cystic Fibrosis Airway Disease, Abstract 692, 7$^{th}$ Annual Meeting of The American Society of Gene Therapy [Jun. 2-6, 2004] Minneapolis, Minnesota, p. 1, e-published May 2, 2004.
Lin J et al., Vaccines Based on Novel Adeno-Associated Virus Vectors Elicit Aberrant CD8+ T-Cell Responses in Mice, J Virol, vol. 81(21):11840-11849, Nov. 2007. (Epub Aug. 22, 2007).
Ling et al., Human Hepatocyte Growth Factor Receptor is a Cellular Coreceptor for Adeno-Associated Virus Serotype 3, Human Gene Therapy, 21:1741-1747 (Dec. 2010).
Ling et al., Selective In Vivo Targeting of Human Liver Tumors by Optimized AAV3 Vectors in a Murine Xenograft Model, Hum Gene Ther. Dec. 2014;25(12):1023-34.
Liu et al., Neutralizing antibodies against AAV2, AAV5 and AAV8 in healthy and HIV-1-infected subjects in China: implications for gene therapy using AAV vectors, Gene Therapy, 21:732-738, May 2014.
Looker et al., An estimate of the global prevalence and incidence of herpes simplex virus type 2, Bull World Health Organ. Oct. 2008;86(10):805-12, A.
Lu Y et al., Analysis of Homologous Recombination Between Different AAV Genomes in In Vitro co-Infections, Abstract 38, Molecular Therapy, vol. 7(5):S15, May 2003.
Lytle AM et al., Effects of FVIII immunity on hepatocyte and hematopoietic stem cell-directed gene therapy of murine hemophilia A, Methods & Clinical Development, vol. 3:15056, Feb. 10, 2016.
Maguire CA et al., Directed evolution of adeno-associated virus for glioma cell transduction. J Neurooncol., vol. 96(3):337-47, Feb. 2010. (Epub Jul. 19, 2009).

Mao et al. Angiotensin 1-7 Overexpression Mediated by a Capsid-optimized AAV8 Vector Leads to Significant Growth Inhibition of Hepatocellular Carcinoma In vivo, Int. J. Biol. Sci, Jan. 14, 2018.
Mao Y et al, Persistent suppression of ocular neovascularization with intravitreal administration of AAVrh.10 coding for bevacizumab, Human Gene Therapy, vol. 22(12):1525-35. doi: 10.1089/hum.2011.090. Dec. 2011. (Epub Oct. 27, 2011).
Messina et al., Adeno-Associated Viral Vectors Based on Serotype 3b Use Components of the Fibroblast Growth Factor Receptor Signaling Complex for Efficient Transduction, Hum Gene Ther. Oct. 2012; 23(10): 1031-1042.
Mimuro et al., The Prevalence of Neutralizing Antibodies Against Adeno-Associated Virus Capsids Is Reduced in Young Japanese Individuals, J. Med Virol, 86:1990-7 Oct. 2013.
Monahan PE and Semulski RJ, Adeno-Associated Virus Vectors for Gene Therapy: More Pros than Cons, Molecular Medicine Today, vol. 6(11):433-40, Nov. 2000.
Mori S et al., Two Novel Adeno-Associated Viruses from Cynomolgus Monkey: Pseudotyping Characterization of Capsid Protein, Virology, vol. 330(2):375-383, Dec. 20, 2004.
Moskaleno et al., Epitope Mapping of Human Anti-Adeno-Associated Virus Type 2 Neutralizing Antibodies: Implications for Gene Therapy and Virus Structure, J Virol, Feb. 2000, 74(4):1761-6.
Mountz JD et al., Monkey See, Monkey Do, Gene Therapy, vol. 10(3):194-6, Feb. 2003.
Nam et al., Structure of Adeno-Associated Virus Serotype 8, a Gene Therapy Vector, J Virol, 81(22) :12260-71, Nov. 2007.
Nathwani AC et al., Enhancing transduction of the liver by adeno-associated viral vectors, Gene Therapy, vol. 16(1):60-9. doi: 10.1038/gt.2008.137. Jan. 2009. (Epub Aug. 14, 2008).
Nzilambi et al., The prevalence of infection with human immunodeficiency virus over a 10-year period in rural zaire, NE J Med, 318(5):276-279, Feb. 1988.
Pacak CA et al., Long-term skeletal muscle protection after gene transfer in a mouse model of LGMD-2D, Molecular Therapy, vol. 15(10):1775-81, Oct. 2007. (Epub Jul. 24, 2007).
Pignataro D et al., Adeno-Associated Viral Vectors Serotype 8 for Cell-Specific Delivery of Therapeutic Genes in the Central Nervous System, Frontiers in Neuroanatomy, vol. 11(2):1-13, Feb. 10, 2017.
Piguet F et al., Correction of brain oligodendrocytes by AAVrh.10 intracerebral gene therapy in metachromatic leukodystrophy mice, Human Gene Therapy, vol. 23(8):903-14. doi: 10.1089/hum.2012.015. Aug. 2012. (Epub Jul. 23, 2012).
Price A et al., Targeted Gene Transfer to Lung Airway Epithelium Using Plasmid or Adenoviral Vectors Formulated with an Anti-Inflammatory Dexamathasone-Spermine conjugate, Abstract 498, 7$^{th}$ Annual Meeting of The American Society of Gene Therapy [Jun. 2-6, 2004] Minneapolis, Minnesota, p. 1, e-published May 2, 2004.
Quesada O et al., Production, purification and preliminary x-ray crystallographic studies of adeno-associated virus serotype 7, Acta Crystallographica, vol. F(63):1073-6, Dec. 2007. (Epub Nov. 30, 2007).
Rafi MA et al., Extended normal life after AAVrh10-mediated gene therapy in the mouse model of krabbe disease, Molecular Therapy, vol. 20(11):2031-42. doi: 10.1038/mt.2012.153. Nov. 2012. (Epub Jul. 31, 2012).
Research Genetics, Designer PCR (advertisement), Nucleic Acids Research, vol. 22(15):2882, Aug. 11, 1994.
Rick ME et al., ASH education Book—Congenital Bleeding Disorders, Hematology/American Society of Hematology Educational Program, vol. 2003(1):559-74, Jan. 1, 2003.
Rosenberg JB et al., AAVrh.10-mediated expression of an anti-cocaine antibody mediates persistent passive immunization that suppresses cocaine-induced behavior, Human Gene Therapy, vol. 23(5):451-9. doi: 10.1089/hum.2011.178. May 2012.
Ruffing M et al., Assembly of viruslike particles by recombinant structural proteins of adeno-associated virus type 2 in insect cells, J Virol., vol. 66(12):6922-30, Dec. 1992.
Rutledge EA et al., Infectious clones and vectors derived from adeno-associated virus (AAV) serotypes other than AAV type 2, Journal of Virology, vol. 72(1):309-319, XP-002137089, Jan. 1998.

(56) References Cited

OTHER PUBLICATIONS

Samaranch L et al., Strong Cortical and Spinal Cord Transduction after AAV7 and AAV9 Delivery into the Cerebrospinal Fluid of Nonhuman Primates, Human Gene Therapy, vol. 24:526-53, May 2013. (Epub May 2, 2013).

Sanmiguel J et al., Real-time PCR as an Analytic Tool in Gene Therapy, Abstract 913, vol. 7(5):S352, May 2003.

Schnell MA et al., Activation of innate immunity in nonhuman primates following intraportal administration of adenoviral vectors, Molecular Therapy, vol. 3(5):708-722, May 2001.

Shen et al., Characterization of the Relationship of AAV Capsid Domain Swapping to Liver Transduction Efficiency, Mol Ther, Aug. 2007, 15(11):1955-62.

Skaricic D et al., Genetic delivery of an anti-RSV antibody to protect against pulmonary infection with RSV, Jour. Virol., vol. 378(1):79-85. doi: 10.1016/j.virol.2008.04.016. Aug. 2008. (Epub Jun. 16, 2008).

Sommer S and Tautz D, Minimal homology requirement for PCR primers, Nucleic Acids Research, vol. 17(16):6749. Aug. 25, 1989.

Sondhi D et al., Enhanced survival of the LINCL mouse following CLN2 gene transfer using the rh.10 rhesus macaque-derived adeno-associated virus vector, Mol Ther., vol. 15(3):481-91, Mar. 2007. (Epub Dec. 19, 2006).

Sondhi D et al., Long-term expression and safety of administration of AAVrh.10hCLN2 to the brain of rats and nonhuman primates for the treatment of late infantile neuronal ceroid lipofuscinosis, Human Gene Therapy, vol. 23(5):324-35. doi: 10.1089/hgtb.2012.120, Oct. 2012. (Epub Nov. 6, 2012).

Sondhi D et al., Survival advantage of neonatal CNS gene transfer for late infantile neuronal ceroid lipofuscinosis, Jour Exp Neurol, vol. 213(1):18-27. doi: 10.1016/j.expneurol.2008.04.022. Sep. 2008. (Epub Apr. 30, 2008).

Sonntag et al., A viral assembly factor promotes AAV2 capsid formation in the nucleolus, PNAS, 107(22):10220-5, Jun. 2010.

Suhy et al. Safe, Long-term Hepatic Expression of Anti-HCV shRNA in a Nonhuman Primate Model, Mol Ther. Sep. 2012;20(9):1737-49. doi: 10.1038/mt.2012.119. Epub Jun. 26, 2012.

Tal J, Adeno-associated virus-based vectors in gene therapy, Journal of Biomedical Science, vol. 7(4):279-291, Jul. 2000.

Tobiasch E et al., Discrimination between different types of human adeno-associated viruses clinical samples by PCR, Journal of Virology Methods, vol. 71(1):17-25, Mar. 1998.

Trempe et al., Alternate mRNA splicing is required for synthesis of adeno-associated virus VP1 capsid protein. J Virol. Sep. 1988;62(9):3356-63, Sep. 1988.

Vandenberghe LH et al., AAV Clades: Their Ability to Recombine and Cross Species-Barriers, Abstract 88, 7th Annual Meeting of The American Society of Gene Therapy [Jun. 2-6, 2004] Minneapolis, Minnesota, p. 1, e-published May 2, 2004.

Vandenberghe LH et al., AAV9 Targets Cone Photoreceptors in the Nonhuman Primate Retina, PLoS One, vol. 8(1):e53463. doi: 10.1371/journal.pone.0053463, 2013. (Epub Jan. 30, 2013).

Vandenberghe LH et al., Naturally occurring singleton residues in AAV capsid impact vector performance and illustrate structural constraints. Gene Ther., vol. 16(12):1416-28, Dec. 2009.

Vandenberghe LH et al., Structure-Function Relationship of the Novel Non-Human Primate Adeno-associated Viruses, Abstract 99, Molecular Therapy, vol. 7(5):S15, May 2003.

Vercauteren, Superior In vivo Transduction of Human Hepatocytes Using Engineered AAV3 Capsid, Mol Therapy, 24(6):1042-1049, Jun. 2016.

Vincent M et al., Comparison of the efficacy of five adeno-associated virus vectors for transducing dorsal raphé nucleus cells in the mouse. J Neurosci Methods, vol. 30(235):189-92, Sep. 30, 2014. (Epub Jul. 18, 2014).

Wang et al., Comparative Study of Liver Gene Transfer With AAV Vectors Based on Natural and Engineered AAV Capsids, Molecular Therapy, Dec. 2015, 23(12):1877-87.

Wang G et al., Persistent expression of biologically active anti-HER2 antibody by AAVrh.10-mediated gene transfer, Cancer Gene Therapy, vol. 17(8):559-70. doi: 10.1038/cgt.2010.11, Aug. 2010. (Epub May 7, 2010).

Wang L et al., Enhancing Transgene Expression from Recombinant AAV8 Vectors in Different Tissues Using Woodchuck Hepatitis Virus Post-Transcriptional Regulatory Element, International Journal of Medical Sciences, vol. 13(4):286-291, Apr. 1, 2016.

Wang L et al., Production of AAV Vectors with Different Serotypes, Abstract 906, Molecular Therapy, vol. 7(5):S350, May 2003.

Wang L et al., Systematic evaluation of AAV vectors for liver directed gene transfer in murine models, Mol Ther., vol. 18(1):118-25. doi: 10.1038/mt.2009.246. Jan. 2010. (Epub Oct. 27, 2009).

Wang L et al., The pleiotropic effects of natural AAV infections on liver-directed gene transfer in macaques, Molecular Therapy, vol. 18(1):126-34, doi: 10.1038/mt.2009.245, Jan. 2010. (Epub Nov. 3, 2009).

Warrington et al., Adeno-Associated Virus Type 2 VP2 Capsid Protein Is Nonessential and Can Tolerate Large Peptide Insertions at Its N Terminus, J Virol, 78(1):6595-6609, Jun. 2004.

Watanabe M et al., AAVrh.10-mediated genetic delivery of bevacizumab to the pleura to provide local anti-VEGF to suppress growth of metastatic lung tumors. Gene Ther., vol. 17(8):1042-51. doi: 10.1038/gt.2010.87, Aug. 2010. (Epub Jul. 1, 2010).

Weitzman MD et al., Adeno-associated virus (AAV) Rep proteins mediate complex formation between AAV DNA and its integration site in human DNA, PNAS, vol. 91:5808-5812, Jun. 21, 1994.

wikipedia.com, "Fungus", accessed Jun. 3, 2013 from https://en.wikipedia.org/wiki/Fungus (last modified Nov. 17, 2015).

wikipedia.com, "List of sequenced bacterial genomes", accessed Jan. 24, 2014 from https://en.wikipedia.org/wiki/List_of_sequenced_bacterial_genomes (last modified Oct. 19, 2015).

wikipedia.com, "Mammal", accessed Sep. 22, 2011 from https://en.wikipedia.org/wiki/Mammal (last modified Nov. 19, 2015).

wikipedia.com, "Murinae", accessed Mar. 18, 2013 from https://en.wikipedia.org/wiki/Murinae (last modified Nov. 7, 2015).

wikipedia.com, "Plant", accessed Mar. 8, 2013 from https://en.wikipedia.org/wiki/Plant (last modified Oct. 5, 2015).

wikipedia.com, "Virus", accessed Nov. 24, 2012 from https://en.wikipedia.org/wiki/Virus (last modified Nov. 1, 2015).

Wobus et al., Monoclonal Antibodies against the Adeno-Associated Virus Type 2 (AAV-2) Capsid: Epitope Mapping and identification of Capsid Domains Involved in AAV-2-Cell Interaction and Neutralization of AAV-2 Infection, J Virol, Oct. 2000, 74(19):9281-93.

Wu et al., Adeno-associated Virus Serotypes: Vector Toolkit for Human Gene Therapy, Molecular Therapy, 14(3):316-327, Sep. 2006.

Wu P et al. Mutational analysis of the adeno-associated virus type 2 (AAV2) capsid gene and construction of AAV2 vectors with altered tropism. J Virol. 74(18):8635-47, Sep. 2000.

Xiao W et al., Gene therapy vectors based on adeno-associated virus type 1, Journal of Virology, 73(5):3994-4003, May 1999.

Xiao X et al., Production of High-titer Recombinant Adeno-Associated Virus Vectors in the Absence of Helper Adenovirus, Journal of Virology, 72(3):2224-32, Mar. 1998.

Xie Q et al., Towards the atomic structure of the adeno-associated virus 2 capsid, Infectious Disease Review, from the VIIIth Parvovirus Workshop, Mont Tremblant, Quebec, Canada, vol. 2(3):136, (Jun. 28-Jul. 20, 2000).

Xin KQ et al., Induction of Robust Immune Response Against Human Immunodeficiency Virus is Supported by the Inherent Tropism of Adeno-Associated Virus Type 5 for Dendritic Cells, J. Virol, vol. 80(24):11899-910, Dec. 2006. (Epub Sep. 27, 2006).

Yan Z et al., Inverted terminal repeat sequences are important for intermolecular recombination and circularization of adeno-associated virus genomes, J Virol. 79(1):364-79, Jan. 2005.

Yang B et al., Global CNS transduction of adult mice by intravenously delivered rAAVrh.8 and rAAVrh.10 and nonhuman primates by rAAVrh.10., Mol Ther., vol. 22(7):1299-309, Jul. 2014. (Epub Apr. 30, 2014).

Zadori Z et al., A viral phospholipase A2 is required for parvovirus infectivity, Developmental Cell, vol. 1:291-302, Aug. 2001.

(56) References Cited

OTHER PUBLICATIONS

Zhang H et al., Several rAAV vectors efficiently cross the blood-brain barrier and transduce neurons and astrocytes in the neonatal mouse central nervous system, Molecular Therapy, vol. 19(8):1440-8, Aug. 2011.
Zhou X et al., Evaluation of Novel Gene Transfer Vectors Derived from Infectious Molecular Clones of Primate AAVs, Abstract 90, 7th Annual Meeting of The American Society of Gene Therapy [Jun. 2-6, 2004] Minneapolis, Minnesota, p. 1, e-published May 2, 2004.
Zhou XY et al., Direct Rescue and Cloning of Infectious Novel AAV Genomes From Non-Human Primate Tissues, Abstract 907, Molecular Therapy, 7(5):S350, May 2003.
Zhu T et al., Sustained Whole-Body Functional Rescue by Systemic Delivery of AAV8 Vectors in Heart Failure and Muscular Dystrophy Hamsters, Molecular Therapy, vol. 11(suppl 1):916, May 2005.
Office Action issued in parent U.S. Appl. No. 10/291,583, dated Dec. 22, 2005.
Response to Office Action dated Dec. 22, 2005 issued in parent U.S. Appl. No. 10/291,583, dated May 15, 2006.
Office Action issued in parent U.S. Appl. No. 10/291,583, dated Feb. 16, 2007.
Response to Office Action dated Feb. 16, 2007 issued in parent U.S. Appl. No. 10/291,583, dated May 3, 2007.
Office Action issued in parent U.S. Appl. No. 10/291,583, dated Jun. 11, 2007.
Response to Office Action dated Jun. 11, 2007 issued in parent U.S. Appl. No. 10/291,583, dated Aug. 10, 2007.
Office Action dated Feb. 6, 2008 issued in parent U.S. Appl. No. 10/291,583, dated Feb. 6, 2008.
Response submitted Apr. 7, 2008 to Office Action dated Feb. 6, 2008 issued in parent U.S. Appl. No. 10/291,583, dated Apr. 7, 2008.
Office Action dated May 1, 2008 issued in parent U.S. Appl. No. 10/291,583, dated May 1, 2008.
Response submitted Sep. 29, 2008 to Office Action dated May 1, 2008 issued in parent U.S. Appl. No. 10/291,583, dated Sep. 29, 2008.
Office Action dated Apr. 15, 2009 issued in parent U.S. Appl. No. 10/291,583, dated Apr. 15, 2009.
Response submitted Jul. 15, 2009 to Office Action dated Apr. 15, 2009 issued in parent U.S. Appl. No. 10/291,583, dated Jul. 15, 2009.
Office Action dated Sep. 18, 2009 issued in parent U.S. Appl. No. 10/291,583, dated Sep. 18, 2009.
Response submitted Mar. 17, 2010 to Office Action dated Sep. 18, 2009 issued in parent U.S. Appl. No. 10/291,583, dated Mar. 17, 2010.
Office Action dated Jun. 8, 2010 issued in parent U.S. Appl. No. 10/291,583, dated Jun. 8, 2010.
Office Action issued in related U.S. Appl. No. 11/985,096, dated Dec. 12, 2011.
Response submitted to Office Action dated Dec. 12, 2011 issued in related U.S. Appl. No. 11/985,096, dated Jun. 12, 2012.
Office Action issued in related U.S. Appl. No. 11/985,096, dated Jul. 30, 2012.
Response to Office Action dated Jul. 30, 2012 issued in related U.S. Appl. No. 11/985,096, dated Jan. 30, 2013.
Advisory action issued in related U.S. Appl. No. 11/985,096, dated Mar. 1, 2013.
Response to Advisory action dated Mar. 1, 2013 issued in related U.S. Appl. No. 11/985,096, dated Mar. 18, 2013.
Office Action issued in related U.S. Appl. No. 11/985,096 and response dated Mar. 17, 2014, dated Sep. 18, 2013.
Office Action issued in related U.S. Appl. No. 11/985,096, dated Jun. 27, 2014.
Notice of Allowance and Interview Summary issued on related U.S. Appl. No. 11/985,096, dated Sep. 25, 2014.
Amendment after Notice of Allowance submitted in related U.S. Appl. No. 11/985,096, dated Oct. 14, 2014.
Amendment after Notice of Allowance submitted in related U.S. Appl. No. 11/985,096, dated Oct. 28, 2014.
Office Action issued in related U.S. Appl. No. 12/962,793, dated Dec. 19, 2011.
Response to Office Action dated Dec. 19, 2011 issued in related U.S. Appl. No. 12/962,793, dated Jun. 19, 2012.
Office Action issued in related U.S. Appl. No. 12/962,793, dated Aug. 30, 2012.
Response to Office Action dated Aug. 30, 2012 issued in related U.S. Appl. No. 12/962,793, dated Feb. 28, 2013.
Advisory Action issued in U.S. Appl. No. 12/962,793, dated Mar. 20, 2013.
Supplemental Amendment filed in U.S. Appl. No. 12/962,793, dated May 13, 2013.
Advisory Action dated issued in U.S. Appl. No. 12/962,793, dated May 24, 2013.
Notice of Allowance issued on U.S. Appl. No. 12/962,793, dated Jun. 11, 2013.
Amendment after Notice of Allowance filed in U.S. Appl. No. 12/962,793, dated Jul. 25, 2013.
Office Action issued on corresponding Chinese application No. 201310326978.2, dated Nov. 19, 2014.
Response to Office Action dated Nov. 19, 2014 issued in corresponding Chinese application No. 201310326978.2, dated Apr. 2, 2015.
Second Office Action issued on corresponding Chinese application No. 201310326978.2, dated Aug. 10, 2015.
Communication in corresponding EP Patent Application No. 10178940.2 including search report dated May 18, 2011, dated May 26, 2011.
Response to Communication dated May 26, 2011, dated Dec. 30, 2011.
Communication in corresponding EP Patent Application No. 10178940.2 pursuant to Article 94(3) and Rule 71(1), invitation to amend claims, dated Feb. 3, 2012.
Response to Communication dated Feb. 3, 2012 issued on corresponding EP Patent Application No. 10178940.2, dated Jun. 13, 2012.
Communication under Rule 71(3) EPC—Intention to Grant issued on corresponding EP Patent Application No. 10178940.2, dated Nov. 5, 2012.
Amended claims filed in response to Communication from EPO dated Nov. 5, 2012 issued on corresponding EP Patent Application No. 10178940.2, dated Mar. 15, 2013.
Communication under Rule 71(3) Epc—Intention to Grant issued on corresponding EP Patent Application No. 10178940.2, dated May 2, 2013.
Response to Communication dated May 2, 2013 issued on corresponding EP Patent Application No. 10178940.2, dated Jul. 11, 2013.
Communication under Rule 71(3) EPC—Intention to Grant issued on corresponding EP Patent Application No. 10178940.2, dated Aug. 1, 2013.
Communication under Artile 91(1) EPC—Decision to Grant issued on corresponding EP Patent Application No. 10178940.2, dated Aug. 29, 2013.
Office Action issued in corresponding Japanese Patent Application No. 2009-102988, dated Oct. 4, 2011.
Final Office Action issued in corresponding Japanese Patent Application No. 2009-102988, dated Jun. 19, 2012.
Response to Office Action dated Jun. 19, 2012 issued in corresponding Japanese Patent Application No. 2009-102988, dated Sep. 12, 2012.
Decision to Grant issued in corresponding Japanese Patent Application No. 2009-102988, dated Nov. 14, 2012.
Office Action dated Dec. 31, 2014 issued in corresponding Chinese Patent Application No. 201310326869.
Office Action dated Sep. 24, 2015 issued in corresponding Chinese Patent Application No. 201310326869.
Office Action dated Jul. 9, 2014 issued in corresponding Australian Patent Application No. 2013202568.
Applicant's response dated Aug. 20, 2015 to Office Action dated Jul. 9, 2014 issued in corresponding Australian Patent Application No. 2013202568.
Office Action dated Jul. 28, 2016 issued in related U.S. Appl. No. 13/633,971.

(56) References Cited

OTHER PUBLICATIONS

Office Action dated May 31, 2016 issued in corresponding Chinese Patent Application No. 201310326869.
Notice of Reasons for Rejection in Japanese Patent Application No. 2014-122390 dated Aug. 13, 2015.
Office Action issued in Canadian Patent Application No. 2,915,124, dated Aug. 15, 2016.
Office Action issued in Japanese Patent Application No. 2016-093699, dated Feb. 24, 2017 and dispatched Mar. 1, 2017.
Extended European Search Report issued in European Patent Application No. 16154948.0, dated Aug. 23, 2016.
Communication of a notice of opposition issued in European Patent Application No. 02795539.2 / 1453547 by the European Patent Office dated Jun. 26, 2017 as well as the statement of opposition dated Jun. 20, 2017 enclosed therein.
Response dated Dec. 5, 2017 in reply to the communication of a notice of opposition dated Jun. 26, 2017 in European Patent Application No. 02795539.2 / 1453547.
Examination Report issued in corresponding Australian Patent Application No. 2015258271 dated Aug. 30, 2017.
Declaration of Olivier Danos, Ph.D. dated Aug. 14, 2018, submitted in Opposition of EP Patent No. 02795539.2.
Declaration of Prof Asokan, dated Aug. 23, 2018, submitted in Opposition of EP Patent No. 02795539.2.
Declaration of Roberto Calcedo, PhD dated Sep. 24, 2018, submitted in Opposition of EP Patent No. 02795539.2.
Second declaration of Olivier Danos, Ph.D. dated Sep. 25, 2018, submitted in Opposition of EP Patent No. 02795539.2.
Proprietor's Submission pursuant to Rule 116 prior to oral proceedings dated Aug. 24, 2018 submitted in Opposition of EP Patent No. 02795539.2.
Opposer's Submission pursuant to Rule 116 prior to oral proceedings dated Aug. 24, 2018 submitted in Opposition of EP Patent No. 02795539.2.
Proprietor's Further Submission prior to oral proceedings dated Sep. 26, 2018 submitted in Opposition of EP Patent No. 02795539.2.
Opposer's Further Submission prior to oral proceedings dated Oct. 23, 2018 submitted in Opposition of EP Patent No. 02795539.2.
Summons to attend oral proceedings and Communication dated Mar. 29, 2018, issued in related European Patent No. 1453547.
Interlocutory decision in Opposition proceedings issued in related European Patent No. 1453547 dated Nov. 30, 2018.
Notice of Opposition and Opponent's Brief in European Patent No. 2359869, dated Sep. 26, 2019.
Office Action dated Oct. 12, 2017 in U.S. Appl. No. 15/584,674.
Response to Office Action dated Oct. 12, 2017 in U.S. Appl. No. 15/584,674, filed Dec. 12, 2017.
Office Action dated Mar. 3, 2018 in U.S. Appl. No. 15/584,674.
Response to Office Action dated Mar. 3, 2018 in U.S. Appl. No. 15/584,674, filed Jun. 8, 2018.
Office Action dated Sep. 19, 2019 in U.S. Appl. No. 15/584,674.
Response to Office Action dated Sep. 19, 2019 in U.S. Appl. No. 15/584,674, filed Jul. 17, 2019.
Notice of Allowance dated Sep. 19, 2019 in U.S. Appl. No. 15/584,674.
International Search Report issued in corresponding International Application No. PCT/US2002/033629, dated Jul. 28, 2003.
Written Opinion issued in corresponding International Application No. PCT/US2002/033629, dated Aug. 11, 2004.
Office Action dated Dec. 4, 2018 in U.S. Appl. No. 16/145,848.
Response to Office Action dated Dec. 4, 2018 in U.S. Appl. No. 16/145,848, filed Feb. 4, 2019.
Office Action dated Apr. 19, 2019 in U.S. Appl. No. 16/145,848.
Response to Office Action dated Apr. 19, 2019 in U.S. Appl. No. 16/145,848, filed Jul. 11, 2019.
Notice of Allowance dated Nov. 14, 2019 in U.S. Appl. No. 16/145,848.
Office Action dated Jul. 28, 2018 in U.S. Appl. No. 13/633,971.

FIG. 1A

|        | 1                                                                      50 |
|--------|---------------------------------------------------------------------------|
| 42_2   | .......... .......... .......... .......... .......... |
| 42_8   | .......... .......... .......... .......... .......... |
| 42_15  | .......... .......... .......... .......... .......... |
| 42_5b  | .......... .......... .......... .......... .......... |
| 42_1b  | .......... .......... .......... .......... .......... |
| 42_13  | .......... .......... .......... .......... .......... |
| 42_3a  | .......... .......... .......... .......... .......... |
| 42_4   | .......... .......... .......... .......... .......... |
| 42_5a  | .......... .......... .......... .......... .......... |
| 42_10  | .......... .......... .......... .......... .......... |
| 42_3b  | .......... .......... .......... .......... .......... |
| 42_11  | .......... .......... .......... .......... .......... |
| 42_6b  | .......... .......... .......... .......... .......... |
| 43_1   | .......... .......... .......... .......... .......... |
| 43_5   | .......... .......... .......... .......... .......... |
| 43_12  | .......... .......... .......... .......... .......... |
| 43_20  | .......... .......... .......... .......... .......... |
| 43_21  | .......... .......... .......... .......... .......... |
| 43_23  | .......... .......... .......... .......... .......... |
| 43_25  | .......... .......... .......... .......... .......... |
| 44_1   | .......... .......... .......... .......... .......... |
| 44_5   | .......... .......... .......... .......... .......... |
| 223_10 | .......... .......... .......... .......... .......... |
| 223_2  | .......... .......... .......... .......... .......... |
| 223_4  | .......... .......... .......... .......... .......... |
| 223_5  | .......... .......... .......... .......... .......... |
| 223_6  | .......... .......... .......... .......... .......... |
| 223_7  | .......... .......... .......... .......... .......... |
| A3_4   | .......... .......... .......... .......... .......... |
| A3_5   | .......... .......... .......... .......... .......... |
| A3_7   | .......... .......... .......... .......... .......... |
| A3_3   | .......... .......... .......... .......... .......... |
| 42_12  | .......... .......... .......... .......... .......... |
| AAV1   | TTGCCCACTC CCTCTCTGCG CGCTCGCTCG CTCGGTGGGG CCTGCGGACC |
| AAV2   | TTGGCCACTC CCTCTCTGCG CGCTCGCTCG CTCACTGAGG CCGGGCGACC |
| AAV3   | TTGGCCACTC CCTCTATGCG CACTCCTCG CTCGGTGGGG CCTGGCGACC |
| AAV8   | .......... .......... .......... .......... .......... |
| AAV9   | .......... .......... .......... .......... .......... |
| AAV7   | TTGGCCACTC CCTCTATGCG CGCTCGCTCG CTCGGTGGGG CCTGCGGACC |
| 44_2   | .......... .......... .......... .......... .......... |

FIG. 1B

```
                       51                                                          100
                                                                   Rep binding site
    42_2      .........  .........  .........  .........  .........
    42_8      .........  .........  .........  .........  .........
    42_15     .........  .........  .........  .........  .........
    42_5b     .........  .........  .........  .........  .........
    42_1b     .........  .........  .........  .........  .........
    42_13     .........  .........  .........  .........  .........
    42_3a     .........  .........  .........  .........  .........
    42_4      .........  .........  .........  .........  .........
    42_5a     .........  .........  .........  .........  .........
    42_10     .........  .........  .........  .........  .........
    42_3b     .........  .........  .........  .........  .........
    42_11     .........  .........  .........  .........  .........
    42_6b     .........  .........  .........  .........  .........
    43_1      .........  .........  .........  .........  .........
    43_5      .........  .........  .........  .........  .........
    43_12     .........  .........  .........  .........  .........
    43_20     .........  .........  .........  .........  .........
    43_21     .........  .........  .........  .........  .........
    43_23     .........  .........  .........  .........  .........
    43_25     .........  .........  .........  .........  .........
    44_1      .........  .........  .........  .........  .........
    44_5      .........  .........  .........  .........  .........
    223_10    .........  .........  .........  .........  .........
    223_2     .........  .........  .........  .........  .........
    223_4     .........  .........  .........  .........  .........
    223_5     .........  .........  .........  .........  .........
    223_6     .........  .........  .........  .........  .........
    223_7     .........  .........  .........  .........  .........
    A3_4      .........  .........  .........  .........  .........
    A3_5      .........  .........  .........  .........  .........
    A3_7      .........  .........  .........  .........  .........
    A3_3      .........  .........  .........  .........  .........
    42_12     .........  .........  .........  .........  .........
    AAV1      AAAGGTCCGC AGACGGCAGA GCTCTGCTCT GCCGGCCCCA CCGAGCGAGC
    AAV2      AAAGGTCGCC CGACGCCCGG GCTTTGCCCG GGCGGCCTCA GTGAGCGAGC
    AAV3      AAAGGTCGCC AGACGGACGT GCTTTGCACG TCCGGCCCCA CCGAGCGAGC
    AAV8      .........  .........  .........  .........  .........
    AAV9      .........  .........  .........  .........  .........
    AAV7      AAAGGTCCGC AGACGGCAGA GCTCTGCTCT GCCGGCCCCA CCGAGCGAGC
    44_2      .........  .........  .........  .........  .........
                                                         Rep binding site
```

FIG. 1C

```
Rep binding site                                                              150
 ◄──────────────────────────┐         TRS
    42_2      ..........  ..|.......  ...|.....  .........  .........
    42_8      ..........  ..|.......  ...........  .........  .........
    42_15     ..........  ..........  ..........  .........  .........
    42_5b     ..........  ..........  ..........  .........  .........
    42_1b     ..........  ..........  ..........  .........  .........
    42_13     ..........  ..........  ..........  .........  .........
    42_3a     ..........  ..........  ..........  .........  .........
    42_4      ..........  ..........  ..........  .........  .........
    42_5a     ..........  ..........  ..........  .........  .........
    42_10     ..........  ..........  ..........  .........  .........
    42_3b     ..........  ..........  ..........  .........  .........
    42_11     ..........  ..........  ..........  .........  .........
    42_6b     ..........  ..........  ..........  .........  .........
    43_1      ..........  ..........  ..........  .........  .........
    43_5      ..........  ..........  ..........  .........  .........
    43_12     ..........  ..........  ..........  .........  .........
    43_20     ..........  ..........  ..........  .........  .........
    43_21     ..........  ..........  ..........  .........  .........
    43_23     ..........  ..........  ..........  .........  .........
    43_25     ..........  ..........  ..........  .........  .........
    44_1      ..........  ..........  ..........  .........  .........
    44_5      ..........  ..........  ..........  .........  .........
    223_10    ..........  ..........  ..........  .........  .........
    223_2     ..........  ..........  ..........  .........  .........
    223_4     ..........  ..........  ..........  .........  .........
    223_5     ..........  ..........  ..........  .........  .........
    223_6     ..........  ..........  ..........  .........  .........
    223_7     ..........  ..........  ..........  .........  .........
    A3_4      ..........  ..........  ..........  .........  .........
    A3_5      ..........  ..........  ..........  .........  .........
    A3_7      ..........  ..........  ..........  .........  .........
    A3_3      ..........  ..........  ..........  .........  .........
    42_12     ..........  ..........  ..........  .........  .........
    AAV1      GAGCGCGCAG  AGAGGGAGTG  GGCAACTCCA  TCACTAGGGG  TAATCGCGAA
    AAV2      GAGCGCGCAG  AGAGGGAGTG  GCCAACTCCA  TCACTAGGGG  TTC.......
    AAV3      GAGTGCGCAT  AGAGGGAGTG  GCCAACTCCA  TCACTAGACG  T.........
    AAV8      .......CAG  AGAGGGAGTG  GCCAACTCCA  TCACTAGGGG  TAG.CGCGAA
    AAV9      .......CAG  AGAGGGAGTG  GCCAACTCCA  TCACTAGGGG  TAATCGCGAA
    AAV7      GAGCGCGCAT  AGAGGGAGTG  GCCAACTCCA  TCACTAGGGG  TA.CCGCGAA
    44_2      ..........  ..|.......  ...|......  .........  .........
 ◄──────────────────────────┘         TRS
   Rep binding site
```

FIG. 1D

```
              151                                                              200
   42_2       ..........  ..........  ..........  ..........  ..........
   42_8       ..........  ..........  ..........  ..........  ..........
   42_15      ..........  ..........  ..........  ..........  ..........
   42_5b      ..........  ..........  ..........  ..........  ..........
   42_1b      ..........  ..........  ..........  ..........  ..........
   42_13      ..........  ..........  ..........  ..........  ..........
   42_3a      ..........  ..........  ..........  ..........  ..........
   42_4       ..........  ..........  ..........  ..........  ..........
   42_5a      ..........  ..........  ..........  ..........  ..........
   42_10      ..........  ..........  ..........  ..........  ..........
   42_3b      ..........  ..........  ..........  ..........  ..........
   42_11      ..........  ..........  ..........  ..........  ..........
   42_6b      ..........  ..........  ..........  ..........  ..........
   43_1       ..........  ..........  ..........  ..........  ..........
   43_5       ..........  ..........  ..........  ..........  ..........
   43_12      ..........  ..........  ..........  ..........  ..........
   43_20      ..........  ..........  ..........  ..........  ..........
   43_21      ..........  ..........  ..........  ..........  ..........
   43_23      ..........  ..........  ..........  ..........  ..........
   43_25      ..........  ..........  ..........  ..........  ..........
   44_1       ..........  ..........  ..........  ..........  ..........
   44_5       ..........  ..........  ..........  ..........  ..........
  223_10      ..........  ..........  ..........  ..........  ..........
  223_2       ..........  ..........  ..........  ..........  ..........
  223_4       ..........  ..........  ..........  ..........  ..........
  223_5       ..........  ..........  ..........  ..........  ..........
  223_6       ..........  ..........  ..........  ..........  ..........
  223_7       ..........  ..........  ..........  ..........  ..........
   A3_4       ..........  ..........  ..........  ..........  ..........
   A3_5       ..........  ..........  ..........  ..........  ..........
   A3_7       ..........  ..........  ..........  ..........  ..........
   A3_3       ..........  ..........  ..........  ..........  ..........
   42_12      ..........  ..........  ..........  ..........  ..........
   AAV1       GCGCCTCCCA  CGCTGCCGCG  TCAGCGCTGA  CGTAAATTAC  GTCATAGGGG
   AAV2       .......CTG  GAGGGGTGGA  GTCGTGACGT  GAATTACGTC  ATAGGGTTAG
   AAV3       .......ATG  GCAGTGACGT  AACGCGAAGC  GCGCGAAGCG  AGACCACGCC
   AAV8       GCGCCTCCCA  CGCTGCCGCG  TCAGCGCTGA  CGTAAATTAC  GTCATAGGGG
   AAV9       GCGCCTCCCA  CGCTGCCGCG  TCAGCGCTGA  CGTAGATTAC  GTCATAGGGG
   AAV7       GCGCCTCCCA  CGCTGCCGCG  TCAGCGCTGA  CGTAAATCAC  GTCATAGGGG
   44_2       ..........  ..........  ..........  ..........  ..........
```

FIG. 1H

```
           351                                                           400
42_2       ..........  ..........  ..........  ..........  ..........
42_8       ..........  ..........  ..........  ..........  ..........
42_15      ..........  ..........  ..........  ..........  ..........
42_5b      ..........  ..........  ..........  ..........  ..........
42_1b      ..........  ..........  ..........  ..........  ..........
42_13      ..........  ..........  ..........  ..........  ..........
42_3a      ..........  ..........  ..........  ..........  ..........
42_4       ..........  ..........  ..........  ..........  ..........
42_5a      ..........  ..........  ..........  ..........  ..........
42_10      ..........  ..........  ..........  ..........  ..........
42_3b      ..........  ..........  ..........  ..........  ..........
42_11      ..........  ..........  ..........  ..........  ..........
42_6b      ..........  ..........  ..........  ..........  ..........
43_1       ..........  ..........  ..........  ..........  ..........
43_5       ..........  ..........  ..........  ..........  ..........
43_12      ..........  ..........  ..........  ..........  ..........
43_20      ..........  ..........  ..........  ..........  ..........
43_21      ..........  ..........  ..........  ..........  ..........
43_23      ..........  ..........  ..........  ..........  ..........
43_25      ..........  ..........  ..........  ..........  ..........
44_1       ..........  ..........  ..........  ..........  ..........
44_5       ..........  ..........  ..........  ..........  ..........
223_10     ..........  ..........  ..........  ..........  ..........
223_2      ..........  ..........  ..........  ..........  ..........
223_4      ..........  ..........  ..........  ..........  ..........
223_5      ..........  ..........  ..........  ..........  ..........
223_6      ..........  ..........  ..........  ..........  ..........
223_7      ..........  ..........  ..........  ..........  ..........
A3_4       ..........  ..........  ..........  ..........  ..........
A3_5       ..........  ..........  ..........  ..........  ..........
A3_7       ..........  ..........  ..........  ..........  ..........
A3_3       ..........  ..........  ..........  ..........  ..........
42_12      ..........  ..........  ..........  ..........  ..........
AAV1       CGAGATCGTG  ATCAAGGTGC  CGAGCGACCT  GGACGAGCAC  CTGCCGGGCA
AAV2       CGAGATTGTG  ATTAAGGTCC  CCAGCGACCT  TGACGGGCAT  CTGCCCGGCA
AAV3       CGAGATTGTC  CTGAAGGTCC  CGAGTGACCT  GGACGAGCGC  CTGCCGGGCA
AAV8       CGAGATCGTG  ATCAAGGTGC  CGAGCGACCT  GGACGAGCAC  CTGCCGGGCA
AAV9       CGAGATTGTG  ATCAAGGTGC  CGAGCGACCT  GGACGAGCAC  CTGCCGGGCA
AAV7       CGAGATCGTG  ATCAAGGTGC  CGAGCGACCT  GGACGAGCAC  CTGCCGGGCA
44_2       ..........  ..........  ..........  ..........  ..........
```

FIG. 1I

```
         401                                                              450
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   TTTCTGACTC  GTTTGTGAGC  TGGGTGGCCG  AGAAGGAATG  GGAGCTGCCC
  AAV2   TTTCTGACAG  CTTTGTGAAC  TGGGTGGCCG  AGAAGGAATG  GGAGTTGCCG
  AAV3   TTTCTAACTC  GTTTGTTAAC  TGGGTGGCCG  AGAAGGAATG  GGACGTGCCG
  AAV8   TTTCTGACTC  GTTTGTGAAC  TGGGTGGCCG  AGAAGGAATG  GGAGCTGCCC
  AAV9   TTTCTGACTC  TTTTGTGAAC  TGGGTGGCCG  AGAAGGAATG  GGAGCTGCCC
  AAV7   TTTCTGACTC  GTTTGTGAAC  TGGGTGGCCG  AGAAGGAATG  GGAGCTGCCC
  44_2   ..........  ..........  ..........  ..........  ..........
```

FIG. 1J

```
         451                                                              500
 42_2    ..........  ..........  ..........  ..........  ..........
 42_8    ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
 42_4    ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
 43_1    ..........  ..........  ..........  ..........  ..........
 43_5    ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
 44_1    ..........  ..........  ..........  ..........  ..........
 44_5    ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
 A3_4    ..........  ..........  ..........  ..........  ..........
 A3_5    ..........  ..........  ..........  ..........  ..........
 A3_7    ..........  ..........  ..........  ..........  ..........
 A3_3    ..........  ..........  ..........  ..........  ..........
 42_12   ..........  ..........  ..........  ..........  ..........
 AAV1    CCGGATTCTG  ACATGGATCT  GAATCTGATT  GAGCAGGCAC  CCCTGACCGT
 AAV2    CCAGATTCTG  ACATGGATCT  GAATCTGATT  GAGCAGGCAC  CCCTGACCGT
 AAV3    CCGGATTCTG  ACATGGATCC  GAATCTGATT  GAGCAGGCAC  CCCTGACCGT
 AAV8    CCGGATTCTG  ACATGGATCG  GAATCTGATC  GAGCAGGCAC  CCCTGACCGT
 AAV9    CCGGATTCTG  ACATGGATCG  GAATCTGATC  GAGCAGGCAC  CCCTGACCGT
 AAV7    CCGGATTCTG  ACATGGATCT  GAATCTGATC  GAGCAGGCAC  CCCTGACCGT
 44_2    ..........  ..........  ..........  ..........  ..........
```

FIG. 1K

```
        501                                                      550
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    GGCCGAGAAG  CTGCAGCGCG  ACTTCCTGGT  CCAATGGCGC  CGCGTGAGTA
AAV2    GGCCGAGAAG  CTGCAGCGCG  ACTTTCTGAC  GGAATGGCGC  CGTGTGAGTA
AAV3    GGCCGAAAAG  CTTCAGCGCG  AGTTCCTGGT  GGAGTGGCGC  CGCGTGAGTA
AAV8    GGCCGAGAAG  CTGCAGCGCG  ACTTCCTGGT  CCAATGGCGC  CGCGTGAGTA
AAV9    GGCCGAGAAG  CTGTAGCGCG  ACTTCCTGGT  CCAATGGCGC  CGCGTGAGTA
AAV7    GGCCGAGAAG  CTGCAGCGCG  ACTTCCTGGT  CCAATGGCGC  CGCGTGAGTA
44_2    ..........  ..........  ..........  ..........  ..........
```

FIG. 1L

```
              551                                                              600
   42_2       ..........  ..........  ..........  ..........  ..........
   42_8       ..........  ..........  ..........  ..........  ..........
  42_15       ..........  ..........  ..........  ..........  ..........
  42_5b       ..........  ..........  ..........  ..........  ..........
  42_1b       ..........  ..........  ..........  ..........  ..........
  42_13       ..........  ..........  ..........  ..........  ..........
  42_3a       ..........  ..........  ..........  ..........  ..........
   42_4       ..........  ..........  ..........  ..........  ..........
  42_5a       ..........  ..........  ..........  ..........  ..........
  42_10       ..........  ..........  ..........  ..........  ..........
  42_3b       ..........  ..........  ..........  ..........  ..........
  42_11       ..........  ..........  ..........  ..........  ..........
  42_6b       ..........  ..........  ..........  ..........  ..........
   43_1       ..........  ..........  ..........  ..........  ..........
   43_5       ..........  ..........  ..........  ..........  ..........
  43_12       ..........  ..........  ..........  ..........  ..........
  43_20       ..........  ..........  ..........  ..........  ..........
  43_21       ..........  ..........  ..........  ..........  ..........
  43_23       ..........  ..........  ..........  ..........  ..........
  43_25       ..........  ..........  ..........  ..........  ..........
   44_1       ..........  ..........  ..........  ..........  ..........
   44_5       ..........  ..........  ..........  ..........  ..........
  223_10      ..........  ..........  ..........  ..........  ..........
  223_2       ..........  ..........  ..........  ..........  ..........
  223_4       ..........  ..........  ..........  ..........  ..........
  223_5       ..........  ..........  ..........  ..........  ..........
  223_6       ..........  ..........  ..........  ..........  ..........
  223_7       ..........  ..........  ..........  ..........  ..........
   A3_4       ..........  ..........  ..........  ..........  ..........
   A3_5       ..........  ..........  ..........  ..........  ..........
   A3_7       ..........  ..........  ..........  ..........  ..........
   A3_3       ..........  ..........  ..........  ..........  ..........
  42_12       ..........  ..........  ..........  ..........  ..........
   AAV1       AGGCCCCGGA  GGCCCTCTTC  TTTGTTCAGT  TCGAGAAGGG  CGAGTCCTAC
   AAV2       AGGCCCCGGA  GGCCCTTTTC  TTTGTGCAAT  TTGAGAAGGG  AGAGAGCTAC
   AAV3       AGGCCCCGGA  GGCCCTCTTT  TTTGTCCAGT  TCGAAAAGGG  GGAGACCTAC
   AAV8       AGGCCCCGGA  GGCCCTCTTC  TTTGTTCAGT  TCGAGAAGGG  CGAGAGCTAC
   AAV9       AGGCCCCGGA  GGCCCTCTTC  TTTGTTCAGT  TCGAGAAGGG  CGAGAGCTAC
   AAV7       AGGCCCCGGA  GGCCCTGTTC  TTTGTTCAGT  TCGAGAAGGG  CGAGAGCTAC
   44_2       ..........  ..........  ..........  ..........  ..........
```

FIG. 1M

```
      601                                                          650
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    TTCCACCTCC  ATATTCTGGT  GGAGACCACG  GGGGTCAAAT  CCATGGTGCT
AAV2    TTCCACATGC  ACGTGCTCGT  GGAAACCACC  GGGGTGAAAT  CCATGGTTTT
AAV3    TTCCACCTGC  ACGTGCTGAT  TGAGACCATC  GGGGTCAAAT  CCATGGTGGT
AAV8    TTTCACCTGC  ACGTTCTGGT  CGAGACCACG  GGGGTCAAGT  CCATGGTGCT
AAV9    TTTCACCTGC  ACGTTCTGGT  CGAGACCACG  GGGGTCAAGT  CCATGGTGCT
AAV7    TTCCACCTTC  ACGTTCTGGT  GGAGACCACG  GGGGTCAAGT  CCATGGTGCT
44_2    ..........  ..........  ..........  ..........  ..........
```

FIG. 1N

```
         651                                                              700
  42_2   ..........  ..........  ..........  ..........  ..........
  42_8   ..........  ..........  ..........  ..........  ..........
  42_15  ..........  ..........  ..........  ..........  ..........
  42_5b  ..........  ..........  ..........  ..........  ..........
  42_1b  ..........  ..........  ..........  ..........  ..........
  42_13  ..........  ..........  ..........  ..........  ..........
  42_3a  ..........  ..........  ..........  ..........  ..........
  42_4   ..........  ..........  ..........  ..........  ..........
  42_5a  ..........  ..........  ..........  ..........  ..........
  42_10  ..........  ..........  ..........  ..........  ..........
  42_3b  ..........  ..........  ..........  ..........  ..........
  42_11  ..........  ..........  ..........  ..........  ..........
  42_6b  ..........  ..........  ..........  ..........  ..........
  43_1   ..........  ..........  ..........  ..........  ..........
  43_5   ..........  ..........  ..........  ..........  ..........
  43_12  ..........  ..........  ..........  ..........  ..........
  43_20  ..........  ..........  ..........  ..........  ..........
  43_21  ..........  ..........  ..........  ..........  ..........
  43_23  ..........  ..........  ..........  ..........  ..........
  43_25  ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
  42_12  ..........  ..........  ..........  ..........  ..........
   AAV1  GGGCCGCTTC  CTGAGTCAGA  TTAGGGACAA  GCT.GGTGCA  GACCATCTAC
   AAV2  GGGACGTTTC  CTGAGTCAGA  TTCGCGAAAA  ACT..GATTC  AGAGAATTTA
   AAV3  CGGCCGCTAC  GTGAGCCAGA  TTAAAGAGAA  GCT..GGTGA  CCCGCATCTA
   AAV8  AGGCCGCTTC  CTGAGTCAGA  TTCGGGAAAA  GCTTGGTCCA  GACCATCTAC
   AAV9  AGGCCGCTTC  CTGAGTCAGA  TTCGGGAGAA  GCT.GGTCCA  GACCATCTAC
   AAV7  AGGCCGCTTC  CTGAGTCAGA  TTCGGGAGAA  GCT....G..  GTCCAGACCA
  44_2   ..........  ..........  ..........  ..........  ..........
```

FIG. 10

```
        701                                                      750
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    C.GCGGGATC  GAGCCG.ACC  CTGCCCAACT  GGTTCGCGGT  GACCAA.GAC
AAV2    CCGCGGGATC  GAGCCG.ACT  TTGCCAAACT  GGTTCGCGGT  CACAAA...G
AAV3    CCGCGGGGTC  GAGCCG.CAG  CTTCCGAACT  GGTTCGCGGT  GACCAA...A
AAV8    CCGCGGGGTC  GAGCCCACC   TTGCCCAACT  GGTTCGCGGT  GACCAAAGAC
AAV9    C.GCGGGATC  GAGCCG.ACC  CTGCCCAACT  GGTTCGCGGT  GACCAA.GAC
AAV7    TCTACCGCGG  GGTCGAGCCC  ACGCTGCCCA  ACTGGTTCGC  GGTGACCAAG
44_2    ..........  ..........  ..........  ..........  ..........
```

FIG. 1P

```
         751                                                              800
 42_2    ..........  ..........  ..........  ..........  ..........
 42_8    ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
 42_4    ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
 43_1    ..........  ..........  ..........  ..........  ..........
 43_5    ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
 44_1    ..........  ..........  ..........  ..........  ..........
 44_5    ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
 A3_4    ..........  ..........  ..........  ..........  ..........
 A3_5    ..........  ..........  ..........  ..........  ..........
 A3_7    ..........  ..........  ..........  ..........  ..........
 A3_3    ..........  ..........  ..........  ..........  ..........
 42_12   ..........  ..........  ..........  ..........  ..........
 AAV1    GCG.TAATGG  CGCCGGAGGG  GGG.AACAAG  GTGGTGGACG  AGTGCTACAT
 AAV2    ACCAGAAATG  GCGCCGGAGG  CGGGAACAAG  GTGGTGGATG  AGTGCTACAT
 AAV3    ACGCGAAATG  GCGCCGGGGG  CGGGAACAAG  GTGGTGGACG  ACTGCTACAT
 AAV8    GCGGTAATGG  CGCCGGCGGG  GGGAACAAG   GTGGTGGACG  AGTGCTACAT
 AAV9    GCG.TAATGG  CGCCGGCGGG  GGG.AACAAG  GTGGTGGACG  AGTGCTACAT
 AAV7    ACGCGTAATG  GCGCCGGCGG  GGGGAACAAG  GTGGTGGACG  AGTGCTACAT
 44_2    ..........  ..........  ..........  ..........  ..........
```

FIG. 1Q

```
           801                                                              850
 42_2      ..........  ..........  ..........  ..........  ..........
 42_8      ..........  ..........  ..........  ..........  ..........
 42_15     ..........  ..........  ..........  ..........  ..........
 42_5b     ..........  ..........  ..........  ..........  ..........
 42_1b     ..........  ..........  ..........  ..........  ..........
 42_13     ..........  ..........  ..........  ..........  ..........
 42_3a     ..........  ..........  ..........  ..........  ..........
 42_4      ..........  ..........  ..........  ..........  ..........
 42_5a     ..........  ..........  ..........  ..........  ..........
 42_10     ..........  ..........  ..........  ..........  ..........
 42_3b     ..........  ..........  ..........  ..........  ..........
 42_11     ..........  ..........  ..........  ..........  ..........
 42_6b     ..........  ..........  ..........  ..........  ..........
 43_1      ..........  ..........  ..........  ..........  ..........
 43_5      ..........  ..........  ..........  ..........  ..........
 43_12     ..........  ..........  ..........  ..........  ..........
 43_20     ..........  ..........  ..........  ..........  ..........
 43_21     ..........  ..........  ..........  ..........  ..........
 43_23     ..........  ..........  ..........  ..........  ..........
 43_25     ..........  ..........  ..........  ..........  ..........
 44_1      ..........  ..........  ..........  ..........  ..........
 44_5      ..........  ..........  ..........  ..........  ..........
223_10     ..........  ..........  ..........  ..........  ..........
223_2      ..........  ..........  ..........  ..........  ..........
223_4      ..........  ..........  ..........  ..........  ..........
223_5      ..........  ..........  ..........  ..........  ..........
223_6      ..........  ..........  ..........  ..........  ..........
223_7      ..........  ..........  ..........  ..........  ..........
 A3_4      ..........  ..........  ..........  ..........  ..........
 A3_5      ..........  ..........  ..........  ..........  ..........
 A3_7      ..........  ..........  ..........  ..........  ..........
 A3_3      ..........  ..........  ..........  ..........  ..........
 42_12     ..........  ..........  ..........  ..........  ..........
 AAV1      CCCCAACTAC  CTCCTGCCCA  AGACTCAGCC  CGAGCTGCAG  TGGGCGTGGA
 AAV2      CCCCAATTAC  TTGCTCCCCA  AAACCCAGCC  TGAGCTCCAG  TGGGCGTGGA
 AAV3      CCCCAACTAC  CTGCTCCCCA  AGACCCAGCC  CGAGCTCCAG  TGGGCGTGGA
 AAV8      CCCCAACTAC  CTCCTGCCCA  AGACTCAGCC  CGAGCTGCAG  TGGGCGTGGA
 AAV9      CCCCAACTAC  CTCCTGCCCA  AGACTCAGCC  CGAGCTGCAG  TGGGCGTGGA
 AAV7      CCCCAACTAC  CTCCTGCCCA  AGACCCAGCC  CGAGCTGCAG  TGGGCGTGGA
 44_2      ..........  ..........  ..........  ..........  ..........
```

FIG. 1S

```
          901                                                         950
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
 223_10   ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   CGGCTCGTGG  CGCAGCACCT  GACCCACGTC  AGCCAGACCC  AGGAGCAGAA
   AAV2   CGGTTGGTGG  CGCAGCATCT  GACGCACGTG  TCGCAGACGC  AGGAGCAGAA
   AAV3   CGGCTGGTGG  CGCAGCATCT  GACGCACGTG  TCGCAGACGC  AGGAGCAGAA
   AAV8   CGGCTCGTGG  CGCAGCACCT  GACCCACGTC  AGCCAGACGC  AGGAGCAGAA
   AAV9   CGGCTCGTGG  CGCAGCACCT  GACCCACGTC  AGCCAGACGC  AGGAGCAGAA
   AAV7   CGGCTCGTGG  CGCAGCACCT  GACCCACGTC  AGCCAGACGC  AGGAGCAGAA
   44_2   ..........  ..........  ..........  ..........  ..........
```

FIG. 1T

```
           951                                                              1000
   42_2    ..........  ..........  ..........  ..........  ..........
   42_8    ..........  ..........  ..........  ..........  ..........
  42_15    ..........  ..........  ..........  ..........  ..........
  42_5b    ..........  ..........  ..........  ..........  ..........
  42_1b    ..........  ..........  ..........  ..........  ..........
  42_13    ..........  ..........  ..........  ..........  ..........
  42_3a    ..........  ..........  ..........  ..........  ..........
   42_4    ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    ..........  ..........  ..........  ..........  ..........
   43_1    ..........  ..........  ..........  ..........  ..........
   43_5    ..........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
   44_1    ..........  ..........  ..........  ..........  ..........
   44_5    ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
   A3_4    ..........  ..........  ..........  ..........  ..........
   A3_5    ..........  ..........  ..........  ..........  ..........
   A3_7    ..........  ..........  ..........  ..........  ..........
   A3_3    ..........  ..........  ..........  ..........  ..........
  42_12    ..........  ..........  ..........  ..........  ..........
   AAV1    CAAGGAGAAT  CTGAACCCCA  ATTCTGACGC  GCCTGTCATC  CGGTCAAAAA
   AAV2    CAAAGAGAAT  CAGAATCCCA  ATTCTGATGC  GCCGGTGATC  AGATCAAAAA
   AAV3    CAAAGAGAAT  CAGAACCCCA  ATTCTGACGC  GCCGGTCATC  AGGTCAAAAA
   AAV8    CAAGGAGAAT  CTGAACCCCA  ATTCTGACGC  GCCCGTGATC  AGGTCAAAAA
   AAV9    CAAGGAGAAT  CTGAACCCCA  ATTCTGACGC  GCCCGTGATC  AGGTCAAAAA
   AAV7    CAAGGAGAAT  CTGAACCCCA  ATTCTGACGC  GCCCGTGATC  AGGTCAAAAA
   44_2    ..........  ..........  ..........  ..........  ..........
```

FIG. 1U 1001                                                                              1050

Rep52/40 start codon

| | | | | |
|---|---|---|---|---|
| 42_2 | | | | |
| 42_8 | | | | |
| 42_15 | | | | |
| 42_5b | | | | |
| 42_1b | | | | |
| 42_13 | | | | |
| 42_3a | | | | |
| 42_4 | | | | |
| 42_5a | | | | |
| 42_10 | | | | |
| 42_3b | | | | |
| 42_11 | | | | |
| 42_6b | | | | |
| 43_1 | | | | |
| 43_5 | | | | |
| 43_12 | | | | |
| 43_20 | | | | |
| 43_21 | | | | |
| 43_23 | | | | |
| 43_25 | | | | |
| 44_1 | | | | |
| 44_5 | | | | |
| 223_10 | | | | |
| 223_2 | | | | |
| 223_4 | | | | |
| 223_5 | | | | |
| 223_6 | | | | |
| 223_7 | | | | |
| A3_4 | | | | |
| A3_5 | | | | |
| A3_7 | | | | |
| A3_3 | | | | |
| 42_12 | | | | |
| AAV1 | CCTCCGCGCG | CTACATGGAG | CTGGTCGGGT | GGCTGGTGGA | CCGGGGCATC |
| AAV2 | CTTCAGCCAG | GTACATGGAG | CTGGTCGGGT | GGCTCGTGGA | CAAGGGGATT |
| AAV3 | CCTCAGCCAG | GTACATGGAG | CTGGTCGGGT | GGCTGGTGGA | CCGCGGGATC |
| AAV8 | CCTCCGCGCG | CTATATGGAG | CTGGTCGGGT | GGCTGGTGGA | CCGGGGCATC |
| AAV9 | CCTCCGCGCG | CTACATGGAG | CTGGTCGGGT | GGCTGGTGGA | CCGGGGCATC |
| AAV7 | CCTCCGCGCG | CTACATGGAG | CTGGTCGGGT | GGCTGGTGGA | CCGGGGCATC |
| 44_2 | | | | |

Rep 52/40 start

FIG. 1V

```
         1051                                                              1100
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     ACCTCCGAGA  AGCAGTGGAT  CCAGGAGGAC  CAGGCCTCGT  ACATCTCCTT
AAV2     ACCTCGGAGA  AGCAGTGGAT  CCAGGAGGAC  CAGGCCTCAT  ACATCTCCTT
AAV3     ACGTCAGAAA  AGCAATGGAT  TCAGGAGGAC  CAGGCCTCGT  ACATCTCCTT
AAV8     ACCTCCGAGA  AGCAGTGGAT  CCAGGAGGAC  CAGGCCTCGT  ACATCTCCTT
AAV9     ACCTCCGAGA  AGCAGTGGAT  CCAGGAGGAC  CAGGCCTCGT  ACATCTCCTT
AAV7     ACCTCCGAGA  AGCAGTGGAT  CCAGGAGGAC  CAGGCCTCGT  ACATCTCCTT
44_2     ..........  ..........  ..........  ..........  ..........
```

FIG. 1W

```
         1101                                                           1150
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     CAACGCCGCT  TCCAACTCGC  GGTCCCAGAT  CAAGGCCGCT  CTGGACAATG
AAV2     CAATGCGGCC  TCCAACTCGC  GGTCCCAAAT  CAAGGCTGCC  TTGGACAATG
AAV3     CAACGCCGCC  TCCAACTCGC  GGTCCCAGAT  CAAGGCCGCG  CTGGACAATG
AAV8     CAACGCCGCC  TCCAACTCGC  GGTCCCAGAT  CAAGGCCGCG  CTGGACAATG
AAV9     CAACGCCGCC  TCCAACTCGC  GGTCCCAGAT  CAAGGCCGCG  CTGGACAATG
AAV7     CAACGCCGCC  TCCAACTCGC  GGTCCCAGAT  CAAGGCCGCG  CTGGACAATG
44_2     ..........  ..........  ..........  ..........  ..........
```

FIG. 1X

```
              1151                                                        1200
   42_2       ..........  ..........  ..........  ..........  ..........
   42_8       ..........  ..........  ..........  ..........  ..........
   42_15      ..........  ..........  ..........  ..........  ..........
   42_5b      ..........  ..........  ..........  ..........  ..........
   42_1b      ..........  ..........  ..........  ..........  ..........
   42_13      ..........  ..........  ..........  ..........  ..........
   42_3a      ..........  ..........  ..........  ..........  ..........
   42_4       ..........  ..........  ..........  ..........  ..........
   42_5a      ..........  ..........  ..........  ..........  ..........
   42_10      ..........  ..........  ..........  ..........  ..........
   42_3b      ..........  ..........  ..........  ..........  ..........
   42_11      ..........  ..........  ..........  ..........  ..........
   42_6b      ..........  ..........  ..........  ..........  ..........
   43_1       ..........  ..........  ..........  ..........  ..........
   43_5       ..........  ..........  ..........  ..........  ..........
   43_12      ..........  ..........  ..........  ..........  ..........
   43_20      ..........  ..........  ..........  ..........  ..........
   43_21      ..........  ..........  ..........  ..........  ..........
   43_23      ..........  ..........  ..........  ..........  ..........
   43_25      ..........  ..........  ..........  ..........  ..........
   44_1       ..........  ..........  ..........  ..........  ..........
   44_5       ..........  ..........  ..........  ..........  ..........
  223_10      ..........  ..........  ..........  ..........  ..........
  223_2       ..........  ..........  ..........  ..........  ..........
  223_4       ..........  ..........  ..........  ..........  ..........
  223_5       ..........  ..........  ..........  ..........  ..........
  223_6       ..........  ..........  ..........  ..........  ..........
  223_7       ..........  ..........  ..........  ..........  ..........
   A3_4       ..........  ..........  ..........  ..........  ..........
   A3_5       ..........  ..........  ..........  ..........  ..........
   A3_7       ..........  ..........  ..........  ..........  ..........
   A3_3       ..........  ..........  ..........  ..........  ..........
   42_12      ..........  ..........  ..........  ..........  ..........
   AAV1       CCGGCAAGAT  CATGGCGCTG  ACCAAATCCG  CGCCCGACTA  CCTGGTAGGC
   AAV2       CGGGAAAGAT  TATGAGCCTG  ACTAAAACCG  CCCCCGACTA  CCTGGTGGGC
   AAV3       CCTCCAAGAT  CATGAGCCTG  ACAAAGACGG  CTCCGGACTA  CCTGGTGGGC
   AAV8       CCGGCAAGAT  CATGGCGCTG  ACCAAATCCG  CGCCCGACTA  CCTGGTGGGG
   AAV9       CCGGCAAGAT  CATGGCGCTG  ACCAAATCCG  CGCCCGACTA  CCTGGTAGGC
   AAV7       CCGGCAAGAT  CATGGCGCTG  ACCAAATCCG  CGCCCGACTA  CCTGGTGGGG
   44_2       ..........  ..........  ..........  ..........  ..........
```

FIG 1Y

```
           1201                                                           1250
   42_2    ..........  ..........  ..........  ..........  ..........
   42_8    ..........  ..........  ..........  ..........  ..........
   42_15   ..........  ..........  ..........  ..........  ..........
   42_5b   ..........  ..........  ..........  ..........  ..........
   42_1b   ..........  ..........  ..........  ..........  ..........
   42_13   ..........  ..........  ..........  ..........  ..........
   42_3a   ..........  ..........  ..........  ..........  ..........
   42_4    ..........  ..........  ..........  ..........  ..........
   42_5a   ..........  ..........  ..........  ..........  ..........
   42_10   ..........  ..........  ..........  ..........  ..........
   42_3b   ..........  ..........  ..........  ..........  ..........
   42_11   ..........  ..........  ..........  ..........  ..........
   42_6b   ..........  ..........  ........GA  ATTCGCCCTT  TCTACGGCTG
   43_1    ..........  ..........  ..........  ..........  ..........
   43_5    ..........  ..........  ..........  ..........  ..........
   43_12   ..........  ..........  ..........  ..........  ..........
   43_20   ..........  ..........  ..........  ..........  ..........
   43_21   ..........  ..........  ..........  ..........  ..........
   43_23   ..........  ..........  ..........  ..........  ..........
   43_25   ..........  ..........  ..........  ..........  ..........
   44_1    ..........  ..........  ..........  ..........  ..........
   44_5    ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
   A3_4    ..........  ..........  ..........  ..........  ..........
   A3_5    ..........  ..........  ..........  ..........  ..........
   A3_7    ..........  ..........  ..........  ..........  ..........
   A3_3    ..........  ..........  ..........  ..........  ..........
   42_12   ..........  ..........  ..........  ..........  ..........
   AAV1    CCCGCTCCGC  CCGCGGACAT  TAAAACCAAC  CGCATCTACC  GCATCCTGGA
   AAV2    CAGCAGCCCG  TGGAGGACAT  TTCCAGCAAT  CGGATTTATA  AAATTTTGGA
   AAV3    AGCAACCCGC  CGGAGGACAT  TACCAAAAAT  CGGATCTACC  AAATCCTGGA
   AAV8    CCCTCGCTGC  CCGCGGACAT  TACCCAGAAC  CGCATCTACC  GCATCCTCGC
   AAV9    CCTTCACTTC  CGGTGGACAT  TACGCAGAAC  CGCATCTACC  GCATCCTGCA
   AAV7    CCCTCGCTGC  CCGCGGACAT  TAAAACCAAC  CGCATCTACC  GCATCCTGGA
   44_2    ..........  ..........  ..........  ..........  ..........
```

FIG. 1Z

```
        1251                                                       1300
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   CGTCAACTGG  ACCAATGAGA  ACTTTCCCTT  CAACGATTGC  GTCGACAAGA
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    GCTGAACGGC  TACGAACCTG  CCTACGCCGG  CTCCGTCTTT  CTCGGCTGGG
AAV2    ACTAAACGGG  TACGATCCCC  AATATGCGGC  TTCCGTCTTT  CTGGGATGGG
AAV3    GCTGAACGGG  TACGATCCGC  AGTACGCGGC  CTCCGTCTTC  CTGGGCTGGG
AAV8    TCTCAACGGC  TACGACCCTG  CCTACGCCGG  CTCCGTCTTT  CTCGGCTGGG
AAV9    GCTCAACGGC  TACGACCCTG  CCTACGCCGG  CTCCGTCTTT  CTCGGCTGGG
AAV7    GCTGAACGGG  TACGATCCTG  CCTACGCCGG  CTCCGTCTTT  CTCGGCTGGG
44_2    ..........  ..........  ..........  ..........  ..........
```

FIG. 1AA

```
           1301                                                       1350
   42_2    ..........  ..........  ..........  ..........  ..........
   42_8    ..........  ..........  ..........  ..........  ..........
   42_15   ..........  ..........  ..........  ..........  ..........
   42_5b   ..........  ..........  ..........  ..........  ..........
   42_1b   ..........  ..........  ..........  ..........  ..........
   42_13   ..........  ..........  ..........  ..........  ..........
   42_3a   ..........  ..........  ..........  ..........  ..........
   42_4    ..........  ..........  ..........  ..........  ..........
   42_5a   ..........  ..........  ..........  ..........  ..........
   42_10   ..........  ..........  ..........  ..........  ..........
   42_3b   ..........  ..........  ..........  ..........  ..........
   42_11   ..........  ..........  ..........  ..........  ..........
   42_6b   TGGTGATCTG  GTGGGAGGAG  GGCAAGATGA  CGGCCAAGGT  CGTGGAGTCC
   43_1    ..........  ..........  ..........  ..........  ..........
   43_5    ..........  ..........  ..........  ..........  ..........
   43_12   ..........  ..........  ..........  ..........  ..........
   43_20   ..........  ..........  ..........  ..........  ..........
   43_21   ..........  ..........  ..........  ..........  ..........
   43_23   ..........  ..........  ..........  ..........  ..........
   43_25   ..........  ..........  ..........  ..........  ..........
   44_1    ..........  ..........  ..........  ..........  ..........
   44_5    ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
   A3_4    ..........  ..........  ..........  ..........  ..........
   A3_5    ..........  ..........  ..........  ..........  ..........
   A3_7    ..........  ..........  ..........  ..........  ..........
   A3_3    ..........  ..........  ..........  ..........  ..........
   42_12   ..........  ..........  ..........  ..........  ..........
   AAV1    CCCAGAAAAG  GTTCGGGAAG  CGCAACACCA  TCTGGCTGTT  TGGGCCGGCC
   AAV2    CCACGAAAAA  GTTCGGCAAG  AGGAACACCA  TCTGGCTGTT  TGGGCCTGCA
   AAV3    CGCAAAAGAA  GTTCGGGAAG  AGGAACACCA  TCTGGCTCTT  TGGGCCGGCC
   AAV8    CTCAGAAAAA  GTTCGGGAAA  CGCAACACCA  TCTGGCTGTT  TGGACCCGCC
   AAV9    CACAAAAGAA  GTTCGGGAAA  CGCAACACCA  TCTGGCTGTT  TGGGCCGGCC
   AAV7    CCCAGAAAAA  GTTCGGGAAG  CGCAACACCA  TCTGGCTGTT  TGGGCCCGCC
   44_2    ..........  ..........  ..........  ..........  ..........
```

42_2   ..........  ..........  ..........  .......GAA  TTCGCCCTTT
    42_8   ..........  ..........  ..........  .......GAA  TTCGCCCTTT
   42_15   ..........  ..........  ..........  .......GAA  TTCGCCCTTT
   42_5b   ..........  ..........  ..........  .......GAA  TTCGCCCTTT
   42_1b   ..........  ..........  ..........  ..........  ..........
   42_13   ..........  ..........  ..........  .......GAA  TTCGCCCTTT
   42_3a   ..........  ..........  ..........  .......GAA  TTCGCCCTTT
    42_4   ..........  ..........  ..........  ..........  ..........
   42_5a   ..........  ..........  ..........  ........GA  ATTCGCCCTT
   42_10   ..........  ..........  ..........  ..........  ..........
   42_3b   ..........  ..........  ..........  ..........  ..........
   42_11   ..........  ..........  ..........  .......GAA  TTCGCCCTTT
   42_6b   GCCAACGCCA  TTCTCGGCGG  CAGCAAGGTG  CGCGTGGACC  AAAAGTGCAA
    43_1   ..........  ..........  ..........  .......GAA  TTCGCCCTTT
    43_5   ..........  ..........  ..........  .......GAA  TTCGCCCTTT
   43_12   ..........  ..........  ..........  .......GAA  TTCGCCCTT.
   43_20   ..........  ..........  ..........  .......GAA  TTCGCCCTTT
   43_21   ..........  ..........  ..........  .......GAA  TTCGCCCTT.
   43_23   ..........  ..........  ..........  .......GAA  TTCGCCCTT.
   43_25   ..........  ..........  ..........  .......GAA  TTCGCCCTTT
    44_1   ..........  ..........  ..........  .......GAA  TTCGCCCTTT
    44_5   ..........  ..........  ..........  .......GAA  TTCGCCCTTT
  223_10   ..........  ..........  ..........  ..........  ..........
   223_2   ..........  ..........  ..........  ..........  ..........
   223_4   ..........  ..........  ..........  ..........  ..........
   223_5   ..........  ..........  ..........  ..........  ..........
   223_6   ..........  ..........  ..........  ..........  ..........
   223_7   ..........  ..........  ..........  ..........  ..........
    A3_4   ..........  ..........  ..........  ........GA  ATTCGCCCTT
    A3_5   ..........  ..........  ..........  ........GA  ATTCGCCCTT
    A3_7   ..........  ..........  .........A  GCGGCCGCGA  ATTCGCCCTT
    A3_3   ..........  ..........  ..........  ........GA  ATTCGCCCTT
   42_12   ..........  ..........  ..........  .......GAA  TTCGCCCTTT
    AAV1   ACCACGGGCA  AGACCAACAT  CGCGGAAGCC  ATCGCCCACG  CCGTGCCCTT
    AAV2   ACTACCGGGA  AGACCAACAT  CGCGGAGGCC  ATAGCCCACA  CTGTGCCCTT
    AAV3   ACGACGGGTA  AAACCAACAT  CGCGGAAGCC  ATCGCCCACG  CCGTGCCCTT
    AAV8   ACCACCGGCA  AGACCAACAT  TGCGGAAGCC  ATCGCCCACG  CCGTGCCCTT
    AAV9   ACCACGGGAA  AGACCAACAT  CGCAGAAGCC  ATTGCCCACG  CCGTGCCCTT
    AAV7   ACCACCGGCA  AGACCAACAT  TGCGGAAGCC  ATCGCCCACG  CCGTGCCCTT
    44_2   ..........  ..........  ..........  ........GA  ATTCGCCCTT
```

FIG. 1AC

```
           1401                                                          1450
    42_2   .CTACGGCTG CGTCAACTGG ACCAATGAGA ACTTTCCCTT CAACGATTGC
    42_8   .CTACGGCTG CGTCAACTGG ACCAATGAGA ACTTTCCCTT CAACGATTGC
   42_15   .CTACGGCTG CGTCAACTGG ACCAATGAGA ACTTTCCCTT CAACGATTGC
   42_5b   .CTACGGCTG CGTCAACTGG ACCAATGAGA ACTTTCCCTT CAACGATTGC
   42_1b   .......... .......... .......... .......... ..........
   42_13   .CTACGGCTG CGTCAACTGG ACCAATGAGA ACTTTCCCTT CAACGATTGC
   42_3a   .CTACGGCTG CGTCAACTGG ACCAATGAGA ACTTTCCCTT CAACGATTGC
    42_4   .......... .......... .......... .......... ..........
   42_5a   .CTACGGCTG CGTCAACTGG ACCAATGAGA ACTTTCCCTT CAACGATTGC
   42_10   .......... .......... .......... .......... ..........
   42_3b   .......... .......... .......... .......... ..........
   42_11   .CTACGGCTG CGTCAACTGG ACCAATGAGA ACTTTCCCTT CAACGATTGC
   42_6b   .GTCTTCCGC CCAGATCGAT CCCACCCCCG TGATCGTCAC TTCCAACACC
    43_1   .CTACGGCTG CATCAACTGG ACCAATGAGA ACTTTCCCTT CAACGATTGC
    43_5   .CTACGGCTG CGTCAACTGG ACCAATGAGA ACTTTCCCTT CAACGATTGC
   43_12   .....GGCTG CGTCAACTGG ACCAATGAGA ACTTTCCCTT CAACGATTGC
   43_20   .CTACGGCTG CGTCAACTGG ACCAATGAGA ACTTTCCCTT CAACGATTGC
   43_21   .....GGCTG CGTCAACTGG ACCAATGAGA ACTTTCCCTT CAACGATTGC
   43_23   .CTACGGCTG CGTCAACTGG ACCAATGAGA ACTTTCCCTT CAACGATTGC
   43_25   .CTACGGCTG CGTCAACTGG ACCAATGAGA ACTTTCCCTT CAACGATTGC
    44_1   .CTACGGCTG CGTCAACTGG ACCAATGAGA ACTTTCCCTT CAACGATTGC
    44_5   .CTACGGCTG CGTCAACTGG ACCAATGAGA ACTTTCCCTT CAACGATTGC
  223_10   .......... .......... .......... .......... ..........
   223_2   .......... .......... .......... .......... ..........
   223_4   .......... .......... .......... .......... ..........
   223_5   .......... .......... .......... .......... ..........
   223_6   .......... .......... .......... .......... ..........
   223_7   .......... .......... .......... .......... ..........
    A3_4   TCTACGGCTG CGTCAACTGG ACCAATGAAA ACTTTCCCTT CAACGATTGC
    A3_5   TCTACGGCTG CGTCAACTGG ACCAATGAAA ACTTTCCCTT CAACGATTGC
    A3_7   TCTACGGCTG CGTCAACTGG ACCAATGAAA ACTTTCCCTT CAACGATTGC
    A3_3   TCTACGGCTG CGTCAACTGG ACCAATGAAA ACTTTCCCTT CAACGATTGC
   42_12   .CTACGGCTG CGTCAACTGG ACCAATGAGA ACTTTCCCTT CAACGATTGC
    AAV1   .CTACGGCTG CGTCAACTGG ACCAATGAGA ACTTTCCCTT CAATGATTGC
    AAV2   .CTACGGGTG CGTAAACTGG ACCAATGAGA ACTTTCCCTT CAACGACTGT
    AAV3   .CTACGGCTG CGTAAACTGG ACCAATGAGA ACTTTCCCTT CAACGATTGC
    AAV8   .CTACGGCTG CGTCAACTGG ACCAATGAGA ACTTTCCCTT CAATGATTGC
    AAV9   .CTACGGCTG CGTCAACTGG ACCAATGAGA ACTTTCCCTT CAACGATTGC
    AAV7   .CTACGGCTG CGTCAACTGG ACCAATGAGA ACTTTCCCTT CAACGATTGC
    44_2   TCTACGGCTG CGTCAACTGG ACCAATGAGA ACTTTCCCTT CAACGATTGC
```

FIG. 1AD

```
        1451                                                             1500
42_2    GTCGACAAGA TGGTGATCTG GTGGGAGGAG GGCAAGATGA CGGCCAAGGT
42_8    GTCGACAAGA TGGTGATCTG GTGGGAGGAG GGCAAGATGA CGGCCAAGGT
42_15   GTCGACAAGA TGGTGATCTG GTGGGAGGAG GGCAAGATGA CGGCCAAGGT
42_5b   GTCGACAAGA TGGTGATCTG GTGGGAGGAG GGCAAGATGA CGGCCAAGGT
42_1b   .......... .......... .......... .......... ..........
42_13   GTCGACAAGA TGGTGATCTG GTGGGAGGAG GGCAAGATGA CGGCCAAGGT
42_3a   GTCGACAAGA TGGTGATCTG GTGGGAGGAG GGCAAGATGA CGGCCAAGGT
42_4    .......... .......... .......... .......... ..........
42_5a   GTCGACAAGA TGGTGATCTG GTGGGAGGAG GGCAAGATGA CGGCCAAGGT
42_10   .......... .......... .......... .......... ..........
42_3b   .......... .......... .......... .......... ..........
42_11   GTCGACAAGA TGGTGATCTG GTGGGAGGAG GGCAAGATGA CGGCCAAGGT
42_6b   AACATGTGCG CCGTGATTGA CGGGAACAGC ACCACCTTCG AGCACCAGCA
43_1    GTCGACAAGA TGGTGATCTG GTGGGAGGAG GGCAAGATGA CGGCCAAGGT
43_5    GTCGACAAGA TGGTGATCTG GTGGGAGGAG GGCAAGATGA CGGCCAAGGT
43_12   GTCGACAAGA TGGTGATCTG GTGGGAGGAG GGCAAGATGA CGGCCAAGGT
43_20   GTCGACAAGA TGGTGATCTG GTGGGAGGAG GGCAAGATGA CGGCCAAGGT
43_21   GTCGACAAGA TGGTGATCTG GTGGGAGGAG GGCAAGATGA CGGCCAAGGT
43_23   GTCGACAAGA TGGTGATCTG GTGGGAGGAG GGCAAGATGA CGGCCAAGGT
43_25   GTCGACAAGA TGGTGATCTG GTGGGAGGAG GGCAAGATGA CGGCCAAGGT
44_1    GTCGACAAGA TGTTGATCTG GTGGGAGGAG GGCAAGATGA CGGCCAAGGT
44_5    GTCGACAAGA TGGTGATCTG GTGGGAGGAG GGCAAGATGA CGGCCAAGGT
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
A3_4    GTCGACAAGA TGGTGATCTG GTGGGAGGAG GGAAAGATGA CCGCCAAGGT
A3_5    GTCGACAAGA TGGTGATCTG GTGGGAGGAG GGAAAGATGA CCGCCAAGGT
A3_7    GTCGACAAGA TGGTGATCTG GTGGGAGGAG GGAAAGATGA CCGCCAAGGT
A3_3    GTCGACAAGA TGGTGATCTG GTGGGAGGAG GGAAAGATGA CCGCCAAGGT
42_12   GTCGACAAGA TGGTGATCTG GTGGGAGGAG GGCAAGATGA CGGCCAAGGT
AAV1    GTCGACAAGA TGGTGATCTG GTGGGAGGAG GGCAAGATGA CGGCCAAGGT
AAV2    GTCGACAAGA TGGTGATCTG GTGGGAGGAG GGGAAGATGA CCGCCAAGGT
AAV3    GTCGACAAGA TGGTGATCTG GTGGGAGGAG GGCAAGATGA CGGCCAAGGT
AAV8    GTCGACAAGA TGGTGATCTG GTGGGAGGAG GGCAAGATGA CGGCCAAGGT
AAV9    GTCGACAAGA TGGTGATCTG GTGGGAGGAG GGCAAGATGA CGGCCAAGGT
AAV7    GTCGACAAGA TGGTGATCTG GTGGGAGGAG GGCAAGATGA CGGCCAAGGT
44_2    GTCGACAAGA TGGTGATCTG GTGGGAGGAG GGCAAGATGA CGGCCAAGGT
```

FIG. 1AE

```
         1501                                                          1550
42_2     CGTGGAGTCC GCCAAGGCCA TTCTCGGCGG CAGCAAGGTG CGCGTGGACC
42_8     CGTGGAGTCC GCCAAGGCCA TTCTCGGCGG CAGCAAGGTG CGCGTGGACC
42_15    CGTGGAGTCC GCCAAGGCCA TTCTCGGCGG CAGCAAGGTG CGCGTGGACC
42_5b    CGTGGAGTCC GCCAAGGCCA TTCTCGGCGG CAGCAAGGTG CGCGTGGACC
42_1b    .......... .......... .......... .......... ..........
42_13    CGTGGAGTCC GCCAAGGCCA TTCTCGGCGG CAGCAAGGTG CGCGTGGACC
42_3a    CGTGGAGTCC GCCAAGGCCA TTCTCGGCGG CAGCAAGGTG CGCGTGGACC
42_4     .......... .......... .......... .......... ..........
42_5a    CGTGGAGTCC GCCAAGGCCA TTCTCGGCGG CAGCAAGGTG CGCGTGGACC
42_10    .......... .......... .......... .......... ..........
42_3b    .......... .......... .......... .......... ..........
42_11    CGTGGAGTCC GCCAAGGCCA TTCTCGGCGG CAGCAAGGTG CGCGTGGACC
42_6b    GCCGTTGCAG GACCGGATGT TCAAATTTGA ACTCACCCGC CGTCTGGAGC
43_1     CGTGGAGTCC GCCAAGGCCA TTCTCGGCGG CAGCAAGGTG CGCGTGGACC
43_5     CGTGGAGTCC GCCAAGGCCA TTCTCGGCGG CAGCAAGGTG CGCGTGGACC
43_12    CGTGGAGTCC GCCAAGGCCA TTCTCGGCGG CAGCAAGGTG CGCGTGGACC
43_20    CGTGGAGTCC GCCAAGGCCA TTCTCGGCGG CAGCAAGGTG CGTGTGGACC
43_21    CGTGGAGTCC GCCAAGGCCA TTCTCGGCGG CAGCAAGGTG CGTGTGGACC
43_23    CGTGGAGTCC GCCAAGGCCA TTCTCGGCGG CAGCAAGGTG CGTGTGGACC
43_25    CGTGGAGTCC GCCAAGGCCA TTCTCGGCGG CAGCAAGGTG CGTGTGGACC
44_1     CGTGGAGTCC GCCAAGGCCA TTCTCGGCGG CAGCAAAGTG CGCGTGGACC
44_5     CGTGGAGTCC GCCAAGGCCA TTCTCGGCGG CAGCAAAGTG CGCGTGGACC
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
A3_4     CGTGGAATCT GCCAAAGCCA TTCTGGGTGG AAGCAAGGTT CGTGTGGACC
A3_5     CGTGGAATCT GCCAAAGCCA TTCTGGGTGG AAGCAAGGTT CGTGTGGACC
A3_7     CGTGGAATCT GCCAAAGCCA TTCTGGGTGG AAGCAAGGTT CGTGTGGACC
A3_3     CGTGGAATCT GCCAAAGCCA TTCTGGGTGG AGGCAAGGTT CGTGTGGACC
42_12    CGTGGAGTCC GCCAAGGCCA TTCTCGGCGG CAGCAAGGTG CGCGTGGACC
AAV1     CGTGGAGTCC GCCAAGGCCA TTCTCGGCGG CAGCAAGGTG CGCGTGGACC
AAV2     CGTGGAGTCG GCCAAAGCCA TTCTCGGAGG AAGCAAGGTG CGCGTGGACC
AAV3     CGTGGAGAGC GCCAAGGCCA TTCTGGGCGG AAGCAAGGTG CGCGTGGACC
AAV8     CGTGGAGTCC GCCAAGGCCA TTCTCGGCGG CAGCAAGGTG CGCGTGGACC
AAV9     CGTGGAGTCC GCCAAGGCCA TTCTCGGCGG CAGCAAGGTG CGCGTGGACC
AAV7     CGTGGAGTCC GCCAAGGCCA TTCTCGGCGG CAGCAAGGTG CGCGTGGACC
44_2     CGTGGAGTCC GCCAAGGCCA TTCTCGGCGG CAGCAAAGTG CGCGTGGACC
```

FIG. 1AF

```
         1551                                                          1600
  42_2   AAAAGTGCAA GTCTTCCGCC CAGATCGATC CCACCCCCGT GATCGTCACT
  42_8   AAAAGTGCAA GTCTTCCGCC CAGATCGATC CCACCCCCGT GATCGTCACT
  42_15  AAAAGTGCAA GTCGTCCGCC CAGATCGACC CCACCCCCGT GATCGTCACC
  42_5b  AAAAGTGCAA GTCGTCCGCC CAGATCGACC CCACCCCCGT GATCGTCACC
  42_1b  .......... .......... .......... .......... ..........
  42_13  AAAAGTGCAA GTCGTCCGCC CAGATCGATC CCACCCCCGT GATCGTCACT
  42_3a  AAAAGTGCAA GTCGTCCGCC CAGATCGATC CCACCCCCGT GATCGTCACT
  42_4   .......... .......... .......... .......... ..........
  42_5a  AAAAGTGCAA GTCGTCCGCC CAGATCGACC CCACCCCCGT GATCGTCACC
  42_10  .......... .......... .......... .......... ..........
  42_3b  .......... .......... .......... .......... ..........
  42_11  AAAAGTGCAA GTCTTCCGCC CAGATCGATC CCACCCCCGT GATCGTCACT
  42_6b  ATGACTTTGG CAAGGTGACA AAGCAGGAAG TCAAAGAGTT CTTCCGCTGG
  43_1   AAAAGTGCAA GTCGTCCGCC CAGATCGACC CCACCCCCGT GATCGTCACC
  43_5   AAAAGTGCAA GTCGTCCGCC CAGATCGACC CCACCCCCGT GATCGTCACC
  43_12  AAAAGTGCAA GTCGTCCGCC CAGATCGACC CCACCCCCGT GATCGTCACC
  43_20  AAAAGTGCAA GTCTTCCGCC CAGATCGATC CCACCCCCGT GATCGTCACC
  43_21  AAAAGTGCAA GTCTTCCGCC CAGATCGATC CCACCCCCGT GATCGTCACC
  43_23  AAAAGTGCAA GTCTTCCGCC CAGATCGATC CCACCCCCGT GATCGTCACC
  43_25  AAAAGTGCAA GTCTTCCGCC CAGATCGATC CCACCCCCGT GATCGTCACC
  44_1   AAAAGTGCAA GCCGTCCGCC CAGATCGACC CCACCCCCGT GATCGTCACC
  44_5   AAAAGTGCAA GTCGTCCGCC CAGATCGACC CCACCCCCGT GATCGTCACC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   AGAAATGCAA GTCTTCGGCC CAGATCGACC CGACTCCGGT GATTGTCACC
  A3_5   AGAAATGCAA GTCTTCGGCC CAGATCGACC CGACTCCGGT GATTGTCACC
  A3_7   AGAAATGCAG GTCTTCGGCC CAGATCGACC CGACTCCGGT GATTGTCACC
  A3_3   AGAAATGCAA GTCTTCGGCC CAGATCGACC CGACTCCGGT GATTGTCACC
  42_12  AAAAGTGCAA GTCGTCCGCC CAGATCGACC CCACCCCCGT GATCGTCACC
  AAV1   AAAAGTGCAA GTCGTCCGCC CAGATCGACC CCACCCCCGT GATCGTCACC
  AAV2   AGAAATGCAA GTCCTCCGCC CAGATAGACC CGACTCCCGT GATCGTCACC
  AAV3   AAAAGTGCAA GTCATCGGCC CAGATCGAAC CCACTCCCGT GATCGTCACC
  AAV8   AAAAGTGCAA GTCGTCCGCC CAGATCGACC CCACCCCCGT GATCGTCACC
  AAV9   AAAAGTGCAA GTCGTCCGCC CAGATCGACC CCACTCCCGT GATCGTCACC
  AAV7   AAAAGTGCAA GTCGTCCGCC CAGATCGACC CCACCCCCGT GATCGTCACC
  44_2   AAAAGTGCAA GTCGTCCGCC CAGATCGACC CCACCCCCGT GATCGTCACC
```

FIG. 1AG

```
         1601                                                   1650
42_2     TCCAACACCA ACATGTGCGC TGTGATTGAC GGGAACAGCA CCACCTTCGA
42_8     TCCAACACCA ACATGTGCGC CGTGATTGAC GGGAACAGCA CCACCTTCGA
42_15    TCCAACACCA ACATGTGCGC CGTGATTGAC GGGAACAGCA CCACCTTCGA
42_5b    TCCAACACCA ACATGTGCGC CGTGATTGAC GGGAACAGCA CCACCTTCGA
42_1b    .......... .......... .......... .......... ..........
42_13    TCCAACACCA ACATGTGCGC CGTGATTGAC GGGAACAGCA CCACCTTCGA
42_3a    TCCAACACCA ACATGTGCGC CGTGATTGAC GGGAACAGCA CCACCTTCGA
42_4     .......... .......... .......... .......... ..........
42_5a    TCCAACACCA ACATGTGCGC CGTGATTGAC GGGAACAGCA CCACCTTCGA
42_10    .......... .......... .......... .......... ..........
42_3b    .......... .......... .......... .......... ..........
42_11    TCCAACACCA ACATGTGCGC CGTGATTGAC GGGAACAGCA CCACCTTCGA
42_6b    GCGCAGGATC ACGTGACCGA GGTGGCGCAT GAGTTCTACG TCAGAAAGGG
43_1     TCCAACACCA ACATGTGCGC CGTGATTGAC GGGAACAGCA CCACCTTCGA
43_5     TCCAACACCA ACATGTGCGC CGTGATTGAC GGGAACAGCA CCACCTTCGA
43_12    TCCAACACCA ACATGTGCGC CGTGATTGAC GGGAACAGCA CCACCTTCGA
43_20    TCCAACACCA ACATGTGCGC CGTGATTGAC GGGAACAGCG CCACCTTCGA
43_21    TCCAACACCA ACATGTGCGC CGTGATTGAC GGGAACAGCA CCACCTTCGA
43_23    TCCAACACCA ACATGTGCGC CGTGATTGAC GGGAACAGCA CCACCTTCGA
43_25    TCCAACACCA ACATGTGCGC CGTGATTGAC GGGAACAGCA CCACCTTCGA
44_1     TCCAACACCA ACATGTGCGC CGTGATTGAC GGGAACAGCA CCACCTTCGA
44_5     TCCAACACCA ACATGTGCGC CGTGATTGAC GGGAACAGCA CCACCTTCGA
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
A3_4     TCTAACACCA ACATGTGCGC CGTGATTGAC GGAAACTCGA CCACCTTCGA
A3_5     TCTAACACCA ACATGTGCGC CGTGATTGAC GGAAACTCGA CCACCTTCGA
A3_7     TCTAACACCA ACATGTGCGC CGTGATTGAC GGAAACTCGA CCACCTTCGA
A3_3     TCTAACACCA ACATGTGCGC CGTGATTGAC GGAAACTCGA CCACCTTCGA
42_12    TCCAACACCA ACATGTGCGC CGTGATTGAC GGGAACAGCA CCACCTTCGA
AAV1     TCCAACACCA ACATGTGCGC CGTGATTGAC GGGAACAGCA CCACCTTCGA
AAV2     TCCAACACCA ACATGTGCGC CGTGATTGAC GGGAACTCAA CGACCTTCGA
AAV3     TCCAACACCA ACATGTGCGC CGTGATTGAC GGGAACAGCA CCACCTTCGA
AAV8     TCCAACACCA ACATGTGCGC CGTGATTGAC GGGAACAGCA CCACCTTCGA
AAV9     TCCAACACCA ACATGTGCGC CGTGATTGAC GGGAACAGCA CCACCTTCGA
AAV7     TCCAACACCA ACATGTGCGC CGTGATTGAC GGGAACAGCA CCACCTTCGA
44_2     TCCAACACCA ACATGTGCGC CGTGATTGAC GGGAACAGCA CCACCTTCGA
```

FIG. 1AH

```
           1651                                                          1700
    42_2   GCACCAGCAG CCGTTACAAG ACCGGATGTT CAAATTTGAA CTCACCCGCC
    42_8   GCACCAGCAG CCGTTACAAG ACCGGATGTT CAAATTTGAA CTCACCCGCC
   42_15   GCACCAGCAG CCGTTGCAGG ACCGGATGTT CAAATTTGAA CTCACCCGCC
   42_5b   GCACCAGCAG CCGTTACAAG ACCGGATGTT CAAATTTGAA CTCACCCGCC
   42_1b   .......... .......... .......... .......... ..........
   42_13   GCACCAGCAG CCGTTACAAG ACCGGATGTT CAAATTTGAA CTCACCCGCC
   42_3a   GCACCAGCAG CCGTTACAAG ACCGGATGTT CAAATTTGAA CTCACCCGCC
    42_4   .......... .......... .......... .......... ..........
   42_5a   GCACCAGCAG CCGTTGCAGG ACCGGATGTT CAAATTTGAA CTCACCCGCC
   42_10   .......... .......... .......... .......... ..........
   42_3b   .......... .......... .......... .......... ..........
   42_11   GCACCAGCAG CCGTTACAAG ACCGGATGTT CAAATTTGAA CTCACCCGCC
   42_6b   TGGAGCCAAC AAGAGACCCG CCCCCGATGA CGCGGATAAA AGCGAGCCCA
    43_1   GCACCAGCAG CCGTTGCAGG ACCGGATGTT CAAGTTCGAA CTCACCCGCC
    43_5   GCACCAGCAG CCGTTGCAGG ACCGGATGTT CAAGTTCGAA CTCACCCGCC
   43_12   GCACCAGCAG CCGTTGCAGG ACCGGATGTT CAAGTTCGAA CTCACCCGCC
   43_20   GCACCAGCAG CCGTTGCAGG ACCGGATGTT CAAATTTGAA CTCACCCGCC
   43_21   GCACCAGCAG CCGTTGCAGG ACCGGATGTT CAAATTTGAA CTCACCCGCC
   43_23   GCACCAGCAG CCGTTGCAGG ACCGGATGTT CAAATTTGAA CTCACCCGCC
   43_25   GCACCAGCAG CCGTTGCAGG ACCGGATGTT CAAATTTGAA CTCACCCGCC
    44_1   GCACCAGCAG CCGTTGCGGG ACCGGATGTT CAAGTTTGAA CTCACCCGCC
    44_5   GCACCAGCAG CCGTTGCAGG ACCGGATGTT CAAGTTTGAA CTCACCCGCC
  223_10   .......... .......... .......... .......... ..........
   223_2   .......... .......... .......... .......... ..........
   223_4   .......... .......... .......... .......... ..........
   223_5   .......... .......... .......... .......... ..........
   223_6   .......... .......... .......... .......... ..........
   223_7   .......... .......... .......... .......... ..........
    A3_4   GCACCAGCAG CCGTTGCAAG ACCGGATGTT CAAATTTGAA CTTACCCGCC
    A3_5   GCACCAGCAG CCGTTGCAAG ACCGGATGTT CAAATTTGAA CTTACCCGCC
    A3_7   GCACCAGCAG CCGTTGCAAG ACCGGATGTT CAAATTTGAA CTTACCCGCC
    A3_3   GCACCAGCAG CCGTTGCAAG ACCGGATGTT CAAATTTGAA CTTACCCGCC
   42_12   GCACCAGCAG CCGTTACAAG ACCGGATGTT CAAATTTGAA CTCACCCGCC
    AAV1   GCACCAGCAG CCGTTGCAGG ACCGGATGTT CAAATTTGAA CTCACCCGCC
    AAV2   ACACCAGCAG CCGTTGCAAG ACCGGATGTT CAAATTTGAA CTCACCCGCC
    AAV3   GCATCAGCAG CCGCTGCAGG ACCGGATGTT TGAATTTGAA CTTACCCGCC
    AAV8   GCACCAGCAG CCTCTCCAGG ACCGGATGTT TAAGTTCGAA CTCACCCGCC
    AAV9   GCACCAGCAG CCTCTCCAGG ACCGGATGTT TAAGTTCGAA CTCACCCGCC
    AAV7   GCACCAGCAG CCGTTGCAGG ACCGGATGTT CAAATTTGAA CTCACCCGCC
    44_2   GCACCAGCAG CCGTTGCAGG ACCGGATGTT CAAGTTTGAA CTCACCCGCC
```

FIG. 1Ai

```
           1701                                                              1750
  42_2    GTCTGGAGCA CGACTTTGGC AAGGTGACAA AGCAGGAAGT CAAAGAGTTC
  42_8    GTCTGGAGCA CGACTTTGGC AAGGTGACAA AGCAGGAAGT CAAAGAGTTC
  42_15   GTCTGGAGCA TGACTTTGGC AAGGTGACAA AGCAGGAAGT CAAAGAGTTC
  42_5b   GTCTGGAGCA CGACTTTGGC AAGGTGACAA AGCAGGAAGT CAAAGAGTTC
  42_1b   .......... .......... .......... .......... ..........
  42_13   GTCTGGAGCA TGACTTTGGC AAGGTGACAA AGCAGGAAGT CAAAGAGTTC
  42_3a   GTCTGGAGCA TGACTTTGGC AAGGTGACAA AGCAGGAAGT CAAAGAGTTC
  42_4    .......... .......... .......... .......... ..........
  42_5a   GTCTGGAGCA TGACTTTGGC AAGGCGACAA AGCAGGAAGT CAAAGAGTTC
  42_10   .......... .......... .......... .......... ..........
  42_3b   .......... .......... .......... .......... ..........
  42_11   GTCTGGAGCA CGACTTTGGC AAGGTGACAA AGCAGGAAGT CAAAGAGTTC
  42_6b   AGCGGGCCTG CCCCTCAGTC GCGGATCCAT CGACGTCAGA CGCGGAAGGA
  43_1    GTCTGGAGCA CGACTTTGGC AAGGTGACCA AGCAGGAAGT CAAAGAGTTC
  43_5    GTCTGGAGCA CGACTTTGGC AAGGTGACCA AGCAGGAAGT CAAAGAGTTC
  43_12   GTCTGGAGCA CGACTTTGGC AAGGTGACCA AGCAGGAAGT CAAAGAGTTC
  43_20   GTCTGGAGCA TGACTTTGGC AAGGTGACGA AGCAGGAAGT CAAAGAGTTC
  43_21   GTCTGGAGCA TGACTTTGGC AAGGTGACGA AGCAGGAAGT CAAAGAGTTC
  43_23   GTCTGGAGCA TGACTTTGGC AAGGTGACGA AGCAGGAAGT CAAAGAGTTC
  43_25   GTCTGGAGCA TGACTTTGGC AAGGTGACGA AGCAGGAAGT CAAAGGGTTC
  44_1    GTCTGGAGCA CGACTTTGGC AAGGTGACAA AGCAGGAAGT CAGAGAGTTC
  44_5    GTCTGGAGCA CGACTTTGGC AAGGTGACAA AGCAGGAAGT CAGAGAGTTC
 223_10   .......... .......... .......... .......... ..........
 223_2    .......... .......... .......... .......... ..........
 223_4    .......... .......... .......... .......... ..........
 223_5    .......... .......... .......... .......... ..........
 223_6    .......... .......... .......... .......... ..........
 223_7    .......... .......... .......... .......... ..........
  A3_4    GTTTGGATCA TGACTTTGGG AAGGTCACCA AGCAGGAAGT CAAAGACTTT
  A3_5    GTTTGGATCA TGACTTTGGG AAGGTCACCA AGCAGGAAGT CAAAGACTTT
  A3_7    GTTTGGATCA TGACTTTGGG AAGGTCACCA AGCAGGAAGT CAAAGACTTT
  A3_3    GTTTGGATCA TGACTTTGGG AAGGTCACCA AGCAGGAAGT CAAAGACTTT
  42_12   GTCTGGAGCA CGACTTTGGC AAGGTGACAA AGCAGGAAGT CAAAGAGTTC
  AAV1    GTCTGGAGCA TGACTTTGGC AAGGTGACAA AGCAGGAAGT CAAAGAGTTC
  AAV2    GTCTGGATCA TGACTTTGGG AAGGTCACCA AGCAGGAAGT CAAAGACTTT
  AAV3    GTTTGGACCA TGACTTTGGG AAGGTCACCA AACAGGAAGT AAAGGACTTT
  AAV8    GTCTGGAGCA CGACTTTGGC AAGGTGACAA AGCAGGAAGT CAAAGAGTTC
  AAV9    GTCTGGAGCA CGACTTTGGC AAGGTGACAA AGCAGGAAGT CAAAGAGTTC
  AAV7    GTCTGGAGCA CGACTTTGGC AAGGTGACGA AGCAGGAAGT CAAAGAGTTC
  44_2    GTCTGGAGCA CGACTTTGGC AAGGTGACAA AGCAGGAAGT CAGAGAGTTC
```

FIG. 1AJ

```
        1751                                                              1800
 42_2   TTCCGCTGGG CGCAGGATCA CGTGACCGAG GTGGCGCATG AGTTCTACGT
 42_8   TTCCGCTGGG CGCAGGATCA CGTGACCGAG GTGGCGCATG AGTTCTACGT
 42_15  TTCCGCTGGG CGCAGGATCA CGTGACCGAG GTGGCGCATG AGTTCTACGT
 42_5b  TTCCGCTGGG CGCAGGATCA CGTGACCGAG GTGGCGCATG AGTTCTACGT
 42_1b  .......... .......... .......... .......... ..........
 42_13  TTCCGCTGGG CGCAGGATCA CGTGACCGAG GTGGCGCATG AGTTCTACGT
 42_3a  TTCCGCTGGG CGCAGGATCA CGTGACCGAG GTGGCGCATG AGTTCTACGT
 42_4   .......... .......... .......... .......... ..........
 42_5a  TTCCGCTGGG CGCAGGATCA CGTGACCGAG GTGGCGCATG AGTTCTACGT
 42_10  .......... .......... .......... .......... ..........
 42_3b  .......... .......... .......... .......... ..........
 42_11  TTCCGCTGGG CGCAGGATCA CGTGACCGAG GTGGCGCATG AGTTCTACGT
 42_6b  GCTCCGGTGG ACTTTGCCGA CAGGTACCAA AACAAATGTT CTCGTCACGC
 43_1   TTCCGCTGGG CGCAGGATCA CGTGACCGAG GTGGCGCATG AGTTCTACGT
 43_5   TTCCGCTGGG CGCAGGATCA CGTGACCGAG GTGGCGCATG AGTTCTACGT
 43_12  TTCCGCTGGG CGCAGGATCA CGTGACCGAG GTGGCGCATG AGTTCTACGT
 43_20  TTCCGCTGGG CGCAGGATCA CGTGACCGAG GTGGCGCATG AGTTCCACGT
 43_21  TTCCGCTGGG CGCAGGATCA CGTGACCGAG GTGGCGCATG AGTTCCACGT
 43_23  TTCCGCTGGG CGCAGGATCA CGTGACCGAG GTGGCGCATG AGTTCCACGT
 43_25  TTCCGCTGGG CGCAGGATCA CGTGACCGAG GTGGCGCATG AGTTCCACGT
 44_1   TTCCGCTGGG CGCAGGATCA CGTGACCGAG GTGGCGCACG AGTTCTACGT
 44_5   TTCCGCTGGG CGCAGGATCA CGTGACCGAG GTGGCGCACG AGTTCTACGT
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   TTCCGGTGGG CTCAAGATCA CGTGACTGAG GTGGAGCATG AGTTCTACGT
 A3_5   TTCCGGTGGG CTCAAGATCA CGTGACTGAG GTGGAGCATG AGTTCTACGT
 A3_7   TTCCGGTGGG CTCAAGATCA CGTGACTGAG GTGGAGCATG AGTTCTACGT
 A3_3   TTCCGGTGGG CTCAAGATCA CGTGACTGAG GTGGAGCATG AGTTCTACGT
 42_12  TTCCGCTGGG CGCAGGATCA CGTGACCGAG GTGGCGCATG AGTTCTACGT
 AAV1   TTCCGCTGGG CGCAGGATCA CGTGACCGAG GTGGCGCATG AGTTCTACGT
 AAV2   TTCCGGTGGG CAAAGGATCA CGTGGTTGAG GTGGAGCATG AATTCTACGT
 AAV3   TTCCGGTGGG CTTCCGATCA CGTGACTGAC GTGGCTCATG AGTTCTACGT
 AAV8   TTCCGCTGGG CCAGTGATCA CGTGACCGAG GTGGCGCATG AGTTTTACGT
 AAV9   TTCCGCTGGG CCAGTGATCA CGTGACCGAG GTGGCGCATG AGTTTTACGT
 AAV7   TTCCGCTGGG CCAGTGATCA CGTGACCGAG GTGGCGCATG AGTTCTACGT
 44_2   TTCCGCTGGG CGCAGGATCA CGTGACCGAG GTGGCGCACG AGTTCTACGT
```

FIG. 1AK

```
                1801                                                                    1850
                                                                                   P40/TATA
       42_2     CAGAAAGGGT GGAGCCAACA AGAGACCCGC CCCCGATGAC GCGGATAAAA
       42_8     CAGAAAGGGT GGAGCCAACA AGAGACCCGC CCCCGATGAC GCGGATAAAA
      42_15     CAGAAAGGGT GGAGCCAACA AGAGACCCGC CCCCGATGAC GCGGATAAAA
      42_5b     CAGAAAGGGT GGAGCCAACA AGAGACCCGC CCCCGATGAC GCGGATAAAA
      42_1b     .......... .......... .......... .......... ..........
      42_13     CAGAAAGGGT GGAGCCAACA AGAGACCCGC CCCCGATGAC GCGGATAAAA
      42_3a     CAGAAAGGGT GGAGCCAACA AGAGACCCGC CCCCGATGAC GCGGATAAAA
       42_4     .......... .......... .......... .......... ..........
      42_5a     CAGAAAGGGT GGAGCCAACA AGAGACCCGC CCCCGATGAC GCGGATAAAA
      42_10     .......... .......... .......... .......... ..........
      42_3b     .......... .......... .......... .......... ..........
      42_11     CAGAAAGGGT GGAGCCAACA AGAGACCCGC CCCCGATGAC GCGGATAAAA
      42_6b     GGGCATAGCG CTGACGTAAA TCACGTCATA GGGGAGTGGT CCTGTATTAG
       43_1     CAGAAAGGGC GGAGCCAGCA AAAGACCCGC CCCCGATGAC GCGGATATAA
       43_5     CAGAAAGGGC GGAGCCAGCA AAAGACCCGC CCCCGATGAC GCGGATATAA
      43_12     CAGAAAGGGC GGAGCCAGCA AAAGACCCGC CCCCGATGAC GCGGATATAA
      43_20     CAGAAAGGGT GGAGCCAACA AGAGACCCGC CCCCGATGAC GCGGATATAA
      43_21     CAGAAAGGGT GGAGCCAACA AGAGACCCGC CCCCGATGAC GCGGATATAA
      43_23     CAGAAAGGGT GGCGCCAACA AGAGACCCGC CCCCGATGAC GCGGATATAA
      43_25     CAGAAAGGGT GGAGCCAACA AGAGACCCGC CCCCGATGAC GCGGATATAA
       44_1     CAGAAAGGGT GGAGCCAACA AGAGACCCGC CCCCGATGAC GCGGATAAAA
       44_5     CAGAAAGGGT GGAGCCAACA AGAGACCCGC CCCCGATGAC GCGGATAAAA
      223_10    .......... .......... .......... .......... ..........
      223_2     .......... .......... .......... .......... ..........
      223_4     .......... .......... .......... .......... ..........
      223_5     .......... .......... .......... .......... ..........
      223_6     .......... .......... .......... .......... ..........
      223_7     .......... .......... .......... .......... ..........
       A3_4     CAAAAAGGGT GGAGCCAAGA AAAGGCCCGC CCCCGATGAT GTATATATAA
       A3_5     CAAAAAGGGT GGAGCCAAGA AAAGGCCCGC CCCCGATGAT GTATATATAA
       A3_7     CAAAAAGGGT GGAGCCAAGA AAAGGCCCGC CCCCGATGAT GTATATATAA
       A3_3     CAAAAAGGGT GGAGCCAAGA AAAGGCCCGC CCCCGATGAT GTATATATAA
      42_12     CAGAAAGGGT GGAGCCAACA AGAGACCCGC CCCCGATCAC GCGGATAAAA
       AAV1     CAGAAAGGGT GGAGCCAACA AAAGACCCGC CCCCGATGAC GCGGATAAAA
       AAV2     CAAAAAGGCT GGAGCCAAGA AAAGACCCGC CCCAGTGAC  GCAGATATAA
       AAV3     CAGAAAGGGT GGAGCTAAGA AACGCCCCGC CTCCAATGAC GCGGATGTAA
       AAV8     CAGAAAGGGC GGAGCCAGCA AAAGACCCGC CCCCGATGAC GCGGATAAAA
       AAV9     CAGAAAGGGC GGAGCCAGCA AAAGACCCGC CCCCGATGAC GCGGATAAAA
       AAV7     CAGAAAGGGC GGAGCCAGCA AAAGACCCGC CCCCGATGAC GCGGATATAA
       44_2     CAGAAAGGGT GGAGCCAACA AGAGACCCGC CCCCGATGAC GCGGATAAAA
                                                                                   P40/TATA
```

FIG. 1AL

```
         1851                                                              1900
                                              P40 RNA
  42_2    GCGAGCCCAA  GCGGGCCTGC  CCCTCAGTCG  CGGATCCATC  GACGTCAGAC
  42_8    GCGAGCCCAA  GCGGGCCTGC  CCCTCAGTCG  CGGATCCATC  GACGTCAGAC
  42_15   GCGAGCCCAA  GCGGGCCTGC  CCCTCAGTCG  CGGATCCATC  GACGTCAGAC
  42_5b   GCGAGCCCAA  GCGGGCCTGC  CCCTCAGTCG  CGGATCCATC  GACGTCAGAC
  42_1b   ..........  ..........  ..........  ..........  ..........
  42_13   GCGAGCCCAA  GCGGGCCTGC  CCCTCAGTCG  CGGATCCATC  GACGTCAGAC
  42_3a   GCGAGCCCAA  GCGGGCCTGC  CCCTCAGTCG  CGGATCCATC  GACGTCAGAC
  42_4    ..........  ..........  ..........  ..........  ..........
  42_5a   GCGAGCCCAA  GCGGGCCCGC  CCCTCAGTCG  CGGATCCATC  GACGTCAGAC
  42_10   ..........  ..........  ..........  ..........  ..........
  42_3b   ..........  ..........  ..........  ..........  ..........
  42_11   GCGAGCCCAA  GCGGGCCTGC  CCCTCAGTCG  CGGATCCATC  GACGTCAGAC
  42_6b   CTGTCACGTG  AGTGCTTTTG  CGACATTTTG  C..ATCCATC  GACGTCAGAC
  43_1    GCGAGCCCAA  GCGGGCCTGC  CCCTCAGTCG  CGGATCCATC  GACGTCAGAC
  43_5    GCGAGCCCAA  GCGGGCCTGC  CCCTCAGTCG  CGGATCCATC  GACGTCAGAC
  43_12   GCGAGCCCAA  GCGGGCCTGC  CCCTCAGTCG  CGGATCCATC  GACGTCAGAC
  43_20   GCGAGCCCAA  GCGGGCCTGC  CCCTCAGTCG  CGGATCCATC  GACGTCAGAC
  43_21   GCGAGCCCAA  GCGGGCCTGC  CCCTCAGTCG  CGGATCCATC  GACGTCAGAC
  43_23   GCGAGCCCAA  GCGGGCCTGC  CCCTCAGTCG  CGGATCCATC  GACGTCAGAC
  43_25   GCGAGCCCAA  GCGGGCCTGC  CCCTCAGTCG  CGGATCCATC  GACGTCAGAC
  44_1    GCGAGCCCAA  GCGGGCCTGC  CCCTCAGTCG  CGGATCCATC  GACGTCAGAC
  44_5    GCGAGCCCAA  GCGGGCCTGC  CCCTCAGTCG  CGGATCCATC  GACGTCAGAC
 223_10   ..........  ..........  ..........  ..........  ..........
 223_2    ..........  ..........  ..........  ..........  ..........
 223_4    ..........  ..........  ..........  ..........  ..........
 223_5    ..........  ..........  ..........  ..........  ..........
 223_6    ..........  ..........  ..........  ..........  ..........
 223_7    ..........  ..........  ..........  ..........  ..........
  A3_4    ATGAGCCCAA  GCGGGCGCGC  GAGTCAGTTG  CGCAGCCATC  GACGTCAGAC
  A3_5    ATGAGCCCAA  GCGGGCGCGC  GAGTCAGTTG  CGCAGCCATC  GACGTCAGAC
  A3_7    ATGAGCCCAA  GCGGGCGCGC  GAGTCAGTTG  CGCAGCCATC  GACGTCAGAC
  A3_3    ATGAGCCCAA  GCGGGCGCGC  GAGTCAGTTG  CGCAGCCATC  GACGTCAGAC
  42_12   GCGAGCCCAA  GCGGGCCTGC  CCCTCAGTCG  CGGATCCATC  GACGTCAGAC
  AAV1    GCGAGCCCAA  GCGGGCCTGC  CCCTCAGTCG  CGGATCCATC  GACGTCAGAC
  AAV2    GTGAGCCCAA  ACGGGTGCGC  GAGTCAGTTG  CGCAGCCATC  GACGTCAGAC
  AAV3    GCGAGCCAAA  ACGGAGTGC   ACGTCACTTG  CGCAGCCGAC  AACGTCAGAC
  AAV8    GCGAGCCCAA  GCGGGCCTGC  CCCTCAGTCG  CGGATCCATC  GACGTCAGAC
  AAV9    GCGAGCCCAA  GCGGGCCTGC  CCCTCAGTCG  CGGATCCATC  GACGTCAGAC
  AAV7    GCGAGCCCAA  GCGGGCCTGC  CCCTCAGTCG  CGGATCCATC  GACGTCAGAC
  44_2    GCGAGCCCAA  GCGGGCCTGC  CCCTCAGTCG  CGGATCCATC  GACGTCAGAC
                                                P40 RNA
```

FIG. 1AM

```
          1901                                                              1950
  42_2    GCGGAAGGAG CTCCGGTGGA CTTTGCCGAC AGGTACCAAA ACAAATGTTC
  42_8    GCGGAAGGAG CTCCGGTGGA CTTTGCCGAC AGGTACCAAA ACAAATGTTC
  42_15   GCGGAAGGAG CTCCGGTGGA CTTTGCCGAC AGGTACCAAA ACAAATGTTC
  42_5b   GCGGAAGGAG CTCCGGTGGA CTTTGCCGAC AGGTACCAAA ACAAATGTTC
  42_1b   .......... .......... .......... .......... ..........
  42_13   GCGGAAGGAG CTCCGGTGGA CTTTGCCGAC AGGTACCAAA ACAAATGTTC
  42_3a   GCGGAAGGAG CTCCGGTGGA CTTTGCCGAC AGGTACCAAA ACAAATGTTC
  42_4    .......... .......... .......... .......... ..........
  42_5a   GCGGAAGGAG CTCCGGTGGA CTTTGCCGAC AGGTACCAAA ACAAATGTTC
  42_10   .......... .......... .......... .......... ..........
  42_3b   .......... .......... .......... .......... ..........
  42_11   GCGGAAGGAG CTCCGGTGA CTTTGCCGAC AGGTACCAAA ACAAATGTTC
  42_6b   GCGGAAGGAG CTCCGGTGGA CTTTGCCGAC AGGTACCAAA ACAAGTGTTC
  43_1    GCGGAAGGAG CTCCGGTGGA CTTTGCCGAC AGGTACCAAA ACAAATGTTC
  43_5    GCGGAAGGAG CTCCGGTGGA CTTTGCCGAC AGGTACCAAA ACAAATGTTC
  43_12   GCGGAAGGAG CTCCGGTGGA CTTTGCCGAC AGGTACCAAA ACAAATGTTC
  43_20   GCGGAAGGAG CTCCGGTGGA CTTTGCCGAC AGGTACCAAA ACAAATGTTC
  43_21   GCGGAAGGAG CTCCGGTGGA CTTTGCCGAC AGGTACCAAA ACAAATGTTC
  43_23   GCGGAAGGAG CTCCGGTGGA CTTTGCCGAC AGGTACCAAA ACAAATGTTC
  43_25   GCGGAAGGAG CTCCGGTGGA CTTTGCCGAC AGGTACCAAA ACAAATGTTC
  44_1    GCGGAAGGAG CTCCGGTGGA CTTTGCCGAC AGGTACCAAA ACAAATGTTC
  44_5    GCGGAAGGAG CTCCGGTGGA CTTTGCCGAC AGGTACCAAA ACAAATGTTC
  223_10  .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
  A3_4    GCGGA...AG CTTCGATAAA CTACGCGGGC AGGTACCAAA ACAAATGTTC
  A3_5    GCGGA...AG CTTCGATAAA CTACGCGGAC AGGTACCAAA ACAAATGTTC
  A3_7    GCGGA...AG CTTCGATAAA CTACGCGGAC AGGTACCAAA ACAAATGTTC
  A3_3    GCGGA...AG CTTCGATAAA CTACGCGGAC AGGTACCAAA ACAAATGTTC
  42_12   GCGGAAGGAG CTCCGGTGGA CTTTGCCGAC AGGTACCAAA ACAAATGTTC
  AAV1    GCGGAAGGAG CTCCGGTGGA CTTTGCCGAC AGGTACCAAA ACAAATGTTC
  AAV2    GCGGA...AG CTTCGATCAA CTACGCAGAC AGGTACCAAA ACAAATGTTC
  AAV3    GCGGA...AG CACCGGCGGA CTACGCGGAC AGGTACCAAA ACAAATGTTC
  AAV8    GCGGAAGGAG CTCCGGTGGA CTTTGCCGAC AGGTACCAAA ACAAATGTTC
  AAV9    GCGGAAGGAG CTCCGGTGGA CTTTGCCGAC AGGTACCAAA ACAAATGTTC
  AAV7    GCGGAAGGAG CTCCGGTGGA CTTTGCCGAC AGGTACCAAA ACAAATGTTC
  44_2    GCGGAAGGAG CTCCGGTGGA CTTTGCCGAC AGGTACCAAA ACAAATGTTC
```

FIG. 1AN

```
          1951                                                              2000
 42_2    TCGTCACGCG  GGCATGCTTC  AGATGCTGTT  TCCCTG.CAA  GACATGCGAG
 42_8    TCGTCACGCG  GGCATGCTTC  AGATGCTGTT  TCCCTG.CAA  GACATGCGAG
 42_15   TCGTCACGCG  GGCATGCTTC  AGATGCTGTT  TCCCTG.CAA  GACATGCGAG
 42_5b   TCGTCACGCG  GGCATGCTTC  AGATGCTGTT  TCCCTG.CAA  GACATGCGAG
 42_1b   ..........  ..........  ....GAATTC  GCCCTT....  .GGCTGCGTC
 42_13   TCGTCACGCG  GGCATGCTTC  AGATGCTGTT  TCCCTG.CAA  GACATGCGAG
 42_3a   TCGTCACGCG  GGCATGCTTC  AGATGCTGCT  TCCCTG.CAA  GACATGCGAG
 42_4    ..........  ..........  ....GAATTC  GCCCTTCTA   CGGCTGCGTC
 42_5a   TCGTCACGCG  GGCATGCTTC  AGATGCTGTT  TCCCTG.CAA  AACATGCGAG
 42_10   ..........  ..........  ....GAATTC  GCCCTTCTA   CGGCTGCGTC
 42_3b   ..........  ..........  ....GAATTC  GCCCTTCTA   CGGCTGCGTC
 42_11   TCGTCACGCG  GGCATGCTTC  AGATGCTGTT  TCCCTG.CAA  GACATGCGAG
 42_6b   TCGTCACGCG  GGCATGCTTC  AGATGCTGTT  TCCCTG.CAA  GACATGCGAG
 43_1    TCGTCACGCG  GGCATGCTTC  AGATGCTGTT  TCCCTG.CAA  AACGTGCGAG
 43_5    TCGTCACGCG  GGCATGCTTC  AGACGCTGTT  TCCCTG.CAA  AACGTGCGAG
 43_12   TCGTCACGCG  GGCATGCTCC  AGATGCTGTT  TCCCTG.CAA  AACGTGCGAG
 43_20   TCGTCACGCG  GGCATGCTTC  AGATGCTGTT  TCCCTG.CAA  GACATGCGAG
 43_21   TCGTCACGCG  GGCATGCTTC  AGATGCTGTT  TCCCTG.CAA  GACATGCGAG
 43_23   TCGTCACGCG  GGCATGCTTC  AGATGCTGTT  TCCCTG.CAA  GACATGCGAG
 43_25   TCGTCACGCG  GGCATGCTTC  AGATGCTGTT  TCCCTG.CAA  GACATGCGAG
 44_1    TCGTCACGCG  GGCATGCTTC  AGATGCTGTT  TCCCTG.CAA  AACATGCGAG
 44_5    TCGTCACGCG  GGCATGCTTC  AGATGCTGTT  TCCCTG.CAA  AACATGCGAG
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
 A3_4    TCGTCACGTG  GGCATGAATC  TGATGCTGTT  TCCCTG.TCG  ACAATGCGAA
 A3_5    TCGTCACGTG  GGCATGAATC  TGATGCTGTT  TCCCTG.TCG  ACAATGCGAA
 A3_7    TCGTCACGTG  GGCATGAATC  TGATGCTGTT  TCCCTG.TCG  ACAATGCGAA
 A3_3    TCGTCACGTG  GGCATGAATC  TGATGCTGTT  TCCCTG.TCG  ACAATGCGAA
 42_12   TCGTCACGCG  GGCATGCTTC  AGATGCTGTT  TCCCTG.CAA  GACATGCGAG
 AAV1    TCGTCACGCG  GGCATGCTTC  AGATGCTGTT  TCCCTG.CAA  GACATGCGAG
 AAV2    TCGTCACGTG  GGCATGAATC  TGATGCTGTT  TCCCTG.CAG  ACAATGCGAG
 AAV3    TCGTCACGTG  GGCATGAATC  TGATGCTTTT  TCCCTG.TAA  AACATGCGAG
 AAV8    TCGTCACGCG  GGCATGCTTC  AGATGCTGTT  TCCCTG.CAA  AACGTGCGAG
 AAV9    TCGTCACGCG  GGCATGCTTC  AGATGCTGCT  TCCCTG.CAA  AACGTGCGAG
 AAV7    TCGTCACGCG  GGCATGATTC  AGATGCTGTT  TCCCTG.CAA  AACGTGCGAG
 44_2    TCGTCACGCG  GGCATGCTTC  AGATGCTGTT  TCCCTG.CAA  AACATGCGAG
```

FIG. 1AO

```
         2001                                                    2050
 42_2    AGAATGAATC AGAATTTCAA CATTTGCTTC ACGCACGGGA CCAGAGACTG
 42_8    AGAATGAATC AGAATTTCAA CATTTGCTTC ACGCACGGGA CCAGAGACTG
 42_15   AGAATGAATC AGAATTTCAA CATTTGCTTC ACGCGCGGGA CCAGAGACTG
 42_5b   AGAATGAATC AGAATTTCAA CATTTGCTTC ACGCACGGGA CCAGAGACTG
 42_1b   A.ACTGGACC A..ATGAGAA CTTTCCCTTC A........A CGATTGCGTC
 42_13   AGAATGAATC AGAATTTCAA CATTTGCTTC ACGCACGGGA CCAGAGACTG
 42_3a   AGAATGAATC AGAATTTCAG CATTTGCTTC ACGCACGGGA CCAGAGACTG
 42_4    A.ACTGGACC A..ATGAGAA CTTTCCCTTC A........A CGATTGCGTC
 42_5a   AGAATGAATC AGAATTTCAA CATTTGCTTC ACGCACGGGA CCAGAGACTG
 42_10   A.ACTGGACC A..ATGAGAA CTTTCCCTTC A........A CGATTGCGTC
 42_3b   A.ACTAGACC A..ATGAGAA CTTTCCCTTC A........A CGATTGCGTC
 42_11   AGAATGAATC AGAATTTCAA CATTTGCTTC ACGCACGGGA CCGGAGACTG
 42_6b   AGAATGAATC AGAATTTCAA CATTTGCTTC ACGCACGGGA CCAGAGACTG
 43_1    AAAATGAATC AGAATTTCAA CATTTGCTTC ACGCACGGGG TCAGAGACTG
 43_5    AGAATGAATC AGAATTTCAA CATTTGCTTC ACGCACGGGG TCAGAGACTG
 43_12   AGAATGAATC AGAATTTCAA CATTTGCTTC ACGCACGGGG TCAGAGACTG
 43_20   AGAATGAATC AGAATTTCAA CATTTGCTTC ACGCACGGGA CCAGAGACTG
 43_21   AGAATGAATC AGAATTTCAA CATTTGCTTC ACGCACGGGA CCAGAGACTG
 43_23   AGAATGAATC AGAATTTCAA CATTTGCTTC ACGCACGGGA CCAGAGACTG
 43_25   AGAATGAATC AGAATTTCAA CATTTGCTTC ACGCACGGGA CCAGAGACTG
 44_1    AGAATGAATC AGAATTTCAA CATTTGCTTC ACGCACGGGA CCAGAGACTG
 44_5    AGAATGAATC AGAATTTCAA CATTTGCTTC ACGCACGGGA CCAGAGACTG
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    AGAATGAATC AGAATTCAAA TATCTGCTTC ACACACGGGC AAAAAGACTG
 A3_5    AGAATGAATC AGAATTCAAA TATCTGCTTC ACACACGGGC AAAAAGACTG
 A3_7    AGAATGAATC AGAATTCAAA TATCTGCTTC ACACACGGGC AAAAAGACTG
 A3_3    AGAATGAATC AGAATTCAAA TATCTGCTTC ACACACGGGC AAAAAGACTG
 42_12   AGAATGAATC AGAATTTCAA CATTTGCTTC ACGCACGGGA CCAGAGACTG
 AAV1    AGAATGAATC AGAATTTCAA CATTTGCTTC ACGCACGGGA CGAGAGACTG
 AAV2    AGAATGAATC AGAATTCAAA TATCTGCTTC ACTCACGGAC AGAAAGACTG
 AAV3    AGAATGAATC AAATTTCCAA TGTCTGTTTT ACGCATGGTC AAAGAGACTG
 AAV8    AGAATGAATC AGAATTTCAA CATTTGCTTC ACACACGGGG TCAGAGACTG
 AAV9    AGAATGAATC AGAATTTCAA CATTTGCTTC ACACACGGGG TCAGAGACTG
 AAV7    AGAATGAATC AGAATTTCAA CATTTGCTTC ACACACGGGG TCAGAGACTG
 44_2    AGAATGAATC AGAATTTCAA CATTTGCTTC ACGCACGGGA CCAGAGACTG
```

FIG. 1AP

```
             2051                                              2100
   42_2   TTCAGAATGT TTCCCCGGCG TGTCAGAATC TCAACC.... ..GGTCGTCA

42_8   TTCAGAATGT TTCCCCGGCG TGTCAGAATC TCAACC.... ..GGTCGTCA
  42_15   TTCAGAATGT TTCCCGGGCG TGTCAGAATC TCAACC.... ..GGTCGTCA
  42_5b   TTCAGAATGT TTCCCCGGCG TGTCAGAATC TCAACC.... ..GGTCGTCA
  42_1b   GACAAGATGG TGATCTGGTG GG..AGGAGG GCAAGA.... ..TGACGGCC
  42_13   TTCAGAATGT TTCCCCGGCG TGTCAGAATC TCAACC.... ..GGTCGTCA
  42_3a   TTCAGAATGT TTCCCCGGCG TGTCAGAATC TCAACC.... ..GGTCGTCA
   42_4   GACAAGATGG TGATCTGGTG GG..AGGAGG GCAAGA.... ..TGACGGCC
  42_5a   TTCAGAATGT TTCCCCGGCG TGTCAGAATC TCAACC.... ..GGTCGTCA
  42_10   GACAAGATGG TGATCTGGTG GG..AGGAGG GCAAGA.... ..TGACGGCC
  42_3b   GACAAGATGG TGATCTGGTG GG..AGGAGG GCAAGA.... ..TGACGGCC
  42_11   TTCAGAATGT TTCCCCGGCG TGTCAGAATC TCAACC.... ..GGTCGTCA
  42_6b   TTCAGAATGT TTCCCCGGCG TGTCAGAATC TCAACC.... ..GGTCGTCA
   43_1   CTCAGAATGT TTCCCCGGTG CATCAGAATC TCAACC.... ..GGTCGTCA
   43_5   CTCAGAATGT TTCCCCGGTG CATCAGAATC TCAACC.... ..GGTCGTCA
  43_12   CTCAGAATGT TTCCCCGGTG CATCAGAATC TCAACC.... ..GGTCGTCA
  43_20   TTCAGAATGT TTCCCCGGCG TGTCAGAATC TCAACC.... ..GGTCGTCA
  43_21   TTCAGAATGT TTCCCCGGCG TGTCAGAATC TCAACC.... ..GGTCGTCA
  43_23   TTCAGAATGT TTCCCCGGCG TGTCAGAATC TCAACC.... ..GGTCGTCA
  43_25   TTCAGAATGT TTCCCCGGCG TGTCAGAATC TCAACC.... ..GGTCGTCA
   44_1   TTCAGAATGT TTCCCCGGCG TGTCAGAATC TCAACC.... ..GGTCGTCA
   44_5   TTCAGAATGT TTCCCCGGCG TGTCAGAATC TCAACC.... ..GGTTGTCA
 223_10   .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
   A3_4   TTTGGAATGC TTTCCCG... TGTCAGAATC TCAACCCGTT TCTGTCGTCA
   A3_5   TTTGGAATGC TTTCCCG... TGTCAGAATC TCAACCCGTT CCTGTCGTCA
   A3_7   TTTGGAATGC TTTCCCG... TGTCAGAATC TCAACCCGTT TCTGTCGTCA
   A3_3   TTTGGAATGC TTTCCCG... TGTCAGAATC TCAACCCGTT TCTGTCGTCA
  42_12   TTCAGAATGT TTCCCCGGCG TGTCAGAATC TCAACC.... ..GGTCGTCA
   AAV1   TTCAGAGTGC TTCCCCGGCG TGTCAGAATC TCAACC.... ..GGTCGTCA
   AAV2   TTTAGAGTGC TTTCCCG... TGTCAGAATC TCAACCCGTT TCTGTCGTCA
   AAV3   TGGGAATGC  TTCCCTGGAA TGTCAGAATC TCAACCCGTT TCTGTCGTCA
   AAV8   CTCAGAGTGT TTCCCCGGCG TGTCAGAATC TCAACC.... ..GGTCGTCA
   AAV9   CTCAGAGTGT TTCCCCGGCG TGTCAGAATC TCAACC.... ..GGTCGTCA
   AAV7   TTTAGAGTGT TTCCCCGGCG TGTCAGAATC TCAACC.... ..GGTCGTCA
   44_2   TTCAGAATGT TTCCCCGGCG TGTCAGAATC TCAACC.... ..GGTCGTCA
```

FIG. 1AQ

```
        2101                                                    2150
42_2    GAAAGAGGAC GTATCGGAAA CTCTGTGCCA TTCATCATCT GCTGGGG.CG

42_8    GAAAGAGGAC GTATCGGAAA CTCTGTGCCA TTCATCATCT GCTAGGG.CG
42_15   GAAAGAGGAC GTATCGGAAA CTCTGTGCCA TTCATCATCT GCTGGGG.CG
42_5b   GAAAGAGGAC GTATCGGAAA CTCTGTGCCA TTCATCATCT GCTGGGG.CG
42_1b   .AAGGTCGTG GAGTCCGCCA AG....GCCA TTCATCATCT GCTGGGG.CG
42_13   GAAAGAGGAC GTATCGGAAA CTCTGTGCCA TTCATCATCT GCTGGGG.CG
42_3a   GAAAGAGGAC GTATCGGAAA CTCTGTGCCA TTCATCATCT GCTGGGG.CG
42_4    .AAGGTCGTG GAGTCCGCCA AG....GCCA TTCATCATCT GCTGGGG.CG
42_5a   GAAAGAGGAC GTATCGGAAA CTCTGTGCCA TTCATCATCT GCTGGGG.CG
42_10   AA....GGTC GTGAAGTCCG CCAAG.GCCA TTCATCATCT GCTGGGG.CG
42_3b   AA....GGTC GTGGAGTCCG CCAAG.GCCA TTCATCATCT GCTGGGG.CG
42_11   GAAAGAGGAC GTATCGGAAA CTCTGTGCCA TTCATCATCT GCTGGGG.CG
42_6b   GAAAGAGGAC GTATCGGAAA CTCTGTGCCA TTCATCATCT GCTGGGG.CG
43_1    GAAAAAAAAC GTATCAGAAA CTGTGTGCCA TTCATCATCT GCTGGGG.CG
43_5    GAAAAAAAAC GTATCAGAAA CTGTGTGCCA TTCATCATCT GCTGGGG.CG
43_12   GAAAAAAAAC GTATCAGAAA CTGTGTGCCA TTCATCATCT GCTGGGG.CG
43_20   GAAAGAGGAC GTATCGGAAA CTCTGTGCGA TTCATCATCT GCTGGGG.CG
43_21   GAAAGAGGAC GTATCGGAAA CTCTGTGCGA TTCATCATCT GCTGGGG.CG
43_23   GAAAGAGGAC GTATCGGAAA CTCTGTGCGA TTCATCATCT GCTGGGG.CG
43_25   GAAAGAGGAC GTATCGGAAA CTCTGTGCGA TTCATCATCT GCTGGGG.CG
44_1    GAAAAAGAC. GTATCGGAAA CTCTGTGCGA TTCATCATCT GCTGGGG.CG
44_5    GAAAAAGAC. GTATCGGAAA CTCTGTGCGA TTCATCATCT GCTGGGG.CG
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
A3_4    GAAAAACG.. .TATCAGAAA CTTTGTTACA TTCATCATAT CATGGGA.AA
A3_5    GAAAAACG.. .TATCAGAAA CTTTGTTACA TTCATCATAT CATGGGA.AA
A3_7    GAAAAACG.. .TATCAGAAA CTTTGTTACA TTCATCATAT CATGGGA.AA
A3_3    GAAAAACG.. .TATCAGAAA CTTTGTTACA TTCATCATAT CATGGGA.AA
42_12   GAAAGAGGAC GTATCGGAAA CTCTGTGCCA TTCATCATCT GCTGGGG.CG
AAV1    GAAAGAGGAC GTATCGGAAA CTCTGTGCCA TTCATCATCT GCTGGGG.CG
AAV2    AAAAGGCG.. .TATCAGAAA CTGTGCTACA TTCATCATAT CATGGGA.AA
AAV3    AAAAGAACAC TTATCAGAAA CTGTGTCCAA TTCATCATAT CCTGGGA.AG
AAV8    GAAAGAGGAC GTATCGGAAA CTCTGTGCGA TTCATCATCT GCTGGGG.CG
AAV9    GAAAGAGGAC GTATCGGAAA CTCTGTGCGA TTCATCATCT GCTGGGG.CG
AAV7    GAAAAAGAC. GTATCGGAAA CTCTGCGCGA TTCATCATCT GCTGGGG.CG
44_2    GAAAAAGAC. GTATCGGAAA CTCTGTGCGA TTCATCATCT GCTGGGGGCG
```

FIG. 1AR

```
        2151                                                                2200
42_2    GGCTCCCGAG ATTGCTTGCT CGGCCTGCGA TCTGGTCAAC GTGGACCTGG
42_8    GGCTCCCGAG ATTGCTTGCT CGGCCTGCGA TCTGGTCAAC GTGGACCTGG
42_15   GGCTCCCGAG ATTGCTTGCT CGGCCTGCGA TCTGGTCAAC GTGGACCTGG
42_5b   GGCTCCCGAG ATTGCTTGCT CGGCCTGCGA TCTGGTCAAC GTGGACCTGG
42_1b   GGCTCCCGAG ATTGCTTGCT CGGCCTGCGA TCTGGTCAAC GTGGACCTGG
42_13   GGCTCCCGAG ATTGCTTGCT CGGCCTGCGA TCTGGTCAAC GTGGACCTGG
42_3a   GGCTCCCGAG ATTGCTTGCT CGGCCTGCGA TCTGGTCAAC GTGGACCTGG
42_4    GGCTCCCGAG ATTGCTTGCT CGGCCTGCGA TCTGGTCAAC GTGGACCTGG
42_5a   GGCTCCCGAG ATTGCTTGCT CGGCCTGCGA TCTGGTCAAC GTGGACCTGG
42_10   GGCTCCCGAG ATTGCTTGCT CGGCCTGCGA TCTGGTCAAC GTGGACCTGG
42_3b   GGCTCCCGAG ATTGCTTGCT CGGCCTGCGA TCTGGTCAAC GTGGACCTGG
42_11   GGCTCCCGAG ATTGCTTGCT CGGCCTGCGA TCTGGTCAAC GTGGACCTGG
42_6b   GGCTCCCGAG ATTGCTTGCT CGGCCTGCGA TCTGGTCAAC GTGGACCTGG
43_1    GGCACCCGAG ATTGCTTGCT CGGCCTGCGA TCTGGTCAAC GTGGACCTGG
43_5    GGCACCCGAG ATTGCTTGCT CGGCCTGCGA TCTGGTCAAC GTGGACCTGG
43_12   GGCACCCGAG ATTGCTTGCT CGGCCTGCGA TCTGGTCAAC GTGGACCTGG
43_20   GGCTCCCGAG ATTGCTTGCT CGGCCTGCGA TCTGGTCAAC GTGGACCTGG
43_21   GGCTCCCGAG ATTGCTTGCT CGGCCTGCGA TCTGGTCAAC GTGGACCTGG
43_23   GGCTCCCGAG ATTGCTTGCT CGGCCTGCGA TCTGGTCAAC GTGGACCTGG
43_25   GGCTCCCGAG ATTGCTTGCT CGGCCTGCGA TCTGGTCAAC GTGGACCTGG
44_1    GGCACCCGAG ATTGCTTGCT CGGCCTGCGA TCTGGTCAAC GTGGACCTAG
44_5    GGCACCCGAG ATTGCTTGCT CGGCCTGCGA TCTGGTCAAC GTGGACCTAG
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
A3_4    AGAACCAGAC ...GCCTGCA CTGCCTGCGA CCTGGTAAAT GTGGACTTGG
A3_5    AGTACCAGAC ...GCCTGCA CTGCCTGCGA CCTGGTAAAT GTGGACTTGG
A3_7    AGTACCAGAC ...GCCTGCA CTGCCTGCGA CCTGGTAAAT GTGGACTTGG
A3_3    AGTACCAGAC ...GCCTGCA CTGCCTGCGA CCTGGTAAAT GTGGACTTGG
42_12   GGCTCCCGAG ATTGCTTGCT CGGCCTGCGA TCTGGTCAAC GTGGACCTGG
AAV1    GGCTCCCGAG ATTGCTTGCT CGGCCTGCGA TCTGGTCAAC GTGGACCTGG
AAV2    GGTGCCAGAC ...GCTTGCA CTGCCTGCGA TCTGGTCAAT GTGGATTTGG
AAV3    GGCACCCGAG ATTGCCTGTT CGGCCTGCGA TTTGGCAAT GTGGACTTGG
AAV8    GGCTCCCGAG ATTGCTTGCT CGGCCTGCGA TCTGGTCAAC GTGGACCTGG
AAV9    GGCTCCCGAG ATTGCTTGCT CGGCCTGCGA TCTGGTCAAC GTGGACCTGG
AAV7    GGCGCCCGAG ATTGCTTGCT CGGCCTGCGA CCTGGTCAAC GTGGACCTGG
44_2    GGCACCCGAG ATTGCTTGCT CGGCCTGCGA TCTGGTCAAC GTGGACCTAG
```

FIG. 1A5

```
        2201                                                              2250
                                    Rep 78 stop       vp1 start
  42_2   ATGACCGTGT TTCTGAGCAA TAAATGACTT AAACCAGGTA TGGCTGCCGA
  42_8   ATGACTGTGT TTCTGAGCAA TAAATGACTT AAACCAGGTA TGGCTGCCGA
 42_15   ATGACTGTGT TTCTGAGCAA TAAATGACTT AAACCAGGTA TGGCTGCCGA
 42_5b   ATGACTGTGT TTCTGAGCAA TAAATGACTT AAACCAGGTA TGGCTGCCGA
 42_1b   ATGACTGTGT TTCTGAGCAA TAAATGACTT AAACCAGGTA TGGCTGCCGA
 42_13   ATGACTGTGT TTCTGAGCAA TAAATGACTT AAACCAGGTA TGGCTGCCGA
 42_3a   ATGACTGTGT TTCTGAGCAA TAAATGACTT AAACCAGGTA TGGCTGCCGA
  42_4   ATGACTGTGT TTCTGAGCAA TAAATGACTT AAACCAGGTA TGGCTGCCGA
 42_5a   ATGACTGTGT TTCTGAGCAA TAAATGACTT AAACCAGGTA TGGCTGCCGA
 42_10   ATGACTGTGT TTCTGAGCAA TAAATGACTT AAACCAGGTA TGGCTGCCGA
 42_3b   ATGACTGTGT TTCTGAGCAA TAAATGACTT AAACCAGGTA TGGCTGCCGA
 42_11   ATGACTGTGT TTCTGAGCAA TAAATGACTT AAACCAGGTA TGGCTGCCGA
 42_6b   ATGACTGTGT TTCTGAGCAA TAAATGACTT AAACCAGGTA TGGCTGCCGA
  43_1   ACGACTGTGT TTCTGAGCAA TAAATGACTT AAACCAGGTA TGGCTGCCGA
  43_5   ACGACTGTGT TTCTGAGCAA TAAATGACTT AAACCAGGTA TGGCTGCCGA
 43_12   ACGACTGTGT TTCTGAGCAA TAAATGACTT AAACCAGGTA TGGCTGCCGA
 43_20   ATGACTGTGT TTCTGAGCAA TAAATGACTT AAACCAGGTA TGGCTGCCGA
 43_21   ATGACTGTGT TTCTGAGCAA TAAATGACTT AAACCAGGTA TGGCTGCCGA
 43_23   ATGACTGTGT TTCTGAGCAA TAAATGACTT AAACCAGGTA TGGCTGCCGA
 43_25   ATGACTGTGT TTCTGAGCAA TAAATGACTT AAACCAGGTA TGGCTGCCGA
  44_1   ATGACTGTGT TTCTGAGCAA TAAATGACTT AAACCAGGTA TGGCTGCCGA
  44_5   ATGACTGTGT TTCTGAGCAA TAAATGACTT AAACCAGGTA TGGCTGCCGA
223_10   .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   ATGACTGTAT TTCTGAGCAA TAAATGACTT AAATCAGGTA TGGCTGCTGA
  A3_5   ATGACTGTAT TTCTGAGCAA TAAATGACTT AAATCAGGTA TGGCTGCTGA
  A3_7   ATGACTGTAT TTCTGAGCAA TAAATGACTT AAATCAGGTA TGGCTGCTGA
  A3_3   ATGACTGTAT TTCTGAGCAA TAAATGACTT AAATCAGGTA TGGCTGCTGA
 42_12   ATGACTGTGT TTCTGAGCAA TAAATGACTT AAACCAGGTA TGGCTGCCGA
  AAV1   ATGACTGTGT TTCTGAGCAA TAAATGACTT AAACCAGGTA TGGCTGCCGA
  AAV2   ATGACTGCAT CTTTGAACAA TAAATGATTT AAATCAGGTA TGGCTGCCGA
  AAV3   ATGACTGTGT TTCTGAGCAA TAAATGACTT AAACCAGGTA TGGCTGCTGA
  AAV8   ATGACTGTGT TTCTGAGCAA TAAATGACTT AAACCAGGTA TGGCTGCCGA
  AAV9   ATGACTGTGT TTCTGAGCAA TAAATGACTT AAACCAGGTA TGGCTGCCGA
  AAV7   ACGACTGCGT TTCTGAGCAA TAAATGACTT AAACCAGGTA TGGCTGCCGA
  44_2   ATGACTGTGT TTCTGAGCAA TAAATGACTT AAACCAGGTA TGGCTGCCGA
                                    Rep78 stop        vp1 start
```

FIG. 1AT

```
           2251                                                              2300
                                                           Rep68 stop
   42_2    TGGTTATCTT CCAGATTGGC TCGAGGACAA CCTCTCTGAG GGCATTCGCG
   42_8    TGGTTATCTT CCAGATTGGC TCGAGGACAA CCTCTCTGAG GGCATTCGCG
   42_15   TGGTTATCTT CCAGATTGGC TCGAGGACAA CCTCTCTGAG GGCATTCGCG
   42_5b   TGGTTATCTT CCAGATTGGC TCGAGGACAA CCTCTCTGAG GGCATTCGCG
   42_1b   TGGTTATCTT CCAGATTGGC TCGAGGACAA CCTCTCTGAG GGCATTCGCG
   42_13   TGGTTATCTT CCAGATTGGC TCGAGGACAA CCTCTCTGAG GGCATTCGCG
   42_3a   TGGTCATCTT CCAGATTGGC TCGAGGACAA CCTCTCTGAG GGCATTCGCG
   42_4    TGGTTATCTT CCAGATTGGC TCGAGGACAA CCTCTCTGAG GGCATTCGCG
   42_5a   TGGTTATCTT CCAGATTGGC TCGAGGACAA CCTCTCTGAG GGCATTCGCG
   42_10   TGGTTATCTT CCAGATTGGC TCGAGGACAA CCTCTCTGAG GGCATTCGCG
   42_3b   TGGTTATCTT CCAGATTGGC TCGAGGACAA CCTCTCTGAG GGCATTCGCG
   42_11   TGGTTATCTT CCAGATTGGC TCGAGGACAA CCTCTCTGAG GGCATTCGCG
   42_6b   TGGTTATCTT CCAGATTGGC TCGAGGACAA CCTCTCTGAG GGCATTCGCG
   43_1    TGGTTATCTT CCAGATTGGC TTGAGGACAA CCTCTCTGAG GGCATTCGCG
   43_5    TGGTTATCTT CCAGATTGGC TTGAGGACAA CCTCTCTGAG GGCATTCGCG
   43_12   TGGTTATCTT CCAGATTGGC TTGAGGACAA CCTCTCTGAG GGCATTCGCG
   43_20   TGGTTATCTT CCAGATTGGC TCGAGGACAA CCTCTCTGAG GGCATTCGCG
   43_21   TGGTTATCTT CCAGATTGGC TCGAGGACAA CCTCTCTGAG GGCATTCGCG
   43_23   TGGTTATCTT CCAGATTGGC TCGAGGACAA CCTCTCTGAG GGCATTCGCG
   43_25   TGGTTATCTT CCAGATTGGC TCGAGGACAA CCTCTCTGAG GGCATTCGCG
   44_1    TGGTTATCTT CCAGATTGGC TCGAGGACAA CCTCTCTGAG GGCATTCGCG
   44_5    TGGTTATCTT CCAGATTGGC TCGAGGACAA CCTCTCTGAG GGCATTCGCG
  223_10   .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    CGGTTATCTT CCAGATTGGC TCGAGGACAC TCTCTCTGAA GGAATCAGAC
   A3_5    CGGTTATCTT CCAGATTGGC TCGAGGACAC TCTCTCTGAA GGAATCAGAC
   A3_7    CGGTTATCTT CCAGATTGGC TCGAGGACAC TCTCTCTGAA GGAATCAGAC
   A3_3    CGGTTATCTT CCAGATTGGC TCGAGGACAC TCTCTCTGAA GGAATCAGAC
   42_12   TGGTTATCTT CCAGATTGGC TCGAGGACAA CCTCTCTGAG GGCATCCGCG
   AAV1    TGGTTATCTT CCAGATTGGC TCGAGGACAA CCTCTCTGAG GGCATTCGCG
   AAV2    TGGTTATCTT CCAGATTGGC TCGAGGACAC TCTCTCTGAA GGAATAAGAC
   AAV3    CGGTTATCTT CCAGATTGGC TCGAGGACAA CCTTTCTGAA GGCATTCGTG
   AAV8    TGGTTATCTT CCAGATTGGC TCGAGGACAA CCTCTCTGAG GGCATTCGCG
   AAV9    TGGTTATCTT CCAGATTGGC TCGAGGACAA CCTCTCTGAG GGCATTCGCG
   AAV7    TGGTTATCTT CCAGATTGGC TCGAGGACAA CCTCTCTGAG GGCATTCGCG
   44_2    TGGTTATCTT CCAGATTGGC TCGAGGACAA CCTCTCTGAG GGCATTCGCG
                                                    Rep 68 stop
```

FIG. 1AU

```
         2301                                                                    2350
42_2     AGTGGTGGGA  CTTGAAACCT  GGAGCCCCGA  AACCCAAAGC  CAACCAGCAA

42_8     AGTGGTGGGA  CTTGAAACCT  GGAGCCCCGA  AACCCAAAGC  CAACCAGCAA
42_15    AGTGGTGGGA  CTTGAAACCT  GGAGCCCCGA  AACCCAAAGC  CAACCAGCAA
42_5b    AGTGGTGGGA  CTTGAAACCT  GGAGCCCCGA  AACCCAAAGC  CAACCAGCAA
42_1b    AGTGGTGGGA  CTTGAGACCT  GGAGCCCCGA  AACCCAAAGC  CAACCAGCAA
42_13    AGTGGTGGGA  CTTGAAACCT  GGAGCCCCGA  AACCCAAAGC  CAACCAGCAA
42_3a    AGTGGTGGGA  CTTGAAACCT  GGAGCCCCGA  AACCCAAAGC  CAACCAGCAA
42_4     AGTGGTGGGA  CTTGAAACCT  GGAGCCCCGA  AACCCAAAGC  CAACCAGCAA
42_5a    AGTGGTGGGA  CTTGAAACCT  GGAGCCCCGA  AACCCAAAGC  CAACCAGCAA
42_10    AGTGGTGGGA  CTTGAAACCT  GGAGCCCCGA  AACCCAAAGC  CAACCAGCAA
42_3b    AGTGGTGGGA  CTTGAAACCT  GGAGCCCCGA  AACCCAAAGC  CAACCAGCAA
42_11    AGTGGTGGGA  CTTGAAACCT  GGAGCCCCGA  AACCCAAAGC  CAACCAGCAA
42_6b    AGTGGTGGGA  CTTGAAACCT  GGAGCCCCGA  AACCCAAAGC  CAACCAGCAA
43_1     AGTGGTGGGA  CCTGAAACCT  GGAGCCCCGA  AACCCAAAGC  CAACCAGCAA
43_5     AGTGGTGGGA  CCTGAAACCT  GGAGCCCCGA  AACCCAAAGC  CAACCAGCAA
43_12    AGTGGTGGGA  CCTGAAACCT  GGAGCCCCGA  AACCCAAAGC  CAACCAGCAA
43_20    AGTGGTGGGA  CTTGAAACCT  GGAGCCCCGA  AACCCAAAGC  CAACCAGCAA
43_21    AGTGGTGGGA  CTTGAAACCT  GGAGCCCCGA  AACCCAAAGC  CAACCAGCAA
43_23    AGTGGTGGGA  CTTGAAACCT  GGAGCCCCGA  AACCCAAAGC  CAACCAGCAA
43_25    AGTGGTGGGA  CTTGAAACCT  GGAGCCCCGA  AACCCAAAGC  CAACCAGCAA
44_1     AGTGGTGGGA  CTTGAAACCT  GGAGCCCCGA  AACCCAAAGC  CAACCAGCAA
44_5     AGTGGTGGGA  CTTGAAACCT  GGAGCCCCGA  AACCCAAAGC  CAACCAGCAA
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     AGTGGTGGAA  GCTCAAACCT  GGCCCACCAC  CGCCGAAACC  TAACCAACAA
A3_5     AGTGGTGGAA  GCTCAAACCT  GGCCCACCAC  CGCCGAAACC  TAACCAACAA
A3_7     AGTGGTGGAA  GCTCAAACCT  GGCCCACCAC  CGCCGAAACC  TAACCAACAA
A3_3     AGTGGTGGAA  GCTCAAACCT  GGCCCACCAC  CGCCGAAACC  TAACCAACAA
42_12    AGTGGTGGGA  CTTGAAACCT  GGAGCCCCGA  AACCCAAAGC  CAACCAGCAA
AAV1     AGTGGTGGGA  CTTGAAACCT  GGAGCCCCGA  AGCCCAAAGC  CAACCAGCAA
AAV2     AGTGGTGGAA  GCTCAAACCT  GGCCCACCAC  CACCAAAGCC  CGCAGAGCGG
AAV3     AGTGGTGGGC  TCTGAAACCT  GGAGTCCCTC  AACCCAAAGC  GAACCAACAA
AAV8     AGTGGTGGGC  GCTGAAACCT  GGAGCCCCGA  AGCCCAAAGC  CAACCAGCAA
AAV9     AGTGGTGGGC  GCTGAAACCT  GGAGCCCCGA  AGCCCAAAGC  CAACCAGCAA
AAV7     AGTGGTGGGA  CCTGAAACCT  GGAGCCCCGA  AACCCAAAGC  CAACCAGCAA
44_2     AGTGGTGGGA  CTTGAAACCT  GGAGCCCCGA  AACCCAAAGC  CAACCAGCAA
```

FIG. 1AV

```
         2351                                                          2400
  42_2   AAGCAGGACG ACGGCCGGGG TCTGGTGCTT CCTGGCTACA AGTACCTCGG
  42_8   AAGCAGGACG ACGGCCGGGG TCTGGTGCTT CCTGGCTACA AGTACCTCGG
  42_15  AAGCAGGACG ACGGCCGGGG TCTGGTGCTT CCTGGCTACA AGTACCTCGG
  42_5b  AAGCAGGACG ACGGCCGGGG TCTGGTGCTT CCTGGCTACA AGTACCTCGG
  42_1b  AAGCAGGACG ACGGCCGGGG TCTGGTGCTT CCTGGCTACA AGTACCTCGG
  42_13  AAGCAGGACG ACGGCCGGGG TCTGGTGCTT CCTGGCTACA AGTACCTCGG
  42_3a  AAGCAGGACG ACGGCCGGGG TCTGGTGCTT CCTGGCTACA AGTACCTCGG
  42_4   AAGCAGGACG ACGGCCGGGG TCTGGTGCTT CCTGGCTACA AGTACCTCGG
  42_5a  AAGCAGGACG ACGGCCGGGG TCTGGTGCTT CCTGGCTACA AGTACCTCGG
  42_10  AAGCAGGACG ACGGCCGGGG TCTGGTGCTT CCTGGCTACA AGTACCTCGG
  42_3b  AAGCAGGACG ACGGCCGGGG TCTGGTGCTT CCTGGCTACA AGTACCTCGG
  42_11  AAGCAGGACG ACGGCCGGGG TCTGGTGCTT CCTGGCTACA AGTACCTCGG
  42_6b  AAGCAGGACG ACGGCCGGGG TCTGGTGCTT CCTGGCTACA AGTACCTCGG
  43_1   AAGCAGGACG ACGGCCGGGG TCTGGTGCTT CCTGGCTACA AGTACCTCGG
  43_5   AAGCAGGACG ACGGCCGGGG TCTGGTGCTT CCTGGCTACA AGTACCTCGG
  43_12  AAGCAGGACG ACGGCCGGGG TCTGGTGCTT CCTGGCTACA AGTACCTCGG
  43_20  AAGCAGGACG ACGGCCGGGG TCTGGTGCTT CCTGGCTACA AGTACCTCGG
  43_21  AAGCAGGACG ACGGCCGGGG TCTGGTGCTT CCTGGCTACA AGTACCTCGG
  43_23  AAGCAGGACG ACGGCCGGGG TCTGGTGCTT CCTGGCTACA AGTACCTCGG
  43_25  AAGCAGGACG ACGGCCGGGG TCTGGTGCTT CCTGGCTACA AGTACCTCGG
  44_1   AAGCAGGACG ACGGCCGGGG TCTGGTGCTT CCTGGCTACA AGTACCTCGG
  44_5   AAGCAGGACG ACGGCCGGGG TCTGGTGCTT CCTGGCTACA AGTACCTCGG
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   CACCGGGACG ACAGTAGGGG TCTTGTGCTT CCTGGGTACA AGTACCTCGG
  A3_5   CACCGGGACG ACAGTAGGGG TCTTGTGCTT CCTGGGTACA AGTACCTCGG
  A3_7   CACCGGGACG ACAGTAGGGG TCTTGTGCTT CCTGGGTACA AGTACCTCGG
  A3_3   CACCGGGACG ACAGTAGGGG TCTTGTGCTT CCTGGGTACA AGTACCTCGG
  42_12  AAGCAGGACG ACGGCCGGGG TCTGGTGCTT CCTGGCTACA AGTACCTCGG
  AAV1   AAGCAGGACG ACGGCCGGGG TCTGGTGCTT CCTGGCTACA AGTACCTCGG
  AAV2   CATAAGGACG ACAGCAGGGG TCTTGTGCTT CCTGGGTACA AGTACCTCGG
  AAV3   CACCAGGACA ACCGTCGGGG TCTTGTGCTT CCGGGTTACA AATACCTCGG
  AAV8   AAGCAGGACG ACGGCCGGGG TCTGGTGCTT CCTGGCTACA AGTACCTCGG
  AAV9   AAGCAGGACG ACGGCCGGGG TCTGGTGCTT CCTGGCTACA AGTACCTCGG
  AAV7   AAGCAGGACA ACGGCCGGGG TCTGGTGCTT CCTGGCTACA AGTACCTCGG
  44_2   AAGCAGGACG ACGGCCGGGG TCTGGTGCTT CCTGGCTACA AGTACCTCGG
```

FIG. 1AW

```
         2401                                                              2450
 42_2    ACCCTTCAAC GGACTCGACA AGGGAGAGCC GGTCAACGAG GCAGACGCCG
 42_8    ACCCTTCAAC GGACTCGACA AGGGGGAGCC CGTCAACGCG GCGGACGCAG
 42_15   ACCCTTCAAC GGACTCGACA AGGGGGAGCC CGTCAACGCG GCGGACGCAG
 42_5b   ACCCTTCAAC GGACTCGACA AGGGAGAGCC GGTCAACGAG GCAGACGCCG
 42_1b   ACCCTTCAAC GGACTCGACA AGGGAGAGCC GGTCAACGAG GCAGACGCCG
 42_13   ACCCTTCAAC GGACTCGACA AGGGGGAGCC CGTCAACGCG GCGGACGCAG
 42_3a   ACCCTTCAAC GGACTCGACA AGGGGGAGCC CGTCAACGCG GCGGACGCAG
 42_4    ACCCTTCAAC GGACTCGACA AGGGAGAGCC GGTCAACGAG GCAGACGCCG
 42_5a   ACCCTTCAAC GGACTCGACA AGGGAGAGCC GGTCAACGAG GCAGACGCCG
 42_10   ACCCTTCAAC GGACTCGACA AGGGAGAGCC GGTCAACGAG GCAGACGCCG
 42_3b   ACCCTTCAAC GGACTCGACA AGGGAGAGCC GGTCAACGAG GCAGACGCCG
 42_11   ACCCTTCAAC GGACTCGACA AGGGAGAGCC GGTCAACGCG GCGGACGCAG
 42_6b   ACCCTTCAAC GGACTCGACA AGGGAGAGCC GGTCAACGAG GCAGACGCCG
 43_1    ACCCTTCAAC GGACTCGACA AGGGGGAGCC CGTCAACGCG GCGGACGCAG
 43_5    ACCCTTCAAC GGACTCGACA AGGGGGAGCC CGTCAACGCG GCGGACGCAG
 43_12   ACCCTTCAAC GGACTCGACA AGGGGGAGCC CGTCAACGCG GCGGACGCAG
 43_20   ACCCTTCAAC GGACTCGACA AGGGGGAGCC CGTCAACGCG GCGGACGCAG
 43_21   ACCCTTCAAC GGACTCGACA AGGGGGAGCC CGTCAACGCG GCGGACGCAG
 43_23   ACCCTTCAAC GGACTCGACA AGGGGGAGCC CGTCAACGCG GCGGACGCAG
 43_25   ACCCTTCAAC GGACTCGACA AGGGGGAGCC CGTCAACGCG GCGGACGCAG
 44_1    ACCCTTCAAC GGACTCGACA AGGGGGAGCC CGTCAACGCG GCGGACGCAG
 44_5    ACCCTTCAAC GGACTCGACA AGGGGGAGCC CGTCAACGCG GCGGACGCAG
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    ACCCTTCAAC GGACTCGACA AAGGAGAGCC GGTCAACGAG GCAGACGCCG
 A3_5    ACCCTTCAAC GGACTCGACA AAGGAGAGCC GGTCAACGAG GCAGACGCCG
 A3_7    ACCCTTCAAC GGACTCGACA AAGGAGAGCC GGTCAACGAG GCAGACGCCG
 A3_3    ACCCTTCAAC GGACTCGACA AAGGAGAGCC GGTCAACGAG GCAGACGCCG
 42_12   ACCCTTCAAC GGACTCGACA AGGGAGAGCC GGTCAACGAG GCAGACGCCG
 AAV1    ACCCTTCAAC GGACTCGACA AGGGGGAGCC CGTCAACGCG GCGGACGCAG
 AAV2    ACCCTTCAAC GGACTCGACA AGGGAGAGCC GGTCAACGAG GCAGACGCCG
 AAV3    ACCCGGTAAC GGACTCGACA AAGGAGAGCC GGTCAACGAG GCGGACGCGG
 AAV8    ACCCTTCAAC GGACTCGACA AGGGGGAGCC CGTCAACGCG GCGGACGCAG
 AAV9    ACCCTTCAAC GGACTCGACA AGGGGGAGCC CGTCAACGCG GCGGACGCAG
 AAV7    ACCCTTCAAC GGACTCGACA AGGGGGAGCC CGTCAACGCG GCGGACGCAG
 44_2    ACCCTTCAAC GGACTCGACA AGGGGGAGCC CGTCAACGCG GCGGACGCAG
```

FIG. 1AX

```
           2451                                                      2500
  42_2    CGGCCCTCGA GCACG.ACAA GGCCTACGAC AAGCAGCTCG AGCAGGGGGA
  42_8    CGGCCCTCGA GCACG.ACAA GGCCTACGAC CAGCAGCTCA AAGCGGGTGA
  42_15   CGGCCCTCGA GCACG.ACAA GGCCTACGAC CAGCAGCTCA AAGCGGGTGA
  42_5b   CGGCCCTCGA GCACG.ACAA GGCCTACGAC AAGCAGCTCG AGCAGGGGGA
  42_1b   CGGCCCTCGA GCACG.ACAA GGCCTACGAC AAGCAGCTCG AGCAGGGGGA
  42_13   CGGCCCTCGA GCACG.ACAA GGCCTACGAC CAGCAGCTCA AAGCGGGTGA
  42_3a   CGGCCCTCGA GCACG.ACAA GGCCTACGAC CAGCAGCTCA AAGCGGGTGA
  42_4    CGGCCCTCGA GCACG.ACAA GGCCTACGAC AAGCAGCTCG AGCAGGGGGA
  42_5a   CGGCCCTCGA GCACG.ACAA GGCCTACGAC AAGCAGCTCG AGCAGGGGGA
  42_10   CGGCCCTCGA GCACG.ACAA GGCCTACGAC AAGCAGCTCG AGCAGGGGGA
  42_3b   CGGCCCTCGA GCACG.ACAA GGCCTACGAC AAGCAGCTCG AGCAGGGGGA
  42_11   CGGCCCTCGA GCACG.ACAA GGCCTACGAC CAGCAGCTCA AAGCGGGTGA
  42_6b   CGGCCCTCGA GCACG.ACAA GGCCTACGAC AAGCAGCTCG AGCAGGGGGA
  43_1    CGGCCCTCGA GCACG.ACAA GGCCTACGAC CAGCAGCTCA AAGCGGGTGA
  43_5    CGGCCCTCGA GCACG.ACAA GGCCTACGAC CAGCAGCTCA AAGCGGGTGA
  43_12   CGGCCCTCGA GCACG.ACAA GGCCTACGAC CAGCAGCTCA AAGCGGGTGA
  43_20   CGGCCCTCGA GCACG.ACAA AGCCTACGAC CAGCAGCTCA AAGCGGGTGA
  43_21   CGGCCCTCGA GCACG.ACAA AGCCTACGAC CAGCAGCTCA AAGCGGGTGA
  43_23   CGGCCCTCGA GCACG.ACAA AGCCTACGAC CAGCAGCTCA AAGCGGGTGA
  43_25   CGGCCCTCGA GCACG.ACAA AGCCTACGAC CAGCAGCTCA AAGCGGGTGA
  44_1    CGGCCCTCGA GCACG.ACAA GGCCTACGAC CAGCAGCTCA AAGCGGGTGA
  44_5    CGGCCCTCGA GCACG.ACAA GGCCTACGAC CAGCAGCTCA AAGCGGGTGA
 223_10   .......... .......CAA GGCCTACGAC CAGCAGCTCA AAGCGGGTGA
 223_2    .......... .......CAA GGCCTACGAC CAGCAGCTCA AAGCGGGTGA
 223_4    .......... .......CAA GGCCTACGAC CAGCAGCTCA AAGCGGGTGA
 223_5    .......... .......CAA GGCCTACGAC CAGCAGCTCA AAGCGGGTGA
 223_6    .......... .......CAA GGCCTACGAC CAGCAGCTCA AAGCGGGTGA
 223_7    .......... .......CAA GGCCTACGAC CAGCAGCTCA AAGCGGGTGA
  A3_4    CGGCCCTCGA GCACG.ACAA AGCCTACGAC CACCAGCTCA AGCAAGGGGA
  A3_5    CGGCCCTCGA GCACG.ACAA AGCCTACGAC CACCAGCTCA AGCAAGGGGA
  A3_7    CGGCCCTCGA GCACG.ACAA AGCCTACGAC CACCAGCTCA AGCAAGGGGA
  A3_3    CGGCCCTCGA GCACG.ACAA AGCCTACGAC CACCAGCTCA AGCAAGGGGA
  42_12   CGGCCCTCGA GCACG.ACAA GGCCTACGAC AAGCAGCTCG AGCAGGGGGA
  AAV1    CGGCCCTCGA GCACG.ACAA GGCCTACGAC CAGCAGCTCA AAGCGGGTGA
  AAV2    CGGCCCTCGA GCACGTACAA AGCCTACGAC CGGCAGCTCG ACAGCGGAGA
  AAV3    CAGCCCTCGA ACACG.ACAA AGCTTACGAC CAGCAGCTCA AGGCCGGTGA
  AAV8    CGGCCCTCGA GCACG.ACAA GGCCTACGAC CAGCAGCTGC AGGCGGGTGA
  AAV9    CGGCCCTCGA GCACG.GCAA GGCCTACGAC CAGCAGCTGC AGGCGGGTGA
  AAV7    CGGCCCTCGA GCACG.ACAA GGCCTACGAC CAGCAGCTCA AAGCGGGTGA
  44_2    CGGCCCTCGA GCACG.ACAA GGCCTACGAC CAGCAGCTCA AAGCGGGTGA
```

FIG. 1AY

```
           2501                                                       2550
  42_2     CAACCCGTAC CTCAAGTACA ACCACGCCGA CGCCGAGTTT CAGGAGCGTC
  42_8     CAATCCGTAC CTGCGGTATA ACCACGCCGA CGCCGAGTTT CAGGAGCGTC
  42_15    CAATCCGTAC CTGCGGTATA ACCACGCCGA CGCCGAGTTT CAGGAGCGTC
  42_5b    CAACCCGTAC CTCAAGTACA ACCACGCCGA CGCCGAGTTT CAGGAGCGTC
  42_1b    CAACCCGTAC CTCAAGTACA ACCACGCCGA CGCCGAGTTT CAGGAGCGTC
  42_13    CAATCCGTAC CTGCGGTATA ACCACGCCGA CGCCGAGTTT CAGGAGCGTC
  42_3a    CAATCCGTAC CTGCGGTATA ACCACGCCGA CGCCGAGTTT CAGGAGCGTC
  42_4     CAACCCGTAC CTCAAGTACA ACCACGCCGA CGCCGAGTTT CAGGAGCGTC
  42_5a    CAACCCGTAC CTCAAGTACA ACCACGCCGA CGCCGAGTTT CAGGAGCGTC
  42_10    CAACCCGTAC CTCAAGTACA ACCACGCCGA CGCCGAGTTT CAGGAGCGTC
  42_3b    CAACCCGTAC CTCAAGTACA ACCACGCCGA CGCCGAGTTT CAGGAGCGTC
  42_11    CAATCCGTAC CTGCGGTATA ACCACGCCGA CGCCGAGTTT CAGGAGCGTC
  42_6b    CAACCCGTAC CTCAAGTACA ACCACGCCGA CGCCGAGTTT CAGGAGCGTC
  43_1     CAATCCGTAC CTGCGGTATA ACCACGCCGA CGCCGAGTTT CAGGAGCGTC
  43_5     CAATCCGTAC CTGCGGTATA ACCACGCCGA CGCCGAGTTT CAGGAGCGTC
  43_12    CAATCCGTAC CTGCGGTATA ACCACGCCGA CGCCGAGTTT CAGGAGCGTC
  43_20    CAATCCGTAC CTGCGGTATA ATCACGCCGA CGCCGAGTTT CAGGAGCGTC
  43_21    CAATCCGTAC CTGCGGTATA ATCACGCCGA CGCCGAGTTT CAGGAGCGTC
  43_23    CAATCCGTAC CTGCGGTATA ATCACGCCGA CGCCGAGTTT CAGGAGCGTC
  43_25    CAATCCGTAC CTGCGGTATA ATCACGCCGA CGCCGAGTTT CAGGAGCGTC
  44_1     CAATCCGTAC CTGCGGTATA ACCACGCCGA CGCCGAGTTT CAGGAGCGTC
  44_5     CAATCCGTAC CTGCGGTATA ACCACGCCGA CGCCGAGTTT CAGGAGCGTC
  223_10   CAATCCGTAC CTGCGGTATA ACCACGCCGA CGCCGAGTTT CAGGAGCGTC
  223_2    CAATCCGTAC CTGCGGTATA ACCACGCCGA CGCCGAGTTT CAGGAGTGTC
  223_4    CAATCCGTAC CTGCGGTATA ACCACGCCGA CGCCGAGTTT CAGGAGCGTC
  223_5    CAATCCGTAC CTGCGGTATA ACCACGCCGA CGCCGAGTTT CAGGAGCGTC
  223_6    CAATCCGTAC CTGCGGTATA ACCACGCCGA CGCCGAGTTT CAGGAGCGTC
  223_7    CAATCCGTAC CTGCGGTATA ACCACGCCGA CGCCGAGTTT CAGGAGCGTC
  A3_4     CAACCCGTAC CTCAAATACA ACCACGCGGA CGCTGAATTT CAGGAGCGTC
  A3_5     CAACCCGTAC CTCAAATACA ACCACGCGGA CGCTGAATTT CAGGAGCGTC
  A3_7     CAACCCGTAC CTCAAATACA ACCACGCGGA CGCTGAATTT CAGGAGCGTC
  A3_3     CAACCCGTAC CTCAAATACA ACCACGCGGA CGCTGAATTT CAGGAGCGTC
  42_12    CAACCCGTAC CTCAAGTACA ACCACGCCGA CGCCGAGTTT CAGGAGCGTC
  AAV1     CAATCCGTAC CTGCGGTATA ACCACGCCGA CGCCGAGTTT CAGGAGCGTC
  AAV2     CAACCCGTAC CTCAAGTACA ACCACGCCGA CGCGGAGTTT CAGGAGCGCC
  AAV3     CAACCCGTAC CTCAAGTACA ACCACGCCGA CGCCGAGTTT CAGGAGCGTC
  AAV8     CAATCCGTAC CTGCGGTATA ACCACGCCGA CGCCGAGTTT CAGGAGCGTC
  AAV9     CAATCCGTAC CTGCGGTATA ACCACGCCGA CGCCGAGTTT CAGGAGCGTC
  AAV7     CAATCCGTAC CTGCGGTATA ACCACGCCGA CGCCGAGTTT CAGGAGCGTC
  44_2     CAATCCGTAC CTGCGGTATA ACCACGCCGA CGCCGAGTTT CAGGAGCGTC
```

FIG. 1AZ

```
         2551                                                    2600
  42_2   TTCAAGAAGA TACGTCTTTT GGGGGCAACC TCGGGCGAGC AGTCTTCCAG
  42_8   TGCAAGAAGA TACGTCTTTT GGGGGCAACC TCGGGCGAGC AGTCTTCCAG
 42_15   TGCAAGAAGA TACGTCTTTT GGGGGCAACC TCGGGCGAGC AGTCTTCCAG
 42_5b   TTCAAGAAGA TACGTCTTTT GGGGGCAACC TCGGGCGAGC AGTCTTCCAG
 42_1b   TTCAAGAAGA TACGTCTTTT GGGGGCAACC TCGGGCGAGC AGTCTTCCAG
 42_13   TTCAAGAAGA TACGTCTTTT GGGGGCAACC TCGGGCGAGC AGTCTTCCAG
 42_3a   TTCAAGAAGA TACGTCTTTT GGGGGCAACC TCGGGCGAGC AGTCTTCCAG
  42_4   TTCAAGAAGA TACGTCTTTT GGGGGCAACC TCGGGCGAGC AGTCTTCCAG
 42_5a   TTCAAGAAGA TACGTCTTTT GGGGGCAACC TCGGGCGAGC AGTCTTCCGG
 42_10   TTCAAGAAGA TACGTCTTTT GGGGGCAACC TCGGGCGAGC AGTCTTCCAG
 42_3b   TTCAAGAAGA TACGTCTTTT GGGGGCAACC TCGGGCGAGC AGTCTTCCAG
 42_11   TTCAAGAAGA TACGTCTTTT GGGGGCAACC TCGGGCGAGC AGTCTTCCAG
 42_6b   TTCAAGAAGA TACGTCTTTT GGGGGCAACC TCGGGCGAGC AGTCTTCCAG
  43_1   TGCAAGAAGA TACGTCTTTT GGGGGCAACC TCGGGCGAGC AGTCTTCCAG
  43_5   TGCAAGAAGA TACGTCTTTT GGGGGCAACC TCGGGCGAGC AGTCTTCCAG
 43_12   TGCAAGAAGA TACGTCTTTT GGGGGCAACC TCGGGCGAGC AGTCTTCCAG
 43_20   TGCAAGAAGA TACGTCTTTT GGGGGCAACC TCGGGCGAGC AGTCTTCCAG
 43_21   TGCAAGAAGA TACGTCTTTT GGGGGCAACC TCGGGCGAGC AGTCTTCCAG
 43_23   TGCAAGAAGA TACGTCCTTT GGGGGCAACC TCGGGCGAGC AGTCTTCCAG
 43_25   TGCAAGAAGA TACGTCTTTT GGGGGCAACC TCGGGCGAGC AGTCTTCCAG
  44_1   TGCAAGAAGA TACGTCTTTT GGGGGCAACC TCGGGCGAGC AGTCTTCCAG
  44_5   TGCAAGAAGA TACGTCTTTT GGGGGCAACC TCGGGCGAGC AGTCTTCCAG
 223_10  TTCAAGAAGA TACGTCTTTT GGGGGCAACC TCGGGCGAGC AGTCTTCCAG
 223_2   TTCAAGAAGA TACGTCTTTT GGGGGCAACC TCGGGCGAGC AGTCTTCCAG
 223_4   TTCAAGAAGA TACGTCTTTT GGGGGCAACC TCGGGCGAGC AGTCTTCCAG
 223_5   TTCAAGAAGA TACGTCTTTT GGGGGCAACC TCGGGCGAGC AGTCTTCCAG
 223_6   TTCAAGAAGA TACGTCTTTT GGGGGCAACC TCGGGCGAGC AGTCTTCCAG
 223_7   TTCAAGAAGA TACGTCTTTT GGGGGCAACC TCGGGCGAGC AGTCTTCCAG
  A3_4   TTCAAGAAGA TACGTCTTTC GGGGGCAACC TCGGGCGAGC AGTCTTCCAG
  A3_5   TTCAAGAAGA TACGTCTTTC GGGGGCAACC TCGGGCGAGC AGTCTTCCAG
  A3_7   TTCAAGAAGA TACGTCTTTC GGGGGCAACC TCGGGCGAGC AGTCTTCCAG
  A3_3   TTCAAGAAGA TACGTCTTTC GGGGGCAACC TCGGGCGAGC AGTCTTCCAG
 42_12   TTCAAGAAGA TACGTCTTTT GGGGGCAACC TCGGGCGAGC AGTCTTCCAG
  AAV1   TGCAAGAAGA TACGTCTTTT GGGGGCAACC TCGGGCGAGC AGTCTTCCAG
  AAV2   TTAAGAAGA  TACGTCTTTT GGGGGCAACC TCGGACGAGC AGTCTTCCAG
  AAV3   TTCAAGAAGA TACGTCTTTT GGGGGCAACC TTGGCAGAGC AGTCTTCCAG
  AAV8   TGCAAGAAGA TACGTCTTTT GGGGGCAACC TCGGGCGAGC AGTCTTCCAG
  AAV9   TGCAAGAAGA TACGTCTTTT GGGGGCAACC TCGGGCGAGC AGTCTTCCAG
  AAV7   TGCAAGAAGA TACGTCATTT GGGGGCAACC TCGGGCGAGC AGTCTTCCAG
  44_2   TGCAAGAAGA TACGTCTTTT GGGGGCAACC TCGGGCGAGC AGTCTTCCAG
```

FIG. 1AAA

```
            2601                                                              2650
  42_2    GCCAAGAAGC GGGTTCTCGA ACCTCTCGGT CTGGTTGAGG AAGGCGCTAA
  42_8    GCCAAGAAGC GGGTTCTCGA ACCTCTCGGT CTGGTTGAGG AAGGCGCTAA
  42_15   GCCAAGAAGC GGGTTCTCGA ACCTCTCGGT CTGGTTGAGG AAGGCGCTAA
  42_5b   GCCAAGAAGC GGGTTCTCGA ACCTCTCGGT CTGGTTGAGG AAGGCGCTAA
  42_1b   GCCAAGAAGC GGGTTCTCGA ACCTCTCGGT CTGGTTGAGG AAGGCGCTAA
  42_13   GCCAAGAAGC GGGTTCTCGA ACCTCTCGGT CTGGTTGAGG AAGGCGCTAA
  42_3a   GCCAAGAAGC GGGTTCTCGA ACCTCTCGGT CTGGTTGAGG AAGGCGCTAA
  42_4    GCCAAGAAGC GGGTTCTCGA ACCTCTCGGT CTGGTTGAGG AAGGCGCTAA
  42_5a   GCCAAGAAGC GGGTTCTCGA ACCTCTCGGT CTGGTTGAGG AAGGCGCTAA
  42_10   GCCAAGAAGC GGGTTCTCGA ACCTCTCGGT CTGGTTGAGG AAGGCGCTAA
  42_3b   GCCAAGAAGC GGGTTCTCGA ACCTCTCGGT CTGGTTGAGG AAGGCGCTAA
  42_11   GCCAAGAAGC GGGTTCTCGA ACCTCTCGGT CTGGTTGAGG AAGGCGCTAA
  42_6b   GCCAAGAAGC GGGTTCTCGA ACCTCTCGGT CTGGTTGAGG AAGGCGCTAA
  43_1    GCCAAGAAGC GGGTTCTCGA ACCTCTCGGT CTGGTTGAGG AAGGCGCTAA
  43_5    GCCAAGAAGC GGGTTCTCGA ACCTCTCGGT CTGGTTGAGG AAGGCGCTAA
  43_12   GCCAAGAAGC GGGTTCTCGA ACCTCTCGGT CTGGTTGAGG AAGGCGCTAA
  43_20   GCCAAGAAGC GGGTTCTCGA ACCTCTCGGT CTGGTTGAGG AAGGCGCTAA
  43_21   GCCAAGAAGC GGGTTCTCGA ACCTCTCGGT CTGGTTGAGG AAGGCGCTAA
  43_23   GCCAAGAAGC GGGTTCTCGA ACCTCTCGGT CTGGTTGAGG AAGGCGCTAA
  43_25   GCCAAGAAGC GGGTTCTCGA ACCTCTCGGT CTGGTTGAGG AAGGCGCTAA
  44_1    GCCAAGAAGC GGGTTCTCGA ACCTCTCGGT CTGGTTGAGG AAGGCGCTAA
  44_5    GCCAAGAAGC GGGTTCTCGA ACCTCTCGGT CTGGTTGAGG AAGGCGCTAA
 223_10   GCCAAAAAGC GGGTTCTCGA ACCTCTTGGT CTGGTTGAGA CGCCAGCTAA
 223_2    GCCAAAAAGC GGGTTCTCGA ACCTCTTGGT CTGGTTGAGA CGCCAGCTAA
 223_4    GCCAAAAAGC GGGTTCTCGA ACCTCTTGGT CTGGTTGAGA CGCCAGCTAA
 223_5    GCCAAAAAGC GGGTTCTCGA ACCTCTTGGT CTGGTTGAGA CGCCAGCTAA
 223_6    GCCAAAAAGC GGGTTCTCGA ACCTCTTGGT CTGGTTGACA CGCCAGCTAA
 223_7    GCCAAAAAGC GGGTTCTCGA ACCTCTTGGT CTGGTTGAGA CGCCAGCTAA
  A3_4    GCCAAAAAGA GGGTACTCGA GCCTCTTGGT CTGGTTGAGG AAGCTGTTAA
  A3_5    GCCAAAAAGA GGGTACTCGA GCCTCTTGGT CTGGTTGAGG AAGCTGTTAA
  A3_7    GCCAAAAAGA GGGTACTCGA GCCTCTTGGT CTGGTTGAGG AAGCTGTTAA
  A3_3    GCCAAAAAGA GGGTACTCGA GCCTCTTGGT CTGGTTGAGG AAGCTGTTAA
  42_12   GCCAAGAAGC GGGTTCTCGA ACCTCTCGGT CTGGTTGAGG AAGGCGCTAA
  AAV1    GCCAAGAAGC GGGTTCTCGA ACCTCTCGGT CTGGTTGAGG AAGGCGCTAA
  AAV2    GCGAAAAAGA GGGTTCTTGA ACCTCTGGGC CTGGTTGAGG AACCTGTTAA
  AAV3    GCCAAAAAGA GGATCCTTGA GCCTCTTGGT CTGGTTGAGG AAGCAGCTAA
  AAV8    GCCAAGAAGC GGGTTCTCGA ACCTCTCGGT CTGGTTGAGG AAGGCGCTAA
  AAV9    GCCAAGAAGC GGGTTCTCGA ACCTCTCGGT CTGGTTGAGG AAGGCGCTAA
  AAV7    GCCAAGAAGC GGGTTCTCGA ACCTCTCGGT CTGGTTGAGG AAGGCGCTAA
  44_2    GCCAAGAAGC GGGTTCTCGA ACCTCTCGGT CTGGTTGAGG AAGGCGCTAA
```

FIG. 1AAB

```
                 2651                                                      2700
          vp2 start
   42_2   GACGGCTCCT GGAAAGAAGA GACCCATAGA ...ATCCCCC ..........
   42_8   GACGGCTCCT GGAAAGAAGA GACCGGTAGA GCCATCACCC CAGCGTTCTC
   42_15  GACGGCTCCT GGAAAGAAGA GACCGGTAGA GCCATCACCC CAGCGTTCTC
   42_5b  GACGGCTCCT GGAAAGAAGA GACCGGTAGA GCCATCACCC CAGCGTTCTC
   42_1b  GACGGCTCCT GGAAAGAAGA GACCCATAGA ...ATCCCCC ..........
   42_13  GACGGCTCCT GGAAAGAAGA GACCCATAGA ...ATCCCCC ..........
   42_3a  GACGGCTCCT GGAAAGAAGA GACCCATAGA ...ATCCCCC ..........
   42_4   GACGGCTCCT GGAAAGAAGA GACCCATAGA ...ATCCCCC ..........
   42_5a  GACGGCTCCT GGAAAGAAGA GACCCATAGA ...ATCCCCC ..........
   42_10  GACGGCTCCT GGAAAGAAGA GACCCATAGA ...ATCCCCC ..........
   42_3b  GACGGCTCCT GGAAAGAAGA GACCCATAGA ...ATCCCCC ..........
   42_11  GACGGCTCCT GGAAAGAAGA GACCCATAGA ...ATCCCCC ..........
   42_6b  GACGGCTCCT GGAAAGAAGA GACCGGTAGA GCCATCACCC CAGCGTTCTC
   43_1   GACGGCTCCT GGAAAGAAGA GACCGGTAGA GCCATCACCT CAGCGTTCCC
   43_5   GACGGCTCCT GGAAAGAAGA GACCGGTAGA GCCATCACCT CAGCGTTCCC
   43_12  GACGGCTCCT GGAAAGAAGA GACCGGTAGA GCCATCACCT CAGCGTTCCC
   43_20  GACGGCTCCT GGAAAGAAGA GACTGGTAGA GCAGTCGCCA CAAGAG...C
   43_21  GACGGCTCCT GGAAAGAAGA GACCGGTAGA GCAGTCGCCA CAAGAG...C
   43_23  GACGGCTCCT GGAAAGAAGA GACCGGTAGA GCAGTCGCCA CAAGAG...C
   43_25  GACGGCTCCT GGAAAGAAGA GACCGGTAGA GCAGTCGCCA CAAGAG...C
   44_1   GACGGCTCCT GGAAAGAAGA GACCGGTAGA GCCATCACCC CAGCGTTCTC
   44_5   GACGGCTCCT GGAAAGAAGA GACCGGTAGA GCCATCACCC CAGCGTTCTC
   223_10 GACGGCACCT GGAAAGAAGC GACCGGTAGA CTCGCCA... ..........
   223_2  GACGGCACCT GGAAAGAAGC GACCGGTAGA CTCGCCA... ..........
   223_4  GACGGCACCT GGAAAGAAGC GACCGGTAGA CTCGCCA... ..........
   223_5  GACGGCACCT GGAAAGAAGC GACCGGTAGA CTCGCCA... ..........
   223_6  GACGGCACCT GGAAAGAAGC GACCGGTAGA CTCGCCA... ..........
   223_7  GACGGCACCT GGAAAGAAGC GACCGGTAGA CTCGCCA... ..........
   A3_4   GACGGCTCCT GGAAAAAAGA GACCTATAGA GCAGTCTCCT GCAGAA...C
   A3_5   GACGGCTCCT GGAAAAAAGA GACCTATAGA GCAGTCTCCT GCAGAA...C
   A3_7   GACGGCTCCT GGAAAAAAGA GACCTATAGA GCAGTCTCCT GCAGAA...C
   A3_3   GACGGCTCCT GGAAAAAAGA GACCTATAGA GCAGTCTCCT GCAGAA...C
   42_12  GACGGCTCCT GGAAAGAAGA GACCGGTAGA GCCATCACCC CAGCGTTCTC
   AAV1   GACGGCTCCT GGAAAGAAAC GTCCGGTAGA GCAGTCGCCA CAAGAG...C
   AAV2   GACGGCTCCG GGAAAAAAGA GGCCGGTAGA GCACTCTCCT GTGGAG...C
   AAV3   AACGGCTCCT GGAAAGAAGG GGGCTGTAGA TCAGTCTCCT CAGGAA...C
   AAV8   GACGGCTCCT GGAAAGAAGA GACCGGTAGA GCCATCACCC CAGCGTTCTC
   AAV9   GACGGCTCCT GGAAAGAAGA GACCGGTAGA GCCATCACCC CAGCGTTCTC
   AAV7   GACGGCTCCT GCAAAGAAGA GACCGGTAGA GCCGTCACCT CAGCGTTCCC
   44_2   GACGGCTCCT GGAAAGAAGA GACCGGTAGA GCCATCACCC CAGCGTTCTC
          vp2 start
```

FIG. 1AAC

```
          2701                                                          2750
   42_2    ..GACTCCTC CACGGGCATC GGCAAGAAAG GCCAGCAGCC CGCTAAAAAG
   42_8    CAGACTCCTC TACGGGCATC GGCAAGACAG GCCAGCAGCC CGCGAAAAAG
   42_15   CAGACTCCTC TACGGGCATC GGCAAGACAG GCCAGCAGCC CGCGAAAAAG
   42_5b   CAGACTCCTC TACGGGCATC GGCAAGACAG GCCAGCAGCC CGCGAAAAAG
   42_1b   ..GACTCCTC CACGGGCATC GGCAAGAAAG GCCAGCAGCC CGCTAAAAAG
   42_13   ..GACTCCTC CACGGGCATC GGCAAGAAAG GCCAGCAGCC CGCTAAAAAG
   42_3a   ..GACTCCTC CACGGGCATC GGCAAGAAAG GCCAGCAGCC CGCTAAAAAG
   42_4    ..GACTCCTC CACGGGCATC GGCAAGAAAG GCCAGCAGCC CGCTAAAAAG
   42_5a   ..GACTCCTC CACGGGCATC GGCAAGAAAG GCCAGCAGCC CGCTAAAAAG
   42_10   ..GACTCCTC CACGGGCATC GGCAGGAAAG GCCAGCAGCC CGCTAAAAAG
   42_3b   ..GACTCCTC CACGGGCATC GGCAAGAAAG GCCAGCAGCC CGCTAAAAAG
   42_11   ..GACTCCTC CACGGGCATC GGCAAGAAAG GCCAGCAGCC CGCTAAAAAG
   42_6b   CAGACTCCTC TACGGGCATC GGCAAGACAG GCCAGCAGCC CGCGAAAAAG
   43_1    CCGACTCCTC CACGGGCATC GGCAAGAAAG GCCACCAGCC CGCGAGAAAG
   43_5    CCGACTCCTC CACGGGCATC GGCAAGAAAG GCCACCAGCC CGCGAGAAAG
   43_12   CCGACTCCTC CACGGGCATC GGCAAGAAAG GCCACCAGCC CGCGAGAAAG
   43_20   CAGACTCCTC CTCGGGCATC GGCAAGACAG GCCAGCAGCC CGCTAAAAAG
   43_21   CAGACTCCTC CTCGGGCATC GGCAAGACAG GCCAGCAGCC CGCTAAAAAG
   43_23   CAGACTCCTC CTCGGGCATC GGCAAGACAG GCCAGCAGCC CGCTAAAAAG
   43_25   CAGACTCCTC CTCGGGCATC GGCAAGACAG GCCAGCAGCC CGCTAAAAAG
   44_1    CAGACTCCTC TACGGGCATC GGCAAGAAAG GCCAGCAGCC CGCGAAAAAG
   44_5    CAGACTCCTC TACGGGCATC GGCAAGAAAG GCCAGCAGCC CGCGAAAAAG
  223_10   ..GACTCCAC CTCGGGCATC GGCAAGAAAG GCCAGCAGCC CGCGAAAAAG
  223_2    ..GACTCCAC CTCGGGCATC GGCAAGAAAG GCCAGCAGCC CGCGAAAAAG
  223_4    ..GACTCCAC CTCGGGCATC GGCAAGAAAG GCCAGCAGCC CGCGAAAAAG
  223_5    ..GACTCCAC CTCGGGCATC GGCAAGAAAG GCCAGCAGCC CGCGAAAAAG
  223_6    ..GACTCCAC CTCGGGCATC GGCAAGAAAG GCCAGCAGCC CGCGAAAAAG
  223_7    ..GACTCCAC CTCGGGCATC GGCAAGAAAG GCCAGCAGCC CGCGAAAAAG
   A3_4    CGGACTCTTC CTCGGGCATC GGCGAATCAG GCCAGCAGCC CGCTAAGAAA
   A3_5    CGGACTCTTC CTCGGGCATC GGCAAATCAG GCCAGCAGCC CGCTAAGAAA
   A3_7    CGGACTCTTC CTCGGGCATC GGCAAATCAG GCCAGCAGCC CGCTAAGAAA
   A3_3    CGGACTCTTC CTCGGGCATC GGCAAATCAG GCCAGCAGCC CGCTAAGAAA
   42_12   CAGACTCCTC TACGGGCATC GGCAAGACAG GCCAGCAGCC CGCGAAAAAG
   AAV1    CAGACTCCTC CTCGGGCATC GGCAAGACAG GCCAGCAGCC CGCTAAAAAG
   AAV2    CAGACTCCTC CTCGGGAACC GGAAAGGCGG GCCAGCAGCC TGCAAGAAAA
   AAV3    CGGACTCATC ATCTGGTGTT GGCAAATCGG GCAAACAGCC TGCCAGAAAA
   AAV8    CAGACTCCTC TACGGGCATC GGCAAGAAAG GCCAACAGCC CGCCAGAAAA
   AAV9    CAGACTCCTC TACGGGCATC GGCAAGAAAG GCCAACAGCC CGCCAGAAAA
   AAV7    CCGACTCCTC CACGGGCATC GGCAAGAAAG GCCAGCAGCC CGCCAGAAAG
   44_2    CAGACTCCTC TACGGGCATC GGCAAGAAAG GCCAGCAGCC CGCGAAAAAG
```

FIG. 1AAD

```
         2751                                                    2800
 42_2    AAGCTCAACT TTGGGCAGAC TGGCGACTCA GAGTCAGTGC CCGACCCCCA
 42_8    AGACTCAACT TTGGGCAGAC TGGCGACTCA GAGTCAGTGC CCGACCCTCA
 42_15   AGACTCAACT TTGGGCAGAC TGGCGACTCA GAGTCAGTGC CCGACCCTCA
 42_5b   AGACTCAACT TTGGGCAGAC TGGCGACTCA GAGTCAGTGC CCGACCCTCA
 42_1b   AGACTCAACT TTGGGCAGAC TGGCGACTCA GAGTCAGTGC CCGACCCTCA
 42_13   AAGCTCAACT TTGGGCAGAC TGGCGACTCA GAGTCAGTGC CCGACCCTCA
 42_3a   AAGCTCAACT TTGGGCAGAC TGGCGACTCA GAGTCAGTGC CCGACCCTCA
 42_4    AAGCTCAACT TTGGGCAGAC TGGCGACTCA GAGTCAGTGC CCGACCCTCA
 42_5a   AAGCTCAACT TTGGGCAGAC TGGCGACTCA GAGTCAGTGC CCGACCCCCA
 42_10   AAGCTCAACT TTGGGCAGAC TGGCGACTCA GAGTCAGTGC CCGACCCTCA
 42_3b   AAGCTCAACT TTGGGCAGAC TGGCGACTCA GAGTCAGTGC CCGACCCTCA
 42_11   AAGCTCAACT TTGGGCAGAC TGGCGACTCA GAGTCAGTGC CCGACCCTCA
 42_6b   AGACTCAACT TTGGGCAGAC TGGCGACTCA GAGTCAGTGC CCGACCCTCA
 43_1    AGACTCAACT TTGGGCAGAC TGGCGACTCG GAGTCAGTCC CCGACCCTCA
 43_5    AGACTGAACT TTGGGCAGAC TGGCGACTCG GAGTCAGTCC CCGACCCTCA
 43_12   AGACTGAACT TTGGGCAGAC TGGCGACTCG GAGTCAGTCC CCGACCCTCA
 43_20   AGACTCAATT TTGGTCAGAC TGGCGACTCA GAGTCAGTCC CCGACCCACA
 43_21   AGACTCAATT TTGGTCAGAC TGGCGACTCA GAGTCAGTCC CCGACCCACA
 43_23   AGACTCAATT TTGGTCAGAC TGGCGACTCA GAGTCAGTCC CCGACCCACA
 43_25   AGACTCAATT TTGGTCAGAC TGGCGACTCA GAGTCAGTCC CCGACCCACA
 44_1    AGACTCAACT TTGGGCAGAC TGGCGACTCA GAGTCAGTGC CCGACCCTCA
 44_5    AGACTCAACT TTGGGCAGAC TGGCGACTCA GAGTCAGTGC CCGACCCTCA
 223_10  AGACTCAACT TTGGGCAGAC TGGCGACTCA GAGTCAGTCC CCGACCCTCA
 223_2   AGACTCAACT TTGGGCAGAC TGGCGACTCA GAGTCAGTCC CCGACCCTCA
 223_4   AGACTCAACT TTGGGCAGAC TGGCGACTCA GAGCCAGTCC CCGACCCTCA
 223_5   AGACTCAACT TTGGGCAGAC TGGCGACTCA GAGCCAGTCC CCGACCCTCA
 223_6   AGACTCAACT TTGGGCAGAC TGGCGACTCA GAGTCAGTCC CCGACCCTCA
 223_7   AGACTCAACT TTGGGCAGAC TGGCGACTCA GAGTCAGTCC CCGACCCTCA
 A3_4    AGACTCAATT TTGGTCAGAC TGGCGACACA GAGTCAGTCC CAGACCCTCA
 A3_5    AGACTCAATT TTGGTCAGAC TGGCGACACA GAGTCAGTCC CAGACCCTCA
 A3_7    AGACTCAATT TTGGTCAGAC TGGCGACACA GAGTCAGTCC CAGACCCTCA
 A3_3    AGACTCAATT TTGGTCAGAC TGGCGACACA GAGTCAGTCC CAGGCCCTCA
 42_12   AGACTCAACT TTGGGCAGAC TGGCGACTCA GAGTCAGTGC CCGACCCTCA
 AAV1    AGACTCAATT TTGGTCAGAC TGGCGACTCA GAGTCAGTCC CCGATCCACA
 AAV2    AGATGAATT  TTGGTCAGAC TGGAGACGCA GACTCAGTAC CTGACCCCCA
 AAV3    AGACTAAATT TCGGTCAGAC TGGAGACTCA GAGTCAGTCC CAGACCCTCA
 AAV8    AGACTCAATT TTGGTCAGAC TGGCGACTCA GAGTCAGTTC CAGACCCTCA
 AAV9    AGACTCAATT TTGGTCAGAC TGGCGACTCA GAGTCAGTTC CAGACCCTCA
 AAV7    AGACTCAATT TCGGTCAGAC TGGCGACTCA GAGTCAGTCC CCGACCCTCA
 44_2    AGACTCAACT TTGGGCAGAC TGGCGACTCA GAGTCAGTGC CCGACCCTCA
```

FIG. 1AAE

```
           2801                                                        2850
                                                                       vp3 start
   42_2    ACCTCTCGGA  GAACCTCCCG  CCGCGCCCTC  AGGTCTGGGA  TCTGGTACAA
   42_8    ACCAATCGGA  GAACCCCCCG  CAGGCCCCTC  TGGTCTGGGA  TCTGGTACAA
   42_15   ACCAATCGGA  GAACCCCCCG  CAGGCCCCTC  TGGTCTGGGA  TCTGGTACAA
   42_5b   ACCAATCGGA  GAACCCCCCG  CAGGCCCCTC  TGGTCTGGGA  TCTGGTACAA
   42_1b   ACCAATCGGA  GAACCCCCCG  CAGGCCCCTC  TGGTCTGGGA  TCTGGCACAA
   42_13   ACCAATCGGA  GAACCCCCCG  CAGGCCCCTC  TGGTCTGGGA  TCTGGTACAA
   42_3a   ACCAATCGGA  GAACCCCCCG  CAGGCCCCTC  TGGTCTGGGA  TCTGGTACAA
   42_4    ACCAATCGGA  GAACCCCCCG  CAGGCCCCTC  TGGTCTGGGA  TCTGGTACAA
   42_5a   ACCTCTCGGA  GAACCTCCCG  CCGCGCCCTC  AGGTCTGGGA  TCTGGTACAA
   42_10   ACCAATCGGA  GAACCCCCCG  CAGGCCCCTC  TGGTCTGGGA  TCTGGTACAA
   42_3b   ACCAATCGGA  GAACCCCCCG  CAGGCCCCTC  TGGTCTGGGA  TCTGGTACAA
   42_11   ACCAATCGGA  GAACCCCCCG  CAGGCCCCTC  TGGTCTGGGA  TCTGGTACAA
   42_6b   ACCAATCGGA  GAACCCCCCG  CAGGCCCCTC  TGGTCTGGGA  TCTGGTACAA
   43_1    ACCAATCGGA  GAACCACCAG  CAGCCCCCTC  TGGTCTGGGA  TCTGGTACAA
   43_5    ACCAATCGGA  GAACCACCAG  CAGGCCCCTC  TGGTCTGGGA  TCTGGTACAA
   43_12   ACCAATCGGA  GAACCACCAG  CAGGCCCCTC  TGGTCTGGGA  TCTGGTACAA
   43_20   ACCTCTCGGA  GAACCTCCAG  CAGCCCCCTC  AGGTCTGGGA  CCTAATACAA
   43_21   ACCTCTCGGA  GAACCTCCAG  CAGCCCCCTC  AGGTCTGGGA  CCTAATACAA
   43_23   ACCTCTCGGA  GAACCTCCAG  CAGCCCCCTC  AGGTCTGGGA  CCTAATACAA
   43_25   ACCTCTCGGA  GAACCTCCAG  CAGCCCCCTC  AGGTCTGGGA  CCTAATACAA
   44_1    ACCAATCGGA  GAACCCCCCG  CAGGCCCCTC  TGGTCTGGGA  TCTGGTACAA
   44_5    ACCAATCGGA  GAACCCCCCG  CAGGCCCCTC  TGGTCTGGGA  TCTGGTACAA
   223_10  ACCAATCGGA  GAACCACCAG  CAGGCCCCTC  TGGTCTGGGA  TCTGGTACAA
   223_2   ACCAATCGGA  GAACCACCAG  CAGGCCCCTC  TGGTCTGGGA  TCTGGTACAA
   223_4   ACCAATCGGA  GAACCACCAG  CAGGCCCCTC  TGGTCTGGGA  TCTGGTACAA
   223_5   ACCAATCGGA  GAACCACCAG  CAGGCCCCTC  TGGTCTGGGA  TCTGGTACAA
   223_6   ACCAATCGGA  GAACCACCAG  CAGGCCCCTC  TGGTCTGGGA  TCTGGTACAA
   223_7   ACCAATCGGA  GAACCACCAG  CAGGCCCCTC  TGGTCTGGGA  TCTGGTACAA
   A3_4    ACCAATCGGA  GAACCCCCCG  CAGCCCCCTC  TGGTGTGGGA  TCTAATACAA
   A3_5    ACCAATCGGA  GAACCCCCCG  CAGCCCCCTC  TGGTGTGGGA  TCTAATACAA
   A3_7    ACCAATCGGA  GAACCCCCCG  CAGCCCCCTC  TGGTGTGGGA  TCTAATACAA
   A3_3    ACCAATCGGA  GAACCCCCCG  CAGCCCCCTC  TGGTGTGGGA  TCTAATACAA
   42_12   ACCAATCGGA  GAACCCCCCG  CAGGCCCCTC  TGGTCTGGGA  TCTGGTACAA
   AAV1    ACCTCTCGGA  GAACCTCCAG  CAACCCCGC   TGCTGTGGGA  CCTACTACAA
   AAV2    GCCTCTCGGA  CAGCCACCAG  CAGCCCCCTC  TGGTCTGGGA  ACTAATACGA
   AAV3    ACCTCTCGGA  GAACCACCAG  CAGCCCCCAC  AAGTTTGGGA  TCTAATACAA
   AAV8    ACCTCTCGGA  GAACCTCCTC  CAGCGCCCTC  TGGTGTGGGA  CCTAATACAA
   AAV9    ACCTCTCGGA  GAACCTCCAG  CAGCGCCCTC  TGGTGTGGGA  CCTAATACAA
   AAV7    ACCTCTCGGA  GAACCTCCAG  CAGCGCCCTC  TAGTGTGGGA  TCTGGTACAG
   44_2    ACCAATCGGA  GAACCCCCCG  CAGGCCCCTC  TGGTCTGGGA  TCTGGTACAA
                                                                       vp3 start
```

FIG. 1AAF

```
         2851                                                      2900
         vp3 start codon
  42_2   TGGCTGCAGG CGGTGGCGCA CCAATGGCAG ACAATAACGA AGGCGCCGAC
  42_8   TGGCTGCAGG CGGTGGCGCT CCAATGGCAG ACAATAACGA AGGCGCCGAC
  42_15  TGGCTGCAGG CGGTGGCGCT CCAATGGCAG ACAATAACGA AGGCGCCGAC
  42_5b  TGGCTGCAGG CGGTGGCGCT CCAATGGCAG ACAATAACGA AGGCGCCGAC
  42_1b  TGGCTGCAGG CGGTGGCGCT CCAATGGCAG ACAATAACGA AGGCGCCGAC
  42_13  TGGCTGCAGG CGGTGGCGCT CCAATGGCAG ACAATAACGA AGGCGCCGAC
  42_3a  TGGCTGCAGG CGGTGGCGCT CCAATGGCAG ACAATAACGA AGGCGCCGAC
  42_4   TGGCTGCAGG CGGTGGCGCT CCAATGGCAG ACAATAACGA AGGCGCCGAC
  42_5a  TGGCTGCAGG CGGTGGCGCA CCAATGGCAG ACAATAACGA AGGCGCCGAC
  42_10  TGGCTGCAGG CGGTGGCGCT CCAATGGCAG ACAATAACGA AGGCGCCGAC
  42_3b  TGGCTGCAGG CGGTGGCGCT CCAATGGCAG ACAATAACGA AGGCGCCGAC
  42_11  TGGCTGCAGG CGGTGGCGCT CCAATGGCAG ACAATAACGA AGGCGCCGAC
  42_6b  TGGCTGCAGG CGGTGGCGCT CCAATGGCAG ACAATAACGA AGGCGCCGAC
  43_1   TGGCTGCAGG CGGTGGCGCT CCAATGGCAG ACAATAACGA AGGCGCCGAC
  43_5   TGGCTGCAGG CGGTGGCGCT CCAATGGCAG ACAATAACGA AGGCGCCGAC
  43_12  TGGCTGCAGG CGGTGGCGCT CCAATGGCAG ACAATAACGA AGGCGCCGAC
  43_20  TGGCTTCAGG CGGTGGCGCT CCAATGGCAG ACAATAACGA AGGCGCCGAC
  43_21  TGGCTTCAGG CGGTGGCGCT CCAATGGCAG ACAATAACGA AGGCGCCGAC
  43_23  TGGCTTCAGG CGGTGGCGCT CCAATGGCAG ACAATAACGA AGGCGCCGAC
  43_25  TGGCTTCAGG CGGTGGCGCT CCAATGGCAG ACAATAACGA AGGCGCCGAC
  44_1   TGGCTGCAGG CGGTGGCGCT CCAATGGCAG ACAATAACGA AGGCGCCGAC
  44_5   TGGCTGCAGG CGGTGGCGCT CCAATGGCAG ACAATAACGA AGGCGCCGAC
  223_10 TGGCTGCAGG CGGTGGCGCA CCAATGGCTG ACAATAACGA GGGCGCCGAC
  223_2  TGGTTGCAGG CGGTGGCGCA CCAATGGCTG ACAATAACGA GGGCGCCGAC
  223_4  TGGCTGCAGG CGGTGGCGCA CCAATGGCTG ACAATAACGA GGGCGCCGAC
  223_5  TGGCTGCAGG CGGTGGCGCA CCAATGGCTG ACAATAACGA GGGCGCCGAC
  223_6  TGGCTGCAGG CGGTGGCGCA CCAATGGCTG ACAATAGCGA GGGCGCCGAC
  223_7  TGGCTGCAGG CGGTGGCGCA CCAATGGCTG ACAATAACGA GGGCGCCGAC
  A3_4   TGGCTTCAGG CGGTGGGGCA CCAATGGCAG ACGATAACGA AGGCGCCGAC
  A3_5   TGGCTTCAGG CGGTGGGGCA CCAATGGCAG ACAATAACGA AGGCGCCGAC
  A3_7   TGGCTTCAGG CGGTGGGGCA CCAATGGCAG ACAATAACGA AGGCGCCGAC
  A3_3   TGGCTTCAGG CGGTGGGGCA CCAATGGCAG ACAATAACGA AGGCGCCGAC
  42_12  TGGCTGCAGG CGGTGGCGCT CCAATGGCAG ACAATAACGA AGGCGCCGAC
  AAV1   TGGCTTCAGG CGGTGGCGCA CCAATGGCAG ACAATAACGA AGGCGCCGAC
  AAV2   TGGCTACAGG CAGTGGCGCA CCAATGGCAG ACAATAACGA GGGCGCCGAC
  AAV3   TGGCTTCAGG CGGTGGCGCA CCAATGGCAG ACAATAACGA GGGTGCCGAT
  AAV8   TGGCTGCAGG CGGTGGCGCA CCAATGGCAG ACAATAACGA AGGCGCCGAC
  AAV9   TGGCTGCAGG CGGTGGCGCA CCAATGGCAG ACAATAACGA AGGCGCCGAC
  AAV7   TGGCTGCAGG CGGTGGCGCA CCAATGGCAG ACAATAACGA AGGTGCCGAC
  44_2   TGGCTGCAGG CGGTGGCGCT CCAATGGCAG ACAATAACGA AGGCGCCGAC
         vp3 start codon (cont'd)
```

FIG. 1AAG

```
         2901                                                              2950
  42_2   GGAGTGGGTA ATGCCTCCGG AAATTGGCAT TGCGATTCCA CATGGCTGGG
  42_8   GGAGTGGGTA GTTCCTCAGG AAATTGGCAT TGCGATTCCA CATGGCTGGG
  42_15  GGAGTGGGTA GTTCCTCAGG AAATTGGCAT TGCGATTCCA CATGGCTGGG
  42_5b  GGAGTGGGTA GTTCCTCAGG AAATTGGCAT TGCGATTCCA CATGGCTGGG
  42_1b  GGAGTGGGTA GTTCCTCAGG AAATTGGCAT TGCGATTCCA CATGGCTGGG
  42_13  GGAGTGGGTA GTTCCTCAGG AAATTGGCAT TGCGATTCCA CATGGCTGGG
  42_3a  GGAGTGGGTA GTTCCTCAGG AAATTGGCAT TGCGATTCCA CATAGCTGGG
  42_4   GGAGTGGGTA ATGCCTCCGG AAATTGGCAT TGCGATTCCA CATGGCTGGG
  42_5a  GGAGTGGGTA ATGCCTCCGG AAATTGGCAT TGCGATTCCA CATGGCTGGG
  42_10  GGAGTGGGTA ATGCCTCCGG AAATTGGCAT TGCGATTCCA CATGGCTGGG
  42_3b  GGAGTGGGTA ATGCCTCCGG AAATTGGCAT TGCGATTCCA CATGGCTGGG
  42_11  GGAGTGGGTA ATGCCTCCGG AAATTGGCAT TGCGATTCCA CATGGCTGGG
  42_6b  GGAGTGGGTA GTTCCTCAGG AAATTGGCAT TGCGATTCCA CATGGCTGGG
  43_1   GGAGTGGGTA GTTCCTCAGG AAATTGGCAT TGCGATTCCA CATGGCTGGG
  43_5   GGAGTGGGTA GTTCCTCAGG AAATTGGCAT TGCGATTCCA CATGGCTGGG
  43_12  GGAGTGGGTA GTTCCTCAGG AAATTGGCAT TGCGATTCCA CATGGCTGGG
  43_20  GGAGTGGGTA ATTCCTCGGG AAATTGGCAT TGCGATTCCA CATGGCTGGG
  43_21  GGAGTGGGTA ATTCCTCGGG AAATTGGCAT TGCGATTCCA CATGGCTGGG
  43_23  GGAGTGGGTA ATTCCTCGGG AAATTGGCAT TGCGATTCCA CATGGCTGGG
  43_25  GGAGTGGGTA ATTCCTCGGG AAATTGGCAT TGCGATTCCA CATGGCTGGG
  44_1   GGAGTGGGTA GTTCCTCAGG AAATTGGCAT TGCGATTCCA CATGGCTGGG
  44_5   GGAGTGGGTA GTTCCTCAGG AAATTGGCAT TGCGATTCCA CATGGCTGGG
  223_10 GGAGTGGGTA ATGCCTCAGG AAATTGGCAT TGCGATTCCA CATGGCTGGG
  223_2  GGAGTGGGTA ATGCCTCAGG AAATTGGCAT TGCGATTCCA CATGGCTGGG
  223_4  GGAGTGGGTA ATGCCTCAGG AAATTGGCAT TGCGATTCCA CACGGCTGGG
  223_5  GGAGTGGGTA ATGCCTCAGG AAATTGGCAT TGCGATTCCA CACGGCTGGG
  223_6  GGAGTGGGTA ATGCCTCAGG AAATTGGCAT TGCGATTCCA CATGGCTGGG
  223_7  GGAGTGGGTA ATGCCTCAGG AAATTGGCAT TGCGATTCCA CATGGCTGGG
  A3_4   GGAGTGGGTA ATTCCTCGGG AAATTGGCAT TGCGATTCCA CATGGATGGG
  A3_5   GGAGTGGGTA ATTCCTCGGG AAATTGGCAT TGCGATTCCA CATGGATGGG
  A3_7   GGAGTGGGTA ATTCCTCGGG AAATTGGCAT TGCGATTCCA CATGGATGGG
  A3_3   GGAGTGGGTA ATTCCTCGGG AAATTGGCAT TGCGATTCCA CATGGATGGG
  42_12  GGAGTGGGTA GTTCCTCAGG AAATTGGCAT TGCGATTCCA CATGGCTGGG
  AAV1   GGAGTGGGTA ATGCCTCAGG AAATTGGCAT TGCGATTCCA CATGGCTGGG
  AAV2   GGAGTGGGTA ATTCCTCCGG AAATTGGCAT TGCGATTCCA CATGGATGGG
  AAV3   GGAGTGGGTA ATTCCTCAGG AAATTGGCAT TGCGATTCCC AATGGCTGGG
  AAV8   GGAGTGGGTA GTTCCTCGGG AAATTGGCAT TGCGATTCCA CATGGCTGGG
  AAV9   GGAGTGGGTA ATTCCTCGGG AAATTGGCAT TGCGATTCCA CATGGCTGGG
  AAV7   GGAGTGGGTA ATGCCTCAGG AAATTGGCAT TGCGATTCCA CATGGCTGGG
  AAV10       GGTA ATTCCTCCGG AAATTGGCAT TGCGATTCCA CATGGCTGGG
  AAV11       GGTA ATTCCTCCGG AAATTGGCAT TGCGATTCCA CATGGCTGGG
  AAV12       GGTA ATTCCTCCGG AAATTGGCAT TGCGATTCCA CATGGCTGGG
  44_2   GGAGTGGGTA GTTCCTCAGG AAATTGGCAT TGCGATTCCA CATGGCTGGG
```

FIG. 1AAH

```
          2951                                                      3000
   42_2   CGACAGAGTC ATCACCACCA GCACCCGCAC CTGGGCCCTG CCCACCTACA
   42_8   CGACAGAGTC ATCACCACCA GCACCCGAAC CTGGGCCCTC CCCACCTACA
  42_15   CGACAGAGTC ATCACCACCA GCACCCGAAC CTGGGCCCTC CCCACCTACA
  42_5b   CGACAGAGTC ATCACCACCA GCACCCGAAC CTGGGCCCTC CCCACCTACA
  42_1b   CGACAGAGTC ATCACCACCA GCACCCGAAC CTGGGCCCTC CCCACCTACA
  42_13   CGACAGAGTC ATCACCACCA GCACCCGAAC CTGGGCCCTC CCCACCTACA
  42_3a   CGACAGAGTC ATCACCACCA GCACCCGAAC CTGGGCCCTC CCCACCTACA
   42_4   CGACAGAGTC ATCACCACCA GCACCCGCAC CTGGGCCCTG CCCACCTACA
  42_5a   CGACAGAGTC ATCACCACCA GCACCCGCAC CTGGGCCCTG CCCACCTACA
  42_10   CGACAGAGTC ATCACCACCA GCACCCGCAC CTGGGCCCTG CCCACCTACA
  42_3b   CGACAGAGTC ATCACCACCA GCACCCGCAC CTGGGCCCTG CCCACCTACA
  42_11   CGACAGAGTC ATCACCACCA GCACCCGCAC CTGGGCCCTG CCCACCTACA
  42_6b   CGACAGAGTC ATCACCACCA GCACCCGAAC CTGGGCCCTC CCCACCTACA
   43_1   CGACAGAGTC ATCACCACCA GCACCCGAAC CTGGGCCCTG CCCACCTACA
   43_5   CGACAGAGTC ATCACCACCA GCACCCGAAC CTGGGCCCTG CCCACCTACA
  43_12   CGACAGAGTC ATCACCACCA GCACCCGAAC CTGGGCCCTG CCCACCTACA
  43_20   GGACAGAGTC ATCACCACCA GCACCCGAAC CTGGGCCCTG CCCACCTACA
  43_21   GGACAGAGTC ATCACCACCA GCACCCGAAC CTGGGCCCTG CCCACCTACA
  43_23   GGACAGAGTC ATCACCACCA GCACCCGAAC CTGGGCCCTG CCCACCTACA
  43_25   GGACAGAGTC ATCACCACCA GCACCCGAAC CTGGGCCCTG CCCACCTACA
   44_1   CGACAGAGTC ATCACCACCA GCACCCGAAC CTGGGCCCTC CCCACCTACA
   44_5   CGACAGAGTC ATCACCACCA GCACCCGAAC CTGGGCCCTC CCCACCTACA
  223_10  CGACAGAGTC ATCACCACCA GCACCCGAAC CTGGGCCCTG CCCACCTACA
  223_2   CGACAGAGTC ATCACCACCA GCACCCGAAC CTGGGCCCTG CCCACCTACA
  223_4   CGACAGAGTC ATCACCACCA GCACCCGAAC CTGGGCCCTG CCCACCTACA
  223_5   CGACAGAGTC ATCACCACCA GCACCCGAAC CTGGGCCCTG CCCACCTACA
  223_6   CGACAGAGTC ATCACCACCA GCACCCGAAC CTGGGCCCTG CCCACCTACA
  223_7   CGACAGAGTC ATCACCACCA GCACCCGAAC CTGGGCCCTG CCCACCTACA
   A3_4   CGACAGAGTT ATCACCACCA GCACAAGAAC CTGGGCCCTC CCCACCTACA
   A3_5   CGACAGAGTT ATCACCACCA GCACAAGAAC CTGGGCCCTC CCCACCTACA
   A3_7   CGACAGAGTT ATCACCACCA GCACAAGAAC CTGGGCCCTC CCCACCTACA
   A3_3   CGACAGAGTT ATCACCACCA GCACAAGAAC CTGGGCCCTC CCCACCTACA
  42_12   CGACAGAGTC ATCACCACCA GCACCCGAAC CTGGGCCCTC CCCACCTACA
   AAV1   CGACAGAGTC ATCACCACCA GCACCCGCAC CTGGGCCTTG CCCACCTACA
   AAV2   CGACAGAGTC ATCACCACCA GCACCCGAAC CTGGGCCCTG CCCACCTACA
   AAV3   CGACAGAGTC ATCACCACCA GCACCAGAAC CTGGGCCCTG CCCACTTACA
   AAV8   CGACAGAGTC ATCACCACCA GCACCCGAAC CTGGGCCCTG CCCACCTACA
   AAV9   GGACAGAGTC ATCACCACCA GCACCCGAAC CTGGGCATTG CCCACCTACA
   AAV7   CGACAGAGTC ATTACCACCA GCACCCGAAC CTGGGCCCTG CCCACCTACA
  AAV10   CGACAGAGTC ATCACCACCA GCACCCGAAC CTGGGTCCTG CCCACCTACA
  AAV11   CGACAGAGTC ATCACCACCA GCACCCGAAC CTGGGCCCTG CCAACCTACA
  AAV12   CGACCGAGTC ATTACCACCA GCACCCGGAC TTGGGCCCTG CCCACCTACA
   44_2   CGACAGAGTC ATCACCACCA GCACCCGAAC CTGGGCCCTC CCCACCTACA
```

FIG. 1AAI

```
         3001                                              3050
 42_2    ACAACCACCT CTACAAGCAG ATATCAA..G TCAGAGCGGG GCT....ACC
 42_8    ACAACCACCT CTACAAGCAA ATCTCCAACG GGACATCGGG AGGAAGCACC
 42_15   ACAACCACCT CTACAAGCAA ATCTCCAACG GGACATCGGG AGGAAGCACC
 42_5b   ACAACCACCT CTACAAGCAA ATCTCCAACG GGACATCGGG AGGAAGCACC
 42_1b   ACAACCACCT CTACAAGCAA ATCTCCAACG GGACATCGGG AGGAAGCACC
 42_13   ACAACCACCT CTACAAGCAA ATCTCCAACG GGACATCGGG AGGAAGCACC
 42_3a   ACAACCACCT CTACAAGCAA ATCTCCAACG GGACATCGGG AGGAAGCACC
 42_4    ACAACCACCT CTACAAGCAG ATATCAA... .GTCAGAGCG GGC..TACC
 42_5a   ACAACCACCT CTACAAGCAG ATATCAA... .GTCAGAGCG GGC..TACC
 42_10   ACAACCACCT CTACAAGCAG ATATCAA..G TCAGAGCGGG GCTA....CC
 42_3b   ACAACCACCT CTACAAGCAG ATATCAA..G TCAGAGCGGG GCTA....CC
 42_11   ACAACCACCT CTACAAGCAG ATATCAA..G TCAGAGCGGG GCTA....CC
 42_6b   ACAACCACCT CTACAAGCAA ATCTCCAACG GGACATCGGG AGGAAGCACC
 43_1    ACAACCATCT CTACAAGCAA ATCTCCAACG GGACATCGGG AGGAAGCACT
 43_5    ACAACCATCT CTACAAGCAA ATCTCCAACG GGACATCGGG AGGAAGCACT
 43_12   ACAACCATCT CTACAAGCAA ATCTCCAACG GGACATCGGG AGGAAGCACT
 43_20   ACAACCACCT CTACAAGCAA ATCTCCAACG GCACCTCGGG AGGAAGCACC
 43_21   ACAACCACCT CTACAAGCAA ATCTCCAACG GCACCTCGGG AGGAAGCACC
 43_23   ACAACCACCT CTACAAGCAA ATCTCCAACG GCACCTCGGG AGGAAGCACC
 43_25   ACAACCACCT CTACAAGCAA ATCTCCAACG GCACCTCGGG AGGAAGCACC
 44_1    ACAACCACCT CTACAAGCAA ATCTCCAACG GGACTTCGGG AGGAAGCACC
 44_5    ACAACCACCT CTACAAGCAA ATCTCCAACG GGACTTCGGG AGGAAGCACC
 223_10  ACAACCACCT CTACAAGCAA ATCTCCAGTC AGTCAGCAGG GAG...CACC
 223_2   ACAACCACCT CTACAAGCAA ATCTCCAGTC AGTCAGCAGG GAG...CACC
 223_4   ACAACCACCT CTACAAGCAA ATCTCCAGTC AGTCAGCAGG GAG...CACC
 223_5   ACAACCACCT CTACAAGCAA ATCTCCAGTC AGTCAGCAGG GAG...CACC
 223_6   ACAACCACCT CTACAAGCAA ATCTCCAGTC AGTCAGCAGG GAG...CACC
 223_7   ACAACCACCT CTACAAGCAA ATCTCCAGTC AGTCAGCAGG GAG...CACC
 A3_4    ATAATCACCT CTACAAGCAA ATCTCCA... GCGAATCGGG AGC...CACC
 A3_5    ATAATCACCT CTACAAGCAA ATCTCCA... GCGAATCGGG AGC...CACC
 A3_7    ATAATCGCCT CTACAAGCAA ATCTCCA... GCGAATCGGG AGC...CACC
 A3_3    ATAATCACCT CTACAAGCAA ATCTCCA... GCGAATCGGG AGC...CACC
 42_12   ACAACCACCT CTACAAGCAA ATCTCCAACG GGACATCGGG AGGAAGCACC
 AAV1    ATAACCACCT CTACAAGCAA ATCTCCAGTG CTTCAACGGG .GG..CCAGC
 AAV2    ACAACCACCT CTACAAACAA ATTTCCA... GCCAATCAGG AGC...CTCG
 AAV3    ACAACCATCT CTACAAGCAA ATCTCCA... GCCAATCAGG AGC...TTCA
 AAV8    ACAACCACCT CTACAAGCAA ATCTCCAACG GGACATCGGG AGGAGCACC
 AAV9    ACAACCACCT CTACAAGCAA ATCTCCAATG GAACATCGGG AGGAAGCACC
 AAV7    ACAACCACCT CTACAAGCAA ATCTCCAGTG AAACTGCAGG TAG...TACC
 AAV10   ACAACCACAT CTACAAGCAA ATCTCCAGCG AGACAGGAGC CACCAACGAC
 AAV11   ACAACCACCT CTACAAACAA ATCTCCAGCG CTTCAACGGG GGCCAGCAAC
 AAV12   ACAACCACCT CTACAAGCAA ATCTCCAGCC AATCGGGTGC CACCAACGAC
 44_2    ACAACCACCT CTACAAGCAA ATCTCCAACG GGACTTCGGG AGGAAGCACC
```

FIG. 1AAJ

```
         3051                                                              3100
  42_2   AACGACAACC ACTTCTTCGG CTACAGCACC CCCTGGGGCT ATTTTGACTT
  42_8   AACGACAACA CCTACTTCGG CTACAGCACC CCCTGGGGT  ATTTTGACTT
  42_15  AACGACAACA CCTACTTCGG CTACAGCACC CCCTGGGGGT ATTTTGACTT
  42_5b  AACGACAACA CCTACTTCGG CTACAGCACC CCCTGGGGGT ATTTTGACTT
  42_1b  AACGACAACA CCTACTTCGG CTACAGCACC CCCTGGGGGT ATTTTGACTT
  42_13  AACGACAACA CCTACTTCGG CTACAGCACC CCCTGGGGGT ATTTTGACTT
  42_3a  AACGACAACA CCTACTTCGG CTACAGCACC CCCTGGGGGT ATTTTGACTT
  42_4   AACGACAACC ACTTCTTCGG CTACAGCACC CCCTGGGGCT ATTTTGACTT
  42_5a  AACGACAACC ACTTCTTCGG CTACAGCACC CCCTGGGGCT ATTTTGACTT
  42_10  AACGACAACC ACTTCTTCGG CTACAGCACC CCCTGGGGCT ATTTTGACTT
  42_3b  AACGACAACC ACTTCTTCGG CTACAGCACC CCCTGGGGCT ATTTTGACTT
  42_11  AACGACAACC ACTTCTTCGG CTACAGCACC CCCTGGGGCT ATTTTGACTT
  42_6b  AACGACAACA CCTACTTCGG CTACAGCACC CCCTGGGGGT ATTTTGACTT
  43_1   AACGACAACA CCTACTTTGG CTACAGCACC CCCTGGGGGT ATTTTGACTT
  43_5   AACGACAACA CCTACTTTGG CTACAGCACC CCCTGGGGGT ATTTTGACTT
  43_12  AACGACAACA CCTACTTTGG CTACAGCACC CCCTGGGGGT ATTTTGACTT
  43_20  AACGACAACA CCTATTTTGG CTACAGCACC CCCTGGGGGT ATTTTGACTT
  43_21  AACGACAACA CCTATTTTGG CTACAGCACC CCCTGGGGGT ATTTTGACTT
  43_23  AACGACAACA CCTATTTTGG CTACAGCACC CCCTGGGGGT ATTTTGACTT
  43_25  AACGACAACA CCTATTTTGG CTACAGCACC CCCTGGGGGT ATTTTGACTT
  44_1   AACGACAACA CCTACTTCGG CTACAGCACC CCCTGGGGGT ATTTTGACTT
  44_5   AACGACAACA CCTACTTCGG CTACAGCACC CCCTGGGGGT ATTTTGACTT
  223_10 AACGATAACG TCTATTTCGG CTACAGCACC CCCTGGGGGT ATTTTGACTT
  223_2  AACGATAACG TCTATTTCGG CTACAGCACC CCCTGGGGGT ATTTTGACTT
  223_4  AACGATAACG TCTATTTCGG CTACAGCACC CCCTGGGGGT ATTTTGACTT
  223_5  AACGATAACG TCTATTTCGG CTACAGCACC CCCTGGGGGT ATTTTGACTT
  223_6  AACGATAACG TCTATTTCGG CTACAGCACC CCCTGGGGGT ATTTTGACTT
  223_7  AACGATAACG TCTATTTCGG CTACAGCACC CCCTGGGGGT ATTTTGACTT
  A3_4   AACGACAACC ACTACTTCGG CTACAGCACC CCCTGGGGGT ATTTTGACTT
  A3_5   AACGACAACC ACTACTTCGG CTACAGCACC CCCTGGGGGT ATTTTGACTT
  A3_7   AACGACAACC ACTACTTCGG CTACAGCACC CCCTGGGGGT ATTTTGACTT
  A3_3   AACGACAACC ACTACTTCGG CTACAGCACC CCCTGGGGGT ATTTTGACTT
  42_12  AACGACAACA CCTACTTCGG CTACAGCACC CCCTGGGGGT ATTTTGACTT
  AAV1   AACGACAACC ACTACTTCGG CTACAGCACC CCCTGGGGGT ATTTTGATTT
  AAV2   AACGACAATC ACTACTTTGG CTACAGCACC CCTTGGGGGT ATTTTGACTT
  AAV3   AACGACAACC ACTACTTTGG CTACAGCACC CCTTGGGGGT ATTTTGACTT
  AAV8   AACGACAACA CCTACTTCGG CTACAGCACC CCCTGGGGGT ATTTTGACTT
  AAV9   AACGACAACA CCTACTTTGG CTACAGCACC CCCTGGGGGT ATTTTGACTT
  AAV7   AACGACAACA CCTACTTCGG CTACAGCACC CCCTGGGGGT ATTTTGACTT
  AAV10  AACCACTACT TCGGCTACAG C......ACC CCCTGGGGGT ATTTTGACTT
  AAV11  ...GACAACC ACTACTTTGG CTACAGCACC CCCTGGGGGT ATTTTGACTT
  AAV12  AACCACTACT TCGGCTA... ...CAGCACC CCTTGGGGGT ATTTTGATTT
  44_2   AACGACAACA CCTACTTCGG CTACAGCACC CCCTGGGGGT ATTTTGACTT
```

FIG. 1AAK

```
         3101                                                    3150
 42_2    TAACAGATTC CACTGCCACT TCTCACCACG TGACTGGCAG CGACTCATCA
 42_8    TAACAGATTC CACTGCCACT TCTCACCACG TGACTGGCAG CGACTCATCA
 42_15   TAACAGATTC CACTGCCACT TCTCACCACG TGACTGGCAG CGACTCATCA
 42_5b   TAACAGATTC CACTGCCACT TCTCACCACG TGACTGGCAG CGACTCATCA
 42_1b   TAACAGATTC CACTGCCACT TCTCACCACG TGACTGGCAG CGACTCATCA
 42_13   TAACAGATTC CACTGCCACT TCTCACCACG TGACTGGCAG CGACTCATCA
 42_3a   TAACAGATTC CACTGCCACT TCTCACCACG TGACTGGCAG CGACTCATCA
 42_4    CAACAGATTC CACTGCCACT TCTCATCACG TGACTGGCAG CGACTCATCA
 42_5a   CAACAGATTC CACTGCCACT TCTCACCACG TGACTGGCAG CGACTCATCA
 42_10   CAACAGATTC CACTGCCACT TCTCACCACG TGACTGGCAG CGACTCATCA
 42_3b   CAACAGATTC CACTGCCACT TCTCACCACG TGACTGGCAG CGACTCATCA
 42_11   CAACAGATTC CACTGCCACT TCTCACCACG TGACTGGCAG CGACTCATCA
 42_6b   TAACAGATTC CACTGCCACT TCTCACCACG TGACTGGCAG CGACTCATCA
 43_1    CAACAGATTC CACTGCCACT TCTCACCACG TGACTGGCAG CGACTCATCA
 43_5    CAACAGATTC CACTGCCACT TCTCACCACG TGACTGGCAG CGACTCATCA
 43_12   CAACAGATTC CACTGCCACT TCTCACCACG TGACTGGCAG CGACTCATCA
 43_20   CAACAGATTC CACTGTCACT TTTCACCACG TGACTGGCAA CGACTCATCA
 43_21   CAACAGATTC CACTGTCACT TTTCACCACG TGACTGGCAA CGACTCATCA
 43_23   CAACAGATTC CACTGTCACT TTTCACCACG TGACTGGCAA CGACTCATCA
 43_25   CAACAGATTC CACTGTCACT TTTCACCACG TGACTGGCAA CGACTCATCA
 44_1    TAACAGATTC CACTGCCACT TCTCACCACG TGACTGGCAG CGACTCATCA
 44_5    TAACAGATTC CACTGCCACT TCTCACCACG TGACTGGCAG CGACTCATCA
 223_10  CAACAGATTC CATTGCCACT TCTCACCACG TGACTGGCAG CGACTTATCA
 223_2   CAACAGATTC CATTGCCACT TCTCACCACG TGACTGGCAG CGACTTATCA
 223_4   CAACAGATTC CATTGCCACT TCTCACCACG TGACTGGCAG CGACTTATCA
 223_5   CAACAGATTC CATTGCCACT TCTCACCACG TGACTGGCAG CGACTTATCA
 223_6   CAACAGATTC CATTGCCACT TCTCACCACG TGACTGGCAG CGACTTATCA
 223_7   CAACAGATTC CATTGCCACT TCTCACCACG TGACTGGCAG CGACTTATCA
 A3_4    TAACAGATTC CACTGTCACT TCTCACCACG TGACTGGCAG CGACTCATCA
 A3_5    TAACAGATTC CACTGTCACT TCTCACCACG TGACTGGCAG CGACTCATCA
 A3_7    TAACAGATTC CACTGTCACT TCTCACCACG TGACTGGCAG CGACTCATCA
 A3_3    TAACAGATTC CACTGTCACT TCTCACCACG TGACTGGCAG CGACTCATCA
 42_12   TAACAGATTC CACTGCCACT TCTCACCACG TGACTGGCAG CGACTCATCA
 AAV1    CAACAGATTC CACTGCCACT TTTCACCACG TGACTGGCAG CGACTCATCA
 AAV2    CAACAGATTC CACTGCCACT TTTCACCACG TGACTGGCAA AGACTCATCA
 AAV3    TAACAGATTC CACTGCCACT TCTCACCACG TGACTGGCAG CGACTCATTA
 AAV8    TAACAGATTC CACTGCCACT TTTCACCACG TGACTGGCAG CGACTCATCA
 AAV9    CAACAGATTC CACTGCCACT TCTCACCACG TGACTGGCAG CGACTCATCA
 AAV7    TAACAGATTC CACTGCCACT TCTCACCACG TGACTGGCAG CGACTCATCA
 AAV10   TAACAGATTC CACTGCCACT TTTCACCACG TGACTGGCAG CGACTCATCA
 AAV11   TAACAGATTC CACTGCCACT TCTCACCACG TGACTGGCAG CGACTCATCA
 AAV12   CAACAGATTC CACTGCCATT TCTCACCACG TGACTGGCAG CGACTCATCA
 44_2    TAACAGATTC CACTGCCACT TCTCACCACG TGACTGGCAG CGACTCATCA
```

FIG. 1AAL

|  | 3151 |  |  |  | 3200 |
|---|---|---|---|---|---|
| 42_2 | ACAACAACTG | GGGATTCCGG | CCCAGAAAGC | TGCGGTTCAA | GTTGTTCAAC |
| 42_8 | ACAACAACTG | GGGATTCCGG | CCCAAGAGAC | TCAACTTCAA | GCTCTTCAAC |
| 42_15 | ACAACAACTG | GGGATTCCGG | CCCAAGAGAC | TCAACTTCAA | GCTCTTCAAC |
| 42_5b | ACAACAACTG | GGGATTCCGG | CCCAAGAGAC | TCAACTTCAA | GCTCTTCAAC |
| 42_1b | ACAACAACTG | GGGATTCCGG | CCCAAGAGAC | TCAACTTCAA | GCTCTTCAAC |
| 42_13 | ACAACAACTG | GGGATTCCGG | CCCAAGAGAC | TCAACTTCAA | GCTCTTCAAC |
| 42_3a | ACAACAGCTG | GGGATTCCGG | CCCAAGAGAC | TCAACTTCAA | GCTCTTCAAC |
| 42_4 | ACAACAACTG | GGGATTCCGG | CCCAAGAGAC | TCAACTTCAA | GCTCTTCAAC |
| 42_5a | ACAACAACCG | GGGATTCCGG | CCCAGAAAGC | TGCGGTTCAA | GTTGTTCAAC |
| 42_10 | ACAACAACTG | GGGATTCCGG | CCCAGAAAGC | TGCGGTTCAA | GTTGTTCAAC |
| 42_3b | ACAACAACTG | GGGATTCCGG | CCCAGAAAGC | TGCGGTTCAA | GTTGTTCAAC |
| 42_11 | ACAACAACTG | GGGATTCCGG | CCCAGAAAGC | TGCGGTTCAA | GTTGTTCAAC |
| 42_6b | ACAACAACTG | GGGATTCCGG | CCCAGAAAGC | TGCGGTTCAA | GTTGTTCAAC |
| 43_1 | ACAATAACTG | GGGATTCCGG | CCCAAGAGAC | TCAACTTCAA | GCTCTTCAAC |
| 43_5 | ACAATAACTG | GGGATTCCGG | CCCAAGAGAC | TCAACTTCAA | GCTCTTCAAC |
| 43_12 | ACAATAACTG | GGGATTCCGG | CCCAAGAGAC | TCAACTTCAA | GCTCTTCAAC |
| 43_20 | ACAACAATTG | GGGATTCCGG | CCCAAAAGAC | TCAACTTCAA | GCTGTTCAAC |
| 43_21 | ACAACAATTG | GGGATTCCGG | CCCAAAAGAC | TCAACTTCAA | GCTGTTCAAC |
| 43_23 | ACAACAATTG | GGGATTCCGG | CCCAAAAGAC | TCAACTTCAA | GCTGTTCAAC |
| 43_25 | ACAACAATTG | GGGATTCCGG | CCCAAAAGAC | TCAACTTCAA | GCTGTTCAAC |
| 44_1 | ACAACAACTG | GGGATTCCGG | CCCAAGAGAC | TCAACTTCAA | GCTCTTCAAC |
| 44_5 | ACAACAACTG | GGGATTCCGG | CCCAAGAGAC | CCAACTTCAA | GCTCTTCAAC |
| 223_10 | ACAACAACTG | GGGATTCCGG | CCCAAGAAGC | TCAACTTCAA | GCTCTTCAAC |
| 223_2 | ACAACAACTG | GGGATTCCGG | CCCAAGAAGC | TCAACTTCAA | GCTCTTCAAC |
| 223_4 | ACAACAACTG | GGGATTCCGG | CCCAAGAAGC | TCAACTTCAA | GCTCTTCAAC |
| 223_5 | ACAACAACTG | GGGATTCCGG | CCCAAGAAGC | TCAACTTCAA | GCTCTTCAAC |
| 223_6 | ACAACAACTG | GGGATTCCGG | CCCAAGAAGC | TCAACTTCAA | GCTCTTCAAC |
| 223_7 | ACAACAACTG | GGGATTCCGG | CCCAAGAAGC | TCAACTTCAA | GCTCTTCAAC |
| A3_4 | ACAACAACTG | GGGATTTAGA | CCCAAGAAAC | TCAATTTCAA | GCTCTTCAAC |
| A3_5 | ATAACAACTG | GGGATTTAGA | CCCAAGAAAC | TCAATTTCAA | GCTCTTCAAC |
| A3_7 | ACAACAACTG | GGGATTTAGA | CCCAAGAAAC | TCAATTTCAA | GCTCTTCAAC |
| A3_3 | ACAACAACTG | GGGATTTAGA | CCCAAGAAAC | TCAATTTCAA | GCTCTTCAAC |
| 42_12 | ACAACAACTG | GGGATTCCGG | CCCAAGAGAC | TCAACTTCAA | GCTCTTCAAC |
| AAV1 | ACAACAATTG | GGGATTCCGG | CCCAAGAGAC | TCAACTTCAA | ACTCTTCAAC |
| AAV2 | ACAACAACTG | GGGATTCCGA | CCCAAGAGAC | TCAACTTCAA | GCTCTTTAAC |
| AAV3 | ACAACAACTG | GGGATTCCGG | CCCAAGAAAC | TCAGCTTCAA | GCTCTTCAAC |
| AAV8 | ACAACAACTG | GGGATTCCGG | CCCAAGAGAC | TCAGCTTCAA | GCTCTTCAAC |
| AAV9 | ACAACAACTG | GGGATTCCGG | CCAAAGAGAC | TCAACTTCAA | GCTGTTCAAC |
| AAV7 | ACAACAACTG | GGGATTCCGG | CCCAAGAAGC | TGCGGTTCAA | GCTCTTCAAC |
| AAV10 | ACAACAACTG | GGGATTC |  |  |  |
| AAV11 | ACAACAACTG | GGGATTC |  |  |  |
| AAV12 | ACAACAACTG | GGGATTC |  |  |  |
| 44_2 | ACAACAACTG | GGGATTCCGG | CCCAAGAGAC | TCAACTTCAA | GCTCTTCAAC |

FIG. 1AAM

```
          3201                                                    3250
  42_2    ATCCAGGTCA AGGAGGTCAC GACGAACGAC GGCGTTACGA CCATCGCTAA
  42_8    ATCCAGGTCA AGGAGGTCAC GCAGAATGAA GGCACCAAGA CCATCGCCAA
  42_15   ATCCAGGTCA AGGAGGTCAC GCAGAATGAA GGCACCAAGA CCATCGCCAA
  42_5b   ATCCAGGTCA AGGAGGTCAC GCAGAATGAA GGCACCAAGA CCATCGCCAA
  42_1b   ATCCAGGTCA AGGAGGTCAC GCAGAATGAA GGCACCAAGA CCATCGCCAA
  42_13   ATCCAGGTCA AGGAGGTCAC GCAGAATGAA GGCACCAAGA CCATCGCCAA
  42_3a   ATCCAGGTCA AGGAGGTCAC GCAGAATGAA GGCACCAAGA CCATCGCCAA
  42_4    ATCCAGGTCA AGGAGGTCAC GCAGAATGAA GGCACCAAGA CCATCGCCAA
  42_5a   ATCCAGGTCA AGGAGGTCAC GACGAACGAC GGCGTTACGA CCATCGCTAA
  42_10   ATCCAGGTCA AGGAGGTCAC GACGAACGAC GGCGTTACGA CCATCGCCAA
  42_3b   ATCCAGGTCA AGGAGGTCAC GACGAACGAC GGCGTTACGA CCATCGCTAA
  42_11   ATCCAGGTCA AGGAGGTCAC GACGAACGAC GGCGTTACGA CCATCGCTAA
  42_6b   ATCCAGGTCA AGGAGGTCAC GACGGACGAC GGCGTTACGA CCATCGCTAA
  43_1    ATCCAGGTCA AGGAGGTCAC GCAGAATGAA GGCACCAAGA CCATCGCCAA
  43_5    ATCCAGGTCA AGGAGGTCAC GCAGAATGAA GGCACCAAGA CCATCGCCAA
  43_12   ATCCAGGTCA AGGAGGTCAC GCAGAATGAA GGCACCAAGA CCATCGCCAA
  43_20   ATCCAGGTCA AGGAAGTCAC GACGAACGAA GGCACCAAGA CCATCGCCAA
  43_21   ATCCAGGTCA AGGAAGTCAC GACGAACGAA GGCACCAAGA CCATCGCCAA
  43_23   ATCCAGGTCA AGGAAGTCAC GACGAACGAA GGCACCAAGA CCATCGCCAA
  43_25   ATCCAGGTCA AGGAAGTCAC GACGAACGAA GGCACCAAGA CCATCGCCAA
  44_1    ATCCAGGTCA AGGAGGTCAC GCAGAATGAA GGCACCAAGA CCATCGCCAA
  44_5    ATCCAGGTCA AGGAGGTCAC GCAGAATGAA GGCACCAAGA CCATCGCCAA
  223_10  ATCCAGGTCA AGGAGCTCAC GACGAATGAC GGTGTCACAA CCATCGCTAA
  223_2   ATCCAGGTCA AGGAGGTCAC GACGAATGAC GGTGTCACAA CCATCGCTAA
  223_4   ATCCAGGTCA AGGAGGTCAC GACGAATGAC GGCGTCACAA CCATCGCTAA
  223_5   ATCCAGGTCA AGGAGGTCAC GACGAATGAC GGCGTCACAA CCATCGCTAA
  223_6   ATCCAGGTCA AGGAGGTCAC GACGAATGAC GGTGTCACAA CCATCGCTAA
  223_7   ATCCAGGTCA AGGAGGTCAC GACGAATGAC GGCGTCACAA CCATCGCTAA
  A3_4    ATCCAAGTCA AGGAGGTCAC GCAGAATGAT GGAACCACGA CCATCGCCAA
  A3_5    ATCCAAGTCA AGGAGGTCAC GCAGAATGAT GGAACCACGA CCATCGCCAA
  A3_7    ATCCAAGTCA AGGAGGTCAC GCAGAATGAT GGAACCACGA CCATCGCCAA
  A3_3    ATCCAAGTCA AGGAGGTCAC GCAGAATGAT GGAACCACGA CCATCGCCAA
  42_12   ATCCAGGTCA AGGAGGTCAC GCAGAATGAA GGCACCAAGA CCATCGCCAA
  AAV1    ATCCAAGTCA AGGAGGTCAC GACGAATGAT GGCGTCACAA CCATCGCTAA
  AAV2    ATTCAAGTCA AAGAGGTCAC GCAGAATGAC GGTACGACGA CGATTGCCAA
  AAV3    ATCCAAGTTA GAGGGTCAC GCAGAACGAT GGCACGACGA CTATTGCCAA
  AAV8    ATCCAGGTCA AGGAGGTCAC GCAGAATGAA GGCACCAAGA CCATCGCCAA
  AAV9    ATCCAGGTCA AGGAGGTTAC GACGAACGAA GGCACCAAGA CCATCGCCAA
  AAV7    ATCCAGGTCA AGGAGGTCAC GACGAATGAC GGCGTTACGA CCATCGCTAA
  44_2    ATCCAGGTCA AGGAGGTCAC GCAGAATGAA GGCACCAAGA CCATCGCCAA
```

FIG. 1AAN

```
            3251                                                      3300
   42_2    TAACCTTACC AGCACGATTC AGGTCTTCTC GGACTCGGAG TACCAACTGC
   42_8    TAACCTTACC AGCACGATTC AGGTCTTTAC GGACTCGGAA TACCAGCTCC
   42_15   TAACCTTACC AGCACGATTC AGGTCTTTAC GGACTCGGAA TACCAGCTCC
   42_5b   TAACCTTACC AGCACGATTC AGGTCTTTAC GGACTCGGAA TACCAGCTCC
   42_1b   TAACCTTACC AGCACGATTC AGGTCTTTAC GGACTCGGAA TACCAGCTCC
   42_13   TAACCTTACC AGCACGATTC AGGTCTTTAC GGACTCGGAA TACCAGCTCC
   42_3a   TAACCTTACC AGCACGATTC AGGTCTTTAC GGACTCGGAA TACCAGCTCC
   42_4    TAACCTTACC AGCACGATTC AGGTCTTTAC GGACTCGGAA TACCGGCTCC
   42_5a   TAACCTTACC AGCACGATTC AGGTCTTCTC GGACTCGGAG TACCAACTGC
   42_10   TAACCTTACC AGCACGATTC AGGTCTTCTC GGACTCGGAG TACCAACTGC
   42_3b   TAACCTTACC AGCACGATTC AGGTCTTCTC GGACTCGGAG TACCAACTGC
   42_11   TAACCTTACC AGCACGATTC AGGTCTTCTC GGACTCGGAG TACCAACTGC
   42_6b   TAACCTTACC AGCACGATTC AGGTCTTCTC GGACTCGGAG TACCAACTGC
   43_1    TAACCTTACC AGCACGATTC AGGTGTTTAC GGACTCGGAA TACCAGCTCC
   43_5    TAACCTTACC AGCACGATTC AGGTGTTTAC GGACTCGGAA TACCAGCTCC
   43_12   TAACCTTACC AGCACGATTC AGGTGTTTAC GGACTCGGAA TACCAGCTCC
   43_20   TAATCTCACC AGCACCGTGC AGGTCTTTAC GGACTCGGAG TACCAGTTAC
   43_21   TAATCTCACC AGCACCGTGC GGGTCTTTAC GGACTCGGAG TACCAGTTAC
   43_23   TAATCTCACC AGCACCGTGC AGGTCTTTAC GGACTTGGAG TACCAGTTAC
   43_25   TAATCTCACC AGCACCGTGC AGGTCTTTAC GGACTCGGAG TACCAGTTAC
   44_1    TAACCTTACC AGCACGATTC AGGTCTTTAC GGACTCGGAA TACCAGCTCC
   44_5    TAACCTTACC AGCACGATTC AGGTCTTTAC GGACTCGGAA TACCAGCTCC
  223_10   TAACCTTACC AGCACGGTTC AGGTCTTTTC GGACTCGGAA TATCAACTGC
  223_2    TAACCTTACC AGCACGGTTC AGGTCTTTTC GGACTCGGAA TATCAACTGC
  223_4    TAACCTTACC AGCACGGTTC AGGTCTTTTC GGACTCGGAA TATCAACTGC
  223_5    TAACCTTACC AGCACGGTTC AGGTCTTTTC GGACTCGGAA TATCAACTGC
  223_6    TAACCTTACC AGCACGGTTC AGGTCTTTTC GGACTCGGAA TATCAACTGC
  223_7    TAACCTTACC AGCACGGTTC AGGTCTTTTC GGACCCGGAA TATCAACTGC
   A3_4    TAACCTTACC AGCACGGTGC AGGTCTTCAC AGACTCTGAG TACCAGCTGC
   A3_5    TAACCTTACC AGCACGGTGC AGGTCTTCAC AGACTCTGAG TACCAGCTGC
   A3_7    TAACCTTACC AGCACGGTGC AGGTCTTCAC AGACTCTGAG TACCAGCTGC
   A3_3    TAACCTTACC AGCGCGGTGC AGGTCTTCAC AGACTCTGAG TACCAGCTGC
   42_12   TAACCTTACC AGCACGATTC AGGTCTTTAC GGACTCGGAA TACCAGCTCC
   AAV1    TAACCTTACC AGCACGGTTC AAGTCTTCTC GGACTCGGAG TACCAGCTTC
   AAV2    TAACCTTACC AGCACGGTTC AGGTGTTTAC TGACTCGGAG TACCAGCTCC
   AAV3    TAACCTTACC AGCACGGTTC AAGTGTTTAC GGACTCGGAG TATCAGCTCC
   AAV8    TAACCTCACC AGCACCATCC AGGTGTTTAC GGACTCGGAG TACCAGCTGC
   AAV9    TAACCTTACC AGCACCGTCC AGGTCTTTAC GGACTCGGAG TACCAGCTAC
   AAV7    TAACCTTACC AGCACGATTC AGGTATTCTC GGACTCGGAA TACCAGCTGC
   44_2    TAACCTTACC AGCACGATTC AGGTCTTTAC GGACTCGGAA TACCAGCTCC
```

FIG. 1AAO

```
           3301                                                          3350
  42_2    CGTACGTCCT CGGCTCTGCG CACCAGGGCT GCCTCCCTCC GTTCCCTGCG
  42_8    CGTACGTCCT CGGCTCTGCG CACCAGGGCT GCCTGCCTCC GTTCCCGGCG
  42_15   CGTACGTCCT CGGCTCTGCG CACCAGGGCT GCCCGCCTCC GTTCCCGGCG
  42_5b   CGTACGTCCT CGGCTCTGCG CACCAGGGCT GCCTGCCTCC GTTCCCGGCG
  42_1b   CGTACGTCCT CGGCTCTGCG CACCAGGGCT GCCTGCCTCC GTTCCCGGCG
  42_13   CGTACGTCCT CGGCTCTGCG CACCAGGGCT GCCTGCCTCC GTTCCCGGCG
  42_3a   CGTACGTCCT CGGCTCTGCG CACCAGGGCT GCCTGCCTCC GTTCCCGGCG
  42_4    CGTACGTCCT CGGCTCTGCG CACCAGGGCT GCCTGCCTCC GTTCCCGGCG
  42_5a   CGTACGTCCT CGGCTCTGCG CACCAGGGCT GCCTCCCTCC GTTCCCTGCG
  42_10   CGTACGTCCT CGGCTCTGCG CACCAGGGCT GCCTCCCTCC GTTCCCTGCG
  42_3b   CGTACGTCCT CGGCTCTGCG CACCAGGGCT GCCTCCCTCC GTTCCCTGCG
  42_1    CGTACGTCCT CGGCTCTGCG CACCAGGGCT GCCTCCCTCC GTTCCCTGCG
  42_6b   CGTACGTCCT CGGCTCTGCG CACCAGGGCT GCCTCCCTCC GTTCCCTGCG
  43_1    CGTACGTCCC CGGCTCTGCG CACCAGGGCT GCCTCCCTCC GTTCCCGGCG
  43_5    CGTACGTCCT CGGCTCTGCG CACCAGGGCT GCCTCCCTCC GTTCCCGGCG
  43_12   CGTACGTCCT CGGCTCTGCG CACCAGGGCT GCCTCCCTCC GTTCCCGGCG
  43_20   CGTACGTGCT AGGATCCGCT CACCAGGGAT GTCTGCCTCC GTTCCCGGCG
  43_21   CGTACGTGCT AGGATCCGCT CACCAGGGAT GTCTGCCTCC GTTCCCGGCG
  43_23   CGTACGTGCT AGGATCCGCT CACCAGGGAT GTCTGCCTCC GTTCCCGGCG
  43_25   CGTACGTGCT AGGATCCGCT CACCAGGGAT GTCTGCCTCC GTTCCCGGCG
  44_1    CGTACGTCCT CGGCTCTGCG CACCAGGGCT GCCTGCCTCC GTTCCCGGCG
  44_5    CGTACGTCCT CGGCTCTGCG CACCAGGGCT GCCTGCCTCC GTTCCCGGCG
  223_10  CGTACGTCCT CGGCTCCGCG CACCAGGGCT GCCTGCCTCC GTTCCCGGCA
  223_2   CGTACGTCCT CGGCTCCGCG CACCAGGGCT GCCTGCCTCC GTTCCCGGCA
  223_4   CGTACGTCCT CGGCTCCGCG CACCAGGGCT GCCTGCCTCC GTTCCCGGCA
  223_5   CGTACGTCCT CGGCTCCGCG CACCAGGGCT GCCTGCCTCC GTTCCCGGCA
  223_6   CGTACGTCCT CGGCTCCGCG CACCAGGGCT GCCTGCCTCC GTTCCCGGCA
  223_7   CGTACGTCCT CGGCTCCGCG CACCAGGGCT GCCTGCCTCC GTTCCCGGCA
  A3_4    CCTACGTCCT CGGTTCGGCT CACCAGGGCT GCCTTCCGCC GTTCCCAGCA
  A3_5    CCTACGTCCT CGGTTCGGCT CACCAGGGCT GCCTTCCGCC GTTCCCAGCA
  A3_7    CCTACGTCCT CGGTTCGGCT CACCAGGGCT GCCTTCCGCC GTTCCCAGCA
  A3_3    CCTACGTCCT CGGTTCGGCT CACCAGGGCT GCCTTCCGCC GTTCCCAGCA
  42_12   CGTACGTCCT CGGCTCTGCG CACCAGGGCT GCCTGCCTCC GTTCCCGGCG
  AAV1    CGTACGTCCT CGGCTCTGCG CACCAGGGCT GCCTCCCTCC GTTCCCGGCG
  AAV2    CGTACGTCCT CGGCTCGGCG CATCAAGGAT GCCTCCCGCC GTTCCCAGCA
  AAV3    CGTACGTGCT CGGGTCGGCG CACCAAGGCT GTCTCCCGCC GTTTCCAGCG
  AAV8    CGTACGTTCT CGGCTCTGCC CACCAGGGCT GCCTGCCTCC GTTCCCGGCG
  AAV9    CGTACGTCCT AGGCTCTGCC CACCAAGGAT GCCTGCCACC GTTCCTGCA
  AAV7    CGTACGTCCT CGGCTCTGCG CACCAGGGCT GCCTGCCTCC GTTCCCGGCG
  44_2    CGTACGTCCT CGGCTCTGCG CACCAGGGCT GCCTGCCTCC GTTCCCGGCG
```

FIG. 1AAP

```
          3351                                                              3400
   42_2   GACGTGTTCA TGATTCCTCA GTACGGATAT CTGACTCTAA ACAACGGCAG
   42_8   GACGTCTTCA TGATTCCTCA GTACGGGTAC CTGACTCTGA ACAACGGCAG
  42_15   GACGTCTTCA TGATTCCTCA GTACGGGTAC CTGACTCTGA ACAACGGCAG
  42_5b   GACGTCTTCA TGATTCCTCA GTACGGGTAC CTGACTCTGA ACAACGGCAG
  42_1b   GACGTCTTCA TGATTCCTCA GTACGGGTAC CTGACTCTGA ACAACGGCAG
  42_13   GACGTCTTCA TGATTCCTCA GTACGGGTAC CTGACTCTGA ACAACGGCAG
  42_3a   GACGTCTTCA TGATTCCTCA GTACGGGTAC CTGACTCTGA ACAACGGCAG
   42_4   GACGTCTTCA TGATTCCTCA GTACGGGTAC CTGACTCTGA ACAACGGCAG
  42_5a   GACGTGTTCA TGATTCCTCA GTACGGATAT CTGACTCTAA ACAACGGCAG
  42_10   GACGTGTTCA TGATTCCTCA GTACGGATAT CTGACTCTAA ACAACGGCAG
  42_3b   GACGTGTTCA TGATTCCTCA GTACGGATAT CTGACTCTAA ACAACGGCAG
   42_1   GACGTGTTCA TGATTCCTCA GTACGGATAT CTGACTCTAA ACAACGGCAG
  42_6b   GACGTGTTCA TGATTCCTCA GTACGGATAT CTGACTCTAA ACAACGGCAG
   43_1   GACGTCTTCA TGATTCCTCA GTACGGGTAT CTGACCCTAA ACAATGGCAG
   43_5   GACGTCTTCA TGATTCCTCA GTACGGGTAT CTGACCCTAA ACAATGGCAG
  43_12   GACGTCTTCA TGATTCCTCA GTACGGGTAT CTGACCCTAA ACAATGGCAG
  43_20   GACGTCTTCA CGGTTCCTCA GTACGGCTAT TTAACTTTAA ACAATGGAAG
  43_21   GACGTCTTCA TGGTTCCTCA GTACGGCTAT TTAACTTTAA ACAATGGAAG
  43_23   GACGTCTTCA TGGTTCCTCA GTACGGCTAT TTAACTTTAA ACAATGGAAG
  43_25   GACGTCTTCA TGGTTCCTCA GTACGGCTAT TTAACTTTAA ACAATGGAAG
   44_1   GACGTCTTCA TGATTCCTCA GTACGGGTAC CTGACTCTGA ACAATGGCAG
   44_5   GACGTCTTCA TGATTCCTCA GTACGGGTAC CTGACTCTGA ACAATGGCAG
  223_10  GACGTGTTCA TGATTCCGCA GTACGGATAC CTGACTCTGA ACAATGGCAG
  223_2   GACGTGTTCA TGATTCCGCA GTACGGATAC CTGACTCTGA ACAATGGCAG
  223_4   GACGTGTTCA TGATTCCGCA GTACGGATAC CTGACTCTGA ACAATGGCAG
  223_5   GACGTGTTCA TGATTCCGCA GTACGGATAC CTGACTCTGA ACAATGGCAG
  223_6   GACGTGTTCA TGATTCCGCA GTACGGATAC CTGACTCTGA ACAATGGCAG
  223_7   GACGTGTTCA TGATTCCGCA GTACGGATAC CTGACTCTGA ACAATGGCAG
   A3_4   GACGTCTTCA TGATTCCTCA GTACGGCTAC TTGACTCTGA ACAATGGCAG
   A3_5   GACGTCTTCA TGATTCCTCA GTACGGCTAC TTGACTCTGA ACAATGGCAG
   A3_7   GACGTCTTCA TGATTCCTCA GTACGGCTAC TTGACTCTGA ACAATGGCAG
   A3_3   GACGTCTTCA TGATTCCTCA GTACGGCTAC TTGACTCTGA ACAATGGCAG
  42_12   GACGTCTTCA TGATTCCTCA GTACGGGTAC CTGACTCTGA ACAACGGCAG
   AAV1   GACGTGTTCA TGATTCCGCA ATACGGCTAC CTGACGCTCA ACAATGGCAG
   AAV2   GACGTCTTCA TGGTGCCACA GTATGGATAC CTCACCCTGA ACAACGGGAG
   AAV3   GACGTCTTCA TGGTCCTCA  GTATGGATAC CTCACCCTGA ACAACGGAAG
   AAV8   GACGTGTTCA TGATTCCCCA GTACGGCTAC CTAACACTCA ACAACGGTAG
   AAV9   GACGTCTTCA TGGTTCCTCA GTACGGCTAC CTGACGCTCA ACAATGGAAG
   AAV7   GACGTCTTCA TGATTCCTCA GTACGGCTAC CTGACTCTCA ACAATGGCAG
   44_2   GACGTCTTCA TGATTCCTCA GTACGGGTAC CTGACTCTGA ACAATGGCAG
```

FIG. 1AAQ

|  | 3401 |  |  |  | 3450 |
|---|---|---|---|---|---|
| 42_2 | TCAGTCTGTG | GGACGTTCCT | CCTTCTACTG | CCTGGAGTAC | TTTCCTTCTC |
| 42_8 | TCAGGCCGTG | GGCCGTTCCT | CCTTCTACTG | CCTGGAGTAC | TTTCCTTCTC |
| 42_15 | TCAGGCCGTG | GGCCGTTCCT | CCTTCTACTG | CCTGGAGTAC | TTTCCTTCTC |
| 42_5b | TCAGGCCGTG | GGCCGTTCCT | CCTTCTACTG | CCTGGAGTAC | TTTCCTTCTC |
| 42_1b | TCAGGCCGTG | GGCCGTTCCT | CCTTCTACTG | CCTGGAGTAC | TTTCCTTCTC |
| 42_13 | TCAGGCCGTG | GGCCGTTCCT | CCTTCTACTG | CCTGGAGTAC | TTTCCTTCTC |
| 42_3a | TCAGGCCGTG | GGCCGTTCCT | CCTTCTACTG | CCTGGAGTAC | TTTCCTTCTC |
| 42_4 | TCAGGCCGTG | GGCCGTTCCT | CCTTCTACTG | CCTGGAGTAC | TTTCCTTCTC |
| 42_5a | TCAGTCTGTG | GGACGTTCCT | CCTTCTACTG | CCTGGAGTAC | TTTCCTTCTC |
| 42_10 | TCAGTCTGTG | GGACGTTCCT | CCTTCTACTG | CCTGGAGTAC | TTTCCTTCTC |
| 42_3b | TCAGTCTGTG | GGACGTTCCT | CCTTCTACTG | CCTGGAGTAC | TTTCCTTCTC |
| 42_11 | TCAGTCTGTG | GGACGTTCCT | CCTTCTACTG | CCTGGAGTAC | TTTCCTTCTC |
| 42_6b | TCAGTCTGTG | GGACGTTCCT | CCTTCTACTG | CCTGGAGTAC | TTTCCTTCTC |
| 43_1 | TCAGGCTGTG | GGCCGTTCCT | CCTTCTACTG | CCTGGAATAC | TTCCCTTCTC |
| 43_5 | TCAGGCTGTG | GGCCGTTCCT | CCTTCTACTG | CCTGGAATAC | TTCCCTTCTC |
| 43_12 | TCAGGCTGTG | GGCCGTTCCT | CCTTCTACTG | CCTGGAATAC | TTCCCTTCTC |
| 43_20 | CCAAGCCCTG | GGACGTTCCT | CCTTCTACTG | TCTGGAGTAT | TTCCCATCGC |
| 43_21 | CCAAGCCCTG | GGACGTTCCT | CCTTCTACTG | TCTGGAGTAT | TTCCCATCGC |
| 43_23 | CCAAGCCCTG | GGACGTTCCT | CCTTCTACTG | TCTGGAGTAT | TTCCCATCGC |
| 43_25 | CCAAGCCCTG | GGACGTTCCT | CCTTCTACTG | TCTGGAGTAT | TTCCCATCGC |
| 44_1 | TCAGGCCGTG | GGCCGTTCCT | CCTTCTACTG | CCTGGAGTAC | TTTCCTTCTC |
| 44_5 | TCAGGCCGTG | GGCCGTTCCT | CCTTCTACTG | CCTGGAGTAC | TTTCCTTCTC |
| 223_10 | CCAATCGGTA | GGCCGTTCCT | CCTTCTACTG | CCTGGAGTAC | TTTCCTTCTC |
| 223_2 | CCAATCGGTA | GGCCGTTCCT | CCTTCTACTG | CCTGGAGTAC | TTTCCTTCTC |
| 223_4 | CCAATCGGTA | GGCCGTTCCT | CCTTCTACTG | CCTGGAGTAC | TTTCCTTCTC |
| 223_5 | CCAATCGGTA | GGCCGTTCCT | CCTTCTACTG | CCTGGAGTAC | TTTCCTTCTC |
| 223_6 | CCAATCGGTA | GGCCGTTCCT | CCTTCTACTG | CCTGGAGTAC | TTTCCTTCTC |
| 223_7 | CCAATCGGTA | GGCCGTTCCT | CCTTCTACTG | CCTGGAGTAC | TTTCCTTCTC |
| A3_4 | CCAAGCGGTA | GGACGTTCTT | CATTCTACTG | TCTAGAGTAT | TTTCCCTCTC |
| A3_5 | CCAAGCGGTA | GGACGTTCTT | CATTCTACTG | TCTAGAGTAT | TTTCCCTCTC |
| A3_7 | CCAAGCGGTA | GGACGTTCTT | CATTCTACTG | TCTAGAGTAT | TTTCCCTCTC |
| A3_3 | CCAAGCGGTA | GGACGTTCTT | CATTCTACTG | TCTAGAGTAT | TTTCCCTCTC |
| 42_12 | TCAGGCCGTG | GGCCGTTCCT | CCTTCTACTG | CCTGGAGTAC | TTTCCTTCTC |
| AAV1 | CCAAGCCGTG | GGACGTTCAT | CCTTTTACTG | CCTGGAATAT | TTCCCTTCTC |
| AAV2 | TCAGGCAGTA | GGACGCTCTT | CATTTTACTG | CCTGGAGTAC | TTTCCTTCTC |
| AAV3 | TCAAGCGGTG | GGACGCTCAT | CCTTTACTG | CCTGGAGTAC | TTCCCTTCGC |
| AAV8 | TCAGGCCGTG | GGACGCTCCT | CCTTCTACTG | CCTGGAATAC | TTCCCTTCGC |
| AAV9 | TCAAGCGTTA | GGACGTTCTT | CTTTCTACTG | TCTGGAATAC | TTCCCTTCTC |
| AAV7 | TCAGTCTGTG | GGACGTTCCT | CCTTCTACTG | CCTGGAGTAC | TTCCCCTCTC |
| 44_2 | TCAGGCCGTG | GGCCGTTCCT | CCTTCTACTG | CCTGGAGTAC | TTTCCTTCTC |

FIG. 1AAR

```
          3451                                                      3500
  42_2    AGATGCTGAG AACGGGCAAT AACTTTGAAT TCAGCTACAC CTTTGAGGAA
  42_8    AAATGCTGAG AACGGGCAAC AACTTTGAGT TCAGCTACCA GTTTGAGGAC
  42_15   AAATGCGGAG AACGGGCAAC AACTTTGAGT TCAGCTACCA GTTTGAGGAC
  42_5b   AAATGCTGAG AACGGGCAAC AACTTTGAGT TCAGCTACCA GTTTGAGGAC
  42_1b   AAATGCTGAG AACGGGCAAC AACTTTGAGT TCAGCTACCA GTTTGAGGAC
  42_13   AAATGCTGAG AACGGGCAAC AACTTTGAGT TCAGCTACCA GTTTGAGGAC
  42_3a   AAATGCTGAG AACGGGCAAC AACTTTGAGT TCAGCTACCA GTTTGAGGAC
  42_4    AAATGCTGAG AACGGGCAAC AACTTTGAGT TCAGCTACCA GTTTGAGGAC
  42_5a   AGATGCTGAG AACGGGCAAT AACTTTGAAT TCAGCTACCA GTTTGAGGAC
  42_10   AGATGCTGAG AACGGGCAAT AACTTTGAAT TCAGCTACAC CTTTGAGGAA
  42_3b   AGATGCTGAG AACGGGCAAT AACTTTGAAT TCAGCTACAC CTTTGAGGAA
  42_11   AGATGCTGAG AACGGGCAAT AACTTTGAAT TCAGCTACAC CTTTGAGGAA
  42_6b   AGATGCTGAG AACGGGCAAT AACTTTGAAT TCAGCTACAC CTTTGAGGAA
  43_1    AAATGCTGAG GACGGGCAAC AACTTTGAAT TCAGCTACAC CTTCGAGGAC
  43_5    AAATGCTGAG GACGGGCAAC AACTTTGAAT TCAGCTACAC CTTCGAGGAC
  43_12   AAATGCTGAG GACGGGCAAC AACTTTGAAT TCAGCTACAC CTTCGAGGAC
  43_20   AGATGCTGAG AACCGGCAAC AACTTTCAGT TCAGCTACAC CTTCGAGGAC
  43_21   AGATGCTGAG AACCGGCAAC AACTTTCAGT TCAGCTACAC CTTCGAGGAC
  43_23   AGATGCCGAG AACCGGCAAC AACTTTCAGT TCAGCTACAC CTTCGAGGAC
  43_25   AGATGCTGAG AACCGGCAAC AACTTTCAGT TCAGCTACAC CTTCGAGGAC
  44_1    AAATGCTGAG AACGGGCAAC AACTTTGAGT TCAGCTACCA GTTTGAGGAC
  44_5    AAATGCTGAG AACGGGCAAC AACTTTGAGT TCAGCTACCA GTTTGAGGAC
  223_10  AGATGCTGAG AACGGGCAAC AACTTCACCT TTAGCTACAC CTTCGAGGAC
  223_2   AGATGCTGAG AACGGGCAAC AACTTCACCT TTAGCTACAC CTTCGAGGAC
  223_4   AGATGCTGAG AACGGGCAAC AACTTCACCT TTAGCTACAC CTTCGAGGAC
  223_5   AGATGCTGAG AACGGGCAAC AACTTCACCT TTAGCTACAC CTTCGAGGAC
  223_6   AGATGCTGAG AACGGGCAAC AACTTCACCT TTAGCTACAC CTTCGAGGAC
  223_7   AGATGCTGAG AACGGGCAAC AACTTCACCT TTAGCTACAC CTTCGAGGAC
  A3_4    AGATGCTGAG GACGGGAAAC AACTTCACCT TCAGCTACAC TTTTGAAGAC
  A3_5    AGATGCTGAG GACGGGAAAC AACTTCACCT TCAGCTACAC TTTTGAAGAC
  A3_7    AGATGCTGAG GACGGGAAAC AACTTCACCT TCAGCTACAC TTTTGAAGAC
  A3_3    AGATGCTGAG GACGGGAAAC AACTTCACCT TCAGCTACAC TTTTGAAGAC
  42_12   AAATGCTGAG AACGGGCAAC AACTTTGAGT TCAGCTACCA GTTTGAGGAC
  AAV1    AGATGCTGAG AACGGGCAAC AACTTTACCT TCAGCTACAC CTTTGAGGAA
  AAV2    AGATGCTGCG TACCGGAAAC AACTTTACCT TCAGCTACAC TTTTGAGGAC
  AAV3    AGATGCTAAG GACTGGAAAT AACTTCCAAT TCAGCTATAC CTTCGAGGAT
  AAV8    AGATGCTGAG AACCGGCAAC AACTTCCAGT TTACTTACAC CTTCGAGGAC
  AAV9    AGATGCTGAG AACCGGCAAC AACTTTCAGT TCAGCTACAC TTTCGAGGAC
  AAV7    AGATGCTGAG AACGGGCAAC AACTTTGAGT TCAGCTACAG CTTCGAGGAC
  44_2    AAATGCTGAG AACGGGCAAC AACTTTGAGT TCAGCTACCA GTTTGAGGAC
```

FIG. 1AAS

```
              3501                                                          3550
     42_2     GTGCCTTTCC ACAGCAGCTA TGCGCACAGC CAGAGCCTGG ACCGGCTGAT
     42_8     GTGCCTTTTC ACAGCAGCTA CGCGCACAGC CAAAGCCTGG ACCGGCTGAT
    42_15     GTGCCTTTTC ACAGCAGCTA CGCGCATAGC CAAAGCCTGG ACCGGCTGAT
    42_5b     GTGCCTTTTC ACAGCAGCTA CGCGCACAGC CAAAGCCTGG ACCGGCTGAT
    42_1b     GTGCCTTTTC ACAGCAGCTA TGCGCACAGC CAAAGCCTGG ACCGGCTGAT
    42_13     GTGCCTTTTC ACAGCAGCTA TGCGCACAGC CAAAGCCTGG ACCGGCTGAT
    42_3a     GTGCCTTTTC ACAGCAGCTA CGCGCACAGC CAAAGCCTGG ACCGGCTGAT
     42_4     GTGCCTTTTC ACAGCAGCTA CGCGCACAGC CAAAGCCTGG ACCGGCTGAT
    42_5a     GTGCCCTTTC ACAGCAGCTA CGCGCACAGC CAAAGCCTGG ACCGGCTGAT
    42_10     GTGCCTTTCC ACAGCAGCTA TGCGCACAGC CAGAGCCTGG ACCGGCTGAT
    42_3b     GTGCCTTTCC ACAGCAGCTA TGCGCACAGC CAGAGCCTGG ACCGGCTGAT
    42_11     GTGCCTTTCC ACAGCAGCTA TGCGCACAGC CAGAGCCTGG ACCGGCTGAT
    42_6b     GTGCCTTTCC ACAGCAGCTA TGCGCATAGC CAGAGCCTGG ACCGGCTGAT
     43_1     GTGCCTTTCC ACAGCAGCTA CGCGCACAGC CAGAGCCTGG ACCGGCTGAT
     43_5     GTGCCTTTCC ACAGCAGCTA CGCGCACAGC CAGAGCCTGG ACCGGCTGAT
    43_12     GTGCCTTTCC ACAGCAGCTA CGCGCACAGC CAGAGCCTGG ACCGGCTGAT
    43_20     GTGCCTTTCC ACAGCAGCTA CGCGCACAGC CAGAGCCTGG ACAGGCTGAT
    43_21     GTGCCTTTCC ACAGCAGCTA CGCGCACAGC CAGAGCCTGG ACAGGCTGAT
    43_23     GTGCCTTTCC ACAGCAGCTA CGCGCACAGC CAGAGCCTGG ACAGGCTGAT
    43_25     GTGCCTTTCC ACAGCAGCTA CGCGCACAGC CAGAGCCTGG ACAGGCTGAT
     44_1     GTGCCTTTTC ACAGCAGCTA CGCGCACAGC CAAAGCCTGG ACCGGCTGAT
     44_5     GTGCCTTTTC ACAGCAGCTA CGCGCACAGC CAAAGCCTGG ACCGGCTGAT
   223_10     GTGCCTTTCC ACAGCAGCTA CGCGCACAGC CAGAGTCTGG ACCGGCTGAT
    223_2     GTGCCTTTCC ACAGCAGCTA CGCGCACAGC CAGAGTCTGG ACCGGCTGAT
    223_4     GTGCCTTTCC ACAGCAGCTA CGCGCACAGC CAGAGTCTGG GCCGGCTGAT
    223_5     GTGCCTTTCC ACAGCAGCTA CGCGCACAGC CAGAGTCTGG GCCGGCTGAT
    223_6     GTGCCTTTCC ACAGCAGCTA CGCGCACAGC CAGAGTCTGG ACCGGCTGAT
    223_7     GTGCCTTTCC ACAGCAGCTA CGCGCACAGC CAGAGTCTGG ACCGGCTGAT
     A3_4     GTGCCTTTCC ACAGCAGCTA CGCGCACAGC CAGAGTCTGG ATCGGCTGAT
     A3_5     GTGCCTTTCC ACAGCAGCTA CGCGCACAGC CAGAGTCTGG ATCGGCTGAT
     A3_7     GTGCCTTTCC ACAGCAGCTA CGCGCACAGC CAGAGTCTGG ATCGGCTGAT
     A3_3     GTGCCTTTCC ACAGCAGCTA CGCGCACAGC CAGAGTCTGG ATCGGCTGAT
    42_12     GTGCCTTTTC ACAGCAGCTA CGCGCACAGC CAAAGCCTGG ACCGGCTGAC
     AAV1     GTGCCTTTCC ACAGCAGCTA CGCGCACAGC CAGAGCCTGG ACCGGCTGAT
     AAV2     GTTCCTTTCC ACAGCAGCTA CGCTCACAGC CAGAGTCTGG ACCGTCTCAT
     AAV3     GTACCTTTTC ACAGCAGCTA CGCTCACAGC CAGAGTTTGG ATCGTTGAT
     AAV8     GTGCCTTTCC ACAGCAGCTA CGCCCACAGC CAGAGCTTGG ACCGGCTGAT
     AAV9     GTGCCTTTCC ACAGCAGCTA CGCACACAGC CAGAGTCTAG ATCGACTGAT
     AAV7     GTGCCTTTCC ACAGCAGCTA CGCACACAGC CAGAGCCTGG ACCGGCTGAT
     44_2     GTGCCTTTTC ACAGCAGCTA CGCGCACAGC CAAAGCCTGG ACCGGCTGAT
```

FIG. 1AAT

```
            3551                                                              3600
  42_2    GAATCCCCTC ATCGACCAGT ACCTGTACTA CCTGGCCCGG ACCCAGAGCA
  42_8    GAACCCCCTC ATCGACCAGT ACCTGTACTA CCTGTCTCGG ACTCAGTCCA
  42_15   GAACCCCCTC ATCGACCAGT ACCTGTACTA CCTGTCTCGG ACTCAGTCCA
  42_5b   GAACCCCCTC ATCGACCAGT ACCTGTACTA CCTGTCTCGG ACTCAGTCCA
  42_1b   GAACCCCCTC ATCGACCAGT ACCTGTACTA CCTGTCTCGG ACTCAGTCCA
  42_13   GAACCCCCTC ATCGACCAGT ACCTGTACTA CCTGTCTCGG ACTCAGTCCA
  42_3a   GAACCCCCTC ATCGACCAGT ACCTGTACTA CCTGTCTCGG ACTCAGTCCA
  42_4    GAACCCCCTC ATCGACCAGT ACCTGTACTA CCTGTCTCGG ACTCAGTCCA
  42_5a   GAACCCCCTC ATCGACCAGT ACCTGTACTA CCTGTCTCGG ACTCAGTCCA
  42_10   GAATCCCCTC ATCGACCAGT ACCTGTACTA CCTGGCCCGG ACCCAGAGCA
  42_3b   GAATCCCCTC ATCGACCAGT ACCTGTACTA CCTGGCCCGG ACCCAGAGCA
  42_11   GAATCCCCTC ATCGACCAGT ACCTGTACTA CCTGGCCCGG ACCCAGAGCA
  42_6b   GAATCCCCTC ATCGACCAGT ACCTGTACTA CCTGGCCCGG ACCCAGAGCA
  43_1    GAACCCTCTC ATCGACCAGT ACCTGTATTA CTTATCCAGA ACTCAGTCCA
  43_5    GAACCCTCTC ATCGACCAGT ACCTGTATTA CTTATCCAGA ACTCAGTCCA
  43_12   GAACCCTCTC ATCGACCAGT ACCTGTATTA CTTATCCAGA ACTCAGTCCA
  43_20   GAATCCCCTC ATCGACCAGT ACCTGTACTA CCTGGTCAGA ACGCAAACGA
  43_21   GAATCCCCTC ATCGACCAGT ACCTGTACTA CCTGGTCAGA ACGCAAACGA
  43_23   GAATCCCCTC ATCGACCAGT ACCTGTACTA CCTGGTCAGA ACGCAAACGA
  43_25   GAATCCCCTC ATCGACCAGT ACCTGTACTA CCTGGTCAGA ACGCAAACGA
  44_1    GAACCCCCTC ATCGACCAGT ACCTGTACTA CCTGTCTCGG ACTCAGTCCA
  44_5    GAACCCCCTC ATCGACCAGT ACCTGTACTA CCTGTCTCGG ACTCAGTCCA
  223_10  GAATCCCCTC ATCGACCAGT ACCTGTACTA CTTGGCCAGA ACACAGAGCA
  223_2   GAATCCCCTC ATCGACCAGT ACCTGTACTA CTTGGCCAGA ACACAGAGCA
  223_4   GAATCCCCTC ATCGACCAGT ACCTGTACTA CTTGGCCAGA ACACAGAGCA
  223_5   GAATCCCCTC ATCGACCAGT ACCTGTACTA CTTGGCCAGA ACACAGAGCA
  223_6   GAATCCCCTC ATCGACCAGT ACCTGTACTA CTTGGCCAGA ACACAGAGCA
  223_7   GAATCCCCTC ATCGACCAGT ACCTGTACTA CTTGGCCAGA ACACAGAGCA
  A3_4    GAATCCTCTC ATTGACCAGT ACCTGTATTA CCTGAGCAAA ACTCAGGGTA
  A3_5    GAATCCTCTC ATTGACCAGT ACCTGTATTA CCTGAGCAAA ACTCAGGGTA
  A3_7    GAATCCTCTC ATTGACCAGT ACCTGTATTA CCTGAGCAAA ACTCAGGGTA
  A3_3    GAATCCTCTC ATTGACCAGT ACCTGTATTA CCTGAGCAAA ACTCAGGGTA
  42_12   GAACCCCCTC ATCGACCAGT ACCTGTACTA CCTGGCCCGG ACCCAGAGCA
  AAV1    GAATCCTCTC ATCGACCAAT ACCTGTATTA CCTGAACAGA ACTCAAA.AT
  AAV2    GAATCCTCTC ATCGACCAGT ACCTGTATTA CTTGAGCAGA ACAAACACTC
  AAV3    GAATCCTCTT ATTGATCAGT ATCTGTACTA CCTGAACAGA ACGCAAGGAA
  AAV8    GAATCCTCTG ATTGACCAGT ACCTGTACTA CTTGTCTCGG ACTCAAACAA
  AAV9    GAACCCCCTC ATCGACCAGT ACCTATACTA CCTGGTCAGA ACACAGACAA
  AAV7    GAATCCCCTC ATCGACCAGT ACTTGTACTA CCTGGCCAGA ACACAGAGTA
  44_2    GAACCCCCTC ATCGACCAGT ACCTGTACTA CCTGTCTCGG ACTCAGTCCA
```

FIG. 1AAU

```
         3601                                                              3650
 42_2    CTACGG..GG  TCCACAAGGG  AGCTGCA.GT  TCCA......  TCAGGCTGGG
 42_8    CGGGA...GG  TACCGCAGGA  ACTCAGCAGT  TGCTATTTTC  TCAGGCCGGG
 42_15   CGGGA...GG  TACCGCAGGA  ACTCAGCAGT  TGCTATTTTC  TCAGGCCGGG
 42_5b   CGGGA...GG  TACCGCAGGA  ACTCAGCAGT  TGCTATTTTC  TCAGGCCGGG
 42_1b   CGGGA...GG  TACCGCAGGA  ACTCAGCAGT  TGCTATTTTC  TCAGGCCGGG
 42_13   CGGGA...GG  TACCGCAGGA  ACTCAGCAGT  TGCTATTTTC  TCAGGCCGGG
 42_3a   CGGGA...GG  TACCGCAGGA  ACTCAGCAGT  TGCTATTTTC  TCAGGCCGGG
 42_4    CGGGA...GG  TACCGCAGGA  ACTCAGCAGT  TGCTATTTTC  TCAGGCCGGG
 42_5a   CGGGA...GG  TACCGCAGGA  ACTCAGCAGT  TGCTATTTTC  TCAGGCCGGG
 42_10   CTACG...GG  GTCCACAAGG  GAGCTGCAGT  TCCA......  TCAGGCTGGG
 42_3b   CTACG...GG  GTCCACAAGG  GAGCTGCAGT  TCCA......  TCAGGCTGGG
 42_11   CTACG...GG  GTCCACAAGG  GAGCTGCAGT  TCCA......  TCAGGCTGGG
 42_6b   CTACG...GG  GTCCACAAGG  GAGCTGCAGT  TCCA......  TCAGGCTGGG
 43_1    CAGGA...GG  AACTCAAGGT  ACTCAGCAAT  TGTTATTTTC  TCAAGCCGGG
 43_5    CAGGA...GG  AACTCAAGGT  ACTCAGCAAT  TGTTATTTTC  TCAAGCCGGG
 43_12   CAGGA...GG  AACTCAAGGT  ACTCAGCAAT  TGTTATTTTC  TCAAGCCGGG
 43_20   CT......GG  AACTGGAGGG  ACGCAGACTC  TGGCATTCAG  CCAAGCGGGT
 43_21   CT......GG  AACTGGAGGG  ACGCAGACTC  TGGCATTCAG  CCAAGCGGGT
 43_23   CT......GG  AACTGGAGGG  ACGCAGACTC  TGGCATTCAG  CCAAGCGGGT
 43_25   CT......GG  AACTGGAGGG  ACGCAGACTC  TGGCATTCAG  CCAAGCGGGT
 44_1    CGGGA...GG  TACCGCAGGA  ACTCAGCAGT  TGCTATTTTC  TCAGGCCGGG
 44_5    CGGGA...GG  TACCGCAGGA  ACTCAGCAGT  TGCTATTTTC  TCAGGCCGGG
 223_10  ACGCAGGAGG  TACTGCTGGC  AATCGGGAAC  TGCAGTTTTA  TCAGGGCGGA
 223_2   ACGCAGGAGG  TACTGCTGGC  AATCGGGAAC  TGCAGTTTTA  TCAGGGCGGA
 223_4   ACGCAGGAGG  TACTGCTGGC  AATCGGGAAC  TGCAGTTTTA  TCAGGGCGGA
 223_5   ACGCAGGAGG  TACTGCTGGC  AATCGGGAAC  TGCAGTTTTA  TCAGGGCGGA
 223_6   ACGCAGGAGG  TACTGCTGGC  AATCGGGAAC  TGCAGTTTTA  TCAGGGCGGA
 223_7   ACGCAGGAGG  TACTGCTGGC  AATCGGGAAC  TGCAGTTTTA  TCAGGGCGGA
 A3_4    CAAG...TGG  AACAACGCAG  CAATCGAGAC  TGCAGTTCAG  CCAAGCTGGG
 A3_5    CAAG...TGG  AACAACGCAG  CAATCGAGAC  TGCAGTTCAA  CCAAGCTGGG
 A3_7    CAAG...TGG  AACAACGCAG  CAATCGAGAC  TGCAGTTCAG  CCAAGCTGGG
 A3_3    CAAG...TGG  AACAACGCAG  CAATCGAGAC  TGCAGTTCAG  CCAAGCTGGG
 42_12   CTACG...GG  GTCCACAAGG  GGGCTGCAGT  TCCA......  TCAGGCTGGG
 AAV1    CAGTCC..GG  AAGTGCCCAA  AACAAGGACT  TGCTGTTTAG  CCGTGGGTCT
 AAV2    CAAG...TGG  AACCACCACG  CAGTCAAGGC  TTCAGTTTTC  TCAGGCCGGA
 AAV3    CAACCTCTGG  AACAACCAAC  CAATCACGGC  TGCTTTTTAG  CCAGGCTGGG
 AAV8    CAGGAG..GC  .ACGGCAAAT  ACGCAGACTC  TGGGCTTCAG  CCAAGGTGGG
 AAV9    CTGGA.....  .ACTGGGGGA  ACTCAAACTT  TGGCATTCAG  CCAAGCAGGC
 AAV7    ACCCAGGAGG  CACAGCTGGC  AATCGGGAAC  TGCAGTTTTA  CCAGGGCGGG
 44_2    CGGGA...GG  TACCGCAGGA  ACTCAGCAGT  TGCTATTTTC  TCAGGCCGGG
```

FIG. 1AAV

```
           3651                                                              3700
  42_2    CCCAACACCA  TGGCCGAGCA  ATCAAAGAAC  TGGCTGCCCG  GACCCTGTTA
  42_8    CCTAATAACA  TGTCGGCTCA  GGCCAAAAAC  TGGCTACCCG  GGCCCTGCTA
  42_15   CCTAATAACA  TGTCGGCTCA  GGCCAAAAAC  TGGCTACCCG  GGCCCTGCTA
  42_5b   CCTAATAACA  TGTCGGCTCA  GGCCAAAAAC  TGGCTACCCG  GGCCCTGCTA
  42_1b   CCTAATAACA  TGTCGGCTCA  GGCCAAAAAC  TGGCTACCCG  GGCCCTGCTA
  42_13   CCTAATAACA  TGTCGGCTCA  GGCCAAAAAC  TGGCTACCCG  GGCCCTGCTA
  42_3a   CCTAATAACA  TGTCGGCTCA  GGCCAAAAAC  TGGCTACCCG  GGCCCTGCTA
  42_4    CCTAATAACA  TGTCGGCTCA  GGCCAAAAAC  TGGCTACCCG  GGCCCTGCTA
  42_5a   CCTAATAACA  TGTCGGCTCA  GGCCAAAAAC  TGGCTACCCG  GGCCCTGCTA
  42_10   CCCAACACCA  TGGCCGAGCA  ATCAAAGAAC  TGGCTGCCCG  GACCCTGTTA
  42_3b   CCCAACACCA  TGGCCGAGCA  ATCAAAGAAC  TGGCTGCCCG  GACCCTGTTA
  42_11   CCCAACACCA  TGGCCGAGCA  ATCAAAGAAC  TGGCTGCCCG  GACCCTGTTA
  42_6b   CCCAACACCA  TGGCCGAGCA  ATCAAAGAAC  TGGCTGCCCG  GACCCTGTTA
  43_1    CCCGCAAACA  TGTCGGCTCA  GGCCAAGAAC  TGGCTACCTG  GACCGTGTTA
  43_5    CCCGCAAACA  TGTCGGCTCA  GGCCAAGAAC  TGGCTACCTG  GACCGTGTTA
  43_12   CCCGCAAACA  TGTCGGCTCA  GGCCAAGAAC  TGGCTACCTG  GACCGTGTTA
  43_20   CCTAGCTCAA  TGGCCAACCA  GGCTAGAAAT  TGGGTGCCCG  GACCTTGCTA
  43_21   CCTAGCTCAA  TGGCCAACCA  GGCTAGAAAT  TGGGTGCCCG  GACCTTGCTA
  43_23   CCTAGCTCAA  TGGCCAACCA  GGCTAGAAAT  TGGGTGCCCG  GACCTTGCTA
  43_25   CCTAGCTCAA  TGGCCAACCA  GGCTAGAAAT  TGGGTGCCCG  GACCTTGCTA
  44_1    CCTAATAACA  TGTCGGCTCA  GGCCAAAAAC  TGGCTACCCG  GGCCCTGCTA
  44_5    CCTAATAACA  TGTCGGCTCA  GGCCAAAAAC  TGGCTACCCG  GGCCCTGCTA
 223_10   CCTACCACCA  TGGCCGAACA  AGCAAAGAAC  TGGCTGCCCG  GACCTTGCTT
 223_2    CCTACCACCA  TGGCCGAACA  AGCAAAGAAC  TGGCTGCCCG  GACCTTGCTT
 223_4    CCTACCACCA  TGGCCGAACA  AGCAAAGAAC  TGGCTGCCCG  GACCTTGCTT
 223_5    CCTACCACCA  TGGCCGAACA  AGCAAAGAAC  TGGCTGCCCG  GACCTTGCTT
 223_6    CCTACCACCA  TGGCCGAACA  AGCAAAGAAC  TGGCTGCCCG  GACCTTGCTT
 223_7    CCTACCACCA  TGGCCGAACA  AGCAAAGAAC  TGGCTGCCCG  GACCTTGCTT
  A3_4    CCTAGCTCCA  TGGCTCAGCA  GGCCAAAAAC  TGGCTACCGG  GACCCAGCTA
  A3_5    CCTAGCTCCA  TGGCTCAGCA  GGCCAAAAAC  TGGCTACCGG  GACCCAGCTA
  A3_7    CCTAGCTCCA  TGGCTCAGCA  GGCCAAAAAC  TGGCTACCGG  GACCCAGCTA
  A3_3    CCTAGCTCCA  TGGCTCAGCA  GGCCAAAAAC  TGGCTACCGG  GACCCAGCTA
  42_12   CCCAACACCA  TGGCCGAGCA  ATCAAAGAAC  TGGCTGCCCG  GACCCTGTTA
  AAV1    CCAGCTGGCA  TGTCTGTTCA  GCCCAAAAAC  TGGCTACCTG  GACCCTGTTA
  AAV2    GCGAGTGACA  TTCGGGACCA  GTCTAGGAAC  TGGCTTCCTG  GACCCTGTTA
  AAV3    CCTCAGTCTA  TGTCTTTGCA  GGCCAGAAAT  TGGCTACCTG  GGCCCTGCTA
  AAV8    CCTAATACAA  TGGCCAATCA  GGCAAAGAAC  TGGCTGCCAG  GACCCTGTTA
  AAV9    CCTAGCTCAA  TGGCCAATCA  GGCTAGAAAC  TGGGTACCCG  GGCCTTGCTA
  AAV7    CCTTCAACTA  TGGCCGAACA  AGCCAAGAAT  TGGTTACCTG  GACCTTGCTT
  44_2    CCTAATAACA  TGTCGGCTCA  GGCCAAAAAC  TGGCTACCCG  GGCCCTGCTA
```

FIG. 1AAW

```
          3701                                                      3750
 42_2     TCGGCAGCAG  AGACTGTCAA  AAAACATAGA  CAGCAACAAC  AACAGTAACT
 42_8     CCGGCAGCAA  CGCGTCTCCA  CGACACTGTC  GCAAAATAAC  AACAGCAACT
 42_15    CCGGCAGCAA  CGCGTCTCCA  CGACACTGTC  GCAAAATAAC  AACAGCAACT
 42_5b    CCGGCAGCAA  CGCGTCTCCA  CGACACTGTC  GCAAAATAAC  AACAGCAACT
 42_1b    CCGGCAGCAA  CGCGTCTCCA  CGACAGTGTC  GCAAAATAAC  AACAGCAACT
 42_13    CCGGCAGCAA  CGCGTCTCCA  CGACAGTGTC  GCAAAATAAC  AACAGCAACT
 42_3a    CCGGCAGCAA  CGCGTCTCCA  CGACACTGTC  GCAAAATAAC  AACAGCAACT
 42_4     CCGGCAGCAA  CGCGTCTCCA  CGACACTGTC  GCAAAATAAC  AACAGCAACT
 42_5a    CCGGCAGCAA  CGCGTCTCCA  CGACACTGTC  GCAAAATAAC  AACAGCAACT
 42_10    TCGGCAGCAG  AGACTGTCAA  AAAACATAGA  CAGCAACAAC  AACAGTAACT
 42_3b    TCGGCAGCAG  AGACTGTCAA  AAAACATAGA  CAGCAACAAC  ACCAGTAACT
 42_11    TCGGCGGCAG  AGACTGTCAA  AAGACATAGA  CAGCAACAAC  AACAGTAACT
 42_6b    TCGGCAGCAG  AGACTGTCAA  AAAACATAGA  CAGCAACAAC  AACAGTAACT
 43_1     CCGTCAGCAA  CGAGTTTCCA  CGACACTGTC  GCAAAACAAC  AACAGCAATT
 43_5     CCGTCAGCAA  CGAGTTTCCA  CGACACTGTC  GCAAAACAAC  AACAGCAATT
 43_12    CCGTCAGCAA  CGAGTTTCCA  CGACACTGTC  GCAAAACAAC  AACAGCAATT
 43_20    CCGGCAGCAG  CGCGTCTCCA  CGACAACCAA  CCAGAACAAC  AACAGCAACT
 43_21    CCGGCAGCAG  CGCGTCTCCA  CGACAACCAA  CCAGAGCAAC  AACAGCAACT
 43_23    CCGGCAGCAG  CGCGTCTCCA  CGACAACCAA  CCAGAACAAC  AACAGCAACT
 43_25    CCGGCAGCAG  CGCGTCTCCA  CGACAACCAA  CCAGAACAAC  AACAGCAACT
 44_1     CCGGCAGCAA  CGCGTCTCCA  CGACACTGTC  GCAAAATAAC  AACAGCAACT
 44_5     CCGGCAGCAA  CGCGTCTCCA  CGACACTGTC  GCAAAATAAC  AACAGCAACT
 223_10   CCGGCAACAG  AGAGTATCCA  AGACGCTGGA  TCAAAATAAC  AACAGCAACT
 223_2    CCGGCAACAG  AGAGTATCCA  AGACGCTGGA  TCAAAATAAC  AACAGCAACT
 223_4    CCGGCAACAG  AGAGTATCCA  AGACGCTGGA  TCAAAATAAC  AACAGCAACT
 223_5    CCGGCAACAG  AGAGTATCCA  AGACGCTGGA  TCAAAATAAC  AACAGCAACT
 223_6    CCGGCAACAG  AGAGTATCCA  AGACGCTGGA  TCAAAATAAC  AACAGCAACT
 223_7    CCGGCAACAG  AGAGTATCCA  AGACGCTGGA  TCAAAATAAC  AACAGCAACT
 A3_4     CCGACAGCAG  CGAATGTCTA  AGACGGCTAA  TGACAACAAC  AACAGTGAAT
 A3_5     CCGACAGCAG  CGAATGTCTA  AGACGGCTAA  TGACAACAAC  AACAGTGAAT
 A3_7     CCGACAGCAG  CGAATGTCTA  AGACGGCTAA  TGACAACAAC  AACAGTGAAT
 A3_3     CCGACAGCAG  CGAATGTCTA  AGACGGCTAA  TGACAACAAC  AACAGTGAAT
 42_12    TCGGCAGCAG  AGACTGTCAA  AAAACATAGA  CAGCAACAAC  AACAGTAACT
 AAV1     TCGGCAGCAG  CGCGTTTCTA  AAACAAAAAC  AGACAACAAC  AACAGCAATT
 AAV2     CCGCCAGCAG  CGAGTATCAA  AGACATCTGC  GGATAACAAC  AACAGTGAAT
 AAV3     CCGGCAACAG  AGACTTTCAA  AGACTGCTAA  CGACAACAAC  AACAGTAACT
 AAV8     CCGCCAACAA  CGCGTCTCAA  CGACAACCGG  GCAAACAAC   AATAGCAACT
 AAV9     CCGTCAGCAG  CGCGTCTCCA  CAACCACCAA  CCAAAATAAC  AACAGCAACT
 AAV7     CCGGCAACAA  AGAGTCTCCA  AAACGCTGGA  TCAAACAAC   AACAGCAACT
 44_2     CCGGCAGCAA  CGCGTCTCCA  CGACACTGTC  GCAAAATAAC  AACAGCAACT
```

FIG. 1AAX

```
         3751                                                           3800
 42_2    TTGCCTGGAC CGGGGCCACT AAATACCATC TGAATGGTAG AAATTCATTA
 42_8    TTGCTTGGAC CGGTGCCACC AAGTATCATC TGAATGGCAG AGACTCTCTG
 42_15   TTGCTTGGAC CGGTGCCACC AAGTATCATC TGAATGGCAG AGACTCTCTG
 42_5b   TTGCTTGGAC CGGTGCCACC AAGTATCATC TGAATGGCAG AGACTCTCTG
 42_1b   TTGCTTGGAC CGGTGCCACC AAGTATCATC TGAATGGCAG AGACTCTCTG
 42_13   TTGCTTGGAC CGGTGCCACC AAGTATCATC TGAATGGCAG AGACTCTCTG
 42_3a   TTGCTTGGAC CGGTGCCACC AAGTATCATC TGAATGGCAG AGACTCTCTG
 42_4    TTGCTTGGAC CGGTGCCACC AAGTATCATC TGAATGGCAG AGACTCTCTG
 42_5a   TTGCTTGGAC CGGTGCCACC AAGTATCATC TGAATGGCAG AGACTCTCTG
 42_10   TTGCCTGGAC CGGGGCCACT AAATACCATC TGAATGGTAG AAATTCATTA
 42_3b   TTGCCTGGAC CGGGGCCACT AAATACCATC TGAATGGTAG AAATTCATTA
 42_11   TTGCCTGGAC CGGGGCCACT AAATACCATC TGAATGGTAG AAATTCATTA
 42_6b   TTGCCTGGAC CGGGGCCACT AAATACCATC TGAATGGTAG AAATTCATTA
 43_1    TTGCTTGGAC CGGTGCCACC AAGTATCACC TGAATGGCAG AGACTCCCTG
 43_5    TTGCTTGGAC CGGTGCCACC AAGTATCACC TGAATGGCAG AGACTCCCTG
 43_12   TTGCTTGGAC CGGTGCCACC AAGTATCACC TGAATGGCAG AGACTCCCTG
 43_20   TTGCCTGGAC GGGAGCTGCC AAGTTTAAGC TGAACGGCCG AGACTCTCTA
 43_21   TTGCCTGGAC GGGAGCTGCC AAGTTTAAGC TGAACGGCCG AGACTCTCTA
 43_23   TTGCCTGGAC GGGAGCTGCC AAGTTTAAGC TGAACGGCCG AGACTCTCTA
 43_25   TTGCCTGGAC GGGAGCTGCC AAGTTTAAGC TGAACGGCCG AGACTCTCTA
 44_1    TTGCCTGGAC CGGTGCCACC AAGTATCATC TGAATGGCAG AGACTCTCTG
 44_5    TTGCCTGGAC CGGTGCCACC AAGTATCATC TGAATGGCAG AGACTCTCTG
 223_10  TTGCCTGGAC TGGTGCCACA AAATACCATT TAAATGNAAG AAATTCATTG
 223_2   TTGCCTGGAC TGGTGCCACA AAATACCATT TAAATGGAAG AAATTCATTG
 223_4   TTGCCTGGAC TGGTGCCACA AAATACCATT TAAATGGAAG AAATTCATTG
 223_5   TTGCCTGGAC TGGTGCCACA AAATACCATT TAAATGGAAG AAATTCATTG
 223_6   TTGCCTGGAC TGGTGCCACA AAATACCATT TAAATGGAAG AAATTCATTG
 223_7   TTGCCTGGAC TGGTGCCACA AAATACCATT TAAATGGAAG AAATTCATTG
 A3_4    TTGCTTGGAC TGCAGCCACC AAATATTACC TGAATGGAAG AAATTCTCTG
 A3_5    TTGCTTGGAC TGCAGCCACC AAATATTACC CGAATGGAAG AAATTCTCTG
 A3_7    TTGCTTGGAC TGCAGCCACC AAATATTACC TGAATGGAAG AAATTCTCTG
 A3_3    TTGCTTGGAC TGCAGCCACC AAATATTACC TGAATGGAAG AAATTCTCTG
 42_12   TTGCCTGGAC CGGGGCCACT AAATACCATC TGAATGGTAG AAATTCATTA
 AAV1    TTACCTGGAC TGGTGCTTCA AAATATAACC TCAATGGGCG TGAATCCATC
 AAV2    ACTCGTGGAC TGGAGCTACC AAGTACCACC TCAATGGCAG AGACTCTCTG
 AAV3    TTCCTTGGAC AGCGGCCAGC AAATATCATC TCAATGGCCG CGACTCGCTG
 AAV8    TTGCCTGGAC TGCTGGACC AAATACCATC TGAATGGAAG AAATTCATTG
 AAV9    TTGCGTGGAC GGGAGCTGCT AAATTCAAGC TGAACGGGAG AGACTCGCTA
 AAV7    TTGCTTGGAC TGGTGCCACC AAATATCACC TGAACGGCAG AAACTCGTTG
 44_2    TTGCCTGGAC CGGTGCCACC AAGTATCATC TGAATGGCAG AGACTCTCTG
```

FIG. 1AAY

```
          3801                                                           3850
  42_2    ACCAACCCGG GCGTAGCCAT GGCCACCAAC AAGGACGACG AGGACCAGTT
  42_8    GTAAATCCCG GTGTCGCTAT GGCAACGCAC AAGGACGACG AAGAGCGATT
  42_15   GTAAATCCCG GTGTCGCTAT GGCAACGCAC AAGGACGACG AAGAGCGATT
  42_5b   GTAAATCCCG GTGTCGCTAT GGCAACGCAC AAGGACGACG AAGAGCGATT
  42_1b   GTAAATCCCG GTGTCGCTAT GGCAACGCAC AAGGGCGACG AAGAGCGATT
  42_13   GTAAATCCCG GTGTCGCTAT GGCAACGCAC AAGGGCGACG AAGAGCGATT
  42_3a   GTAAATCCCG GTGTCGCTAT GGCAACGCAC AAGGACGACG AAGAGCGATT
  42_4    GTAAATCCCG GTGTCGCTAT GGCAACGCAC AAGGACGACG AAGAGCGATT
  42_5a   GTAAATCCCG GTGTCGCTAT GGCAACGCAC AAGGACGACG AAGAGCGATT
  42_10   ACCAACCCGG GCGTAGCCAT GGCCACCAAC AAGGACGACG AGGACCAGTT
  42_3b   ACCAACCCGG GCGTAGCCAT GGCCACCAAC AAGGACGACG AGGACCAGTT
  42_11   ACCAACCCGG GCGTAGCCAT GGCCACCAAC AAGGACGACG AGGACCAGTT
  42_6b   ACCAACCCGG GCGTAGCCAT GGCCACCAAC AAGGACGACG AGGACCAGTT
  43_1    GTTAATCCCG GCGTTGCCAT GGCTACCCAC AAGGACGACG AGGAGCGCTT
  43_5    GTTAATCCCG GCGTTGCCAT GGCTACCCAC AAGGACGACG AGGAGCGCTT
  43_12   GTTAATCCCG GCGTTGCCAT GGCTACCCAC AAGGACGACG AGGAGCGCTT
  43_20   ATGAATCCGG GCGTGGCAAT GGCTTCCCAC AAGGATGACG ACGACCGCTT
  43_21   ATGAATCCGG GCGTGGCAAT GGCTTCCCAC AAGGATGACG ACGACCGCTT
  43_23   ATGAATCCGG GCGTGGCAAT GGCTTCCCAC AAGGATGACG ACGACCGCTT
  43_25   ATGAATCCGG GCGTGGCAAT GGCTTCCCAC AAGGATGACG ACGACCGCTT
  44_1    GTAAATCCCG GTGTCGCTAT GGCAACCCAC AAGGACGACG AAGAGCGATT
  44_5    GTAAATCCCG GTGTCGCTAT GGCAACCCAC AAGGACGACG AAGAGCGATT
  223_10  GTTAATCCCG GTGTCGCCAT GGCAACCCAC AAGGACGACG AGGAACGCTT
  223_2   GTTAATCCCG GTGTCGCCAT GGCAACCCAC AAGGACGACG AGGAACGCTT
  223_4   GTTAATCCCG GTGTCGCCAT GGCAACCCAC AAGGACGACG AGGAACGCTT
  223_5   GTTAATCCCG GTGTCGCCAT GGCAACCCAC AAGGACGACG AGGAACGCTT
  223_6   GTTAATCCCG GTGTCGCCAT GGCAACCCAC AAGGACGACG AGGAACGCTT
  223_7   GTTAATCCCG GTGTCGCCAT GGCAACCCAC AAGGACGACG AGGAACGCTT
  A3_4    GTCAATCCCG GGCCCCAAT  GGCCAGTCAC AAGGACGATG AGGAAAAGTA
  A3_5    GTCAATCCCG GGCCCCAAT  GGCCAGTCAC AAGGACGATG AGGAAAAGTA
  A3_7    GTCAATCCCG GGCCCCAAT  GGCCAGTCAC AAGGACGATG AGGAAAAGTA
  A3_3    GTCAATCCCG GGCCCCAGT  GGCCAGTCAC AAGGACGATG AGGAAAAGTA
  42_12   ACCAACCCGG GCGTAGCCAT GGCCACCAAC AAGGACGACG AGGACCAGTT
  AAV1    ATCAACCCTG GCACTGCTAT GGCCTCACAC AAAGACGACG AAGACAAGTT
  AAV2    GTGAATCC.. GGCC....AT GGCAAGCCAC AAGGACGATG AAGAAAGTT
  AAV3    GTGAATCCAG GACCAGCTAT GGCCAGTCAC AAGGACGATG AAGAAAAATT
  AAV8    GCTAATCCTG GCATCGCTAT GGCAACACAC AAAGACGACG AGGAGCGTTT
  AAV9    ATGAATCCTG GCGTGGCTAT GGCATCGCAC AAAGACGACG AGGACCGCTT
  AAV7    GTTAATCCCG GCGTCGCCAT GGCAACTCAC AAGGACGACG AGGACCGCTT
  44_2    GTAAATCCCG GTGTCGCTAT GGCAACCCAC AAGGACGACG AAGAGCGATT
```

FIG. 1AAZ

```
         3851                                                        3900
 42_2    CTTTCCCATC AACGGAGTGC TGGTTTTTGG CGAAACGGGG GCTGCCAACA
 42_8    TTTTCCATCC AGCGGAGTCT TGATGTTTGG GAAACAGGGA GCTGGAAA..
 42_15   TTTTCCATCC AGCGGAGTCT TGATGTTTGG GAAACAGGGA GCTGGAAA..
 42_5b   TTTTCCATCC AGCGGAGTCT TGATGTTTGG GAAACAGGGA GCTGGAAA..
 42_1b   TTTTCCATCC AGCGGAGTCT TGATGTTTGG GAAACAGGGA GCTGGAAA..
 42_13   TTTTCCATCC AGCGGAGTCT TGATGTTTGG GAAACAGGGA GCTGGAAA..
 42_3a   TTTTCCATCC AGCGGAGTCT TGATGTTTGG GAAACAGGGA GCTGGAAA..
 42_4    TTTTCCATCC AGCGGAGTCT TGATGTTTGG GAAACAGGGA GCTGGAAA..
 42_5a   TTTTCCATCC AGCGGAGTCT TGATGTTTGG GAAACAGGGA GCTGGAAA..
 42_10   CTTTCCCATC AACGGAGTGC TGGTTTTTGG CAAAACGGGG GCTGCCAACA
 42_3b   CTTTCCCATC AACGGAGTGC TGGTTTTTGG CAAAACGGGG GCTGCCAACA
 42_11   CTTTCCCATC AACGGAGTGC TGGTTTTTGG CAAAACGGGG GCTGCCAACA
 42_6b   CTTTCCCATC AACGGAGTGC TGGTTTTTGG CAAAACGGGG GCTGCCAACA
 43_1    CTTCCCGTCA AGCGGAGTTC TAATGTTTGG CAAGCAGGGG GCTGGAAA..
 43_5    CTTCCCGTCA AGCGGAGTTC TAATGTTTGG CAAGCAGGGG GCTGGAAA..
 43_12   CTTCCCGTCA AGCGGAGTTC TAATGTTTGG CAAGCAGGGG GCTGGAAA..
 43_20   CTTCCCTTCG AGCGGGGTCC TGATTTTTGG CAAGCAAGGA GCCGGGAA..
 43_21   CTTCCCTTCG AGCGGGGTCC TGATTTTTGG CAAGCAAGGA GCCGGGAA..
 43_23   CTTCCCTTCG AGCGGGGTCC TGATTTTTGG CAAGCAAGGA GCCGGGAA..
 43_25   CTTCCCTTCG AGCGGGGTCC TGATTTTTGG CAAGCAAGGA GCCGGGAA..
 44_1    TTTTCCGTCC AGCGGAGTCT TAATGTTTGG GAAACAGGGA GCTGGAAA..
 44_5    TTTTCCGTCC AGCGGAGTCT TAATGTTTGG GAAACAGGGA GCTGGAAA..
 223_10  CTTCCCTTCG AGCGGAGTTC TAATTTTTGG CAAAACTGGA GCAGCTAATA
 223_2   CTCCCCTTCG AGCGGAGTTC TAATTTTTGG CAAAACTGGA GCAGCTAATA
 223_4   CTTCCCTTCG AGCGGAGTTC TAATTTTTGG CAAAACTGGA GCAGCTAATA
 223_5   CTTCCCTTCG AGCGGAGTTC TAATTTTTGG CAAAACTGGA GCAGCTAATA
 223_6   CTTCCCTTCG AGCGGAGTTC TAATTTTTGG CAAAACTGGA GCAGCTAATA
 223_7   CTTCCCTTCG AGCGGAGTTC TAATTTTTGG CAAAACTGGA GCAGCTAATA
 A3_4    TTTCCCCATG CACGGAAATC TCATCTTTGG AAAACAAGGC ACAGGAAC..
 A3_5    TTTCCCCATG CACGGAAATC TCATCTTTGG AAAACAAGGC ACAGGAAC..
 A3_7    TTTCCCCATG CACGGAAATC TCATCTTTGG AAAACAAGGC ACAGGAAC..
 A3_3    TTTCCCCATG CACGGAAATC TCATCTTTGG AAAACAAGGC ACAGGAAC..
 42_12   CTTTCCCATC AACGGAGTGC TGGTTTTTGG CAAAACGGGG GCTGCCAACA
 AAV1    CTTCCCATG  AGCGGTGTCA TGATTTTTGG AAAAGAGAGC GCCGGAGC..
 AAV2    TTTTCCTCAG AGCGGGGTTC TCATCTTTGG GAAGCAAGGC TCAGAGAA..
 AAV3    TTTCCCTATG CACGGCAATC TAATATTTGG CAAAGAAGGG ACAACGGC..
 AAV8    TTTTCCAGT  AACGGGATCC TGATTTTTGG CAAACAAAAT GCTGCCAG..
 AAV9    CTTTCCATCA AGTGGCGTTC TCATATTTGG CAAGCAAGGA GCCGGGAA..
 AAV7    TTTCCCATCC AGCGGAGTCC TGATTTTTGG AAAAACTGGA GCAACTAACA
 44_2    TTTTCCGTCC AGCGGAGTCT TAATGTTTGG GAAACAGGGA GCTGGAAA..
```

FIG. 1AAAA

```
            3901                                                               3950
  42_2    AGACAACGCT  GGAA......  AACGTGCTAA  TGACCAGCGA  GGAGGAGATC
  42_8    AGACAACG.T  GGACTATAGC  AGCGTTATGC  TAACCAGTGA  GGAAGAAATC
  42_15   AGACAACG.T  GGACTATAGC  AGCGTTATGC  TAACCAGTGA  GGAAGAAATC
  42_5b   AGACAACG.T  GGACTATAGC  AGCGTTATGC  TAACCAGTGA  GGAAGAAATC
  42_1b   AGACAACG.T  AGACTATAGC  AGCGTTATGC  TAACCAGTGA  GGAAGAAATC
  42_13   AGACAACG.T  GGACTATAGC  AGCGTTATGC  TAACCAGTGA  GGAAGAAATC
  42_3a   AGACAACG.T  GGACTATAGC  AGCGTTATGC  TAACCAGTGA  GGAAGAAATC
  42_4    AGACAACG.T  GGACTATAGC  AGCGTTATGC  TAACCAGTGA  GGAAGAAATC
  42_5a   AGACAACG.T  GGACTATAGC  AGCGTTATGC  TAACCAGTGA  GGAAGAAATC
  42_10   AGACAACGCT  GGAA......  AACGTGCTAA  TGACCAGCGA  GGAGGAGATC
  42_3b   AGACAACGCT  GGAA......  AACGTGCTAA  TGACCAGCGA  GGAGGAGATC
  42_11   AGACAACGCT  GGAA......  AACGTGCTAA  TGACCAGCGA  GGAGGAGATC
  42_6b   AGACAACGCT  GGAA......  AACGTGCTAA  TGACCAGCGA  GGAGGAGATC
  43_1    AGACAATG.T  GGACTACAGC  AGCGTGATGC  TCACCAGCGA  AGAAGAAATT
  43_5    AGACAATG.T  GGACTACAGC  AGCGTGATGC  TCACCAGCGA  AGAAGAAATT
  43_12   AGACAATG.T  GGACTACAGC  AGCGTGATGC  TCACCAGCGA  AGAAGAAATT
  43_20   CGATGGAG.T  GGATTACAGC  CAAGTGCTGA  TTACAGATGA  GGAAGAAATC
  43_21   CGATGGAG.T  GGATTACAGC  CAAGTGCTGA  TTACAGATGA  GGAAGAAATC
  43_23   CGATGGAG.T  GGATTACAGC  CAAGTGCTGA  TTACAGATGA  GGAAGAAATC
  43_25   CGATGGAG.T  GGATTACAGC  CAAGTGCTGA  TTACAGATGA  GGAAGAAATC
  44_1    AGACAACG.T  GGACTATAGC  AGCGTTATGC  TAACCAGTGA  GGAAGAAATT
  44_5    AGACAACG.T  GGACTATAGC  AGCGTTATGC  TAACCAGTGA  GGAAGAAATT
  223_10  AAACTACATT  AGAA......  AACGTGCTCA  TGACAAATGA  AGAAGAAATT
  223_2   AAACTACATT  AGAA......  AACGTGCTCA  TGACAAATGA  AGAAGAAATT
  223_4   AAACTACATT  AGAA......  AACGTGCTCA  TGACAAATGA  AGAAGAAATT
  223_5   AAACTACATT  AGAA......  AACGTGCTCA  TGACAAATGA  AGAAGAAATT
  223_6   AAACTACATT  AGAA......  AACGTGCTCA  TGACAAATGA  AGAAGAAATT
  223_7   AAACTACATT  AGAA......  AACGTGCTCA  TGACAAATGA  AGAAGAAATT
  A3_4    TACCAATG.T  GGACATTGAA  TCAGTGCTTA  TTACAGACGA  AGAAGAAATC
  A3_5    TACCAATG.T  GGACATTGAA  TCAGTGCTTA  TTACAGACGA  AGAAGAAATC
  A3_7    TACCAATG.T  GGACATTGAA  TCAGTGCTTA  TTACAGACGA  AGAAGAAATC
  A3_3    TACCAATG.T  GGACATTGAA  TCAGTGCTTA  TTACAGACGA  AGAAGAAATC
  42_12   AGACAACGCT  GGAA......  AACGTGCTAA  TGACCAGCGA  GGAGGAGATC
  AAV1    TTCAAACA.C  TGCATTGGAC  AATGTCATGA  TTACAGACGA  AGAGGAAATT
  AAV2    AACAAATG.T  GAACATTGAA  AAGGTCATGA  TTACAGACGA  AGAGGAAATC
  AAV3    AAGTAACG.C  AGAATTAGAT  AATGTAATGA  TTACGGATGA  AGAAGAGATT
  AAV8    AGACAATG.C  GGATTACAGC  GATGTCATGC  TCACCAGCGA  GGAAGAAATC
  AAV9    CGATGGAG.T  CGACTACAGC  CAGGTGCTGA  TTACAGATGA  GGAAGAAATT
  AAV7    AAACTACATT  GGAA......  AATGTGTTAA  TGACAAATGA  AGAAGAAATT
  44_2    AGACAACG.T  GGACTATAGC  AGCGTTATGC  TAACCAGTGA  GGAAGAAATT
```

FIG. 1AAAB

```
              3951                                                              4000
   42_2    AAAACCACCA ATCCCGTGGC TACAGAAGAA TACGGTGTGG TCTCCAGCAA
   42_8    AAAACCACCA ACCCAGTGGC CACAGAACAG TACGGCGTGG TGGCCGATAA
   42_15   AAAACCACCA ACCCAGTGGC CACAGAACAG TACGGCGTGG TGGCCGATAA
   42_5b   AAAACCACCA ACCCAGTGGC CACAGAACAG TACGGCGTGG TGGCCGATAA
   42_1b   AAAACCACCA ACCCAGTGGC CACAGAACAG TACGGCGTGG TGGCCGATAA
   42_13   AAAACCACCA ACCCAGTGGC CACAGAACAG TACGGCGTGG TGGCCGATAA
   42_3a   AAAACCACCA ACCCAGTGGC CACAGAACAG TACGGCGTGG TGGCCGATAA
   42_4    AAAACCACCA ACCCAGTGGC CACAGAACAG TACGGCGTGG TGGCCGATAA
   42_5a   AAAACCACCA ACCCAGTGGC CACAGAACAG TACGGCGTGG TGGCCGATAA
   42_10   AAAACCACCA ATCCCGTGGC TACAGAAGAA TACGGTGTGG TCTCCAGCAA
   42_3b   AAAACCACCA ATCCCGTGGC TACAGAACAG TACGGTGTGG TCTCCAGCAA
   42_11   AAAACCACCA ATCCCGTGGC TACAGAAGAA TACGGTGTGG TCTCCAGCAA
   42_6b   AAAACCACCA ATCCCGTGGC TACAGAAGAA TACGGTGTGG TCTCCAGCAA
   43_1    AAAACTACTA ACCCAGTGGC TACAGAGCAG TATGGTGTGG TGGCAGACAA
   43_5    AAAACTACTA ACCCAGTGGC TACAGAGCAG TATGGTGTGG TGGCAGACAA
   43_12   AAAACTACTA ACCCAGTGGC TACAGAGCAG TATGGTGTGG TGGCAGACAA
   43_20   AAGGCTACCA ACCCGTGGC CACAGAAGAA TATGGAGCAG TGGCCATCAA
   43_21   AAGGCTACCA ACCCGTGGC CACAGAAGAA TATGGAGCAG TGGCCATCAA
   43_23   AAGGCTACCA ACCCGTGGC CACAGAAGAA TATGGAGCAG TGGCCATCAA
   43_25   AAGGCTACCA ACCCGTGGC CACAGAAGAA TATGGAGCAG TGGCCATCAA
   44_1    AAAACCACCA ACCCAGTGGC CACGGAACAG TACGGCGTGG TGGCCGATAA
   44_5    AAAACCACCA ACCCAGTGGC CACAGAACAG TACGGCGTGG TGGCCGATAA
  223_10   CGTCCTACCA ACCCGGTAGC TACCGAGGAA TACGGGATTG TAAGCAGCAA
  223_2    CGTCCTACCA ACCCGGTAGC TACCGAGGAA TACGGGATTG TAAGCAGCAA
  223_4    CGTCCTACCA ACCCGGTAGC TACCGAGGAA TACGGGATTG TAAGCAGCAA
  223_5    CGTCCTACCA ACCCGGTAGC TACCGAGGAA TACGGGATTG TAAGCAGCAA
  223_6    CGTCCTACCA ACCCGGTAGC TACCGAGGAA TACGGGATTG TAAGCAGCAA
  223_7    CGTCCTACCA ACCCGGTAGC TACCGAGGAA TACGGGATTG TAAGCAGCAA
   A3_4    AGAACAACTA ATCCTGTGGC TACAGAACAA TACGGACAGG TTGCCACCAA
   A3_5    AGAACGACTA ATCCTGTGGC TACAGAACAA TACGGACAGG TTGCCACCAA
   A3_7    AGAACAACTA ATCCTGTGGC TACAGAACAA TACGGACAGG TTGCCACCAA
   A3_3    AGAACAACTA ATCCTGTGGC TACAGAACAA TACGGACAGG TTGCCACCAA
   42_12   AAAACCACCA ATCCCGTGGC TACAGAAGAA TACGGTGTGG TCTCCAGCAA
   AAV1    AAAGCCACTA ACCCTGTGGC CACCGAAAGA TTTGGGACCG TGGCAGTCAA
   AAV2    GGAACAACCA ATCCCGTGGC TACGGAGCAG TATGGTTCTG TATCTACCAA
   AAV3    CGTACCACCA ATCCTGTGGC AACAGAGCAG TATGGAACTG TGGCAAATAA
   AAV8    AAAACCACTA ACCCTGTGGC TACAGAGGAA TACGGTATCG TGGCAGATAA
   AAV9    AAAGCCACCA ACCCTGTAGC CACAGAGGAA TACGGAGCAG TGGCCATCAA
   AAV7    CGTCCTACTA ATCCTGTAGC CACGGAAGAA TACGGGATAG TCAGCAGCAA
   44_2    AAAACCACCA ACCCAGTGGC CACAGAACAG TACGGCGTGG TGGCCGATAA
```

FIG. 1AAAC

```
         4001                                                    4050
  42_2   CCTGCAATCG TCTACGGCCG GACCCCAGAC ACAGACTGTC AACAGCCAGG
  42_8   CCTGCAACAG CAAAACGCCG CTCCTATTGT AGGGGCCGTC AACAGTCAAG
  42_15  CCTGCAACAG CAAAACGCCG CTCCTATTGT AGGGGCCGTC AACAGTCAAG
  42_5b  CCTGCAACAG CAAAACGCCG CTCCTATTGT AGGGGCCGTC AACAGTCAAG
  42_1b  CCTGCAACAG CAAAACGCCG CTCCTATTGT AGGGGCCGTC AACAGTCAAG
  42_13  CCTGCAACAG CAAAACGCCG CTCCTATTGT AGGGGCCGTC AACAGTCAAG
  42_3a  CCTGCAACAG CAAAACGCCG CTCCTATTGT AGGGGCCGTC AACAGTCAAG
  42_4   CCTGCAACAG CAAAACGCCG CTCCTATTGT AGGGGCCGTC AACAGTCAAG
  42_5a  CCTGCAACAG CAAAACGCCG CTCCTATTGT AGGGGCCGTC AACAGTCAAG
  42_10  CCTGCAATCG TCTACGGCCG GACCCCAGAC ACAGACTGTC AACAGCCAGG
  42_3b  CCTGCAATCG TCTACGGCCG GACCCCAGAC ACAGACTGTC AACAGCCAGG
  42_11  CCTGCAATCG TCTACGGCCG GACCCCAGAC ACAGACTGTC AACAGCCAGG
  42_6b  CCTGCAATCG TCTACGGCCG GACCCCAGAC ACAGACTGTC AACAGCCAGG
  43_1   CCTGCAGCAG ACCAACGGAG CTCCCATTGT GGGAACTGTC AACAGCCAGG
  43_5   CCTGCAGCAG ACCAACGGAG CTCCCATTGT GGGAACTGTC AACAGCCAGG
  43_12  CCTGCAGCAG ACCAACGGAG CTCCCATTGT GGGAACTGTC AACAGCCAGG
  43_20  CAACCAGGCC GCCAATACGC AGGCGCAGAC CGGACTCGTG CACAACCAGG
  43_21  CAACCAGGCC GCCAATACGC AGGCGCAGAC CGGACTCGTG CACAACCAGG
  43_23  CAACCAGGCC GCCAATACGC AGGCGCAGAC CGGACTCGTG CACAACCAGG
  43_25  CAACCAGGCC GCCAATACGC AGGCGCAGAC CGGACTCGTG CACAACCAGG
  44_1   CCTGCAACAG CAAAACGCCG CTCCTATTGT AGGGGCCGTC AACAGTCAAG
  44_5   CCTGCAACAG CAAAACGCCG CTCCTATTGT AGGGGCCGTC AACAGTCAAG
  223_10 CTTGCAGGCG GCTAGCACCG CAGCCCAGAC ACAAGTTGTT AACAACCAGG
  223_2  CTTGCAGGCG GCTAGCACCG CAGCCCAGAC ACAAGTTGTT AACAACCAGG
  223_4  CTTGCAGGCG GCTAGCACCG CAGCCCAGAC ACAAGTTGTT AACAACCAGG
  223_5  CTTGCAGGCG GCTAGCACCG CAGCCCAGAC ACAAGTTGTT AACAACCAGG
  223_6  CTTGCAGGCG GCTAGCACCG CAGCCCAGAC ACAAGTTGTT AACAACCAGG
  223_7  CTTGCAGGCG GCTAGCACCG CAGCCCAGAC ACAAGTTGTT AACAACCAGG
  A3_4   CCATCAGAGT CAGGACACCA CAGCTTCCTA TGGAAGTGTG GACAGCCAGG
  A3_5   CCGTCAGAGT CAGAACACCA CAGCTTCCTA TGGAAGTGTG GACAGCCAGG
  A3_7   CCATCAGAGT CAGAACACCA CAGCTTCCTA TGGAAGTGTG GACAGCCAGG
  A3_3   CCATCAGAGT CAGAACACCA CAGCTTCCTA TGGAAGTGTG GACAGCCAGG
  42_12  CCTGCAATCG TCTACGGCCG GACCCCAGAC ACAGACTGTC AACAGCCAGG
  AAV1   TTTCCAGAGC AGCAGCACAG ACCCTGCGAC CGGAGATGTG CATGCTATGG
  AAV2   CCTCCAGAGA GGCAACAGAC AAGCAGCTAC CGCAGATGTC AACACACAAG
  AAV3   CTTGCAGAGC TCAAATACAG CTCCCACGAC TGGAACTGTC AATCATCAGG
  AAV8   CTTGCAGCAG CAAAACACGG CTCCTCAAAT TGGAACTGTC AACAGCCAGG
  AAV9   CAACCAGGCC GCTAACACGC AGGCGCAAAC TGGACTTGTG CATAACCAGG
  AAV7   CTTACAAGCG GCTAATACTG CAGCCCAGAC ACAAGTTGTC AACAACCAGG
  44_2   CCTGCAACAG CAAAACGCCG CTCCTATTGT AGGGGCCGTC AACAGTCAAG
```

FIG. 1AAAD

```
        4051                                                                          4100
 42_2   GGGCTCTGCC  CGGCATGGTC  TGGCAGAACC  GGGACGTGTA  CCTGCAGGGT
 42_8   GAGCCTTACC  TGGCATGGTC  TGGCAGAACC  GGGACGTGTA  CCTGCAGGGT
 42_15  GAGCCTTACC  TGGCATGGTC  TGGCAGAACC  GGGACGTGTA  CCTGCAGGGT
 42_5b  GAGCCTTACC  TGGCATGGTC  TGGCAGAACC  GGGACGTGTA  CCTGCAGGGT
 42_1b  GAGCCTTACC  TGGCATGGTC  TGGCAGAACC  GGGACGTGTA  CCTGCAGGGT
 42_13  GAGCCTTACC  TGGCATGGTC  TGGCAGAACC  GGGACGTGTA  CCTGCAGGGT
 42_3a  GAGCCTTACC  TGGCATGGTC  TGGCAGAACC  GGGACGTGTA  CCTGCAGGGT
 42_4   GAGCCTTACC  TGGCATGGTC  TGGCAGAACC  GGGACGTGTA  CCTGCAGGGT
 42_5a  GAGCCTTACC  TGGCATGGCC  TGGCAGAACC  GGGACGTGTA  CCTGCAGGGT
 42_10  GGGCTCTGCC  CGGCATGGTC  TGGCAGAACC  GGGACGTGTA  CCTGCAGGGT
 42_3b  GGGCTCTGCC  CGGCATGGTC  TGGCAGAACC  GGGACGTGTA  CCTGCAGGGT
 42_11  GGGCTCTGCC  CGGCATGGTC  TGGCAGAACC  GGGACGTGTA  CCTGCAGGGT
 42_6b  GGGCTCTGCC  CGGCATGGTC  TGGCAGAACC  GGGACGTGTA  CCTGCAGGGT
 43_1   GGGCCTTACC  TGGTATGGTC  TGGCAAAACC  GGGACGTGTA  CCTGCAGGGC
 43_5   GGGCCTTACC  TGGTATGGTC  TGGCAAAACC  GGGACGTGTA  CCTGCAGGGC
 43_12  GGGCCTTACC  TGGTATGGTC  TGGCAAAACC  GGGACGTGTA  CCTGCAGGGC
 43_20  GGGTGATTCC  CGGCATGGTG  TGGCAGAATA  GAGACGTGTA  CCTGCAGGGT
 43_21  GGGTGATTCC  CGGCATGGTG  TGGCAGAATA  GAGACGTGTA  CCTGCAGGGT
 43_23  GGGTGATTCC  CGGCATGGTG  TGGCAGAATA  GAGACGTGTA  CCTGCAGGGT
 43_25  GGGTGATTCC  CGGCATGGTG  TGGCAGAATA  GAGACGTGTA  CCTGCAGGGT
 44_1   GAGCCTTACC  TGGCATGGTC  TGGCAGAACC  GGGACGTGTA  CCTGCAGGGT
 44_5   GAGCCTTACC  TGGCATGGTC  TGGCAGAACC  GGGACGTGTA  CCTGCAGGGT
223_10  GAGCCTTACC  TGGCATGGTC  TGGCAGAACC  GGGACGTGTA  CCTGCAAGGT
223_2   GAGCCTTACC  TGGCATGGTC  TGGCAGAACC  GGGACGTGTA  CCTGCAAGGT
223_4   GAGCCTTACC  TGGCATGGTC  TGGCAGAACC  GGGACGTGTA  CCTGCAAGGT
223_5   GAGCCTTACC  TGGCATGGTC  TGGCAGAACC  GGGACGTGTA  CCTGCAAGGT
223_6   GAGCCTTACC  TGGCATGGTC  TGGCAGAACC  GGGACGTGTA  CCTGCAAGGT
223_7   GAGCCTTACC  TGGCATGGTC  TGGCAGAACC  GGGACGTGTA  CCTGCAAGGT
 A3_4   GAATCTTACC  TGGAATGGTG  TGGCAGGACC  GCGATGTCTA  TCTTCAAGGT
 A3_5   GAATCTTACC  TGGAATGGTG  TGGCAGGACC  GCGATGTCTA  TCTTCAAGGT
 A3_7   GAATCTTACC  TGGAATGGTG  TGGCAGGACC  GCGATGTCTA  TCTTCAAGGT
 A3_3   GAATCTTACC  TGGAATGGTG  TGGCAGGACC  GCGATGTCTA  TCTTCAAGGT
 42_12  GGGCTCTGCC  CGGCATGGTC  TGGCAGAACC  GGGACGTGTA  CCTGCAGGGT
 AAV1   GAGCATTACC  TGGCATGGTG  TGGCAAGATA  GAGACGTGTA  CCTGCAGGGT
 AAV2   GCGTTCTTCC  AGGCATGGTC  TGGCAGGACA  GAGATGTGTA  CCTTCAGGGG
 AAV3   GGGCCTTACC  TGGCATGGTG  TGGCAAGATC  GTGACGTGTA  CCTTCAAGGA
 AAV8   GGGCCTTACC  CGGTATGGTC  TGGCAGAACC  GGGACGTGTA  CCTGCAGGGT
 AAV9   GAGTTATTCC  TGGTATGGTC  TGGCAGAACC  GGGACGTGTA  CCTGCAGGGC
 AAV7   GAGCCTTACC  TGGCATGGTC  TGGCAGAACC  GGGACGTGTA  CCTGCAGGGT
 44_2   GAGCCTTACC  TGGCATGGTC  TGGCAGAACC  GGGACGTGTA  CCTGCAGGGT
```

FIG. 1AAAE

```
           4101                                                    4150
   42_2    CCC.ATCTGG  GCCAAAATTC  CTCACACGGA  CGGCAACTTT  CACCCGTCTC
   42_8    CCT.ATCTGG  GCCAAGATTC  CTCACACGGA  CGGCAACTTT  CATCCTTCGC
  42_15    CCT.ATCTGG  GCCAAGATTC  CTCACACGGA  CGGCAACTTT  CATCCTTCGC
  42_5b    CCT.ATCTGG  GCCAAGATTC  CTCACACGGA  CGGCAACTTT  CATCCTTCGC
  42_1b    CCT.ATCTGG  GCCAAGATTC  CTCACACGGA  CGGCAACTTT  CATCCTTCGC
  42_13    CCT.ATCTGG  GCCAAGATTC  CTCACACGGA  CGGCAACTTT  CATCCTTCGC
  42_3a    CCT.ATCTGG  GCCAAGATTC  CTCACACGGA  CGGCAACTTT  CATCCTTCGC
   42_4    CCT.ATCTGG  GCCAAGATTC  CTCACACGGA  CGGCAACTTT  CATCCTTCGC
  42_5a    CCT.ATCTGG  GCCAAGATTC  CTCACACGGA  CGGCAACTTT  CATCCTTCGC
  42_10    CCC.ATCTGG  GCCAAAATTC  CTCACACGGA  CGGCAACTTT  CACCCGTCTC
  42_3b    CCC.ATCTGG  GCCAAAATTC  CTCACACGGA  CGGCAACTTT  CACCCGTCTC
  42_11    CCC.ATCTGG  GCCAAAATTC  CTCACACGGA  CGGCAACTTT  CACCCGTCTC
  42_6b    CCC.ATCTGG  GCCAAAATTC  CTCACACGGA  CGGCAACTTT  CACCCGTCTC
   43_1    CCC.ATCTGG  GCCAAAATTC  CTCACACGGA  CGGCAACTTT  CATCCTTCGC
   43_5    CCC.ATCTGG  GCCAAAATTC  CTCACACGGA  CGGCAACTTT  CATCCTTCGC
  43_12    CCC.ATCTGG  GCCAAAATTC  CTCACACGGA  CGGCAACTTT  CATCCTTCGC
  43_20    CCC.ATCTGG  GCCAAAATTC  CTCACACGGA  CGGCAACTTT  CACCCGTCTC
  43_21    CCC.ATCTGG  GCCAAAATTC  CTCACACGGA  CGGCAACTTT  CACCCGTCTC
  43_23    CCC.ATCTGG  GCCAAAATTC  CTCACACGGA  CGGCAACTTT  CACCCGTCTC
  43_25    CCC.ATCTGG  GCCAAAATTC  CTCACACGGA  CGGCAACTTT  CACCCGTCTC
   44_1    CCT.ATCTGG  GCCAAGATTC  CTCACACGGA  CGGAAACTTT  CATCCCTCGC
   44_5    CCT.ATCTGG  GCCAAGATTC  CTCACACGGA  CGGAAACTTT  CATCCCTCGC
  223_10   CCC.ATTTGG  GCCAAGATTC  CTCACACGGA  CGGCAACTTT  CACCCGTCTC
  223_2    CCC.ATTTGG  GCCAAGATTC  CTCACACGGA  CGGCAACTTT  CACCCGTCTC
  223_4    CCC.ATTTGG  GCCAAGATTC  CTCACACGGA  CGGCAACTTT  CACCCGTCTC
  223_5    CCC.ATTTGG  GCCAAGATTC  CTCACACGGA  CGGCAACTTT  CACCCGTCTC
  223_6    CCC.ATTTGG  GCCAAGATTC  CTCACACGGA  CGGCAACTTT  CACCCGTCTC
  223_7    CCC.ATTTGG  GCCAAGATTC  CTCACACGGA  CGGCAACTTT  CACCCGTCTC
   A3_4    CCC.ATTTGG  GCCAAAACTC  CTCACACGGA  CGGACACTTT  CATCCTTCTC
   A3_5    CCC.ATTTGG  GCCAAAACTC  CTCACACGGA  CGGACACTTT  CATCCTTCTC
   A3_7    CCC.ATTTGG  GCCAAAACTC  CTCACACGGA  CGGACACTTT  CATCCTTCTC
   A3_3    CCC.ATTTGG  GCCAAAACTC  CTCACACGGA  CGGACACTTT  CATCCTTCTC
  42_12    CCC.ATCTGG  GCCAAAATTC  CTCACACGGA  CGGCAACTTT  CACCCGTCTC
   AAV1    CCC.ATTTGG  GCCAAAATTC  CTCACACAGA  TGGACACTTT  CACCCGTCTC
   AAV2    CCC.ATCTGG  GCAAAGATTC  CACACACGGA  CGGACATTTT  CACCCCTCTC
   AAV3    CCT.ATCTGG  GCAAAGATTC  CTCACACGGA  TGGACACTTT  CATCCTTCTC
   AAV8    CCC.ATCTGG  GCCAAGATTC  CTCACACGGA  CGGCAACTTC  CACCCGTCTC
   AAV9    CCCTATTTGG  GCTAAATAC   CTCACACAGA  TGGCAACTTT  CACCCGTCTC
   AAV7    CCC.ATCTGG  GCCAAGATTC  CTCACACGGA  TGGCAACTTT  CACCCGTCTC
   44_2    CCT.ATCTGG  GCCAAGATTC  CTCACACGGA  CGGAAACTTT  CATCCCTCGC
```

FIG. 1AAAF

|  | 4151 |  |  |  | 4200 |
|---|---|---|---|---|---|
| 42_2 | CCCTGATGGG | CGGATTTGGA | CTCAAACACC | CGCCTCCTCA | AATTCTCATC |
| 42_8 | CGCTGATGGG | AGGCTTTGGA | CTGAAACACC | CGCCTCCTCA | GATCCTGATT |
| 42_15 | CGCTGATGGG | AGGCTTTGGA | CTGAAACACC | CGCCTCCTCA | GATCCTGATT |
| 42_5b | CGCTGATGGG | AGGCTTTGGA | CTGAAACACC | CGCCTCCTCA | GATCCTGATT |
| 42_1b | CGCTGATGGG | AGGCTTTGGA | CTGAAACACC | CGCCTCCTCA | GATCCTGATT |
| 42_13 | CGCTGATGGG | AGGCTTTGGA | CTGAAACACC | CGCCTCCTCA | GATCCTGATT |
| 42_3a | CGCTGATGGG | AGGCTTTGGA | CTGAAACACC | CGCCTCCTCA | GATCCTGATT |
| 42_4 | CGCTGATGGG | AGGCTTTGGA | CTGAAACACC | CGCCTCCTCA | GATCCTGATT |
| 42_5a | CGCTGATGGG | AGGCTTTGGA | CTGAAACACC | CGCCTCCTCA | GATCCTGATT |
| 42_10 | CCCTGATGGG | CGGATTTGGA | CTCAAACACC | CGCCTCCTCA | AATTCTCATC |
| 42_3b | CCCTGATGGG | CGGATTTGGA | CTCAAACACC | CGCCTCCTCA | AATTCTCATC |
| 42_11 | CCCTGATGGG | CGGATTTGGA | CTCAAACACC | CGCCTCCTCA | AATTCTCATC |
| 42_6b | CCCTGATGGA | CGGATTTGGA | CTCAAACACC | CGCCTCCTCA | AATTCTCATC |
| 43_1 | CGCTGATGGG | AGGCTTTGGA | CTGAAACACC | CGCCTCCTCA | GATCCTGGTG |
| 43_5 | CGCTGATGGG | AGGCTTTGGA | CTGAAACACC | CGCCTCCTCA | GATCCTGGTG |
| 43_12 | CGCTGATGGG | AGGCTTTGGA | CTGAAACACC | CGCCTCCTCA | GATCCTGGTG |
| 43_20 | CCCTGATGGG | CGGCTTTGGA | CTGAAGCACC | CGCCTCCTCA | AATTCTCATC |
| 43_21 | CCCTGATGGG | CGGCTTTGGA | CTGAAGCACC | CGCCTCCTCA | AATTCTCATC |
| 43_23 | CCCTGATGGG | CGGCTTTGGA | CTGAAGCACC | CGCCTCCTCA | AATTCTCATC |
| 43_25 | CCCTGATGGG | CGGCTTTGGA | CTGAAGCACC | CGCCTCCTCA | AATTCTCATC |
| 44_1 | CGCTGATGGG | AGGCTTTGGA | CTGAAACACC | CGCCTCCTCA | GATCCTGATT |
| 44_5 | CGCTGATGGG | AGGCTTTGGA | CTGAAACACC | CGCCTCCTCA | GATCCTGATT |
| 223_10 | CTCTAATGGG | TGGCTTTGGA | CTGAAACACC | CGCCTCCCCA | GATCCTGATC |
| 223_2 | CTCTAATGGG | TGGCTTTGGA | CTGAAACACC | CGCCTCCCCA | GATCCTGATC |
| 223_4 | CTCTAATGGG | TGGCTTTGGA | CTGAAACACC | CGCCTCCCCA | GATCCTGATC |
| 223_5 | CTCTAATGGG | TGGCTTTGGA | CTGAAACACC | CGCCTCCCCA | GATCCTGATC |
| 223_6 | CTCTAATGGG | TGGCTTTGGA | CTGAAACACC | CGCCTCCCCA | GATCCTGATC |
| 223_7 | CTCTAATGGG | TGGCTTTGGA | CTGAAACACC | CGCCTCCCCA | GATCCTGATC |
| A3_4 | CGCTCATGGG | AGGCTTTGGA | CTGAAACACC | CTCCTCCCCA | GATCCTGATC |
| A3_5 | CGCTCATGGG | AGGCTTTGGA | CTGAAACACC | CTCCTCCCCA | GATCCTGATC |
| A3_7 | CGCTCATGGG | AGGCTTTGGA | CTGAAACACC | CTCCTCCCCA | GATCCTGATC |
| A3_3 | CGCTCATGGG | AGGCTTTGGA | CTGAAACACC | CTCCTCCCCA | GATCCTGATC |
| 42_12 | CCCTGATGGG | CGGATTTGGA | CTCAAACACC | CGCCTCCTCA | AATTCTCATC |
| AAV1 | CTCTTATGGG | CGGCTTTGGA | CTCAAGAACC | CGCCTCCTCA | GATCCTCATC |
| AAV2 | CCCTCATGGG | TGGATTCGGA | CTTAAACACC | CTCCTCCACA | GATTCTCATC |
| AAV3 | CTCTGATGGG | AGGCTTTGGA | CTGAAACATC | CGCCTCCTCA | AATCATGATC |
| AAV8 | CGCTGATGGG | CGGCTTTGGC | CTGAAACATC | CTCCGCCTCA | GATCCTGATC |
| AAV9 | CTCTGATGGG | TGGATTTGGA | CTGAAACACC | CACCTCCACA | GATTCTAATT |
| AAV7 | CTTTGATGGG | CGGCTTTGGA | CTTAAACATC | CGCCTCCTCA | GATCCTGATC |
| 44_2 | CGCTGATGGG | AGGCTTTGGA | CTGAAACACC | CGCCTCCTCA | GATCCTGATT |

FIG. 1AAAG

```
           4201                                                              4250
  42_2    AAAAACACCC CGGTACCTGC TAATCCTCCA GAGGTGTTTA CTCCTGCCAA
  42_8    AAGAATACAC CTGTTCCCGC GGATCCTCCA ACTACCTTCA GTCAAGCCAA
  42_15   AAGAATACAC CTGTTCCCGC GGATCCTCCA ACTACCTTCA GTCAAGCCAA
  42_5b   AAGAATACAC CTGTTCCCGC GGATCCTCCA ACTACCTTCA GTCAAGCCAA
  42_1b   AAGAATACAC CTGTTCCCGC GGATCCTCCA ACTACCTTCA GTCAAGCCAA
  42_13   AAGAATACAC CTGTTCCCGC GGATCCTCCA ACTACCTTCA GTCAAGCCAA
  42_3a   AAGAATACAC CTGTTCCCGC GGATCCTCCA ACTACCTTCA GTCAAGCCAA
  42_4    AAGAATACAC CTGTTCCCGC GGATCCTCCA ACTACCTTCA GTCAAGCCAA
  42_5a   AAGAATACAC CTGTTCCCGC GGATCCTCCA ACTACCTTCA GTCAAGCCAA
  42_10   AAAAACACCC CGGTACCTGC TAATCCTCCA GAGGTGTTTA CTCCTGCCAA
  42_3b   AAAAACACCC CGGTACCTGC TAATCCTCCA GAGGTGTTTA CTCCTGCCAA
  42_11   AAAAACACCC CGGTACCTGC TAATCCTCCA GAGGTGTTTA CTCCTGCCAA
  42_6b   AAAAACACCC CGGTACCTGC TAATCCTCCA GAGGTGTTTA CTCCTGCCAA
  43_1    AAAAACACTC CTGTTCCTGC GGATCCTCCG ACCACCTTCA GCCAGGCCAA
  43_5    AAAAACACTC CTGTTCCTGC GGATCCTCCG ACCACCTTCA GCCAGGCCAA
  43_12   AAAAACACTC CTGTTCCTGC GGATCCTCCG ACCACCTTCA GCCAGGCCAA
  43_20   AAGAACACAC CGGTTCCAGC GGACCCGCCG CTTACCTTCA ACCAGGCCAA
  43_21   AAGAACACAC CGGTTCCAGC GGACCCGCCG CTTACCTTCA ACCAGGCCAA
  43_23   AAGAACACAC CGGTTCCAGC GGACCCGCCG CTTACCTTCA ACCAGGCCAA
  43_25   AAGAACACAC CGGTTCCAGC GGACCCGCCG CTTACCTTCA ACCAGGCCAA
  44_1    AAGAATACAC CTGTTCCCGC GGATCCTCCA ACTACCTTCA GTCAAGCTAA
  44_5    AAGAATACAC CTGTTCCCGC GGATCCTCCA ACTACCTTCA GTCAAGCTAA
 223_10   AAAAACACAC CGGTACCTGC TAATCCTCCA GAAGTGTTTA CTCCTGCCAA
 223_2    AAAAACACGC CGGTACCTGC TAATCCTCCA GAAGTGTTTA CTCCTGCCAA
 223_4    AAAAACACAC CGGTACCTGC TAATCCTCCA GAAGTGTTTA CTCCTGCCAA
 223_5    AAAAACACAC CGGTACCTGC TAATCCTCCA GAAGTGTTTA CTCCTGCCAA
 223_6    AAAAACACAC CGGTACCTGC TAATCCTCCA GAAGTGTTTA CTCCTGCCAA
 223_7    AAAAACACAC CGGTACCTGC TAATCCTCCA GAAGTGTTTA CTCCTGCCAA
  A3_4    AAAAACACAC CTGTGCCAGC GAATCCCGCG ACCACTTTCA CTCCTGGAAA
  A3_5    AAAAACACAC CTGTGCCAGC GAATCCCGCG ACCACTTTCA CTCCTGGAAA
  A3_7    AAAAACACAC CTGTGCCAGC GAATCCCGCG ACCACTTTCA CTCCTGGAAA
  A3_3    AAAAACACAC CTGTGCCAGC GAATCCCGCG ACCACTTTCA CTCCTGGAAA
  42_12   A...A..... .......... .......... .......... ..........
  AAV1    AAAAACACGC CTGTTCCTGC GAATCCTCCG GCGGAGTTTT CAGCTACAAA
  AAV2    AAGAACACCC CGGTACCTGC GAATCCTTCG ACCACCTTCA GTGCGGCAAA
  AAV3    AAAAATACTC CGGTACCGGC AAATCCTCCG ACGACTTTCA GCCCGGCCAA
  AAV8    AAGAACACGC CTGTACCTGC GGATCCTCCG ACCACCTTCA ACCAGTCAAA
  AAV9    AAAAATACAC CAGTGCCGGC AGATCCTCCT CTTACCTTCA ATCAAGCCAA
  AAV7    AAGAACACTC CCGTTCCCGC TAATCCTCCG GAGGTGTTTA CTCCTGCCAA
  44_2    AAGAATACAC CTGTTCCCGC GGATCCTCCA ACTACCTTCA GTCAAGCTAA
```

FIG. 1AAAH

```
         4251                                                              4300
 42_2    GTTTGCCTCA TTTATCACGC AGTACAGCAC CGGCCA.GGT CAGCGTGGAG
 42_8    GCTGGCGTCG TTCATCACGC AGTACAGCAC CGGACA.GGT CAGCGTGGAA
 42_15   GCTGGCGTCG TTCATCACGC AGTACAGCAC CGGACA.GGT CAGCGTGGAA
 42_5b   GCTGGCGTCG TTCATCACGC AGTACAGCAC CGGACA.GGT CAGCGTGGAA
 42_1b   GCTGGCGTCG TTCATCACGC AGTACAGCAC CGGACA.GGT CAGCGTGGAA
 42_13   GCTGGCGTCG TTCATCACGC AGTACAGCAC CGGACA.GGT CAGCGTGGAA
 42_3a   GCTGGCGTCG TTCATCACGC AGTACAGCAC CGGACA.GGT CAGCGTGGAA
 42_4    GCCGGCGTCG TTCATCACGC AGTACAGCAC CGGACA.GGT CAGCGTGGAA
 42_5a   GCTGGCGTCG TTCATCACGC AGTACAGCAC CGGACA.GGT CAGCGTGGAA
 42_10   GTTTGCCTCA TTTATCACGC AGTACAGCAC CGGCCA.GGT CAGCGTGGAG
 42_3b   GTTTGCCTCA TTTATCACGC AGTACAGCAC CGGCCA.GGT CAGCGTGGAG
 42_11   GTTTGCCTCA TTTATCACGC AGTACAGCAC CGGCCA.GGT CAGCGTGGAG
 42_6b   GTTTGCCTCA TTTATCACGC AGTACAGCAC CGGCCA.GGT CAGCGTGGAG
 43_1    GCTGGCTTCT TTTATCACGC AGTACAGCAC CGGACA.GGT CAGCGTGGAA
 43_5    GCTGGCTTCT TTTATCACGC AGTACAGCAC CGGACA.GGT CAGCGTGGAA
 43_12   GCTGGCTTCT TTTATCACGC AGTACAGCAC CGGACA.GGT CAGCGTGGAA
 43_20   GCTGAACTCT TTCATCACGC AGTACAGCAC CGGACA.GGT CAGCGTGGAA
 43_21   GCTGAACTCT TTCATCACGC AGTACAGCAC CGGACA.GGT CAGCGTGGAA
 43_23   GCTGAACTCT TTCATCACGC AGTACAGCAC CGGACA.GGT CAGCGTGGAA
 43_25   GCTGAACTCT TTCATCACGC AGTACAGCAC CGGACA.GGT CAGCGTGGAA
 44_1    GCTGGCGTCG TTCATCACGC AGTACAGCAC CGGACA.GGT CAGCGTGGAA
 44_5    GCTGGCGTCG TTCATCACGC AGTACAGCAC CGGACA.GGT CAGCGTGGAA
 223_10  GTTTGCTTCC TTCATCACGC AGTACAGCAC CGGGCA.AGT CAGCGTTGAG
 223_2   GTTTGCTTCC TTCATCACGC AGTACAGCAC CGGGCA.AGT CAGCGTTGAG
 223_4   GTTTGCTTCC TTCATCACGC AGTACAGCAC CGGGCA.AGT CAGCGTTGAG
 223_5   GTTTGCTTCC TTCATCACGC AGTACAGCAC CGGGCA.AGT CAGCGTTGAG
 223_6   GCTTGCTTCC TTCATCACGC AGTACAGCAC CGGGCA.AGT CAGCGTTGAG
 223_7   GATTGCTTCC TTCATCACGC AGTACAGCAC CGGGCA.AGT CAGCGTTGAG
 A3_4    GTTTGCTTCG TTCATTACCC AGTATTCCAC CGGACA.GGT CAGCGTGGAA
 A3_5    GTTTGCTTCG TTCATTACCC AGTATTCCAC CGGACA.GGT CAGCGTGGAA
 A3_7    GTTTGCTTCG TTCATTACCC AGTATTCCAC CGGACA.GGT CAGCGTGGAA
 A3_3    GTTTGCTTCG TTCATTACCC AGTATTCCAC CGGACA.GGT CAGCGTGGAA
 42_12   .......... .......... .......... .......... ..........
 AAV1    GTTTGCTTCA TTCATCACCC AATACTCCAC AGGACA.AGT GAGTGTGGAA
 AAV2    GTTTGCTTCC TTCATCACAC AGTACTCCAC GGGACACGGT CAGCGTGGAG
 AAV3    GTTTGCTTCA TTTATCACTC AGTACTCCAC TGGACA.GGT CAGCGTGGAA
 AAV8    GCTGAACTCT TTCATCACGC AATACAGCAC CGGACA.GGT CAGCGTGGAA
 AAV9    GCTGAACTCT TTCATCACGC AGTACAGCAC GGGACA.AGT CAGCGTGGAA
 AAV7    GTTTGCTTCG TTCATCACAC AGTACAGCAC CGGACA.AGT CAGCGTGGAA
 44_2    GCTGGCGTCG TTCATCACGC AGTACAGCAC CGGACA.GGT CAGCGTGGAA
```

FIG. 1AAAI

```
        4301                                                                    4350
  42_2   ATCGAGTGGG AACTGCAGAA AGAAAACAGC AAACGCTGGA ATCCAGAGAT
  42_8   ATTGAATGGG AGCTGCAGAA AGAGAACAGC AAGCGCTGGA ACCCAGAGAT
 42_15   ATTGAATGGG AGCTGCAGAA AGAGAACAGC AAGCGCTGGA ACCCAGAGAT
 42_5b   ATTGAATGGG AGCTGCAGAA AGAGAACAGC AAGCGCTGGA ACCCAGAGAT
 42_1b   ATTGAATGGG AGCTGCAGAA AGAGAACAGC AAGCGCTGGA ACCCAGAGAT
 42_13   ATTGAATGGG AGCTGCAGAA AGAGAACAGC AAGCGCTGGA ACCCAGAGAT
 42_3a   ATTGAATGGG AGCTGCAGAA AGAGAACAGC AAGCGCTGGA ACCCAGAGAT
  42_4   ATTGAATGGG AGCTGCAGAA AGAGAACAGC AAGCGCTGGA ACCCAGAGAT
 42_5a   ATTGAATGGG AGCTGCAGAA AGAGAACAGC AAGCGCTGGA ACCCAGAGAT
 42_10   ATCGAGTGGG AACTGCAGAA AGAAAACAGC AAACGCTGGA ATCCAGAGAT
 42_3b   ATCGAGTGGG AACTGCAGAA AGAAAACAGC AAACGCTGGA ATCCAGAGAT
 42_11   ATCGAGTGGG AACTGCAGAA AGAGAACAGC AAACGCTGGA ATCCAGAGAT
 42_6b   ATCGAGTGGG AACTGCAGAA AGAAAACAGC AAACGCTGGA ATCCAGAGAT
  43_1   ATCGAATGGG AGCTGCAGAA AGAAAACAGC AAGCGCTGGA ACCCAGAGAT
  43_5   ATCGAATGGG AGCTGCAGAA AGAAAACAGC AAGCGCTGGA ACCCAGAGAT
 43_12   ATCGAATGGG AGCTGCAGAA AGAAAACAGC AAGCGCTGGA ACCCAGAGAT
 43_20   ATCGAGTGGG AGCTGCAGAA AGAAAACAGC AAACGCTGGA ATCCAGAGAT
 43_21   ATCGAGTGGG AGCTGCAGAA AGAAAACAGC AAACGCTGGA ATCCAGAGAT
 43_23   ATCGAGTGGG AGCTGCAGAA AGAAAACAGC AAACGCTGGA ATCCAGAGAT
 43_25   ATCGAGTGGG AGCTGCAGAA AGAAAACAGC AAACGCTGGA ATCCAGAGAT
  44_1   ATTGAATGGG AGCTGCAGAA AGAAAACAGC AAACGCTGGA ACCCAGAGAT
  44_5   ATTGAATGGG AGCTGCAGAA AGAAAACAGC AAACGCTGGA ACCCAGAGAT
 223_10  ATCGAGTGGG AGCTGCAGAA AGAGAACAGC AAGCGCTGGA ACCCAGAGAT
 223_2   ATCGAGTGGG AGCTGCAGAA AGAGAACAGC AAGCGCTGGA ACCCAGAGAT
 223_4   ATCGAATGGG AGCTGCAGAA AGAGAACAGC AAGCGCTGGA ACCCAGAGAT
 223_5   ATCGAATGGG AGCTGCAGAA AGAGAACAGC AAGCGCTGGA ACCCAGAGAT
 223_6   ATCGAGTGGG AGCTGCAGAA AGAGAACAGC AAGCGCTGGA ACCCAGAGAT
 223_7   ATCGAGTGGG AGCTGCAGAA AGAGAACAGC AAGCGCTGGA ACCCAGAGAT
  A3_4   ATAGAGTGGG AGCTGCAGAA AGAAAACAGC AAACGCTGGA ACCCAGAAAT
  A3_5   ATAGAGTGGG AGCTGCAGAA AGAAAACAGC AAACGCTGGA ACCCGGAAAT
  A3_7   ATAGAGTGGG AGCTGCAGAA AGAAAACAGC AAACGCTGGA ACCCAGAAAT
  A3_3   ATAGAGTGGG AGCTGCAGAA AGAAAACAGC AAACGCTGGA ACCCAGAAAT
 42_12   .......... .......... .......... .......... ..........
  AAV1   ATTGAATGGG AGCTGCAGAA AGAAAACAGC AAGCGCTGGA ATCCCGAAGT
  AAV2   ATCGAGTGGG AGCTGCAGAA GGAAAACAGC AAACGCTGGA ATCCCGAAAT
  AAV3   ATTGAGTGGG AGCTACAGAA AGAAAACAGC AAACGTTGGA ATCCAGAGAT
  AAV8   ATTGAATGGG AGCTGCAGAA GGAAAACAGC AAGCGCTGGA ACCCCGAGAT
  AAV9   ATCGAGTGGG AGCTGCAGAA AGAAAACAGC AAGCGCTGGA ATCCAGAGAT
  AAV7   ATCGAGTGGG AGCTGCAGAA GGAAAACAGC AAGCGCTGGA ACCCGGAGAT
  44_2   ATTGAATGGG AGCTGCAGAA AGAAAACAGC AAACGCTGGA ACCCAGAGAT
```

FIG. 1AAAJ

```
           4351                                                           4400
  42_2     TCAGTACACC TCAAATTATG CCAAGTCTAA TAAT.GTGGA ATTTGCTGTC
  42_8     TCAGTATACT TCCAACTACT ACAAATCTAC AAAT.GTGGA CTTTGCTGTC
  42_15    TCAGTATACT TCCAACTACT ACAAATCTAC AAAT.GTGGA CTTTGCTGTC
  42_5b    TCAGTATACT TCCAACTACT ACAAATCTAC AAAT.GTGGA CTTTGCTGTC
  42_1b    TCAGTATACT TCCAACTACT ACAAATCTAC AAAT.GTGGA CTTTGCTGTC
  42_13    TCAGTATACT TCCAACTACT ACAAATCTAC AAAT.GTGGA CTTTGCTGTC
  42_3a    TCAGTATACT TCCAACTACT ACAAATCTAC AAAT.GTGGA CTTTGCTGTC
  42_4     TCAGTATACT TCCAACTACT ACAAATCTAC AAAT.GTGGA CTTTGCTGTC
  42_5a    TCAGTATACT TCCAACTACT ACAAATCTAC AAAT.GTGGA CTTTGCTGTC
  42_10    TCAGTACACC TCAAATTATG CCAAGTCTAA TAAT.GTGGA ATTTGCTGTC
  42_3b    TCAGTACACC TCAAATTATG CCAAGTCTAA TAAT.GTGGA ATTTGCTGTC
  42_11    TCAGTACACC TCAAATTATG CCAAGTCTAA TAAT.GTGGA ATTTGCTGTC
  42_6b    TCAGTACACC TCAAATTATG CCAAGTCTAA TAAT.GTGGA ATTTGCTGTC
  43_1     TCAGTATACT TCCAACTACT ACAAATCTAC AAAT.GTGGA CTTTGCTGTC
  43_5     TCAGTATACT TCCAACTACT ACAAATCTAC AAAT.GTGGA CTTTGCTGTC
  43_12    TCAGTATACT TCCAACTACT ACAAATCTAC AAAT.GTGGA CTTTGCTGTC
  43_20    TCAATACACT TCCAACTACT ACAAATCTAC AAAT.GTGGA CTTTGCTGTC
  43_21    TCAATACACT TCCAACTACT ACAAATCTAC AAAT.GTGGA CTTTGCTGTC
  43_23    TCAATACACT TCCAACTACT ACAAATCTAC AAAT.GTGGA CTTTGCTGTC
  43_25    TCAATACACT TCCAACTACT ACAAATCTAC AAAT.GTGGA CTTTGCTGTC
  44_1     TCAATACACT TCCAACTACT ACAAATCTAC AAAT.GTGGA CTTCGCTGTT
  44_5     TCAATACACT TCCAACTACT ACAAATCTAC AAAT.GTGGA CTTTGCTGTT
 223_10    TCAGTACACC TCCAACTTTG ACAAACAGAC TGGA.GTGGA CTTTGCTGTT
 223_2     TCAGTACACC TCCAACTTTG ACAAACAGAC TGGA.GTGGA CTTTGCTGTT
 223_4     TCAGTACACC TCCAACTTTG ACAAACAGAC TGGA.GTGGA CTTTGCTGTT
 223_5     TCAGTACACC TCCAACTTTG ACAAACAGAC TGGA.GTGGA CTTTGCTGTT
 223_6     TCAGTACACC TCCAACTTTG ACAAACAGAC TGGA.GTGGA CTTTGCTGTT
 223_7     TCAGTACACC TCCAACTTTG ACAAACAGAC TGGA.GTGGA CTTTGCTGTT
  A3_4     TCAGTACACC TCCAACTACA ACAAGTCGGT GAAT.GTGGA GTTACCGTG
  A3_5     TCAGTACACC TCCAACTACA ACAAGTCGGT GAAT.GTGGA GTTACCGTG
  A3_7     TCAGTACACC TCCAACTACA ACAAGTCGGT GAAT.GTGGA GTTACCGTG
  A3_3     TCAGTACACC TCCAACTACA ACAAGTCGGT GAAT.GTGGA GTTACCGTG
  42_12    ...GTATACT TCCAACTACT ACAAATCTAC AAAT.GTGGA CTTTGCTGTC
  AAV1     GCAGTACACA TCCAATTATG CAAAATCTGC CAAC.GTTGA TTTACTGTG
  AAV2     TCAGTACACT TCCAACTACA ACAAGTCTGT TAATCGTGGA CTT.ACCGTG
  AAV3     TCAGTACACT TCCAACTACA ACAAGTCTGT TAAT.GTGGA CTTACTGTA
  AAV8     CCAGTACACC TCCAACTACT ACAAATCTAC AAGT.GTGGA CTTTGCTGTT
  AAV9     CCAGTATACT TCAAACTACT ACAAATCTAC AAAT.GTGGA CTTTGCTGTC
  AAV7     TCAGTACACC TCCAACTTTG AAAAGCAGAC TGGT.GTGGA CTTTGCCGTT
  44_2     TCAATACACT TCCAACTACT ACAAATCTAC AAAT.GTGGA CTTTGCTGTT
```

FIG. 1AAAK

```
        4401                                                              4450
 42_2    AACAACGAAG  GGGTTTATAC  TGAGCCTCGC  CCCATTGGCA  CCCGTTACCT
 42_8    AATACTGAGG  GTACTTATTC  AGAGCCTCGC  CCCATTGGCA  CCCGTTACCT
 42_15   AATACTGAGG  GTACTTATTC  AGAGCCTCGC  CCCATTGGCA  CCCGTTACCT
 42_5b   AATACTGAGG  GTACTTATTC  AGAGCCTCGC  CCCATTGGCA  CCCGTTACCT
 42_1b   AATACTGAGG  GTACTTATTC  AGAGCCTCGC  CCCATTGGCA  CCCGTTACCT
 42_13   AATACTGAGG  GTACTTATTC  AGAGCCTCGC  CCCATTGGCA  CCCGTTACCT
 42_3a   AATACTGAGG  GTACTTATTC  AGAGCCTCGC  CCCATTGGCA  CCCGTTACCT
 42_4    AATACTGAGG  GTACTTATTC  AGAGCCTCGC  CCCATTGGCA  CCCGTTACCT
 42_5a   AATACTGAGG  GTACTTATTC  AGAGCCTCGC  CCCATTGGCA  CCCGTTACCT
 42_10   AACAACGAAG  GGGTTTATAC  TGAGCCTCGC  CCCATTGGCA  CCCGTTACCT
 42_3b   AACAACGAAG  GGGTTTATAC  TGAGCCTCGC  CCCATTGGCA  CCCGTTACCT
 42_11   AACAACGAAG  GGGTTTATAC  TGAGCCTCGC  CCCATTGGCA  CCCGTTACCT
 42_6b   AACAACGAAG  GGGTTTATAC  TGAGCCTCGC  CCCATTGGCA  CCCGTTACCT
 43_1    AATACTGAGG  GTACTTATTC  AGAGCCTCGC  CCCATTGGCA  CTCGTTATCT
 43_5    AATACCGAGG  GTACTTATTC  AGAGCCTCGC  CCCATTGGCA  CTCGTTATCT
 43_12   AATACTGAGG  GTACTTATTC  AGAGCCTCGC  CCCATTGGCA  CTCGTTATCT
 43_20   AACACGGAAG  GAGTTTATAG  CGAGCCTCGC  CCCATTGGCA  CCCGTTACCT
 43_21   AACACGGAAG  GAGTTTATAG  CGAGCCTCGC  CCCATTGGCA  CCCGTTACCT
 43_23   AACACGGAAG  GAGTTTATAG  CGAGCCTCGC  CCCATTGGCA  CCCGTTACCT
 43_25   AACACGGAGG  GGGTTTATAG  CGAGCCTCGC  CCCATTGGCA  CCCGTTACCT
 44_1    AACACAGATG  GCACTTATTC  TGAGCCTCGC  CCCATTGGCA  CCCGTTACCT
 44_5    AACACAGATG  GCACTTATTC  TGAGCCTCGC  CCCATTGGCA  CCCGTTACCT
 223_10  GACAGCCAGG  GTGTTTACTC  TGAGCCT...  ..........  ..........
 223_2   GACAGCCAGG  GTGTTTACTC  TGAGCCT...  ..........  ..........
 223_4   GACAGCCAGG  GTGTTTACTC  TGAGCCT...  ..........  ..........
 223_5   GACAGCCAGG  GTGTTTACTC  TGAGCCT...  ..........  ..........
 223_6   GACAGCCAGG  GTGTTTACTC  TGAGCCT...  ..........  ..........
 223_7   GACAGCCAGG  GTGTTTACTC  TGAGCCT...  ..........  ..........
 A3_4    GACGCAAACG  GTGTTTATTC  TGAACCCCGC  CCTATTGGCA  CTCGTTACCT
 A3_5    GACGCAAACG  GTGTTTATTC  TGAACCCCGC  CCTATTGGCA  CTCGTTACCT
 A3_7    GACGCAAACG  GTGTTTATTC  TGAACCCCGC  CCTATTGGCA  CTCGTTACCT
 A3_3    GACGCAAACG  GTGTTTATTC  TGAACCCCGC  CCTATTGGCA  CTCGTTACCT
 42_12   AATACTGAGG  GTACTTATTC  AGAGCCTCGC  CCCATTGGCA  CCCGTTACCT
 AAV1    GACAACAATG  GACTTATAC   TGAGCCTCGC  CCCATTGGCA  CCCGTTACCT
 AAV2    GATACTAATG  GCGTGTATTC  AGAGCCTCGC  CCCATTGGCA  CCAGATACCT
 AAV3    GACACTAATG  GTGTTTATAG  TGAACCTCGC  CCTATTGGAA  CCCGGTATCT
 AAV8    AATACAGAAG  GCGTGTACTC  TGAACCCCGC  CCCATTGGCA  CCCGTTACCT
 AAV9    AATACCGAAG  GTGTTTACTC  TGAGCCTCGC  CCCATTGGTA  CTCGTTACCT
 AAV7    GACAGCCAGG  GTGTTTACTC  TGAGCCTCGC  CCTATTGGCA  CTCGTTACCT
 44_2    AACACAGATG  GCACTTATTC  TGAGCCTCGC  CCCATCGGCA  CCCGTTACCT
```

FIG. 1AAAL

```
            4451                                                              4500
                    VP1-3 stop        Poly A signal
   42_2     CACCCGTAAC CTGTAATTGC CTGTTAATCA ATAAACCGGT TAATTCGTTT
   42_8     CACCCGTAAC CTGTAATTGC CTGTTAATCA ATAAACCGGC TAATTCGTTT
   42_15    CACCCGTAAC CTGTAATTGC CTGTTAATCA ATAAACCGGT TAATTCGTTT
   42_5b    CACCCGTAAC CTGTAATTGC CTGTTAATCA ATAAACCGGT TAATTCGTTT
   42_1b    CACCCGTAAC CTGTAATTGC CTGTTAATCA ATAAACCGGT TGATTCGTTT
   42_13    CACCCGTAGC CTGTAATTGC CTGTTAATCA ATAAACCGGT TGATTCGTTT
   42_3a    CACCCGTAAC CTGTAATTGC CTGTTAATCA ATAAACCGGT TAATTCGTTT
   42_4     CACCCGTAAC CTGTAATTGC CTGTTAATCA ATAAACCGGT TAATTCGTTT
   42_5a    CACCCGTAAC CTGTAATTGC CTGTTAATCA ATAAACCGGT TAATTCGTTT
   42_10    CACCCGTAAC CTGTAATTGC CTGTTAATCA ATAAACCGGT TAATTCGTTT
   42_3b    CACCCGTAAC CTGTAATTGC CTGTTAATCA ATAAACCGGT TAATTCGTTT
   42_11    CACCCGTAAC CTGTAATTAC TTGTTAATCA ATAAACCGGT TGATTCGTTT
   42_6b    CACCCGTAAC CTGTAATTGC CTGTTAATCA ATAAACCGGT TAATTCGTTT
   43_1     CACCCGTAAT CTGTAATTGC TTGTTAATCA ATAAACCGGT ..........
   43_5     CACCCGTAAT CTGTAATTGC TTGTTAATCA ATAAACCGGT TAATTCGTTT
   43_12    CACCCGTAAT CTGTAATTGC TTGTTAATCA ATAAACCGGT TAATTCGTTT
   43_20    CACCCGCAAC CTGTAATTAC ATGTTAATCA ATAAACCGGT TAATTCGTTT
   43_21    CACCCGCAAC CTGTAATTAC ATGTTAATCA ATAAACCGGT TAATTCGTTT
   43_23    CACCCGCAAC CTGTAATTAC ATGTTAATCA ATAAACCGGT TAATTCGTTT
   43_25    CACCCGCAAC CTGTAATTAC ATGTTAATCA ATAAACCGGT TAATTCGTTT
   44_1     CACCCGTAAT CTGTAATTGC TCGTTAATCA ATAAACCGGT TGATTCGTTT
   44_5     CACCCGTAAT CTGTAATTGC TTGTTAATCA ATAAACCGGT TGATTCGTTT
   223_10   .......... .......... .......... .......... ..........
   223_2    .......... .......... .......... .......... ..........
   223_4    .......... .......... .......... .......... ..........
   223_5    .......... .......... .......... .......... ..........
   223_6    .......... .......... .......... .......... ..........
   223_7    .......... .......... .......... .......... ..........
   A3_4     TACCCGGAAC TTGTAATTTC CTGTTAATGA ATAAACCGAT TTATGCGTTT
   A3_5     TACCCGGAAC TTGTAATTTC CTGTTAATGA ATAAACCGAT TTATGCGTTT
   A3_7     TACCCGGAAC TTGTAATTTC CTGTTAATGA ATAAACCGAT TTATGCGTTT
   A3_3     TACCCGGAAC TTGTAATTTC CTGTTAATGA ATAAGCCGAT TTATGCGTTT
   42_12    CACCCGTAAC CTGTAATTGC CTGTTAATCA ATAAACCGGT TAATTCGTTT
   AAV1     TACCCGTCCC CTGTAATTAC GTGTTAATCA ATAAACCGGT TGATTCGTTT
   AAV2     GACTCGTAAT CTGTAATTGC TTGTTAATCA ATAAACCGTT TAATTCGTTT
   AAV3     CACACGAAAC TTGTGAATCC TGGTTAATCA ATAAACCGTT TAATTCGTTT
   AAV8     CACCCGTAAT CTGTAATTGC CTGTTAATCA ATAAACCGGT TGATTCGTTT
   AAV9     CACCCGTAAT TTGTAATTGC CTGTTAATCA ATAAACCGGT TAATTCGTTT
   AAV7     CACCCGTAAT CTGTAATTGC ATGTTAATCA ATAAACCGGT TGATTCGTTT
   44_2     CACCCGTAAT CTGTAATTGC TTGTTAATCA ATAAACCGGT TGATTCGTTT
                    vp1-3 stop        PolyA signal
```

FIG. 1AAAM

```
                4501                                                        4550
       42_2     CAGTTGAACT TTGGTCTC.T GCGAAGGGCG AATTC..... ..........
       42_8     CAGTTGAACT TTGGTCTC.T GCGAAGGGCG AATTC..... ..........
       42_15    CAGTTGAACT TTGGTCTC.T GCGAAGGGCG AATTC..... ..........
       42_5b    CAGTTGAACT TTGGTCTC.T GCGAAGGGCG AATTCGTTTA AACCTGCAGG
       42_1b    CAGTTGAACT TTGGTCTC.. ...AAGGGCG AATTC..... ..........
       42_13    CAGTTGAACT TTGGTCTC.T GCGAAGGGCG AATTC..... ..........
       42_3a    CAGTTGAACT TTGGTCTC.T GCGAAGGGCG AATTC..... ..........
       42_4     CAGTTGAACT TTGGTCTC.T GCGAAGGGCG AATTC..... ..........
       42_5a    CAGTTGAACT TTGGTCTC.T GCGAAGGGCG AATTC..... ..........
       42_10    CAGTTGAACT TTGGTC.... ...AAGGGCG AATTC..... ..........
       42_3b    CAGTTGAACT TTGGTCTC.T GCGAAGGGCG AATTC..... ..........
       42_11    CAGTTGAACT TTGGTCTC.T GCGAAGGGCG AATTC..... ..........
       42_6b    CAGTTGAACT TTGGTCTC.T GCGAAGGGCG AATTC..... ..........
       43_1     .......... .......... .......... .......... ..........
       43_5     CAGTTGAACT TTGGTCTC.T GCGAAGGGCG AATTCGTTTA AACCTGCAGG
       43_12    CAGTTGAACT TTGGTCTC.T GCGAAGGGCG AATTC..... ..........
       43_20    CAGTTGAACT TTGGTCTC.T GCGAAGGGCG AATTC..... ..........
       43_21    CAGTTGAACT TTGGTCTC.T GCGAAGGGCG AATTC..... ..........
       43_23    CAGTTGAACT TTGGTCTC.T GCGAAGGGCG AATTC..... ..........
       43_25    CAGTTGAACT TTGGTCTC.T GCGAAGGGCG AATTC..... ..........
       44_1     CAGTTGAACT TTGGTCTC.T GCGAAGGGCG AATTC..... ..........
       44_5     CAGTTGAACT TTGGTCTC.T GCGAAGGGCG AATTC..... ..........
       223_10   .......... .......... .......... .......... ..........
       223_2    .......... .......... .......... .......... ..........
       223_4    .......... .......... .......... .......... ..........
       223_5    .......... .......... .......... .......... ..........
       223_6    .......... .......... .......... .......... ..........
       223_7    .......... .......... .......... .......... ..........
       A3_4     CAGTTGAACT TTGGTCTC.T GCGAAGGGCG AATTCGC.GG CCGCTA....
       A3_5     CAGTTGAACT TTGGTCTC.T GCGAAGGGCG AATTC..... ..........
       A3_7     CAGTTGAACT TTGGTCTC.T GCGAAGGGCG AATTC..... ..........
       A3_3     CAGTTGAACT TTGGTCTC.T GCGAAGGGCG AATTCGT.TT AAACCT....
       42_12    CAGTTGAACT TTGGTCTC.T GCGAAGGGCG AATTC..... ..........
       AAV1     CAGTTGAACT TTGGTCTCCT GTCCTTCTTA TCTTATCGGT TACCATGGTT
       AAV2     CAGTTGAACT TTGGTCTC.T GCGTATTTCT ..TCTT.AT  CTAGTTTCCA
       AAV3     CAGTTGAACT TTGGCTCT.T GTGCACTTCT TTATCTTTAT CTTGTTTCCA
       AAV8     CAGTTGAACT TTGGTCTC.T GCG....... .......... ..........
       AAV9     CAGTTGAACT TTGGTCTC.T GCG....... .......... ..........
       AAV7     CAGTTGAACT TTGGTCTCCT GTGCTTCTTA TCTTATCGGT TTCCATAGCA
       44_2     CAGTTGAACT TTGGTCTC.T GCGAAGGGCG AATTC..... ..........
```

FIG. 1AAAN

```
           4551                                                          4600
   42_2    ..........  ..........  ..........  ..........  ..........
   42_8    ..........  ..........  ..........  ..........  ..........
   42_15   ..........  ..........  ..........  ..........  ..........
   42_5b   ACTAGTCCCT  TTAGTGAGGG  TTAATTCTGA  G.........  ..........
   42_1b   ..........  ..........  ..........  ..........  ..........
   42_13   ..........  ..........  ..........  ..........  ..........
   42_3a   ..........  ..........  ..........  ..........  ..........
   42_4    ..........  ..........  ..........  ..........  ..........
   42_5a   ..........  ..........  ..........  ..........  ..........
   42_10   ..........  ..........  ..........  ..........  ..........
   42_3b   ..........  ..........  ..........  ..........  ..........
   42_11   ..........  ..........  ..........  ..........  ..........
   42_6b   ..........  ..........  ..........  ..........  ..........
   43_1    ..........  ..........  ..........  ..........  ..........
   43_5    AC........  ..........  ..........  ..........  ..........
   43_12   ..........  ..........  ..........  ..........  ..........
   43_20   ..........  ..........  ..........  ..........  ..........
   43_21   ..........  ..........  ..........  ..........  ..........
   43_23   ..........  ..........  ..........  ..........  ..........
   43_25   ..........  ..........  ..........  ..........  ..........
   44_1    ..........  ..........  ..........  ..........  ..........
   44_5    ..........  ..........  ..........  ..........  ..........
   223_10  ..........  ..........  ..........  ..........  ..........
   223_2   ..........  ..........  ..........  ..........  ..........
   223_4   ..........  ..........  ..........  ..........  ..........
   223_5   ..........  ..........  ..........  ..........  ..........
   223_6   ..........  ..........  ..........  ..........  ..........
   223_7   ..........  ..........  ..........  ..........  ..........
   A3_4    ..........  ..........  ..........  ..........  ..........
   A3_5    ..........  ..........  ..........  ..........  ..........
   A3_7    ..........  ..........  ..........  ..........  ..........
   A3_3    ..........  ..........  ..........  ..........  ..........
   42_12   ..........  ..........  ..........  ..........  ..........
   AAV1    ATAGCTTACA  CATTAACTGC  TTGGTTGCGC  T.........  ..........
   AAV2    TGGCTAC...  GTAGATAAGT  AGC.......  ..........  ..........
   AAV3    TGGCTACTGC  GTAGATAAGC  AGCGGCCTGC  GGCGCTTGCG  CTTCGCGGTT
   AAV8    ..........  ..........  ..........  ..........  ..........
   AAV9    ..........  ..........  ..........  ..........  ..........
   AAV7    ACTGGTTACA  CATTAACTGC  TTGGGTGCGC  TTCACGATAA  GAACACTGAC
   44_2    ..........  ..........  ..........  ..........  ..........
```

FIG. 1AAAO

```
       4601                                                        4650
42_2   ..........  ..........  ..........  ..........  ..........
42_8   ..........  ..........  ..........  ..........  ..........
42_15  ..........  ..........  ..........  ..........  ..........
42_5b  ....CTTGGC  GTAATCATGG  GTCATAG...  ..........  ..........
42_1b  ..........  ..........  ..........  ..........  ..........
42_13  ..........  ..........  ..........  ..........  ..........
42_3a  ..........  ..........  ..........  ..........  ..........
42_4   ..........  ..........  ..........  ..........  ..........
42_5a  ..........  ..........  ..........  ..........  ..........
42_10  ..........  ..........  ..........  ..........  ..........
42_3b  ..........  ..........  ..........  ..........  ..........
42_11  ..........  ..........  ..........  ..........  ..........
42_6b  ..........  ..........  ..........  ..........  ..........
43_1   ..........  ..........  ..........  ..........  ..........
43_5   ..........  ..........  ..........  ..........  ..........
43_12  ..........  ..........  ..........  ..........  ..........
43_20  ..........  ..........  ..........  ..........  ..........
43_21  ..........  ..........  ..........  ..........  ..........
43_23  ..........  ..........  ..........  ..........  ..........
43_25  ..........  ..........  ..........  ..........  ..........
44_1   ..........  ..........  ..........  ..........  ..........
44_5   ..........  ..........  ..........  ..........  ..........
223_10 ..........  ..........  ..........  ..........  ..........
223_2  ..........  ..........  ..........  ..........  ..........
223_4  ..........  ..........  ..........  ..........  ..........
223_5  ..........  ..........  ..........  ..........  ..........
223_6  ..........  ..........  ..........  ..........  ..........
223_7  ..........  ..........  ..........  ..........  ..........
A3_4   ..........  ..........  ..........  ..........  ..........
A3_5   ..........  ..........  ..........  ..........  ..........
A3_7   ..........  ..........  ..........  ..........  ..........
A3_3   ..........  ..........  ..........  ..........  ..........
42_12  ..........  ..........  ..........  ..........  ..........
AAV1   ....TCGCGA  TAAAAGACTT  ACGTCATCGG  GTTACCCCTA  GTGATGGAGT
AAV2   ....ATGGCG  GGTTAATCAT  TAACTACAAG  GA.ACCCCTA  GTGATGGAGT
AAV3   TACAACTGCT  GGTTAATATT  TAACTCTCGC  CATACCTCTA  GTGATGGAGT
AAV8   ..........  ..........  ..........  ..........  ..........
AAV9   ..........  ..........  ..........  ..........  ..........
AAV7   ..........  ..........  ..GTCACCGC  GGTACCCCTA  GTGATGGAGT
44_2   ..........  ..........  ..........  ..........  ..........
```

FIG. 1AAAP

```
       4651                                                    4700
42_2   ..........  ..........  ..........  ..........  ..........
42_8   ..........  ..........  ..........  ..........  ..........
42_15  ..........  ..........  ..........  ..........  ..........
42_5b  ..........  ..........  ..........  ..........  ..........
42_1b  ..........  ..........  ..........  ..........  ..........
42_13  ..........  ..........  ..........  ..........  ..........
42_3a  ..........  ..........  ..........  ..........  ..........
42_4   ..........  ..........  ..........  ..........  ..........
42_5a  ..........  ..........  ..........  ..........  ..........
42_10  ..........  ..........  ..........  ..........  ..........
42_3b  ..........  ..........  ..........  ..........  ..........
42_11  ..........  ..........  ..........  ..........  ..........
42_6b  ..........  ..........  ..........  ..........  ..........
43_1   ..........  ..........  ..........  ..........  ..........
43_5   ..........  ..........  ..........  ..........  ..........
43_12  ..........  ..........  ..........  ..........  ..........
43_20  ..........  ..........  ..........  ..........  ..........
43_21  ..........  ..........  ..........  ..........  ..........
43_23  ..........  ..........  ..........  ..........  ..........
43_25  ..........  ..........  ..........  ..........  ..........
44_1   ..........  ..........  ..........  ..........  ..........
44_5   ..........  ..........  ..........  ..........  ..........
223_10 ..........  ..........  ..........  ..........  ..........
223_2  ..........  ..........  ..........  ..........  ..........
223_4  ..........  ..........  ..........  ..........  ..........
223_5  ..........  ..........  ..........  ..........  ..........
223_6  ..........  ..........  ..........  ..........  ..........
223_7  ..........  ..........  ..........  ..........  ..........
A3_4   ..........  ..........  ..........  ..........  ..........
A3_5   ..........  ..........  ..........  ..........  ..........
A3_7   ..........  ..........  ..........  ..........  ..........
A3_3   ..........  ..........  ..........  ..........  ..........
42_12  ..........  ..........  ..........  ..........  ..........
AAV1   TGCCCACTCC  CTCTCTGCGC  GCTCGCTCGC  TCGGTGGGGC  CTGCGGACCA
AAV2   TGGCCACTCC  CTCTCTGCGC  GCTCGCTCGC  TCACTGAGGC  CGGGCGACCA
AAV3   TGGCCACTCC  CTCTATGCGC  ACTCGCTCGC  TCGGTGGGGC  CTGGCGACCA
AAV8   ..........  ..........  ..........  ..........  ..........
AAV9   ..........  ..........  ..........  ..........  ..........
AAV7   TGGCCACTCC  CTCTATGCGC  GCTCGCTCGC  TCGGTGGGGC  CTGCGGACCA
44_2   ..........  ..........  ..........  ..........  ..........
```

FIG. 1AAAQ

```
         4701                                                         4750
  42_2    ..........  ..........  ..........  ..........  ..........
  42_8    ..........  ..........  ..........  ..........  ..........
 42_15    ..........  ..........  ..........  ..........  ..........
 42_5b    ..........  ..........  ..........  ..........  ..........
 42_1b    ..........  ..........  ..........  ..........  ..........
 42_13    ..........  ..........  ..........  ..........  ..........
 42_3a    ..........  ..........  ..........  ..........  ..........
  42_4    ..........  ..........  ..........  ..........  ..........
 42_5a    ..........  ..........  ..........  ..........  ..........
 42_10    ..........  ..........  ..........  ..........  ..........
 42_3b    ..........  ..........  ..........  ..........  ..........
 42_11    ..........  ..........  ..........  ..........  ..........
 42_6b    ..........  ..........  ..........  ..........  ..........
  43_1    ..........  ..........  ..........  ..........  ..........
  43_5    ..........  ..........  ..........  ..........  ..........
 43_12    ..........  ..........  ..........  ..........  ..........
 43_20    ..........  ..........  ..........  ..........  ..........
 43_21    ..........  ..........  ..........  ..........  ..........
 43_23    ..........  ..........  ..........  ..........  ..........
 43_25    ..........  ..........  ..........  ..........  ..........
  44_1    ..........  ..........  ..........  ..........  ..........
  44_5    ..........  ..........  ..........  ..........  ..........
 223_10   ..........  ..........  ..........  ..........  ..........
 223_2    ..........  ..........  ..........  ..........  ..........
 223_4    ..........  ..........  ..........  ..........  ..........
 223_5    ..........  ..........  ..........  ..........  ..........
 223_6    ..........  ..........  ..........  ..........  ..........
 223_7    ..........  ..........  ..........  ..........  ..........
  A3_4    ..........  ..........  ..........  ..........  ..........
  A3_5    ..........  ..........  ..........  ..........  ..........
  A3_7    ..........  ..........  ..........  ..........  ..........
  A3_3    ..........  ..........  ..........  ..........  ..........
 42_12    ..........  ..........  ..........  ..........  ..........
  AAV1    AAGGTCCGCA  GACGGCAGAG  CTCTGCTCTG  CCGGCCCCAC  CGAGCGAGCG
  AAV2    AAGGTCGCCC  GACGCCCGGG  CTTTGCCCGG  GCGGCCTCAG  TGAGCGAGCG
  AAV3    AAGGTCGCCA  GACGGACGTG  CTTTGCACGT  CCGGCCCCAC  CGAGCGAGCG
  AAV8    ..........  ..........  ..........  ..........  ..........
  AAV9    ..........  ..........  ..........  ..........  ..........
  AAV7    AAGGTCCGCA  GACGGCAGAG  CTCTGCTCTG  CCGGCCCCAC  CGAGCGAGCG
  44_2    ..........  ..........  ..........  ..........  ..........
```

FIG. 1AAAR

```
              4751                            4774
     42_2     ..........    ..........    ....
     42_8     ..........    ..........    ....
    42_15     ..........    ..........    ....
    42_5b     ..........    ..........    ....
    42_1b     ..........    ..........    ....
    42_13     ..........    ..........    ....
    42_3a     ..........    ..........    ....
     42_4     ..........    ..........    ....
    42_5a     ..........    ..........    ....
    42_10     ..........    ..........    ....
    42_3b     ..........    ..........    ....
    42_11     ..........    ..........    ....
    42_6b     ..........    ..........    ....
     43_1     ..........    ..........    ....
     43_5     ..........    ..........    ....
    43_12     ..........    ..........    ....
    43_20     ..........    ..........    ....
    43_21     ..........    ..........    ....
    43_23     ..........    ..........    ....
    43_25     ..........    ..........    ....
     44_1     ..........    ..........    ....
     44_5     ..........    ..........    ....
   223_10     ..........    ..........    ....
    223_2     ..........    ..........    ....
    223_4     ..........    ..........    ....
    223_5     ..........    ..........    ....
    223_6     ..........    ..........    ....
    223_7     ..........    ..........    ....
     A3_4     ..........    ..........    ....
     A3_5     ..........    ..........    ....
     A3_7     ..........    ..........    ....
     A3_3     ..........    ..........    ....
    42_12     ..........    ..........    ....
     AAV1     AGCGCGCAGA    GAGGGAGTGG    GCAA
     AAV2     AGCGCGCAGA    GAGGGAGTGG    CCAA
     AAV3     AGTGCGCATA    GAGGGAGTGG    CCAA
     AAV8     ..........    ..........    ....
     AAV9     ..........    ..........    ....
     AAV7     AGCGCGCATA    GAGGGAGTGG    CCAA
     44_2     ..........    ..........    ....
```

```
                     10         20         30         40         50         60
                     ....|....|....|....|....|....|....|....|....|....|....|....|
C1\VP1         MAADGYLPDWLEDNLSEGIREWWDLKPGAPKPKANQQKQDDGRGLVLPGYKYLGPFNGLD
C2\VP1         MAADGYLPDWLEDNLSEGIREWWDLKPGAPKLKANQQKQDDGRGLVLPGYKYLGPFHGLD
C5\VP1@2       MAADGYLPDWLEDNLSEGIREWWDLKPGAPKPKANQQKQDDGRGLVLPGYEYLGPFNGLD
AAV4\VP1       -MTDGYLPDWLEDNLSEGVREWWALQPGAPKPKANQQHQDNARGLVLPGYKYLGPGNGLD
AAV1           MAADGYLPDWLEDNLSEGIREWWDLKPGAPKPKANQQKQDDGRGLVLPGYKYLGPFNGLD
AAV6\VP1       MAADGYLPDWLEDNLSEGIREWWDLKPGAPKPKANQQKQDDGRGLVLPGYKYLGPFNGLD
A3_3           MAADGYLPDWLEDTLSEGIRQWWKLKPGPPPPKPNQQHRDDSRGLVLPGYKYLGPFNGLD
A3_7           MAADGYLPDWLEDTLSEGIRQWWKLKPGPPPPKPNQQHRDDSRGLVLPGYKYLGPFNGLD
A3_4           MAADGYLPDWLEDTLSEGIRQWWKLKPGPPPPKPNQQHRDDSRGLVLPGYKYLGPFNGLD
A3_5           MAADGYLPDWLEDTLSEGIRQWWKLKPGPPPPKPNQQHRDDSRGLVLPGYKYLGPFNGLD
AAV2           MAADGYLPDWLEDTLSEGIRQWWKLKPGPPPPKPAERHKDDSRGLVLPGYKYLGPFNGLD
AAV3           MAADGYLPDWLEDNLSEGIREWWALKPGVPQPKANQQHQDNRRGLVLPGYKYLGPGNGLD
13.3b\VP1      MAADGYLPDWLEDNLSEGIREWWDLKPGAPKPKANQQKQDNGRGLVLPGYKYLGPFNGLD
AAV7           MAADGYLPDWLEDNLSEGIREWWDLKPGAPKPKANQQKQDNGRGLVLPGYKYLGPFNGLD
223_4          ------------------------------------------------------------
223_5          ------------------------------------------------------------
223_10         ------------------------------------------------------------
223_2          ------------------------------------------------------------
223_7          ------------------------------------------------------------
223_6          ------------------------------------------------------------
44_1           MAADGYLPDWLEDNLSEGIREWWDLKPGAPKPKANQQKQDDGRGLVLPGYKYLGPFNGLD
44_5           MAADGYLPDWLEDNLSEGIREWWDLKPGAPKPKANQQKQDDGRGLVLPGYKYLGPFNGLD
44_2           MAADGYLPDWLEDNLSEGIREWWDLKPGAPKPKANQQKQDDGRGLVLPGYKYLGPFNGLD
29.3\VP1       MAADGYLPDWLEDNLSEGIREWWALKPGAPKPKANQQKQDDGRGLVLPGYKYLGPFNGLD
29.5\VP1       MAADGYLPDWLEDNLSEGIREWWALKPGAPKPKANQQKQDDGRGLVLPGYKYLGPFNGLD
42_15          MAADGYLPDWLEDNLSEGIREWWDLKPGAPKPKANQQKQDDGRGLVLPGYKYLGPFNGLD
42_8           MAADGYLPDWLEDNLSEGIREWWDLKPGAPKPKANQQKQDDGRGLVLPGYKYLGPFNGLD
42_13          MAADGYLPDWLEDNLSEGIREWWDLKPGAPKPKANQQKQDDGRGLVLPGYKYLGPFNGLD
42_3A          MAADGHLPDWLEDNLSEGIREWWDLKPGAPKPKANQQKQDDGRGLVLPGYKYLGPFNGLD
42_4           MAADGYLPDWLEDNLSEGIREWWDLKPGAPKPKANQQKQDDGRGLVLPGYKYLGPFNGLD
42_5A          MAADGYLPDWLEDNLSEGIREWWDLKPGAPKPKANQQKQDDGRGLVLPGYKYLGPFNGLD
42_1B          MAADGYLPDWLEDNLSEGIREWWDLKPGAPKPKANQQKQDDGRGLVLPGYKYLGPFNGLD
42_5B          MAADGYLPDWLEDNLSEGIREWWDLKPGAPKPKANQQKQDDGRGLVLPGYKYLGPFNGLD
43_1           MAADGYLPDWLEDNLSEGIREWWDLKPGAPKPKANQQKQDDGRGLVLPGYKYLGPFNGLD
43_12          MAADGYLPDWLEDNLSEGIREWWDLKPGAPKPKANQQKQDDGRGLVLPGYKYLGPFNGLD
43_5           MAADGYLPDWLEDNLSEGIREWWDLKPGAPKPKANQQKQDDGRGLVLPGYKYLGPFNGLD
AAV8           MAADGYLPDWLEDNLSEGIREWWALKPGAPKPKANQQKQDDGRGLVLPGYKYLGPFNGLD
43_21          MAADGYLPDWLEDNLSEGIREWWDLKPGAPKPKANQQKQDDGRGLVLPGYKYLGPFNGLD
43_25          MAADGYLPDWLEDNLSEGIREWWDLKPGAPKPKANQQKQDDGRGLVLPGYKYLGPFNGLD
43_23          MAADGYLPDWLEDNLSEGIREWWDLKPGAPKPKANQQKQDDGRGLVLPGYKYLGPFNGLD
43_20          MAADGYLPDWLEDNLSEGIREWWDLKPGAPKPKANQQKQDDGRGLVLPGYKYLGPFNGLD
AAV_9          MAADGYLPDWLEDNLSEGIREWWDLKPGAPKPKANQQKQDDGRGLVLPGYKYLGPFNGLD
24.1           MAADGYLPDWLEDNLSEGIREWWDLKPGAPKPKANQQKQDDGRGLVLPGYKYLRPFNGLD
42.2REAL       MAADGYLPDWLEDNLSEGIREWWDLKPGAPKPKANQQKQDDGRGLVLPGYKYLGPFNGLD
7.2\VP1        MAADGYLPDWLEGNLSEGIREWWDLKPGAPKPKANQQKQDDGRGLVLPGYRYLGPFNGLD
27.3\VP1       MAADGYLPDWLEDNLSEGIREWWDLKPGAPKPKANQQKQDDGRGLVLPGYKYLGPFNGLD
16.3\VP1       MAADGYLPDWLEDNLSEGIREWWDLKPGAPKPKANQQKQDDGRGLVLPGYKYLGPFNGLD
42_10          MAADGYLPDWLEDNLSEGIREWWDLKPGAPKPKANQQKQDDGRGLVLPGYKYLGPFNGLD
42_3B          MAADGYLPDWLEDNLSEGIREWWDLKPGAPKPKANQQKQDDGRGLVLPGYKYLGPFNGLD
42_11          MAADGYLPDWLEDNLSEGIREWWDLKPGAPKPKANQQKQDDGRGLVLPGYKYLGPFNGLD
F1\VP1         MAADGYLPDWLEDNLSEGIREWWDLKPGAPKPKANQQKQDDGRGLVLPGYKYLGPFNGLD
F5\VP1@3       MAADGYLPDWLEDNLSEGIREWWDLKPGAPKPKANQQKQDDGRGLVLPGYKYLGPFNGLD
F3\VP1         MAADGYLPDWLEDNLSEGIREWWDLKPGAPKPKANQQKQDDGRGLVLPGYKYLGPFNGLD
42_6B          MAADGYLPDWLEDNLSEGIREWWDLKPGAPKPKANQQKQDDGRGLVLPGYKYLGPFNGLD
42_12          MAADGYLPDWLEDNLSEGIREWWDLKPGAPKPKANQQKQDDGRGLVLPGYKYLGPFNGLD
AAV5\CAP       MSFVDHPPDWLEE-VGEGLREFLGLEAGPPKPKPNQQHQDQARGLVLPGYNYLGPGNGLD
```

FIG. 2A

```
                    70        80        90        100       110       120
             ....|....|....|....|....|....|....|....|....|....|....|....|
C1\VP1       KGEPVNAADAAALEHDKAYDQQLKAGDNPYLRYNHADAEFQERLQEDTSFGGNLGRAVFQ
C2\VP1       KGEPVNAADAAALEHDKAYDQQLKAGDNPYLRYNHADAEFQERLQEDTSFGGNLGRAVFQ
C5\VP1@2     KGEPVNAADAAALEHDKAYDQQLKAGDNPYLRYNHADAEFQERLQEDTSFGGNLGRAVFQ
AAV4\VP1     KGEPVNAADAAALEHDKAYDQQLKAGDNPYLKYNHADAEFQQRLQGDTSFGGNLGRAVFQ
AAV1         KGEPVNAADAAALEHDKAYDQQLKAGDNPYLRYNHADAEFQERLQEDTSFGGNLGRAVFQ
AAV6\VP1     KGEPVNAADAAALEHDKAYDQQLKAGDNPYLRYNHADAEFQERLQEDTSFGGNLGRAVFQ
A3_3         KGEPVNEADAAALEHDKAYDHQLKQGDNPYLKYNHADAEFQERLQEDTSFGGNLGRAVFQ
A3_7         KGEPVNEADAAALEHDKAYDHQLKQGDNPYLKYNHADAEFQERLQEDTSFGGNLGRAVFQ
A3_4         KGEPVNEADAAALEHDKAYDHQLKQGDNPYLKYNHADAEFQERLQEDTSFGGNLGRAVFQ
A3_5         KGEPVNEADAAALEHDKAYDHQLKQGDNPYLKYNHADAEFQERLQEDTSFGGNLGRAVFQ
AAV2         KGEPVNEADAAALEHDKAYDRQLDSGDNPYLKYNHADAEFQERLKEDTSFGGNLGRAVFQ
AAV3         KGEPVNEADAAALEHDKAYDQQLKAGDNPYLKYNHADAEFQERLQEDTSFGGNLGRAVFQ
13.3b\VP1    KGEPVNAADAAALEHDKAYDQQLNAGDNPYLRYNHADAEFQERLQEDTSFGGNLGRAVFQ
AAV7         KGEPVNAADAAALEHDKAYDQQLKAGDNPYLRYNHADAEFQERLQEDTSFGGNLGRAVFQ
223_4        ------------------KAYDQQLKAGDNPYLRYNHADAEFQERLQEDTSFGGNLGRAVFQ
223_5        ------------------KAYDQQLKAGDNPYLRYNHADAEFQERLQEDTSFGGNLGRAVFQ
223_10       ------------------KAYDQQLKAGDNPYLRYNHADAEFQERLQEDTSFGGNLGRAVFQ
223_2        ------------------KAYDQQLKAGDNPYLRYNHADAEFQECLQEDTSFGGNLGRAVFQ
223_7        ------------------KAYDQQLKAGDNPYLRYNHADAEFQERLQEDTSFGGNLGRAVFQ
223_6        ------------------KAYDQQLKAGDNPYLRYNHADAEFQERLQEDTSFGGNLGRAVFQ
44_1         KGEPVNAADAAALEHDKAYDQQLKAGDNPYLRYNHADAEFQERLQEDTSFGGNLGRAVFQ
44_5         KGEPVNAADAAALEHDKAYDQQLKAGDNPYLRYNHADAEFQERLQEDTSFGGNLGRAVFQ
44_2         KGEPVNAADAAALEHDKAYDQQLKAGDNPYLRYNHADAEFQERLQEDTSFGGNLGRAVFQ
29.3\VP1     KGEPVNAADAAALEHDKAYDQQLKAGDNPYLRYNHADAEFQERLQEDTSFGGNLGRAVFQ
29.5\VP1     KGEPVNAADAAALEHDKAYDQQLKAGDNPYLRYNHADAEFQERLQEDTSFGGNLGRAVFQ
42_15        KGEPVNAADAAALEHDKAYDQQLKAGDNPYLRYNHADAEFQERLQEDTSFGGNLGRAVFQ
42_8         KGEPVNAADAAALEHDKAYDQQLKAGDNPYLRYNHADAEFQERLQEDTSFGGNLGRAVFQ
42_13        KGEPVNAADAAALEHDKAYDQQLKAGDNPYLRYNHADAEFQERLQEDTSFGGNLGRAVFQ
42_3A        KGEPVNAADAAALEHDKAYDQQLKAGDNPYLRYNHADAEFQERLQEDTSFGGNLGRAVFQ
42_4         KGEPVNEADAAALEHDKAYDKQLEQGDNPYLKYNHADAEFQERLQEDTSFGGNLGRAVFQ
42_5A        KGEPVNEADAAALEHDKAYDKQLEQGDNPYLKYNHADAEFQERLQEDTSFGGNLGRAVFR
42_1B        KGEPVNEADAAALEHDKAYDKQLEQGDNPYLKYNHADAEFQERLQEDTSFGGNLGRAVFQ
42_5B        KGEPVNEADAAALEHDKAYDKQLEQGDNPYLKYNHADAEFQERLQEDTSFGGNLGRAVFQ
43_1         KGEPVNAADAAALEHDKAYDQQLKAGDNPYLRYNHADAEFQERLQEDTSFGGNLGRAVFQ
43_12        KGEPVNAADAAALEHDKAYDQQLKAGDNPYLRYNHADAEFQERLQEDTSFGGNLGRAVFQ
43_5         KGEPVNAADAAALEHDKAYDQQLKAGDNPYLRYNHADAEFQERLQEDTSFGGNLGRAVFQ
AAV8         KGEPVNAADAAALEHDKAYDQQLQAGDNPYLRYNHADAEFQERLQEDTSFGGNLGRAVFQ
43_21        KGEPVNAADAAALEHDKAYDQQLKAGDNPYLRYNHADAEFQERLQEDTSFGGNLGRAVFQ
43_25        KGEPVNAADAAALEHDKAYDQQLKAGDNPYLRYNHADAEFQERLQEDTSFGGNLGRAVFQ
43_23        KGEPVNAADAAALEHDKAYDQQLKAGDNPYLRYNHADAEFQERLQEDTSFGGNLGRAVFQ
43_20        KGEPVNAADAAALEHDKAYDQQLKAGDNPYLRYNHADAEFQERLQEDTSFGGNLGRAVFQ
AAV_9        KGEPVNAADAAALEHDKAYDQQLKAGDNPYLRYNHADAEFQERLQEDTSFGGNLGRAVFQ
24.1         KGEPVNAADAAALEHDKAYDKQLEQGDNPYLKYNHADAEFQERLQEDTSFGGNLGRAVFQ
42.2REAL     KGEPVNEADAAALEHDKAYDKQLEQGDNPYLKYNHADAEFQERLQEDTSFGGNLGRAVFQ
7.2\VP1      KGEPVNEADAAALEHDKAYDKQLEQGDNPYLKYNHADAEFQERLQEDTSFGGNLGRAVFQ
27.3\VP1     KGEPVNEADAAALEHDKAYDKQLEQGDNPYLKYNHADAEFQERLQEDTSFGGNLGRAVFQ
16.3\VP1     KGEPVNEADAAALEHDKAYDKQLEQGDNPYLKYNHADAEFQERLQEDTSFGGNLGRAVFQ
42_10        KGEPVNEADAAALEHDKAYDKQLEQGDNPYLKYNHADAEFQERLQEDTSFGGNLGRAVFQ
42_3B        KGEPVNEADAAALEHDKAYDKQLEQGDNPYLKYNHADAEFQERLQEDTSFGGNLGRAVFQ
42_11        KGEPVNAADAAALEHDKAYDQQLKAGDNPYLRYNHADAEFQERLQEDTSFGGNLGRAVFQ
F1\VP1       KGEPVNAADAAALEHDKAYDQQLKAGDNPYLRYNHADAEFQERLQEDTSFGGNLGRAVFQ
F5\VP1@3     KGEPVNAADAAALEHDKAYDQQLKAGDNPYLRYNHADAEFQERLQEDTSFGGNLGRAVFQ
F3\VP1       KGEPVNAADAAALEHDKAYDQQLKAGDNPYLRYNHADAEFQERLQEDTSFGGNLGRAVFQ
42_6B        KGEPVNEADAAALEHDKAYDKQLEQGDNPYLKYNHADAEFQERLQEDTSFGGNLGRAVFQ
42_12        KGEPVNEADAAALEHDKAYDKQLEQGDNPYLKYNHADAEFQERLQEDTSFGGNLGRAVFQ
AAV5\CAP     RGEPVNRADEVAREHDISYNEQLEAGDNPYLKYNHADAEFQEKLADDTSFGGNLGKAVFQ
```

FIG. 2B

```
                  130        140        150        160        170        180
         ....|....|....|....|....|....|....|....|....|....|....|....|....|
C1\VP1    AKKRVLEPLGLVEEGAKTAPGKKRP-LESPQ-EPDSSSGIGKKGKQPAKKRLNFEEDTGA
C2\VP1    AKKRVLEPLGLVEEGAKTAPGKKRP-LESPQ-EPDSSSGIGKKGKQPAKKRLNFEEDTGA
C5\VP1@2  AKKRVLEPLGLVEEGAKTAPGKKRP-LESPQ-EPDSSSGIGKKGKQPAKKRLNFEEDTGA
AAV4\VP1  AKKRVLEPLGLVEQAGETAPGKKRPLIESPQ-QPDSSTGIGKKGKQPAKKKLVFEDETGA
AAV1      AKKRVLEPLGLVEEGAKTAPGKKRPVEQSPQ-EPDSSSGIGKTGQQPAKKRLNFGQTGDS
AAV6\VP1  AKKRVLEPFGLVEEGAKTAPGKKRPVEQSPQ-EPDSSSGIGKTGQQPAKKRLNFGQTGDS
A3_3      AKKRVLEPLGLVEEAVKTAPGKKRPIEQSPA-EPDSSSGIGKSGQQPAKKRLNFGQTGDT
A3_7      AKKRVLEPLGLVEEAVKTAPGKKRPIEQSPA-EPDSSSGIGKSGQQPAKKRLNFGQTGDT
A3_4      AKKRVLEPLGLVEEAVKTAPGKKRPIEQSPA-EPDSSSGIGESGQQPAKKRLNFGQTGDT
A3_5      AKKRVLEPLGLVEEAVKTAPGKKRPIEQSPA-EPDSSSGIGKSGQQPAKKRLNFGQTGDT
AAV2      AKKRVLEPLGLVEEPVKTAPGKKRPVEHSPV-EPDSSSGTGKAGQQPARKRLNFGQTGDA
AAV3      AKKRILEPLGLVEEAAKTAPGKKGAVDQSPQ-EPDSSSGVGKSGKQPARKRLNFGQTGDS
13.3b\VP1 AKKRVLEPLGLVEEGAKTAPAKKRPVEPSPQRSPDSSTGIGKKGQQPARKRLNFGQTGDS
AAV7      AKKRVLEPLGLVEEGAKTAPAKKRPVEPSPQRSPDSSTGIGKKGQQPARKRLNFGQTGDS
223_4     AKKRVLEPLGLVETPAKTAPGKKRPVD-----SPDSTSGIGKKGQQPAKKRLNFGQTGDS
223_5     AKKRVLEPLGLVETPAKTAPGKKRPVD-----SPDSTSGIGKKGQQPAKKRLNFGQTGDS
223_10    AKKRVLEPLGLVETPAKTAPGKKRPVD-----SPDSTSGIGKKGQQPAKKRLNFGQTGDS
223_2     AKKRVLEPLGLVETPAKTAPGKKRPVD-----SPDSTSGIGKKGQQPAKKRLNFGQTGDS
223_7     AKKRVLEPLGLVETPAKTAPGKKRPVD-----SPDSTSGIGKKGQQPAKKRLNFGQTGDS
223_6     AKKRVLEPLGLVETPAKTAPGKKRPVD-----SPDSTSGIGKKGQQPAKKRLNFGQTGDS
44_1      AKKRVLEPLGLVEEGAKTAPGKKRPVEPSPQRSPDSSTGIGKKGQQPAKKRLNFGQTGDS
44_5      AKKRVLEPLGLVEEGAKTAPGKKRPVEPSPQRSPDSSTGIGKKGQQPAKKRLNFGQTGDS
44_2      AKKRVLEPLGLVEEGAKTAPGKKRPVEPSPQRSPDSSTGIGKKGQQPAKKRLNFGQTGDS
29.3\VP1  AKKRVLEPLGLVEEGAKTAPGKKRPVEPSPQRSPDSTTGIGKKGQQPAKKRLNFGQTGDS
29.5\VP1  AKKRVLEPLGLVEEGAKTAPGKKRPVEPSPQRSPDSSTGIGKKGQQPAKKRLNFGQTGDS
42_15     AKKRVLEPLGLVEEGAKTAPGKKRPVEPSPQRSPDSSTGIGKTGQQPAKKRLNFGQTGDS
42_8      AKKRVLEPLGLVEEGAKTAPGKKRPVEPSPQRSPDSSTGIGKTGQQPAKKRLNFGQTGDS
42_13     AKKRVLEPLGLVEEGAKTAPGKKRPIE------SPDSSTGIGKKGQQPAKKKLNFGQTGDS
42_3A     AKKRVLEPLGLVEEGAKTAPGKKRPIE------SPDSSTGIGKKGQQPAKKKLNFGQTGDS
42_4      AKKRVLEPLGLVEEGAKTAPGKKRPIE------SPDSSTGIGKKGQQPAKKKLNFGQTGDS
42_5A     AKKRVLEPLGLVEEGAKTAPGKKRPIE------SPDSSTGIGKKGQQPAKKKLNFGQTGDS
42_1B     AKKRVLEPLGLVEEGAKTAPGKKRPIE------SPDSSTGIGKKGQQPAKKKLNFGQTGDS
42_5B     AKKRVLEPLGLVEEGAKTAPGKKRPVEPSPQRSPDSSTGIGKTGQQPAKKRLNFGQTGDS
43_1      AKKRVLEPLGLVEEGAKTAPGKKRPVEPSPQRSPDSSTGIGKKGHQPARKRLNFGQTGDS
43_12     AKKRVLEPLGLVEEGAKTAPGKKRPVEPSPQRSPDSSTGIGKKGHQPARKRLNFGQTGDS
43_5      AKKRVLEPLGLVEEGAKTAPGKKRPVEPSPQRSPDSSTGIGKKGHQPARKRLNFGQTGDS
AAV8      AKKRVLEPLGLVEEGAKTAPGKKRPVEPSPQRSPDSSTGIGKKGQQPARKRLNFGQTGDS
43_21     AKKRVLEPLGLVEEGAKTAPGKKRPVEQSPQ-EPDSSSGIGKTGQQPAKKRLNFGQTGDS
43_25     AKKRVLEPLGLVEEGAKTAPGKKRPVEQSPQ-EPDSSSGIGKTGQQPAKKRLNFGQTGDS
43_23     AKKRVLEPLGLVEEGAKTAPGKKRPVEQSPQ-EPDSSSGIGKTGQQPAKKRLNFGQTGDS
43_20     AKKRVLEPLGLVEEGAKTAPGKKRLVEQSPQ-EPDSSSGIGKTGQQPAKKRLNFGQTGDS
AAV_9     AKKRVLEPLGLVEEGAKTAPGKKRPVEQSPQ-EPDSSSGIGKSGQQPAKKRLNFGQTGDS
24.1      AKKRVLEPLGLVEEVAKTAPGKKRPIE------SPDSSTGIGKKGQQPAKKKLNFGQTGDS
42.2REAL  AKKRVLEPLGLVEEGAKTAPGKKRPIE------SPDSSTGIGKKGQQPAKKKLNFGQTGDS
7.2\VP1   AKKRVLEPLGLVEEGAKTAPGKKRPIE------SPDSSTGIGKNGQPPAKKKLNFGQTGDS
27.3\VP1  AKKRVLEPLGLVEEGAKTASGKKRPIE------SPDSSTGIGKKGQQPAKKKLNFGQTGDS
16.3\VP1  AKKRVLEPLGLVEEGAKTAPGKKRPIE------SPDSSTGIGKKGQQPAKKKLNFGQTGDS
42_10     AKKRVLEPLGLVEEGAKTAPGKKRPIE------SPDSSTGIGRKGQQPAKKKLNFGQTGDS
42_3B     AKKRVLEPLGLVEEGAKTAPGKKRPIE------SPDSSTGIGKKGQQPAKKKLNFGQTGDS
42_11     AKKRVLEPLGLVEEGAKTAPGKKRPIE------SPDSSTGIGKKGQQPAKKKLNFGQTGDS
F1\VP1    AKKRVLEPLGLVEEGAKTAPGKKRPID------SPDSSTGIGKKGQQPAKKKLNFGQTGDS
F5\VP1@3  AKKRVLEPLGLVEEGAKTAPGKKRPID------SPDSSTGIGKKGQQPAKKKLNFGQTGDS
F3\VP1    AKKRVLEPLGLVEEGAKTAPGKKRPIG------SPDSSTGIGKKGQQPAKKKLNFGQTGDS
42_6B     AKKRVLEPLGLVEEGAKTAPGKKRPVEPSPQRSPDSSTGIGKTGQQPAKKRLNFGQTGDS
42_12     AKKRVLEPLGLVEEGAKTAPGKKRPVEPSPQRSPDSSTGIGKTGQQPAKKRLNFGQTGDS
AAV5\CAP  AKKRVLEPFGLVEEGAKTAPTGKR---------IDDHFPKRKKARTEEDSKP--STSSDA
```

FIG. 2C

```
                          190       200       210       220       230       240
                          ....|....|....|....|....|....|....|....|....|....|....|....|
C1\VP1          GDGP----PEGSDTSAMS--SDIEMRAAPGGNAVDAGQGSDGVGNASGDWHCDSTWSEGK
C2\VP1          GDGP----PEGSDTSAMS--SDIEMRAAPGGNAVDAGQGSDGVGNASGDWHCDSTWSEGK
C5\VP1@2        GDGP----PEGSDTSAMS--SDIEMRAAPGGNAVDAGQGSDGVGNASGDWHCDSTWSEGK
AAV4\VP1        GDGP----PEGSTSGAMS--DDSEMRAAAGGAAVEGGQGADGVGNASGDWHCDSTWSEGH
AAV1            ESVPD-PQPLGEPPATPAAVGPTTMASGGGAPMADNNEGADGVGNSGNWHCDSTWLGDR
AAV6\VP1        ESVPD-PQPLGEPPATPAAVGPTTMASGGGAPMADNNEGADGVGNSGNWHCDSTWLGDR
A3_3            ESVPG-PQPIGEPPAAPSGVGSNTMASGGGAPMADNNEGADGVGNSSGNWHCDSTWMGDR
A3_7            ESVPD-PQPIGEPPAAPSGVGSNTMASGGGAPMADNNEGADGVGNSSGNWHCDSTWMGDR
A3_4            ESVPD-PQPIGEPPAAPSGVGSNTMASGGGAPMADDNEGADGVGNSSGNWHCDSTWMGDR
A3_5            ESVPD-PQPIGEPPAAPSGVGSNTMASGGGAPMADNNEGADGVGNSSGNWHCDSTWMGDR
AAV2            DSVPD-PQPLGQPPAAPSGLGTNTMATGSGAPMADNNEGADGVGNSSGNWHCDSTWMGDR
AAV3            ESVPD-PQPLGEPPAAPTSLGSNTMASGGGAPMADNNEGADGVGNSSGNWHCDSQWLGDR
13.3b\VP1       ESVPD-PQPLGEPPAAPSSVGSGTVAAGGGAPMADNNEGADGVGNASGNWHCDSTWLGDR
AAV7            ESVPD-PQPLGEPPAAPSSVGSGTVAAGGGAPMADNNEGADGVGNASGNWHCDSTWLGDR
223_4           EPVPD-PQPIGEPPAGPSGLGSGTMAAGGGAPMADNNEGADGVGNASGNWHCDSTRLGDR
223_5           EPVPD-PQPIGEPPAGPSGLGSGTMAAGGGAPMADNNEGADGVGNASGNWHCDSTRLGDR
223_10          ESVPD-PQPIGEPPAGPSGLGSGTMAAGGGAPMADNNEGADGVGNASGNWHCDSTWLGDR
223_2           ESVPD-PQPIGEPPAGPSGLGSGTMVAGGGAPMADNNEGADGVGNASGNWHCDSTWLGDR
223_7           ESVPD-PQPIGEPPAGPSGLGSGTMAAGGGAPMADNNEGADGVGNASGNWHCDSTWLGDR
223_6           ESVPD-PQPIGEPPAGPSGLGSGTMAAGGGAPMADNSEGADGVGNASGNWHCDSTWLGDR
44_1            ESVPD-PQPIGEPPAGPSGLGSGTMAAGGGAPMADNNEGADGVGSSSGNWHCDSTWLGDR
44_5            ESVPD-PQPIGEPPAGPSGLGSGTMAAGGGAPMADNNEGADGVGSSSGNWHCDSTWLGDR
44_2            ESVPD-PQPIGEPPAGPSGLGSGTMAAGGGAPMADNNEGADGVGSSSGNWHCDSTWLGDR
29.3\VP1        ESVPD-PQPIGEPPAGPSGLGSGTMAAGGGAPMADNNEGADGVGSSSGNWHCDSTWLGDR
29.5\VP1        ESVPD-PQPIGEPPAGPSGLGSGTMAAGGGAPMADNNEGADGVGSSSGNWHCDSTWLGDG
42_15           ESVPD-PQPIGEPPAGPSGLGSGTMAAGGGAPMADNNEGADGVGSSSGNWHCDSTWLGDR
42_8            ESVPD-PQPIGEPPAGPSGLGSGTMAAGGGAPMADNNEGADGVGSSSGNWHCDSTWLGDR
42_13           ESVPD-PQPIGEPPAGPSGLGSGTMAAGGGAPMADNNEGADGVGSSSGNWHCDSTWLGDR
42_3A           ESVPD-PQPIGEPPAGPSGLGSGTMAAGGGAPMADNNEGADGVGSSSGNWHCDSTWLGDR
42_4            ESVPD-PQPIGEPPAGPSGLGSGTMAAGGGAPMADNNEGADGVGNASGNWHCDSTWLGDR
42_5A           ESVPD-PQPLGEPPAAPSGLGSGTMAAGGGAPMADNNEGADGVGNASGNWHCDSTWLGDR
42_1B           ESVPD-PQPIGEPPAGPSGLGSGTMAAGGGAPMADNNEGADGVGSSSGNWHCDSTWLGDR
42_5B           ESVPD-PQPIGEPPAGPSGLGSGTMAAGGGAPMADNNEGADGVGSSSGNWHCDSTWLGDR
43_1            ESVPD-PQPIGEPPAGPSGLGSGTMAAGGGAPMADNNEGADGVGSSSGNWHCDSTWLGDR
43_12           ESVPD-PQPIGEPPAGPSGLGSGTMAAGGGAPMADNNEGADGVGSSSGNWHCDSTWLGDR
43_5            ESVPD-PQPIGEPPAGPSGLGSGTMAAGGGAPMADNNEGADGVGSSSGNWHCDSTWLGDR
AAV8            ESVPD-PQPLGEPPAAPSGVGPNTMAAGGGAPMADNNEGADGVGSSSGNWHCDSTWLGDR
43_21           ESVPD-PQPLGEPPAAPSGLGPNTMASGGGAPMADNNEGADGVGNSSGNWHCDSTWLGDR
43_25           ESVPD-PQPLGEPPAAPSGLGPNTMASGGGAPMADNNEGADGVGNSSGNWHCDSTWLGDR
43_23           ESVPD-PQPLGEPPAAPSGLGPNTMASGGGAPMADNNEGADGVGNSSGNWHCDSTWLGDR
43_20           ESVPD-PQPLGEPPAAPSGLGPNTMASGGGAPMADNNEGADGVGNSSGNWHCDSTWLGDR
AAV_9           ESVPD-PQPLGEPPEAPSGLGPNTMASGGGAPMADNNEGADGVGNSSGNWHCDSTWLGDR
24.1            ESVPD-PQPLGEPPAAPSGLGSGTMAAGGGAPMADNNEGADGVGNASGNWHCDSTWLGDR
42.2REAL        ESVPD-PQPLGEPPAAPSGLGSGTMAAGGGAPMADNNEGADGVGNASGNWHCDSTWLGDR
7.2\VP1         ESVPD-PQPLGEPPAAPSGLGSGTMAAGGGAPMADNNEGADGVGNASGNWHCDSTWLGDR
27.3\VP1        ESVPD-PQPLGEPPAAPSGLGSGTMAAGGGAPMADNNEGADGVGNASGNWHCDSTWLGDR
16.3\VP1        ESVPD-PQPLGEPPAAPSGLGSGTMAAGGGAPMADNNEGADGVGNASGNWHCDSTWLGDR
42_10           ESVPD-PQPIGEPPAGPSGLGSGTMAAGGGAPMADNNEGADGVGNASGNWHCDSTWLGDR
42_3B           ESVPD-PQPIGEPPAGPSGLGSGTMAAGGGAPMADNNEGADGVGNASGNWHCDSTWLGDR
42_11           ESVPD-PQPIGEPPAGPSGLGSGTMAAGGGAPMADNNEGADGVGNASGNWHCDSTWLGDR
F1\VP1          ESVPD-PQPLGEPPAAPSSVGSGTMAAGGGAPMADNNEGADGVGNASGNWHCDSTWLGDR
F5\VP1@3        ESVPD-PQPLGEPPAAPSSVGSGTMAAGGGAPTADNNEGADGVGNASGNWHCDSTWLGDR
F3\VP1          ESVPD-PQPLGEPPAAPSSVGSGTMAAGGGAPMADNNEGADGVGNASGNWHCDSTWLGDR
42_6B           ESVPD-PQPIGEPPAGPSGLGSGTMAAGGGAPMADNNEGADGVGSSSGNWHCDSTWLGDR
42_12           ESVPD-PQPIGEPPAGPSGLGSGTMAAGGGAPMADNNEGADGVGSSSGNWHCDSTWLGDR
AAV5\CAP        EAGPSGSQQLQIPAQPASSLGADTMSAGGGGPLGDNNQGADGVGNASGDWHCDSTWMGDR
```

FIG. 2D

```
                     250        260        270        280        290        300
                     ....|....|....|....|....|....|....|....|....|....|....|....|
C1\VP1               VTTTSTRTWVLPTYNNHLYLRLG-----TTSNSNTYNGFSTPWGYFDFNRFHCHFSPRDW
C2\VP1               VTTTSTRTWVLPTYNNHLYLRLG-----TTSNSNTYNGFSTPWGYFDFNRFHCHFSPRDW
C5\VP1@2             VTTTSTRTWVLPTYNNHLYLRLG-----TTSNSNTYNGFSTPWGYFDFNRFHCHFSPRDW
AAV4\VP1             VTTTSTRTWVLPTYNNHLYKRLG-----ESLQSNTYNGFSTPWGYFDFNRFHCHFSPRDW
AAV1                 VITTSTRTWALPTYNNNHLYKQIS-SASTGASNDNHYFGYSTPWGYFDFNRFHCHFSPRDW
AAV6\VP1             VITTSTRTWALPTYNNNHLYKQIS-SASTGASNDNHYFGYSTPWGYFDFNRFHCHFSPRDW
A3_3                 VITTSTRTWALPTYNNHLYKQIS--SESGATNDNHYFGYSTPWGYFDFNRFHCHFSPRDW
A3_7                 VITTSTRTWALPTYNNRLYKQIS--SESGATNDNHYFGYSTPWGYFDFNRFHCHFSPRDW
A3_4                 VITTSTRTWALPTYNNHLYKQIS--SESGATNDNHYFGYSTPWGYFDFNRFHCHFSPRDW
A3_5                 VITTSTRTWALPTYNNHLYKQIS--SESGATNDNHYFGYSTPWGYFDFNRFHCHFSPRDW
AAV2                 VITTSTRTWALPTYNNHLYKQIS--SQSGASNDNHYFGYSTPWGYFDFNRFHCHFSPRDW
AAV3                 VITTSTRTWALPTYNNHLYKQIS--SQSGASNDNHYFGYSTPWGYFDFNRFHCHFSPRDW
13.3b\VP1            VITTSTRTWALPTYNNHLYEQIS-SETAGSTNDNTYFGYSTPWGYFDFNRFHCHFSPRDW
AAV7                 VITTSTRTWALPTYNNHLYKQIS-SETAGSTNDNTYFGYSTPWGYFDFNRFHCHFSPRDW
223_4                VITTSTRTWALPTYNNHLYKQIS-SQSAGSTNDNVYFGYSTPWGYFDFNRFHCHFSPRDW
223_5                VITTSTRTWALPTYNNHLYKQIS-SQSAGSTNDNVYFGYSTPWGYFDFNRFHCHFSPRDW
223_10               VITTSTRTWALPTYNNHLYKQIS-SQSAGSTNDNVYFGYSTPWGYFDFNRFHCHFSPRDW
223_2                VITTSTRTWALPTYNNHLYKQIS-SQSAGSTNDNVYFGYSTPWGYFDFNRFHCHFSPRDW
223_7                VITTSTRTWALPTYNNHLYKQIS-SQSAGSTNDNVYFGYSTPWGYFDFNRFHCHFSPRDW
223_6                VITTSTRTWALPTYNNHLYKQIS-SQSAGSTNDNVYFGYSTPWGYFDFNRFHCHFSPRDW
44_1                 VITTSTRTWALPTYNNHLYKQISNGTSGGSTNDNTYFGYSTPWGYFDFNRFHCHFSPRDW
44_5                 VITTSTRTWALPTYNNHLYKQISNGTSGGSTNDNTYFGYSTPWGYFDFNRFHCHFSPRDW
44_2                 VITTSTRTWALPTYNNHLYKQISNGTSGGSTNDNTYFGYSTPWGYFDFNRFHCHFSPRDW
29.3\VP1             VITTSTRTWALPTYNNHLYKQISNGTSGGSTNDNTYFGYSTPWGYFDFNRFHCHFSPRDW
29.5\VP1             VITTSTRTWALPTYNNHLYKQISNGTSGGSTNDNTYFGYSTPWGYFDFNRFHCHFSPRDW
42_15                VITTSTRTWALPTYNNHLYKQISNGTSGGSTNDNTYFGYSTPWGYFDFNRFHCHFSPRDW
42_8                 VITTSTRTWALPTYNNHLYKQISNGTSGGSTNDNTYFGYSTPWGYFDFNRFHCHFSPRDW
42_13                VITTSTRTWALPTYNNHLYKQISNGTSGGSTNDNTYFGYSTPWGYFDFNRFHCHFSPRDW
42_3A                VITTSTRTWALPTYNNHLYKQISNGTSGGSTNDNTYFGYSTPWGYFDFNRFHCHFSPRDW
42_4                 VITTSTRTWALPTYNNHLYKQIS--SQSGATNDNHFFGYSTPWGYFDFNRFHCHFSSRDW
42_5A                VITTSTRTWALPTYNNHLYKQIS--SQSGATNDNHFFGYSTPWGYFDFNRFHCHFSPRDW
42_1B                VITTSTRTWALPTYNNHLYKQISNGTSGGSTNDNTYFGYSTPWGYFDFNRFHCHFSPRDW
42_5B                VITTSTRTWALPTYNNHLYKQISNGTSGGSTNDNTYFGYSTPWGYFDFNRFHCHFSPRDW
43_1                 VITTSTRTWALPTYNNHLYKQISNGTSGGSTNDNTYFGYSTPWGYFDFNRFHCHFSPRDW
43_12                VITTSTRTWALPTYNNHLYKQISNGTSGGSTNDNTYFGYSTPWGYFDFNRFHCHFSPRDW
43_5                 VITTSTRTWALPTYNNHLYKQISNGTSGGSTNDNTYFGYSTPWGYFDFNRFHCHFSPRDW
AAV8                 VITTSTRTWALPTYNNHLYKQISNGTSGGATNDNTYFGYSTPWGYFDFNRFHCHFSPRDW
43_21                VITTSTRTWALPTYNNHLYKQISNGTSGGSTNDNTYFGYSTPWGYFDFNRFHCHFSPRDW
43_25                VITTSTRTWALPTYNNHLYKQISNGTSGGSTNDNTYFGYSTPWGYFDFNRFHCHFSPRDW
43_23                VITTSTRTWALPTYNNHLYKQISNGTSGGSTNDNTYFGYSTPWGYFDFNRFHCHFSPRDW
43_20                VITTSTRTWALPTYNNHLYKQISNGTSGGSTNDNTYFGYSTPWGYFDFNRFHCHFSPRDW
AAV_9                VITTSTRTWALPTYNNHLYKQISNGTSGGSTNDNTYFGYSTPWGYFDFNRFHCHFSPRDW
24.1                 VITTSTRTWALPTYNNHLYKQIS-SQS-GATNDNHFFSYSTPWGYFDFNRFHCHFSPRDW
42.2REAL             VITTSTRTWALPTYNNHLYKQIS-SQS-GATNDNHFFGYSTPWGYFDFNRFHCHFSPRDW
7.2\VP1              VITTSTRTWALPTYNNHLYKQIS-SQS-GATNDNHFFGYSTPWGYFDFNRFHCHFSPRDW
27.3\VP1             VITTSTRTWALPTYNNHLYKQIS-SQS-GATNDNHFFGYSTPWGYFDFNRFHCHFSPRDW
16.3\VP1             VITTSTRTWALPTYNNHLYKQIS-SQS-GATNDNHFFGYSTPWGYFDFNRFHCHFSPRDW
42_10                VITTSTRTWALPTYNNHLYKQIS-SQS-GATNDNHFFGYSTPWGYFDFNRFHCHFSPRDW
42_3B                VITTSTRTWALPTYNNHLYKQIS-SQS-GATNDNHFFGYSTPWGYFDFNRFHCHFSPRDW
42_11                VITTSTRTWALPTYNNHLYKQIS-SQS-GATNDNHFFGYSTPWGYFDFNRFHCHFSPRDW
F1\VP1               VITTSTRTWALPTYNNHLYKQIS-SSSSGATNDNHYFGYSTPWGYFDFNRFHCHFSPRDW
F5\VP1@3             VITTSTRTWALPTYNNHLYKQIS-SSSSGATNDNHYFGYSTPWGYFDFNRFHCHFSPRDW
F3\VP1               VITTSTRTWALPTYNNHLYKQIS-SSSSGATNDNHYFGYSTPWGYFDFNRFHCHFSPRDW
42_6B                VITTSTRTWALPTYNNHLYKQISNGTSGGSTNDNTYFGYSTPWGYFDFNRFHCHFSPRDW
42_12                VITTSTRTWALPTYNNHLYKQISNGTSGGSTNDNTYFGYSTPWGYFDFNRFHCHFSPRDW
AAV5\CAP             VVTKSTRTWVLPSYNNHQYREIK-SGSVDGSNANAYFGYSTPWGYFDFNRFHSHWSPRDW
```

FIG. 2E

```
                   310        320        330        340        350        360
                   ....|....|....|....|....|....|....|....|....|....|....|....|
C1\VP1             QRLINNNWGLRPKAMRVKIFNIQVKEVTTSNGETTVANNLTSTVQIFADSSYELPYVMDA
C2\VP1             QRLINNNWGLRPKAMRVKIFNIQVKEVTTSNGETTVANNLTSTVQIFADSSYELPYVMDA
C5\VP1@2           QRLINNNWGLRPKAMRVKIFNIQVKEVTTSNGETTVANNLTSTVQIFADSSYELPYVMDA
AAV4\VP1           QRLINNNWGMRPKAMRVKIFNIQVKEVTTSNGETTVANNLTSTVQIFADSSYELPYVMDA
AAV1               QRLINNNWGFRPKRLNFKLFNIQVKEVTTNDGVTTIANNLTSTVQVFSDSEYQLPYVLGS
AAV6\VP1           QRLINNNWGFRPKRLNFKLFNIQVKEVTTNDGVTTIANNLTSTVQVFSDSEYQLPYVLGS
A3_3               QRLINNNWGFRPKKLNFKLFNIQVKEVTQNDGTTTIANNLTSAVQVFTDSEYQLPYVLGS
A3_7               QRLINNNWGFRPKKLNFKLFNIQVKEVTQNDGTTTIANNLTSTVQVFTDSEYQLPYVLGS
A3_4               QRLINNNWGFRPKKLNFKLFNIQVKEVTQNDGTTTIANNLTSTVQVFTDSEYQLPYVLGS
A3_5               QRLINNNWGFRPKKLNFKLFNIQVKEVTQNDGTTTIANNLTSTVQVFTDSEYQLPYVLGS
AAV2               QRLINNNWGFRPKRLNFKLFNIQVKEVTQNDGTTTIANNLTSTVQVFTDSEYQLPYVLGS
AAV3               QRLINNNWGFRPKKLSFKLFNIQVRGVTQNDGTTTIANNLTSTVQVFTDSEYQLPYVLGS
13.3b\VP1          QRLINNNWGFRPKKLRFKLFNIQVKEVTTNDGVTTIANNLTSTIQVFSDSEYQLPYVLGS
AAV7               QRLINNNWGFRPKKLRFKLFNIQVKEVTTNDGVTTIANNLTSTIQVFSDSEYQLPYVLGS
223_4              QRLINNNWGFRPKKLNFKLFNIQVKEVTTNDGVTTIANNLTSTVQVFSDSEYQLPYVLGS
223_5              QRLINNNWGFRPKKLNFKLFNIQVKEVTTNDGVTTIANNLTSTVQVFSDSEYQLPYVLGS
223_10             QRLINNNWGFRPKKLNFKLFNIQVKEVTTNDGVTTIANNLTSTVQVFSDSEYQLPYVLGS
223_2              QRLINNNWGFRPKKLNFKLFNIQVKEVTTNDGVTTIANNLTSTVQVFSDSEYQLPYVLGS
223_7              QRLINNNWGFRPKKLNFKLFNIQVKEVTTNDGVTTIANNLTSTVQVFSDPEYQLPYVLGS
223_6              QRLINNNWGFRPKKLNFKLFNIQVKEVTTNDGVTTIANNLTSTVQVFSDSEYQLPYVLGS
44_1               QRLINNNWGFRPKRLNFKLFNIQVKEVTQNEGTKTIANNLTSTIQVFTDSEYQLPYVLGS
44_5               QRLINNNWGFRPKRPNFKLFNIQVKEVTQNEGTKTIANNLTSTIQVFTDSEYQLPYVLGS
44_2               QRLINNNWGFRPKRLNFKLFNIQVKEVTQNEGTKTIANNLTSTIQVFTDSEYQLPYVLGS
29.3\VP1           QRLINNNWGFRPKRLNFKLFNIQVKEVTQNEGTKTIANNLTSTIQVFTDSEYQLPYVLGS
29.5\VP1           QRLINNNWGFRPKSLNFKLFNIQVKEVTQNEGTKTIANNLTSTIQVFTDSEYQLPYVLGS
42_15              QRLINNNWGFRPKRLNFKLFNIQVKEVTQNEGTKTIANNLTSTIQVFTDSEYQLPYVLGS
42_8               QRLINNNWGFRPKRLNFKLFNIQVKEVTQNEGTKTIANNLTSTIQVFTDSEYQLPYVLGS
42_13              QRLINNNWGFRPKRLNFKLFNIQVKEVTQNEGTKTIANNLTSTIQVFTDSEYQLPYVLGS
42_3A              QRLINNSWGFRPKRLNFKLFNIQVKEVTQNEGTKTIANNLTSTIQVFTDSEYQLPYVLGS
42_4               QRLINNNWGFRPKRLNFKLFNIQVKEVTQNEGTKTIANNLTSTIQVFTDSEYRLPYVLGS
42_5A              QRLINNNRGFRPRKLRFKLFNIQVKEVTTNDGVTTIANNLTSTIQVFSDSEYQLPYVLGS
42_1B              QRLINNNWGFRPKRLNFKLFNIQVKEVTQNEGTKTIANNLTSTIQVFTDSEYQLPYVLGS
42_5B              QRLINNNWGFRPKRLNFKLFNIQVKEVTQNEGTKTIANNLTSTIQVFTDSEYQLPYVLGS
43_1               QRLINNNWGFRPKRLNFKLFNIQVKEVTQNEGTKTIANNLTSTIQVFTDSEYQLPYVPGS
43_12              QRLINNNWGFRPKRLNFKLFNIQVKEVTQNEGTKTIANNLTSTIQVFTDSEYQLPYVLGS
43_5               QRLINNNWGFRPKRLNFKLFNIQVKEVTQNEGTKTIANNLTSTIQVFTDSEYQLPYVLGS
AAV8               QRLINNNWGFRPKRLSFKLFNIQVKEVTQNEGTKTIANNLTSTIQVFTDSEYQLPYVLGS
43_21              QRLINNNWGFRPKRLNFKLFNIQVKEVTTNEGTKTIANNLTSTVRVFTDSEYQLPYVLGS
43_25              QRLINNNWGFRPKRLNFKLFNIQVKEVTTNEGTKTIANNLTSTVQVFTDSEYQLPYVLGS
43_23              QRLINNNWGFRPKRLNFKLFNIQVKEVTTNEGTKTIANNLTSTVQVFTDLEYQLPYVLGS
43_20              QRLINNNWGFRPKRLNFKLFNIQVKEVTTNEGTKTIANNLTSTVQVFTDSEYQLPYVLGS
AAV_9              QRLINNNWGFRPKRLNFKLFNIQVKEVTTNEGTKTIANNLTSTVQVFTDSEYQLPYVLGS
24.1               QRLINNNWGFRPRKLRFKLFNIQVKEVTTNDGVTTIANNLTSTIQVFSDSEYQLPYVLGS
42.2REAL           QRLINNNWGFRPRKLRFKLFNIQVKEVTTNDGVTTIANNLTSTIQVFSDSEYQLPYVLGS
7.2\VP1            QRLINNNWGFRPRKLRFKLFNIQVKEVTTNDGVTTIANNLTSTIQVFSDSEYQLPYVLGS
27.3\VP1           QRLINNNWGFRPRKLRFKLFNIQVKEVTTNDGVTTIANNLTSTIQVFSDSEYQLPYVLGS
16.3\VP1           QRLINNNWGFRPRKLRFKLFNIQVKEVTTNDGVTTIANNLTSTIQVFSDSEYQLPYVLGS
42_10              QRLINNNWGFRPRKLRFKLFNIQVKEVTTNDGVTTIANNLTSTIQVFSDSEYQLPYVLGS
42_3B              QRLINNNWGFRPRKLRFKLFNIQVKEVTTNDGVTTIANNLTSTIQVFSDSEYQLPYVLGS
42_11              QRLINNNWGFRPRKLRFKLFNIQVKEVTTNDGVTTIANNLTSTIQVFSDSEYQLPYVLGS
F1\VP1             QRLINNNWGFRPKKLRFKLFNIQVKEVTTNDGVTTIANNLTSTIQVFSDSEYQLPYVLGS
F5\VP1@3           QRLINNNWGFRPKKLRFKLFNIQVKEVTTNDGVTTIANNLTSTVQVFSDSEYQLPYVLGS
F3\VP1             QRLINNNWGFRPKKLRFKLLNIQVKEVTTNDGVTTIANNLTSTVQVFSDSEYQLPYVLGS
42_6B              QRLINNNWGFRPRKLRFKLFNIQVKEVTTDDGVTTIANNLTSTIQVFSDSEYQLPYVLGS
42_12              QRLINNNWGFRPKRLNFKLFNIQVKEVTQNEGTKTIANNLTSTIQVFTDSEYQLPYVLGS
AAV5\CAP           QRLINNYWGFRPRSLRVKIFNIQVKEVTVQDSTTTIANNLTSTVQVFTDDDYQLPYVVGN
```

FIG. 2F

```
                    370        380        390        400        410        420
              ....|....|....|....|....|....|....|....|....|....|....|....|
C1\VP1        GQEGSLSPFPNDVFMVPQYGYCGIVTG-ENQNQTDRNAFYCLEYFPSQMLRTGNNFEMAY
C2\VP1        GQEGSLPPFPNDVFMVPQYGYCGIVTG-ENQNQTDRNAFYCLEYFPSQMLRTGNNFEMAY
C5\VP1@2      GQEGSLPPFPNDVFMVPQYGYCGIVTG-ENQNQTDRNAFYCLEYFPSQMLRTGNNFETAY
AAV4\VP1      GQEGSLPPFPNDVFMVPQYGYCGLVTGNTSQQQTDRNAFYCLEYFPSQMLRTGNNFEITY
AAV1          AHQGCLPPFPADVFMIPQYGYLTLNNG---SQAVGRSSFYCLEYFPSQMLRTGNNFTFSY
AAV6\VP1      AHQGCLPPFPADVFMIPQYGYLTLNNG---SQAVGRSSFYCLEYFPSQMLRTGNNFTFSY
A3_3          AHQGCLPPFPADVFMIPQYGYLTLNNG---SQAVGRSSFYCLEYFPSQMLRTGNNFTFSY
A3_7          AHQGCLPPFPADVFMIPQYGYLTLNNG---SQAVGRSSFYCLEYFPSQMLRTGNNFTFSY
A3_4          AHQGCLPPFPADVFMIPQYGYLTLNNG---SQAVGRSSFYCLEYFPSQMLRTGNNFTFSY
A3_5          AHQGCLPPFPADVFMIPQYGYLTLNNG---SQAVGRSSFYCLEYFPSQMLRTGNNFTFSY
AAV2          AHQGCLPPFPADVFMVPQYGYLTLNNG---SQAVGRSSFYCLEYFPSQMLRTGNNFTFSY
AAV3          AHQGCLPPFPADVFMVPQYGYLTLNNG---SQAVGRSSFYCLEYFPSQMLRTGNNFQFSY
13.3b\VP1     AHQGCLPPFPADVFMIPQYGYLTLNNG---SQSVGRSSFYCLEYFPSQMLRTGNNFEFSY
AAV7          AHQGCLPPFPADVFMIPQYGYLTLNNG---SQSVGRSSFYCLEYFPSQMLRTGNNFEFSY
223_4         AHQGCLPPFPADVFMIPQYGYLTLNNG---SQSVGRSSFYCLEYFPSQMLRTGNNFTFSY
223_5         AHQGCLPPFPADVFMIPQYGYLTLNNG---SQSVGRSSFYCLEYFPSQMLRTGNNFTFSY
223_10        AHQGCLPPFPADVFMIPQYGYLTLNNG---SQSVGRSSFYCLEYFPSQMLRTGNNFTFSY
223_2         AHQGCLPPFPADVFMIPQYGYLTLNNG---SQSVGRSSFYCLEYFPSQMLRTGNNFTFSY
223_7         AHQGCLPPFPADVFMIPQYGYLTLNNG---SQSVGRSSFYCLEYFPSQMLRTGNNFTFSY
223_6         AHQGCLPPFPADVFMIPQYGYLTLNNG---SQSVGRSSFYCLEYFPSQMLRTGNNFTFSY
44_1          AHQGCLPPFPADVFMIPQYGYLTLNNG---SQAVGRSSFYCLEYFPSQMLRTGNNFEFSY
44_5          AHQGCLPPFPADVFMIPQYGYLTLNNG---SQAVGRSSFYCLEYFPSQMLRTGNNFEFSY
44_2          AHQGCLPPFPADVFMIPQYGYLTLNNG---SQAVGRSSFYCLEYFPSQMLRTGNNFEFSY
29.3\VP1      ARQGCLPPFPADVFMIPQYGYLTLNNG---SQAVGRSSFYCLEYFPSQMLRTGNNFEFSY
29.5\VP1      AHQGCLPPFPADVFMIPQYGYLTLNNG---SQAVGRSSFYCLEYFPSQMLRTGNNFEFSY
42_15         AHQGCPPPFPADVFMIPQYGYLTLNNG---SQAVGRSSFYCLEYFPSQMRRTGNNFEFSY
42_8          AHQGCLPPFPADVFMIPQYGYLTLNNG---SQAVGRSSFYCLEYFPSQMLRTGNNFEFSY
42_13         AHQGCLPPFPADVFMIPQYGYLTLNNG---SQAVGRSSFYCLEYFPSQMLRTGNNFEFSY
42_3A         AHQGCLPPFPADVFMIPQYGYLTLNNG---SQAVGRSSFYCLEYFPSQMLRTGNNFEFSY
42_4          AHQGCLPPFPADVFMIPQYGYLTLNNG----SQAVGRSSFYCLEYFPSQMLRTGNNFEFSY
42_5A         AHQGCLPPFPADVFMIPQYGYLTLNNG---SQSVGRSSFYCLEYFPSQMLRTGNNFEFSY
42_1B         AHQGCLPPFPADVFMIPQYGYLTLNNG---SQAVGRSSFYCLEYFPSQMLRTGNNFEFSY
42_5B         AHQGCLPPFPADVFMIPQYGYLTLNNG----SQAVGRSSFYCLEYFPSQMLRTGNNFEFSY
43_1          AHQGCLPPFPADVFMIPQYGYLTLNNG---SQAVGRSSFYCLEYFPSQMLRTGNNFEFSY
43_12         AHQGCLPPFPADVFMIPQYGYLTLNNG---SQAVGRSSFYCLEYFPSQMLRTGNNFEFSY
43_5          AHQGCLPPFPADVFMIPQYGYLTLNNG---SQAVGRSSFYCLEYFPSQMLRTGNNFEFSY
AAV8          AHQGCLPPFPADVFMIPQYGYLTLNNG---SQAVGRSSFYCLEYFPSQMLRTGNNFQFTY
43_21         AHQGCLPPFPADVFMVPQYGYLTLNNG---SQALGRSSFYCLEYFPSQMLRTGNNFQFSY
43_25         AHQGCLPPFPADVFMVPQYGYLTLNNG---SQALGRSSFYCLEYFPSQMLRTGNNFQFSY
43_23         AHQGCLPPFPADVFMVPQYGYLTLNNG---SQALGRSSFYCLEYFPSQMPRTGNNFQFSY
43_20         AHQGCLPPFPADVFTVPQYGYLTLNNG---SQALGRSSFYCLEYFPSQMLRTGNNFQFSY
AAV_9         AHQGCLPPFPADVFMVPQYGYLTLNNG---SQALGRSSFYCLEYFPSQMLRTGNNFQFSY
24.1          AHQGCLPPFPADVFMIPQYGYLTLNNG---SQSVGRSSFYCLEYFPSQMLRTGNNFEFSY
42.2REAL      AHQGCLPPFPADVFMIPQYGYLTLNNG----SQSVGRSSFYCLEYFPSQMLRTGNNFEFSY
7.2\VP1       AHQGCLPPFPADVFMIPQYGYLTLNNG---SQSVGRSSFYCLEYFPSQMLRTGDNFEFSY
27.3\VP1      AHQGCLPPFPADVFMIPQYGYLTLNNG---SQSVGRSSFCCLEYFPSQMLRTGNNFEFSY
16.3\VP1      AHQGCLPPFPADVFMIPQYGYLTLNNG---SQSMGRSSFYCLEYFPSQMLRTGNNFEFSY
42_10         AHQGCLPPFPADVFMIPQYGYLTLNNG---SQSVGRSSFYCLEYFPSQMLRTGNNFEFSY
42_3B         AHQGCLPPFPADVFMIPQYGYLTLNNG---SQSVGRSSFYCLEYFPSQMLRTGNNFEFSY
42_11         AHQGCLPPFPADVFMIPQYGYLTLNNG---SQSVGRSSFYCLEYFPSQMLRTGNNFEFSY
F1\VP1        AHQGCLPPFPADVFMIPQYGYLTLNNG---SQSVGRSSFYCLEYFPSQMLRTGNNFEFSY
F5\VP1@3      AHQGCLPPFPADVFMIPQYGYLTLNNG---SQSVGRSSFYCLEYFPSQMLRTGNNFEFSY
F3\VP1        AHQGCLPPFPADVFMIPQYGYLTLDNG---SQSVGRSSFYCLEYFPSQMLRTGNNFEFSY
42_6B         AHQGCLPPFPADVFMIPQYGYLTLNNG----SQSVGRSSFYCLEYFPSQMLRTGNNFEFSY
42_12         AHQGCLPPFPADVFMIPQYGYLTLNNG----SQAVGRSSFYCLEYFPSQMLRTGNNFEFSY
AAV5\CAP      GTEGCLPAFPPQVFTLPQYGYATLNRD-NTENPTERSSFFCLEYFPSKMLRTGNNFEFTY
```

FIG. 2G

```
                      430        440        450        460        470        480
                 ....|....|....|....|....|....|....|....|....|....|....|....|
C1\VP1           NFGKVPFHSMYAYSQSPDRLMNPLLDQYLWHLQSTTSGETLNQGNAATTFGKIRSGDFAF
C2\VP1           NFEKVPFHSMYAHSQSLDRLMNPLLDQYLWHLQSTTSGETLNQGNAATTFGKIRSGDFAF
C5\VP1@2         NFEKVPFHSMYAHSQSLDGLMNPLLDQYLWHLQSTTSGETLNQGNAATTFGKIRSGDFAF
AAV4\VP1         SFEKVPFHSMYAHSQSLDRLMNPLIDQYLWGLQSTTTGTTLNAGTATTNFTKLRPTNFSN
AAV1             TFEEVPFHSSYAHSQSLDRLMNPLIDQYLYYLNRTQNQSG-SAQNKDLLFSRGSPAGMSV
AAV6\VP1         TFEDVPFHSSYAHSQSLDRLMNPLIDQYLYYLNRTQNQSG-SAQNKDLLFSRGSPAGMSV
A3_3             TFEDVPFHSSYAHSQSLDRLMNPLIDQYLYYLSKTQ-GTSGTTQQSRLQFSQAGPSSMAQ
A3_7             TFEDVPFHSSYAHSQSLDRLMNPLIDQYLYYLSKTQ-GTSGTTQQSRLQFSQAGPSSMAQ
A3_4             TFEDVPFHSSYAHSQSLDRLMNPLIDQYLYYLSKTQ-GTSGTTQQSRLQFSQAGPSSMAQ
A3_5             TFEDVPFHSSYAHSQSLDRLMNPLIDQYLYYLSKTQ-GTSGTTQQSRLQFNQAGPSSMAQ
AAV2             TFEDVPFHSSYAHSQSLDRLMNPLIDQYLYYLSRTN-TPSGTTTQSRLQFSQAGASDIRD
AAV3             TFEDVPFHSSYAHSQSLDRLMNPLIDQYLYYLNRTQGTTSGTTNQSRLLFSQAGPQSMSL
13.3b\VP1        SFEDVPFHSSYAHSQSLDRLMNPLIDQYLYYLARTQSDPGGTAGNRELQFYQGGPSTMAE
AAV7             SFEDVPFHSSYAHSQSLDRLMNPLIDQYLYYLARTQSNPGGTAGNRELQFYQGGPSTMAE
223_4            TFEDVPFHSSYAHSQSLGRLMNPLIDQYLYYLARTQSNAGGTAGNRELQFYQGGPTTMAE
223_5            TFEDVPFHSSYAHSQSLGRLMNPLIDQYLYYLARTQSNAGGTAGNRELQFYQGGPTTMAE
223_10           TFEDVPFHSSYAHSQSLGRLMNPLIDQYLYYLARTQSNAGGTAGNRELQFYQGGPTTMAE
223_2            TFEDVPFHSSYAHSQSLGRLMNPLIDQYLYYLARTQSNAGGTAGNRELQFYQGGPTTMAE
223_7            TFEDVPFHSSYAHSQSLGRLMNPLIDQYLYYLARTQSNAGGTAGNRELQFYQGGPTTMAE
223_6            TFEDVPFHSSYAHSQSLGRLMNPLIDQYLYYLARTQSNAGGTAGNRELQFYQGGPTTMAE
44_1             QFEDVPFHSSYAHSQSLDRLMNPLIDQYLYYLSRTQSTGG-TAGTQQLLFSQAGPNNMSA
44_5             QFEDVPFHSSYAHSQSLDRLMNPLIDQYLYYLSRTQSTGG-TAGTQQLLFSQAGPNNMSA
44_2             QFEDVPFHSSYAHSQSLDRLMNPLIDQYLYYLSRTQSTGG-TAGTQQLLFSQAGPNNMSA
29.3\VP1         QFEDVPFHSSYAHSQSLDRLMNPLIDQYLYYLSRTQSTGG-TAGTQQLLFSQAGPNNMSA
29.5\VP1         QFEDVPFHSSYAHSQSLDRLMNPLIDQYLYYLSRTQSTGG-TAGTQQLLFSQAGPNNMSA
42_15            QFEDVPFHSSYAHSQSLDRLMNPLIDQYLYYLSRTQSTGG-TAGTQQLLFSQAGPNNMSA
42_8             QFEDVPFHSSYAHSQSLDRLMNPLIDQYLYYLSRTQSTGG-TAGTQQLLFSQAGPNNMSA
42_13            QFEDVPFHSSYAHSQSLDRLMNPLIDQYLYYLSRTQSTGG-TAGTQQLLFSQAGPNNMSA
42_3A            QFEDVPFHSSYAHSQSLDRLMNPLIDQYLYYLSRTQSTGG-TAGTQQLLFSQAGPNNMSA
42_4             QFEDVPFHSSYAHSQSLDRLMNPLIDQYLYYLSRTQSTGG-TAGTQQLLFSQAGPNNMSA
42_5A            QFEDVPFHSSYAHSQSLDRLMNPLIDQYLYYLSRTQSTGG-TAGTQQLLFSQAGPNNMSA
42_1B            QFEDVPFHSSYAHSQSLDRLMNPLIDQYLYYLSRTQSTGG-TAGTQQLLFSQAGPNNMSA
42_5B            QFEDVPFHSSYAHSQSLDRLMNPLIDQYLYYLSRTQSTGG-TAGTQQLLFSQAGPNNMSA
43_1             TFEDVPFHSSYAHSQSLDRLMNPLIDQYLYYLSRTQSTGG-TQGTQQLLFSQAGPANMSA
43_12            TFEDVPFHSSYAHSQSLDRLMNPLIDQYLYYLSRTQSTGG-TQGTQQLLFSQAGPANMSA
43_5             TFEDVPFHSSYAHSQSLDRLMNPLIDQYLYYLSRTQSTGG-TQGTQQLLFSQAGPANMSA
AAV8             TFEDVPFHSSYAHSQSLDRLMNPLIDQYLYYLSRTQTTGG-TANTQTLGFSQGGPNTMAN
43_21            TFEDVPFHSSYAHSQSLDRLMNPLIDQYLYYLVRTQTTG--TGGTQTLAFSQAGPSSMAN
43_25            TFEDVPFHSSYAHSQSLDRLMNPLIDQYLYYLVRTQTTG--TGGTQTLAFSQAGPSSMAN
43_23            TFEDVPFHSSYAHSQSLDRLMNPLIDQYLYYLVRTQTTG---TGGTQTLAFSQAGPSSMAN
43_20            TFEDVPFHSSYAHSQSLDRLMNPLIDQYLYYLVRTQTTG--TGGTQTLAFSQAGPSSMAN
AAV_9            TFEDVPFHSSYAHSQSLDRLMNPLIDQYLYYLVRTQTTG---TGGTQTLAFSQAGPSSMAN
24.1             TFEEVPFHSSYVHSQSLDRLMNPLIDQYLYYLARTQST----TGSTRELQFHQAGPNTMAE
42.2REAL         TFEEVPFHSSYAHSQSLDRLMNPLIDQYLYYLARTQST-----TGSTRELQFHQAGPNTMAE
7.2\VP1          TFEEVPFHSSYAHSQSLDRLMNPLIDQYLYYLARTQST----TGSTRELQFHQAGPNTMAE
27.3\VP1         TFEEVPFHSSYAHSQSLDRLMNPLIDQYLYYLARTQST----TGSTRELQFHQAGPNTVAE
16.3\VP1         TFEEVPFHSSYAHSQSLDRLMNPLIDQYLYYLARTQST----TGSTRELQFHQAGPNTMAE
42_10            TFEEVPFHSSYAHSQSLDRLMNPLIDQYLYYLARTQST-----TGSTRELQFHQAGPNTMAE
42_3B            TFEEVPFHSSYAHSQSLDRLMNPLIDQYLYYLARTQST----TGSTRELQFHQAGPNTMAE
42_11            TFEEVPFHSSYAHSQSLDRLMNPLIDQYLYYLARTQST----TGSTRELQFHQAGPNTMAE
F1\VP1           SFEDVPFHSSYAHSQSLDRLMNPLIDQYLYYLARTQST----TGSTRELQFHQAGPNTMAE
F5\VP1@3         SFEDVPFHSSYAHSQSLDRLMNPLIDQYLYYLARTQST-----TGSTRELQFHQAGPNTMAE
F3\VP1           SFEDVPFHSSYAHSQSLDRLMNPLIDQYLYYLARTQST----TGSTRELQFHQAGPNTMAE
42_6B            TFEEVPFHSSYAHSQSLDRLMNPLIDQYLYYLARTQST-----TGSTRELQFHQAGPNTMAE
42_12            QFEDVPFHSSYAHSQSLDRLTNPLIDQYLYYLARTQST----TGSTRGLQFHQAGPNTMAE
AAV5\CAP         NFEEVPFHSSFAPSQNLFKLANPLVDQYLYRFVSTNNTGG-------VQFNKNLAGRYAN
```

FIG. 2H

```
                  490       500       510       520       530       540
             ....|....|....|....|....|....|....|....|....|....|....|....|
C1\VP1       YRKNWLPGPCVKQQRLSKTASQNYKIPASGGNALLKYDTHYTLNNRWSNIAPGPPMATAG
C2\VP1       YRKNWLPGPCVKQQRFSKTASQNYKIPASGGNALLKYDTHYTLNNRWSNIAPGPPMATAG
C5\VP1@2     YRKNWLPGPCVKQQRFSKTASQNYKIPASGGNALLKYDTHYTLNNRWSNIAPGPPMATAG
AAV4\VP1     FKKNWLPGPSIKQQGFSKTANQNYKIPATGSDSLIKYETHSTLDGRWSALTPGPPMATAG
AAV1         QPKNWLPGPCYRQQRVSKTKTDN-----NNSNFTWTGASKYNLNGRESIINPGTAMASHK
AAV6\VP1     QPKNWLPGPCYRQQRVSKTKTDN-----NNSNFTWTGASKYNLNGRESIINPGTAMASHK
A3_3         QAKNWLPGPSYRQQRMSKTANDN-----NNSEFAWTAATKYYLNGRNSLVNPGPPVASHK
A3_7         QAKNWLPGPSYRQQRMSKTANDN-----NNSEFAWTAATKYYLNGRNSLVNPGPPMASHK
A3_4         QAKNWLPGPSYRQQRMSKTANDN-----NNSEFAWTAATKYYLNGRNSLVNPGPPMASHK
A3_5         QAKNWLPGPSYRQQRMSKTANDN-----NNSEFAWTAATKYYPNGRNSLVNPGPPMASHK
AAV2         QSRNWLPGPCYRQQRVSKTSADN-----NNSEYSWTGATKYHLNGRDSLVNPGPAMASHK
AAV3         QARNWLPGPCYRQQRLSKTANDN-----NNSNFPWTAASKYHLNGRDSLVNPGPAMASHK
13.3b\VP1    QAKNWLPGPCFRQQRVSKTLDQN-----NNSNFAWTGATKYHLNGRNSLVNPGVAMATHK
AAV7         QAKNWLPGPCFRQQRVSKTLDQN-----NNSNFAWTGATKYHLNGRNSLVNPGVAMATHK
223_4        QAKNWLPGPCFRQQRVSKTLDQN-----NNSNFAWTGATKYHLNGRNSLVNPGVAMATHK
223_5        QAKNWLPGPCFRQQRVSKTLDQN-----NNSNFAWTGATKYHLNGRNSLVNPGVAMATHK
223_10       QAKNWLPGPCFRQQRVSKTLDQN-----NNSNFAWTGATKYHLNXRNSLVNPGVAMATHK
223_2        QAKNWLPGPCFRQQRVSKTLDQN-----NNSNFAWTGATKYHLNGRNSLVNPGVAMATHK
223_7        QAKNWLPGPCFRQQRVSKTLDQN-----NNSNFAWTGATKYHLNGRNSLVNPGVAMATHK
223_6        QAKNWLPGPCFRQQRVSKTLDQN-----NNSNFAWTGATKYHLNGRNSLVNPGVAMATHK
44_1         QAKNWLPGPCYRQQRVSTTLSQN-----NNSNFAWTGATKYHLNGRDSLVNPGVAMATHK
44_5         QAKNWLPGPCYRQQRVSTTLSQN-----NNSNFAWTGATKYHLNGRDSLVNPGVAMATHK
44_2         QAKNWLPGPCYRQQRVSTTLSQN-----NNSNFAWTGATKYHLNGRDSLVNPGVAMATHK
29.3\VP1     QAKNWLPGPCYRQQRVSTTLSQN-----NNSNFAWTGATKYHLNGRDSLVNPGVAMATHK
29.5\VP1     QAKNWLPGPCYRQQRVSTTLSQN-----DNSNFAWTGATKYHLNGRDSLVNPGVAMATHK
42_15        QAKNWLPGPCYRQQRVSTTLSQN-----NNSNFAWTGATKYHLNGRDSLVNPGVAMATHK
42_8         QAKNWLPGPCYRQQRVSTTLSQN-----NNSNFAWTGATKYHLNGRDSLVNPGVAMATHK
42_13        QAKNWLPGPCYRQQRVSTTVSQN-----NNSNFAWTGATKYHLNGRDSLVNPGVAMATHK
42_3A        QAKNWLPGPCYRQQRVSTTLSQN-----NNSNFAWTGATKYHLNGRDSLVNPGVAMATHK
42_4         QAKNWLPGPCYRQQRVSTTLSQN-----NNSNFAWTGATKYHLNGRDSLVNPGVAMATHK
42_5A        QAKNWLPGPCYRQQRVSTTLSQN-----NNSNFAWTGATKYHLNGRDSLVNPGVAMATHK
42_1B        QAKNWLPGPCYRQQRVSTTVSQN-----NNSNFAWTGATKYHLNGRDSLVNPGVAMATHK
42_5B        QAKNWLPGPCYRQQRVSTTLSQN-----NNSNFAWTGATKYHLNGRDSLVNPGVAMATHK
43_1         QAKNWLPGPCYRQQRVSTTLSQN-----NNSNFAWTGATKYHLNGRDSLVNPGVAMATHK
43_12        QAKNWLPGPCYRQQRVSTTLSQN-----NNSNFAWTGATKYHLNGRDSLVNPGVAMATHK
43_5         QAKNWLPGPCYRQQRVSTTLSQN-----NNSNFAWTGATKYHLNGRDSLVNPGVAMATHK
AAV8         QAKNWLPGPCYRQQRVSTTTGQN-----NNSNFAWTAGTKYHLNGRNSLANPGIAMATHK
43_21        QARNWVPGPCYRQQRVSTTTNQS-----NNSNFAWTGAAKFKLNGRDSLMNPGVAMASHK
43_25        QARNWVPGPCYRQQRVSTTTNQN-----NNSNFAWTGAAKFKLNGRDSLMNPGVAMASHK
43_23        QARNWVPGPCYRQQRVSTTTNQN-----NNSNFAWTGAAKFKLNGRDSLMNPGVAMASHK
43_20        QARNWVPGPCYRQQRVSTTTNQN-----NNSNFAWTGAAKFKLNGRDSLMNPGVAMASHK
AAV_9        QARNWVPGPCYRQQRVSTTTNQN-----NNSNFAWTGAAKFKLNGRDSLMNPGVAMASHK
24.1         QSKNWLPGPCYRQQRLSKNIDSN-----NNSNFAWTGATKYHLNGRNSLTNPGVAMATNK
42.2REAL     QSKNWLPGPCYRQQRLSKNIDSN-----NNSNFAWTGATKYHLNGRNSLTNPGVAMATNK
7.2\VP1      QSKNWLPGPCYRQQRLSKNIDSN-----NNSNFAWTGATKYHLNGRNSLTNPGVAMATNK
27.3\VP1     QSKNWLPGPCYRQQRLSKNIDSN-----NNSNFAWTGATKYHLNGRNSLTNPGVAMATNK
16.3\VP1     QSKNWLPGPCYRQQRLSKNIDSN-----NNSNFAWTGATKYHLNGRNSLTNPGVAMATNK
42_10        QSKNWLPGPCYRQQRLSKNIDSN-----NNSNFAWTGATKYHLNGRNSLTNPGVAMATNK
42_3B        QSKNWLPGPCYRQQRLSKNIDSN-----NTSNFAWTGATKYHLNGRNSLTNPGVAMATNK
42_11        QSKNWLPGPCYRRQRLSKDIDSN-----NNSNFAWTGATKYHLNGRNSLTNPGVAMATNK
F1\VP1       QSKNWLPGPCYRQQGLSKNLDFN-----NNSNFAWTAATKYHLNGRNSLTNPGIPMATNK
F5\VP1@3     QSKNWLPGPCYRQQRLSKNLDFN-----NNSNFAWTAATKYHLNGRNSLTNPGIPMATNK
F3\VP1       QSKNWLPGPCYRQQRLSKNLDFN-----NNSNFAWTAATKYHLNGRNSLTNPGIPMATNK
42_6B        QSKNWLPGPCYRQQRLSKNIDSN-----NNSNFAWTGATKYHLNGRNSLTNPGVAMATNK
42_12        QSKNWLPGPCYRQQRLSKNIDSN-----NNSNFAWTGATKYHLNGRNSLTNPGVAMATNK
AAV5\CAP     TYKNWFPGPMGRTQGWNLGSGVN-----RASVSAFATTNRMELEGASYQVPPQPNGMTNN
```

FIG. 21

```
                         550        560        570        580        590        600
                   ....|....|....|....|....|....|....|....|....|....|....|....|
C1\VP1             PSDGDFS-NAQLIFPGPS--VTGNTTTSAN-NLLFTSEEEIAATNPRDTDMFGQIADNNQ
C2\VP1             PSDGDFS-NAQLIFPGPS--VTGNTTTSAN-NLLFTSEGEIAATNPRDTDMFGQIADNNQ
C5\VP1@2           PSDGDFS-NAQLIFPGPS--VTGNTTTSAN-NLLFTSEEEIAATNPRDTDMFGQIADNNQ
AAV4\VP1           PADSKFS-NSQLIFAGPK--QNGNTATVPG-TLIFTSEEELAATNATDTDMWGNLPGGDQ
AAV1               DDEDKFFPMSGVMIFGKE--SAGASNTALD-NVMITDEEEIKATNPVATERFGTVAVNFQ
AAV6\VP1           DDKDKFFPMSGVMIFGKE--SAGASNTALD-NVMITDEEEIKATNPVATERFGTVAVNLQ
A3_3               DDEEKYFPMHGNLIFGKQ--GTGTTNVDIE-SVLITDEEEIRTTNPVATEQYGQVATNHQ
A3_7               DDEEKYFPMHGNLIFGKQ--GTGTTNVDIE-SVLITDEEEIRTTNPVATEQYGQVATNHQ
A3_4               DDEEKYFPMHGNLIFGKQ--GTGTTNVDIE-SVLITDEEEIRTTNPVATEQYGQVATNHQ
A3_5               DDEEKYFPMHGNLIFGKQ--GTGTTNVDIE-SVLITDEEEIRTTNPVATEQYGQVATNRQ
AAV2               DDEEKFFPQSGVLIFGKQ--GSEKTNVDIE-KVMITDEEEIRTTNPVATEQYGSVSTNLQ
AAV3               DDEEKFFPMHGNLIFGKE--GTTASNAELD-NVMITDEEEIRTTNPVATEQYGTVANNLQ
13.3b\VP1          DDEDRFFPSSGVLIFGKT--GATN-KTTLE-NVLMTNEEEIRPTNPVATEEYGIVSSNLQ
AAV7               DDEDRFFPSSGVLIFGKT--GATN-KTTLE-NVLMTNEEEIRPTNPVATEEYGIVSSNLQ
223_4              DDEERFFPSSGVLIFGKT--GAAN-KTTLE-NVLMTNEEEIRPTNPVATEEYGIVSSNLQ
223_5              DDEERFFPSSGVLIFGKT--GAAN-KTTLE-NVLMTNEEEIRPTNPVATEEYGIVSSNLQ
223_10             DDEERFFPSSGVLIFGKT--GAAN-KTTLE-NVLMTNEEEIRPTNPVATEEYGIVSSNLQ
223_2              DDEERFSPSSGVLIFGKT--GAAN-KTTLE-NVLMTNEEEIRPTNPVATEEYGIVSSNLQ
223_7              DDEERFFPSSGVLIFGKT--GAAN-KTTLE-NVLMTNEEEIRPTNPVATEEYGIVSSNLQ
223_6              DDEERFFPSSGVLIFGKT--GAAN-KTTLE-NVLMTNEEEIRPTNPVATEEYGIVSSNLQ
44_1               DDEERFFPSSGVLMFGKQ--GAGKDNVDYS-SVMLTSEEEIKTTNPVATEQYGVVADNLQ
44_5               DDEERFFPSSGVLMFGKQ--GAGKDNVDYS-SVMLTSEEEIKTTNPVATEQYGVVADNLQ
44_2               DDEERFFPSSGVLMFGKQ--GAGKDNVDYS-SVMLTSEEEIKTTNPVATEQYGVVADNLQ
29.3\VP1           DDEERFFPSSGVLMFGKQ--GAGKGNVDYS-SVMLTSEEEIKTTNPVATEQYGVVADNLQ
29.5\VP1           DDEERFFPSSGVLMFGKQ--GAGKDNVDYS-SVMLTSEEEIKTTNPVATEQYGVVADNLQ
42_15              DDEERFFPSSGVLMFGKQ--GAGKDNVDYS-SVMLTSEEEIKTTNPVATEQYGVVADNLQ
42_8               DDEERFFPSSGVLMFGKQ--GAGKDNVDYS-SVMLTSEEEIKTTNPVATEQYGVVADNLQ
42_13              GDEERFFPSSGVLMFGKQ--GAGKDNVDYS-SVMLTSEEEIKTTNPVATEQYGVVADNLQ
42_3A              DDEERFFPSSGVLMFGKQ--GAGKDNVDYS-SVMLTSEEEIKTTNPVATEQYGVVADNLQ
42_4               DDEERFFPSSGVLMFGKQ--GAGKDNVDYS-SVMLTSEEEIKTTNPVATEQYGVVADNLQ
42_5A              DDEERFFPSSGVLMFGKQ--GAGKDNVDYS-SVMLTSEEEIKTTNPVATEQYGVVADNLQ
42_1B              GDEERFFPSSGVLMFGKQ--GAGKDNVDYS-SVMLTSEEEIKTTNPVATEQYGVVADNLQ
42_5B              DDEERFFPSSGVLMFGKQ--GAGKDNVDYS-SVMLTSEEEIKTTNPVATEQYGVVADNLQ
43_1               DDEERFFPSSGVLMFGKQ--GAGKDNVDYS-SVMLTSEEEIKTTNPVATEQYGVVADNLQ
43_12              DDEERFFPSSGVLMFGKQ--GAGKDNVDYS-SVMLTSEEEIKTTNPVATEQYGVVADNLQ
43_5               DDEERFFPSSGVLMFGKQ--GAGKDNVDYS-SVMLTSEEEIKTTNPVATEQYGVVADNLQ
AAV8               DDEERFFPSNGILIFGKQ--NAARDNADYS-DVMLTSEEEIKTTNPVATEEYGIVADNLQ
43_21              DDDDRFFPSSGVLIFGKQ--GAGNDVDYS-QVLITDEEEIKATNPVATEEYGAVAINNQ
43_25              DDDDRFFPSSGVLIFGKQ--GAGNDVDYS-QVLITDEEEIKATNPVATEEYGAVAINNQ
43_23              DDDDRFFPSSGVLIFGKQ--GAGNDVDYS-QVLITDEEEIKATNPVATEEYGAVAINNQ
43_20              DDDDRFFPSSGVLIFGKQ--GAGNDVDYS-QVLITDEEEIKATNPVATEEYGAVAINNQ
AAV_9              DDEDRFFPSSGVLIFGKQ--GAGNDVDYS-QVLITDEEEIKATNPVATEEYGAVAINNQ
24.1               DDEDQFFPINGVLVFGKT--GAAN-KTTLE-NVLMTSEEEIKTTNPVATEEYGVVSSNLQ
42.2REAL           DDEDQFFPINGVLVFGET--GAAN-KTTLE-NVLMTSEEEIKTTNPVATEEYGVVSSNLQ
7.2\VP1            DDEDQFFPINGVLVFGKT--GAAN-KTTLE-NVLMTSEEEIKTTNPVATEEYGVVSSNLQ
27.3\VP1           DDEDQFLPINGVLVFGKT---GAAN-KTTLE-NVLMTSEEEIKTTNPVATEEYGVVSSNLQ
16.3\VP1           DDEGQFFPINGVLVFGKT---GAAN-KTTLE-NVLMTSEEEIKTTNPVATEEYGVVSSNLQ
42_10              DDEDQFFPINGVLVFGKT---GAAN-KTTLE-NVLMTSEEEIKTTNPVATEEYGVVSSNLQ
42_3B              DDEDQFFPINGVLVFGKT---GAAN-KTTLE-NVLMTSEEEIKTTNPVATEQYGVVSSNLQ
42_11              DDEDQFFPINGVLVFGKT---GAAN-KTTLE-NVLMTSEEEIKTTNPVATEEYGVVSSNLQ
F1\VP1             DDEDQFFPINGVLVFGKT---GAAN-KTTLE-NVLMTSEEEIKTTNPVATEEYGVVSSNLQ
F5\VP1@3           DDEDQFFPINGVLVFGKT---GAAN-KTTLE-NVLMTSEEEIKTTNPVATEEYGVVSSNLQ
F3\VP1             DDEDQFFPINGVLVFGKT---GAAN-KTTLE-NVLMTSEEEIKTTNPVATEEYGVVSSNLQ
42_6B              DDEDQFFPINGVLVFGKT---GAAN-KTTLE-NVLMTSEEEIKTTNPVATEEYGVVSSNLQ
42_12              DDEDQFFPINGVLVFGKT---GAAN-KTTLE-NVLMTSEEEIKTTNPVATEEYGVVSSNLQ
AAV5\CAP           LQGSNTYALENTMIFNSQPANPGTTATYLEGNMLITSESETQPVNRVAYNVGGQMATNNQ
```

FIG. 2J

```
                      610        620        630        640        650        660
                 ....|....|....|....|....|....|....|....|....|....|....|....|
C1\VP1           NATTAPITGNVTAMGVLPGMVWQNRDIYYQGPIWAKIPHADGHFHPSPLIGGFGLKHPPP
C2\VP1           NATTAPITGNVTAMGVLPGMVWQNRDIYYQGPIWAKIPHADGHFHPSPLIGGFGLKHPPP
C5\VP1@2         NATTAPITGNVTAMGVLPGMVWQNRDIYYQGPIWAKIPHADGHFHPSPLIGGFGLKHPPP
AAV4\VP1         SNSNLPTVDRLTALGAVPGMVWQNRDIYYQGPIWAKIPHTDGHFHPSPLIGGFGLKHPPP
AAV1             SSSTDPATGDVHAMGALPGMVWQDRDVYLQGPIWAKIPHTDGHFHPSPLMGGFGLKNPPP
AAV6\VP1         SSSTDPATGDVHVMGALPGMVWQDRDVYLQGPIWAKIPHTDGHFHPSPLMGGFGLKHPPP
A3_3             SQNTTASYGSVDSQGILPGMVWQDRDVYLQGPIWAKTPHTDGHFHPSPLMGGFGLKHPPP
A3_7             SQNTTASYGSVDSQGILPGMVWQDRDVYLQGPIWAKTPHTDGHFHPSPLMGGFGLKHPPP
A3_4             SQDTTASYGSVDSQGILPGMVWQDRDVYLQGPIWAKTPHTDGHFHPSPLMGGFGLKHPPP
A3_5             SQNTTASYGSVDSQGILPGMVWQDRDVYLQGPIWAKTPHTDGHFHPSPLMGGFGLKHPPP
AAV2             RGNRQAATADVNTQGVLPGMVWQDRDVYLQGPIWAKIPHTDGHFHPSPLMGGFGLKHPPP
AAV3             SSNTAPTTGTVNHQGALPGMVWQDRDVYLQGPIWAKIPHTDGHFHPSPLMGGFGLKHPPP
13.3b\VP1        AANTAAQTQVVNNQGALPGMVWQNRDVYLQGPIWAKIPHTDGNFHPSPLMGGFGLKHPPP
AAV7             AANTAAQTQVVNNQGALPGMVWQNRDVYLQGPIWAKIPHTDGNFHPSPLMGGFGLKHPPP
223_4            AASTAAQTQVVNNQGALPGMVWQNRDVYLQGPIWAKIPHTDGNFHPSPLMGGFGLKHPPP
223_5            AASTAAQTQVVNNQGALPGMVWQNRDVYLQGPIWAKIPHTDGNFHPSPLMGGFGLKHPPP
223_10           AASTAAQTQVVNNQGALPGMVWQNRDVYLQGPIWAKIPHTDGNFHPSPLMGGFGLKHPPP
223_2            AASTAAQTQVVNNQGALPGMVWQNRDVYLQGPIWAKIPHTDGNFHPSPLMGGFGLKHPPP
223_7            AASTAAQTQVVNNQGALPGMVWQNRDVYLQGPIWAKIPHTDGNFHPSPLMGGFGLKHPPP
223_6            AASTAAQTQVVNNQGALPGMVWQNRDVYLQGPIWAKIPHTDGNFHPSPLMGGFGLKHPPP
44_1             QQNAAPIVGAVNSQGALPGMVWQNRDVYLQGPIWAKIPHTDGNFHPSPLMGGFGLKHPPP
44_5             QQNAAPIVGAVNSQGALPGMVWQNRDVYLQGPIWAKIPHTDGNFHPSPLMGGFGLKHPPP
44_2             QQNAAPIVGAVNSQGALPGMVWQNRDVYLQGPIWAKIPHTDGNFHPSPLMGGFGLKHPPP
29.3\VP1         QQNAAPIVGAVNSQGALPGMVWQNRDVYLQGPIWAKIPHTDGNFHPSPLMGGFGLKHPPP
29.5\VP1         QQNAAPIVGAVNSQGALPGMVWQNRDVYLQGPIWAKIPHTDGNFHPSPLMGGFGLKHPPP
42_15            QQNAAPIVGAVNSQGALPGMVWQNRDVYLQGPIWAKIPHTDGNFHPSPLMGGFGLKHPPP
42_8             QQNAAPIVGAVNSQGALPGMVWQNRDVYLQGPIWAKIPHTDGNFHPSPLMGGFGLKHPPP
42_13            QQNAAPIVGAVNSQGALPGMVWQNRDVYLQGPIWAKIPHTDGNFHPSPLMGGFGLKHPPP
42_3A            QQNAAPIVGAVNSQGALPGMVWQNRDVYLQGPIWAKIPHTDGNFHPSPLMGGFGLKHPPP
42_4             QQNAAPIVGAVNSQGALPGMVWQNRDVYLQGPIWAKIPHTDGNFHPSPLMGGFGLKHPPP
42_5A            QQNAAPIVGAVNSQGALPGMAWQNRDVYLQGPIWAKIPHTDGNFHPSPLMGGFGLKHPPP
42_1B            QQNAAPIVGAVNSQGALPGMVWQNRDVYLQGPIWAKIPHTDGNFHPSPLMGGFGLKHPPP
42_5B            QQNAAPIVGAVNSQGALPGMVWQNRDVYLQGPIWAKIPHTDGNFHPSPLMGGFGLKHPPP
43_1             QTNGAPIVGTVNSQGALPGMVWQNRDVYLQGPIWAKIPHTDGNFHPSPLMGGFGLKHPPP
43_12            QTNGAPIVGTVNSQGALPGMVWQNRDVYLQGPIWAKIPHTDGNFHPSPLMGGFGLKHPPP
43_5             QTNGAPIVGTVNSQGALPGMVWQNRDVYLQGPIWAKIPHTDGNFHPSPLMGGFGLKHPPP
AAV8             QQNTAPQIGTVNSQGALPGMVWQNRDVYLQGPIWAKIPHTDGNFHPSPLMGGFGLKHPPP
43_21            AANTQAQTGLVHNQGVIPGMVWQNRDVYLQGPIWAKIPHTDGNFHPSPLMGGFGLKHPPP
43_25            AANTQAQTGLVHNQGVIPGMVWQNRDVYLQGPIWAKIPHTDGNFHPSPLMGGFGLKHPPP
43_23            AANTQAQTGLVHNQGVIPGMVWQNRDVYLQGPIWAKIPHTDGNFHPSPLMGGFGLKHPPP
43_20            AANTQAQTGLVHNQGVIPGMVWQNRDVYLQGPIWAKIPHTDGNFHPSPLMGGFGLKHPPP
AAV_9            AANTQAQTGLVHNQGVIPGMVWQNRDVYLQGPIWAKIPHTDGNFHPSPLMGGFGLKHPPP
24.1             SSTAGPQTQTVNSQGALPGMVWQNRDVCLQGPIWAKIPHTDGNFHPSPLMGGFGLKHPPP
42.2REAL         SSTAGPQTQTVNSQGALPGMVWQNRDVYLQGPIWAKIPHTDGNFHPSPLMGGFGLKHPPP
7.2\VP1          SSTAGPQTQTVNSQGALPGMVWQNRDVYLQGPIWAKIPHTDGNFHPSPLMGGFGLKHPPP
27.3\VP1         SSTAGPRTQTVNSQGALPGMVWQNRDVYLQGPIWAEIPHTDGNFHPSPLMGGFGLKHPPP
16.3\VP1         SSTAGPQTQTVNSQGALPGMVWQNRDVYLQGPIWAKIPHTDGNFHPSPLMGGFGLKHPPP
42_10            SSTAGPQTQTVNSQGALPGMVWQNRDVYLQGPIWAKIPHTDGNFHPSPLMGGFGLKHPPP
42_3B            SSTAGPQTQTVNSQGALPGMVWQNRDVYLQGPIWAKIPHTDGNFHPSPLMGGFGLKHPPP
42_11            SSTAGPQTQTVNSQGALPGMVWQNRDVYLQGPIWAKIPHTDGNFHPSPLMGGFGLKHPPP
F1\VP1           PSTAGPQSQTINSQGALPGMVWQNRDVYLQGPIWAKIPHTDGNFHPSPLMGGFGLKHPPP
F5\VP1@3         SSTAGPQSQTINSQGALPGMVWQNRDVYLQGPIWAKIPHTDGNFHPSPLMGGFGLEHPPP
F3\VP1           SSTAGPQSQTINSQGALPGMVWQNRDVYLQGPIWAKIPHTDGNFHPSPLMGGFGLKHPPP
42_6B            SSTAGPQTQTVNSQGALPGMVWQNRDVYLQGPIWAKIPHTDGNFHPSPLMDGFGLKHPPP
42_12            SSTAGPQTQTVNSQGALPGMVWQNRDVYLQGPIWAKIPHTDGNFHPSPLMGGFGLKHPPP
AAV5\CAP         SSTTAPATGTYNLQEIVPGSVWMERDVYLQGPIWAKIPETGAHFHPSPAMGGFGLKHPPP
```

FIG. 2K

```
                      670        680        690        700        710        720
              ....|....|....|....|....|....|....|....|....|....|....|....|....|
C1\VP1        QIFIKNTPVPANPATTFTAARVDSFITQYSTGQVAVQIEWEIEKERSKRWNPEVQFTSNY
C2\VP1        QIFIKNTPVPANPATTFTAARVDSFITQYSTGQVAVQIEWEIEKERSKRRNPEVQFTSNY
C5\VP1@2      QIFIKNTPVPAYPATTFTAARVDSFITQYSTGQVAVQIEWEIEKERSKRWNPEVQFTSNC
AAV4\VP1      QIFIKNTPVPANPATTFSSTPVNSFITQYSTGQVSVQIDWEIQKERSKRWNPEVQFTSNY
AAV1          QILIKNTPVPANPPAEFSATKFASFITQYSTGQVSVEIEWELQKENSKRWNPEVQYTSNY
AAV6\VP1      QILIKNTPVPANPPAEFSATKFASFITQYSTGQVSVEIEWELQKENSKRWNPEVQYTSNY
A3_3          QILIKNTPVPANPATTFTPGKFASFITQYSTGQVSVEIEWELQKENSKRWNPEIQYTSNY
A3_7          QILIKNTPVPANPATTFTPGKFASFITQYSTGQVSVEIEWELQKENSKRWNPEIQYTSNY
A3_4          QILIKNTPVPANPATTFTPGKFASFITQYSTGQVSVEIEWELQKENSKRWNPEIQYTSNY
A3_5          QILIKNTPVPANPATTFTPGKFASFITQYSTGQVSVEIEWELQKENSKRWNPEIQYTSNY
AAV2          QILIKNTPVPANPSTTFSAAKFASFITQYSTGQVSVEIEWELQKENSKRWNPEIQYTSNY
AAV3          QIMIKNTPVPANPPTTFSPAKFASFITQYSTGQVSVEIEWELQKENSKRWNPEIQYTSNY
13.3b\VP1     QILIKNTPVPANPPEVFTPAKFASFITQYSTGQVSVEIEWELQKENSKRWDPEIQYTSNF
AAV7          QILIKNTPVPANPPEVFTPAKFASFITQYSTGQVSVEIEWELQKENSKRWNPEIQYTSNF
223_4         QILIKNTPVPANPPEVFTPAKFASFITQYSTGQVSVEIEWELQKENSKRWNPEIQYTSNF
223_5         QILIKNTPVPANPPEVFTPAKFASFITQYSTGQVSVEIEWELQKENSKRWNPEIQYTSNF
223_10        QILIKNTPVPANPPEVFTPAKFASFITQYSTGQVSVEIEWELQKENSKRWNPEIQYTSNF
223_2         QILIKNTPVPANPPEVFTPAKFASFITQYSTGQVSVEIEWELQKENSKRWNPEIQYTSNF
223_7         QILIKNTPVPANPPEVFTPAKIASFITQYSTGQVSVEIEWELQKENSKRWNPEIQYTSNF
223_6         QILIKNTPVPANPPEVFTPAKLASFITQYSTGQVSVEIEWELQKENSKRWNPEIQYTSNF
44_1          QILIKNTPVPADPPTTFSQAKLASFITQYSTGQVSVEIEWELQKENSKRWNPEIQYTSNY
44_5          QILIKNTPVPADPPTTFSQAKLASFITQYSTGQVSVEIEWELQKENSKRWNPEIQYTSNY
44_2          QILIKNTPVPADPPTTFSQAKLASFITQYSTGQVSVEIEWELQKENSKRWNPEIQYTSNY
29.3\VP1      QILIKNTPVPADPPTTFSQAKLASFITQYSTGQVSVEIEWELQKENSKRWNPEIQYTSNY
29.5\VP1      QILIKNTPVPADPPTTFSQAKLASFITQYSTGQVSVEIEWELQKENSKRWNPEIQYTSNY
42_15         QILIKNTPVPADPPTTFSQAKLASFITQYSTGQVSVEIEWELQKENSKRWNPEIQYTSNY
42_8          QILIKNTPVPADPPTTFSQAKLASFITQYSTGQVSVEIEWELQKENSKRWNPEIQYTSNY
42_13         QILIKNTPVPADPPTTFSQAKLASFITQYSTGQVSVEIEWELQKENSKRWNPEIQYTSNY
42_3A         QILIKNTPVPADPPTTFSQAKLASFITQYSTGQVSVEIEWELQKENSKRWNPEIQYTSNY
42_4          QILIKNTPVPADPPTTFSQAKPASFITQYSTGQVSVEIEWELQKENSKRWNPEIQYTSNY
42_5A         QILIKNTPVPADPPTTFSQAKLASFITQYSTGQVSVEIEWELQKENSKRWNPEIQYTSNY
42_1B         QILIKNTPVPADPPTTFSQAKLASFITQYSTGQVSVEIEWELQKENSKRWNPEIQYTSNY
42_5B         QILIKNTPVPADPPTTFSQAKLASFITQYSTGQVSVEIEWELQKENSKRWNPEIQYTSNY
43_1          QILVKNTPVPADPPTTFSQAKLASFITQYSTGQVSVEIEWELQKENSKRWNPEIQYTSNY
43_12         QILVKNTPVPADPPTTFSQAKLASFITQYSTGQVSVEIEWELQKENSKRWNPEIQYTSNY
43_5          QILVKNTPVPADPPTTFSQAKLASFITQYSTGQVSVEIEWELQKENSKRWNPEIQYTSNY
AAV8          QILIKNTPVPADPPTTFNQSKLNSFITQYSTGQVSVEIEWELQKENSKRWNPEIQYTSNY
43_21         QILIKNTPVPADPPLTFNQAKLNSFITQYSTGQVSVEIEWELQKENSKRWNPEIQYTSNY
43_25         QILIKNTPVPADPPLTFNQAKLNSFITQYSTGQVSVEIEWELQKENSKRWNPEIQYTSNY
43_23         QILIKNTPVPADPPLTFNQAKLNSFITQYSTGQVSVEIEWELQKENSKRWNPEIQYTSNY
43_20         QILIKNTPVPADPPLTFNQAKLNSFITQYSTGQVSVEIEWELQKENSKRWNPEIQYTSNY
AAV_9         QILIKNTPVPADPPLTFNQAKLNSFITQYSTGQVSVEIEWELQKENSKRWNPEIQYTSNY
24.1          QILIKNTPVPANPPEVFTPAKFASFITQYSTGQVSVEIEWELQKENSKRWNPEIQYTSNY
42.2REAL      QILIKNTPVPANPPEVFTPAKFASFITQYSTGQVSVEIEWELQKENSKRWNPEIQYTSNY
7.2\VP1       QILIKNTPVPANPPEVFTPAKFASFITQYSTGQVSVEIEWELQKENSKRWNPEIQYTSNY
27.3\VP1      QILIKNTPVPANPPEVFTPAKFASFITQYSTGQVSVEIEWELQKENSKRWNPEIQYTSNY
16.3\VP1      QILIKNTPVPANPPGVFTPALFASFITQYSTGQVSVEIEWELQKENSKRWNPEIQYTSNY
42_10         QILIKNTPVPANPPEVFTPAKFASFITQYSTGQVSVEIEWELQKENSKRWNPEIQYTSNY
42_3B         QILIKNTPVPANPPEVFTPAKFASFITQYSTGQVSVEIEWELQKENSKRWNPEIQYTSNY
42_11         QILIKNTPVPANPPEVFTPAKFASFITQYSTGQVSVEIEWELQKENSKRWNPEIQYTSNY
F1\VP1        QILIKNTPVPANPPEVFTPAKFASFITQYSTGQVSVEIEWELQKENSKRWNPEIQYTSNY
F5\VP1@3      QILIKNTPVPANPPEVFTPAKFASFITQYSTGQVSVEIEWELQKENSKRWNPEIQYTSNY
F3\VP1        QILIKNTPVPANPPEVFTPAKFASFITQYSTGQVSVEIEWELQKENSKRWNPEIQYTSNY
42_6B         QILIKNTPVPANPPEVFTPAKFASFITQYSTGQVSVEIEWELQKENSKRWNPEIQYTSNY
42_12         QILIK-------------------------------------------------YTSNY
AAV5\CAP      MMLIKNTPVPGN-ITSFSDVPVSSFITQYSTGQVTVEMEWELKKENSKRWNPEIQYTNNY
```

FIG. 2L

```
                        730       740       750
                  ....|....|....|....|....|....|.
C1\VP1            GNQSSMLWAPDTTGKYTEPRVIGSRYLTNHL
C2\VP1            GNQSSMLWAPDTTGKYTEPRVIGSRYLTNHL
C5\VP1@2          GNQSSMLWAPDTTGKYTEPRVIGSRYLTNHL
AAV4\VP1          GQQNSLLWAPDAAGKYTEPRAIGTRYLTHHL
AAV1              AKSANVDFTVDNNGLYTEPRPIGTRYLTRPL
AAV6\VP1          AKSANVDFTVDNNGLYTEPRPIGTRYLTRPL
A3_3              NKSVNVEFTVDANGVYSEPRPIGTRYLTRNL
A3_7              NKSVNVEFTVDANGVYSEPRPIGTRYLTRNL
A3_4              NKSVNVEFTVDANGVYSEPRPIGTRYLTRNL
A3_5              NKSVNVEFTVDANGVYSEPRPIGTRYLTRNL
AAV2              NKSVNVDFTVDTNGVYSEPRPIGTRYLTRNL
AAV3              NKSVNVDFTVDTNGVYSEPRPIGTRYLTRNL
13.3b\VP1         EKQTGVDFAVDSQGVYSEPRPIGTRYLTRNL
AAV7              EKQTGVDFAVDSQGVYSEPRPIGTRYLTRNL
223_4             DKQTGVDFAVDSQGVYSEP------------
223_5             DKQTGVDFAVDSQGVYSEP------------
223_10            DKQTGVDFAVDSQGVYSEP------------
223_2             DKQTGVDFAVDSQGVYSEP------------
223_7             DKQTGVDFAVDSQGVYSEP------------
223_6             DKQTGVDFAVDSQGVYSEP------------
44_1              YKSTNVDFAVNTDGTYSEPRPIGTRYLTRNL
44_5              YKSTNVDFAVNTDGTYSEPRPIGTRYLTRNL
44_2              YKSTNVDFAVNTDGTYSEPRPIGTRYLTRNL
29.3\VP1          YKSTNVDFAVNTDGTYSEPRPIGTRYLTRNL
29.5\VP1          YKSTNVDFAVNTDGTYSEPRPIGTRYLTRNL
42_15             YKSTNVDFAVNTEGTYSEPRPIGTRYLTRNL
42_8              YKSTNVDFAVNTEGTYSEPRPIGTRYLTRNL
42_13             YKSTNVDFAVNTEGTYSEPRPIGTRYLTRSL
42_3A             YKSTNVDFAVNTEGTYSEPRPIGTRYLTRNL
42_4              YKSTNVDFAVNTEGTYSEPRPIGTRYLTRNL
42_5A             YKSTNVDFAVNTEGTYSEPRPIGTRYLTRNL
42_1B             YKSTNVDFAVNTEGTYSEPRPIGTRYLTRNL
42_5B             YKSTNVDFAVNTEGTYSEPRPIGTRYLTRNL
43_1              YKSTNVDFAVNTEGTYSEPRPIGTRYLTRNL
43_12             YKSTNVDFAVNTEGTYSEPRPIGTRYLTRNL
43_5              YKSTNVDFAVNTEGTYSEPRPIGTRYLTRNL
AAV8              YKSTSVDFAVNTEGVYSEPRPIGTRYLTRNL
43_21             YKSTNVDFAVNTEGVYSEPRPIGTRYLTRNL
43_25             YKSTNVDFAVNTEGVYSEPRPIGTRYLTRNL
43_23             YKSTNVDFAVNTEGVYSEPRPIGTRYLTRNL
43_20             YKSTNVDFAVNTEGVYSEPRPIGTRYLTRNL
AAV_9             YKSTNVDFAVNTEGVYSEPRPIGTRYLTRNL
24.1              AKSNNVEFAVNNEGVYTEPRPIGTRYLTRNL
42.2REAL          AKSNNVEFAVNNEGVYTEPRPIGTRYLTRNL
7.2\VP1           AKSNNVEFAVNNEGVYTEPRPIGTRYLTRNL
27.3\VP1          AKSNNVEFAVNNEGVYTEPRPIGTRYLTRNL
16.3\VP1          AKSNNVEFAVNNEGVYTEPRPIGTRYLTRNL
42_10             AKSNNVEFAVNNEGVYTEPRPIGTRYLTRNL
42_3B             AKSNNVEFAVNNEGVYTEPRPIGTRYLTRNL
42_11             AKSNNVEFAVNNEGVYTEPRPIGTRYLTRNL
F1\VP1            AKSNNVEFAVNPDGVYTEPRPIGTRYLPRNL
F5\VP1@3          AKSNNVEFAVNPDGVYTEPRPIGTRYLTRNL
F3\VP1            AKSNNVEFAVNPDGVYTEPRPIGTRYLTRNL
42_6B             AKSNNVEFAVNNEGVYTEPRPIGTRYLTRNL
42_12             YKSTNVDFAVNTEGTYSEPRPIGTRYLTPNL
AAV5\CAP          NDPQFVDFAPDSTGEYRTTRPIGTRYLTRPL
```

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
            50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
                100                 105                 110

Arg Glu Lys Leu Val Gln Thr Ile Tyr Arg Gly Val Glu Pro Thr Leu
                115                 120                 125

Pro Asn Trp Phe Ala Val Thr Lys Thr Arg Asn Gly Ala Gly Gly Gly
            130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Leu Asn
                195                 200                 205

Pro Asn Ser Asp Ala Pro Val Ile Arg Ser Lys Thr Ser Ala Arg Tyr
                210                 215                 220

Fig. 3B

Met Glu Leu Val Gly Trp Leu Val Asp Arg Gly Ile Thr Ser Glu Lys
225             230             235             240

Gln Trp Ile Gln Glu Asp Gln Ala Ser Tyr Ile Ser Phe Asn Ala Ala
        245             250             255

Ser Asn Ser Arg Ser Gln Ile Lys Ala Ala Leu Asp Asn Ala Gly Lys
            260             265             270

Ile Met Ala Leu Thr Lys Ser Ala Pro Asp Tyr Leu Val Gly Pro Ser
        275             280             285

Leu Pro Ala Asp Ile Lys Thr Asn Arg Ile Tyr Arg Ile Leu Glu Leu
    290             295             300

Asn Gly Tyr Asp Pro Ala Tyr Ala Gly Ser Val Phe Leu Gly Trp Ala
305             310             315             320

Gln Lys Lys Phe Gly Lys Arg Asn Thr Ile Trp Leu Phe Gly Pro Ala
            325             330             335

Thr Thr Gly Lys Thr Asn Ile Ala Glu Ala Ile Ala His Ala Val Pro
            340             345             350

Phe Tyr Gly Cys Val Asn Trp Thr Asn Glu Asn Phe Pro Phe Asn Asp
        355             360             365

Cys Val Asp Lys Met Val Ile Trp Trp Glu Glu Gly Lys Met Thr Ala
    370             375             380

Lys Val Val Glu Ser Ala Lys Ala Ile Leu Gly Gly Ser Lys Val Arg
385             390             395             400

Val Asp Gln Lys Cys Lys Ser Ser Ala Gln Ile Asp Pro Thr Pro Val
            405             410             415

Ile Val Thr Ser Asn Thr Asn Met Cys Ala Val Ile Asp Gly Asn Ser
        420             425             430

Thr Thr Phe Glu His Gln Gln Pro Leu Gln Asp Arg Met Phe Lys Phe
        435             440             445

Fig. 3C

Glu Leu Thr Arg Arg Leu Glu His Asp Phe Gly Lys Val Thr Lys Gln
    450             455             460

Glu Val Lys Glu Phe Phe Arg Trp Ala Ser Asp His Val Thr Glu Val
465             470             475                         480

Ala His Glu Phe Tyr Val Arg Lys Gly Gly Ala Ser Lys Arg Pro Ala
                485             490             495

Pro Asp Asp Ala Asp Ile Ser Glu Pro Lys Arg Ala Cys Pro Ser Val
            500             505             510

Ala Asp Pro Ser Thr Ser Asp Ala Glu Gly Ala Pro Val Asp Phe Ala
            515             520             525

Asp Arg Tyr Gln Asn Lys Cys Ser Arg His Ala Gly Met Ile Gln Met
    530             535             540

Leu Phe Pro Cys Lys Thr Cys Glu Arg Met Asn Gln Asn Phe Asn Ile
545             550             555                         560

Cys Phe Thr His Gly Val Arg Asp Cys Leu Glu Cys Phe Pro Gly Val
                565             570             575

Ser Glu Ser Gln Pro Val Val Arg Lys Lys Thr Tyr Arg Lys Leu Cys
            580             585             590

Ala Ile His His Leu Leu Gly Arg Ala Pro Glu Ile Ala Cys Ser Ala
        595             600             605

Cys Asp Leu Val Asn Val Asp Leu Asp Asp Cys Val Ser Glu Gln
    610             615             620

US 11,034,977 B2

METHOD OF DETECTING AND/OR IDENTIFYING ADENO-ASSOCIATED VIRUS (AAV) SEQUENCES AND ISOLATING NOVEL SEQUENCES IDENTIFIED THEREBY

CROSS-REFERENCE TO RELATED APPLICATIONS

This application is a continuation of U.S. patent application Ser. No. 15/584,674, filed May 5, 2017, which is a continuation of U.S. patent application Ser. No. 14/956,934, filed Dec. 2, 2015, now U.S. Pat. No. 10,041,090, issued Aug. 7, 2018, which is a continuation of U.S. patent application Ser. No. 13/633,971, filed Oct. 3, 2012, now U.S. Pat. No. 9,790,472, issued Oct. 17, 2017, which is a divisional of U.S. patent application Ser. No. 12/962,793, filed Dec. 8, 2010, now U.S. Pat. No. 8,524,446, issued Sep. 3, 2013, which is a continuation of U.S. patent application Ser. No. 10/291,583, filed Nov. 12, 2002, now abandoned, which claims the benefit under 35 USC 119(e) of U.S. Provisional Patent Application No. 60/386,675, filed Jun. 5, 2002, U.S. Provisional Patent Application No. 60/377,066, filed May 1, 2002, U.S. Provisional Patent Application No. 60/341,117, filed Dec. 17, 2001, and U.S. Provisional Patent Application No. 60/350,607, filed Nov. 13, 2001. These applications are incorporated by reference herein.

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recent studies suggest that AAV vectors may be the preferred vehicle for gene therapy. To date, there have been 6 different serotypes of AAVs isolated from human or non-human primates (NHP) and well characterized. Among them, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B.

What are desirable are AAV-based constructs for gene delivery.

SUMMARY OF THE INVENTION

In one aspect, the invention provides a novel method of detecting and identifying AAV sequences from cellular DNAs of various human and non-human primate (NHP) tissues using bioinformatics analysis, PCR based gene amplification and cloning technology, based on the nature of latency and integration of AAVs in the absence of helper virus co-infection.

In another aspect, the invention provides method of isolating novel AAV sequences detected using the above described method of the invention. The invention further comprises methods of generating vectors based upon these novel AAV serotypes, for serology and gene transfer studies solely based on availability of capsid gene sequences and structure of rep/cap gene junctions.

In still another aspect, the invention provides a novel method for performing studies of serology, epidemiology, biodistribution and mode of transmission, using reagents according to the invention, which include generic sets of primers/probes and quantitative real time PCR.

In yet another aspect, the invention provides a method of isolating complete and infectious genomes of novel AAV serotypes from cellular DNA of different origins using RACE and other molecular techniques.

In a further aspect, the invention provides a method of rescuing novel serotypes of AAV genomes from human and NHP cell lines using adenovirus helpers of different origins.

In still a further aspect, the invention provides novel AAV serotypes, vectors containing same, and methods of using same.

These and other aspects of the invention will be readily apparent from the following detailed description of the invention.

BRIEF DESCRIPTION OF THE DRAWINGS

FIGS. 2A through 2M are an alignment of the amino acid sequences of the proteins of the vp1 capsid proteins of previously published AAV serotypes 1 [SEQ ID NO:64], AAV2 [SEQ ID NO:70], AAV3 [SEQ ID NO: 71], AAV4 [SEQ ID NO:63], AAV5 [SEQ ID NO:114], and AAV6 [SEQ ID NO:65] and novel AAV sequences of the invention, including: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], 42-12 [SEQ ID NO: 113]. Novel serotypes AAV8 [SEQ ID NO:95] and AAV9 [SEQ ID NO:100] are the subject of co-filed patent applications.

FIGS. 3A through 3C provide the amino acid sequences of the AAV7 rep proteins [SEQ ID NO:3].

DETAILED DESCRIPTION OF THE INVENTION

Figure 1E:
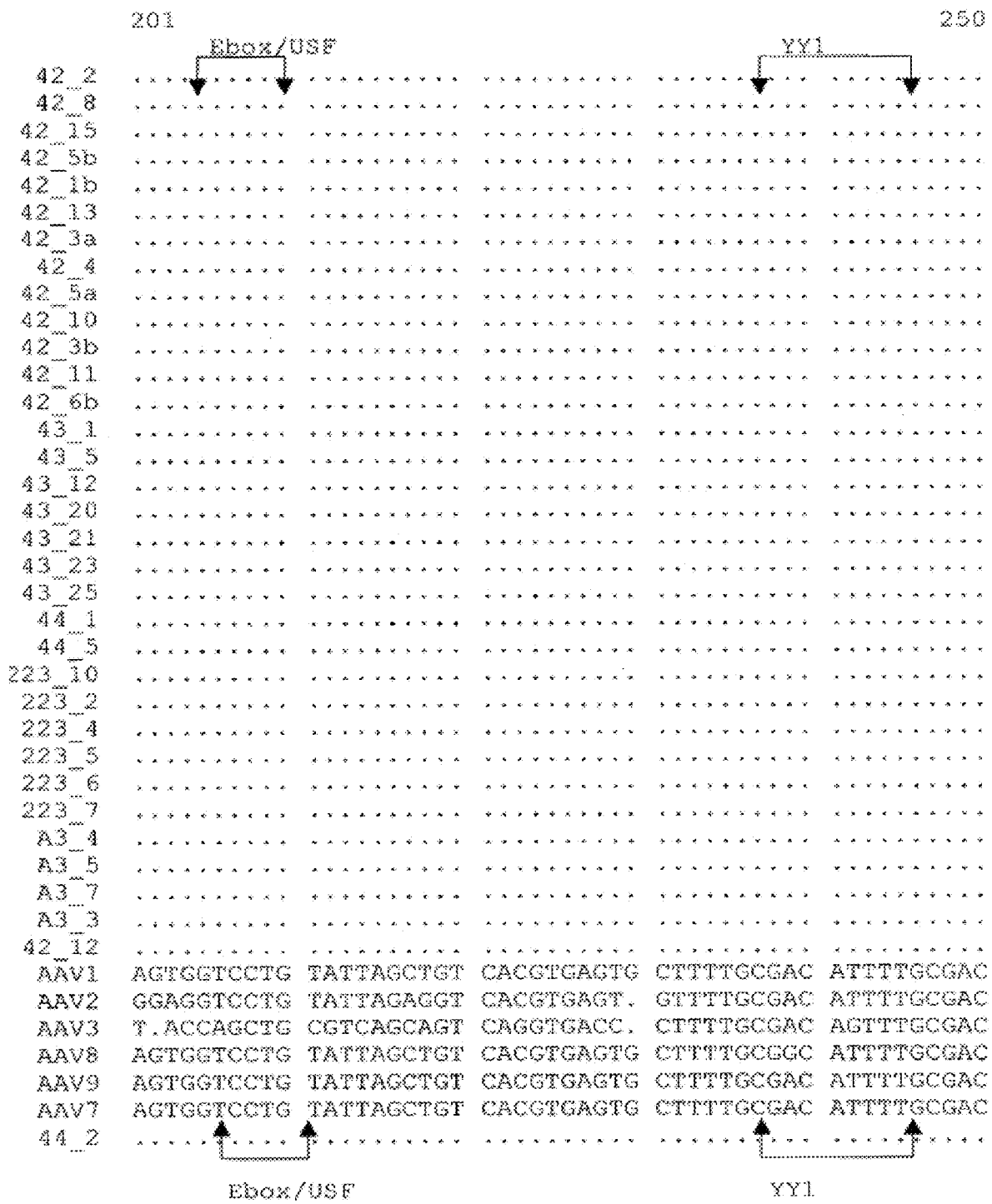
FIGS. 1A through 1AAAR provide an alignment of the nucleic acid sequences encoding at least the cap proteins for the AAV serotypes. The full-length sequences including the ITRs, the rep region, and the capsid region are provided for novel AAV serotype 7 [SEQ ID NO:1], and for previously published AAV1 [SEQ IN NO:6], AAV2 [SEQ ID NO:7]; and AAV3 [SEQ ID NO:8]. Novel AAV serotypes AAV8 [SEQ ID NO:4] and AAV9 [SEQ ID NO:5] are the subject of co-filed applications. The other novel clones of the invention provided in this alignment include: 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], 44.2 [SEQ ID NO: 59]. The nucleotide sequences of the signature regions of AAV10 [SEQ ID NO: 117], AAV11 [SEQ ID NO: 118] and AAV12 [SEQ ID NO:119] are provided in this figure. Critical landmarks in the structures of AAV genomes are shown. Gaps are demonstrated by dots. The 3' ITR of AAV1 [SEQ ID NO:6] is shown in the same configuration as in the published sequences. TRS represents terminal resolution site. Notice that AAV7 is the only AAV reported that uses GTG as the initiation codon for VP3.

In the present invention, the inventors have found a method which takes advantage of the ability of adeno-associated virus (AAV) to penetrate the nucleus, and, in the absence of a helper virus co-infection, to integrate into cellular DNA and establish a latent infection. This method utilizes a polymerase chain reaction (PCR)-based strategy for detection, identification and/or isolation of sequences of AAVs from DNAs from tissues of human and non-human primate origin as well as from other sources. Advantageously, this method is also suitable for detection, identification and/or isolation of other integrated viral and non-viral sequences, as described below.

The invention further provides nucleic acid sequences identified according to the methods of the invention. One such adeno-associated virus is of a novel serotype, termed herein serotype 7 (AAV7). Other novel adeno-associated virus serotypes provided herein include AAV10, AAV11, and AAV12. Still other novel AAV serotypes identified according to the methods of the invention are provided in the present specification. See, Figures and Sequence Listing, which is incorporated by reference.

Also provided are fragments of these AAV sequences. Among particularly desirable AAV fragments are the cap proteins, including the vp1, vp2, vp3, the hypervariable regions, the rep proteins, including rep 78, rep 68, rep 52, and rep 40, and the sequences encoding these proteins. Each of these fragments may be readily utilized in a variety of vector systems and host cells. Such fragments may be used alone, in combination with other AAV sequences or fragments, or in combination with elements from other AAV or non-AAV viral sequences. In one particularly desirable embodiment, a vector contains the AAV cap and/or rep sequences of the invention.

As described herein, alignments are performed using any of a variety of publicly or commercially available Multiple Sequence Alignment Programs, such as AClustal accessible through Web Servers on the internet. Alternatively, Vector NTI utilities are also used. There are also a number of algorithms known in the art which can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similar programs are available for amino acid sequences, e.g., the "Clustal X" program. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The term "substantial homology" or "substantial similarity," when referring to amino acids or fragments thereof, indicates that, when optimally aligned with appropriate amino acid insertions or deletions with another amino acid, there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

The AAV sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV sequences of the invention.

As described herein, the vectors of the invention containing the AAV capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below. As used throughout this specification and the claims, the terms A comprising≅ and "including" and their variants are inclusive of other components, elements, integers, steps and the like. Conversely, the term "consisting" and its variants is exclusive of other components, elements, integers, steps and the like.

I. Methods of the Invention

A. Detection of Sequences Via Molecular Cloning

In one aspect, the invention provides a method of detecting and/or identifying target nucleic acid sequences in a sample. This method is particularly well suited for detection of viral sequences which are integrated into the chromosome of a cell, e.g., adeno-associated viruses (AAV) and retroviruses, among others. The specification makes reference to AAV, which is exemplified herein. However, based on this information, one of skill in the art may readily perform the methods of the invention on retroviruses [e.g., feline leukemia virus (FeLV), HTLVI and HTLVII], and lentivirinae [e.g., human immunodeficiency virus (HIV), simian immunodeficiency virus (SIV), feline immunodeficiency virus (FIV), equine infectious anemia virus, and spumavirinal)], among others. Further, the method of the invention may also be used for detection of other viral and non-viral sequences, whether integrated or non-integrated into the genome of the host cell.

As used herein, a sample is any source containing nucleic acids, e.g., tissue, tissue culture, cells, cell culture, and biological fluids including, without limitation, urine and blood. These nucleic acid sequences may be DNA or RNA from plasmids, natural DNA or RNA from any source, including bacteria, yeast, viruses, and higher organisms such as plants or animals. DNA or RNA is extracted from the sample by a variety of techniques known to those of skill in the art, such as those described by Sambrook, Molecular Cloning: A Laboratory Manual (New York: Cold Spring Harbor Laboratory). The origin of the sample and the method by which the nucleic acids are obtained for application of the method of the invention is not a limitation of the present invention. Optionally, the method of the invention can be performed directly on the source of DNA, or on nucleic acids obtained (e.g., extracted) from a source.

The method of the invention involves subjecting a sample containing DNA to amplification via polymerase chain reaction (PCR) using a first set of primers specific for a first region of double-stranded nucleic acid sequences, thereby obtaining amplified sequences.

As used herein, each of the Aregions≅ is predetermined based upon the alignment of the nucleic acid sequences of at least two serotypes (e.g., AAV) or strains (e.g., lentiviruses), and wherein each of said regions is composed of sequences having a 5' end which is highly conserved, a middle which is preferably, but necessarily, variable, and a 3' end which is highly conserved, each of these being conserved or variable relative to the sequences of the at least two aligned AAV serotypes. Preferably, the 5' and/or 3' end is highly conserved over at least about 9, and more preferably, at least 18 base pairs (bp). However, one or both of the sequences at the 5= or 3=end may be conserved over more than 18 bp, more than 25 bp, more than 30 bp, or more than 50 bp at the 5' end. With respect to the variable region, there is no requirement for conserved sequences, these sequences may be relatively conserved, or may have less than 90, 80, or 70% identity among the aligned serotypes or strains.

Each of the regions may span about 100 bp to about 10 kilobase pairs in length. However, it is particularly desirable that one of the regions is a Asignature≅, i.e., a region which is sufficiently unique to positively identify the amplified sequence as being from the target source. For example, in one embodiment, the first region is about 250 bp in length, and is sufficiently unique among known AAV sequences, that it positively identifies the amplified region as being of AAV origin. Further, the variable sequences within this region are sufficiently unique that can be used to identify the serotype from which the amplified sequences originate. Once amplified (and thereby detected), the sequences can be identified by performing conventional restriction digestion and comparison to restriction digestion patterns for this region in any of AAV1, AAV2, AAV3, AAV4, AAV5, or AAV6, or that of AAV7, AAV10, AAV11, AAV12, or any of the other novel serotypes identified by the invention, which is predetermined and provided by the present invention.

Given the guidance provided herein, one of skill in the art can readily identify such regions among other integrated viruses to permit ready detection and identification of these sequences. Thereafter, an optimal set of generic primers located within the highly conserved ends can be designed and tested for efficient amplification of the selected region from samples. This aspect of the invention is readily adapted to a diagnostic kit for detecting the presence of the target sequence (e.g., AAV) and for identifying the AAV serotype, using standards which include the restriction patterns for the AAV serotypes described herein or isolated using the techniques described herein. For example, quick identification or molecular serotyping of PCR products can be accomplished by digesting the PCR products and comparing restriction patterns.

Figure 1F:
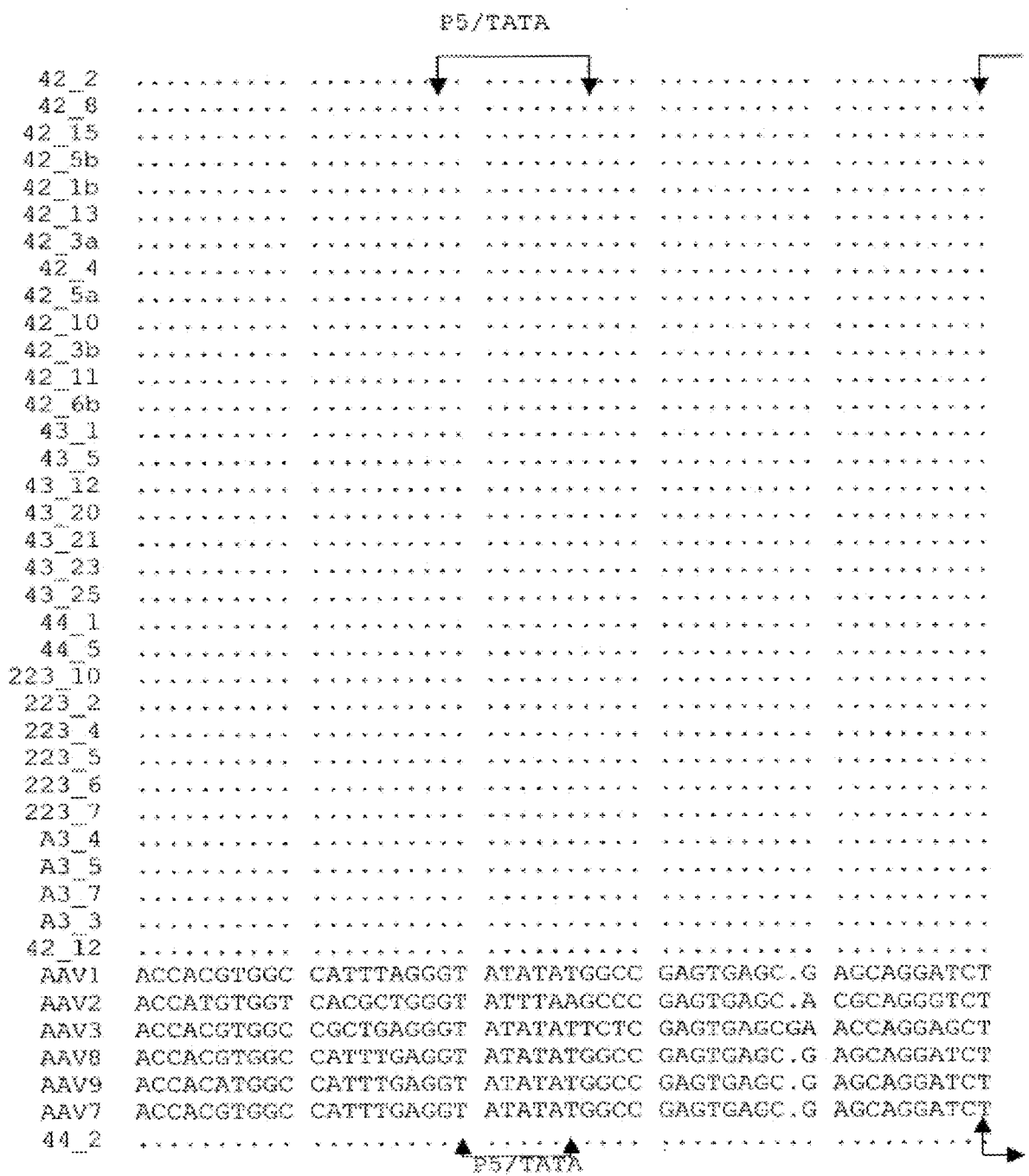
Figure 1G:
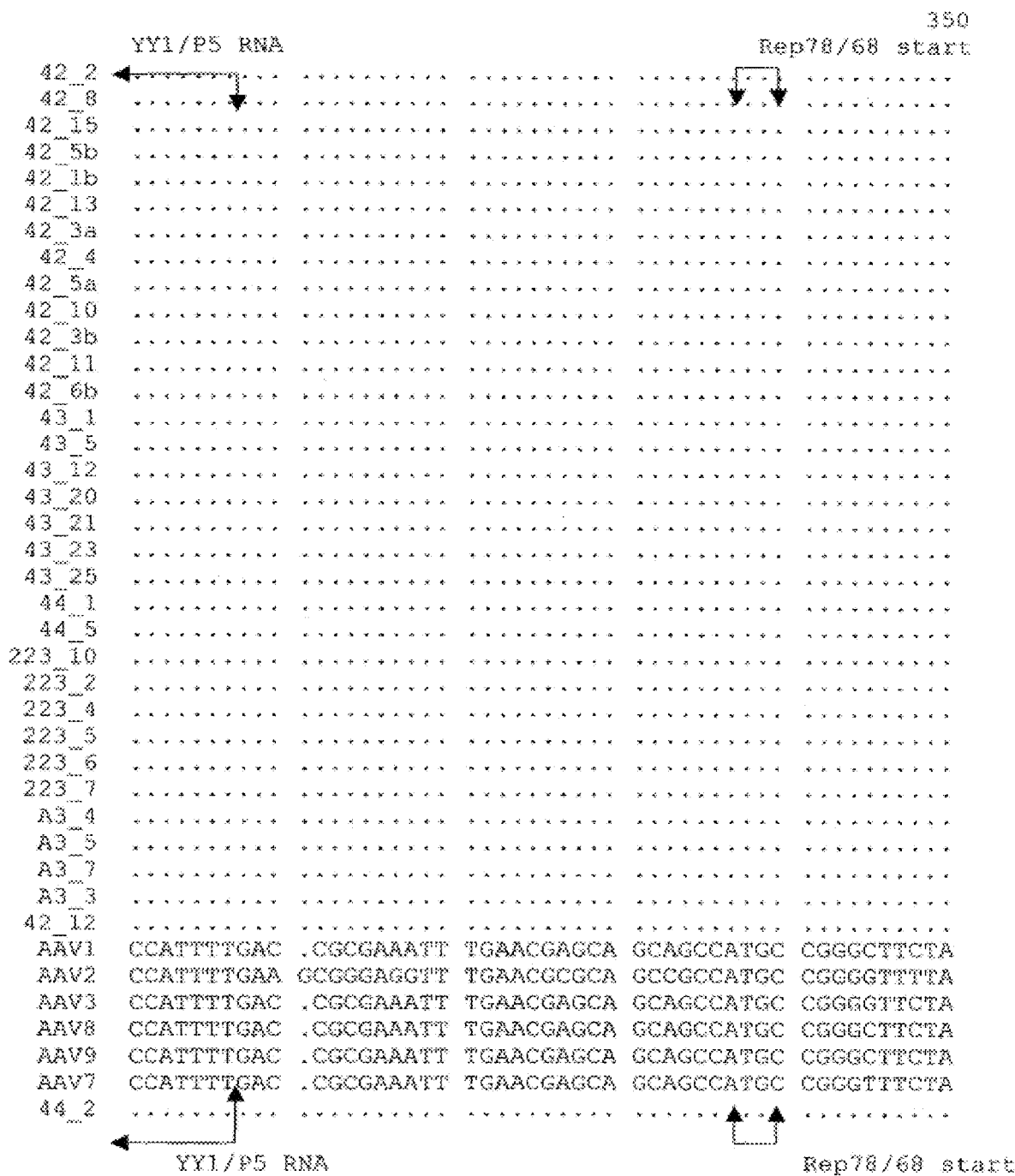
Figure 1R:
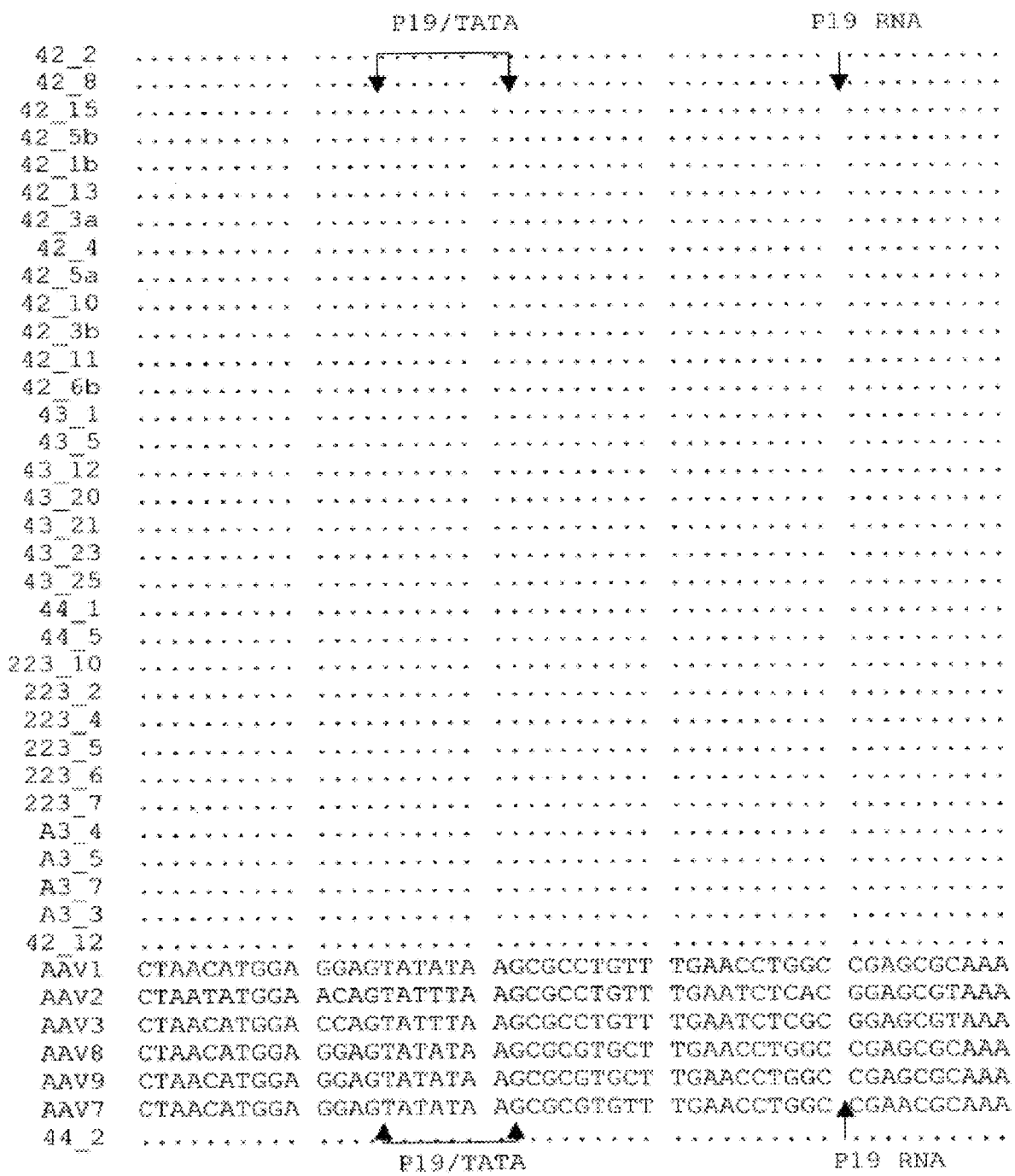

Thus, in one embodiment, the "signature region" for AAV spans about bp 2800 to about 3200 of AAV 1 [SEQ ID NO:6], and corresponding base pairs in AAV 2, AAV3, AAV4, AAV5, and AAV6. More desirably, the region is about 250 bp, located within bp 2886 to about 3143 bp of AAV 1 [SEQ ID NO:6], and corresponding base pairs in AAV 2 [SEQ ID NO:7], AAV3 [SEQ ID NO8], and other AAV serotypes. See, FIG. 1. To permit rapid detection of AAV in the sample, primers which specifically amplify this signature region are utilized. However, the present invention is not limited to the exact sequences identified herein for the AAV signature region, as one of skill in the art may readily alter this region to encompass a shorter fragment, or a larger fragment of this signature region.

The PCR primers are generated using techniques known to those of skill in the art. Each of the PCR primer sets is composed of a 5' primer and a 3' primer. See, e.g., Sambrook et al, cited herein. The term "primer" refers to an oligonucleotide which acts as a point of initiation of synthesis when placed under conditions in which synthesis of a primer extension product which is complementary to a nucleic acid strand is induced. The primer is preferably single stranded. However, if a double stranded primer is utilized, it is treated to separate its strands before being used to prepare extension products. The primers may be about 15 to 25 or more nucleotides, and preferably at least 18 nucleotides. However, for certain applications shorter nucleotides, e.g., 7 to 15 nucleotides are utilized.

The primers are selected to be sufficiently complementary to the different strands of each specific sequence to be amplified to hybridize with their respective strands. Therefore, the primer sequence need not reflect the exact sequence of the region being amplified. For example, a non-complementary nucleotide fragment may be attached to the 5' end of the primer, with the remainder of the primer sequence being completely complementary to the strand. Alternatively, non-complementary bases or longer sequences can be interspersed into the primer, provided that the primer sequence has sufficient complementarity with the sequence of the strand to be amplified to hybridize therewith and form a template for synthesis of the extension product of the other primer.

The PCR primers for the signature region according to the invention are based upon the highly conserved sequences of two or more aligned sequences (e.g., two or more AAV serotypes). The primers can accommodate less than exact identity among the two or more aligned AAV serotypes at the 5' end or in the middle. However, the sequences at the 3' end of the primers correspond to a region of two or more aligned AAV serotypes in which there is exact identity over at least five, preferably, over at least nine base pairs, and more preferably, over at least 18 base pairs at the 3' end of the primers. Thus, the 3' end of the primers is composed of sequences with 100% identity to the aligned sequences over at least five nucleotides. However, one can optionally utilize one, two, or more degenerate nucleotides at the 3' end of the primer.

For example, the primer set for the signature region of AAV was designed based upon a unique region within the AAV capsid, as follows. The 5' primer was based upon nt 2867-2891 of AAV2 [SEQ ID NO:7], 5'-GGTAAT-TCCTCCGGAAATTGGCATT3'. See, FIG. 1. The 3' primer was designed based upon nt 3096-3122 of AAV2 [SEQ ID NO:7], 5'-GACTCATCAACAACAACTGGGGATTC-3'. However, one of skill in the art may have readily designed the primer set based upon the corresponding regions of AAV 1, AAV3, AAV4, AAV5, AAV6, or based upon the information provided herein, AAV7, AAV10, AAV11, AAV12, or another novel AAV of the invention. In addition, still other primer sets can be readily designed to amplify this signature region, using techniques known to those of skill in the art.

B. Isolation of Target Sequences

As described herein, the present invention provides a first primer set which specifically amplifies the signature region of the target sequence, e.g., an AAV serotype, in order to permit detection of the target. In a situation in which further sequences are desired, e.g., if a novel AAV serotype is identified, the signature region may be extended. Thus, the invention may further utilize one or more additional primer sets.

Suitably, these primer sets are designed to include either the 5' or 3' primer of the first primer set and a second primer unique to the primer set, such that the primer set amplifies a region 5' or 3' to the signature region which anneals to either the 5' end or the 3' end of the signature region. For example, a first primer set is composed of a 5' primer, P1 and a 3' primer P2 to amplify the signature region. In order to extend the signature region on its 3' end, a second primer set is composed of primer P1 and a 3' primer P4, which amplifies the signature region and contiguous sequences downstream of the signature region. In order to extend the signature region on its 5' end, a third primer set is composed of a 5' primer, P5, and primer P2, such that the signature region and contiguous sequences upstream of the signature region are amplified. These extension steps are repeated (or performed at the same time), as needed or desired. Thereafter, the products results from these amplification steps are fused using conventional steps to produce an isolated sequence of the desired length.

The second and third primer sets are designed, as with the primer set for the signature region, to amplify a region having highly conserved sequences among the aligned sequences. Reference herein to the term "second" or "third" primer set is for each of discussion only, and without regard to the order in which these primers are added to the reaction mixture, or used for amplification. The region amplified by the second primer set is selected so that upon amplification it anneals at its 5' end to the 3' end of the signature region. Similarly, the region amplified by the third primer set is selected so that upon amplification it anneals at its 3' end anneals to the 5' end of the signature region. Additional primer sets can be designed such that the regions which they amplify anneal to the either the 5' end or the 3' end of the extension products formed by the second or third primer sets, or by subsequent primer sets.

For example, where AAV is the target sequence, a first set of primers (P1 and P2) are used to amplify the signature region from the sample. In one desirable embodiment, this signature region is located within the AAV capsid. A second set of primers (P1 and P4) is used to extend the 3' end of the signature region to a location in the AAV sequence which is just before the AAV 3' ITR, i.e., providing an extension product containing the entire 3' end of the AAV capsid when using the signature region as an anchor. In one embodiment, the P4 primer corresponds to nt 4435 to 4462 of AAV2 [SEQ ID NO:7], and corresponding sequences in the other AAV serotypes. This results in amplification of a region of about 1.6 kb, which contains the 0.25 kb signature region. A third set of primers (P3 and P2) is used to extend the 5' end of signature region to a location in the AAV sequences which is in the 3' end of the rep genes, i.e., providing an extension product containing the entire 5' end of the AAV capsid when using the signature region as an anchor. In one embodiment, the P3 primer corresponds to nt 1384 to 1409 of AAV2 [SEQ ID NO:7], and corresponding sequences in the other AAV serotypes. This results in amplification of a region of about 1.7 kb, which contains the 0.25 kb signature region. Optionally, a fourth set of primers are used to further extend the extension product containing the entire 5' end of the AAV capsid to also include the rep sequences. In one embodiment, the primer designated P5 corresponds to nt 108 to 133 of AAV2 [SEQ ID NO:7], and corresponding sequences in the other AAV serotypes and is used in conjunction with the P2 primer.

Following completion of the desired number of extension steps, the various extension products are fused, making use of the signature region as an anchor or marker, to construct an intact sequence. In the example provided herein, AAV sequences containing, at a minimum, an intact AAV cap gene are obtained. Larger sequences may be obtained, depending upon the number of extension steps performed.

Suitably, the extension products are assembled into an intact AAV sequence using methods known to those of skill in the art. For example, the extension products may be digested with DraIII, which cleaves at the DraIII site located within the signature region, to provide restriction fragments which are re-ligated to provide products containing (at a minimum) an intact AAV cap gene. However, other suitable techniques for assembling the extension products into an intact sequence may be utilized. See, generally, Sambrook et al, cited herein.

As an alternative to the multiple extension steps described above, another embodiment of the invention provides for direct amplification of a 3.1 kb fragment which allows isolation of full-length cap sequences. To directly amplify a 3.1 kb full-length cap fragment from NHP tissue and blood DNAs, two other highly conserved regions were identified in AAV genomes for use in PCR amplification of large fragments. A primer within a conserved region located in the middle of the rep gene is utilized (AV1ns: 5' GCTGCGT-CAACTGGACCAATGAGAAC 3', nt of SEQ ID NO:6) in combination with the 3' primer located in another conserved region downstream of the Cap gene (AV2cas: 5' CGCAGA-GACCAAAGTTCAACTGAAACGA 3', SEQ ID NO: 7) for amplification of AAV sequences including the full-length AAV cap. Typically, following amplification, the products are cloned and sequence analysis is performed with an accuracy of ≥99.9%. Using this method, the inventors have isolated at least 50 capsid clones which have subsequently been characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5). These clones are identified elsewhere in the specification, together with the species of animal from which they were identified and the tissues in that animal these novel sequences have been located.

C. Alternative Method for Isolating Novel AAV

In another aspect, the invention provides an alternative method for isolating novel AAV from a cell. This method involves infecting the cell with a vector which provides helper functions to the AAV; isolating infectious clones containing AAV; sequencing the isolated AAV; and comparing the sequences of the isolated AAV to known AAV serotypes, whereby differences in the sequences of the isolated AAV and known AAV serotypes indicates the presence of a novel AAV.

In one embodiment, the vector providing helper functions provides essential adenovirus functions, including, e.g., E1a, E1b, E2a, E4ORF6. In one embodiment, the helper functions are provided by an adenovirus. The adenovirus may be a wild-type adenovirus, and may be of human or non-human origin, preferably non-human primate (NHP) origin. The DNA sequences of a number of adenovirus types are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified human types [see, e.g., Horwitz, cited above]. Similarly adenoviruses known to infect non-human animals (e.g., chimpanzees) may also be employed in the vector constructs of this invention. See, e.g., U.S. Pat. No. 6,083,716. In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. The selection of the adenovirus type is not anticipated to limit the following invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

In another alternative, infectious AAV may be isolated using genome walking technology (Siebert et al., 1995, *Nucleic Acid Research*, 23:1087-1088, Friezner-Degen et al., 1986, *J Biol. Chem.* 261:6972-6985, BD Biosciences Clontech, Palo Alto, Calif.). Genome walking is particularly well suited for identifying and isolating the sequences adjacent to the novel sequences identified according to the method of the invention. For example, this technique may be useful for isolating inverted terminal repeat (ITRs) of the novel AAV serotype, based upon the novel AAV capsid and/or rep sequences identified using the methods of the invention. This technique is also useful for isolating sequences adjacent to other AAV and non-AAV sequences identified and isolated according to the present invention. See, Examples 3 and 4.

The methods of the invention may be readily used for a variety of epidemiology studies, studies of biodistribution, monitoring of gene therapy via AAV vectors and vector derived from other integrated viruses. Thus, the methods are well suited for use in pre-packaged kits for use by clinicians, researchers, and epidemiologists.

II. Diagnostic Kit

In another aspect, the invention provides a diagnostic kit for detecting the presence of a known or unknown adeno-associated virus (AAV) in a sample. Such a kit may contain a first set of 5' and 3' PCR primers specific for a signature region of the AAV nucleic acid sequence. Alternatively, or additionally, such a kit can contain a first set of 5' and 3' PCR primers specific for the 3.1 kb fragment which includes the full-length AAV capsid nucleic acid sequence identified herein (e.g., the AV1ns and AV2cas primers.) Optionally, a kit of the invention may further contain two or more additional sets of 5' and 3' primers, as described herein, and/or PCR probes. These primers and probes are used according to the present invention amplify signature regions of each AAV serotype, e.g., using quantitative PCR.

The invention further provides a kit useful for identifying an AAV serotype detected according to the method of the invention and/or for distinguishing novel AAV from known AAV. Such a kit may further include one or more restriction enzymes, standards for AAV serotypes providing their "signature restriction enzyme digestions analyses", and/or other means for determining the serotype of the AAV detected.

In addition, kits of the invention may include, instructions, a negative and/or positive control, containers, diluents and buffers for the sample, indicator charts for signature comparisons, disposable gloves, decontamination instructions, applicator sticks or containers, and sample preparator cups, as well as any desired reagents, including media, wash reagents and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

The kits provided by the present invention are useful for performing the methods described herein, and for study of biodistribution, epidemiology, mode of transmission of novel AAV serotypes in human and NHPs.

Thus, the methods and kits of the invention permit detection, identification, and isolation of target viral sequences, particularly integrated viral sequences. The methods and kits are particularly well suited for use in detection, identification and isolation of AAV sequences, which may include novel AAV serotypes.

In one notable example, the method of the invention facilitated analysis of cloned AAV sequences by the inventors, which revealed heterogeneity of proviral sequences between cloned fragments from different animals, all of which were distinct from the known six AAV serotypes, with the majority of the variation localized to hypervariable regions of the capsid protein. Surprising divergence of AAV sequences was noted in clones isolated from single tissue sources, such as lymph node, from an individual rhesus monkey. This heterogeneity is best explained by apparent evolution of AAV sequence within individual animals due, in part, to extensive homologous recombination between a limited number of co-infecting parenteral viruses. These studies suggest sequence evolution of widely disseminated virus during the course of a natural AAV infection that presumably leads to the formation of swarms of quasispecies which differ from one another in the array of capsid hypervariable regions. This is the first example of rapid molecular evolution of a DNA virus in a way that formerly was thought to be restricted to RNA viruses.

Sequences of several novel AAV serotypes identified by the method of the invention and characterization of these serotypes is provided.

III. Novel AAV Serotypes

A. Nucleic Acid Sequences

Nucleic acid sequences of novel AAV serotypes identified by the methods of the invention are provided. See, SEQ ID NO:1, 9-59, and 117-120, which are incorporated by reference herein. See also, FIG. 1 and the sequence listing.

For novel serotype AAV7, the full-length sequences, including the AAV 5' ITRs, capsid, rep, and AAV 3' ITRs are provided in SEQ ID NO:1.

For other novel AAV serotypes of the invention, the approximately 3.1 kb fragment isolated according to the method of the invention is provided. This fragment contains sequences encoding full-length capsid protein and all or part of the sequences encoding the rep protein. These sequences include the clones identified below.

For still other novel AAV serotypes, the signature region encoding the capsid protein is provided. For example, the AAV10 nucleic acid sequences of the invention include those illustrated in FIG. 1 [See, SEQ ID NO:117, which spans 255 bases]. The AAV11 nucleic acid sequences of the invention include the DNA sequences illustrated in FIG. 1 [See, SEQ ID NO:118 which spans 258 bases]. The AAV12 nucleic acid sequences of the invention include the DNA sequences illustrated in FIG. 1 [See, SEQ ID NO:119, which consists of 255 bases]. Using the methodology described above, further AAV10, AAV11 and AAV12 sequences can be readily identified and used for a variety of purposes, including those described for AAV7 and the other novel serotypes herein.

FIG. 1 provides the non-human primate (NHP) AAV nucleic acid sequences of the invention in an alignment with the previously published AAV serotypes, AAV 1 [SEQ ID NO:6], AAV2 [SEQ ID NO:7], and AAV3 [SEQ ID NO:8]. These novel NHP sequences include those provided in the following Table I, which are identified by clone number:

TABLE 1

| AAV Cap Sequence | Clone Number | Source Species | Tissue | SEQ ID NO (DNA) |
|---|---|---|---|---|
| Rh.1 | Clone 9 (AAV9) | Rhesus | Heart | 5 |
| Rh.2 | Clone 43.1 | Rhesus | MLN | 39 |
| Rh.3 | Clone 43.5 | Rhesus | MLN | 40 |
| Rh.4 | Clone 43.12 | Rhesus | MLN | 41 |
| Rh.5 | Clone 43.20 | Rhesus | MLN | 42 |
| Rh.6 | Clone 43.21 | Rhesus | MLN | 43 |
| Rh.7 | Clone 43.23 | Rhesus | MLN | 44 |
| Rh.8 | Clone 43.25 | Rhesus | MLN | 45 |
| Rh.9 | Clone 44.1 | Rhesus | Liver | 46 |
| Rh.10 | Clone 44.2 | Rhesus | Liver | 59 |
| Rh.11 | Clone 44.5 | Rhesus | Liver | 47 |
| Rh.12 | Clone 42.1B | Rhesus | MLN | 30 |
| Rh.13 | 42.2 | Rhesus | MLN | 9 |
| Rh.14 | Clone 42.3A | Rhesus | MLN | 32 |
| Rh.15 | Clone 42.3B | Rhesus | MLN | 36 |
| Rh.16 | Clone 42.4 | Rhesus | MLN | 33 |
| Rh.17 | Clone 42.5A | Rhesus | MLN | 34 |
| Rh.18 | Clone 42.5B | Rhesus | MLN | 29 |
| Rh.19 | Clone 42.6B | Rhesus | MLN | 38 |
| Rh.20 | Clone 42.8 | Rhesus | MLN | 27 |
| Rh.21 | Clone 42.10 | Rhesus | MLN | 35 |
| Rh.22 | Clone 42.11 | Rhesus | MLN | 37 |
| Rh.23 | Clone 42.12 | Rhesus | MLN | 58 |
| Rh.24 | Clone 42.13 | Rhesus | MLN | 31 |
| Rh.25 | Clone 42.15 | Rhesus | MLN | 28 |
| Rh.26 | Clone 223.2 | Rhesus | Liver | 49 |
| Rh.27 | Clone 223.4 | Rhesus | Liver | 50 |
| Rh.28 | Clone 223.5 | Rhesus | Liver | 51 |
| Rh.29 | Clone 223.6 | Rhesus | Liver | 52 |
| Rh.30 | Clone 223.7 | Rhesus | Liver | 53 |
| Rh.31 | Clone 223.10 | Rhesus | Liver | 48 |
| Rh.32 | Clone C1 | Rhesus | Spleen, Duo, Kid & Liver | 19 |
| Rh.33 | Clone C3 | Rhesus |  | 20 |
| Rh.34 | Clone C5 | Rhesus |  | 21 |
| Rh.35 | Clone F1 | Rhesus | Liver | 22 |
| Rh.36 | Clone F3 | Rhesus |  | 23 |
| Rh.37 | Clone F5 | Rhesus |  | 24 |
| Cy.1 | Clone 1.3 | Cyno | Blood | 14 |
| Cy.2 | Clone 13.3B | Cyno | Blood | 15 |
| Cy.3 | Clone 24.1 | Cyno | Blood | 16 |
| Cy.4 | Clone 27.3 | Cyno | Blood | 17 |
| Cy.5 | Clone 7.2 | Cyno | Blood | 18 |
| Cy.6 | Clone 16.3 | Cyno | Blood | 10 |
| bb.1 | Clone 29.3 | Baboon | Blood | 11 |
| bb.2 | Clone 29.5 | Baboon | Blood | 13 |
| Ch.1 | Clone A3.3 | Chimp | Blood | 57 |
| Ch.2 | Clone A3.4 | Chimp | Blood | 54 |
| Ch.3 | Clone A3.5 | Chimp | Blood | 55 |
| Ch.4 | Clone A3.7 | Chimp | Blood | 56 |

A novel NHP clone was made by splicing capsids fragments of two chimp adenoviruses into an AAV2 rep construct. This new clone, A3.1, is also termed Ch.5 [SEQ ID NO:20]. Additionally, the present invention includes two human AAV sequences, termed H6 [SEQ ID NO:25] and H2 [SEQ ID NO:26].

The AAV nucleic acid sequences of the invention further encompass the strand which is complementary to the strands provided in the sequences provided in FIG. 1 and the Sequence Listing [SEQ ID NO:1, 9-59, 117-120], nucleic acid sequences, as well as the RNA and cDNA sequences corresponding to the sequences provided in FIG. 1 and the Sequence Listing [SEQ ID NO:1, 9-59, 117-120], and their complementary strands. Also included in the nucleic acid sequences of the invention are natural variants and engineered modifications of the sequences of FIG. 1 and the Sequence Listing [SEQ ID NO:1, 9-59, 117-120], and their complementary strands. Such modifications include, for example, labels which are known in the art, methylation, and substitution of one or more of the naturally occurring nucleotides with a degenerate nucleotide.

Further included in this invention are nucleic acid sequences which are greater than 85%, preferably at least about 90%, more preferably at least about 95%, and most preferably at least about 98 to 99% identical or homologous to the sequences of the invention, including FIG. 1 and the Sequence Listing [SEQ ID NO:1, 9-59, 117-120]. These terms are as defined herein.

Also included within the invention are fragments of the novel AAV sequences identified by the method described herein. Suitable fragments are at least 15 nucleotides in length, and encompass functional fragments, i.e., fragments which are of biological interest. In one embodiment, these fragments are fragments of the novel sequences of FIG. 1 and the Sequence Listing [SEQ ID NO:1, 9-59, 117-120], their complementary strands, cDNA and RNA complementary thereto.

Examples of suitable fragments are provided with respect to the location of these fragments on AAV1, AAV2, or AAV7. However, using the alignment provided herein (obtained using the Clustal W program at default settings), or similar techniques for generating an alignment with other novel serotypes of the invention, one of skill in the art can readily identify the precise nucleotide start and stop codons for desired fragments.

Examples of suitable fragments include the sequences encoding the three variable proteins (vp) of the AAV capsid which are alternative splice variants: vp1 [e.g., nt 825 to 3049 of AAV7, SEQ ID NO: 1]; vp2 [e.g., nt 1234-3049 of AAV7, SEQ ID NO: 1]; and vp3 [e.g., nt 1434-3049 of AAV7, SEQ ID NO:1]. It is notable that AAV7 has an unusual GTG start codon. With the exception of a few house-keeping genes, such a start codon has not previously been reported in DNA viruses. The start codons for vp1, vp2 and vp3 for other AAV serotypes have been believed to be such that they permit the cellular mechanism of the host cell in which they reside to produce vp1, vp2 and vp3 in a ratio of 10%:10%:80%, respectively, in order to permit efficient assembly of the virion. However, the AAV7 virion has been found to assemble efficiently even with this rare GTG start codon. Thus, the inventors anticipate this it is desirable to alter the start codon of the vp3 of other AAV serotypes to contain this rare GTG start codon, in order to improve packaging efficiency, to alter the virion structure and/or to alter location of epitopes (e.g., neutralizing antibody epitopes) of other AAV serotypes. The start codons may be altered using conventional techniques including, e.g., site directed mutagenesis. Thus, the present invention encompasses altered AAV virions of any selected serotype, composed of a vp3, and/or optionally, vp1 and/or vp2 having start codons altered to GTG.

Other suitable fragments of AAV, include a fragment containing the start codon for the AAV capsid protein [e.g., nt 468 to 3090 of AAV7, SEQ ID NO:1, nt 725 to 3090 of AAV7, SEQ ID NO: 1, and corresponding regions of the other AAV serotypes]. Still other fragments of AAV7 and the other novel AAV serotypes identified using the methods described herein include those encoding the rep proteins, including rep 78 [e.g., initiation codon 334 of FIG. 1 for AAV7], rep 68 [initiation codon nt 334 of FIG. 1 for AAV7], rep 52 [initiation codon 1006 of FIG. 1 for AAV7], and rep 40 [initiation codon 1006 of FIG. 1 for AAV7] Other fragments of interest may include the AAV 5' inverted terminal repeats ITRs, [nt 1 to 107 of FIG. 1 for AAV7]; the AAV 3' ITRs [nt 4704 to 4721 of FIG. 1 for AAV7], P19 sequences, AAV P40 sequences, the rep binding site, and the terminal resolute site (TRS). Still other suitable fragments will be readily apparent to those of skill in the art. The corresponding regions in the other novel serotypes of the invention can be readily determined by reference to FIG. 1, or by utilizing conventional alignment techniques with the sequences provided herein.

In addition to including the nucleic acid sequences provided in the figures and Sequence Listing, the present invention includes nucleic acid molecules and sequences which are designed to express the amino acid sequences, proteins and peptides of the AAV serotypes of the invention. Thus, the invention includes nucleic acid sequences which encode the following novel AAV amino acid sequences: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113], and artificial AAV serotypes generated using these sequences and/or unique fragments thereof.

As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

B. AAV Amino Acid Sequences, Proteins and Peptides

The invention provides proteins and fragments thereof which are encoded by the nucleic acid sequences of the novel AAV serotypes identified herein, including, e.g., AAV7 [nt 825 to 3049 of AAV7, SEQ ID NO: 1] the other novel serotypes provided herein. Thus, the capsid proteins of the novel serotypes of the invention, including: H6 [SEQ ID NO: 25], H2 [SEQ ID NO: 26], 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO: 42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], and 44.2 [SEQ ID NO: 59], can be readily generated using conventional techniques from the open reading frames provided for the above-listed clones.

The invention further encompasses AAV serotypes generated using sequences of the novel AAV serotypes of the invention, which are generated using synthetic, recombinant or other techniques known to those of skill in the art. The invention is not limited to novel AAV amino acid sequences, peptides and proteins expressed from the novel AAV nucleic acid sequences of the invention and encompasses amino acid sequences, peptides and proteins generated by other methods known in the art, including, e.g., by chemical synthesis, by other synthetic techniques, or by other methods. For example, the sequences of any of C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113] by be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Particularly desirable proteins include the AAV capsid proteins, which are encoded by the nucleotide sequences identified above. The sequences of many of the capsid proteins of the invention are provided in an alignment in FIG. 2 and/or in the Sequence Listing, SEQ ID NO: 2 and 60 to 115, which is incorporated by reference herein. The AAV capsid is composed of three proteins, vp1, vp2 and vp3, which are alternative splice variants. The full-length sequence provided in these figures is that of vp1. Based on the numbering of the AAV7 capsid [SEQ ID NO:2], the sequences of vp2 span amino acid 138-737 of AAV7 and the sequences of vp3 span amino acids 203-737 of AAV7. With this information, one of skill in the art can readily determine the location of the vp2 and vp3 proteins for the other novel serotypes of the invention.

Other desirable proteins and fragments of the capsid protein include the constant and variable regions, located between hypervariable regions (HPV) and the sequences of the HPV regions themselves. An algorithm developed to determine areas of sequence divergence in AAV2 has yielded 12 hypervariable regions (HVR) of which 5 overlap or are part of the four previously described variable regions. [Chiorini et al, *J. Virol,* 73:1309-19 (1999); Rutledge et al, *J. Virol.,* 72:309-319] Using this algorithm and/or the alignment techniques described herein, the HVR of the novel AAV serotypes are determined. For example, with respect to the number of the AAV2 vp1 [SEQ ID NO:70], the HVR are located as follows: HVR1, aa 146-152; HVR2, aa 182-186; HVR3, aa 262-264; HVR4, aa 381-383; HVR5, aa 450-474; HVR6, aa 490-495; HVR7, aa500-504; HVR8, aa 514-522; HVR9, aa 534-555; HVR10, aa 581-594; HVR11, aa 658-667; and HVR12, aa 705-719. Utilizing an alignment prepared in accordance with conventional methods and the novel sequences provided herein [See, e.g., FIG. 2], one can readily determine the location of the HVR in the novel AAV serotypes of the invention. For example, utilizing FIG. 2, one can readily determine that for AAV7 [SEQ ID NO:2]. HVR1 is located at aa 146-152; HVR2 is located at 182-187; HVR3 is located at aa 263-266, HVR4 is located at aa 383-385, HVR5 is located at aa 451-475; HVR6 is located at aa 491-496 of AAV7; HVR7 is located at aa 501-505; HVR8 is located at aa 513-521; HVR9 is located at 533-554; HVR10 is located at aa 583-596; HVR11 is located at aa 660-669; HVR12 is located at aa 707-721. Using the information provided herein, the HVRs for the other novel serotypes of the invention can be readily determined.

In addition, within the capsid, amino acid cassettes of identity have been identified. These cassettes are of particular interest, as they are useful in constructing artificial serotypes, e.g., by replacing a HVR1 cassette of a selected serotype with an HVR1 cassette of another serotype. Certain of these cassettes of identity are noted in FIG. 2. See, FIG. 2, providing the Clustal X alignment, which has a ruler is displayed below the sequences, starting at 1 for the first residue position. The line above the ruler is used to mark strongly conserved positions. Three characters (*, : , .) are used. "*" indicates positions which have a single, fully conserved residue. ":" indicates that a "strong" group is fully conserved "." Indicates that a "weaker" group is fully conserved. These are all the positively scoring groups that occur in the Gonnet Pam250 matrix. The strong groups are defined as a strong score >0.5 and the weak groups are defined as weak score <0.5.

Additionally, examples of other suitable fragments of AAV capsids include, with respect to the numbering of AAV2 [SEQ ID NO:70], aa 24-42, aa 25-28; aa 81-85; aa133-165; aa 134-165; aa 137-143; aa 154-156; aa 194-208; aa 261-274; aa 262-274; aa 171-173; aa 413-417; aa 449-478; aa 494-525; aa 534-571; aa 581-601; aa 660-671; aa 709-723. Still other desirable fragments include, for example, in AAV7, amino acids 1 to 184 of SEQ ID NO:2, amino acids 199 to 259; amino acids 274 to 446; amino acids 603 to 659; amino acids 670 to 706; amino acids 724 to 736; aa 185 to 198; aa 260 to 273; aa447 to 477; aa495 to 602; aa660 to 669; and aa707 to 723. Still other desirable regions, based on the numbering of AAV7 [SEQ ID NO:2], are selected from among the group consisting of aa 185 to 198; aa 260 to 273; aa447 to 477; aa495 to 602; aa660 to 669; and aa707 to 723. Using the alignment provided herein performed using the Clustal X program at default settings, or using other commercially or publicly available alignment programs at default settings, one of skill in the art can readily determine corresponding fragments of the novel AAV capsids of the invention.

Other desirable proteins are the AAV rep proteins [aa 1 to 623 of SEQ ID NO:3 for AAV7] and functional fragments thereof, including, e.g., aa 1 to 171, aa 172 to 372, aa 373 to 444, aa 445 to 623 of SEQ ID NO:3, among others. Suitably, such fragments are at least 8 amino acids in length. See, FIG. 3. Comparable regions can be identified in the proteins of the other novel AAV of the invention, using the techniques described herein and those which are known in the art. In addition, fragments of other desired lengths may be readily utilized. Such fragments may be produced recombinantly or by other suitable means, e.g., chemical synthesis.

The sequences, proteins, and fragments of the invention may be produced by any suitable means, including recombinant production, chemical synthesis, or other synthetic means. Such production methods are within the knowledge of those of skill in the art and are not a limitation of the present invention.

IV. Production of rAAV with Novel AAV Capsids

The invention encompasses novel, wild-type AAV serotypes identified by the invention, the sequences of which wild-type AAV serotypes are free of DNA and/or cellular material with these viruses are associated in nature. In another aspect, the present invention provides molecules which utilize the novel AAV sequences of the invention, including fragments thereof, for production of molecules useful in delivery of a heterologous gene or other nucleic acid sequences to a target cell.

The molecules of the invention which contain sequences of a novel AAV serotype of the invention include any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain sequences encoding a novel AAV capsid of the invention (e.g., AAV7 capsid, AAV 44-2 (rh.10), an AAV10 capsid, an AAV11 capsid, an AAV12 capsid), or a fragment of one or more of these AAV capsids. Alternatively, the vectors may contain the capsid protein, or a fragment thereof, itself.

Optionally, vectors of the invention may contain sequences encoding AAV rep proteins. Such rep sequences may be from the same AAV serotype which is providing the cap sequences. Alternatively, the present invention provides vectors in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are expressed from the same source as the cap sequences. In this embodiment, the rep sequences may be fused in frame to cap sequences of a different AAV serotype to form a chimeric AAV vector. Optionally, the vectors of the invention further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV serotype (e.g., AAV7 or another novel AAV). Alternatively, these vectors contain sequences encoding artificial capsids which contain one or more fragments of the AAV7 (or another novel AAV) capsid fused to heterologous AAV or non-AAV capsid proteins (or fragments thereof). These artificial capsid proteins are selected from non-contiguous portions of the AAV7 (or another novel AAV) capsid or from capsids of other AAV serotypes. For example, it may be desirable to modify the coding regions of one or more of the AAV vp1, e.g., in one or more of the hypervariable regions (i.e., HPV1-12), or vp2, and/or vp3. In another example, it may be desirable to alter the start codon of the vp3 protein to GTG. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having an AAV serotype 7 (or another novel AAV) capsid, or a portion thereof. Such a method involves culturing a host cell which contains a nucleic acid sequence encoding an adeno-associated virus (AAV) serotype 7 (or another novel AAV) capsid protein, or fragment thereof, as defined herein; a functional rep gene; a minigene composed of, at a minimum, AAV inverted terminal repeats (ITRs) and a transgene; and sufficient helper functions to permit packaging of the minigene into the AAV7 (or another novel AAV) capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E 1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J Virol.,* 70:520-532 (1993) and U.S. Pat. No. 5,478,745.

A. The Minigene

The minigene is composed of, at a minimum, a transgene and its regulatory sequences, and 5= and 3=AAV inverted terminal repeats (ITRs). It is this minigene which is packaged into a capsid protein and delivered to a selected host cell.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Vivol.,* 78(Pt 1):13-21 (January 1997); Furler, S., et al, *Gene Ther.,* 8(11):864-873 (June 2001); Klump H., et al., *Gene Ther.,* 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner which permits its transcription, translation and/or expression in a cell transfected with the plasmid vector or infected with the virus produced by the invention. As used herein, Aoperably linked≅ sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J Clin. Invest.*, 100:2865-2872 (1997)]. Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Vivol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor a chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5= and 3=ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 µg to about 100 µg DNA, and preferably about 10 to about 50 µg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

B. Rep and Cap Sequences

In addition to the minigene, the host cell contains the sequences which drive expression of the novel AAV capsid protein (e.g., AAV7 or other novel AAV capsid or an artificial capsid protein comprising a fragment of one or more of these capsids) in the host cell and rep sequences of the same serotype as the serotype of the AAV ITRs found in the minigene. The AAV cap and rep sequences may be independently obtained from an AAV source as described above and may be introduced into the host cell in any manner known to one in the art as described above. Additionally, when pseudotyping a novel AAV capsid of the invention, the sequences encoding each of the essential rep proteins may be supplied by the same AAV serotype, or the sequences encoding the rep proteins may be supplied by different AAV serotypes (e.g., AAV1, AAV2, AAV3, AAV4, AAV5, AAV6, or one of the novel serotypes identified herein). For example, the rep78/68 sequences may be from AAV2, whereas the rep52/40 sequences may from AAV1.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By Aadenoviral DNA which expresses the E1a gene products, it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example D. Host Cells And Packaging Cell Lines The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The most desirable cells do not carry any adenovirus gene other than E1, E2a and/or E4 ORF6; nor do they contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6. Yet other cell lines can be constructed using the novel AAV rep and/or novel AAV cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

These novel AAV-based vectors which are generated by one of skill in the art are beneficial for gene delivery to selected host cells and gene therapy patients since no neutralization antibodies to AAV7 have been found in the human population. Further, early studies show no neutralizing antibodies in cyno monkey and chimpanzee populations, and less than 15% cross-reactivity of AAV 7 in rhesus monkeys, the species from which the serotype was isolated. One of skill in the art may readily prepare other rAAV viral vectors containing the AAV7 capsid proteins provided herein using a variety of techniques known to those of skill in the art. One may similarly prepare still other rAAV viral vectors containing AAV7 sequence and AAV capsids of another serotype. Similar advantages are conferred by the vectors based on the other novel AAV of the invention.

Thus, one of skill in the art will readily understand that the AAV7 sequences of the invention can be readily adapted for use in these and other viral vector systems for in vitro, ex vivo or in vivo gene delivery. Similarly, one of skill in the art can readily select other fragments of the novel AAV genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

V. Recombinant Viruses And Uses Thereof

Using the techniques described herein, one of skill in the art may generate a rAAV having a capsid of a novel serotype of the invention, or a novel capsid containing one or more novel fragments of an AAV serotype identified by the method of the invention. In one embodiment, a full-length capsid from a single serotype, e.g., AAV7 [SEQ ID NO: 2] can be utilized. In another embodiment, a full-length capsid may be generated which contains one or more fragments of a novel serotype of the invention fused in frame with sequences from another selected AAV serotype. For example, a rAAV may contain one or more of the novel hypervariable region sequences of an AAV serotype of the invention. Alternatively, the unique AAV serotypes of the invention may be used in constructs containing other viral or non-viral sequences.

It will be readily apparent to one of skill in the art one embodiment, that certain serotypes of the invention will be particularly well suited for certain uses. For example, vectors based on AAV7 capsids of the invention are particularly well suited for use in muscle; whereas vectors based on rh.10 (44-2) capsids of the invention are particularly well suited for use in lung. Uses of such vectors are not so limited and one of skill in the art may utilize these vectors for delivery to other cell types, tissues or organs. Further, vectors based upon other capsids of the invention may be used for delivery to these or other cells, tissues or organs.

A. Delivery of Trans gene

In another aspect, the present invention provides a method for delivery of a transgene to a host which involves transfecting or infecting a selected host cell with a vector generated with the sequences of the AAV of the invention.

Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences which direct expression thereof and AAV capsid proteins.

Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W C Manning et al, *Human Gene Therapy*, 9:477-485 (Mar. 1, 1998). The results of this assay may be used to determine which AAV vector containing capsid proteins of a particular serotype are preferred for delivery, e.g., by the absence of neutralizing antibodies specific for that capsid serotype.

In one aspect of this method, the delivery of vector with a selected AAV capsid proteins may precede or follow delivery of a gene via a vector with a different serotype AAV capsid protein. Similarly, the delivery of vector with other novel AAV capsid proteins of the invention may precede or follow delivery of a gene via a vector with a different serotype AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of serotypes which differ from the first vector. For example, if a first vector has AAV7 capsid proteins [SEQ ID NO:2], subsequently administered vectors may have capsid proteins selected from among the other serotypes, including AAV1, AAV2, AAV3A, AAV3B, AAV4, AAV6, AAV10, AAV11, and AAV12, or any of the other novel AAV capsids identified herein including, without limitation: A3.1, H2, H6, C1, C2, C5, A3-3, A3-7, A3-4, A3-5, 3.3b, 223.4, 223-5, 223-10, 223-2, 223-7, 223-6, 44-1, 44-5, 44-2, 42-15, 42-8, 42-13, 42-3A, 42-4, 42-5A, 42-1B, 42-5B, 43-1, 43-12, 43-5, 43-21, 43-25, 43-20, 24.1, 42.2, 7.2, 27.3, 16.3, 42.10, 42-3B, 42-11, F1, F5, F3, 42-6B, and/or 42-12.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin The viral vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 1 ml to about 100 ml of solution containing concentrations of from about $1 \times 10^9$ to $1 \times 10^{16}$ genomes virus vector. A preferred human dosage may be about $1 \times 10^{13}$ to $1 \times 10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGF β, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, IL-2, IL-4, IL-12, and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce Aself≈-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Trans genes

Alternatively, or in addition, the vectors of the invention may contain AAV sequences of the invention and a transgene encoding a peptide, polypeptide or protein which induces an immune response to a selected immunogen. For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncoriviral which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Between the HIV and SIV, many suitable antigens have been described and can readily be selected. Examples of suitable HIV and SIV antigens include, without limitation the gag, pol, Vif, Vpx, VPR, Env, Tat and Rev proteins, as well as various fragments thereof. In addition, a variety of modifications to these antigens have been described. Suitable antigens for this purpose are known to those of skill in the art. For example, one may select a sequence encoding the gag, pol, Vif, and Vpr, Env, Tat and Rev, amongst other proteins. See, e.g., the modified gag protein which is described in U.S. Pat. No. 5,972,596. See, also, the HIV and SIV proteins described in D. H. Barouch et al, J. Virol., 75(5):2462-2467 (March 2001), and R. R. Amara, et al, Science, 292:69-74 (6 Apr. 2001). These proteins or subunits thereof may be delivered alone, or in combination via separate vectors or from a single vector.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek=s disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; *H. ducreyi* (which causes chancroid); brucella; *Franisella tularensis* (which causes tularemia); yersinia (pasteurella); streptobacillus moniliformis and spirillum; Gram-positive bacilli include *Listeria monocytogenes*; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: *Mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fever, all of which are currently classified as Category A agents; *Coxiella burnetti* (Q fever); *Brucella* species (brucellosis), *Burkholderia mallei* (glanders), *Ricinus communis* and its toxin (ricin toxin), *Clostridium perfringens* and its toxin (epsilon toxin), *Staphylococcus* species and their toxins (enterotoxin B), all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of T cell receptors (TCRs) which are involved in the disease have been characterized. These TCRs include V-3, V-14, V-17 and Va-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Va-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a nucleic acid molecule that encodes at least one of these polypeptides will elicit an immune response that will target T cells involved in scleroderma.

Optionally, vectors containing AAV sequences of the invention may be delivered using a prime-boost regimen. A variety of such regimens have been described in the art and may be readily selected. See, e.g., WO 00/11140, published Mar. 2, 2000, incorporated by reference.

Such prime-boost regimens typically involve the administration of a DNA (e.g., plasmid) based vector to prime the immune system to second, booster, administration with a traditional antigen, such as a protein or a recombinant virus carrying the sequences encoding such an antigen. In one embodiment, the invention provides a method of priming and boosting an immune response to a selected antigen by delivering a plasmid DNA vector carrying said antigen, followed by boosting, e.g., with a vector containing AAV sequences of the invention.

In one embodiment, the prime-boost regimen involves the expression of multiproteins from the prime and/or the boost vehicle. See, e.g., R. R. Amara, Science, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one or example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming vaccine may be administered at various sites in the body in a dose dependent manner, which depends on the antigen to which the desired immune response is being targeted. The invention is not limited to the amount or situs of injection(s) or to the pharmaceutical carrier. Rather, the priming step encompasses treatment regimens which include a single dose or dosage which is administered hourly, daily, weekly or monthly, or yearly. As an example, the mammals may receive one or two priming injection containing between about 10 μg to about 50 μg of plasmid in carrier. A desirable priming amount or dosage of the priming DNA vaccine composition ranges between about 1 μg to about 10,000 μg of the DNA vaccine. Dosages may vary from about 1 μg to 1000 μs DNA per kg of subject body weight. The amount or site of injection is desirably selected based upon the identity and condition of the mammal being vaccinated.

The dosage unit of the DNA vaccine suitable for delivery of the antigen to the mammal is described herein. The DNA vaccine is prepared for administration by being suspended or dissolved in a pharmaceutically or physiologically acceptable carrier such as isotonic saline, isotonic salts solution or other formulations which will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes.

Optionally, the priming step of this invention also includes administering with the priming DNA vaccine composition, a suitable amount of an adjuvant, such as are defined herein.

Preferably, a boosting composition is administered about 2 to about 27 weeks after administering the priming DNA vaccine to the mammalian subject. The administration of the boosting composition is accomplished using an effective amount of a boosting vaccine composition containing or capable of delivering the same antigen as administered by the priming DNA vaccine. The boosting composition may be composed of a recombinant viral vector derived from the same viral source or from another source. Alternatively, the "boosting composition" can be a composition containing the same antigen as encoded in the priming DNA vaccine, but in the form of a protein or peptide, which composition induces an immune response in the host. In another embodiment, the boosting vaccine composition includes a composition containing a DNA sequence encoding the antigen under the control of a regulatory sequence directing its expression in a mammalian cell, e.g., vectors such as well-known bacterial or viral vectors. The primary requirements of the boosting vaccine composition are that the antigen of the vaccine composition is the same antigen, or a cross-reactive antigen, as that encoded by the DNA vaccine.

Suitably, the vectors of the invention are also well suited for use in regimens which use non-AAV vectors as well as proteins, peptides, and/or other biologically useful therapeutic or immunogenic compounds. These regimens are particularly well suited to gene delivery for therapeutic poses and for immunization, including inducing protective immunity. Such uses will be readily apparent to one of skill in the art.

Further, a vector of the invention provides an efficient gene transfer vehicle which can deliver a selected transgene to a selected host cell in vivo or ex vivo even where the organism has neutralizing antibodies to one or more AAV serotypes. In one embodiment, the vector (e.g., an rAAV) and the cells are mixed ex vivo; the infected cells are cultured using conventional methodologies; and the transduced cells are re-infused into the patient. Further, the vectors of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

EXAMPLES

Example 1: PCR Amplification, Cloning and Characterization of Novel AAV Sequences Tissues from nonhuman primates were screened for AAV sequences using a PCR method based on oligonucleotides to highly conserved regions of known AAVs. A stretch of AAV sequence spanning 2886 to 3143 bp of AAV1 [SEQ ID NO:6] was selected as a PCR amplicon in which a hypervariable region of the capsid protein (Cap) that is unique to each known AAV serotype, which is termed herein a "signature region," is flanked by conserved sequences. In later analysis, this signature region was shown to be located between conserved residues spanning hypervariable region 3.

An initial survey of peripheral blood of a number of nonhuman primate species revealed detectable AAV in a subset of animals from species such as rhesus macaques, cynomologous macaques, chimpanzees and baboons. However, there were no AAV sequences detected in some other species tested, including Japanese macaques, pig-tailed macaques and squirrel monkeys. A more extensive analysis of vector distribution was conducted in tissues of rhesus monkeys of the University of Pennsylvania and Tulane colonies recovered at necropsy. This revealed AAV sequence throughout a wide array of tissues.

A. Amplification of an AAV Signature Region

DNA sequences of AAV1-6 and AAVs isolated from Goose and Duck were aligned to each other using "Clustal W" at default settings. The alignment for AAV1-6, and including the information for the novel AAV7, is provided in FIG. 1. Sequence similarities among AAVs were compared.

In the line of study, a 257 bp region spanning 2886 bp to 3143 bp of AAV 1 [SEQ ID NO: 6], and the corresponding region in the genomes of AAV 2-6 genomes [See, FIG. 1], was identified by the inventors. This region is located with the AAV capsid gene and has highly conserved sequences among at both 5' and 3' ends and is relatively variable sequence in the middle. In addition, this region contains a DraIII restriction enzyme site (CACCACGTC, SEQ ID NO:15). The inventors have found that this region serves as specific signature for each known type of AAV DNA. In other words, following PCR reactions, digestion with endonucleases that are specific to each known serotypes and gel electrophoresis analysis, this regions can be used to definitively identify amplified DNA as being from serotype 1, 2, 3, 4, 5, 6, or another serotype.

The primers were designed, validated and PCR conditions optimized with AAV1, 2 and 5 DNA controls. The primers were based upon the sequences of AAV2: 5' primer, 1S: bp 2867-2891 of AAV2 (SEQ ID NO:7) and 3' primer, 18as, bp 3095-3121 of AAV2 (SEQ ID NO:7).

Cellular DNAs from different tissues including blood, brain, liver, lung, testis, etc. of different rhesus monkeys were studied utilizing the strategy described above. The results revealed that DNAs from different tissues of these monkeys gave rise to strong PCR amplifications. Further restriction analyses of PCR products indicated that they were amplified from AAV sequences different from any published AAV sequences.

PCR products (about 255 bp in size) from DNAs of a variety of monkey tissues have been cloned and sequenced. Bioinformatics study of these novel AAV sequences indicated that they are novel AAV sequences of capsid gene and distinct from each other. FIG. 1 includes in the alignment the novel AAV signature regions for AAV10-12 [SEQ ID NO:117, 118 and 119, respectively]. Multiple sequence alignment analysis was performed using the Clustal W (1.81) program. The percentage of sequence identity between the signature regions of AAV 1-7 and AAV 10-12 genomes is provided below.

TABLE 2

Sequences for Analysis

| Sequence # | AAV Serotype | Size (bp) |
|---|---|---|
| 1 | AAV1 | 258 |
| 2 | AAV2 | 255 |
| 3 | AAV3 | 255 |
| 4 | AAV4 | 246 |
| 5 | AAV5 | 258 |
| 6 | AAV6 | 258 |
| 7 | AAV7 | 258 |
| 10 | AAV10 | 255 |
| 11 | AAV11 | 258 |
| 12 | AAV12 | 255 |

TABLE 3

Pairwise Alignment (Percentage of Identity)

|  | AAV2 | AAV3 | AAV4 | AAV5 | AAV6 | AAV7 | AAV10 | AAV11 | AAV12 |
|---|---|---|---|---|---|---|---|---|---|
| AAV1 | 90 | 90 | 81 | 76 | 97 | 91 | 93 | 94 | 93 |
| AAV2 |  | 93 | 79 | 78 | 90 | 90 | 93 | 93 | 92 |
| AAV3 |  |  | 80 | 76 | 90 | 92 | 92 | 92 | 92 |
| AAV4 |  |  |  | 76 | 81 | 84 | 82 | 81 | 79 |
| AAV5 |  |  |  |  | 75 | 78 | 79 | 79 | 76 |
| AAV6 |  |  |  |  |  | 91 | 92 | 94 | 94 |
| AAV7 |  |  |  |  |  |  | 94 | 92 | 92 |
| AAV10 |  |  |  |  |  |  |  | 95 | 93 |
| AAV11 |  |  |  |  |  |  |  |  | 94 |

Over 300 clones containing novel AAV serotype sequences that span the selected 257 bp region were isolated and sequenced. Bioinformatics analysis of these 300+ clones suggests that this 257 bp region is critical in serving as a good land marker or signature sequence for quick isolation and identification of novel AAV serotype.

B. Use of the Signature Region for PCR Amplification.

The 257 bp signature region was used as a PCR anchor to extend PCR amplifications to 5' of the genome to cover the junction region of rep and cap genes (1398 bp-3143 bp, SEQ ID NO:6) and 3' of the genome to obtain the entire cap gene sequence (2866 bp-4600 bp, SEQ ID NO:6). PCR amplifications were carried out using the standard conditions, including denaturing at 95° C. for 0.5-1 min, annealing at 60-65° C. for 0.5-1 min and extension at 72° C. for 1 min per kb with a total number of amplification cycles ranging from 28 to 42.

Using the aligned sequences as described in "A", two other relative conserved regions were identified in the sequence located in 3' end of rep genes and 5' to the 257 bp region and in the sequence down stream of the 257 bp fragment but before the AAV' 3 ITR. Two sets of new primers were designed and PCR conditions optimized for recovery of entire capsid and a part of rep sequences of novel AAV serotypes. More specifically, for the 5' amplification, the 5' primer, AV1Ns, was GCTGCGT-CAACTGGACCAATGAGAAC [nt 1398-1423 of AAV1, SEQ ID NO:6] and the 3' primer was 18as, identified above. For the 3' amplification, the 5' primer was 1s, identified above, and the 3' primer was AV2Las, TCGTTTCAGTT-GAACTTTGGTCTCTGCG [nt 4435-4462 of AAV2, SEQ ID NO:7].

In these PCR amplifications, the 257 bp region was used as a PCR anchor and land marker to generate overlapping fragments to construct a complete capsid gene by fusion at the DraIII site in the signature region following amplification of the 5' and 3' extension fragments obtained as described herein. More particularly, to generate the intact AAV7 cap gene, the three amplification products (a) the sequences of the signature region; (b) the sequences of the 5' extension; and (c) the sequences of the 3' extension were cloned into a pCR4-Topo [Invitrogen] plasmid backbone according to manufacturer's instructions. Thereafter, the plasmids were digested with DraIII and recombined to form an intact cap gene.

In this line of work, about 80% of capsid sequences of AAV7 and AAV 8 were isolated and analyzed. Another novel serotype, AAV9, was also discovered from Monkey #2.

Using the PCR conditions described above, the remaining portion of the rep gene sequence for AAV7 is isolated and cloned using the primers that amplify 108 bp to 1461 bp of AAV genome (calculated based on the numbering of AAV2, SEQ ID NO:7). This clone is sequenced for construction of a complete AAV7 genome without ITRs.

C. Direct Amplification of 3.1 kb Cap Fragment

To directly amplify a 3.1 kb full-length Cap fragment from NHP tissue and blood DNAs, two other highly conserved regions were identified in AAV genomes for use in PCR amplification of large fragments. A primer within a conserved region located in the middle of the rep gene was selected (AV1ns: 5' GCTGCGTCAACTGGACCAAT-GAGAAC 3', nt 1398-1423 of SEQ ID NO:6) in combination with the 3' primer located in another conserved region downstream of the Cap gene (AV2cas: 5' CGCAGAGAC-CAAAGTTCAACTGAAACGA 3', SEQ ID NO:7) for amplification of full-length cap fragments. The PCR products were Topo-cloned according to manufacturer's directions (Invitrogen) and sequence analysis was performed by Qiagengenomics (Qiagengenomics, Seattle, Wash.) with an accuracy of 99.9%. A total of 50 capsid clones were isolated and characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5).

To rule out the possibility that sequence diversity within the novel AAV family was not an artifact of the PCR, such as PCR-mediated gene splicing by overlap extension between different partial DNA templates with homologous sequences, or the result of recombination process in bacteria, a series of experiments were performed under identical conditions for VP1 amplification using total cellular DNAs. First, intact AAV7 and AAV8 plasmids were mixed at an equal molar ratio followed by serial dilutions. The serially diluted mixtures were used as templates for PCR amplification of 3.1 kb VP1 fragments using universal primers and identical PCR conditions to that were used for DNA amplifications to see whether any hybrid PCR products were generated. The mixture was transformed into bacteria and isolated transformants to look for hybrid clones possibly derived from recombination process in bacterial cells. In a different experiment, we restricted AAV7 and AAV8 plasmids with Msp I, Ava I and HaeI, all of which cut both genomes multiple times at different positions, mixed the digestions in different combinations and used them for PCR amplification of VP1 fragments under the same conditions to test whether any PCR products could be generated through overlap sequence extension of partial AAV sequences. In another experiment, a mixture of gel purified 5' 1.5 kb AAV7 VP1 fragment and 3' 1.7 kb AAV8 VP1 fragment with overlap in the signature region was serially diluted and used for PCR amplification in the presence and absence of 200 ng cellular DNA extracted from a monkey cell line that was free of AAV sequences by TaqMan analysis. None of these experiments demonstrated efficient PCR-mediated overlap sequence production under the conditions of the genomic DNA Cap amplification (data not shown). As a further confirmation, 3 pairs of primers were designed, which were located at different HVRs, and were sequence specific to the variants of clone 42s from Rhesus macaque F953, in different combinations to amplify shorter fragments from mesenteric lymph node (MLN) DNA from F953 from which clone 42s were isolated. All sequence variations identified in full-length Cap clones were found in these short fragments (data not shown).

Example 2: Adeno-Associated Viruses Undergo Substantial Evolution in Primates During Natural Infections Sequence analysis of selected AAV isolates revealed divergence throughout the genome that is most concentrated in hypervariable regions of the capsid proteins. Epidemiologic data indicate that all known serotypes are endemic to primates, although isolation of clinical isolates has been restricted to AAV2 and AAV3 from anal and throat swabs of human infants and AAV5 from a human condylomatous wart. No known clinical sequalae have been associated with AAV infection.

In an attempt to better understand the biology of AAV, nonhuman primates were used as models to characterize the sequlae of natural infections. Tissues from nonhuman primates were screened for AAV sequences using the PCR method of the invention based on oligonucleotides to highly conserved regions of known AAVs (see Example 1). A stretch of AAV sequence spanning 2886 to 3143 bp of AAV1 [SEQ ID NO:6] was selected as a PCR amplicon in which conserved sequences are flanked by a hypervariable region that is unique to each known AAV serotype, termed herein a "signature region."

An initial survey of peripheral blood of a number of nonhuman primate species including rhesus monkeys, cynomologous monkeys, chimpanzees, and baboons revealed detectable AAV in a subset of animals from all species. A more extensive analysis of vector distribution was conducted in tissues of rhesus monkeys of the University of Pennsylvania and Tulane colonies recovered at necropsy. This revealed AAV sequence throughout a wide array of tissues.

The amplified signature sequences were subcloned into plasmids and individual transformants were subjected to sequence analysis. This revealed substantial variation in nucleotide sequence of clones derived from different animals. Variation in the signature sequence was also noted in clones obtained within individual animals. Tissues harvested from two animals in which unique signature sequences were identified (i.e., colon from 98E044 and heart from 98E056) were further characterized by expanding the sequence amplified by PCR using oligonucleotides to highly conserved sequences. In this way, complete proviral structures were reconstructed for viral genomes from both tissues as described herein. These proviruses differ from the other known AAVs with the greatest sequence divergence noted in regions of the Cap gene.

Additional experiments were performed to confirm that AAV sequences resident to the nonhuman primate tissue represented proviral genomes of infectious virus that is capable of being rescued and form virions. Genomic DNA from liver tissue of animal 98E056, from which AAV8 signature sequence was detected, was digested with an endonuclease that does not have a site within the AAV sequence and transfected into 293 cells with a plasmid containing an E 1 deleted genome of human adenovirus serotype 5 as a source of helper functions. The resulting lysate was passaged on 293 cells once and the lysate was recovered and analyzed for the presence of AAV Cap proteins using a broadly reacting polyclonal antibody to Cap proteins and for the presence and abundance of DNA sequences from the PCR amplified AAV provirus from which AAV8 was derived. Transfection of endonuclease restricted heart DNA and the adenovirus helper plasmid yielded high quantities of AAV8 virus as demonstrated by the detection of Cap proteins by Western blot analysis and the presence of $10^4$ AAV8 vector genomes per 293 cell. Lysates were generated from a large-scale preparation and the AAV was purified by cesium sedimentation. The purified preparation demonstrated 26 nm icosohedral structures that look identical to those of AAV serotype 2. Transfection with the adenovirus helper alone did not yield AAV proteins or genomes, ruling out contamination as a source of the rescued AAV.

To further characterize the inter and intra animal variation of AAV signature sequence, selected tissues were subjected to extended PCR to amplify entire Cap open reading frames.

The resulting fragments were cloned into bacterial plasmids and individual transformants were isolated and fully sequenced. This analysis involved mesenteric lymph nodes from three rhesus monkeys (Tulane/V223—6 clones; Tulane/T612—7 clones; Tulane/F953—14 clones), liver from two rhesus monkeys (TulaneN251—3 clones; Penn/00E033—3 clones), spleen from one rhesus monkey (Penn/97E043—3 clones), heart from one rhesus monkey (IHGT/98E046-1 clone) and peripheral blood from one chimpanzee (New Iberia/X133—5 clones), six cynomologous macaques (Charles River/A1378, A3099, A3388, A3442, A2821, A3242—6 clones total) and one Baboon (SFRB/8644—2 clones). Of the 50 clones that were sequenced from 15 different animals, 30 were considered non-redundant based on the finding of at least 7 amino acid differences from one another. The non-redundant VP1 clones are numbered sequentially as they were isolated, with a prefix indicating the species of non-human primate from which they were derived. The structural relationships between these 30 non-redundant clones and the previously described 8 AAV serotypes were determined using the SplitsTree program [Huson, D. H. SplitsTree: analyzing and visualizing evolutionary data. *Bioinformatics* 14, 68-73 (1998)] with implementation of the method of split decomposition. The analysis depicts homoplasy between a set of sequences in a tree-like network rather than a bifurcating tree. The advantage is to enable detection of groupings that are the result of convergence and to exhibit phylogenetic relationships even when they are distorted by parallel events. Extensive phylogenetic research will be required in order to elucidate the AAV evolution, whereas the intention here only is to group the different clones as to their sequence similarity.

To confirm that the novel VP1 sequences were derived from infectious viral genomes, cellular DNA from tissues with high abundance of viral DNA was restricted with an endonuclease that should not cleave within AAV and transfected into 293 cells, followed by infection with adenovirus. This resulted in rescue and amplification of AAV genomes from DNA of tissues from two different animals (data not shown).

VP1 sequences of the novel AAVs were further characterized with respect to the nature and location of amino acid sequence variation. All 30 VP1 clones that were shown to differ from one another by greater than 1% amino acid sequence were aligned and scored for variation at each residue. An algorithm developed to determine areas of sequence divergence yielded 12 hypervariable regions (HVR) of which 5 overlap or are part of the 4 previously described variable regions [Kotin, cited above; Rutledge, cited above]. The three-fold-proximal peaks contain most of the variability (HVR5-10). Interestingly the loops located at the 2 and 5 fold axis show intense variation as well. The HVRs 1 and 2 occur in the N-terminal portion of the capsid protein that is not resolved in the X-ray structure suggesting that the N-terminus of the VP1 protein is exposed on the surface of the virion.

Real-time PCR was used to quantify AAV sequences from tissues of 21 rhesus monkeys using primers and probes to highly conserved regions of Rep (one set) and Cap (two sets) of known AAVs. Each data point represents analysis from tissue DNA from an individual animal. This confirmed the wide distribution of AAV sequences, although the quantitative distribution differed between individual animals. The source of animals and previous history or treatments did not appear to influence distribution of AAV sequences in rhesus macaques. The three different sets of primers and probes used to quantify AAV yielded consistent results. The highest levels of AAV were found consistently in mesenteric lymph nodes at an average of 0.01 copies per diploid genome for 13 animals that were positive. Liver and spleen also contained high abundance of virus DNA. There were examples of very high AAV, such as in heart of rhesus macaque 98E056, spleen of rhesus macaque 97E043 and liver of rhesus macaque RQ4407, which demonstrated 1.5, 3 and 20 copies of AAV sequence per diploid genome respectively. Relatively low levels of virus DNA were noted in peripheral blood mononuclear cells, suggesting the data in tissue are not due to resident blood components (data not shown). It should be noted that this method would not necessarily capture all AAVs resident to the nonhuman primates since detection requires high homology to both the oligonucleotides and the real time PCR probe. Tissues from animals with high abundance AAV DNA was further analyzed for the molecular state of the DNA, by DNA hybridization techniques, and its cellular distribution, by in situ hybridization.

The kind of sequence variation revealed in AAV proviral fragments isolated from different animals and within tissues of the same animals is reminiscent of the evolution that occurs for many RNA viruses during pandemics or even within the infection of an individual. In some situations the notion of a wild-type virus has been replaced by the existence of swarms of quasispecies that evolve as a result of rapid replication and mutations in the presence of selective pressure. One example is infection by HIV, which evolves in response to immunologic and pharmacologic pressure. Several mechanisms contribute to the high rate of mutations in RNA viruses, including low fidelity and lack of proof reading capacity of reverse transcriptase and non-homologous and homologous recombination.

Evidence for the formation of quasispecies of AAV was illustrated in this study by the systematic sequencing of multiple cloned proviral fragments. In fact, identical sequences could not be found within any extended clones isolated between or within animals. An important mechanism for this evolution of sequence appears to be a high rate of homologous recombination between a more limited number of parenteral viruses. The net result is extensive swapping of hypervariable regions of the Cap protein leading to an array of chimeras that could have different tropisms and serologic specificities (i.e., the ability to escape immunologic responses especially as it relates to neutralizing antibodies). Mechanisms by which homologous recombination could occur are unclear. One possibility is that + and − strands of different single stranded AAV genomes anneal during replication as has been described during high multiplicity of infections with AAV recombinants. It is unclear if other mechanisms contribute to sequence evolution in AAV infections. The overall rate of mutation that occurs during AAV replication appears to be relatively low and the data do not suggest high frequencies of replication errors. However, substantial rearrangements of the AAV genome have been described during lytic infection leading to the formation of defective interfering particles. Irrespective of the mechanisms that lead to sequence divergence, with few exceptions, vp1 structures of the quasispecies remained intact without frameshifts or nonsense mutations suggesting that competitive selection of viruses with the most favorable profile of fitness contribute to the population dynamics.

These studies have implications in several areas of biology and medicine. The concept of rapid virus evolution, formerly thought to be a property restricted to RNA viruses, should be considered in DNA viruses, which classically have been characterized by serologic assays. It will be important in terms of parvoviruses to develop a new method for describing virus isolates that captures the complexity of its structure and biology, such as with HIV, which are categorized as general families of similar structure and function called Clades. An alternative strategy is to continue to categorize isolates with respect to serologic specificity and develop criteria for describing variants within serologic groups.

Example 3: Vectorology of Recombinant AAV Genomes Equipped with AAV2 ITRs is Using Chimeric Plasmids Containing AAV2 Rep and Novel AAV Cap Genes for Serological and Gene Transfer Studies in Different Animal Models Chimeric packaging constructs are generated by fusing AAV2 rep with cap sequences of novel AAV serotypes. These chimeric packaging constructs are used, initially, for pseudotyping recombinant AAV genomes carrying AAV2 ITRs by triple transfection in 293 cell using Ad5 helper plasmid. These pseudotyped vectors are used to evaluate performance in transduction-based serological studies and evaluate gene transfer efficiency of novel AAV serotypes in different animal models including NHP and rodents, before intact and infectious viruses of these novel serotypes are isolated.

A. pAAV2GFP

The AAV2 plasmid which contains the AAV2 ITRs and green fluorescent protein expressed under the control of a constitutitive promoter. This plasmid contains the following elements: the AAV2 ITRs, a CMV promoter, and the GFP coding sequences.

B. Cloning of Trans Plasmid

To construct the chimeric trans-plasmid for production of recombinant pseudotyped AAV7 vectors, p5E18 plasmid (Xiao et al., 1999, *J Vivol* 73:3994-4003) was partially digested with Xho I to linearize the plasmid at the Xho I site at the position of 3169 bp only. The Xho I cut ends were then filled in and ligated back. This modified p5E18 plasmid was restricted with Xba I and Xho I in a complete digestion to remove the AAV2 cap gene sequence and replaced with a 2267 bp Spe I/Xho I fragment containing the AAV7 cap gene which was isolated from pCRAAV7 6-5+15-4 plasmid.

The resulting plasmid contains the AAV2 rep sequences for Rep78/68 under the control of the AAV2 P5 promoter, and the AAV2 rep sequences for Rep52/40 under the control of the AAV2 P19 promoter. The AAV7 capsid sequences are under the control of the AAV2 P40 promoter, which is located within the Rep sequences. This plasmid further contains a spacer 5' of the rep ORF.

C. Production of Pseudotyped rAAV

The rAAV particles (AAV2 vector in AAV7 capsid) are generated using an adenovirus-free method. Briefly, the cis plasmid (pAAV2.1 lacZ plasmid containing AAV2 ITRs), and the trans plasmid pCRAAV7 6-5+15-4 (containing the AAV2 rep and AAV7 cap) and a helper plasmid, respectively, were simultaneously co-transfected into 293 cells in a ratio of 1:1:2 by calcium phosphate precipitation.

For the construction of the pAd helper plasmids, pBG10 plasmid was purchased from Microbix (Canada). A RsrII fragment containing L2 and L3 was deleted from pBHG10, resulting in the first helper plasmid, pAdΔF13. Plasmid AdΔ F1 was constructed by cloning Asp700/SalI fragment with a PmeI/SgfI deletion, isolating from pBHG10, into Bluescript. MLP, L2, L2 and L3 were deleted in the pAdΔF1. Further deletions of a 2.3 kb NruI fragment and, subsequently, a 0.5 kb RsrII/NruI fragment generated helper plasmids pAdΔF5 and pAdΔF6, respectively. The helper plasmid, termed pΔF6, provides the essential helper functions of E2a and E4 ORF6 not provided by the E1-expressing helper cell, but is deleted of adenoviral capsid proteins and functional E1 regions).

Typically, 50 μg of DNA (cis:trans:helper) was transfected onto a 150 mm tissue culture dish. The 293 cells were harvested 72 hours post-transfection, sonicated and treated with 0.5% sodium deoxycholate (37EC for 10 min) Cell lysates were then subjected to two rounds of a CsCl gradient. Peak fractions containing rAAV vector are collected, pooled and dialyzed against PBS.

Example 4: Creation of Infectious Clones Carrying Intact Novel AAV Serotypes for Study of Basic Virology in Human and NHP Derived Cell Lines and Evaluation of Pathogenesis of Novel AAV Serotypes in NHP and Other Animal Models To achieve this goal, the genome walker system is employed to obtain 5' and 3' terminal sequences (ITRs) and complete construction of clones containing intact novel AAV serotype genomes.

Briefly, utilizing a commercially available Universal Genome Walker Kit [Clontech], genomic DNAs from monkey tissues or cell lines that are identified as positive for the presence of AAV7 sequence are digested with Dra I, EcoR V, Pvu II and Stu I to endonucleases and ligated to Genome Walker Adaptor to generate 4 individual Genome Walker Libraries (GWLs). Using DNAs from GWLs as templates, AAV7 and adjacent genomic sequences will be PCR-amplified by the adaptor primer 1 (AP1, provided in the kit) and an AAV7 specific primer 1, followed by a nested PCR using the adaptor primer 2 (AP2) and another AAV7 specific primer 2, both of which are internal to the first set of primers. The major PCR products from the nested PCR are cloned and characterized by sequencing analysis.

In this experiment, the primers covering the 257 bp or other signature fragment of a generic AAV genome are used for PCR amplification of cellular DNAs extracted from Human and NHP derived cell lines to identify and characterize latent AAV sequences. The identified latent AAV genomes are rescued from the positive cell lines using adenovirus helpers of different species and strains.

To isolate infectious AAV clones from NHP derived cell lines, a desired cell line is obtained from ATCC and screened by PCR to identify the 257 bp amplicon, i.e., signature region of the invention. The 257 bp PCR product is cloned and serotyped by sequencing analysis. For these cell lines containing the AAV7 sequence, the cells are infected with SV-15, a simian adenovirus purchased from ATCC, human Ad5 or transfected with plasmid construct housing the human Ad genes that are responsible for AAV helper functions. At 48 hour post infection or transfection, the cells are harvested and Hirt DNA is prepared for cloning of AAV7 genome following Xiao et al., 1999, J. Virol, 73:3994-4003.

Example 5—Production of AAV Vectors

A pseudotyping strategy similar to that of Example 3 for AAV1/7 was employed to produce AAV2 vectors packaged with AAV1, AAV5 and AAV8 capsid proteins. Briefly, recombinant AAV genomes equipped with AAV2 ITRs were packaged by triple transfection of 293 cells with cis-plasmid, adenovirus helper plasmid and a chimeric packaging construct where the AAV2 rep gene is fused with cap genes of novel AAV serotypes. To create the chimeric packaging constructs, the Xho I site of p5E18 plasmid at 3169 bp was ablated and the modified plasmid was restricted with Xba I and Xho I in a complete digestion to remove the AAV2 cap gene and replace it with a 2267 bp Spe I/Xho I fragment containing the AAV8 cap gene [Xiao, W., et al., (1999) *J Vivol* 73, 3994-4003]. A similar cloning strategy was used for creation of chimeric packaging plasmids of AAV2/1 and AAV2/5. All recombinant vectors were purified by the standard $CsCl_2$ sedimentation method except for AAV2/2, which was purified by single step heparin chromatography.

Genome copy (GC) titers of AAV vectors were determined by TaqMan analysis using probes and primers targeting SV40 poly A region as described previously [Gao, G., et al., (2000) *Hum Gene Ther* 11, 2079-91].

Vectors were constructed for each serotype for a number of in vitro and in vivo studies. Eight different transgene cassettes were incorporated into the vectors and recombinant virions were produced for each serotype. The recovery of virus, based on genome copies, is summarized in Table 4 below. The yields of vector were high for each serotype with no consistent differences between serotypes. Data presented in the table are average genome copy yields with standard deviation$\times 10^{13}$ of multiple production lots of 50 plate (150 mm) transfections.

TABLE 4

Production of Recombinant Vectors

|  | AAV2/1 | AAV2/2 | AAV2/5 | AAV2/7 | AAV2/8 |
|---|---|---|---|---|---|
| CMV LacZ | 7.30 ± 4.33 (n = 9) | 4.49 ± 2.89 (n = 6) | 5.19 ± 5.19 (n = 8) | 3.42 (n = 1) | 0.87 (n = 1) |
| CMV EGFP | 6.43 ± 2.42 (n = 2) | 3.39 ± 2.42 (n = 2) | 5.55 ± 6.49 (n = 4) | 2.98 ± 2.66 (n = 2) | 3.74 ± 3.88 (n = 2) |
| TBG LacZ | 4.18 (n = 1) | 0.23 (n = 1) | 0.704 ± 0.43 (n = 2) | 2.16 (n = 1) | 0.532 (n = 1) |
| Alb A1AT | 4.67 ± 0.75 (n = 2) | 4.77 (n = 1) | 4.09 (n = 1) | 5.04 (n = 1) | 2.02 (n = 1) |
| CB A1AT | 0.567 (n = 1) | 0.438 (n = 1) | 2.82 (n = 1) | 2.78 (n = 1) | 0.816 ± 0.679 (n = 2) |
| TBG rhCG | 8.51 ± 6.65 (n = 6) | 3.47 ± 2.09 (n = 5) | 5.26 ± 3.85 (n = 4) | 6.52 ± 3.08 (n = 4) | 1.83 ± 0.98 (n = 5) |
| TBG cFIX | 1.24 ± 1.29 (n = 3) | 0.63 ± 0.394 (n = 6) | 3.74 ± 2.48 (n = 7) | 4.05 (n = 1) | 15.8 ± 15.0 (n = 5) |

Example 6—Serologic Analysis of Pseudotyped Vectors

C57BL/6 mice were injected with vectors of different serotypes of AAVCBA1AT vectors intramuscularly ($5\times10^{11}$ GC) and serum samples were collected 34 days later. To test neutralizing and cross-neutralizing activity of sera to each serotype of AAV, sera was analyzed in a transduction based neutralizing antibody assay [Gao, G. P., et al., (1996) *J Vivol* 70, 8934-43]. More specifically, the presence of neutralizing antibodies was determined by assessing the ability of serum to inhibit transduction of 84-31 cells by reporter viruses (AAVCMVEGFP) of different serotypes. Specifically, the reporter virus AAVCMVEGFP of each serotype [at multiplicity of infection (MOI) that led to a transduction of 90% of indicator cells] was pre-incubated with heat-inactivated serum from animals that received different serotypes of AAV or from naïve mice. After 1-hour incubation at 37° C., viruses were added to 84-31 cells in 96 well plates for 48 or 72-hour, depending on the virus serotype. Expression of GFP was measured by FluoroImagin (Molecular Dynamics) and quantified by Image Quant Software. Neutralizing antibody titers were reported as the highest serum dilution that inhibited transduction to less than 50%.

The availability of GFP expressing vectors simplified the development of an assay for neutralizing antibodies that was based on inhibition of transduction in a permissive cell line (i.e., 293 cells stably expressing E4 from Ad5). Sera to selected AAV serotypes were generated by intramuscular injection of the recombinant viruses. Neutralization of AAV transduction by 1:20 and 1:80 dilutions of the antisera was evaluated (See Table 5 below). Antisera to AAV1, AAV2, AAV5 and AAV8 neutralized transduction of the serotype to which the antiserum was generated (AAV5 and AAV8 to a lesser extent than AAV1 and AAV2) but not to the other serotype (i.e., there was no evidence of cross neutralization suggesting that AAV 8 is a truly unique serotype).

directed gene transfer, either mouse albumin gene promoter (Alb) [Xiao, W. (1999), cited above] or human thyroid hormone binding globulin gene promoter (TBG) [Wang (1997), cited above] was used to drive liver specific expression of reporter genes. In muscle-directed gene transfer experiments, either cytomegalovirus early promoter (CMV) or chicken β-actin promoter with CMV enhancer (CB) was employed to direct expression of reporters.

For muscle-directed gene transfer, vectors were injected into the right tibialis anterior of 4-6 week old NCR nude or C57BL/6 mice (Taconic, Germantown, N.Y.). In liver-directed gene transfer studies, vectors were infused intraportally into 7-9 week old NCR nude or C57BL/6 mice (Taconic, Germantown, N.Y.). Serum samples were collected intraorbitally at different time points after vector administration. Muscle and liver tissues were harvested at different time points for cryosectioning and Xgal histochemical staining from animals that received the lacZ vectors. For the re-administration experiment, C56BL/6 mice initially received AAV2/1, 2/2, 2/5, 2/7 and 2/8CBA1AT vectors intramuscularly and followed for A1AT gene expression for 7 weeks. Animals were then treated with AAV2/8TBGcFIX intraportally and studied for cFIX gene expression.

TABLE 5

Serological Analysis of New AAV Serotypes.

| | | % Infection on 84-31 cells with AAVCMVEGFP virus: | | | | | | | | |
|---|---|---|---|---|---|---|---|---|---|---|
| | | AAV2/1 Serum dilution: | | AAV2/2 Serum dilution: | | AAV2/5 Serum dilution: | | AAV2/7 Serum dilution: | | AAV2/8 Serum dilution: | |
| Sera: | Immunization Vector | 1/20 | 1/80 | 1/20 | 1/80 | 1/20 | 1/80 | 1/20 | 1/80 | 1/20 | 1/80 |
| Group 1 | AAV2/1 | 0 | 0 | 100 | 100 | 100 | 100 | 100 | 100 | 100 | 100 |
| Group 2 | AAV2/2 | 100 | 100 | 0 | 0 | 100 | 100 | 100 | 100 | 100 | 100 |
| Group 3 | AAV2/5 | 100 | 100 | 100 | 100 | 16.5 | 16.5 | 100 | 100 | 100 | 100 |
| Group 4 | AAV2/7 | 100 | 100 | 100 | 100 | 100 | 100 | 61.5 | 100 | 100 | 100 |
| Group 5 | AAV2/8 | 100 | 100 | 100 | 100 | 100 | 100 | 100 | 100 | 26.3 | 60 |

Human sera from 52 normal subjects were screened for neutralization against selected serotypes. No serum sample was found to neutralize AAV2/7 and AAV2/8 while AAV2/2 and AAV2/1 vectors were neutralized in 20% and 10% of sera, respectively. A fraction of human pooled IgG representing a collection of 60,000 individual samples did not neutralize AAV2/7 and AAV2/8, whereas AAV2/2 and AAV2/1 vectors were neutralized at titers of serum equal to 1/1280 and 1/640, respectively.

Example 7—In Vivo Evaluation of Different Serotypes of AAV Vectors

In this study, 7 recombinant AAV genomes, AAV2CBhA1AT, AAV2AlbhA1AT, AAV2CMVrhCG, AAV2TBGrhCG, AAV2TBGcFIX, AAV2CMVLacZ and AAV2TBGLacZ were packaged with capsid proteins of different serotypes. In all 7 constructs, minigene cassettes were flanked with AAV2 ITRs. cDNAs of human α-antitrypsin (A1AT) [Xiao, W., et al., (1999) J Virol 73, 3994-4003] β-subunit of rhesus monkey choriogonadotropic hormone (CG) [Zoltick, P. W. & Wilson, J. M. (2000) Mol Ther 2, 657-9] canine factor IX [Wang, L., et al., (1997) Proc Natl Acad Sci USA 94, 11563-6] and bacterial β-glactosidase (i.e., Lac Z) genes were used as reporter genes. For liver- ELISA based assays were performed to quantify serum levels of hA1AT, rhCG and cFIX proteins as described previously [Gao, G. P., et al., (1996) J Vivol 70, 8934-43; Zoltick, P. W. & Wilson, J. M. (2000) Mol Ther 2, 657-9; Wang, L., et al., Proc Natl Acad Sci USA 94, 11563-6]. The experiments were completed when animals were sacrificed for harvest of muscle and liver tissues for DNA extraction and quantitative analysis of genome copies of vectors present in target tissues by TaqMan using the same set of primers and probe as in titration of vector preparations [Zhang, Y., et al., (2001) Mol Ther 3, 697-707].

The performance of vectors base on the new serotypes were evaluated in murine models of muscle and liver-directed gene transfer and compared to vectors based on the known serotypes AAV1, AAV2 and AAV5. Vectors expressing secreted proteins (alpha-antitrypsin (A1AT) and chorionic gonadotropin (CG)) were used to quantitate relative transduction efficiencies between different serotypes through ELISA analysis of sera. The cellular distribution of transduction within the target organ was evaluated using lacZ expressing vectors and X-gal histochemistry.

The performance of AAV vectors in skeletal muscle was analyzed following direct injection into the tibialis anterior muscles. Vectors contained the same AAV2 based genome with the immediate early gene of CMV or a CMV enhanced β-actin promoter driving expression of the transgene. Previous studies indicated that immune competent C57BL/6 mice elicit limited humoral responses to the human A1AT protein when expressed from AAV vectors [Xiao, W., et al., (1999) *J Vivol* 73, 3994-4003].

In each strain, AAV2/1 vector produced the highest levels of A1AT and AAV2/2 vector the lowest, with AAV2/7 and AAV2/8 vectors showing intermediate levels of expression. Peak levels of CG at 28 days following injection of nu/nu NCR mice showed the highest levels from AAV2/7 and the lowest from AAV2/2 with AAV2/8 and AAV2/1 in between. Injection of AAV2/1 and AAV2/7 lacZ vectors yielded gene expression at the injection sites in all muscle fibers with substantially fewer lacZ positive fibers observed with AAV2/2 and AAV 2/8 vectors. These data indicate that the efficiency of transduction with AAV2/7 vectors in skeletal muscle is similar to that obtained with AAV2/1, which is the most efficient in skeletal muscle of the previously described serotypes [Xiao, W. (1999), cited above; Chao, H., et al., (2001) *Mol Ther* 4, 217-22; Chao, H., et al., (2000) *Mol Ther* 2, 619-23].

Similar murine models were used to evaluate liver-directed gene transfer. Identical doses of vector based on genome copies were infused into the portal veins of mice that were analyzed subsequently for expression of the transgene. Each vector contained an AAV2 based genome using previously described liver-specific promoters (i.e., albumin or thyroid hormone binding globulin) to drive expression of the transgene. More particularly, CMVCG and TBGCG minigene cassettes were used for muscle and liver-directed gene transfer, respectively. Levels of rhCG were defined as relative units (RUs×10$^3$). The data were from assaying serum samples collected at day 28, post vector administration (4 animals per group). As shown in Table 3, the impact of capsid proteins on the efficiency of transduction of A1AT vectors in nu/nu and C57BL/6 mice and CG vectors in C57BL/6 mice was consistent (See Table 6).

TABLE 6

Expression of β-unit of Rhesus Monkey Chorionic Gonadotropin (rhCG)

| Vector | Muscle | Liver |
| --- | --- | --- |
| AAV2/1 | 4.5 ± 2.1 | 1.6 ± 1.0 |
| AAV2 | 0.5 ± 0.1 | 0.7 ± 0.3 |
| AAV2/5 | ND* | 4.8 ± 0.8 |
| AAV2/7 | 14.2 ± 2.4 | 8.2 ± 4.3 |
| AAV2/8 | 4.0 ± 0.7 | 76.0 ± 22.8 |

*Not determined in this experiment.

In all cases, AAV2/8 vectors yielded the highest levels of transgene expression that ranged from 16 to 110 greater than what was obtained with AAV2/2 vectors; expression from AAV2/5 and AAV2/7 vectors was intermediate with AAV2/7 higher than AAV2/5. Analysis of X-Gal stained liver sections of animals that received the corresponding lacZ vectors showed a correlation between the number of transduced cells and overall levels of transgene expression. DNAs extracted from livers of C57BL/6 mice who received the A1AT vectors were analyzed for abundance of vector DNA using real time PCR technology.

The amount of vector DNA found in liver 56 days after injection correlated with the levels of transgene expression (See Table 7). For this experiment, a set of probe and primers targeting the SV40 polyA region of the vector genome was used for TaqMan PCR. Values shown are means of three individual animals with standard deviations. The animals were sacrificed at day 56 to harvest liver tissues for DNA extraction. These studies indicate that AAV8 is the most efficient vector for liver-directed gene transfer due to increased numbers of transduced hepatocytes.

TABLE 7

Real Time PCR Analysis for Abundance of AAV Vectors in nu/nu Mouse Liver Following Injection of 1 × 10$^{11}$ Genome Copies of Vector.

| AAV vectors/Dose | Genome Copies per Cell |
| --- | --- |
| AAV2/1AlbA1AT | 0.6 ± 0.36 |
| AAV2AlbA1AT | 0.003 ± 0.001 |
| AAV2/5AlbA1AT | 0.83 ± 0.64 |
| AAV2/7AlbA1AT | 2.2 ± 1.7 |
| AAV2/8AlbA1AT | 18 ± 11 |

The serologic data described above suggest that AAV2/8 vector should not be neutralized in vivo following immunization with the other serotypes. C57BL/6 mice received intraportal injections of AAV2/8 vector expressing canine factor IX (10$^{11}$ genome copies) 56 days after they received intramuscular injections of A1AT vectors of different serotypes. High levels of factor IX expression were obtained 14 days following infusion of AAV2/8 into naïve animals (17±2 µg/ml, n=4) which were not significantly different that what was observed in animals immunized with AAV2/1 (31±23 µg/ml, n=4), AAV2/2 (16 µg/ml, n=2), and AAV2/7 (12 µg/ml, n=2). This contrasts to what was observed in AAV2/8 immunized animals that were infused with the AAV2/8 factor IX vector in which no detectable factor IX was observed (<0.1 µg/ml, n=4).

Oligonucleotides to conserved regions of the cap gene did amplify sequences from rhesus monkeys that represented unique AAVs. Identical cap signature sequences were found in multiple tissues from rhesus monkeys derived from at least two different colonies. Full-length rep and cap open reading frames were isolated and sequenced from single sources. Only the cap open reading frames of the novel AAVs were necessary to evaluate their potential as vectors because vectors with the AAV7 or AAV8 capsids were generated using the ITRs and rep from AAV2. This also simplified the comparison of different vectors since the actual vector genome is identical between different vector serotypes. In fact, the yields of recombinant vectors generated using this approach did not differ between serotypes.

Vectors based on AAV7 and AAV8 appear to be immunologically distinct (i.e., they are not neutralized by antibodies generated against other serotypes). Furthermore, sera from humans do not neutralize transduction by AAV7 and AAV8 vectors, which is a substantial advantage over the human derived AAVs currently under development for which a significant proportion of the human population has pre-existing immunity that is neutralizing [Chirmule, N., et al., (1999) *Gene Ther* 6, 1574-83].

The tropism of each new vector is favorable for in vivo applications. AAV2/7 vectors appear to transduce skeletal muscle as efficiently as AAV2/1, which is the serotype that confers the highest level of transduction in skeletal muscle of the primate AAVs tested to date [Xiao, W., cited above; Chou (2001), cited above, and Chou (2000), cited above]. Importantly, AAV2/8 provides a substantial advantage over the other serotypes in terms of efficiency of gene transfer to liver that until now has been relatively disappointing in terms of the numbers of hepatocytes stably transduced. AAV2/8 consistently achieved a 10 to 100-fold improvement in gene transfer efficiency as compared to the other vectors. The basis for the improved efficiency of AAV2/8 is unclear, although it presumably is due to uptake via a different receptor that is more active on the basolateral surface of hepatocytes. This improved efficiency will be quite useful in the development of liver-directed gene transfer where the number of transduced cells is critical, such as in urea cycle disorders and familial hypercholesterolemia.

Thus, the present invention provides a novel approach for isolating new AAVs based on PCR retrieval of genomic sequences. The amplified sequences were easily incorporated into vectors and tested in animals. The lack of pre-existing immunity to AAV7 and the favorable tropism of the vectors for muscle indicates that AAV7 is suitable for use as a vector in human gene therapy and other in vivo applications. Similarly, the lack of pre-existing immunity to the AAV serotypes of the invention, and their tropisms, renders them useful in delivery of therapeutic molecules and other useful molecules.

Example 9—Tissue Tropism Studies

In the design of a high throughput functional screening scheme for novel AAV constructs, a non-tissue specific and highly active promoter, CB promoter (CMV enhanced chicken β actin promoter) was selected to drive an easily detectable and quantifiable reporter gene, human α anti-trypsin gene. Thus only one vector for each new AAV clone needs to be made for gene transfer studies targeting 3 different tissues, liver, lung and muscle to screen for tissue tropism of a particular AAV construct. The following table summarizes data generated from 4 novel AAV vectors in the tissue tropism studies (AAVCBA1AT), from which a novel AAV capsid clone, 44.2, was found to be a very potent gene transfer vehicle in all 3 tissues with a big lead in the lung tissue particularly. Table 8 reports data obtained (inn A1AT/mL serum) at day 14 of the study.

TABLE 8

| Vector | Target Tissue | | |
|---|---|---|---|
| | Lung | Liver | Muscle |
| AAV2/1 | ND | ND | 45 ± 11 |
| AAV2/5 | 0.6 ± 0.2 | ND | ND |
| AAV2/8 | ND | 84 ± 30 | ND |
| AAV2/rh.2 (43.1) | 14 ± 7 | 25 ± 7.4 | 35 ± 14 |
| AAV2/rh.10 (44.2) | 23 ± 6 | 53 ± 19 | 46 ± 11 |
| AAV2/rh.13 (42.2) | 3.5 ± 2 | 2 ± 0.8 | 3.5 ± 1.7 |
| AAV2/rh.21 (42.10) | 3.1 ± 2 | 2 ± 1.4 | 4.3 ± 2 |

A couple of other experiments were then performed to confirm the superior tropism of AAV 44.2 in lung tissue. First, AAV vector carried CC10hA1AT minigene for lung specific expression were pseudotyped with capsids of novel AAVs were given to Immune deficient animals (NCR nude) in equal volume (50 μl each of the original preps without dilution) via intratracheal injections as provided in the following table. In Table 9, 50 μl of each original prep per mouse, NCR Nude, detection limit ≥0.033 μl g/ml, Day 28

TABLE 9

| Vector | Total GC in 50 μl vector | μg of A1AT/ml with 50 μl vector | μg of A1AT/ml with $1 \times 10^{11}$ vector | Relative Gene transfer as compared to rh.10 (clone 44.2) |
|---|---|---|---|---|
| 2/1 | $3 \times 10^{12}$ | 2.6 ± 0.5 | 0.09 ± 0.02 | 2.2 |
| 2/2 | $5.5 \times 10^{11}$ | <0.03 | <0.005 | <0.1 |
| 2/5 | $3.6 \times 10^{12}$ | 0.65 ± 0.16 | 0.02 ± 0.004 | 0.5 |
| 2/7 | $4.2 \times 10^{12}$ | 1 ± 0.53 | 0.02 ± 0.01 | 0.5 |
| 2/8 | $7.5 \times 10^{11}$ | 0.9 ± 0.7 | 0.12 ± 0.09 | 2.9 |
| 2/ch.5 (A.3.1) | $9 \times 10^{12}$ | 1 ± 0.7 | 0.01 ± 0.008 | 0.24 |
| 2/rh.8 (43.25) | $4.6 \times 10^{12}$ | 26 ± 21 | 0.56 ± 0.46 | 13.7 |
| 2/rh.10 (44.2) | $2.8 \times 10^{12}$ | 115 ± 38 | 4.1 ± 1.4 | 100 |
| 2/rh.13 (42.2) | $6 \times 10^{12}$ | 7.3 ± 0.8 | 0.12 ± 0.01 | 2.9 |
| 2/rh.21 (42.10) | $2.4 \times 10^{12}$ | 9 ± 0.9 | 0.38 ± 0.04 | 9.3 |
| 2/rh.22 (42.11) | $2.6 \times 10^{12}$ | 6 ± 0.4 | 0.23 ± 0.02 | 5.6 |
| 2/rh.24 (42.13) | $1.1 \times 10^{11}$ | 0.4 ± 0.3 | 0.4 ± 0.3 | 1 |

The vectors were also administered to immune competent animals (C57BL/6) in equal genome copies ($1 \times 10^{11}$ GC) as shown in the Table 10. ($1 \times 10^{11}$ GC per animal, C57BL/6, day 14, detection limit ≥0.033 μg/ml)

TABLE 10

| AAV Vector | μg of A1AT/ml with $1 \times 10^{11}$ vector | Relative Gene transfer as compared to rh.10 (clone 44.2) |
|---|---|---|
| 2/1 | 0.076 ± 0.031 | 2.6 |
| 2/2 | 0.1 ± 0.09 | 3.4 |
| 2/5 | 0.0840.033 | 2.9 |
| 2/7 | 0.33 ± 0.01 | 11 |
| 2/8 | 1.92 ± 1.3 | 2.9 |
| 2/ch.5 (A.3.1) | 0.048 ± 0.004 | 1.6 |
| 2/rh.8 (43.25) | 1.7 ± 0.7 | 58 |
| 2/rh.10 (44.2) | 2.93 ± 1.7 | 100 |
| 2/rh.13 (42.2) | 0.45 ± 0.15 | 15 |
| 2/rh.21 (42.10) | 0.86 ± 0.32 | 29 |
| 2/rh.22 (42.11) | 0.38 ± 0.18 | 13 |
| 2/rh.24 (42.13) | 0.3 ± 0.19 | 10 |

The data from both experiments confirmed the superb tropism of clone 44.2 in lung-directed gene transfer.

Interestingly, performance of clone 44.2 in liver and muscle directed gene transfer was also outstanding, close to that of the best liver transducer, AAV8 and the best muscle transducer AAV1, suggesting that this novel AAV has some intriguing biological significance.

To study serological properties of those novel AAVs, pseudotyped AAVGFP vectors were created for immunization of rabbits and in vitro transduction of 84-31 cells in the presence and absence of antisera against different capsids. The data are summarized below:

TABLE 11a

| Cross-NAB assay in 8431 cells and adenovirus (Adv) coinfection Infection in 8431 cells (coinfected with Adv) with: | | | | |
|---|---|---|---|---|
| Serum from rabbit immunized with: | $10^9$ GC rh.13 AAV2/42.2 | $10^9$ GC rh.21 AAV2/42.10 | $10^9$ GC rh.22 AAV2/42.11 | $10^{10}$ GC rh.24 AAV2/42.13 |
| AAV2/1 | 1/20 | 1/20 | 1/20 | No NAB |
| AAV2/2 | 1/640 | 1/1280 | 1/5120 | No NAB |
| AAV2/5 | No NAB | 1/40 | 1/160 | No NAB |
| AAV2/7 | 1/81920 | 1/81920 | 1/40960 | 1/640 |
| AAV2/8 | 1/640 | 1/640 | 1/320 | 1/5120 |
| Ch.5 AAV2/A3 | 1/20 | 1/160 | 1/640 | 1/640 |

TABLE 11a-continued

Cross-NAB assay in 8431 cells and adenovirus (Adv) coinfection
Infection in 8431 cells (coinfected with Adv) with:

| Serum from rabbit immunized with: | $10^9$ GC rh.13 AAV2/42.2 | $10^9$ GC rh.21 AAV2/42.10 | $10^9$ GC rh.22 AAV2/42.11 | $10^{10}$ GC rh.24 AAV2/42.13 |
|---|---|---|---|---|
| rh.8 AAV2/43.25 | 1/20 | 1/20 | 1/20 | 1/320 |
| rh.10 AAV2/44.2 | No NAB | No NAB | No NAB | 1/5120 |
| rh.13 AAV2/42.2 | 1/5120 | 1/5120 | 1/5120 | No NAB |
| rh.21 AAV2/42.10 | 1/5120 | 1/10240 | 1/5120 | 1/20 |
| rh.22 AAV2/42.11 | 1/20480 | 1/20480 | 1/40960 | No NAB |
| rh.24 AAV2/42.13 | No NAB | 1/20 | 1/20 | 1/5120 |

TABLE 11b

Cross-NAB assay in 8431 cells and Adv coinfection
Infection in 8431 cells (coinfected with Adv) with:

| Serum from rabbit immunized with: | $10^9$ GC rh.12 AAV2/42.1B | $10^{10}$ GC ch.5 AAV2/A3 | $10^{10}$ GC rh.8 AAV2/43.25 | $10^9$ GC rh.10 AAV2/44.2 | $10^9$ GC rh.20 AAV2/42.8.2 |
|---|---|---|---|---|---|
| AAV2/1 | No NAB | 1/20480 | No NAB | 1/80 | ND |
| AAV2/2 | 1/20 | No NAB | No NAB | No NAB | ND |
| AAV2/5 | No NAB | 1/320 | No NAB | No NAB | ND |
| AAV2/7 | 1/2560 | 1/640 | 1/160 | 1/81920 | ND |
| AAV2/8 | 1/10240 | 1/2560 | 1/2560 | 1/81920 | ND |
| ch.5 AAV2/A3 | 1/1280 | 1/10240 | ND | 1/5120 | 1/320 |
| rh.8 AAV2/43.25 | 1/1280 | ND | 1/20400 | 1/5120 | 1/2560 |
| rh.10 AAV2/44.2 | 1/5120 | ND | ND | 1/5120 | 1/5120 |
| rh.13 AAV2/42.2 | 1/20 | ND | ND | No NAB | 1/320 |
| rh.21 AAV2/42.10 | 1/20 | ND | ND | 1/40 | 1/80 |
| rh.22 AAV2/42.11 | No NAB | ND | ND | ND | No NAB |
| rh.24 AAV2/42.13 | 1/5120 | ND | ND | ND | 1/2560 |

TABLE 12

| | Titer of rabbit sera | Titer after |
|---|---|---|
| Vector | Titer d21 | Boosting |
| ch.5 AAV2/A3 | 1/10,240 | 1/40,960 |
| rh.8 AAV2/43.25 | 1/20,400 | 1/163,840 |
| rh.10 AAV2/44.2 | 1/10,240 | 1/527,680 |
| rh.13 AAV2/42.2 | 1/5,120 | 1/20,960 |
| rh.21 AAV2/42.10 | 1/20,400 | 1/81,920 |
| rh.22 AAV2/42.11 | 1/40,960 | ND |
| rh.24 AAV2/42.13 | 1/5,120 | ND |

TABLE 13a

Infection in 8431 cells (coinfected with Adv) with GFP

| | $10^9$ GC/well AAV2/1 | $10^9$ GC/well AAV2/2 | $10^9$ GC/well AAV2/5 | $10^9$ GC/well AAV2/7 | $10^9$ GC/well AAV2/8 | $10^9$ GC/well ch.5 AAV2/A3 |
|---|---|---|---|---|---|---|
| # GFU/field | 128 | >200 | 95 | 56 | 13 | 1 |
| | 83 | >200 | 65 | 54 | 11 | 1 |

TABLE 13b

| | 10⁹ GC/well rh.8 AAV2/43.25 | 10⁹ GC/well rh.10 AAV2/44.2 | 10⁹ GC/well rh.13 AAV2/42.2 | 10⁹ GC/well rh.21 AAV2/42.10 | 10⁹ GC/well rh.22 AAV2/42.11 | 10⁹ GC/well rh.24 AAV2/42.13 | 10⁹ GC/well rh.12 AAV2/42.1B |
|---|---|---|---|---|---|---|---|
| # GFU/field | 3 | 13 | 54 | 62 | 10 | 3 | 18 |
| | 2 | 12 | 71 | 60 | 14 | 2 | 20 |
| | | | 48 | 47 | 16 | 3 | 12 |

Infection in 8431 cells (coinfected with Adv) with GFP

Example 10—Mouse Model of Familial Hypercholesterolemia

The following experiment demonstrates that the AAV2/7 construct of the invention delivers the LDL receptor and express LDL receptor in an amount sufficient to reduce the levels of plasma cholesterol and triglycerides in animal models of familial hypercholesterolemia.

A. Vector Construction

AAV vectors packaged with AAV7 or AAV8 capsid proteins were constructed using a pseudotyping strategy [Hildinger M, et al., *J Virol* 2001; 75:6199-6203]. Recombinant AAV genomes with AAV2 inverted terminal repeats (ITR) were packaged by triple transfection of 293 cells with the cis-plasmid, the adenovirus helper plasmid and a chimeric packaging construct, a fusion of the capsids of the novel AAV serotypes with the rep gene of AAV2. The chimeric packaging plasmid was constructed as previously described [Hildinger et al, cited above]. The recombinant vectors were purified by the standard $CsCl_2$ sedimentation method. To determine the yield TaqMan (Applied Biosystems) analysis was performed using probes and primers targeting the SV40 poly(A) region of the vectors [Gao G P, et al., *Hum Gene Ther.* 2000 Oct. 10; 11(15):2079-91]. The resulting vectors express the transgene under the control of the human thyroid hormone binding globulin gene promoter (TBG).

B. Animals

LDL receptor deficient mice on the C57Bl/6 background were purchased from the Jackson Laboratory (Bar Harbor, Me., USA) and maintained as a breeding colony. Mice were given unrestricted access to water and obtained a high fat Western Diet (high % cholesterol) starting three weeks prior vector injection. At day −7 as well at day 0, blood was obtained via retroorbital bleeds and the lipid profile evaluated. The mice were randomly divided into seven groups. The vector was injected via an intraportal injection as previously described ([Chen S J et al., *Mol Therapy* 2000; 2(3), 256-261]. Briefly, the mice were anaesthetized with ketamine and xylazine. A laparotomy was performed and the portal vein exposed. Using a 30 g needle the appropriate dose of vector diluted in 100 ul PBS was directly injected into the portal vein. Pressure was applied to the injection site to ensure a stop of the bleeding. The skin wound was closed and draped and the mice carefully monitored for the following day. Weekly bleeds were performed starting at day 14 after liver directed gene transfer to measure blood lipids. Two animals of each group were sacrificed at the time points week 6 and week 12 after vector injection to examine atherosclerotic plaque size as well as receptor expression. The remaining mice were sacrificed at week 20 for plaque measurement and determination of transgene expression.

TABLE 14

| | Vector | dose | n |
|---|---|---|---|
| Group 1 | AAV2/7-TBG-hLDLr | $1 \times 10^{12}$ gc | 12 |
| Group 2 | AAV2/7-TBG-hLDLr | $3 \times 10^{11}$ gc | 12 |
| Group 3 | AAV2/7-TBG-hLDLr | $1 \times 10^{11}$ gc | 12 |
| Group 4 | AAV2/8-TBG-hLDLr | $1 \times 10^{12}$ gc | 12 |
| Group 5 | AAV2/8-TBG-hLDLr | $3 \times 10^{11}$ gc | 12 |
| Group 6 | AAV2/8-TBG-hLDLr | $1 \times 10^{11}$ gc | 12 |
| Group 7 | AAV2/7-TBG-LacZ | $1 \times 10^{11}$ gc | 16 |

C. Serum Lipoprotein and Liver Function Analysis

Blood samples were obtained from the retroorbital plexus after a 6 hour fasting period. The serum was separated from the plasma by centrifugation. The amount of plasma lipoproteins and liver transaminases in the serum were detected using an automatized clinical chemistry analyzer (ACE, Schiapparelli Biosystems, Alpha Wassermann)

D. Detection of Transgene Expression

LDL receptor expression was evaluated by immunofluorescence staining and Western blotting. For Western Blot frozen liver tissue was homogenized with lysis buffer (20 mM Tris, pH7.4, 130 mM NaCl, 1% Triton X 100, proteinase inhibitor (complete, EDTA-free, Roche, Mannheim, Germany). Protein concentration was determined using the Micro BCA Protein Assay Reagent Kit (Pierce, Rockford, Ill.). 40 µg of protein was resolved on 4-15% Tris-HCl Ready Gels (Biorad, Hercules, Calif.) and transferred to a nitrocellulose membrane (Invitrogen,). To generate Anti-hLDL receptor antibodies a rabbit was injected intravenously with an AdhLDLr prep ($1 \times 10^{13}$ GC). Four weeks later the rabbit serum was obtained and used for Western Blot. A 1:100 dilution of the serum was used as a primary antibody followed by a HRP-conjugated anti-rabbit IgG and ECL chemiluminescent detection (ECL Western Blot Detection Kit, Amersham, Arlington Heights, Ill.).

E. Immunocytochemistry

For determination of LDL receptor expression in frozen liver sections immunohistochemistry analyses were performed. 10 um cryostat sections were either fixed in acetone for 5 minutes, or unfixed. Blocking was obtained via a 1 hour incubation period with 10% of goat serum. Sections were then incubated for one hour with the primary antibody at room temperature. A rabbit polyclonal antibody anti-human LDL (Biomedical Technologies Inc., Stoughton, Mass.) was used diluted accordingly to the instructions of the manufacturer. The sections were washed with PBS, and incubated with 1:100 diluted fluorescein goat anti-rabbit IgG (Sigma, St Louis, Mo.). Specimens were finally examined under fluorescence microscope Nikon Microphot-FXA. In all cases, each incubation was followed by extensive washing with PBS. Negative controls consisted of preincubation with PBS, omission of the primary antibody, and substitution of the primary antibody by an isotype-matched nonimmune control antibody. The three types of controls mentioned above were performed for each experiment on the same day.

F. Gene Transfer Efficiency

Liver tissue was obtained after sacrificing the mice at the designated time points. The tissue was shock frozen in liquid nitrogen and stored at −80° C. until further processing. DNA was extracted from the liver tissue using a QIAamp DNA Mini Kit (QIAGEN GmbH, Germany) according to the manufacturers protocol. Genome copies of AAV vectors in the liver tissue were evaluated using Taqman analysis using probes and primers against the SV40 poly(A) tail as described above.

G. Atherosclerotic Plaque Measurement

For the quantification of the atherosclerotic plaques in the mouse aorta the mice were anaesthetized (10% ketamine and xylazine, ip), the chest opened and the arterial system perfused with ice-cold phosphate buffered saline through the left ventricle. The aorta was then carefully harvested, slit down along the ventral midline from the aortic arch down to the femoral arteries and fixed in formalin. The lipid-rich atherosclerotic plaques were stained with Sudan IV (Sigma, Germany) and the aorta pinned out flat on a black wax surface. The image was captured with a Sony DXC-960 MD color video camera. The area of the plaque as well as of the complete aortic surface was determined using Phase 3 Imaging Systems (Media Cybernetics).

H. Clearance of $I^{125}$ LDL

Two animals per experimental group were tested. A bolus of $I^{125}$-labeled LDL (generously provided by Dan Rader, U Penn) was infused slowly through the tail vein over a period of 30 sec (1,000,000 counts of $[I^{125}]$-LDL diluted in 100 μl sterile PBS/animal) At time points 3 min, 30 min, 1.5 hr, 3 hr, 6 hr after injection a blood sample was obtained via the retro-orbital plexus. The plasma was separated off from the whole blood and 10 μl plasma counted in the gamma counter. Finally the fractional catabolic rate was calculated from the lipoprotein clearance data.

I. Evaluation of Liver Lipid Accumulation

Oil Red Staining of frozen liver sections was performed to determine lipid accumulation. The frozen liver sections were briefly rinsed in distilled water followed by a 2 minute incubation in absolute propylene glycol. The sections were then stained in oil red solution (0.5% in propylene glycol) for 16 hours followed by counterstaining with Mayer's hematoxylin solution for 30 seconds and mounting in warmed glycerin jelly solution.

For quantification of the liver cholesterol and triglyceride content liver sections were homogenized and incubated in chloroform/methanol (2:1) overnight. After adding of 0.05% H2SO4 and centrifugation for 10 minutes, the lower layer of each sample was collected, divided in two aliquots and dried under nitrogen. For the cholesterol measurement the dried lipids of the first aliquot were dissolved in 1% Triton X-100 in chloroform. Once dissolved, the solution was dried under nitrogen. After dissolving the lipids in ddH$_2$0 and incubation for 30 minutes at 37° C. the total cholesterol concentration was measured using a Total Cholesterol Kit (Wako Diagnostics). For the second aliquot the dried lipids were dissolved in alcoholic KOH and incubated at 60° C. for 30 minutes. Then 1M MgCl2 was added, followed by incubation on ice for 10 minutes and centrifugation at 14,000 rpm for 30 minutes. The supernatant was finally evaluated for triglycerides (Wako Diagnostics).

All of the vectors pseudotyped in an AAV2/8 or AAV2/7 capsid lowered total cholesterol, LDL and triglycerides as compared to the control. These test vectors also corrected phenotype of hypercholesterolemia in a dose-dependent manner. A reduction in plaque area for the AAV2/8 and AAV2/7 mice was observed in treated mice at the first test (2 months), and the effect was observed to persist over the length of the experiment (6 months).

Example 10—Functional Factor IX Expression and Correction of Hemophilia

A. Knock-Out Mice

Functional canine factor IX (FIX) expression was assessed in hemophilia B mice. Vectors with capsids of AAV1, AAV2, AAV5, AAV7 or AAV8 were constructed to deliver AAV2 5' ITR—liver-specific promoter [LSP]—canine FIX—woodchuck hepatitis post-regulatory element (WPRE)—AAV2 3' ITR. The vectors were constructed as described in Wang et al, 2000, *Molecular Therapy* 2: 154-158), using the appropriate capsids.

Knock-out mice were generated as described in Wang et al, 1997. *Proc. Natl. Acad. Sci. USA* 94: 11563-11566. This model closely mimic the phenotypes of hemophilia B in human.

Vectors of different serotypes (AAV1, AAV2, AAV5, AAV7 and AAV8) were delivered as a single intraportal injection into the liver of adult hemophiliac C57Bl/6 mice in a dose of $1 \times 10^{11}$ GC/mouse for the five different serotypes and one group received an AAV8 vector at a lower dose, $1 \times 10^{10}$ GC/mouse. Control group was injected with $1 \times 10^{11}$ GC of AAV2/8 TBG LacZ3. Each group contains 5-10 male and female mice. Mice were bled bi-weekly after vector administration.

1. ELISA

The canine FIX concentration in the mouse plasma was determined by an ELISA assay specific for canine factor IX, performed essentially as described by Axelrod et al, 1990, *Proc. Natl. Acad Sci. USA*, 87:5173-5177 with modifications. Sheep anti-canine factor IX (Enzyme Research Laboratories) was used as primary antibody and rabbit anti-canine factor IX ((Enzyme Research Laboratories) was used as secondary antibody. Beginning at two weeks following injection, increased plasma levels of cFIX were detected for all test vectors. The increased levels were sustained at therapeutic levels throughout the length of the experiment, i.e., to 12 weeks. Therapeutic levels are considered to be 5% of normal levels, i.e., at about 250 ng/mL.

The highest levels of expression were observed for the AAV2/8 (at $10^{11}$) and AAV2/7 constructs, with sustained superphysiology levels cFIX levels (ten-fold higher than the normal level). Expression levels for AAV2/8 ($10^{11}$) were approximately 10 fold higher than those observed for AAV2/2 and AAV2/8 ($10^{10}$). The lowest expression levels, although still above the therapeutic range, were observed for AAV2/5.

2. In Vitro Activated Partial Thromboplastin Time (aPTT) Assay

Functional factor IX activity in plasma of the FIX knock-out mice was determined by an in vitro activated partial thromboplastin time (aPTT) assay-Mouse blood samples were collected from the retro-orbital plexus into $\frac{1}{10}$ volume of citrate buffer. The aPTT assay was performed as described by Wang et al, 1997, *Proc. Natl. Acad. Sci. USA* 94: 11563-11566.

Clotting times by aPTT on plasma samples of all vector injected mice were within the normal range (approximately 60 sec) when measured at two weeks post-injection, and sustained clotting times in the normal or shorter than normal range throughout the study period (12 weeks).

Lowest sustained clotting times were observed in the animals receiving AAV2/8 ($10^{11}$) and AAV2/7. By week 12, AAV2/2 also induced clotting times similar to those for AAV2/8 and AAV2/7. However, this lowered clotting time was not observed for AAV2/2 until week 12, whereas lowered clotting times (in the 25-40 sec range) were observed for AAV2/8 and AAV2/7 beginning at week two.

Immuno-histochemistry staining on the liver tissues harvested from some of the treated mice is currently being performed. About 70-80% of hepatocytes are stained positive for canine FIX in the mouse injected with AAV2/8.cFIX vector.

B. Hemophilia B Dogs

Dogs that have a point mutation in the catalytic domain of the F.IX gene, which, based on modeling studies, appears to render the protein unstable, suffer from hemophilia B [Evans et al, 1989, Proc. Natl. Acad. Sci. USA, 86:10095-10099). A colony of such dogs has been maintained for more than two decades at the University of North Carolina, Chapel Hill. The homeostatic parameters of these dogs are well described and include the absence of plasma F.IX antigen, whole blood clotting times in excess of 60 minutes, whereas normal dogs are 6-8 minutes, and prolonged activated partial thromboplastin time of 50-80 seconds, whereas normal dogs are 13-28 seconds. These dogs experience recurrent spontaneous hemorrhages. Typically, significant bleeding episodes are successfully managed by the single intravenous infusion of 10 ml/kg of normal canine plasma; occasionally, repeat infusions are required to control bleeding.

Four dogs are injected intraportally with AAV.cFIX according to the schedule below. A first dog receives a single injection with AAV2/2.cFIX at a dose of $3.7 \times 10^{11}$ genome copies (GC)/kg. A second dog receives a first injection of AAV2/2.cFIX ($2.8 \times 10^{11}$ GC/kg), followed by a second injection with AAV2/7.cFIX ($2.3 \times 10^{13}$ GC/kg) at day 1180. A third dog receives a single injection with AAV2/2.cFIX at a dose of $4.6 \times 10^{12}$ GC/kg. The fourth dog receives an injection with AAV2/2.cFIX ($2.8 \times 10^{12}$ GC/kg) and an injection at day 995 with AAV2/7.cFIX ($5 \times 10^{12}$ GC/kg).

The abdomen of hemophilia dogs are aseptically and surgically opened under general anesthesia and a single infusion of vector is administered into the portal vein. The animals are protected from hemorrhage in the pen-operative period by intravenous administration of normal canine plasma. The dog is sedated, intubated to induce general anesthesia, and the abdomen shaved and prepped. After the abdomen is opened, the spleen is moved into the operative field. The splenic vein is located and a suture is loosely placed proximal to a small distal incision in the vein. A needle is rapidly inserted into the vein, then the suture loosened and a 5 F cannula is threaded to an intravenous location near the portal vein threaded to an intravenous location near the portal vein bifurcation. After hemostasis is secured and the catheter balloon inflated, approximately 5.0 ml of vector diluted in PBS is infused into the portal vein over a 5 minute interval. The vector infusion is followed by a 5.0 ml infusion of saline. The balloon is then deflated, the callula removed and venous hemostasis is secured. The spleen is then replaced, bleeding vessels are cauterized and the operative wound is closed. The animal is extubated having tolerated the surgical procedure well. Blood samples are analyzed as described. [Wang et al, 2000, *Molecular Therapy* 2: 154-158]

Results showing correction or partial correction are anticipated for AAV2/7.

All publications cited in this specification and priority applications, including U.S. patent application Ser. No. 15/584,674, U.S. patent application Ser. No. 14/956,934, U.S. patent application Ser. No. 13/633,971, U.S. patent application Ser. No. 12/962,793, U.S. patent application Ser. No. 10/291,583, and U.S. Provisional Patent Application Nos. 60/386,675, 60/377,066, 60/341,117, and 60/350,607, are incorporated herein by reference. While the invention has been described with reference to particularly preferred embodiments, it will be appreciated that modifications can be made without departing from the spirit of the invention. Such modifications are intended to fall within the scope of the claims.

SEQUENCE LISTING

<160> NUMBER OF SEQ ID NOS: 120

<210> SEQ ID NO 1
<211> LENGTH: 4721
<212> TYPE: DNA
<213> ORGANISM: Unknown
<220> FEATURE:
<223> OTHER INFORMATION: adeno-associated virus serotype 7

<400> SEQUENCE: 1

```
ttggccactc cctctatgcg cgctcgctcg ctcggtgggg cctgcggacc aaaggtccgc        60
agacggcaga gctctgctct gccggcccca ccgagcgagc gagcgcgcat agagggagtg       120
gccaactcca tcactagggg taccgcgaag cgcctcccac gctgccgcgt cagcgctgac       180
gtaaatcacg tcatagggga gtggtcctgt attagctgtc acgtgagtgc ttttgcgaca       240
ttttgcgaca ccacgtggcc atttgaggta tatatggccg agtgagcgag caggatctcc       300
attttgaccg cgaaatttga acgagcagca gccatgccgg gtttctacga gatcgtgatc       360
aaggtgccga gcgacctgga cgagcacctg ccgggcattt ctgactcgtt tgtgaactgg       420
gtggccgaga aggaatggga gctgccccg gattctgaca tggatctgaa tctgatcgag       480
caggcacccc tgaccgtggc cgagaagctg cagcgcgact tcctggtcca atggcgccgc       540
```

```
gtgagtaagg ccccggaggc cctgttcttt gttcagttcg agaagggcga gagctacttc      600
caccttcacg ttctggtgga gaccacgggg gtcaagtcca tggtgctagg ccgcttcctg      660
agtcagattc gggagaagct ggtccagacc atctaccgcg gggtcgagcc cacgctgccc      720
aactggttcg cggtgaccaa gacgcgtaat ggcgccggcg gggggaacaa ggtggtggac      780
gagtgctaca tccccaacta cctcctgccc aagacccagc ccgagctgca gtgggcgtgg      840
actaacatgg aggagtatat aagcgcgtgt ttgaacctgg ccgaacgcaa acggctcgtg      900
gcgcagcacc tgacccacgt cagccagacg caggagcaga acaaggagaa tctgaacccc      960
aattctgacg cgcccgtgat caggtcaaaa acctccgcgc gctacatgga gctggtcggg     1020
tggctggtgg accggggcat cacctccgag aagcagtgga tccaggagga ccaggcctcg     1080
tacatctcct tcaacgccgc ctccaactcg cggtcccaga tcaaggccgc gctggacaat     1140
gccggcaaga tcatggcgct gaccaaatcc gcgcccgact acctggtggg gccctcgctg     1200
cccgcggaca ttaaaaccaa ccgcatctac cgcatcctgg agctgaacgg gtacgatcct     1260
gcctacgccg gctccgtctt tctcggctgg gcccagaaaa agttcgggaa gcgcaacacc     1320
atctggctgt ttgggcccgc caccaccggc aagaccaaca ttgcggaagc catcgcccac     1380
gccgtgccct tctacggctg cgtcaactgg accaatgaga actttccctt caacgattgc     1440
gtcgacaaga tggtgatctg gtgggaggag ggcaagatga cggccaaggt cgtggagtcc     1500
gccaaggcca ttctcggcgg cagcaaggtg cgcgtggacc aaaagtgcaa gtcgtccgcc     1560
cagatcgacc ccaccccgt gatcgtcacc tccaacacca acatgtgcgc cgtgattgac     1620
gggaacagca ccaccttcga gcaccagcag ccgttgcagg accggatgtt caaatttgaa     1680
ctcacccgcc gtctggagca cgactttggc aaggtgacga agcaggaagt caaagagttc     1740
ttccgctggg ccagtgatca cgtgaccgag gtggcgcatg agttctacgt cagaaagggc     1800
ggagccagca aaagacccgc ccccgatgac gcggatataa gcgagcccaa gcgggcctgc     1860
ccctcagtcg cggatccatc gacgtcagac gcggaaggag ctccggtgga ctttgccgac     1920
aggtaccaaa acaaatgttc tcgtcacgcg ggcatgattc agatgctgtt tccctgcaaa     1980
acgtgcgaga gaatgaatca gaatttcaac atttgcttca cacacggggt cagagactgt     2040
ttagagtgtt tccccggcgt gtcagaatct caaccggtcg tcagaaaaaa gacgtatcgg     2100
aaactctgcg cgattcatca tctgctgggg cgggcgcccg agattgcttg ctcggcctgc     2160
gacctggtca acgtggacct ggacgactgc gtttctgagc aataaatgac ttaaaccagg     2220 tatgctgcc gatggttatc ttccagattg gctcgaggca aacctctctg agggcattcg     2280
cgagtggtgg gacctgaaac ctggagcccc gaaacccaaa gccaaccagc aaaagcagga     2340
caacggccgg ggtctggtgc ttcctggcta caagtacctc ggacccttca acggactcga     2400 caaggggggag cccgtcaacg cggcggacgc agcggccctc gagcacgaca aggcctacga     2460
ccagcagctc aaagcgggtg acaatccgta cctgcggtat aaccacgccg acgccgagtt     2520
tcaggagcgt ctgcaagaag atacgtcatt tgggggcaac ctcgggcgag cagtcttcca     2580
ggccaagaag cgggttctcg aacctctcgg tctggttgag gaaggcgcta agacggctcc     2640
tgcaaagaag agaccggtag agccgtcacc tcagcgttcc cccgactcct ccacgggcat     2700
cggcaagaaa ggccagcagc ccgccagaaa gagactcaat ttcggtcaga ctggcgactc     2760
agagtcagtc cccgacccte aacctctcgg agaacctcca gcagcgccct ctagtgtggg     2820
atctggtaca gtggctgcag gcggtggcgc accaatggca gacaataacg aaggtgccga     2880
```

```
cggagtgggt aatgcctcag gaaattggca ttgcgattcc acatggctgg gcgacagagt    2940
cattaccacc agcacccgaa cctgggccct gcccacctac aacaaccacc tctacaagca    3000
aatctccagt gaaactgcag gtagtaccaa cgacaacacc tacttcggct acagcacccc    3060
ctggggtat tttgacttta acagattcca ctgccacttc tcaccacgtg actggcagcg    3120
actcatcaac aacaactggg gattccggcc aagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa ctttgagttc agctacagct tcgaggacgt    3480
gcctttccac agcagctacg cacacagcca gagcctggac cggctgatga atccccctcat    3540
cgaccagtac ttgtactacc tggcagaac acagagtaac ccaggaggca cagctggcaa    3600
tcgggaactg cagtttttacc agggcgggcc ttcaactatg ccgaacaag ccaagaattg    3660
gttacctgga ccttgcttcc ggcaacaaag agtctccaaa cgctggatc aaaacaacaa    3720
cagcaacttt gcttggactg gtgccaccaa atatcacctg aacggcagaa actcgttggt    3780
taatcccggc gtcgccatgg caactcacaa ggacgacgag gaccgcttttt cccatccag    3840
cggagtcctg atttttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctggcagaa ccgggacgtg tacctgcagg gtcccatctg    4080
ggccaagatt cctcacacgg atggcaactt tcacccgtct cctttgatgg gcggctttgg    4140
acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga acccggagat    4320
tcagtacacc tccaactttg aaaagcagac tggtgtggac tttgccgttg acagccaggg    4380
tgtttactct gagcctcgcc ctattggcac tcgttacctc acccgtaatc tgtaattgca    4440
tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt acccctagtg atggagttgg ccactccctc tatgcgcgct    4620
cgctcgctcg gtggggcctg cggaccaaag gtccgcagac ggcagagctc tgctctgccg    4680
gccccaccga gcgagcgagc gcgcatagag ggagtggcca a    4721
```

<210> SEQ ID NO 2
<211> LENGTH: 737
<212> TYPE: PRT
<213> ORGANISM: Unknown
<220> FEATURE:
<223> OTHER INFORMATION: capsid protein of adeno-associated virus serotpye 7

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

-continued

Lys Ala Asn Gln Gln Lys Gln Asp Asn Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln

```
                450             455             460
    Phe Tyr Gln Gly Gly Pro Ser Thr Met Ala Glu Gln Ala Lys Asn Trp
    465                 470                 475                 480

Leu Pro Gly Pro Cys Phe Arg Gln Gln Arg Val Ser Lys Thr Leu Asp
                    485                 490                 495

Gln Asn Asn Asn Ser Asn Phe Ala Trp Thr Gly Ala Thr Lys Tyr His
                500                 505                 510

Leu Asn Gly Arg Asn Ser Leu Val Asn Pro Gly Val Ala Met Ala Thr
                    515                 520                 525

His Lys Asp Asp Glu Asp Arg Phe Phe Pro Ser Ser Gly Val Leu Ile
                530                 535                 540

Phe Gly Lys Thr Gly Ala Thr Asn Lys Thr Thr Leu Glu Asn Val Leu
    545                 550                 555                 560

Met Thr Asn Glu Glu Glu Ile Arg Pro Thr Asn Pro Val Ala Thr Glu
                    565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
                    595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
    625                 630                 635                 640

Leu Lys His Pro Pro Pro Gln Ile Leu Ile Lys Asn Thr Pro Val Pro
                    645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
                    675                 680                 685

Gln Lys Glu Asn Ser Lys Arg Trp Asn Pro Glu Ile Gln Tyr Thr Ser
                690                 695                 700

Asn Phe Glu Lys Gln Thr Gly Val Asp Phe Ala Val Asp Ser Gln Gly
    705                 710                 715                 720

Val Tyr Ser Glu Pro Arg Pro Ile Gly Thr Arg Tyr Leu Thr Arg Asn
                    725                 730                 735

Leu

<210> SEQ ID NO 3
<211> LENGTH: 623
<212> TYPE: PRT
<213> ORGANISM: Unknown
<220> FEATURE:
<223> OTHER INFORMATION: rep protein of adeno-associated virus serotype
      7

<400> SEQUENCE: 3

Met Pro Gly Phe Tyr Glu Ile Val Ile Lys Val Pro Ser Asp Leu Asp
    1               5                   10                  15

Glu His Leu Pro Gly Ile Ser Asp Ser Phe Val Asn Trp Val Ala Glu
                    20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Asp Phe Leu
            50                  55                  60

Val Gln Trp Arg Arg Val Ser Lys Ala Pro Glu Ala Leu Phe Phe Val
```

```
               65                  70                  75                  80
          Gln Phe Glu Lys Gly Glu Ser Tyr Phe His Leu His Val Leu Val Glu
                               85                  90                  95

Thr Thr Gly Val Lys Ser Met Val Leu Gly Arg Phe Leu Ser Gln Ile
                              100                 105                 110

Arg Glu Lys Leu Val Gln Thr Ile Tyr Arg Gly Val Glu Pro Thr Leu
                              115                 120                 125

Pro Asn Trp Phe Ala Val Thr Lys Thr Arg Asn Gly Ala Gly Gly Gly
          130                 135                 140

Asn Lys Val Val Asp Glu Cys Tyr Ile Pro Asn Tyr Leu Leu Pro Lys
          145                 150                 155                 160

Thr Gln Pro Glu Leu Gln Trp Ala Trp Thr Asn Met Glu Glu Tyr Ile
                              165                 170                 175

Ser Ala Cys Leu Asn Leu Ala Glu Arg Lys Arg Leu Val Ala Gln His
                              180                 185                 190

Leu Thr His Val Ser Gln Thr Gln Glu Gln Asn Lys Glu Asn Leu Asn
                              195                 200                 205

Pro Asn Ser Asp Ala Pro Val Ile Arg Ser Lys Thr Ser Ala Arg Tyr
          210                 215                 220

Met Glu Leu Val Gly Trp Leu Val Asp Arg Gly Ile Thr Ser Glu Lys
          225                 230                 235                 240

Gln Trp Ile Gln Glu Asp Gln Ala Ser Tyr Ile Ser Phe Asn Ala Ala
                              245                 250                 255

Ser Asn Ser Arg Ser Gln Ile Lys Ala Ala Leu Asp Asn Ala Gly Lys
                              260                 265                 270

Ile Met Ala Leu Thr Lys Ser Ala Pro Asp Tyr Leu Val Gly Pro Ser
                              275                 280                 285

Leu Pro Ala Asp Ile Lys Thr Asn Arg Ile Tyr Arg Ile Leu Glu Leu
                              290                 295                 300

Asn Gly Tyr Asp Pro Ala Tyr Ala Gly Ser Val Phe Leu Gly Trp Ala
          305                 310                 315                 320

Gln Lys Lys Phe Gly Lys Arg Asn Thr Ile Trp Leu Phe Gly Pro Ala
                              325                 330                 335

Thr Thr Gly Lys Thr Asn Ile Ala Glu Ala Ile Ala His Ala Val Pro
                              340                 345                 350

Phe Tyr Gly Cys Val Asn Trp Thr Asn Glu Asn Phe Pro Phe Asn Asp
                              355                 360                 365

Cys Val Asp Lys Met Val Ile Trp Trp Glu Glu Gly Lys Met Thr Ala
          370                 375                 380

Lys Val Val Glu Ser Ala Lys Ala Ile Leu Gly Gly Ser Lys Val Arg
          385                 390                 395                 400

Val Asp Gln Lys Cys Lys Ser Ser Ala Gln Ile Asp Pro Thr Pro Val
                              405                 410                 415

Ile Val Thr Ser Asn Thr Asn Met Cys Ala Val Ile Asp Gly Asn Ser
                              420                 425                 430

Thr Thr Phe Glu His Gln Gln Pro Leu Gln Asp Arg Met Phe Lys Phe
                              435                 440                 445

Glu Leu Thr Arg Arg Leu Glu His Asp Phe Gly Lys Val Thr Lys Gln
                              450                 455                 460

Glu Val Lys Glu Phe Phe Arg Trp Ala Ser Asp His Val Thr Glu Val
          465                 470                 475                 480

Ala His Glu Phe Tyr Val Arg Lys Gly Gly Ala Ser Lys Arg Pro Ala
                              485                 490                 495
```

```
Pro Asp Ala Asp Ile Ser Glu Pro Lys Arg Ala Cys Pro Ser Val
            500                 505                 510
Ala Asp Pro Ser Thr Ser Asp Ala Glu Gly Ala Pro Val Asp Phe Ala
            515                 520                 525
Asp Arg Tyr Gln Asn Lys Cys Ser Arg His Ala Gly Met Ile Gln Met
530                 535                 540
Leu Phe Pro Cys Lys Thr Cys Glu Arg Met Asn Gln Asn Phe Asn Ile
545                 550                 555                 560
Cys Phe Thr His Gly Val Arg Asp Cys Leu Glu Cys Phe Pro Gly Val
                565                 570                 575
Ser Glu Ser Gln Pro Val Val Arg Lys Lys Thr Tyr Arg Lys Leu Cys
            580                 585                 590
Ala Ile His His Leu Leu Gly Arg Ala Pro Glu Ile Ala Cys Ser Ala
            595                 600                 605
Cys Asp Leu Val Asn Val Asp Leu Asp Asp Cys Val Ser Glu Gln
            610                 615                 620

<210> SEQ ID NO 4
<211> LENGTH: 4393
<212> TYPE: DNA
<213> ORGANISM: Unknown
<220> FEATURE:
<223> OTHER INFORMATION: adeno-associated virus serotype 8

<400> SEQUENCE: 4
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag     120
tgcttttgcg gcattttgcg acaccacgtg gccatttgag gtatatatgg ccgagtgagc     180
gagcaggatc tccattttga ccgcgaaatt tgaacgagca gcagccatgc cgggcttcta     240
cgagatcgtg atcaaggtgc cgagcgacct ggacgagcac ctgccgggca tttctgactc     300
gtttgtgaac tgggtggccg agaaggaatg ggagctgccc ccggattctg acatggatcg     360
gaatctgatc gagcaggcac ccctgaccgt ggccgagaag ctgcagcgcg acttcctggt     420
ccaatggcgc gcgtgagta aggccccgga ggccctcttc tttgttcagt cgagaaaggg     480
cgagagctac tttcacctgc acgttctggt cgagaccacg ggggtcaagt ccatggtgct     540
aggccgcttc ctgagtcaga ttcgggaaaa gcttggtcca gaccatctac ccgcggggtc     600
gagccccacc ttgcccaact ggttcgcggt gaccaaagac gcggtaatgg cgccggcggg     660
ggggaacaag gtggtggacg agtgctacat ccccaactac ctcctgccca agactcagcc     720
cgagctgcag tgggcgtgga ctaacatgga ggagtatata agcgcgtgct gaacctggc     780
cgagcgcaaa cggctcgtgg cgcagcacct gacccacgtc agccgacgc aggagcagaa     840
caaggagaat ctgaacccca ttctgacgc gcccgtgatc aggtcaaaaa cctccgcgcg     900
ctatatggag ctggtcgggt ggctggtgga ccggggcatc acctccgaga agcagtggat     960
ccaggaggac caggcctcgt acatctcctt caacgccgcc tccaactcgc ggtcccagat    1020
caaggccgcg ctggacaatg ccggcaagat catggcgctg accaaatccg cgcccgacta    1080
cctggtgggg ccctcgctgc ccgcggacat taccagaac cgcatctacc gcatcctcgc    1140
tctcaacggc tacgaccctg cctacgccgg ctccgtcttt ctcggctggg ctcagaaaaa    1200
gttcgggaaa cgcaacacca tctgctgtt tggacccgcc accaccggca agaccaacat    1260
tgcggaagcc atcgcccacg ccgtgccctt ctacggctgc gtcaactgga ccaatgagaa    1320
```

```
ctttcccttc aatgattgcg tcgacaagat ggtgatctgg tgggaggagg gcaagatgac   1380
ggccaaggtc gtggagtccg ccaaggccat tctcggcggc agcaaggtgc gcgtggacca   1440
aaagtgcaag tcgtccgccc agatcgaccc caccccgtg atcgtcacct ccaacaccaa    1500
catgtgcgcc gtgattgacg ggaacagcac caccttcgag caccagcagc ctctccagga   1560
ccggatgttt aagttcgaac tcacccgccg tctggagcac gactttggca aggtgacaaa   1620
gcaggaagtc aaagagttct ccgctgggc cagtgatcac gtgaccgagg tggcgcatga    1680
gttttacgtc agaaagggcg gagccagcaa aagacccgcc cccgatgacg cggataaaag   1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gacccttcaa cggactcgac aagggggagc cgtcaacgc ggcggacgca gcggccctcg    2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
cagactcctc tacgggcatc ggcaagaaag gccaacagcc cgccagaaaa agactcaatt   2640
ttggtcagac tggcgactca gagtcagttc cagaccctca acctctcgga gaacctccag   2700 cagcgcctc tggtgtggga cctaatacaa tggctgcagg cggtggcgca ccaatggcag    2760
acaataacga aggcgccgac ggagtgggta gttcctcggg aaattggcat tgcgattcca   2820
catggctggg cgacagagtc atcaccacca gcacccgaac ctgggccctg cccacctaca   2880
acaaccacct ctacaagcaa atctccaacg gacatcgggg aggagccacc aacgacaaca   2940
cctacttcgg ctacagcacc ccctgggggt attttgactt taacagattc cactgccact   3000
tttcaccacg tgactggcag cgactcatca acaacaactg gggattccgg cccaagagac   3060
tcagcttcaa gctcttcaac atccaggtca aggaggtcac gcagaatgaa ggcaccaaga   3120
ccatcgccaa taacctcacc agcaccatcc aggtgtttac ggactcggag taccagctgc   3180
cgtacgttct cggctctgcc caccagggct gcctgcctcc gttcccggcg acgtgttca    3240 tgattcccca gtacggctac ctaacactca acaacggtag tcaggccgtg ggacgctcct   3300
ccttctactg cctggaatac tttccttcgc agatgctgag aaccggcaac aacttccagt   3360
ttacttacac cttcgaggac gtgcctttcc acagcagcta cgcccacagc cagagcttgg   3420
accggctgat gaatcctctg attgaccagt acctgtacta cttgtctcgg actcaaacaa   3480
caggaggcac ggcaaatacg cagactctgg gcttcagcca aggtgggcct aatacaatgg   3540
ccaatcaggc aaagaactgg ctgccaggac cctgttaccg ccaacaacgc gtctcaacga   3600
caaccgggca aaacaacaat agcaactttg cctggactgc tggaccaaa taccatctga    3660 atggaagaaa ttcattggct aatcctggca tcgctatggc aacacacaaa gacgacgagg   3720
```

```
agcgttttt  tcccagtaac  gggatcctga  tttttggcaa  acaaaatgct  gccagagaca    3780
atgcggatta  cagcgatgtc  atgctcacca  gcgaggaaga  aatcaaaacc  actaaccctg    3840
tggctacaga  ggaatacggt  atcgtggcag  ataacttgca  gcagcaaaac  acggctcctc    3900
aaattggaac  tgtcaacagc  caggggggcct  tacccggtat  ggtctggcag  aaccgggacg    3960
tgtacctgca  gggtcccatc  tgggccaaga  ttcctcacac  ggacggcaac  ttccacccgt    4020
ctccgctgat  gggcggcttt  ggcctgaaac  atcctccgcc  tcagatcctg  atcaagaaca    4080
cgcctgtacc  tgcggatcct  ccgaccacct  tcaaccagtc  aaagctgaac  tctttcatca    4140
cgcaatacag  caccggacag  gtcagcgtgg  aaattgaatg  ggagctgcag  aaggaaaaca    4200
gcaagcgctg  gaaccccgag  atccagtaca  cctccaacta  ctacaaatct  acaagtgtgg    4260
actttgctgt  taatacagaa  ggcgtgtact  ctgaaccccg  ccccattggc  acccgttacc    4320
tcacccgtaa  tctgtaattg  cctgttaatc  aataaaccgg  ttgattcgtt  tcagttgaac    4380
tttggtctct  gcg                                                           4393
```

<210> SEQ ID NO 5
<211> LENGTH: 4385
<212> TYPE: DNA
<213> ORGANISM: Unknown
<220> FEATURE:
<223> OTHER INFORMATION: adeno-associated virus serotype 9

<400> SEQUENCE: 5

```
cagagaggga  gtggccaact  ccatcactag  gggtaatcgc  gaagcgcctc  ccacgctgcc      60
gcgtcagcgc  tgacgtagat  tacgtcatag  gggagtggtc  ctgtattagc  tgtcacgtga     120
gtgcttttgc  gacattttgc  gacaccacat  ggccatttga  ggtatatatg  gccgagtgag     180
cgagcaggat  ctccattttg  accgcgaaat  ttgaacgagc  agcagccatg  ccgggcttct     240
acgagattgt  gatcaaggtg  ccgagcgacc  tggacgagca  cctgccgggc  atttctgact     300
cttttgtgaa  ctgggtggcc  gagaaggaat  gggagctgcc  cccggattct  gacatggatc     360
ggaatctgat  cgagcaggca  cccctgaccg  tggccgagaa  gctgcagcgc  gacttcctgg     420
tccaatggcg  ccgcgtgagt  aaggcccgg  aggccctctt  ctttgttcag  ttcgagaagg     480
gcgagagcta  ctttcacctg  cacgttctgg  tcgagaccac  gggggtcaag  tccatggtgc     540
taggccgctt  cctgagtcag  attcgggaga  agctggtcca  gaccatctac  cgcgggatcg     600
agccgacct   gcccaactgg  ttcgcggtga  ccaagacgcg  taatggcgcc  ggcggggga     660
acaaggtggt  ggacgagtgc  tacatcccca  actacctcct  gcccaagact  cagcccgagc     720
tgcagtgggc  gtggactaac  atggaggagt  atataagcgc  gtgcttgaac  ctggccgagc     780
gcaaacggct  cgtggcgcag  cacctgaccc  acgtcagcca  gacgcaggag  cagaacaagg     840
agaatctgaa  ccccaattct  gacgcgcccg  tgatcaggtc  aaaaacctcc  gcgcgctaca     900
tggagctggt  cgggtggctg  gtggaccggg  gcatcacctc  cgagaagcag  tggatccagg     960
aggaccaggc  ctcgtacatc  tccttcaacg  ccgcctccaa  ctcgcggtcc  cagatcaagg    1020
ccgcgctgga  caatgccggc  aagatcatgg  cgctgaccaa  atccgcgccc  gactacctgg    1080
taggcccttc  acttccggtg  gacattaccg  agaaccgcat  ctaccgcatc  ctgcagctca    1140
acggctacga  ccctgcctac  gccggctccg  tctttctcgg  ctgggcacaa  agaagttcg     1200
ggaaacgcaa  caccatctgg  ctgtttgggc  cggccaccac  gggaaagacc  aacatcgcag    1260
aagccattgc  ccacgccgtg  cccttctacg  gctgcgtcaa  ctggaccaat  gagaactttc    1320
```

-continued

```
ccttcaacga ttgcgtcgac aagatggtga tctggtggga ggagggcaag atgacggcca    1380
aggtcgtgga gtccgccaag gccattctcg gcggcagcaa ggtgcgcgtg gaccaaaagt    1440
gcaagtcgtc cgcccagatc gaccccactc ccgtgatcgt cacctccaac accaacatgt    1500
gcgccgtgat tgacgggaac agcaccacct tcgagcacca gcagcctctc caggaccgga    1560
tgtttaagtt cgaactcacc cgccgtctgg agcacgactt tggcaaggtg acaaagcagg    1620
aagtcaaaga gttcttccgc tgggccagtg atcacgtgac cgaggtggcg catgagtttt    1680
acgtcagaaa gggcggagcc agcaaaagac ccgcccccga tgacgcggat aaaagcgagc    1740
ccaagcgggc ctgcccctca gtcgcggatc catcgacgtc agacgcggaa ggagctccgg    1800
tggactttgc cgacaggtac caaaacaaat gttctcgtca cgcgggcatg cttcagatgc    1860
tgcttccctg caaaacgtgc gagagaatga atcagaattt caacatttgc ttcacacacg    1920
gggtcagaga ctgctcagag tgtttccccg gcgtgtcaga atctcaaccg gtcgtcagaa    1980
agaggacgta tcggaaactc tgtgcgattc atcatctgct ggggcgggct cccgagattg    2040
cttgctcggc ctgcgatctg gtcaacgtgg acctggatga ctgtgtttct gagcaataaa    2100
tgacttaaac caggtatggc tgccgatggt tatcttccag attggctcga ggacaacctc    2160
tctgagggca ttcgcgagtg gtgggcgctg aaacctggag ccccgaagcc caaagccaac    2220
cagcaaaagc aggacgacgg ccggggtctg gtgcttcctg gctacaagta cctcggaccc    2280
ttcaacggac tcgacaaggg ggagcccgtc aacgcggcgg acgcagcggc cctcgagcac    2340
ggcaaggcct acgaccagca gctgcaggcg ggtgacaatc cgtacctgcg gtataaccac    2400
gccgacgccg agtttcagga gcgtctgcaa gaagatacgt cttttggggg caacctcggg    2460
cgagcagtct tccaggccaa gaagcgggtt ctcgaacctc tcggtctggt tgaggaaggc    2520
gctaagacgc tcctggaaa gaagagaccg gtagagccat caccccagcg ttctccagac    2580
tcctctacgg gcatcggcaa gaaaggccaa cagcccgcca gaaaaagact caattttggt    2640
cagactggcg actcagagtc agttccagac cctcaacctc tcggagaacc tccagcagcg    2700
ccctctggtg tgggacctaa tacaatggct gcaggcggtg gcgcaccaat ggcagacaat    2760
aacgaaggcg ccgacggagt gggtaattcc tcgggaaatt ggcattgcga ttccacatgg    2820
ctgggggaca gagtcatcac caccagcacc cgaacctggg cattgcccac ctacaacaac    2880
cacctctaca gcaaatctc caatggaaca tcgggaggaa gcaccaacga caacacctac    2940
tttggctaca gcacccctg ggggtatttt gacttcaaca gattccactg ccacttctca    3000
ccacgtgact ggcagcgact catcaacaac aactggggat tccggccaaa gagactcaac    3060
ttcaagctgt tcaacatcca ggtcaaggag gttacgacga acgaaggcac caagaccatc    3120
gccaataacc ttaccagcac cgtccaggtc tttacggact cggagtacca gctaccgtac    3180
gtcctaggct ctgcccacca aggatgcctg ccaccgtttc ctgcagacgt cttcatggtt    3240
cctcagtacg gctacctgac gctcaacaat ggaagtcaag cgttaggacg ttcttctttc    3300
tactgtctgg aatacttccc ttctcagatg ctgagaaccg caacaacttt cagttcagc    3360
tacacttcg aggacgtgcc tttccacagc agctacgcac acagccagag tctagatcga    3420
ctgatgaacc cctcatcga ccagtaccta tactacctgg tcagaacaca gacaactgga    3480
actgggggaa ctcaaacttt ggcattcagc caagcaggcc ctagctcaat ggccaatcag    3540
gctagaaact gggtacccgg ccttgctac cgtcagcagc gcgtctccac aaccaccaac    3600
caaaataaca acagcaactt tgcgtggacg ggagctgcta aattcaagct gaacgggaga    3660
gactcgctaa tgaatcctgg cgtggctatg gcatcgcaca aagacgacga ggaccgcttc    3720
```

-continued

```
tttccatcaa gtggcgttct catatttggc aagcaaggag ccgggaacga tggagtcgac    3780
tacagccagg tgctgattac agatgaggaa gaaattaaag ccaccaaccc tgtagccaca    3840
gaggaatacg gagcagtggc catcaacaac caggccgcta acacgcaggc gcaaactgga    3900
cttgtgcata accagggagt tattcctggt atggtctggc agaaccggga cgtgtacctg    3960
cagggcccta tttgggctaa aatacctcac acagatggca actttcaccc gtctcctctg    4020
atgggtggat tggactgaa acacccacct ccacagattc taattaaaaa tacaccagtg    4080
ccggcagatc ctcctcttac cttcaatcaa gccaagctga actctttcat cacgcagtac    4140
agcacgggac aagtcagcgt ggaaatcgag tgggagctgc agaaagaaaa cagcaagcgc    4200
tggaatccag agatccagta cacttcaaac tactacaaat ctacaaatgt ggactttgct    4260
gtcaatacca aaggtgttta ctctgagcct cgccccattg gtactcgtta cctcacccgt    4320
aatttgtaat tgcctgttaa tcaataaacc ggttaattcg tttcagttga actttggtct    4380
ctgcg                                                              4385

<210> SEQ ID NO 6
<211> LENGTH: 4718
<212> TYPE: DNA
<213> ORGANISM: Unknown
<220> FEATURE:
<223> OTHER INFORMATION: adeno-associated virus serotype 1

<400> SEQUENCE: 6
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcataggg agtggtcctg tattagctgt cacgtgagtg cttttgcgac     240
attttgcgac accacgtggc catttagggt atatatggcc gagtgagcga gcaggatctc     300
cattttgacc gcgaaatttg aacgagcagc agccatgccg gcttctacg agatcgtgat     360
caaggtgccg agcgacctgg acgagcacct gccgggcatt tctgactcgt ttgtgagctg     420
ggtggccgag aaggaatggg agctgccccc ggattctgac atggatctga atctgattga     480
gcaggcaccc ctgaccgtgg ccgagaagct gcagcgcgac ttcctggtcc aatggcgccg     540
cgtgagtaag gccccggagg ccctcttctt tgttcagttc gagaagggcg agtcctactt     600
ccacctccat attctggtgg agaccacggg ggtcaaatcc atggtgctgg ccgcttcct      660
gagtcagatt agggacaagc tggtgcagac catctaccgc gggatcgagc cgaccctgcc     720
caactggttc gcggtgacca agacgcgtaa tggcgccgga gggggaaca aggtggtgga     780
cgagtgctac atccccaact acctcctgcc caagactcag cccgagctgc agtgggcgtg     840
gactaacatg gaggagtata taagcgcctg tttgaacctg gccgagcgca acggctcgt      900
ggcgcagcac ctgacccacg tcagccgac ccaggagcag aacaaggaga atctgaaccc     960
caattctgac gcgcctgtca tccggtcaaa aacctccgcg cgctacatgg agctggtcgg    1020
gtggctggtg accggggca tcacctccga gaagcagtgg atccaggagg accaggcctc    1080
gtacatctcc ttcaacgccg cttccaactc gcggtcccag atcaaggcg ctctggacaa    1140
tgccggcaag atcatggcgc tgaccaaatc cgcgcccgac tacctggtag gccccgctcc    1200
gccccgcgga ttaaaaacca accgcatcta ccgcatcctg gagctgaacg gctacgaacc    1260
tgcctacgcc ggctccgtct ttctcggctg ggcccagaaa aggttcggga agcgcaacac    1320
```

```
catctggctg tttgggccgg ccaccacggg caagaccaac atcgcggaag ccatcgccca     1380
cgccgtgccc ttctacggct gcgtcaactg gaccaatgag aactttccct tcaatgattg     1440
cgtcgacaag atggtgatct ggtgggagga gggcaagatg acggccaagg tcgtggagtc     1500
cgccaaggcc attctcggcg gcagcaaggt gcgcgtggac caaaagtgca agtcgtccgc     1560
ccagatcgac cccacccccg tgatcgtcac ctccaacacc aacatgtgcg ccgtgattga     1620
cgggaacagc accaccttcg agcaccagca gccgttgcag gaccggatgt tcaaatttga     1680
actcacccgc cgtctggagc atgactttgg caaggtgaca aagcaggaag tcaaagagtt     1740
cttccgctgg gcgcaggatc acgtgaccga ggtggcgcat gagttctacg tcagaaaggg     1800
tggagccaac aaaagacccg cccccgatga cgcggataaa agcgagccca gcgggcctg     1860
cccctcagtc gcggatccat cgacgtcaga cgcggaagga gctccggtgg actttgccga     1920
caggtaccaa aacaaatgtt ctcgtcacgc gggcatgctt cagatgctgt ttccctgcaa     1980
gacatgcgag agaatgaatc agaatttcaa catttgcttc acgcacggga cgagagactg     2040
ttcagagtgc ttccccggcg tgtcagaatc tcaaccggtc gtcagaaaga ggacgtatcg     2100
gaaactctgt gccattcatc atctgctggg gcgggctccc gagattgctt gctcggcctg     2160
cgatctggtc aacgtggacc tggatgactg tgtttctgag caataaatga cttaaaccag     2220
gtatggctgc cgatggttat cttccagatt ggctcgagga caacctctct gagggcattc     2280
gcgagtggtg ggacttgaaa cctggagccc cgaagcccaa agccaaccag caaaagcagg     2340
acgacggccg gggtctggtg cttcctggct acaagtacct cggacccttc aacggactcg     2400
acaaggggga gcccgtcaac gcggcggacg cagcggccct cgagcacgac aaggcctacg     2460
accagcagct caaagcgggt gacaatccgt acctgcggta taaccacgcc gacgccgagt     2520
ttcaggagcg tctgcaagaa gatacgtctt ttgggggcaa cctcgggcga gcagtcttcc     2580
aggccaagaa gcgggttctc gaacctctcg gtctggttga ggaaggcgct aagacggctc     2640
ctggaaagaa acgtccggta gagcagtcgc acaagagcc agactcctcc tcgggcatcg     2700
gcaagacagg ccagcagccc gctaaaaaga gactcaattt tggtcagact ggcgactcag     2760
agtcagtccc cgatccacaa cctctcggag aacctccagc aaccccgct gctgtgggac     2820
ctactacaat ggcttcaggc ggtggcgcac caatggcaga caataacgaa ggcgccgacg     2880
gagtgggtaa tgcctcagga aattggcatt gcgattccac atggctgggc gacagagtca     2940
tcaccaccag cacccgcacc tgggccttgc ccacctacaa taaccacctc tacaagcaaa     3000
tctccagtgc ttcaacgggg gccagcaacg acaaccacta cttcggctac agcacccct     3060
gggggtattt tgatttcaac agattccact gccacttttc accacgtgac tggcagcgac     3120
tcatcaacaa caattgggga ttccggccca gagactcaa cttcaaactc ttcaacatcc     3180
aagtcaagga ggtcacgacg aatgatggcg tcacaaccat cgctaataac cttaccagca     3240
cggttcaagt cttctcggac tcggagtacc agcttccgta cgtcctcggc tctgcgcacc     3300
agggctgcct ccctccgttc ccggcggacg tgttcatgat tccgcaatac ggctacctga     3360
cgctcaacaa tggcagccaa gccgtgggac gttcatcctt ttactgcctg gaatatttcc     3420
cttctcagat gctgagaacg ggcaacaact ttaccttcag ctacacccttt gaggaagtgc     3480
cttttccacag cagctacgcg cacagccaga gcctggaccg gctgatgaat cctctcatcg     3540
accaatacct gtattacctg aacagaactc aaaatcagtc cggaagtgcc caaacaagg     3600
acttgctgtt tagccgtggg tctccagctg gcatgtctgt tcagcccaaa aactggctac     3660
ctggaccctg ttatcggcag cagcgcgttt ctaaaacaaa aacagacaac aacaacagca     3720
```

```
attttacctg gactggtgct tcaaaatata acctcaatgg gcgtgaatcc atcatcaacc   3780
ctggcactgc tatggcctca cacaaagacg acgaagacaa gttctttccc atgagcggtg   3840
tcatgatttt tggaaaagag agcgccggag cttcaaacac tgcattggac aatgtcatga   3900
ttacagacga agaggaaatt aaagccacta accctgtggc caccgaaaga tttgggaccg   3960
tggcagtcaa tttccagagc agcagcacag accctgcgac cggagatgtg catgctatgg   4020
gagcattacc tggcatggtg tggcaagata gagacgtgta cctgcagggt cccatttggg   4080
ccaaaattcc tcacacagat ggacactttc accgtctcc tcttatgggc ggctttggac   4140
tcaagaaccc gcctcctcag atcctcatca aaaacacgcc tgttcctgcg aatcctccgg   4200
cggagttttc agctacaaag tttgcttcat tcatcaccca atactccaca ggacaagtga   4260
gtgtggaaat tgaatgggag ctgcagaaag aaaacagcaa gcgctggaat cccgaagtgc   4320
agtacacatc caattatgca aaatctgcca acgttgattt tactgtggac aacaatggac   4380
tttatactga gcctcgcccc attggcaccc gttaccttac ccgtcccctg taattacgtg   4440
ttaatcaata aaccggttga ttcgtttcag ttgaactttg gtctcctgtc cttcttatct   4500
tatcggttac catggttata gcttacacat taactgcttg gttgcgcttc gcgataaaag   4560
acttacgtca tcgggttacc cctagtgatg gagttgccca ctccctctct gcgcgctcgc   4620
tcgctcggtg gggcctgcgg accaaaggtc cgcagacggc agagctctgc tctgccggcc   4680
ccaccgagcg agcgagcgcg cagagaggga gtgggcaa                          4718

<210> SEQ ID NO 7
<211> LENGTH: 4675
<212> TYPE: DNA
<213> ORGANISM: adeno-associated virus 2

<400> SEQUENCE: 7
ttggccactc cctctctgcg cgctcgctcg ctcactgagg ccgggcgacc aaaggtcgcc     60
cgacgcccgg gctttgcccg gcggcctcag tgagcgagc gagcgcgcag agagggagtg    120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtatttta agcccgagtg agcacgcagg gtctccattt tgaagcggga    300
ggtttgaacg cgcagccgcc atgccggggt tttacgagat tgtgattaag gtccccagcg    360
accttgacgg gcatctgccc ggcatttctg acagctttgt gaactgggtg gccgagaagg    420
aatgggagtt gccgccagat tctgacatgg atctgaatct gattgagcag caccctga    480 ccgtggccga aagctgcag cgcgactttc tgacggaatg cgccgtgtg agtaaggccc    540 cggaggccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctcccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca agagaatca gaatcccaat tctgatgcgc    960
cggtgatcag atcaaaaact tcagccaggt acatggagct ggtcgggtgg ctcgtggaca   1020 agggattac ctcggagaag cagtggatcc aggaggacca ggcctcatac atctccttca   1080
```

-continued

```
atgcggcctc caactcgcgg tcccaaatca aggctgcctt ggacaatgcg ggaaagatta      1140
tgagcctgac taaaaccgcc cccgactacc tggtgggcca gcagcccgtg gaggacattt      1200
ccagcaatcg gatttataaa attttggaac taaacgggta cgatccccaa tatgcggctt      1260
ccgtctttct gggatgggcc acgaaaaagt tcggcaagag gaacaccatc tggctgtttg      1320
ggcctgcaac taccgggaag accaacatcg cggaggccat agcccacact gtgcccttct      1380
acgggtgcgt aaactggacc aatgagaact ttcccttcaa cgactgtgtc gacaagatgg      1440
tgatctggtg ggaggagggg aagatgaccg ccaaggtcgt ggagtcggcc aaagccattc      1500
tcggaggaag caaggtgcgc gtggaccaga aatgcaagtc ctcggcccag atagacccga      1560
ctcccgtgat cgtcacctcc aacaccaaca tgtgcgccgt gattgacggg aactcaacga      1620
ccttcgaaca ccagcagccg ttgcaagacc ggatgttcaa atttgaactc acccgccgtc      1680
tggatcatga ctttgggaag gtcaccaagc aggaagtcaa agactttttc cggtgggcaa      1740
aggatcacgt ggttgaggtg gagcatgaat tctacgtcaa aaagggtgga gccaagaaaa      1800
gacccgcccc cagtgacgca gatataagtg agcccaaacg ggtgcgcgag tcagttgcgc      1860
agccatcgac gtcagacgcg gaagcttcga tcaactacgc agacaggtac caaaacaaat      1920
gttctcgtca cgtgggcatg aatctgatgc tgtttccctg cagacaatgc gagagaatga      1980
atcagaattc aaatatctgc ttcactcacg gacagaaaga ctgtttagag tgctttcccg      2040
tgtcagaatc tcaacccgtt tctgtcgtca aaaaggcgta tcagaaactg tgctacattc      2100
atcatatcat gggaaaggtg ccagacgctt gcactgcctg cgatctggtc aatgtggatt      2160
tggatgactg catctttgaa caataaatga tttaaatcag gtatggctgc cgatggttat      2220
cttccagatt ggctcgagga cactctctct gaaggaataa dacagtggtg aagctcaaa      2280 cctgcccac caccaccaaa gcccgcagag cggcataagg acgacagcag gggtcttgtg      2340
cttcctgggt acaagtacct cggacccttc aacggactcg acaagggaga gccggtcaac      2400
gaggcagacg ccgcggccct cgagcacgta caaagcctac gaccggcagc tcgacagcgg      2460
agacaacccg tacctcaagt acaaccacgc cgacgcggag tttcaggagc gccttaaaga      2520
agatacgtct tttgggggca acctcggacg agcagtcttc caggcgaaaa agagggttct      2580
tgaacctctg ggcctggttg aggaacctgt taagacggct ccgggaaaaa agaggccggt      2640
agagcactct cctgtggagc cagactcctc ctcgggaacc ggaaaggcgg gccagcagcc      2700
tgcaagaaaa agattgaatt ttggtcagac tggagacgca gactcagtac ctgaccccca      2760
gcctctcgga cagccaccag cagccccctc tggtctggga actaatacga tggctacagg      2820
cagtggcgca ccaatggcag acaataacga gggcgccgac ggagtgggta attcctccgg      2880
aaattggcat tgcgattcca catggatggg cgacagagtc atcaccacca gcacccgaac      2940
ctgggccctg cccacctaca caaccacct ctacaaacaa atttccagcc aatcaggagc      3000
ctcgaacgac aatcactact ttggctacag caccccttgg gggtattttg acttcaacag      3060
attccactgc cacttttcac cacgtgactg gcaaagactc atcaacaaca actgggggatt      3120 ccgacccaag agactcaact tcaagctctt taacattcaa gtcaaagagg tcacgcagaa      3180
tgacggtacg acgacgattg ccaataacct taccagcacg gttcaggtgt ttactgactc      3240
ggagtaccag ctcccgtacg tcctcggctc ggcgcatcaa ggatgcctcc cgccgttccc      3300
agcagacgtc ttcatggtgc acagtatgg atacctcacc ctgaacaacg ggagtcaggc      3360
agtaggacgc tcttcatttt actgcctgga gtactttcct tctcagatgc tgcgtaccgg      3420
aaacaacttt accttcagct acacttttga ggacgttcct ttccacagca gctacgctca      3480
```

-continued

| | |
|---|---|
| cagccagagt ctggaccgtc tcatgaatcc tctcatcgac cagtacctgt attacttgag | 3540 |
| cagaacaaac actccaagtg gaaccaccac gcagtcaagg cttcagtttt ctcaggccgg | 3600 |
| agcgagtgac attcgggacc agtctaggaa ctggcttcct ggaccctgtt accgccagca | 3660 |
| gcgagtatca aagacatctg cggataacaa caacagtgaa tactcgtgga ctggagctac | 3720 |
| caagtaccac ctcaatggca gagactctct ggtgaatccg gccatggcaa gccacaagga | 3780 |
| cgatgaagaa aagttttttc ctcagagcgg ggttctcatc tttgggaagc aaggctcaga | 3840 |
| gaaaacaaat gtgaacattg aaaaggtcat gattacagac gaagaggaaa tcggaacaac | 3900 |
| caatcccgtg ctacggagc agtatggttc tgtatctacc aacctccaga gaggcaacag | 3960 |
| acaagcagct accgcagatg tcaacacaca aggcgttctt ccaggcatgg tctggcagga | 4020 |
| cagagatgtg taccttcagg ggcccatctg ggcaaagatt ccacacacgg acggacattt | 4080 |
| tcaccctct cccctcatgg gtggattcgg acttaaacac cctcctccac agattctcat | 4140 |
| caagaacacc ccggtacctg cgaatccttc gaccaccttc agtgcggcaa gtttgcttc | 4200 |
| cttcatcaca cagtactcca cgggacacgg tcagcgtgga gatcgagtgg gagctgcaga | 4260 |
| aggaaaacag caaacgctgg aatcccgaaa ttcagtacac ttccaactac aacaagtctg | 4320 |
| ttaatcgtgg acttaccgtg gatactaatg gcgtgtattc agagcctcgc cccattggca | 4380 |
| ccagatacct gactcgtaat ctgtaattgc ttgttaatca ataaaccgtt taattcgttt | 4440 |
| cagttgaact ttggtctctg cgtatttctt tcttatctag tttccatggc tacgtagata | 4500 |
| agtagcatgg cgggttaatc attaactaca aggaacccct agtgatggag ttggccactc | 4560 |
| cctctctgcg cgctcgctcg ctcactgagg ccgggcgacc aaaggtcgcc cgacgcccgg | 4620 |
| gctttgcccg ggcggcctca gtgagcgagc gagcgcgcag agagggagtg gccaa | 4675 |

<210> SEQ ID NO 8
<211> LENGTH: 4726
<212> TYPE: DNA
<213> ORGANISM: adeno-associated virus 3

<400> SEQUENCE: 8

| | |
|---|---|
| ttggccactc cctctatgcg cactcgctcg ctcggtgggg cctggcgacc aaaggtcgcc | 60 |
| agacggacgt gctttgcacg tccggcccca ccgagcgagc gagtgcgcat agagggagtg | 120 |
| gccaactcca tcactagagg tatggcagtg acgtaacgcg aagcgcgcga agcgagacca | 180 |
| cgcctaccag ctgcgtcagc agtcaggtga ccctttgcg acagtttgcg acaccacgtg | 240 |
| gccgctgagg gtatatattc tcgagtgagc gaaccaggag ctccattttg accgcgaaat | 300 |
| tgaacgagc agcagccatg ccggggttct acgagattgt cctgaaggtc ccgagtgacc | 360 |
| tggacgagcg cctgccgggc atttctaact cgtttgttaa ctgggtggcc gagaaggaat | 420 |
| gggacgtgcc gccggattct gacatggatc cgaatctgat tgagcaggca ccctgaccg | 480 |
| tggccgaaaa gcttcagcgc gagttcctgg tggagtggcg ccgcgtgagt aaggcccgg | 540 |
| aggccctctt ttttgtccag ttcgaaaagg gggagaccta cttccacctg cacgtgctga | 600 |
| ttgagaccat cggggtcaaa tccatggtgg tcggccgcta cgtgagccag attaaagaga | 660 |
| agctggtgac ccgcatctac cgcggggtcg agccgcagct tccgaactgg ttcgcggtga | 720 |
| ccaaaacgcg aaatggcgcc ggggggcggga acaaggtggt ggacgactgc tacatcccca | 780 |
| actacctgct cccccaagacc cagcccgagc tccagtgggc gtggactaac atggaccagt | 840 |
| atttaagcgc ctgtttgaat ctcgcggagc gtaaacggct ggtggcgcag catctgacgc | 900 |

```
acgtgtcgca gacgcaggag cagaacaaag agaatcagaa ccccaattct gacgcgccgg    960
tcatcaggtc aaaaacctca gccaggtaca tggagctggt cgggtggctg gtggaccgcg   1020
ggatcacgtc agaaaagcaa tggattcagg aggaccaggc ctcgtacatc tccttcaacg   1080
ccgcctccaa ctcgcggtcc cagatcaagg ccgcgctgga caatgcctcc aagatcatga   1140
gcctgacaaa gacggctccg gactacctgg tgggcagcaa cccgccggag acattacca    1200
aaaatcggat ctaccaaatc ctggagctga acgggtacga tccgcagtac gcggcctccg   1260
tcttcctggg ctgggcgcaa aagaagttcg ggaagaggaa caccatctgg ctctttgggc   1320
cggccacgac gggtaaaacc aacatcgcgg aagccatcgc ccacgccgtg cccttctacg   1380
gctgcgtaaa ctggaccaat gagaactttc ccttcaacga ttgcgtcgac aagatggtga   1440
tctggtggga ggagggcaag atgacggcca aggtcgtgga gagcgccaag gccattctgg   1500
gcggaagcaa ggtgcgcgtg gaccaaaagt gcaagtcatc ggcccagatc gaacccactc   1560
ccgtgatcgt cacctccaac accaacatgt gcgccgtgat tgacgggaac agcaccacct   1620
tcgagcatca gcagccgctg caggaccgga tgtttgaatt tgaacttacc cgccgtttgg   1680
accatgactt tgggaaggtc accaaacagg aagtaaagga ctttttccgg tgggcttccg   1740
atcacgtgac tgacgtggct catgagttct acgtcagaaa gggtggagct aagaaacgcc   1800
ccgcctccaa tgacgcggat gtaagcgagc caaaacggga gtgcacgtca cttgcgcagc   1860
cgacaacgtc agacgcggaa gcaccggcgg actacgcgga caggtaccaa aacaaatgtt   1920
ctcgtcacgt gggcatgaat ctgatgcttt ttccctgtaa aacatgcgag agaatgaatc   1980
aaatttccaa tgtctgtttt acgcatggtc aaagagactg tggggaatgc ttccctggaa   2040
tgtcagaatc tcaacccgtt tctgtcgtca aaagaagac ttatcagaaa ctgtgtccaa    2100
ttcatcatat cctgggaagg gcacccgaga ttgcctgttc ggcctgcgat ttggccaatg   2160
tggacttgga tgactgtgtt tctgagcaat aaatgactta aaccaggtat ggctgctgac   2220
ggttatcttc cagattggct cgaggacaac ctttctgaag gcattcgtga gtggtgggct   2280
ctgaaacctg gagtccctca acccaaagcg aaccaacaac accaggacaa ccgtcggggt   2340
cttgtgcttc cgggttacaa atacctcgga cccggtaacg gactcgacaa aggagagccg   2400
gtcaacgagg cggacgcggc agccctcgaa cacgacaaag cttacgacca gcagctcaag   2460
gccggtgaca cccgtacct caagtacaac acgccgacg ccgagtttca ggagcgtctt    2520
caagaagata cgtctttggg gggcaacctt ggcagagcag tcttccaggc caaaaagagg   2580
atccttgagc ctcttggtct ggttgaggaa gcagctaaaa cggctcctgg aaagaagggg   2640
gctgtagatc agtctcctca ggaaccggac tcatcatctg gtgttggcaa atcgggcaaa   2700
cagcctgcca gaaaaagact aaatttcggt cagactggag actcagagtc agtcccagac   2760
cctcaaccct ctcggagaacc accagcagcc cccacaagtt tgggatctaa tacaatggct   2820
tcaggcggtg gcgcaccaat ggcagacaat aacgagggtg ccgatggagt gggtaattcc   2880
tcaggaaatt ggcattgcga ttcccaatgg ctgggcgaca gagtcatcac caccagcacc   2940
agaacctggg ccctgcccac ttacaacaac atctctaca agcaaatctc cagccaatca    3000
ggagcttcaa acgacaacca ctactttggc tacagcaccc cttgggggta ttttgacttt   3060
aacagattcc actgccactt ctcaccacgt gactggcagc gactcattaa caacaactgg   3120
ggattccggc caagaaact cagcttcaag ctcttcaaca tccaagttag aggggtcacg   3180
cagaacgatg gcacgacgac tattgccaat aaccttacca gcacggttca gtgtttacg    3240
gactcggagt atcagctccc gtacgtgctc gggtcggcgc accaaggctg tctcccgccg   3300
```

```
tttccagcgg acgtcttcat ggtccctcag tatggatacc tcaccctgaa caacggaagt    3360
caagcggtgg gacgctcatc cttttactgc ctggagtact tcccttcgca gatgctaagg    3420
actggaaata acttccaatt cagctatacc ttcgaggatg tacctttca cagcagctac    3480
gctcacagcc agagtttgga tcgcttgatg aatcctctta ttgatcagta tctgtactac    3540
ctgaacagaa cgcaaggaac aacctctgga acaaccaacc aatcacggct gcttttagc    3600
caggctgggc ctcagtctat gtctttgcag gccagaaatt ggctacctgg gccctgctac    3660
cggcaacaga gactttcaaa gactgctaac gacaacaaca acagtaactt tccttggaca    3720
gcggccagca aatatcatct caatggccgc gactcgctgg tgaatccagg accagctatg    3780
gccagtcaca aggacgatga agaaaaattt ttccctatgc acggcaatct aatatttggc    3840
aaagaaggga caacggcaag taacgcagaa ttagataatg taatgattac ggatgaagaa    3900
gagattcgta ccaccaatcc tgtggcaaca gagcagtatg gaactgtggc aaataacttg    3960
cagagctcaa atacagctcc cacgactgga actgtcaatc atcaggggc cttacctggc    4020
atggtgtggc aagatcgtga cgtgtacctt caaggaccta tctgggcaaa gattcctcac    4080
acggatggac actttcatcc ttctcctctg atgggaggct ttggactgaa acatccgcct    4140
cctcaaatca tgatcaaaaa tactccggta ccggcaaatc ctccgacgac tttcagcccg    4200
gccaagtttg cttcatttat cactcagtac tccactggac aggtcagcgt ggaaattgag    4260
tgggagctac agaaagaaaa cagcaaacgt tggaatccag agattcagta cacttccaac    4320
tacaacaagt ctgttaatgt ggactttact gtagacacta atggtgttta tagtgaacct    4380
cgccctattg aacccggta tctcacacga aacttgtgaa tcctggttaa tcaataaacc    4440
gtttaattcg tttcagttga actttggctc ttgtgcactt cttatcttt atcttgtttc    4500
catggctact gcgtagataa gcagcggcct gcggcgcttg cgcttcgcgg tttacaactg    4560
ctggttaata tttaactctc gccataccct tagtgatgga gttggccact ccctctatgc    4620
gcactcgctc gctcggtggg gcctggcgac caaaggtcgc cagacggacg tgctttgcac    4680
gtccggcccc accgagcgag cgagtgcgca tagagggagt ggccaa             4726
```

<210> SEQ ID NO 9
<211> LENGTH: 3098
<212> TYPE: DNA
<213> ORGANISM: Unknown
<220> FEATURE:
<223> OTHER INFORMATION: AAV serotype, clone 42.2

<400> SEQUENCE: 9

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcttccg    180
cccagatcga tccaccccc gtgatcgtca cttccaacac caacatgtgc gctgtgattg    240
acgggaacag caccaccttc gagcaccagc agccgttaca agaccggatg ttcaaatttg    300
aactcacccg ccgtctggag cacgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gccccgatg acgcggataa agcgagccc aagcgggcct    480
gccctcagt cgcggatcca tcgacgtcag acgcggaagg agctccggtg actttgccg    540
acaggtacca aaacaaatgt tctcgtcacg cgggcatgct tcagatgctg tttccctgca    600
```

-continued

```
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgacc gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggacccct caacggactc    1020
gacaagggag agccggtcaa cgaggcagac gccgcggccc tcgagcacga caaggcctac    1080
gacaagcagc tcgagcaggg ggacaacccg tacctcaagt acaaccacgc cgacgccgag    1140
tttcaggagc gtcttcaaga agatacgtct tttgggggca acctcgggcg agcagtcttc    1200
caggccaaga agcgggttct cgaacctctc ggtctggttg aggaaggcgc taagacggct    1260
cctggaaaga agagacccat agaatcccc gactcctcca cgggcatcgg caagaaaggc    1320
cagcagcccg ctaaaaagaa gctcaacttt gggcagactg gcgactcaga gtcagtgccc    1380
gaccccaac ctctcggaga acctcccgcc gcgccctcag gtctgggatc tggtacaatg    1440
gctgcaggcg gtggcgcacc aatggcagac aataacgaag gcgccgacgg agtgggtaat    1500
gcctccggaa attggcattg cgattccaca tggctgggcg acagagtcat caccaccagc    1560
acccgcacct gggccctgcc cacctacaac aaccacctct acaagcagat atcaagtcag    1620
agcggggcta ccaacgacaa ccacttcttc ggctacagca ccccctgggg ctattttgac    1680
ttcaacagat tccactgcca cttctcacca cgtgactggc agcgactcat caacaacaac    1740
tggggattcc ggcccagaaa gctgcggttc aagttgttca acatccaggt caaggaggtc    1800
acgacgaacg acggcgttac gaccatcgct aataacctta ccagcacgat tcaggtcttc    1860
tcggactcgg agtaccaact gccgtacgtc ctcggctctg cgcaccaggg ctgcctccct    1920
ccgttccctg cggacgtgtt catgattcct cagtacggat atctgactct aaacaacggc    1980
agtcagtctg tgggacgttc ctccttctac tgcctggagt actttccttc tcagatgctg    2040
agaacgggca ataactttga attcagctac acctttgagg aagtgccttt ccacagcagc    2100
tatgcgcaca gccagagcct ggaccggctg atgaatcccc tcatcgacca gtacctgtac    2160
tacctggccc ggaccagag cactacgggg tccacaaggg agctgcagtt ccatcaggct    2220
gggcccaaca ccatggccga gcaatcaaag aactggctgc ccggaccctg ttatcggcag    2280
cagagactgt caaaaaacat agacagcaac aacaacagta actttgcctg gaccggggcc    2340
actaaatacc atctgaatgg tagaaattca ttaaccaacc cgggcgtagc catggccacc    2400
aacaaggacg acgaggacca gttctttccc atcaacggag tgctggtttt ggcgaaacg    2460
ggggctgcca acaagacaac gctggaaaac gtgctaatga ccagcgagga ggagatcaaa    2520
accaccaatc ccgtggctac agaagaatac ggtgtggtct ccagcaacct gcaatcgtct    2580
acggccggac cccagacaca gactgtcaac agccagggg ctctgccccgg catggtctgg    2640
cagaaccggg acgtgtacct gcagggtccc atctgggcca aaattcctca cacggacggc    2700
aactttcacc cgtctcccct gatggcgga tttggactca acacccgcc tcctcaaatt    2760
ctcatcaaaa acacccggt acctgctaat cctccagagg tgtttactcc tgccaagttt    2820
gcctcattta tcacgcagta cagcaccggc caggtcagcg tggagatcga gtgggaactg    2880
cagaaagaaa acagcaaacg ctggaatcca gagattcagt acacctcaaa ttatgccaag    2940
tctaataatg tggaatttgc tgtcaacaac gaagggggttt atactgagcc tcgccccatt    3000
```

-continued

| | |
|---|---:|
| ggcacccgtt acctcacccg taacctgtaa ttgcctgtta atcaataaac cggttaattc | 3060 |
| gtttcagttg aactttggtc tctgcgaagg gcgaattc | 3098 |

<210> SEQ ID NO 10
<211> LENGTH: 3098
<212> TYPE: DNA
<213> ORGANISM: Unknown
<220> FEATURE:
<223> OTHER INFORMATION: AAV serotype, clone 16.3

<400> SEQUENCE: 10

| | |
|---|---:|
| gaattcgccc ttcgcagaga ccaaagttca actgaaacga atcaaccggt ttattgatta | 60 |
| acaagtaatt acaggttacg ggtgaggtaa cgggtgccaa tggggcgagg ctcagtataa | 120 |
| accccttcgt tgttgacagc aaattccaca ttattagact tggcataatt tgaggtgtac | 180 |
| tgaatctctg gattccagcg tttgctgttt tctttctgca gttcccactc gatctccacg | 240 |
| ctgacctggc cggtgctgta ctgcgtgata aatgaggcaa actaggcagg agtaaacacc | 300 |
| cctggaggat tagcaggtac cggggtgttt ttgatgagaa tttgaggagg cgggtgtttg | 360 |
| agtccaaatc cgcccatcag gggagacggg tgaaagttgc cgtccgtgtg aggaattttg | 420 |
| gcccagatgg gaccctgcag gtacacgtcc cggttctgcc agaccatgcc gggcagagcc | 480 |
| ccctggctgt tgacagtctg tgtctggggt ccggccgtag acgattgcag gttgctggag | 540 |
| accacaccgt attcttctgt agccacggga ttggtggttt tgatctcctc ctcgctggtc | 600 |
| attagcacgt tttccagcgt tgtccttgttg gcagcccccg ttttgccaaa aaccagcact | 660 |
| ccgttgatgg gaaagaactg gccctcgtcg tccttgttgg tggccatggc tacgcccggg | 720 |
| ttggttaatg aatttctacc attcagatgg tatttagtgg ccccggtcca ggcaaagtta | 780 |
| ctgttgttgt tgctgtctat gttttttgac agtctctgct gccgataaca gggtccgggc | 840 |
| agccagttct ttgattgctc ggccatggtg ttgggcccag cctgatgaa ctgcagctcc | 900 |
| cttgtggacc ccgtagtgct ctgggtccgg gccaggtagt acaggtactg gtcgatgagg | 960 |
| ggattcatca gccggtccag gctctggctg tgcgcatagc tgctgtggaa aggcacttcc | 1020 |
| tcaaaggtgt agctgaattc aaagttattg cccgttctca gcatctgaga aggaaagtac | 1080 |
| tccaggcagt agaaggagga acgtcccata gactgactgc cgttgtttag agtcagatat | 1140 |
| ccgtactgag gaatcatgaa cacgtccgca gggaacggag ggaggcagcc ctggtgcgca | 1200 |
| gagccgagga cgtacggcag ttggtactcc gagtccgaga agacctgaat cgtgctggta | 1260 |
| aggttattag cgatggtcgt aacgccgtcg ttcgtcgtga cctccttgac ctggatgttg | 1320 |
| aacaacttga accgcagctt tctgggccgg aatccccagt tgttgttgat gagtcgctgc | 1380 |
| cagtcacgtg gtgagaagtg gcagtggaat ctgttgaagt caaaatagcc caggggggtg | 1440 |
| ctgtagccga agaagtggtt gtcgttggta gccccgctct gacttgatat ctgcttgtag | 1500 |
| aggtggttgt tgtaggtggg cagggcccag gtgcgggtgc tggtggtgat gactctgtcg | 1560 |
| cccagccatg tggaatcgca atgccaattt ccggaggcat tacccactcc gtcggcgcct | 1620 |
| tcgttattgt ctgccattgg tgcgccaccg cctgcagcca ttgtaccaga tcccagacct | 1680 |
| gagggcgcgg cggaggttc tccgagaggt tgggggtcgg gcactgactc tgagtcgcca | 1740 |
| gtctgcccaa agttgagctt cttttttagcg ggctgctggc cttttcttgcc gatgcccgtg | 1800 |
| gaggagtcgg gggattctat gggtctcttc tttccaggag ccgtcttagc gccttcctca | 1860 |
| accagaccga gaggttcgag aacccgcttc ttggcctgga agactgctcg cccgaggttg | 1920 |

```
cccccaaaag acgtatcttc ttgaagacgc tcctgaaact cagcgtcggc gtggttgtac    1980
ttgaggtacg ggttgtcccc ctgctcgagc tgcttgtcgt aggccttgtc gtgctcgagg    2040
gccgcggcgt ctgcctcgtt gaccggctct cccttgtcga gtccgttgaa gggtccgagg    2100
tacttgtagc caggaagcac cagaccccgg ccgtcgtcct gcttttgctg gttggctttg    2160
ggtttcgggg ctccaggttt caagtcccac cactcgcgaa tgccctcaga gaggttgtcc    2220
tcgagccaat ctggaagata accatcggca gccatacctg gtttaagtca tttattgctc    2280
agaaacacag tcatccaggt ccacgttgac cagatcgcag gccgagcaag caatctcggg    2340
agcccgcccc agcagatgat gaatggcaca gagtttccga tacgtcctct ttctgacgac    2400
cggttgagat tctgacacgc cggggaaaca ttctgaacag tctctggtcc cgtgcgtgaa    2460
gcaaatgttg aaattctgat tcattctctc gcatgtcttg cagggaaaca gcatctgaag    2520
catgcccgcg tgacgagaac atttgttttg gtacctgtcg gcaaagtcca ccggagctcc    2580
ttccgcgtct gacgtcgatg gatccgcgac tgagggggcag gcccgcttgg gctcgctttt    2640
atccgcgtca tcggggggcgg gcctcttgtt ggctccaccc tttctgacgt agaactcatg    2700
cgccacctcg gtcacgtgat cctgcgccca gcggaagaac tctttgactt cctgctttgt    2760
caccttgcca aagtcctgct ccagacgcg ggtgagttca aatttgaaca tccggtcttg    2820
taacggctgc tggtgctcga aggtggtgct gttccccgtca atcacggcgc acatgttggt    2880
gttggaagtg acgatcacgg gggtgggatc gatctgggcg gacgacttgc acttttggtc    2940
cacgcgcacc ttgctgccgc cgagaatggc cttggcggac tccacgacct tggccgtcat    3000
cttgccctcc tcccaccaga tcaccatctt gtcgacgcaa tcgttgaagg gaaagttctc    3060
attggtccag ttgacgcagc cgtagaaagg gcgaattc                          3098

<210> SEQ ID NO 11
<211> LENGTH: 3121
<212> TYPE: DNA
<213> ORGANISM: Unknown
<220> FEATURE:
<223> OTHER INFORMATION: AAV serotype, clone 29.3

<400> SEQUENCE: 11
gaattcgccc ttcgcagaga ccaaagttca actgaaacga atcaaccggt ttattgatta     60
acaagcaatt acagattacg ggtgaggtaa cgggtgccga tggggcgagg ctcagaataa    120
gtgccatctg tgttaacagc aaagtccaca tttgtagatt tgtagtagtt ggaagtgtat    180
tgaatctctg ggttccagcg tttgctgttt tctttctgca gctcccattc aatttccacg    240
ctgacctgtc cggtgctgta ctgcgtgatg aacgacgcca gcttagcttg actgaaggta    300
gttggaggat ccgcgggaac aggtgtattc ttaatcagga tctgaggagg cgggtgtttc    360
agtccaaagc ccccatcag cggcgaggga tgaaagtttc cgtccgtgtg aggaatcttg    420
gcccagatag gaccctgcag gtacacgtcc cggttctgcc agaccatgcc aggtaaggct    480
ccttgactgt tgacggcccc tacaatagga gcggcgtttt gctgttgcag ttatcggcc    540 accacgccgt actgttctgt ggccactggg ttggtggttt taatttcttc ctcactggtt    600
agcataacgc tgctatagtc cacgttgcct tttccagctc cctgtttccc aaacattaag    660
actccgctgg acggaaaaaa tcgctcttcg tcgtccttgt gggttgccat agcgacaccg    720
ggatttacca gagagtctct gccattcaga tgatacttgg tggcaccggt ccaggcaaag    780
ttgctgttgt tattttgcga cagtgtcgtg agacgcgtt gctgccggta gcagggcccg    840
ggtagccagt ttttggcctg agccgacatg ttattaggcc cggcctgaga aaatagcaac    900
```

```
tgctgagttc ctgcggtacc tcccgtggac tgagtccgag acaggtagta caggtactgg    960
tcgatgaggg ggttcatcag ccggtccagg ctttggctgt gcgcgtagct gctgtgaaaa   1020
ggcacgtcct caaactggta gctgaactca aagttgttgc ccgttctcag catttgagaa   1080
ggaaagtact ccaggcagta gaaggaggaa cggcccacgg cctgactgcc attgttcaga   1140
gtcaggtacc cgtactgagg aatcatgaag acgtccgccg ggaacggagg caggcagccc   1200
tggcgcgcag agccgaggac gtacgggagc tggtattccg agtccgtaaa gacctgaatc   1260
gtgctggtaa ggttattggc gatggtcttg gtgccttcat tctgcgtgac ctccttgacc   1320
tggatgttga agagcttgaa gttgagtctc ttgggccgga atccccagtt gttgttgatg   1380
agtcgctgcc agtcacgtgg tgagaagtgg cagtggaatc tgttaaagtc aaaataccc   1440 caggggggtgc tgtagccgaa gtaggtgttg tcgttggtgc ttcctcccga agtcccgttg   1500
gagatttgct tgtagaggtg gttgttgtag gtggggaggg cccaggttcg ggtgctggtg   1560
gtgatgactc tgtcgcccag ccatgtggaa tcgcaatgcc aatttcctga ggaactaccc   1620
actccgtcgg cgccttcgtt attgtctgcc attggagcgc caccgcctgc agccattgta   1680
ccagatccca gaccagaggg gcctgcgggg ggttctccga ttggttgagg gtcgggcact   1740
gactctgagt cgccagtctg cccaaagttg agtctctttt tcgcgggctg ctggcctttc   1800
ttgccgatgc ccgtagtgga gtctggagaa cgctggggtg atggctctac cggtctcttc   1860
tttccaggag ccgtcttagc gccttcctca accagaccga gaggttcgag aacccgcttc   1920
ttggcctgga agactgctcg tccgaggttg cccccaaaag acgtatcttc ttgcagacgc   1980
tcctgaaact cggcgtcggc gtggttatac cgcaggtacg gattgtcacc cgctttgagc   2040
tgctggtcgt aggccttgtc gtgctcgagg ccgctgcgt ccgccgcgtt gacgggctcc   2100
cccttgtcga gtccgttgaa gggtccgagg tacttgtagc caggaagcac cagaccccgg   2160
ccgtcgtcct gcttttgctg gttggctttg ggcttcgggg ctccaggttt cagcgcccac   2220
cactcgcgaa tgccctcaga gaggttgtcc tcgagccaat ctggaagata accatcggca   2280
gccatacctg atctaaatca tttattgttc aaagatgcag tcatccaaat ccacattgac   2340
cagatcgcag gcagtgcaag cgtctggcac ctttcccatg atatgatgaa tgtagcacag   2400
tttctgatac gccttttga cgacagaaac gggttgagat tctgacacgg gaaagcactc   2460
taaacagtct ttctgtccgt gagtgaagca gatatttgaa ttctgattca ttctctcgca   2520
ttgtctgcag ggaaacagca tcagattcat gcccacgtga cgagaacatt tgttttggta   2580
cctgtccgcg tagttgatcg aagcttccgc gtctgacgtc gatggctgcg caactgactc   2640
gcgcacccgt ttgggctcac ttatatctgc gtcactgggg gcgggtcttt tcttggctcc   2700 acccttttg acgtagaatt catgctccac ctcaaccacg tgatcctttg cccaccggaa   2760
aaagtctttg acttcctgct tggtgacctt cccaaagtca tgatccagac ggcgggtgag   2820
ttcaaatttg aacatccggt cttgcaacgg ctgctggtgt tcgaaggtcg ttgagttccc   2880
gtcaatcacg gcgcacatgt tggtgttgga ggtgacgatc acgggagtcg ggtctatctg   2940
ggccgaggac ttgcatttct ggtccacgcg caccttgctt cctccagaa tggctttggc    3000 cgactccacg accttggcgg tcatcttccc ctcctcccac cagatcacca tcttgtcgac   3060
acagtcgttg aagggaaagt tctcattggt ccagttgacg cagccgtaga agggcgaatt   3120
c                                                                  3121
```

<210> SEQ ID NO 12

<211> LENGTH: 3121
<212> TYPE: DNA
<213> ORGANISM: Unknown
<220> FEATURE:
<223> OTHER INFORMATION: AAV serotype, clone 29.4

<400> SEQUENCE: 12

| | | | | | |
|---|---|---|---|---|---:|
| gaattcgccc | ttctacggct | gcgtcaactg | gaccaatgag | aactttccct | tcaacgactg | 60 |
| tgtcgacaag | atggtgatct | ggtgggagga | ggggaagatg | accgccaagg | tcgtggagtc | 120 |
| ggccaaagcc | attctcggag | gaagcaaggt | gcgcgtggac | cagaaatgca | agtcctcggc | 180 |
| ccagatagac | ccgactccg | tgatcgtcac | ctccaacacc | aacatgtgcg | ccgtgattga | 240 |
| cgggaactca | acgaccttcg | aacaccagca | gccgttgcaa | gaccggatgt | tcaaatttga | 300 |
| actcacccgc | cgtctggatc | atgactttgg | gaaggtcacc | aagcaggaag | tcaaagactt | 360 |
| tttccggtgg | gcaaaggatc | acgtggttga | ggtggagcac | gaattctacg | tcaaaaaggg | 420 |
| tggagccaag | aaaagacccg | ccccagtga | cgcagatata | agtgagccca | acgggtgcg | 480 |
| cgagtcagtt | gcgcagccat | cgacgtcaga | cgcggaagct | tcgatcaact | acgcagacag | 540 |
| gtaccaaaac | aaatgttctc | gtcacgcggg | catgaatctg | atgctgtttc | cctgcagaca | 600 |
| atgcgagaga | atgaatcaga | attcaaatat | ctgcttcact | cacggacaga | aagactgttt | 660 |
| agagtgcttt | cccgtgtcag | aatctcaacc | cgtttctgtc | gtcaaaaagg | cgtatcagaa | 720 |
| actgtgctac | attcatcata | tcatgggaaa | ggtgccagac | gcttgcactg | cctgcgatct | 780 |
| ggtcgatgtg | gatttggatg | actgcatctt | tgaacaataa | atgatttaaa | tcaggtatgg | 840 |
| ctgccgatgg | ttatcttcca | gattggctcg | aggacaacct | ctctgagggc | attcgcgagt | 900 |
| ggtgggcgct | gaaacctgga | gccccgaagc | caaagccaa | ccagcaaaag | caggacggcg | 960 |
| gccgggtct | ggtgcttcct | ggctacaagt | acctcggacc | cttcaacgga | ctcgacaagg | 1020 |
| gggagcccgt | caacgcggcg | gacgcagcgg | ccctcgagca | cgacaaggcc | tacgaccagc | 1080 |
| agctcaaagc | gggtgacaat | ccgtacctgc | ggtataacca | cgccgacgcc | gagtttcagg | 1140 |
| agcgtctgca | agaagatacg | tcttttgggg | gcaacctcgg | gcgagcagtc | ttccaggcca | 1200 |
| agaagcgggt | tctcgaacct | ctcggtctgg | ttgaggaagg | cgctaagacg | gctcctggaa | 1260 |
| agaagagacc | ggtagagcca | tcaccccagc | gttctccaga | ctcctctacg | ggcatcggca | 1320 |
| agaaaggcca | gcagcccgcg | aaaaagagac | tcaactttgg | gcagactggc | gactcagagt | 1380 |
| cagtgcccga | ccctcaacca | atcggagaac | cccccgcagg | cccctctggt | ctgggatctg | 1440 |
| gtacaatggc | tgcaggcggt | ggcgctccaa | tggcagacaa | taacgaaggc | gccgacggag | 1500 |
| tgggtagttc | ctcaggaaat | tggcattgcg | attccacatg | gctgggcgac | tgagtcatca | 1560 |
| ccaccagcac | ccgaacctgg | gcctccccca | cctacaacaa | ccacctctac | aagcaaatct | 1620 |
| ccaacgggac | ttcgggagga | agcaccaacg | acaacaccta | cttcggctac | agcacccct | 1680 |
| gggggtattt | tgactttaac | agattccact | gccacttctc | accacgtgac | tggcagcgac | 1740 |
| tcatcaacaa | caactgggga | ttccggccca | agagactcaa | cttcaagctc | ttcaacatcc | 1800 |
| aggtcaagga | ggtcacgcag | aatgaaggca | ccaagaccat | cgccaataac | cttaccagca | 1860 |
| cgattcaggt | ctttacggac | tcggaatacc | agctcccgta | cgtcctcggc | tctgcgcacc | 1920 |
| agggctgcct | gcctccgttc | ccggcggacg | tcttcatgat | tcctcagtac | gggtacctga | 1980 |
| ctctgaacaa | tggcagtcag | gccgtgggcc | gttcctcctt | ctactgcctg | gagtactttc | 2040 |
| cttctcaaat | gctgagaacg | ggcaacaact | ttgagttcag | ctaccagttt | gaggacgtgc | 2100 |
| cttttcacag | cagctacgcg | cacagccaaa | gcctggaccg | gctgatgaac | cccctcatcg | 2160 |

-continued

```
accagtacct gtactacctg tctcggactc agtccacggg aggtaccgca ggaactcagc    2220
agttgctatt ttctcaggcc gggcctaata acatgtcggc tcaggccaaa aactggctac    2280
ccgggccctg ctaccggcag taacgcgtct ccacgacact gtcgcaaaat aacaacagca    2340
actttgtctg gaccggtgcc accaagtatc atctgaatgg cagagactct ctggtagatc    2400
ccggtgtcgc tatggcaacc cacaaggacg acgaagagcg attttttccg tccagcggag    2460
tcataatgtt tgggaaacag ggagctggaa aagacaacgt ggactatagc agcgtcatgc    2520
taaccagtga ggaagaaatt aaaaccacca acccagtggc cacagaacag tacggcgtgg    2580
tggccgataa cctgcaacag caaaacgccg ctcctattgt aggggccgtc aacagtcaag    2640
gagccttacc tggcatggtc tggcagaacc gggacgtgta cctgcagggt cctacctggg    2700
ccaagattcc tcacacggac ggaaactttc atccctcgcc gctgatggga ggctttggac    2760
tgaaacaccc gcctcctcag atcctgatta agaatacacc tgttcccgcg gatcctccaa    2820
ctaccttcag tcaagctaag ctggcgtcgt tcatcacgca gtacagcacc ggacaggtca    2880
gcgtggaaat tgaatgggag ctgcaggaag aaaacagcaa acgctggaac ccagagattc    2940
aatacacttc caactactac aaatctacaa atgtggactt tgctgttaac acagatggca    3000
cttattctga gcctcgcccc atcggcaccc gttacctcac ccgtaatctg taattgcttg    3060
ttaatcaata aaccggttga ttcgtttcag ttgaactttg gtctctgcga agggcgaatt    3120
c                                                                   3121
```

<210> SEQ ID NO 13
<211> LENGTH: 3121
<212> TYPE: DNA
<213> ORGANISM: Unknown
<220> FEATURE:
<223> OTHER INFORMATION: AAV serotype, clone 29.5

<400> SEQUENCE: 13

```
gaattcgccc ttcgcgagac caaagttcaa ctgaaacgaa tcaaccggtt tattgattaa      60
caagcaatta cagattacgg gtgaggtaac gggtgccgat ggggcgaggc tcagaataag     120
tgccatctgt gttaacagca aagtccacat ttgtagattt gtagtagttg gaagtgtatt     180
gaatctctgg gttccagcgt ttgctgtttt ctttctgcag ctcccattca atttccacgc     240
tgacctgtcc ggtgctgtac tgcgtgatga acgacgccag cttagcttga ctgaaggtag     300
ttggaggatc cgcgggaaca ggtgtattct taatcaggat ctgaggaggc gggtgtttca     360
gtccaaagcc tcccatcagc ggcgagggat gaaagtttcc gtccgtgtga ggaatcttgg     420
cccagatagg accctgcagg tacacgtccc ggttctgcca gaccatgcca ggtaaggctc     480
cttgactgtt gacggcccct acaataggag cggcgttttg ctgttgcagg ttatcggcca     540
ccacgccgta ctgttctgtg gccactgggt tggtggtttt aatttcttcc tcactggtta     600
gcataacgct gctatagtcc acgttgtctt ttccagctcc ctgtttccca aacattaaga     660
ctccgctgga cggaaaaaat cgctcttcgt cgtccttgtg ggttgccata gcgacaccgg     720
gatttaccag agagtctctg ccattcagat gatacttggt ggcaccggtc caggcaaagt     780
tgctgttgtc attttgcgac agtgtcgtgg agacgcgttc ctgccggtag cagggccgg     840 gtagccagtt tttggcctga ccgacatgt tattaggccc ggcctgagaa aatagcaact     900
gctgagttcc tgcggtacct cccgtggact gagtccgaga caggtagtac aggtactggt     960
cgatgagggg gttcatcagc cggtccaggc tttggctgtg cgcgtagctg ctgtgaaaag    1020
```

```
gcacgtcctc aaactggtag ctgaactcaa agttgttgcc cgttctcagc atttgagaag    1080
gaaagtactc caggcagtag aaggaggaac ggcccacggc ctgactgcca ttgttcagag    1140
tcaggtaccc gtactgagga atcatgaaga cgtccgccgg gaacggaggc aggcagccct    1200
ggtgcgcaga gccgaggacg tacgggagct ggtattccga gtccgtaaag acctgaatcg    1260
tgctggtaag gttattggcg atggtcttgg tgccttcatt ctgcgtgacc tccttgacct    1320
ggatgttgaa gagcttgaag ttgaggctct tgggccggaa tccccagttg ttgttgatga    1380
gtcgctgcca gtcacgtggt gagaagtggc agtggaatct gttaaagtca aatacccccc    1440 aggggggtgct gtagccgaag taggtgttgt cgttggtgct tcctcccgaa gtcccgttgg    1500
agatttgctt gtagaggtgg ttgttgtagg tggggagggc ccaggttcgg gtgctggtgg    1560
tgatgactcc gtcgcccagc catgtggaat cgcaatgcca atttcctgag gaactaccca    1620
ctccgtcggc gccttcgtta ttgtctgcca ttggagcgcc accgcctgca gccattgtac    1680
cagatcccag accagagggg cctgcggggg gttctccgat tggttgaggg tcgggcactg    1740
actctgagtc gccagtctgc ccaaagttga gtctcttttt cgcgggctgc tggccttttct    1800 tgccgatgcc cgtagaggag tctggagaac gctggggtga tggctctacc ggtctcttct    1860
ttccaggagc cgtcttagcg ccttcctcaa ccagaccgag aggttcgaga acccgcttct    1920
tggcctggaa gactgctcgc ccgaggttgc ccccaaaaga cgtatcttct gcagacgct    1980 cctgaaactc ggcgtcggcg tggttatacc gcaggtacgg attgtcaccc gctttgagct    2040
gctggtcgta ggccttgtcg tgctcgaggg ccgctgcgtc cgccgcgttg acgggctccc    2100
ccttgtcgag tccgttgaag gtccgaggt acttgtagcc aggaagcacc agaccccggc    2160
cgtcgtcctg cttttgctgg ttggctttgg gcttcggggc tccaggtttc agcgcccacc    2220
actcgcgaat gccctcagag aggttgtcct cgagccaatc tggaagataa ccatcggcag    2280 ccataccga tttaaatcat ttattgttca aagatgcagt catccaaatc cacattgacc    2340
agatcgcagg cagtgcaagc gtctggcacc tttcccatga tatgatgaat gtagcacagt    2400
ttctgatacg cctttttgac gacagaaacg ggttgagatt ctgacacggg aaagcactct    2460
aaacagtctt tctgtccgtg agtgaagcag atatttgaat tctgattcat tctctcgcat    2520
tgtctgcagg gaaacagcat cagattcatg cccacgtgac gagaacattt gttttggtac    2580
ctgtctgcgt agttgatcga agcttccgcg tctgacgtcg atggctgcgc aactgactcg    2640
cgcacccgtt tgggctcact tatatctgcg tcactggggg cgggtctttt cttggctcca    2700
ccctttttga cgtagaattc atgctccacc tcaaccacgt gatcctttgc ccaccggaaa    2760
aagtctttga cttcctgctt ggtgaccttc ccaaagtcat gatccagacg gcgggtgagt    2820
tcaaatttga acatccggtc ttgcaacggc tgctggtgtt cgaaggtcgt tgagttcccg    2880
tcaatcacgg cgcacatgtt ggtgttggag gtgacgatca cgggagtcgg gtctatctgg    2940
gccgaggact tgcatttctg gtccacgcgc accttgcttc ctccgagaat ggctttggcc    3000
gactccacga ccttggcggt catcttcccc tcctcccacc agatcaccat cttgtcgaca    3060
cagtcgttga aggaaagtt ctcattggtc cagttgacgc agccgtagaa agggcgaatt    3120
c                                                                   3121
```

<210> SEQ ID NO 14  
<211> LENGTH: 3131  
<212> TYPE: DNA  
<213> ORGANISM: Unknown  
<220> FEATURE:  
<223> OTHER INFORMATION: AAV serotype, clone 1-3

<400> SEQUENCE: 14

```
gcggccgcga attcgccctt ggctgcgtca actggaccaa tgagaacttt cccttcaatg        60
attgcgtcga caagatggtg atctggtggg aggagggcaa gatgacggcc aaggtcgtgg       120
agtccgccaa ggccattctc ggcggcagca aggtgcgcgt ggaccaaaag tgcaagtcgt       180
ccgcccagat cgaccccacc cccgtgatcg tcacctccaa caccaacatg tgcgccgtga       240
ttgacgggaa cagcaccacc ttcgagcacc agcagcctct ccaggaccgg atgtttaagt       300
tcgaactcac ccgccgtctg gagcacgact ttggcaaggt gacaaagcag gaagtcaaag       360
agttcttccg ctgggccagt gatcacgtga ccgaggtggc gcatgagttt tacgtcagaa       420
agggcggagc cagcaaaaga cccgcccccg atgacgcgga taaaagcgag cccaagcggg       480
cctgcccctc agtcgcggat ccatcgacgt cagacgcgga aggagctccg gtggactttg       540
ccgacaggta ccaaaacaaa tgttctcgtc acgcgggcat gcttcagatg ctgtttccct       600
gcaaaacgtg cgagagaatg aatcggaatt caacatttg cttcacacac ggggtcagag       660
actgctcaga gtgtttcccc ggcgtgtcag aatctcaacc ggtcgtcaga agaggacgt       720
atcggaaact ccgtgcgatt catcatctgc tggggcgggc tcccgagatt gcttgctcgg       780
cctgcgatct ggtcaacgtg gacctggatg actgtgtttc tgagcaataa atgacttaaa       840
ccaggtatgg ctgccgatgg ttatcttcca gattggctcg aggacaacct ctctgagggc       900
attcgcgagt ggtgggcgct gaaacctgga gccccgaagc caaagccaa ccagcaaaag       960
caggacgacg gccggggtct ggtgcttcct ggctacaagt acctcggacc cttcaacgga      1020
ctcgacaagg gggagcccgt caacgcggcg gacgcagcgg ccctcgagca cgacaaggct      1080
tacgaccagc agctgcaggc gggtgacaat ccgtacctgc ggtataacca cgccgacgcc      1140
gagtttcagg agcgtctgca agaagatacg tcttttgggg gcaacctcgg gcgagcagtc      1200
ttccaggcca agaagcgggt tctcgaacct ctcggtctgg ttgaggaagg cgctaagacg      1260
gctcctggaa agaagagacc ggtagagcca tcaccccagc gttctccaga ctcctctacg      1320
ggcatcggca agaaaggcca acagcccgcc agaaaaagac tcaattttgg tcagactggc      1380
gactcagagt cagttccaga ccctcaacct ctcggagaac ctccagcagc gcctctggt      1440
gtgggaccta atacaatggc tgcaggcggt ggcgcaccaa tggcagacaa taacgaaggc      1500
gccgacgag tgggtagttc ctcgggaaat tggcattgcg attccacatg ctgggcgac      1560
agagtcatca ccaccagcac ccgaacctgg gccctgccca cctacaacaa ccacctctac      1620
aagcaaatct ccaacgggac atcggagga gccaccaacg acaacaccta cttcggctac      1680
agcaccccct gggggtattt tgactttaac agattccact gccacctttc accacgtgac      1740
tggcagcgac tcatcaacaa caactgggga ttccgaccca gagactcag cttcaagctc      1800
ttcaacatcc aggtcaagga ggtcacgcag aatgaaggca ccaagaccat cgccaataac      1860
ctcaccagca atccatccagt gtttacggac tcggagtacc agctgccgta cgttctcggc      1920
tctgtccacc agggctgcct gcctccgttc ccggcggacg tgttcatgat tccccagtac      1980
ggctacctaa cactcaacaa cggtagtcag gccgtgggac gctcctcctt ctactgcctg      2040
gaatactttc cttcgcagat gctgagaacc ggcaacaact tccagtttac ttacaccttc      2100
gaggacgtgc ctttccacag cagctacgcc cacagctaga gcttggaccg gctgatgaat      2160
cctctgattg accagtacct gtactacttg tctcggactc aaacaacagg aggcacggca      2220
aatacgcaga ctctgggctt cagccaaggt gggcctaata caatggccaa tcaggcaaag      2280
```

| | |
|---|---|
| aactggctgc caggaccctg ttaccgccaa caacgcgtct caacgacaac cgggcaaaac | 2340 |
| aacaatagca actttgcctg gactgctggg accaaatacc atctgaatgg aagaaattca | 2400 |
| ttggctaatc ctggcatcgc tatggcaaca cacaaagacg acgaggagcg ttttttttcc | 2460 |
| agtaacggga tcctgatttt tggcaaacaa aatgctgcca gagacaatgc ggattacagc | 2520 |
| gatgtcatgc tcaccagcga ggaagaaatc aaaaccacta accctgtggc tacagaggaa | 2580 |
| tacggtatcg tggcagataa cttgcagcag caaaacacgg ctcctcaaat tggaactgtc | 2640 |
| aacagccagg gggccttacc cggtatggtc tggcagaacc gggacgtgta cctgcagggt | 2700 |
| cccatctggg ccaagattcc tcacacggac ggcaacttcc accgtctccc gctgatgggc | 2760 |
| ggctttggcc tgaaacatcc tccgcctcag atcctgatca gaacacgcc tgtacctgcg | 2820 |
| gatcctccga ccaccttcaa ccagtcaaag ctgaactctt tcatcacgca atacagcacc | 2880 |
| ggacaggtca gcgtggaaat tgaatgggag ctgcagaagg aaaacagcaa gcgctggaac | 2940 |
| cccgagatcc agtacacctc caactactac aaatctataa gtgtggactt tgctgttaat | 3000 |
| acagaaggcg tgtactctga accccgcccc attggcaccc gttacctcac ccgtaatctg | 3060 |
| taattgcctg ttaatcaata aaccggttga ttcgtttcag ttgaactttg gtctctgcga | 3120 |
| agggcgaatt c | 3131 |

<210> SEQ ID NO 15
<211> LENGTH: 3127
<212> TYPE: DNA
<213> ORGANISM: Unknown
<220> FEATURE:
<223> OTHER INFORMATION: AAV serotype, clone 13-3b

<400> SEQUENCE: 15

| | |
|---|---|
| gcggccgcga attcgccctt cgcagagacc aaagttcaac tgaaacgaat caaccggttt | 60 |
| attgattaac atgcaattac agattacggg tgaggtaacg agtgccaata gggcgaggct | 120 |
| cagagtaaac accctggctg tcaacggcaa agtccacacc agtctgcttt tcaaagttgg | 180 |
| aggtgtactg aatctccggg tcccagcgct tgctgttttc cttctgcagc tcccactcga | 240 |
| tttccacgct gacttgtccg gtgctgtact gtgtgatgaa cgaagcaaac ttggcaggag | 300 |
| taaacacctc cggaggatta gcgggaacgg gagtgttctt gatcaggatc tgaggaggcg | 360 |
| gatgtttaag tccaaagccg cccatcaaag gagacgggtg aaagttgcca tccgtgtgag | 420 |
| gaatcttggc ccagatggga ccctgcaggt acacgtcccg gttctgccag accatgccag | 480 |
| gtaaggctcc ctggttgttg acaacttgtg tctgggctgc agtattagcc gcttgtaagt | 540 |
| tgctgctgac tatcccgtat tcttccgtgg ctacaggatt agtaggacga atttcttctt | 600 |
| catttgtcat taacacattt tccaatgtag ttttgttagt tgctccagtt tttccaaaaa | 660 |
| tcaggactcc gctggatggg aaaaagcggt cctcgtcgtc cttgtgagtt gccatggcga | 720 |
| cgccgggatt aaccaacgag tttctgccgt tcaggtgata tttggtggca ccagtccaag | 780 |
| caaagttgct gttgttgttt tgatccgacg ttttggagac cctttgttgc cggaagcagg | 840 |
| gtccaggtaa ccaattcttg gcttgttcgg ccatagttga aggcccgccc tggtaaaact | 900 |
| gcagttcccg attgccagct gtgcctcctg ggtcactctg tgttctgcc aggtagtaca | 960 |
| agtactggtc gatgagggga ttcatcagcc ggtccaggct ctggctgtgt gcgtagctgc | 1020 |
| tgtggaaagg cacgtcctcg aagctgtagc tgaactcaaa gttgttgccc gttctcagca | 1080 |
| tctgagaggg gaagtactcc aggcagtaga aggaggaacg tcccacagac tgactgccat | 1140 |
| tgttgagagt caggtagccg tactgaggaa tcatgaagac gtccgccggg aacggaggca | 1200 |

```
ggcagccctg gtgcgcagag ccgaggacgt acggcagctg gtattccgag tccgagaata    1260
cctgaatcgt gctggtaagg ttattagcga tggtcgtaac gccgtcattc gtcgtgacct    1320
ccttgacctg gatgttgaag agcttgaacc gcagcttctt gggccggaat ccccagttgt    1380
tgttgatgag tcgctgccag tcacgtggtg agaagtggca gtggaatctg ttaaagtcaa    1440
aataccccca gggggtgctg tagccgaagt aggtgttgtc gttggtacta cctgcagttt    1500
cactggagat ttgctcgtag aggtggttgt tgtaggtggg cagggcccag gttcgggtgc    1560
tggtggtaat gactctgtcg cccagccatg tggaatcgca atgccaattt cctgaggcat    1620
tacccactcc gtcggcacct tcgttattgt ctgccattgg tgcgccaccg cctgcagcca    1680
ctgtaccaga tcccacacta gagggcgctg ctggaggttc tccgagaggt tgagggtcgg    1740
ggactgactc tgagtcgcca gtctgaccga aattgagtct ctttctggcg gctgctggc    1800 ccttcttgcc gatgcccgtg gaggagtcgg gggaacgctg aggtgacggc tctaccggtc    1860
tcttctttgc aggagccgtc ttagcgcctt cctcaaccag accgagaggt tcgagaaccc    1920
gcttcttggc ctggaagact gctcgcccga ggttgccccc aaatgacgta tcttcttgca    1980
gacgctcctg aaactcggcg tcggcgtggt tataccgcag gtacgggttg tcacccgcat    2040
tgagctgctg gtcgtaggcc ttgtcgtgct cgagggccgc tgcgtccgcc gcgttgacgg    2100
gctccccctt gtcgagtccg ttgaagggtc gaggtacttg tagccagga agcaccagac    2160 cccggccgtt gtcctgcttt tgctggttgg ctttgggttt cggggctcca ggtttcaggt    2220
cccaccactc gcgaatgccc tcagagaggt tgtcctcgag ccaatctgga agataaccat    2280
cggcagccat acctgattta aatcatttat tgttcaaaga tgcagtcatc caaatccaca    2340
ttgaccagat cgcaggcagt gcaagcgtct ggcacctttc ccatgatatg atgaatgtag    2400
cacagtttct gatacgcctt tttgacgaca gaaacgggtt tagattctga cacgggaaag    2460
cactctaaac agtctttctg tccgtgagtg aagcagatat ttgaattctg attcattctc    2520
tcgcattgtc tgcagggaaa cagcatcaga ttcatgccca cgtgacgaga acatttgttt    2580
tggtacctgt ctgcgtagtt gatcgaagct tccgcgtctg acgtcgatgg ctgcgcaact    2640
gactcgcgca cccgtttggg ctcacttata tctgcgtcac tggggcggg tcttttcttg    2700 gctccaccct ttttgacgta gaattcatgc tccacctcaa ccacgtaatc ctttgcccac    2760
cggaaaaagt ctttgacttc ctgcttggtg accttcccaa agtcatgatc cagacggcgg    2820
gtgagttcaa atttgaacat ccggtcttgc aacggctgct ggtgttcgaa ggtcgttgag    2880
ttcccgtcga tcacggcgca catgttggtg ttggagatga cgatcgcggg agtcgggtct    2940
atctgggccg aggacttgca tttctggtcc acgcgcacct tgcttcctcc gagaatggct    3000
ttggccgact ccacgacctt ggcggtcatc ttcccctcct cccaccagat caccatcttg    3060
tcgacacagt cgttgaaggg aaagttctca ttggtccagt tgacgcagcc gtagaaaggg    3120
cgaattc                                                             3127

<210> SEQ ID NO 16
<211> LENGTH: 3106
<212> TYPE: DNA
<213> ORGANISM: Unknown
<220> FEATURE:
<223> OTHER INFORMATION: AAV serotype, clone 24-1

<400> SEQUENCE: 16
gcggccgcga attcgcccct tcgcagagac caaagttcaac tgaaacgaat caaccggttt      60
```

| | |
|---|---|
| attgattaac aagtaattac aggttacggg tgaggtaacg ggtgccaatg gggcgaggct | 120 |
| cagtataaac cccttcgttg ttgacagcaa attccacatt attagacttg gcataatttg | 180 |
| aggtgtactg aatctctgga ttccagcgtt tgctgttttc tttctgcagt tcccactcga | 240 |
| tctccacgct gacctggccg gtgctgtact gcgtgataaa tgaggcaaac ttggcaggag | 300 |
| taaacacctc tggaggatta gcaggtaccg gggtgttttt gatgagaatt tgaggaggcg | 360 |
| ggtgtttgag tccaaatccg cccatcaggg gagacgggtg aaagttgccg tccgtgtgag | 420 |
| gaattttggc ccagatggga ccctgcaggc acacgtcccg gttctgccag accatgccgg | 480 |
| gcagagcccc ctggctgttg acagtctgtg tctggggtcc ggccgtagac gattgcaggt | 540 |
| tgctggagac cacaccgtat tcttctgtag ccacgggatt ggtggttttg atctcctcct | 600 |
| cgctggtcat tagcacgttt tccagcgttg tcttgttggc agccccgtt ttgccaaaaa | 660 |
| ccagcactcc gttgatggga agaactggt cctcgtcgtc cttgttggtg gccatggcta | 720 |
| cgcccgggtt ggttaatgaa tttctaccat tcagatggta tttagtggcc ccggtccagg | 780 |
| caaagttact gttgttgttg ctgtctatgt tttttgacag tctctgctgc cgataacagg | 840 |
| gtccgggcag ccagttcttt gattgctcgg ccatggtgtt gggcccagcc tgatggaact | 900 |
| gcagctccct tgtggacccc gtagtgctct gggtccgggc caggtagtac aggtactggt | 960 |
| cgatgagggg attcatcagc cggtctaggc tctggctgtg cacatagctg ctgtggaaag | 1020 |
| gcacttcctc aaaggtgtag ctgaattcaa agttattgcc cgttctcagc atctgagaag | 1080 |
| gaaagtactc caggcagtag aaggaggaac gtcccacaga ctgactgccg ttgtttagag | 1140 |
| tcagatatcc gtactgagga atcatgaaca cgtccgcagg gaacggaggg aggcagccct | 1200 |
| ggtgcgcaga gccgaggacg tacggcagtt ggtactccga gtccgagaag acctgaatcg | 1260 |
| tgctggtaag gttattagcg atggtcgtaa cgccgtcgtt cgtcgtgacc tccttgacct | 1320 |
| ggatgttgaa caacttgaac cgcagctttc tgggccggaa tccccagttg ttgttgatga | 1380 |
| gtcgctgcca gtcacgtggt gagaagtggc agtggaatct gttgaagtca aaatagcccc | 1440 |
| aggggggtgct gtagctgaag aagtggttgt cgttggtagc cccgctctga cttgatatct | 1500 |
| gcttgtagag gtggttgttg taggtgggca gggcccaggt gcgggtgctg gtggtgatga | 1560 |
| ctctgtcgcc cagccatgtg gaatcgcaat gccaatttcc ggaggcatta cccactccgt | 1620 |
| cggcgccttc gttattgtct gccattggtg cgccaccgcc tgcagccatt gtaccagatc | 1680 |
| ccagacctga gggcgcggcg ggaggttctc cgagaggttg ggggtcgggc actgactctg | 1740 |
| agtcgccagt ctgcccaaag ttgagcttct ttttagcggg ctgctggcct ttcttgccga | 1800 |
| tgcccgtgga ggagtcgggg gattctatgg gtctcttctt tccaggagcc gtcttagcga | 1860 |
| cttcctcaac cagaccgaga ggttcgagaa cccgcttctt ggcctggaag actgctcgcc | 1920 |
| cgaggttgcc cccaaaagac gtatcttctt gaagacgctc ctgaaactcg gcgtcggcgt | 1980 |
| ggttgtactt gaggtacggg ttgtccccct gctcgagctg cttgtcgtag gccttgtcgt | 2040 |
| gctcgagggc cgcggcgtct gcctcgttga ccggctctcc cttgtcgagt ccgttgaagg | 2100 |
| gtctgaggta cttgtagcca ggaagcacca gaccccggcc gtcgtcctgc ttttgctggt | 2160 |
| tggctttggg tttcggggct ccaggtttca agtcccacca ctcgcgaatg ccctcagaga | 2220 |
| ggttgtcctc gagccaatct ggaagataac catcggcagc cataccctggt ttaagtcatt | 2280 |
| tattgctcag aaacacagtc atccaggtcc acgttgacca gatcgcaggc cgagcaagca | 2340 |
| atctcggag cccgccccag cagatgatga atggcacaga gtttccgata cgtcctcttt | 2400 |
| ctgacgaccg gttgagattc tgacacgccg gggaaacatt ctgaacagtc tctggtcccg | 2460 |

```
tgcgtgaagc aaatgttgaa attctgattc actctctcgc atgtcttgca gggaaacagc    2520
atctgaagca tgcccgcgtg acgagaacat ttgttttggt acctgtcggc aaagtccacc    2580
ggagctcctt ccgcgtctga cgtcgatgga ttcgcgactg aggggcaggc ccgcttgggc    2640 tcgctttttat ccgcgtcatc gggggcgggt ctcttgttgg ccccacccctt tctgacgtag   2700 aacccatgcg ccacctcggt cacgtgatcc tgcgcccagc ggaagaacct tttgacttcc    2760
tgctttgtca ccttgccaaa gttatgctcc agacggcggg tgggttcaaa tttgaacatc    2820
cggtcctgca acggctgctg gtgctcgaag gtggcgctgt tcccgtcaat cacggcgcac    2880
atgttggtgt tggaggtgac ggtcacgggg gtggggtcga tctgggcgga cgacttgcac    2940
ttttggtcca cgcgcacctt gctgccgccg agaatggcct tggcggactc cacgaccttg    3000
gccgtcatct tgccctcctc ccaccagatc accatcttgt cggcgcaatc gttgaaggga    3060
aagttctcat tggtccagtt gacgcagccg tagaaagggc gaattc                   3106
```

<210> SEQ ID NO 17  
<211> LENGTH: 3102  
<212> TYPE: DNA  
<213> ORGANISM: Unknown  
<220> FEATURE:  
<223> OTHER INFORMATION: AAV serotype, clone 27-3

<400> SEQUENCE: 17

```
gcggccgcga attcgccctt cgcagagacc aaagttcaac tgaaacgaat caaccggttt     60
attgattaac aagtaattac aggttacggg tgaggtaacg ggtgccaatg gggcgaggct    120
cagtataaac cccttcgttg ttgacagcaa attccacatt attagacttg cataaatttg    180
aggtgtactg aatctctgga ttccagcgtt tgctgttttc tttctgcagt tcccactcga    240
tctccacgct gacctggccg gtgctgtact gcgtgataaa tgaggcaaac ttggcaggag    300
taaacacctc tggaggatta gcaggtaccg gggtgttttt gatgagaatt tgaggaggcg    360 ggtgttttgag tccaaatccg cccatcaggg gagacgggtg aaagttgccg tccgtgtgag    420
gaatttcggc ccagatggga ccctgcaggt acacgtcccg gttctgccag accatgccgg    480
gcagagcccc ctggctgttg acagtctgtg tccgggtcc ggccgtagac gattgcaggt    540
tgctggagac cacccgtat tcttctgtag ccacgggatt ggtggttttg atctcctcct    600
cgctggtcat tagcacgttt tccagcgttg tcttgttggc agcccccgtt ttgccaaaaa    660
ccagcactcc gttgatggga aggaactggt cctcgtcgtc cttgttggtg gccatggcta    720
cgcccgggtt ggttaatgaa tttctaccat tcagatggta tttagtggcc ccggtccagg    780
caaagttact gttgttgttg ctgtctatgt ttttttgacag tctctgctgc cgataacagg    840
gtccgggcag ccagttcttt gattgctcgg ccacggtgtt gggcccagcc tgatggaact    900
gcagctccct tgtggacccc gtagtgctct gggtccgggc caggtagtac aggtactggt    960
cgatgagggg attcatcagc cggtccaggc tctggctgtg cgcatagctg ctgtggaaag   1020
gcacttcctc aaaggtgtag ctgaattcaa agttattgcc cgttctcagc atctgagaag   1080
gaaagtactc caggcagcag aaggaggaac gtcccacaga ctgactgccg ttgtttagag   1140
tcagatatcc gtactgagga atcatgaaca cgtccgcagg gaacggaggg aggcagcccct  1200 ggtgcgcaga gccgaggacg tacggcagtt ggtactccga gtccgagaag acctgaatcg   1260
tgctggtaag gttattagcg atggtcgtaa cgccgtcgtt cgtcgtgacc tccttgacct   1320
ggatgttgaa caacttgaac cgcagctttc tgggccggaa tccccagttg ttgttgatga   1380
```

```
gtcgctgcca gtcacgtggt gagaagtggc agtggaatct gttgaagtca aaatagcccc    1440
aggggggtgct gtagccgaag aagtggttgt cgttggtagc cccgctctga cttgatatct    1500
gcttgtagag gtggttgttg taggtgggca gggcccaggt gcgggtgctg gtggtgatga    1560
ctctgtcgcc cagccatgtg gaatcgcaat gccaatttcc ggaggcatta cccactccgt    1620
cggcgccttc gttattgtct gccattggtg cgccaccgcc tgcagccatt gtaccagatc    1680
ccagacctga gggcgcggcg ggaggttctc cgagaggttg ggggtcgggc actgactctg    1740
agtcgccagt ctgcccaaag ttgagcttct ttttagcggg ctgctggcct tcttgccga    1800
tgcccgtgga ggagtcgggg gattctatgg gtctcttctt tccggaagcc gtcttagcgc    1860
cttcctcaac cagaccgaga ggttcgagaa cccgcttctt ggcctggaag actgctcgcc    1920
cgaggttgcc cccaaaagac gtatcttctt gaagacgctc ctgaaactcg gcgtcggcgt    1980
ggttgtactt gaggtacggg ttgtcccccct gctcgagctg cttgtcgtag gccttgtcgt    2040
gctcgagggc cgcggcgtct gcctcgttga ccggctctcc cttgtcgagt ccgttgaagg    2100
gtccgaggta cttgtagcca ggaagcacca gaccccggcc gtcgtcctgc ttttgctggt    2160
tggctttggg tttcggggct ccaggtttca agtcccacca ctcgcgaatg ccctcagaga    2220
ggttgtcctc gagccaatct ggaagataac catcggcagc catacctggt ttaagtcatt    2280
tattgctcag aaacacagtc atccaggtcc acgttgacca gatcgcaggc cgagcaagca    2340
atctcgggag cccgccccag cagatgatga atggcacaga gtttccgata cgtcctcttt    2400
ctgacgaccg gttgagattc tgacacgccg gggaaacatt ctgaacagtc tctggtcccg    2460
tgcgtgaagc aaatgttgaa attctgattc attctctcgc atgtcttgca gggaaacagc    2520
atctgaagca tgcccgcgtg acgagaacat ttgttttggt acctgtcggc aaagtccacc    2580
ggagctcctt ccgcgtctga cgtcgatgga tccgcgactg agggggcaagc ccgcttgggc    2640
tcgctttat ccgcgtcatc gggggcgggt ctcttgttgg ctccacccctt tctgacgtag    2700
aactcatgcg ccacctcggt cacgtgatcc tgcgcccagc ggaagaactc tttgacttcc    2760
tgctttgtca ccttgccaaa gtcatgctcc agacggcggg tgagttcaaa tttgaacatc    2820
cggtcttgta acggctgctg gtgctcgaag gtggtgctgt tcccgtcaat cacggcgcac    2880
atgttggtgt tggaagtgac gatcacgggg gtgggatcga tctgggcgga cgacttgcac    2940
ttttggtcca cgcgcacctt gctgccgccg agaatggcct tggcggactc cacgaccttg    3000
gccgtcatct tgccctcctc ccaccagatc accatcttgt cgacgcaatc gttgaaggga    3060
aagttctcat tggtccagtt gacgcagccg aagggcgaat tc                        3102
```

<210> SEQ ID NO 18
<211> LENGTH: 3106
<212> TYPE: DNA
<213> ORGANISM: Unknown
<220> FEATURE:
<223> OTHER INFORMATION: AAV serotype, clone 7-2

<400> SEQUENCE: 18

```
gcggccgcga attcgccctt cgcagagacc aaagttcaac tgaaacgaat cagccggttt      60
attgattaac aagtaattac aggttacggg tgaggtaacg ggtgccaatg gggcgaggct     120
cagtataaac cccttcgttg ttgacagcaa attccacatt attagacttg gcataatttg     180
aggtgtactg aatctctgga ttccagcgtt tgctgttttc tttctgcagt tcccactcga     240
tctccacgct gacctggccg gtgctgtact gcgtgataaa tgaggcaaac ttggcaggag     300
taaacacctc tggaggatta gcaggtaccg gggtgttttt gatgagaatt tgaggaggcg     360
```

```
ggtgtttgag tccaaatccg cccatcaggg gagacgggtg aaagttgccg tccgtgtgag      420
gaattttggc ccagatggga ccctgcaggt acacgtcccg gttctgccag accatgccgg      480
gcagagcccc ctggctgttg acagtctgtg tctggggtcc ggccgtagac gattgcaggt      540
tgctggagac cacaccgtat tcttctgtag ccacgggatt ggtggttttg atctcctcct      600
cgctggtcat tagcacgttt tccagcgttg tcttgttggc agccccgtt ttgccaaaaa       660 ccagcactcc gttgatggga aagaactggt cctcgtcgtc cttgttggtg gccatggcta      720
cgcccgggtt ggttaatgaa tttctaccat tcagatggta tttagtggcc ccggtccagg      780
caaagttact gttgttgttg ctgtctatgt tttttgacag tctctgctgc cgataacagg      840
gtccgggcag ccagttcttt gattgctcgg ccatggtgtt gggcccagcc tgatggaact      900
gcagctccct tgtggacccc gtagtgctct gggtccgggc caggtagtac aggtactggt      960
cgatgagggg attcatcagc cggtccaggc tctggctgtg cgcatagctg ctgtggaaag     1020
gcacttcctc aaaggtgtag ctgaattcaa agttatcgcc cgttctcagc atctgagaag     1080
gaaagtactc caggcagtag aaggaggaac gtcccacaga ctgactgccg ttgtttagag     1140
tcagatatcc gtactgagga atcatgaaca cgtccgcagg gaacggaggg aggcagccct     1200
ggtgcgcaga gccgaggacg tacggcagtt ggtactccga gtccgagaag acctgaatcg     1260
tgctggtaag gttattagcg atggtcgtaa cgccgtcgtt cgtcgtgacc tccttgacct     1320
ggatgttgaa caacttgaac cgcagctttc tgggccggaa tccccagttg ttgttgatga     1380
gtcgctgcca gtcacgtggt gagaagtggc agtggaatct gttgaagtca aaatagcccc     1440 aggggggtgct gtagccgaag aagtggttgt cgttggtagc cccgctctga cttgatatct     1500
gcttgtagag gtggttgttg taggtgggca gggcccaggt gcgggtgctg gtggtgatga     1560
ctctgtcgcc cagccatgtg gaatcgcaat gccaatttcc ggaggcatta cccactccgt     1620
cggcgccttc gttattgtct gccattggtg cgccaccgcc tgcagccatt gtaccagatc     1680
ccagacctga gggcgcggcg ggaggttctc cgagaggttg ggggtcgggc actgactctg     1740
agtcgccagt ctgcccaaag ttgagcttct ttttagcggg cggctggccg ttcttgccga     1800
tgcccgtgga ggagtcgggg gattctatgg gtctcttctt tccaggagcc gtcttagcgc     1860
cttcctcaac cagaccgaga ggttcgagaa cccgcttctt ggcctggaag actgctcgcc     1920
cgaggttgcc cccaaaagac gtatcttctt gaagacgctc ctgaaactcg gcgtcggcgt     1980
ggttgtactt gaggtacggg ttgtccccct gctcgagctg cttgtcgtag gccttgtcgt     2040
gctcgagggc cgcggcgtct gcctcgttga ccggctctcc cttgtcgagt ccgttgaagg     2100
gtccgaggta cctgtagcca ggaagcacca gaccccggcc gtcgtcctgc ttttgctggt     2160
tggctttggg tttcggggct ccaggtttca agtcccacca ctcgcgaatg ccctcagaga     2220
ggttgccctc gagccaatct ggaagataac catcggcagc catacctggt ttaagtcatt     2280
tattgctcag aaacacagtc atccaggtcc acgttggcca gatcgcaggc cgagcaagca     2340
atctcgggag cccgccccag cagatgatga atggcacaga gtttccgata cgtcctcttt     2400
ctgacgaccg gttgagattc tgacacgccg gggaaacatt ctgaacagtc tctggtcccg     2460
tgcgtgaagc aaatgttgaa attctgattc attctctcgc atgtcttgca ggggaacagc     2520
atctgaagca tgcccgcgtg acgagaacat tgttttggt acctgtcggc aaagtccacc      2580
ggagctcctt ccgcgtctga cgtcgatgga tccgcgactg aggggcaggc ccgcttgggc     2640
tcgcttttat ccgcgtcatc gggggcgggt ctcttgttgg ctccacccctt tctgacgtag    2700
```

| | |
|---|---:|
| aactcatacg ccacctcggt cacgtgatcc tgcgcccagc ggaagaactc tttgacttcc | 2760 |
| tgctttgtca ccttgccaaa gtcatgctcc agacggcggg tgagttcaaa tttgaacatc | 2820 |
| cggtcttgta acggctgctg gtgctcgaag gtggtgctgt tcccgtcaat cacggcgcac | 2880 |
| atgttggtgt tggaagtgac gatcacgggg gtgggatcga tctgggcgga cgacttgcac | 2940 |
| ttttggtcca cgcgcacctt gctgccgccg agaatggcct tggcggactc cacgaccttg | 3000 |
| gccgtcatcc tgccctcctc ccaccagatc accatcttgt cgacgcaatc gttgaaggga | 3060 |
| aagttctcat tggtccagtt gacgcagccg tagaaagggc gaattc | 3106 |

<210> SEQ ID NO 19
<211> LENGTH: 3105
<212> TYPE: DNA
<213> ORGANISM: Unknown
<220> FEATURE:
<223> OTHER INFORMATION: AAV serotype, clone C1

<400> SEQUENCE: 19

| | |
|---|---:|
| gaattcgccc ttgctgcgtc aactggacca atgagaactt tcccttcaac gattgcgtcg | 60 |
| acaagatggt gatctggtgg gaggagggca agatgaccgc caaggtcgtg gagtccgcca | 120 |
| aggccattct gggcggaagc aaggtgcgcg tggaccaaaa gtgcaagtca tcggcccaga | 180 |
| tcgaccccac gcccgtgatc gtcacctcca acaccaacat gtgcgccgtg atcgacggga | 240 |
| acagcaccac cttcgagcac cagcagccgc tgcaggaccg catgttcaag ttcgagctca | 300 |
| cccgccgtct ggagcacgac tttggcaagg tgaccaagca ggaagtcaaa gagttcttcc | 360 |
| gctgggctca ggatcacgtg actgaggtgg cgcatgagtt ctacgtcaga aagggcggag | 420 |
| ccaccaaaag acccgccccc agtgacgcgg atataagcga gcccaagcgg gcctgcccct | 480 |
| cagttgcgga gccatcgacg tcagacgcgg aagcaccggt ggactttgcg gacaggtacc | 540 |
| aaaacaaatg ttctcgtcac gcgggcatgc ttcagatgct gtttccctgc aagacatgcg | 600 |
| agagaatgaa tcagaatttc aacgtctgct tcacgcacgg ggtcagagac tgctcagagt | 660 |
| gcttccccgg cgcgtcagaa tctcaacccg tcgtcagaaa aaagacgtat cagaaactgt | 720 |
| gcgcgattca tcatctgctg gggcgggcac ccgagattgc gtgttcggcc cgcgatctcg | 780 |
| tcaacgtgga cttggatgac tgtgtttctg agcaataaat gacttaaacc aggtatggct | 840 |
| gctgacggtt atcttccaga ttggctcgag gacaacctct ctgagggcat tcgcgagtgg | 900 |
| tgggacctga aacctggagc ccccaagccc aaggccaacc agcagaagca ggacgacggc | 960 |
| cggggtctgg tgcttcctgg ctacaagtac ctcggaccct caacggact cgacaagggg | 1020 |
| gagcccgtca acgcggcgga cgcagcggcc ctcgagcacg acaaggccta cgaccagcag | 1080 |
| ctcaaagcgg gtgacaatcc gtacctgcgg tataaccacg ccgacgccga gtttcaggag | 1140 |
| cgtctgcaag aagatacgtc ttttgggggc aacctcgggc gagcagtctt ccaggccaag | 1200 |
| aagagggtac tcgaacctct gggcctggtt gaagaaggtg ctaagacggc tcctggaaag | 1260 |
| aagagaccgt tagagtcacc acaagagccc gactcctcct caggaatcgg caaaaaggc | 1320 |
| aaacaaccag ccaaaaagag actcaacttt gaagaggaca ctggagccgg agacggaccc | 1380 |
| cctgaaggat cagataccag cgccatgtct tcagacattg aaatgcgtgc agcaccgggc | 1440 |
| ggaaatgctg tcgatgcggg acaaggttcc gatggagtgg gtaatgcctc gggtgattgg | 1500 |
| cattgcgatt ccacctggtc tgagggcaag gtcacaacaa cctcgaccag aacctgggtc | 1560 |
| ttgcccacct acaacaacca cttgtacctg cggctcggaa acatcaaa cagcaacacc | 1620 |
| tacaacggat tctccacccc ctgggggatac tttgacttta acagattcca ctgtcacttc | 1680 |

```
tcaccacgtg actggcaaag actcatcaac aacaactggg gactacgacc aaaagccatg    1740
cgcgttaaaa tcttcaatat ccaagttaag gaggtcacaa cgtcgaacgg cgagactacg    1800
gtcgctaata accttaccag cacggttcag atatttgcgg actcgtcgta tgagctcccg    1860
tacgtgatgg acgctggaca agagggaagt ctgtctcctt tccccaatga cgtcttcatg    1920
gtgcctcaat atggctactg tggcattgtg actggcgaaa atcagaacca gacggacaga    1980
aatgctttct actgcctgga gtattttcct tcacaaatgc tgagaactgg caataacttt    2040
gaaatggctt acaactttgg gaaggtgccg ttccactcaa tgtatgctta cagccagagc    2100
ccggacagac tgatgaatcc cctcctggac cagtacctgt ggcacttaca gtcgaccacc    2160
tctggagaga ctctgaatca aggcaatgca gcaaccacat ttggaaaaat caggagtgga    2220
gactttgcct tttacagaaa gaactggctg cctgggcctt gtgttaaaca gcagagactc    2280
tcaaaaactg ccagtcaaaa ttacaagatt cctgccagcg ggggcaacgc tctgttaaag    2340
tatgacaccc actataccct taacaaccgc tggagcaaca tagcgcctgg acctccaatg    2400
gcaacagctg accttcaga tggggacttc agcaacgccc agctcatctt ccctggacca    2460
tcagtcaccg gaaacacaac aacctcagca aacaatctgt tgtttacatc agaagaagaa    2520
attgctgcca ccaacccaag agacacggac atgtttggtc agattgctga caataatcag    2580
aatgctacaa ctgctcccat aaccggcaac gtgactgcta tgggagtgct tcctggcatg    2640
gtgtggcaaa acagagacat ttactaccaa gggccaattt gggccaagat cccacacgcg    2700
gacggacatt tcatccttc accgctaatt ggcggttttg gactgaaaca tccgcctccc    2760
cagatattta tcaaaaacac ccccgtacct gccaatcctg cgacaacctt cactgcagcc    2820
agagtggact ctttcatcac acaatacagc accggccagg tcgctgttca gattgaatgg    2880
gaaatcgaaa aggaacgctc caaacgctgg aatcctgaag tgcagtttac ttcaaactat    2940
gggaaccagt cttctatgtt gtgggctccc gatacaactg gaagtatac agagccgcgg    3000 gttattggct ctcgttattt gactaatcat ttgtaactgc ctagttaatc aataaaccgt    3060
gtgattcgtt tcagttgaac tttggtctct gcgaagggcg aattc                    3105
```

<210> SEQ ID NO 20
<211> LENGTH: 3105
<212> TYPE: DNA
<213> ORGANISM: Unknown
<220> FEATURE:
<223> OTHER INFORMATION: AAV serotype, clone C3

<400> SEQUENCE: 20

```
gaattcgccc ttgctgcgtc aactggacca atgagaactt tcccttcaac gattgcgtcg      60
acaagatggt gatctggtgg gaggagggca agatgaccgc caaggtcgtg gagtccgcca     120
aggccattct gggcggaagc aaggtgcgcg tggaccaaaa gtgcaagtca tcggcccaga     180
tcgaccccac gcccgtgatc gtcacctcca acaccaacat gtgcgccgtg atcgacggga     240
acagcaccac cttcgagcac cagcagccgc tgcaggaccg catgttcaag ttcgagctca     300
cccgccgtct ggagcacgac tttggcaagg tgaccaagca ggaagtcaaa gagttcttcc     360
gctgggctca ggatcacgtg actgaggtgg cgcatgagtt ctacgtcaga aagggcggag     420
ccaccaaaag acccgccccc agtgacgcgg atataagcga gcccaagcgg gcctgcccct     480
cagttgcgga gccatcgacg tcagacgcgg aagcaccggt ggactttgcg gacaggtacc     540
aaaacaaatg ttctcgtcac gcgggcatgc ttcagatgct gtttccctgc aagacatgcg     600
```

-continued

```
agagaatgaa tcagaatttc aacgtctgct tcacgcacgg ggtcagagac tgctcagagt      660
gcttccccgg cgcgtcagaa tctcaacccg tcgtcagaaa aaagacgtat cagaaactgt      720
gcgcgattca tcatctgctg gggcgggcac ccgagattgc gtgttcggcc tgcgatctcg      780
tcaacgtgga cttggatgac tgtgtttctg agcaataaat gacttaaacc aggtatggct      840
gctgacggtt atcttccaga ttggctcgag gacaacctct ctgagggcat tcgcgagtgg      900
tgggacctga aacctggagc ccccaagctc aaggccaacc agcagaagca ggacgacggc      960
cggggtctgg tgcttcctgg ctacaagtac ctcggaccct tccacggact cgacaagggg     1020
gagcccgtca acgcggcgga cgcagcggcc ctcgagcacg acaaggccta cgaccagcag     1080
ctcaaagcgg gtgacaatcc gtacctgcgg tataaccacg ccgacgccga gtttcaggag     1140
cgtctgcaag aagatacgtc ttttgggggc aacctcgggc gagcagtctt ccaggccaag     1200
aagagggtac tcgaaccact gggcctggtt gaagaaggtg ctaagacggc tcctggaaag     1260
aagagaccgt tagagtcacc acaagagccc gactcctcct caggaatcgg caaaaaaggc     1320
aaacaaccag ccaaaaagag actcaacttt gaagaggaca ctggagccgg agacggaccc     1380
cctgaaggat cagataccag cgccatgtct tcagacattg aaatgcgtgc agcaccgggc     1440
ggaaatgctg tcgatgcggg acaaggttcc gatgagtgg gtaatgcctc gggtgattgg      1500
cattgcgatt ccacctggtc tgagggcaag gtcacaacaa cctcgaccag aacctgggtc     1560
ttgcccacct acaacaacca cttgtacctg cggctcggaa caacatcaaa cagcaacacc     1620
tacaacggat tctccacccc ctggggatac tttgacttta acagattcca ctgtcacttc     1680
tcaccacgtg actggcaaag actcatcaac aacaactggg gactacgacc aaaagccatg     1740
cgcgttaaaa tcttcaatat ccaagttaag gaggtcacaa cgtcgaacgg cgagactacg     1800
gtcgctaata accttaccag cacgattcag atatttgcgg actcgtcgta tgagctcccg     1860
tacgtgatgg acgctggaca agagggaagt ctgcctcctt tccccaatga cgtcttcatg     1920
gtgcctcaat atggctactg tggcattgtg actggcgaaa atcagaacca gacggacaga     1980
aatgctttct actgcctgga gtattttcct tcacaaatgc tgagaactgg caataacttt     2040
gaaatggctt acaactttga gaaggtgccg ttccactcaa tgtatgctca cagccagagc     2100
ctggacagac tgatgaatcc cctcctggac cagtacctgt ggcacttaca gtcgaccacc     2160
tctggagaga ctctgaatca aggcaatgca gcaaccacat ttggaaaaat caggagtgga     2220
gactttgcct tttacagaaa gaactggctg cctgggcctt gtgttaaaca gcagagattc     2280
tcaaaaactg ccagtcaaaa ttacaagatt cctgccagcg ggggcaacgc tctgttaaag     2340
tatgacaccc actataccct aaacaaccgc tggagcaaca tagcgcctgg acctccaatg     2400
gcaacagctg gaccttcaga tgggacttc agcaacgccc agctcatctt ccctggacca     2460
tcagtcaccg gaaacacaac aacctcagca acaatctgt tgtttacatc agaaggagaa      2520
attgctgcca ccaacccaag agacacggac atgtttggtc agattgctga caataatcag     2580
aatgctacaa ctgctcccat aaccggcaac gtgactgcta tgggagtgct tcctggcatg     2640
gtgtggcaaa acagagacat ttactaccaa gggccaattt gggccaagat cccacacgcg     2700
gacggacatt ttcatccttc accgctaatt ggcggttttg gactgaaaca tccgcctccc     2760
cagatattta tcaaaaacac ccccgtacct gccaatcctg cgacaacctt cactgcagcc     2820
agagtggact ctttcatcac acaatacagc accggccagg tcgctgttca gattgaatgg     2880
gaaatcgaaa aggaacgctc caaacgccgg aatcctgaag tgcagtttac ttcaaactat     2940
gggaaccagt cttctatgtt gtgggctccc gatacaactg gaagtatac agagccgcgg     3000
```

| | | | | |
|---|---|---|---|---|
| gttattggct | ctcgttattt | gactaatcat | ttgtaactgc | ctagttaatc aataaaccgt | 3060 |
| gtgattcgtt | tcagttgaac | tttggtctct | gcgaagggcg | aattc | 3105 |

<210> SEQ ID NO 21
<211> LENGTH: 3105
<212> TYPE: DNA
<213> ORGANISM: Unknown
<220> FEATURE:
<223> OTHER INFORMATION: AAV serotype, clone C5

<400> SEQUENCE: 21

| | | | | | |
|---|---|---|---|---|---|
| gaattcgccc | ttcgcagaga | ccaaagttca | actgaaacga | atcacacggt | ttattgatta | 60 |
| actaggcagt | tacaaatgat | tagtcaaata | acgagagcca | ataacccgcg | gctctgtata | 120 |
| cttcccagtt | gtatcgggag | cccacaacat | agaagactgg | ttcccacagt | ttgaagtaaa | 180 |
| ctgcacttca | ggattccagc | gtttggagcg | ttccttttcg | atttcccatt | caatctgaac | 240 |
| agcgacctgg | ccgtgctgt | attgtgtgat | gaaagagtcc | actctggctg | cagtgaaggt | 300 |
| tgtcgcagga | taggcaggta | cggggtgtt | tttgataaat | atctggggag | gcggatgttt | 360 |
| cagtccaaaa | ccgccaatta | gcggtgaagg | atgaaaatgt | ccgtccgcgt | gtgggatctt | 420 |
| ggcccaaatt | ggcccttggt | agtaaatgtc | tctgttttgc | cacaccatgc | caggaagcac | 480 |
| tcccatagca | gtcacgttgc | cggttatggg | agcagttgta | gcattctgat | tattgtcagc | 540 |
| aatctgacca | aacatgtccg | tgtctcttgg | gttggtggca | gcaatttctt | cttctgatgt | 600 |
| aaacaacaga | ttgtttgctg | aggttgttgt | gtttccggtg | actgatggtc | cagggaagat | 660 |
| gagctgggcg | ttgctgaagt | ccccatctga | aggtccagct | gttgccattg | gaggtccagg | 720 |
| cgctatgttg | ctccagcggt | tgtttaaggt | atagtgggtg | tcatacttta | acagagcgtt | 780 |
| gcccccgctg | gcaggaatct | tgtaatttg | actggcagtt | tttgagaatc | tctgctgttt | 840 |
| aacacaaggc | ccaggcagcc | agttctttct | gtaaaaggca | aagtctccac | tcctgatttt | 900 |
| tccaaatgtg | gttgctgcat | tgccttgatt | cagagtctct | ccagaggtgg | tcgactgtaa | 960 |
| gtgccacagg | tactggtcca | ggagggggatt | catcagtccg | tccaggctct | ggctgtgagc | 1020 |
| atacattgag | tggaacggca | ccttctcaaa | gttgtaagcc | gtttcaaagt | tattgccagt | 1080 |
| tctcagcatt | tgtgaaggaa | aatactccag | gcagtagaaa | gcatttctgt | ccgtctggtt | 1140 |
| ctgattttcg | ccagtcacaa | tgccacagta | gccatattga | ggcaccatga | agacgtcatt | 1200 |
| ggggaaagga | ggcagacttc | cctcttgtcc | agcgtccatc | acgtacggga | gctcatacga | 1260 |
| cgagtccgca | aatatctgaa | ccgtgctggt | aaggttatta | gcgaccgtag | tctcgccgtt | 1320 |
| cgacgttgtg | acctccttaa | cttggatatt | gaagatttta | acgcgcatgg | cttttggtcg | 1380 |
| tagtccccag | ttgttgttga | tgagtctttg | ccagtcacgt | ggtgagaagt | gacagtggaa | 1440 |
| tctgttaaag | tcaaagtatc | cccagggggt | ggagaatccg | ttgtaggtgt | tgctgtttga | 1500 |
| tgttgttccg | agccgcaggt | acaagtggtt | gttgtaggtg | ggcaagaccc | aggttctggt | 1560 |
| cgaggttgtt | gtgaccttgc | cctcagacca | ggtggaatcg | caatgccaat | cacccgaggc | 1620 |
| attacccact | ccatcggaac | cttgtcccgc | atcgacagca | tttccgcccg | gtgctgcacg | 1680 |
| catttcaatg | tctgaagaca | tggcgctggt | atctgatcct | tcaggggggtc | cgtctccggc | 1740 |
| tccagtgtcc | tcttcaaagt | tgagtctctt | tttggctggt | tgtttgcctt | ttttgccgat | 1800 |
| tcctgaggag | gagtcgggct | cttgtggtga | ctctaacggt | ctcttctttc | caggagccgt | 1860 |
| cttagcacct | tcttcaacca | ggcccagagg | ttcgagtacc | ctcttcttgg | cctggaagac | 1920 |

```
tgctcgcccg aggttgcccc caaaagacgt atcttcttgc agacgctcct gaaactcggc    1980
gtcggcgtgg ttataccgca ggtacggatt gtcacccgct ttgagctgct ggtcgtaggc    2040
cttgtcgtgc tcgagggccg ctgcgtccgc cgcgttgacg ggctccccct tgtcgagtcc    2100
gttgaagggt ccgaggtact cgtagccagg aagcaccaga ccccggccgt cgtcctgctt    2160
ctgctggttg gccttgggct tggggctcc aggtttcagg tcccaccact cgcgaatgcc    2220
ctcagagagg ttgtcctcga gccaatctgg aagataaccg tcagcagcca tacctggttt    2280
aagtcattta ttgctcagaa acacagtcat ccaagtccac gttgacgaga tcgcaggccg    2340
aacacgcaat ctcgggtgcc cgccccagca gatgatgaat cgcgcacagt ttctgatacg    2400
tcttttttct gacgacgggt tgagattctg acgcgccggg aagcactct gagcagtctc    2460 tgacccgtg cgtgaagcag acgttgaaat tctgattcat tctctcgcat gtcttgcagg    2520
gaaacagcat ctgaagcatg cccgcgtgac gagaacattt gttttggtac ctgtccgcaa    2580
ggtccaccgg tgcttccgcg tctgacgtcg atggctccgc aactgagggg caggcccgct    2640
tgggctcgct tatatccgcg tcactggggg cgggtctttt ggtggctccg cccttcctga    2700
cgtagaactc atgcgccacc tcagtcacgt gatcctgagc ccagcggaag aactctttga    2760
cttcctgctt ggtcaccttg ccaaagtcgt gctccagacg gcgggtgagc tcgaacttga    2820
acatgcggtc ctgcagcggc tgctggtgct cgaaggtggt gctgttccg tcgatcacgg    2880 cgcacatgtt ggtgttggag gtgacgatca cgggcgtggg gtcgatctgg gccgatgact    2940 tgcactttg gtccacgcgc accttgcttc cgcccagaat ggccttggcg gactccacga    3000
ccttggcggt catcttgccc tcctcccacc agatcaccat cttgtcgacg caatcgttga    3060
agggaaagtt ctcattggtc cagttgacgc agcaagggcg aattc                   3105

<210> SEQ ID NO 22
<211> LENGTH: 3094
<212> TYPE: DNA
<213> ORGANISM: Unknown
<220> FEATURE:
<223> OTHER INFORMATION: AAV serotype, clone F1

<400> SEQUENCE: 22
gaattcgccc ttgctgcgtc aactggacca agagaacttt cccttcaacg attgcgtcga     60
caagatggtg atctggtggg aggagggcaa gatgacggcc aaggtcgtgg agtccgccaa    120
agccattctg ggcggaagca aggtgcgcgt cgaccaaaag tgcaagtcct cggcccagat    180
cgatcccacc cccgtgatcg tcacctccaa caccaacatg tgcgccgtga tcgacgggaa    240
cagcaccacc ttcgagcacc agcagccgtt gcaggaccgg atgttcaaat ttgaactcac    300
ccgccgtctg gaacacgact ttggcaaggt gaccaagcag gaagtcaaag agttcttccg    360
ctgggctagt gatcacgtga ctgaggtgac gcatgagttc tacgtcagaa agggcggagc    420
cagcaaaaga cccgcccccg atgacgcgga tataagcgag cccaagcggg cctgtccctc    480
agtcacggac ccatcgacgt cagacgcgga aggagctccg gtggactttg ccgacaggta    540
ccaaaacaaa tgttctcgtc acgcgggcat gcttcagatg ctgtttccct gcaaaacgtg    600
cgagagaatg aatcagaatt caacatttg cttcacgcac ggggtcagag actgtttaga    660
atgtttcccc ggcgtgtcag aatctcaacc ggtcgtcaga aaaagacgt atcggaagct    720 gtgtgcgatt catcatctgc tggggcgggc acccgagatt gcttgctcgg cctgcgacct    780
ggtcaacgtg gacctggacg actgtgtttc tgagcaataa atgacttaaa ccgggtatgg    840
ctgccgatgg ttatcttcca gattggctcg aggacaacct ctctgagggc attcgcgagt    900
```

```
ggtgggacct gaaacctgga gccccgaaac ccaaagccaa ccagcaaaag caggacgacg      960
gccggggtct ggtgcttcct ggctacaagt acctcggacc cttcaacgga ctcgacaagg     1020
gggagcccgt caacgcggcg gacgcagcgg ccctcgagca cgacaaggcc tacgaccagc     1080
agctcaaagc gggtgacaat ccgtacctgc ggtataacca cgccgacgcc gagtttcagg     1140
agcgtctgca agaagatacg tcatttgggg caacctcgg gcgagcagtc ttccaggcca      1200
agaagcgggt tctcgaacct ctcggtctgg ttgaggaagg cgctaagacg gctcctggaa     1260
agaagagacc catagactct ccagactcct ccacgggcat cggcaaaaaa ggccagcagc     1320
ccgctaaaaa gaagctcaat tttggtcaga ctggcgactc agagtcagtc cccgaccctc     1380
aacctcttgg agaacctcca gcagcgccct ctagtgtggg atctggtaca atggctgcag     1440
gcggtggcgc accaatggca gacaataacg aaggtgccga cggagtgggt aatgcctcag     1500
gaaattggca ttgcgattcc acatggctgg gcgacagagt catcaccacc agcaccagaa     1560
cctgggccct ccccacctac aacaaccacc tctacaagca aatctccagc agcagctcag     1620
gagccaccaa tgacaaccac tacttcggct acagcacccc ctgggggtat tttgacttta     1680
acagattcca ctgccacttc tcaccacgtg actggcagcg actcatcaac aacaactggg     1740
gattccggcc caagaagctg cggttcaagc tcttcaacat ccaggtcaag gaggtcacaa     1800
cgaatgacgg cgtcacgacc atcgctaata accttaccag cacggttcag gtcttctcgg     1860
actcggaata ccagctgccg tacgtcctcg gctctgcgca ccagggctgc ctgcctccgt     1920
tcccggcgga cgtcttcatg attcctcagt acggctacct gactctgaac aacggcagcc     1980
aatcggtggg ccgttcctcc ttctactgcc tggaatattt ccctctcaa atgctgagaa      2040 cgggcaacaa ctttgagttc agttacagct tcgaggacgt gcctttccac agcagctacg     2100
cgcacagcca gagcctagac cggctgatga accctctcat cgaccagtac ctgtactacc     2160
tggcccggac ccagagcacc acgggttcca cagggaact gcaatttcat caagctgggc      2220
ccaatactat ggccgagcag tcaaagaact ggctgcctgg accctgctat aggcaacagg     2280
gactgtcaaa gaacttggac tttaacaaca acagcaattt tgcctggact gctgccacta     2340
aatatcatct gaatggcaga aactctttga ccaatcctgg cattcccatg gcaaccaaca     2400
aggatgatga ggaccagttc tttcccatca acgggtact ggttttggc aagacgggag       2460 ctgccaacaa aactacgctg gaaaacgttc tgatgaccag cgaggaggag atcaagacca     2520
ctaaccctgt ggctacagaa gaatacggtg tggtctccag caacctgcag ccgtctacag     2580
ccgggcctca atcacagact atcaacagcc agggagcact gcctggcatg gtctggcaga     2640
accgggacgt gtatctgcag ggtcccatct gggccaaaat tcctcacacg gatggcaact     2700
ttcacccgtc tcctctgatg ggcggttttg gactcaaaca cccgcctcca cagatcctga     2760
tcaaaaacac acctgtacct gctaatcctc cggaggtgtt tactcctgcc aagtttgcct     2820
ccttcatcac gcagtacagc accggacaag tcagcgtgga aatcgagtgg gagctgcaga     2880
aagaaaacag caagcgctgg aacccagaaa ttcagtatac ttccaattat gccaagtcta     2940
ataatgttga atttgctgtg aaccctgatg gtgtttatac tgagcctcgc cccattggca     3000
ctcgttacct ccccgtaat ctgtaattgc ttgttaatca ataaaccggt tgattcgttt      3060
cagttgaact ttggtctctg cgaagggcga attc                                 3094
```

<210> SEQ ID NO 23
<211> LENGTH: 3095
<212> TYPE: DNA

```
<213> ORGANISM: Unknown
<220> FEATURE:
<223> OTHER INFORMATION: AAV serotype, clone F3

<400> SEQUENCE: 23
gaattcgccc ttcgcagaga ccaaagttca actgaaacga atcaaccggt ttattgatta      60
acaagcaatt acagattacg ggtgaggtaa cgagtgccaa tggggcgagg ctcagtataa     120
acaccatcag ggttcacagc aaattcaaca ttattagact tggcataatt ggaagtatac     180
tgaatttctg ggttccagcg cttgctgttt tctttctgca gctcccactc gatttccacg     240
ctgacttgtc cggtgctgta ctgcgtgatg aaggaggcaa acttggcagg agtaaacacc     300
tccggaggat tagcaggtac aggtgtgttt ttgatcagga tctgtggagg cgggtgtttg     360
agtccaaaac cgcccatcag aggagacggg tgaaagttgc catccgtgtg aggaattttg     420
gcccagatgg gaccctgcag atacacgtcc cggttctgcc agaccatgcc aggcagtgct     480
ccctggctgt tgatagtctg tgattgaggc ccggctgtag acgactgcag gttgctggag     540
accacaccgt attcttctgt agccacaggg ttagtggtct tgatctcctc ctcgctggtc     600
atcagaacgt tttccagcgt agttttgttg gcagctcccg tcttgccaaa aaccagtacc     660
ccgttgatgg gaaagaactg gtcctcatca tccttgttgg ttgccatggg aatgccagga     720
ttggtcaaag agtttctgcc attcagatga tatttagtgg cagcagtcca ggcaaaattg     780
ctgttgttgt taaagtccaa gttctttgac agtctctgtt gcctatagca gggtccaggc     840
agccagttct ttgactgctc ggccatagta ttgggcccag cttgatgaaa ttgcagttcc     900
ctggtggaac ccgtggtgct ctgggtccgg gccaggtagt acaggtactg gtcgatgaga     960
gggttcatca gccggtctag gctctggctg tgcgcgtagc tgctgtggaa aggcacgtcc    1020
tcgaagctgt aactgaactc aaagttgttg cccgttctca gcatttgaga ggggaaatat    1080
tccaggcagt agaaggagga acggcccacc gattggctgc cgttgtccag agtcaggtag    1140
ccgtactgag gaatcatgaa gacgtccgcc gggaacggag gcaggcagcc ctggtgcgca    1200
gagccgagga cgtacggcag ctggtattcc gagtccgaga agacctgaac cgtgctggta    1260
aggttattag cgatggtcgt gacgccgtca ttcgttgtga cctccttgac ctggatgttg    1320
aggagcttga accgcagctt cttgggccgg aatccccagt tgttgttgat gagtcgctgc    1380
cagtcacgtg gtgagaagtg gcagtggaat ctgttaaagt caaaataccc caggggggtg    1440
ctgtagccga agtagtggtt gtcattggtg gctcctgagc tgctgctgga gatttgcttg    1500
tagaggtggt tgttgtaggt ggggagggcc caggttctgg tgctggtggt gatgactctg    1560
tcgcccagcc atgtggaatc gcaatgccaa tttcctgagg cattacccac tccgtcggca    1620
ccttcgttat tgtctgccat tggtgcgcca ccgcctgcag ccattgtacc agatcccaca    1680
ctagagggcg ctgctggagg ttctccaaga ggttgagggt cggggactga ctctgagtcg    1740
ccagtctgac caaaattgag cttctttta gcgggctgct ggcctttttt gccgatgccc    1800
gtggaggagt ctggagagcc tatgggtctc ttctttccag gagccgtctt agccgcttcc    1860
tcaaccagac cgagaggttc gagaacccgc ttcttggcct ggaagactgc tcgcccgagg    1920
ttgcccccaa atgacgtatc ttcttgcaga cgctcctgaa actcggcgtc ggcgtggtta    1980
taccgcaggt acggattgtc acccgctttg agctgctggt cgtaggcctt gtcgtgctcg    2040
agggccgctg cgtccgccgc gttgacgggc tccccttgt cgagtccgtt gaagggtccg    2100
aggtacttgt agccaggaag caccagaccc cggccgtcgt cctgcttttg ctggttggct    2160
ttgggtttcg gggctccagg tttcaggtcc caccactcgc gaatgccctc agagaggttg    2220
```

-continued

```
tcctcgagcc aatctggaag ataaccatcg gcagccatac ctggtttaag tcatttattg    2280
ctcagaaaca cagtcgtcca ggtccacgtt gaccaggtcg caggccgagc aagcaatctc    2340
gggtgcccgc cccagcagat gatgaatcgc acacagcttc cgatacgtct tttttctgac    2400
gaccggttga gattctgaca cgccggggaa acattctaaa cagtctctga ccccgtgcgt    2460
gaagcaaatg ttgaaattct gattcattct ctcgcacgtt ttgcagggaa acagcacctg    2520
aagcatgccc gcgtgacgag aacatttgtt ttggtacctg tcggcaaagt ccaccggagc    2580
tccttccgcg tctgacgtcg atgggtccgt gactgaggga cgggcccgct tgggctcgct    2640
tatatccgcg tcatcggggg cgggtctttt gctggctccg ccctttctga cgtagaactc    2700
atgcgtcacc tcagtcacgt gatcactagc ccagcggaag aactctttga cttcctgctt    2760
tgtcaccttg ccaaagtcgt gttccagacg gcgggtgagt tcaaatttga acatccggtc    2820
ctgcaacggt tgctggtgct cgaaggtggt gctgttcccg tcgatcacgg cgcacatgtt    2880
ggtgttggag gtgacgatca cggggtgggg atcgatctgg gcggacgact tgcacttttg    2940
gtccacgcgc accttgctgc cgccgagaat ggccttggcg gactccacga ccttggccgt    3000
catcttgccc tcctcccacc agatcaccat cttgtcgacg caatcgttga agggaaagtt    3060
ctcattggtc cagttgacgc agcaagggcg aattc                              3095
```

<210> SEQ ID NO 24
<211> LENGTH: 3095
<212> TYPE: DNA
<213> ORGANISM: Unknown
<220> FEATURE:
<223> OTHER INFORMATION: AAV serotype, clone F5

<400> SEQUENCE: 24

```
gaattcgccc ttcgcagaga ccaaagttca actgaaacga atcaaccggt ttattgatta      60
acaagcaatt acagattacg ggtgaggtaa cgagtgccaa tggggcgagg ctcagtataa     120
acaccatcag ggttcacagc aaattcaaca ttattagact tggcataatt ggaagtatac     180
tgaatttctg ggttccagcg cttgctgttt tctttctgca gctcccactc gatttccacg     240
ctgacttgtc cggtgctgta ctgcgtgatg aaggaggcaa acttggcagg agtaaacacc     300
tccggaggat tagcaggtac aggtgtgttt ttgatcagga tctgtggagg cgggtgttcg     360
agtccaaaac cgcccatcag aggagacggg tgaaagttgc catccgtgtg aggaattttg     420
gcccagatgg gaccctgcag atacacgtcc cggttctgcc agaccatgcc aggcagtgct     480
ccctggctgt tgatagtctg tgattgaggc ccggctgtag acgactgcag gttgctggag     540
accacaccgt attcttctgt agccacaggg ttagtggtct tgatctcctc ctcgctggtc     600
atcagaacgt tttccagcgt agttttgttg gcagctcccg tcttgccaaa accagtacc     660
ccgttgatgg gaaagaactg gtcctcatca tccttgttgg ttgccatggg aatgccagga    720
ttggtcaaag agtttctgcc attcagatga tatttagtgg cagcagtcca ggcaaaattg    780
ctgttgttgt taaagtccaa gttctttgac agtctctgtt gcctatagca gggtccaggc    840
agccagttct ttgactgctc ggccatagta ttgggcccag cttgatgaaa ttgcagttcc    900
ctggtggaac ccgtggtgct ctgggtccgg gccaggtagt acaggtactg gtcgatgaga    960
gggttcatca gccggtctag gctctggctg tgcgcgtagc tgctgtggaa aggcacgtcc   1020
tcgaagctgt aactgaactc aaagttgttg cccgttctca gcatttgaga ggggaaatat   1080
tccaggcagt agaaggagga acggcccacc gattggctgc cgttgttcag agtcaggtag   1140
```

```
ccgtactgag gaatcatgaa gacgtccgcc gggaacggag gcaggcagcc ctggtgcgca      1200
gagccgagga cgtacggcag ctggtattcc gagtccgaga agacctgaac cgtgctggta      1260
aggttattag cgatggtcgt gacgccgtca ttcgttgtga cctccttgac ctggatgttg      1320
aagagcttga accgcagctt cttgggccgg aatccccagt tgttgttgat gagtcgctgc      1380
cagtcacgtg gtgagaagtg gcagtggaat ctgttaaagt caaaataccc ccaggggtg       1440 ctgtagccga agtagtggtt gtcattggtg gctcctgagc tgctgctgga gatttgcttg      1500
tagaggtggt tgttgtaggt ggggagggcc caggttctgg tgctggtggt gatgactctg      1560
tcgcccagcc atgtggaatc gcaatgccaa tttcctgagg cattacccac tccgtcggca      1620
ccttcgttat tgtctgccgt tggtgcgcca ccgcctgcag ccattgtacc agatcccaca      1680
ctagagggcg ctgctggagg ttctccaaga ggttgagggt cggggactga ctctgagtcg      1740
ccagtctgac caaaattgag cttcttttta gcgggctgct ggcctttttt gccgatgccc      1800
gtggaggagt ctggagagtc tatgggtctc ttctttccag gagccgtctt agcgccttcc      1860
tcaaccagac cgagaggttc gagaacccgc ttcttggcct ggaagactgc tcgcccgagg      1920
ttgcccccaa atgacgtatc ttcttgcagg cgctcctgaa actcggcgtc ggcgtggtta      1980
taccgcaggt acgattgtc acccgctttg agctgctggt cgtaggcctt gtcgtgctcg       2040
agggccgctg cgtccgccgc gttgacgggc tccccttgt cgagtccgtt gaagggtccg       2100
aggtacttgt agccaggaag caccagaccc cggccgtcgt cctgcttttg ctggttggct      2160
ttgggtttcg gggctccagg tttcaggtcc caccactcgc gaatgccctc agagaggttg      2220
tcctcgagcc aatctggaag ataaccatcg gcagccatac ctggtttaag ccatttattg      2280
ctcagaaaca cagtcgtcca ggtccacgtt gaccaggtcg caggccgagc aggcaatctc      2340
gggtgcccgc cccagcagat gatgaatcgc acacagcttc cgatacgtct tttttctgac      2400
gaccggttga gattctgaca cgccggggaa acattctaaa cagtctctga ccccgtgcgt      2460
gaagcaaatg ttgaaattct gattcattct ctcgcacgtt ttgcagggaa acagcatctg      2520
aagcatgccc gcgtggcgag aacatttgtt ttggtacctg tcggcaaagt ccaccggagc      2580
tccttccgcg tctgacgtcg atgggtccgt gactgaggga caggcccgct tgggctcgct      2640
tatatccgcg tcatcggggg cgggtctttt gctggctccg ccctttctga cgtagaactc      2700
atgcgtcacc tcagtcacgt gatcactagc ccagcggaag aactctttga cttcctgctt      2760
tgtcaccttg ccaaagtcgt gttccagacg gcgggtgagt tcaaatttga acatccggtc      2820
ctgcaacggc tgctggtgct cgaaggtggt gctgttcccg tcgatcacgg cgcgcatgtt      2880
ggtgttggag gtgacgatca cggggggtggg atcgatctgg gcggacgact tgcacttttg      2940
gtccacgcgc accttgctgc cgccgagaat ggccttggcg gactccacga ccttggccgt      3000
catcttgccc tcctcccacc agatcaccat cttgtcgacg caatcgttga agggaaagtt      3060
ctcattggtc cagttgacgc agcaagggcg aattc                                 3095
```

<210> SEQ ID NO 25
<211> LENGTH: 3142
<212> TYPE: DNA
<213> ORGANISM: Unknown
<220> FEATURE:
<223> OTHER INFORMATION: AAV serotype, clone H6

<400> SEQUENCE: 25

```
aaaacgacgg ccagtgtgatt gtaatacgac tcactatagg gcgaaattga aattagcggc       60
cgcgaattcg cctttcgcag agaccaaagt tcaactgaaa cgaattaaac ggtttattga      120
```

-continued

```
ttaacaagca attacagatt acgagtcagg tatctggtgc caatggggcg aggctctgaa      180
tacacaccat tagtgtccac agtaaagtcc acattaacag acttgttgta gttggaagtg      240
tactgaattt cgggattcca gcgtttgctg ttctccttct gcagctccca ctcgatctcc      300
acgctgacct gtcccgtgga atactgtgtg atgaaagaag caaacttggc agaactgaag      360
tttgtgggag gattggctgg aacgggagtg ttttttgatca tgatctgagg aggcgggtgt     420
ttgagtccaa aacctcccat cagtggagaa ggatgaaagt gtccatcggt gtgaggaatc      480
ttggcccaaa tgggtccctg caggtacacg tctcgatcct gccacaccat accaggtaac      540
gctccttggt gattgacagt tccagtagtt ggaccagtgt ttgagttttg caaattattt      600
gacacagtcc cgtactgctc cgtagccacg ggattggtgg ccctgatttc ttcttcatct      660
gtaatcatga cattttccaa atccgcgtcg ttggcatttg ttccttgttt accaaatatc      720
agggttccat gcatggggaa aaacttttct tcgtcatcct tgtgactggc catagctggt      780
cctggattaa ccaacgagtc ccggccattt agatgatact ttgtagctgc agtccaggga     840
aagttgctgt tgttgttgtc gttgtgcctgt tttgacagac gctgctgtct gtagcaaggt    900
ccaggcagcc agttttttagc ttgaagagac atgttggttg gtccagcttg gctaaacagt   960
agccgagact gctgaagagt tccactattt gtttgtgtct tgttcagata atacaggtac    1020
tggtcgatca gaggattcat cagccgatcc agactctggc tgtgagcgta gctgctgtgg   1080
aaaggcacgt cttcaaaagt gtagctgaac tgaaagttgt ttccagtacg cagcatctga    1140
gaaggaaagt actccaggca gtaaaaggaa gagcgtccta ccgcctgact cccgttgttc    1200
agggtgaggt atccatactg tgggaccatg aagacgtccg ctggaaacgg cgggaggcat    1260
ccttgatgcg ccgagcccag gacgtacggg agctggtact ccgagtcagt aaacacctga    1320
accgtgctgg taaggttatt ggcaatcgtc gtcgtaccgt cattctgcgt gacctctttg    1380
acttgaatat taaagagctt gaagttgagt cttttgggcc ggaatccccg gttgttgttg    1440
acgagtcttt gccagtcacg tggtgaaaag tggcagtgga atctgttgaa gtcaaaatac    1500 ccccagggg tgctgtagcc aaagtagtgg ttgtcgttgc tggctcctga ttggctggag     1560
atttgcttgt agaggtggtt gttgtatgtg ggcagggccc aggttcgggt gctggtggtg    1620
atgactctgt cgcccagcca ttgggaatcg caatgccaat ttcctgagga attacccact    1680
ccatcggcac cctcgttatt gtctgccatt ggtgcgccac tgcctgtagc cattgtagta    1740
gatcccagac cagaggggc tgctggtggc tgtccgagag gctgggggtc aggtacggag     1800
tctgcgtctc cagtctgacc aaaatttaat cttttttcttg caggctgctg gcccgctttt   1860
ccggttcccg aggaggagtc tggctccaca ggagagtgct ctaccggcct ctttttttccc   1920 ggagccgtct taacaggctc ctcaaccagg cccagaggtt caagaaccct ctttttcgcc    1980
tggaagactg ctcgtccgag gttgccccca aaagacgtat cttctttaag gcgctcctga    2040
aactctgcgt cggcgtggtt gtacttgagg tacgggttgt ctccgctgtc gagctgccgg    2100
tcgtaggcct tgtcgtgctc gagggccgcg gcgtctgcct cgttgaccgg ctccccttg     2160 tcgagtccgt tgaagggtcc gaggtacttg tacccaggaa gcacaagacc cctgctgtcg    2220
tccttatgcc gctctgcggg ctttggtggt ggtgggccag gtttgagctt ccaccactgt    2280
cttattcctt cagagagagt gtcctcgagc caatctggaa gataaccatc ggcagccata    2340
cctgatttaa atcatttatt gttcagagat gcagtcatcc aaatccacat tgaccagatc    2400
gcaggcagtg caagcgtctg gcacctttcc catgatatga tgaatgtagc acagtttctg    2460
```

```
atacgccttt ttgacgacag aaacggggttg agattctgac acgggaaagc actctaaaca    2520
gtctttctgt ccgtgagtga agcagatatt tgaattctga ttcattctct cgcattgtct    2580
gcagggaaac agcatcagat tcatgcccac gtgacgagaa catttgtttt ggtacctgtc    2640
cgcgtagttg atcgaagctt ccgcgtctga cgtcgatggc tgcgcaactg actcgcgcgc    2700
ccgtttgggc tcacttatat ctgcgtcact gggggcgggt cttttcttag ctccacccct   2760
tttgacgtag aattcatgct ccacctcaac acgtgatcc tttgcccacc ggaaaaagtc    2820
tttcacttcc tgcttggtga cctttccaaa gtcatgatcc agacggcggg taagttcaaa    2880
tttgaacatc cggtcttgca acggctgctg gtgctcgaag gtcgttgagt tcccgtcaat    2940
cacggcgcac atgttggtgt tggaggtgac gatcacggga gtcgggtcta tctgggccga    3000
ggacttgcat ttctggtcca cacgcacctt gcttcctcca agaatggctt tggccgactc    3060
cacgaccttg gcggtcatct tccccttcctc ccaccagatc accatcttgt cgacgcaatg    3120
gtaaaaggaa agttctcatt gg                                              3142
```

<210> SEQ ID NO 26
<211> LENGTH: 3075
<212> TYPE: DNA
<213> ORGANISM: Unknown
<220> FEATURE:
<223> OTHER INFORMATION: AAV serotype, clone H2

<400> SEQUENCE: 26

```
tgagaacttt cctttcaacg attgcgtcgg acaagatggt gatctggtgg gaggagggga      60
agatgaccgc caaggtcgtg gagtcggcca aagccattct tggaggaagc aaggtgcgtg    120
tggaccagaa atgcaagtcc tcggcccaga tagacccgac tcccgtgatc gtcacctcca    180
acaccaacat gtgcgccgtg attgacggga actcaacgac cttcgagcac cagcagccgt    240
tgcaagaccg gatgttcaaa tttgaactta cccgccgtct ggatcatgac tttggaaagg    300
tcaccaagca ggaagtgaaa gactttttcc ggtgggcaaa ggatcacgtg gttgaggtgg    360
agcatgaatt ctacgtcaaa aagggtggag ctaagaaaag acccgccccc agtgacgcag    420
atataagtga gcccaaacgg gcgcgcgagt cagttgcgca gccatcaacg tcagacgcgg    480
aagcttcgat caactacgcg gacaggtacc aaaaacaaat gttctcgtca cgtgggcatg    540
aatctgatgc tgtttccctg cagacaatgc gagagaatga atcagaattc aaatatctgc    600
ttcactcacg gacagaaaga ctgtttagag tgctttcccg tgtcagaatc tcaacccgtt    660
tctgtcgtca aaaaggcgta tcagaaactg tgctacattc atcatatcat gggaaaggtg    720
ccagacgctt gcactgcctg cgatctggtc aatgtggatt tggatgactg catctctgaa    780
caataaatga tttaaatcag gtatggctgc cgatggttat cctccagatt ggctcgagga    840
cactctctct gaagggataa acagtggtg gaagctcaaa cctggcccac caccaaaa      900 gcccgcagag cggcataagg acgacagcag gggtcttgtg cttcctgggt acaagtacct    960
cggacccttc aacggactcg acaaggggga gccggtcaac gaggcagacg ccgcggccct   1020
cgagcacgac aaggcctacg accggcagct cgacagcgga gacaacccgt acctcaagta   1080
caaccacgcc gacgcagagt ttcaggagcg ccttaaagaa gatacgtctt tgggggcaa    1140 cctcggacga gcagtcttcc aggcgaaaaa gagggttctt gaacctctgg gcctggttga   1200
ggaacctgtt aagacggctc cgggaaaaaa gaggccggta gagcactctc tgtggagcc    1260 agactcctcc tcgggaaccg gaaagcgggg ccagcggcct gcaagaaaaa gattaaattt   1320
tggtcagact ggagacgcag actccgtacc tgaccccccag cctctcggac agccaccagc    1380
```

```
agcccctct ggtctgggat ctactacaat ggctacaggc agtggcgcac caatggcaga    1440
caataacgag ggtgccgatg gagtgggtaa ttcctcagga aattggcatt gcgattccca    1500
atggctgggc gacagagtca tcaccaccag cacccgaacc tgggccctgc ccacatacaa    1560
caaccacctc tacaagcaaa tctccagcca atcaggagcc agcaacgaca accactactt    1620
tggctacagc accccctggg ggtatttga cttcaacaga ttccactgcc acttttcacc    1680
acgtgactgg caaagactca tcaacaacaa ctggggattc cggcccaaaa gactcaactt    1740
caagctcttt aatattcaag tcaaagaggt cacgcagaat gacggtacga cgacgattgc    1800
caataacctt accagcacgg ttcaggtgtt tactgactcg gagtaccagc tcccgtacgt    1860
cctgggctcg gcgcatcaag gatgcctccc gccgtttcca gcggacgtct catggtccc    1920 acagtatgga tacctcaccc tgaacaacgg gagtcaggcg gtaggacgct cttccttta    1980 ctgcctggag tactttcctt ctcagatgct gcgtactgga aacaactttc agttcagcta    2040
cacttttgaa gacgtgcctt tccacagcag ctacgctcac agccagagtc tggatcggct    2100
gatgaatcct ctgatcgacc agtacctgta ttatctgaac aagacacaaa caaatagtgg    2160
aactcttcag cagtctcggc tactgtttag ccaagctgga ccaaccaaca tgtctcttca    2220
agctaaaaac tggctgcctg gaccttgcta cagacagcag cgtctgtcaa acaggcaaa    2280 cgacaacaac aacagcaact ttccctggac tgcagctaca aagtatcatc taaatggccg    2340
ggactcgttg gttaatccag accagctat ggccagtcac aaggatgacg aagaaaagtt    2400 tttcccatg catggaaccc tgatatttgg taaacaagga acaaatgcca acgacgcgga    2460
tttggaaaat gtcatgatta cagatgaaga agaaatcagg gccaccaatc ccgtggctac    2520
ggagcagtac gggactgtgt caaataattt gcaaaactca aacactggtc caactactgg    2580
aactgtcaat cgccaaggag cgttacctgg tatggtgtgg caggatcgag acgtgtacct    2640
gcagggaccc atttgggcca agattcctca caccgatgga cactttcatc cttctccact    2700
gatgggaggt tttggactca acaacccgcc tcctcagatc atgatcaaaa acactcccgt    2760
tccagccaat cctcccacaa acttcagttc tgccaagttt gcttctttca tcacacagta    2820
ttccacggga caggtcagcg tggagatcga gtgggagctg cagaaggaga acagcaaacg    2880
ctggaatccc gaaattcagt acacttccaa ctacaacaag tctgttaatg tggactttac    2940
tgtggacact aatggtgtgt attcagagcc tcgccccatt ggcaccagat acctgactcg    3000
taatctgtaa ttgcttgtta atcaataaac cgtttaattc gtttcagttg aactttggtc    3060
tctgcgaagg gcgaa                                                    3075
```

<210> SEQ ID NO 27
<211> LENGTH: 3128
<212> TYPE: DNA
<213> ORGANISM: Unknown
<220> FEATURE:
<223> OTHER INFORMATION: AAV serotype, clone 42.8

<400> SEQUENCE: 27

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tccaccccc gtgatcgtca cttccaacac caacatgtgc gccgtgattg     240
acgggaacag caccaccttc gagcaccagc agccgttaca agaccggatg ttcaaatttg     300
```

```
aactcacccg ccgtctggag cacgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gccccgatg acgcggataa aagcgagccc aagcgggcct    480 gccctcagt cgcggatcca tcgacgtcag acgcggaagg agctccggtg gactttgccg    540
acaggtacca aaacaaatgt tctcgtcacg cgggcatgct tcagatgctg tttcctgca    600 agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctag ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca aagccaacca gcaaaagcag    960
gacgacggcc ggggtctggt gcttcctggc tacaagtacc tcggacccct caacggactc   1020 gacaagggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctgaaagag agaccggt agagccatca ccccagcgtt ctccagactc ctctacgggc   1320
atcggcaaga caggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca cgggacatc gggaggaagc accaacgaca cacctactt cggctacagc   1680 acccctggg ggtatttga ctttaacaga ttccactgcc acttctcacc acgtgactgg   1740
cagcgactca tcaacaacaa ctggggattc cggcccaaga gactcaactt caagctcttc   1800
aacatccagg tcaaggaggt cacgcagaat gaaggcacca agaccatcgc caataacctt   1860
accagcacga ttcaggtctt tacggactcg gaataccagc tcccgtacgt cctcggctct   1920
gcgcaccagg gctgcctgcc tccgttcccg gcggacgtct tcatgattcc tcagtacggg   1980
tacctgactc tgaacaacgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gatgaacccc   2160
ctcatcgacc agtacctgta ctacctgtct cggactcagt ccacgggagg taccgcagga   2220
actcagcagt tgctattttc tcaggccggg cctaataaca tgtcggctca ggccaaaaac   2280
tggctacccg ggcctgcta ccggcagcaa cgcgtctcca cgacactgtc gcaaaataac   2340
aacagcaact tgcttggac cggtgccacc aagtatcatc tgaatggcag agactctctg   2400 gtaaatccg tgtcgctat ggcaacgcac aaggacgacg aagagcgatt ttttccatcc   2460
agcggagtct tgatgtttgg gaaacaggga gctggaaaag acaacgtgga ctatagcagc   2520
gttatgctaa ccagtgagga agaaatcaaa accaccaacc cagtggccac agaacagtac   2580
ggcgtggtgc ccgataacct gcaacagcaa aacgccgctc ctattgtagg ggccgtcaac   2640
agtcaaggag ccttacctgg catggtctgg cagaaccggg acgtgtacct gcagggtcct   2700
```

-continued

| | |
|---|---|
| atctgggcca agattcctca cacggacggc aactttcatc cttcgccgct gatgggaggc | 2760 |
| tttggactga aacacccgcc tcctcagatc ctgattaaga atacacctgt tcccgcggat | 2820 |
| cctccaacta ccttcagtca agccaagctg gcgtcgttca tcacgcagta cagcaccgga | 2880 |
| caggtcagcg tggaaattga atgggagctg cagaaagaga cagcaagcg ctggaaccca | 2940 |
| gagattcagt atacttccaa ctactacaaa tctacaaatg tggactttgc tgtcaatact | 3000 |
| gagggtactt attcagagcc tcgccccatt ggcacccgtt acctcacccg taacctgtaa | 3060 |
| ttgcctgtta atcaataaac cggctaattc gtttcagttg aactttggtc tctgcgaagg | 3120 |
| gcgaattc | 3128 |

<210> SEQ ID NO 28
<211> LENGTH: 3128
<212> TYPE: DNA
<213> ORGANISM: Unknown
<220> FEATURE:
<223> OTHER INFORMATION: AAV serotype, clone 42.15

<400> SEQUENCE: 28

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgcgtgga ccaaaagtgc aagtcgtccg | 180 |
| cccagatcga ccccaccccc gtgatcgtca cctccaacac caacatgtgc gccgtgattg | 240 |
| acgggaacag caccaccttc gagcaccagc agccgttgca ggaccggatg ttcaaatttg | 300 |
| aactcacccg ccgtctggag catgactttg gcaaggtgac aaagcaggaa gtcaaagagt | 360 |
| tcttccgctg ggcgcaggat cacgtgaccg aggtggcgca tgagttctac gtcagaaagg | 420 |
| gtggagccaa caagagaccc gccccgatg acgcggataa aagcgagccc aagcgggcct | 480 |
| gcccctcagt cgcggatcca tcgacgtcag acgcggaagg agctccggtg gactttgccg | 540 |
| acaggtacca aaacaaatgt tctcgtcacg cgggcatgct tcagatgctg tttccctgca | 600 |
| agacatgcga gagaatgaat cagaatttca acatttgctt cacgcgcggg accagagact | 660 |
| gttcagaatg tttcccgggc gtgtcagaat ctcaaccggt cgtcagaaag aggacgtatc | 720 |
| ggaaactctg tgccattcat catctgctgg ggcgggctcc cgagattgct tgctcggcct | 780 |
| gcgatctggt caacgtggac ctggatgact gtgtttctga gcaataaatg acttaaacca | 840 |
| ggtatggctg ccgatggtta tcttccagat tggctcgagg acaacctctc tgagggcatt | 900 |
| cgcgagtggt gggactgaa acctggagcc ccgaaaccca agccaaccca gcaaaagcag | 960 |
| gacgacggcc ggggtctggt gcttcctggc tacaagtacc tcggaccctt caacggactc | 1020 |
| gacaagggg agcccgtcaa cgcggcggac gcagcggccc tcgagcacga caaggcctac | 1080 |
| gaccagcagc tcaaagcggg tgacaatccg tacctgcggt ataaccacgc cgacgccgag | 1140 |
| tttcaggagc gtctgcaaga agatacgtct tttgggggca acctcgggcg agcagtcttc | 1200 |
| caggccaaga agcgggttct cgaacctctc ggtctggttg aggaaggcgc taagacggct | 1260 |
| cctggaaaga gagaccggt agagccatca ccccagcgtt ctccagactc ctctacgggc | 1320 |
| atcggcaaga caggccagca gcccgcgaaa aagagactca actttgggca gactggcgac | 1380 |
| tcagagtcag tgcccgaccc tcaaccaatc ggagaacccc ccgcaggccc ctctggtctg | 1440 |
| ggatctggta caatggctgc aggcggtggc gctccaatgg cagacaataa cgaaggcgcc | 1500 |
| gacggagtgg gtagttcctc aggaaattgg cattgcgatt ccacatggct gggcgacaga | 1560 |

-continued

| | |
|---|---|
| gtcatcacca ccagcacccg aacctgggcc ctccccacct acaacaacca cctctacaag | 1620 |
| caaatctcca acgggacatc gggaggaagc accaacgaca cacctactt cggctacagc | 1680 |
| acccccotggg ggtatttga ctttaacaga ttccactgcc acttctcacc acgtgactgg | 1740 |
| cagcgactca tcaacaacaa ctggggattc cggcccaaga gactcaactt caagctcttc | 1800 |
| aacatccagg tcaaggaggt cacgcagaat gaaggcacca agaccatcgc caataacctt | 1860 |
| accagcacga ttcaggtctt tacgactcg gaataccagc tcccgtacgt cctcggctct | 1920 |
| gcgcaccagg gctgcccgcc tccgttcccg gcggacgtct tcatgattcc tcagtacggg | 1980 |
| tacctgactc tgaacaacgg cagtcaggcc gtgggccgtt cctccttcta ctgcctggag | 2040 |
| tactttcctt ctcaaatgcg gagaacgggc aacaactttg agttcagcta ccagtttgag | 2100 |
| gacgtgcctt ttcacagcag ctacgcgcat agccaaagcc tggaccggct gatgaacccc | 2160 |
| ctcatcgacc agtacctgta ctacctgtct cggactcagt ccacgggagg taccgcagga | 2220 |
| actcagcagt gctatttttc tcaggccggg cctaataaca tgtcggctca ggccaaaaac | 2280 |
| tggctacccg ggccctgcta ccggcagcaa cgcgtctcca cgacactgtc gcaaaataac | 2340 |
| aacagcaact tgcttggac cggtgccacc aagtatcatc tgaatggcag agactctctg | 2400 |
| gtaaatcccg gtgtcgctat ggcaacgcac aaggacgacg aagagcgatt ttttccatcc | 2460 |
| agcggagtct tgatgttttgg gaaacaggga gctggaaaag acaacgtgga ctatagcagc | 2520 |
| gttatgctaa ccagtgagga gaaaatcaaa accaccaacc cagtggccac agaacagtac | 2580 |
| ggcgtggtgg ccgataacct gcaacagcaa aacgccgctc ctattgtagg ggccgtcaac | 2640 |
| agtcaaggag ccttacctgg catggtctgg cagaaccggg acgtgtacct gcagggtcct | 2700 |
| atctgggcca agattcctca cacggacggc aactttcatc cttcgccgct gatgggaggc | 2760 |
| tttggactga aacacccgcc tcctcagatc ctgattaaga atacacctgt tcccgcggat | 2820 |
| cctccaacta ccttcagtca agccaagctg cgtcgttca tcacgcagta cagcaccgga | 2880 |
| caggtcagcg tggaaattga atgggagctg cagaaagaga cagcaagcg ctggaaccca | 2940 |
| gagattcagt atacttccaa ctactacaaa tctacaaatg tggactttgc tgtcaatact | 3000 |
| gagggtactt attcagagcc tcgccccatt ggcacccgtt acctcacccg taacctgtaa | 3060 |
| ttgcctgtta atcaataaac cggttaattc gtttcagttg aactttggtc tctgcgaagg | 3120 |
| gcgaattc | 3128 |

<210> SEQ ID NO 29
<211> LENGTH: 3197
<212> TYPE: DNA
<213> ORGANISM: Unknown
<220> FEATURE:
<223> OTHER INFORMATION: AAV serotype. clone 42.5b

<400> SEQUENCE: 29

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgcgtgga ccaaaagtgc aagtcgtccg | 180 |
| cccagatcga ccccacccc gtgatcgtca cctccaacac caacatgtgc gccgtgattg | 240 |
| acgggaacag caccaccttc gagcaccagc agccgttaca agaccggatg ttcaaatttg | 300 |
| aactcacccg ccgtctggag cacgactttg gcaaggtgac aaagcaggaa gtcaaagagt | 360 |
| tcttccgctg gcgcaggat cacgtgaccg aggtggcgca tgagttctac gtcagaaagg | 420 |
| gtggagccaa caagagaccc gccccgatg acgcggataa aagcgagccc aagcgggcct | 480 |

```
gcccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat ggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggacccgt caacggactc   1020
gacaagggag agccggtcaa cgaggcagac gccgcggccc tcgagcacga caaggcctac   1080
gacaagcagc tcgagcaggg ggacaacccg tacctcaagt acaaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagccatca ccccagcgtt ctccagactc tctacgggc   1320 atcggcaaga caggccagca gcccgcgaaa aagagactca actttgggca gactggcgac   1380
tcagagtcag tgcccgaccc tcaaccaatc ggagaacccc cgcaggccc ctctggtctg   1440 ggatctggta caatggctgc aggcggtggc gctccaatgg cagacaataa cgaaggcgcc   1500
gacgagtggg tagttcctc aggaaattgg cattgcgatt ccacatggct gggcgacaga   1560
gtcatcacca ccagcacccg aacctgggcc ctccccacct acaacaacca cctctacaag   1620
caaatctcca acgggacatc gggaggaagc accaacgaca cacctactt cggctacagc   1680 accccctggg ggtattttga ctttaacaga ttccactgcc acttctcacc acgtgactgg   1740
cagcgactca tcaacaacaa ctggggattc cgcccaagga gactcaactt caagctcttc   1800
aacatccagg tcaaggaggt cacgcagaat gaaggcacca agaccatcgc caataacctt   1860
accagcacga ttcaggtctt tacgactcg gaataccagc tcccgtacgt cctcggctct   1920
gcgcaccagg gctgcctgcc tccgttcccg gcggacgtct tcatgattcc tcagtacggg   1980
tacctgactc tgaacaacgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gatgaacccc   2160
ctcatcgacc agtacctgta ctacctgtct cggactcagt ccacgggagg taccgcagga   2220
actcagcagt tgctattttc tcaggccggg cctaataaca tgtcggctca ggccaaaaac   2280
tggctacccg gcccctgcta ccggcagcaa cgcgtctcca cgacactgtc gcaaaataac   2340
aacagcaact tgcttggac cggtgccacc aagtatcatc tgaatggcag agactctctg   2400
gtaaatcccg gtgtcgctat ggcaacgcac aaggacgacg aagagcgatt ttttccatcc   2460
agcggagtct tgatgtttgg aaacaggga gctggaaaag acaacgtgga ctatagcagc   2520
gttatgctaa ccagtgagga agaaatcaaa accaccaacc cagtggccac agaacagtac   2580
ggcgtggtgg ccgataacct gcaacagcaa acgccgctc ctattgtagg ggccgtcaac   2640
agtcaaggag ccttacctgg catggtctgg cagaaccggg acgtgtacct gcagggtcct   2700
atctgggcca agattcctca cacggacggc aactttcatc cttcgccgct gatgggaggc   2760
tttggactga aacacccgcc tcctcagatc ctgattaaga atacacctgt tccgcggat   2820
```

```
cctccaacta ccttcagtca agccaagctg gcgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgcccatt ggcacccgtt acctcacccg taacctgtaa     3060
ttgcctgtta atcaataaac cggttaattc gtttcagttg aactttggtc tctgcgaagg    3120
gcgaattcgt ttaaacctgc aggactagtc cctttagtga gggttaattc tgagcttggc    3180
gtaatcatgg gtcatag                                                   3197
```

<210> SEQ ID NO 30
<211> LENGTH: 2501
<212> TYPE: DNA
<213> ORGANISM: Unknown
<220> FEATURE:
<223> OTHER INFORMATION: AAV serotype, clone 42.1b

<400> SEQUENCE: 30

```
gaattcgccc ttggctgcgt caactggacc aatgagaact tcccttcaa cgattgcgtc      60 gacaagatgg tgatctggtg ggaggagggc aagatgacgg ccaaggtcgt ggagtccgcc    120
aaggccattc atcatctgct ggggcgggct cccgagattg cttgctcggc ctgcgatctg    180
gtcaacgtgg acctggatga ctgtgtttct gagcaataaa tgacttaaac caggtatggc    240
tgccgatggt tatcttccag attggctcga ggacaacctc tctgagggca ttcgcgagtg    300
gtgggacttg agacctggag ccccgaaacc caaagccaac cagcaaaagc aggacgacgg    360
ccggggtctg gtgcttcctg gctacaagta cctcggaccc ttcaacggac tcgacaaggg    420
agagccggtc aacgaggcag acgccgcggc cctcgagcac gacaaggcct acgacaagca    480
gctcgagcag gggacaacc cgtacctcaa gtacaaccac gccgacgccg agtttcagga    540
gcgtcttcaa gaagatacgt cttttggggg caacctcggg cgagcagtct tccaggccaa    600
gaagcgggtt ctcgaacctc tcggtctggt tgaggaaggc gctaagacgg ctcctggaaa    660
gaagagaccc atagaatccc ccgactcctc cacgggcatc ggcaagaaag ccagcagcc    720 cgctaaaaag agactcaact ttgggcagac tggcgactca gagtcagtgc ccgaccctca    780
accaatcgga gaaccccccg caggcccctc tggtctggga tctggcacaa tggctgcagg    840
cggtggcgct ccaatggcag acaataacga aggcgccgac ggagtgggta gttcctcagg    900
aaattggcat gcgattcca catggctggg cgacagagtc atcaccacca gcacccgaac    960
ctgggcccct cccacctaca acaaccacct ctacaagcaa atctccaacg gacatcggg   1020 aggaagcacc aacgacaaca cctacttcgg ctacagcacc cctgggggt attttgactt    1080 taacagattc cactgccact tctcaccacg tgactggcag cgactcatca acaacaactg   1140
gggattccgg cccaagagac tcaacttcaa gctcttcaac atccaggtca aggaggtcac    1200
gcagaatgaa ggcaccaaga ccatcgccaa taacctacc agcacgattc aggtctttac    1260
ggactcggaa taccagctcc cgtacgtcct cggctctgcg caccagggct gcctgcctcc    1320
gttcccggcg gacgtcttca tgattcctca gtacgggtac ctgactctga caacggcag    1380 tcaggccgtg ggccgttcct ccttctactg cctggagtac tttccttctc aaatgctgag    1440
aacgggcaac aactttgagt tcagctacca gtttgaggac gtgccttttc acagcagcta    1500
tgcgcacagc caaagcctgg accggctgat gaaccccctc atcgaccagt acctgtacta    1560
cctgtctcgg actcagtcca cgggaggtac cgcaggaact cagcagttgc tatttctca     1620 ggccgggcct aataacatgt cggctcaggc caaaaactgg ctacccgggc cctgctaccg    1680
```

-continued

```
gcagcaacgc gtctccacga cagtgtcgca aaataacaac agcaactttg cttggaccgg    1740
tgccaccaag tatcatctga atggcagaga ctctctggta aatcccggtg tcgctatggc    1800
aacgcacaag ggcgacgaag agcgattttt tccatccagc ggagtcttga tgtttgggaa    1860
acagggagct ggaaaagaca acgtagacta tagcagcgtt atgctaacca gtgaggaaga    1920
aatcaaaacc accaacccag tggccacaga acagtacggc gtggtggccg ataacctgca    1980
acagcaaaac gccgctccta ttgtaggggc cgtcaacagt caaggagcct tacctggcat    2040
ggtctggcag aaccgggacg tgtacctgca gggtcctatc tgggccaaga ttcctcacac    2100
ggacggcaac tttcatcctt cgccgctgat gggaggcttt ggactgaaac cccgcctcc    2160 tcagatcctg attaagaata cacctgttcc cgcggatcct ccaactacct tcagtcaagc    2220
caagctggcg tcgttcatca cgcagtacag caccggacag gtcagcgtgg aaattgaatg    2280
ggagctgcag aaagagaaca gcaagcgctg gaacccagag attcagtata cttccaacta    2340
ctacaaatct acaaatgtgg actttgctgt caatactgag ggtacttatt cagagcctcg    2400
ccccattggc acccgttacc tcacccgtaa cctgtaattg cctgttaatc aataaaccgg    2460
ttgattcgtt tcagttgaac tttggtctca agggcgaatt c                       2501
```

<210> SEQ ID NO 31
<211> LENGTH: 3113
<212> TYPE: DNA
<213> ORGANISM: Unknown
<220> FEATURE:
<223> OTHER INFORMATION: AAV serotype, clone 42.13

<400> SEQUENCE: 31

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga tcccacccc gtgatcgtca cttccaacac caacatgtgc gccgtgattg    240
acgggaacag caccaccttc gagcaccagc agccgttaca agaccggatg ttcaaatttg    300
aactcacccg ccgtctggag catgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gcccccgatg acgcggataa aagcgagccc aagcgggcct    480 gccccctcagt cgcggatcca tcgacgtcag acgcggaagg agctccggtg actttgccg    540 acaggtacca aaacaaatgt ctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccag gcaaaagcag    960
gacgacggcc ggggtctggt gcttcctggc tacaagtacc tcggacccct taacggactc   1020
gacaaggggg agcccgtcaa cgcggcggac gcagcggccc tcgagcacga caaggcctac   1080
gaccagcagc tcaaagcggg tgacaatccg tacctgcgt ataaccacgc cgacgccgag   1140
tttcaggagc gtcttcaaga agatacgtct tttgggggca acctcgggcg agcagtcttc   1200
```

```
caggccaaga agcgggttct cgaacctctc ggtctggttg aggaaggcgc taagacggct    1260
cctggaaaga agagacccat agaatccccc gactcctcca cgggcatcgg caagaaaggc    1320
cagcagcccg ctaaaaagaa gctcaacttt gggcagactg gcgactcaga gtcagtgccc    1380 gacccctcaac caatcggaga accccccgca ggcccctctg gtctgggatc tggtacaatg    1440
gctgcaggcg gtggcgctcc aatggcagac aataacgaag gcgccgacgg agtgggtagt    1500
tcctcaggaa attggcattg cgattccaca tggctgggcg acagagtcat caccaccagc    1560
acccgaacct gggccctccc cacctacaac aaccacctct acaagcaaat ctccaacggg    1620
acatcgggag gaagcaccaa cgacaacacc tacttcggct acagcacccc ctgggggtat    1680 tttgactttta acagattcca ctgccacttc tcaccacgtg actggcagcg actcatcaac    1740
aacaactggg gattccggcc caagagactc aacttcaagc tcttcaacat ccaggtcaag    1800
gaggtcacgc agaatgaagg caccaagacc atcgccaata accttaccag cacgattcag    1860
gtctttacgg actcggaata ccagctcccg tacgtcctcg gctctgcgca ccagggctgc    1920
ctgcctccgt tcccggcgga cgtcttcatg attcctcagt acgggtacct gactctgaac    1980
aacggcagtc aggccgtggg ccgttcctcc ttctactgcc tggagtactt tccttctcaa    2040
atgctgagaa cgggcaacaa ctttgagttc agctaccagt tgaggacgt gccttttcac    2100 agcagctatg cgcacagcca aagcctggac cggctgatga ccccctcat cgaccagtac    2160 ctgtactacc tgtctcggac tcagtccacg ggaggtaccg caggaactca gcagttgcta    2220
ttttctcagg ccgggcctaa taacatgtcg gctcaggcca aaaactggct acccgggccc    2280
tgctaccgga gcaacgcgt ctccacgaca gtgtcgcaaa ataacaacag caactttgct    2340
tggaccggtg ccaccaagta tcatctgaat ggcagagact ctctggtaaa tcccggtgtc    2400
gctatggcaa cgcacaaggg cgacgaagag cgattttttc catccagcgg agtcttgatg    2460
tttgggaaac agggagctgg aaaagacaac gtggactata gcagcgttat gctaaccagt    2520
gaggaagaaa tcaaaaccac caacccagtg gccacagaac agtacggcgt ggtggccgat    2580
aacctgcaac agcaaacgc cgctcctat tgtaggggccg tcaacagtca aggagcctta    2640
cctggcatgg tctggcagaa ccgggacgtg tacctgcagg gtcctatctg gccaagatt    2700 cctcacacgg acggcaactt tcatccttcg ccgctgatgg gaggctttgg actgaaacac    2760
ccgcctcctc agatcctgat taagaataca cctgttcccg cggatcctcc aactaccttc    2820
agtcaagcca agctggcgtc gttcatcacg cagtacagca ccggacaggt cagcgtggaa    2880
attgaatggg agctgcagaa agagaacagc aagcgctgga acccagagat tcagtatact    2940
tccaactact acaaatctac aaatgtggac tttgctgtca atactgaggg tacttattca    3000
gagcctcgcc ccattggcac ccgttacctc accccgtagcc tgtaattgcc tgttaatcaa    3060
taaaccggtt gattcgtttc agttgaactt tggtctctgc gaagggcgaa ttc            3113
```

<210> SEQ ID NO 32
<211> LENGTH: 3113
<212> TYPE: DNA
<213> ORGANISM: Unknown
<220> FEATURE:
<223> OTHER INFORMATION: AAV serotype, clone 42.3a

<400> SEQUENCE: 32

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
```

```
cccagatcga tcccaccccc gtgatcgtca cttccaacac caacatgtgc gccgtgattg    240
acgggaacag caccaccttc gagcaccagc agccgttaca agaccggatg ttcaaatttg    300
aactcacccg ccgtctggag catgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gcccccgatg acgcggataa aagcgagccc aagcgggcct    480
gcccctcagt cgcggatcca tcgacgtcag acgcggaagg agctccggtg gactttgccg    540
acaggtacca aaacaaatgt tctcgtcacg cgggcatgct tcagatgctg cttccctgca    600
agacatgcga gagaatgaat cagaatttca gcatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtca tcttccagat tggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggaccctt caacggactc   1020 gacaagggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagacccat agaatccccc gactcctcca cgggcatcgg caagaaaggc   1320
cagcagcccg ctaaaaagaa gctcaacttt gggcagactg gcgactcaga gtcagtgccc   1380
gaccctcaac caatcggaga accccccgca ggcccctctg gtctgggatc tggtacaatg   1440
gctgcaggcg gtggcgctcc aatggcagac aataacgaag gcgccgacgg agtgggtagt   1500
tcctcaggaa attggcattg cgattccaca tagctgggcg acagagtcat caccaccagc   1560
acccgaacct gggccctccc cacctacaac aaccacctct acaagcaaat ctccaacggg   1620 acatcggag gaagcaccaa cgacaacacc tacttcggct acagcacccc ctgggggtat   1680
tttgacttta acagattcca ctgccacttc tcaccacgtg actggcagcg actcatcaac   1740
aacagctggg gattccggcc caagagactc aacttcaagc tcttcaacat ccaggtcaag   1800
gaggtcacgc agaatgaagg caccaagacc atcgccaata accttaccag cacgattcag   1860
gtctttacgg actcggaata ccagctcccg tacgtcctcg gctctgcgca ccagggctgc   1920
ctgcctccgt tcccggcgga cgtcttcatg attcctcagt acgggtacct gactctgaac   1980
aacggcagtc aggccgtggg ccgttcctcc ttctactgcc tggagtactt tccttctcaa   2040
atgctgagaa cgggcaacaa ctttgagttc agctaccagt ttgaggacgt gccttttcac   2100
agcagctacg cgcacagcca aagcctggac cggctgatga ccccctcat cgaccagtac   2160 ctgtactacc tgtctcggac tcagtccacg ggaggtaccg caggaactca gcagttgcta   2220 tttctcagg ccgggcctaa taacatgtcg gctcaggcca aaaactggct acccgggccc   2280
tgctaccggc agcaacgcgt ctccacgaca ctgtcgcaaa ataacaacag caactttgct   2340
tggaccggtg ccaccaagta tcatctgaat ggcagagact ctctggtaaa tcccggtgtc   2400
gctatggcaa cgcacaagga cgacgaagag cgatttttc catccagcgg agtcttgatg   2460
tttgggaaac agggagctgg aaaagacaac gtggactata gcagcgttat gctaaccagt   2520
```

-continued

| | |
|---|---|
| gaggaagaaa tcaaaaccac caacccagtg ccacagaac agtacggcgt ggtggccgat | 2580 |
| aacctgcaac agcaaaacgc cgctcctatt gtaggggccg tcaacagtca aggagcctta | 2640 |
| cctggcatgg tctggcagaa ccgggacgtg tacctgcagg gtcctatctg ggccaagatt | 2700 |
| cctcacacgg acggcaactt tcatccttcg ccgctgatgg gaggctttgg actgaaacac | 2760 |
| ccgcctcctc agatcctgat taagaataca cctgttcccg cggatcctcc aactaccttc | 2820 |
| agtcaagcca agctggcgtc gttcatcacg cagtacagca ccggacaggt cagcgtggaa | 2880 |
| attgaatggg agctgcagaa agagaacagc aagcgctgga acccagagat tcagtatact | 2940 |
| tccaactact acaaatctac aaatgtggac tttgctgtca atactgaggg tacttattca | 3000 |
| gagcctcgcc ccattggcac ccgttacctc acccgtaacc tgtaattgcc tgttaatcaa | 3060 |
| taaaccggtt aattcgtttc agttgaactt tggtctctgc gaagggcgaa ttc | 3113 |

<210> SEQ ID NO 33
<211> LENGTH: 2504
<212> TYPE: DNA
<213> ORGANISM: Unknown
<220> FEATURE:
<223> OTHER INFORMATION: AAV serotype, clone 42.4

<400> SEQUENCE: 33

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattcatcat ctgctggggc gggctcccga gattgcttgc tcggcctgcg | 180 |
| atctggtcaa cgtggacctg gatgactgtg tttctgagca ataaatgact taaaccaggt | 240 |
| atggctgccg atggttatct tccagattgg ctcgaggaca acctctctga gggcattcgc | 300 |
| gagtggtggg acttgaaacc tggagccccg aaacccaaag ccaaccagca aaagcaggac | 360 |
| gacggccggg gtctggtgct tcctggctac aagtacctcg gacccttcaa cggactcgac | 420 |
| aagggagagc cggtcaacga ggcagacgcc gcggccctcg agcacgacaa ggcctacgac | 480 |
| aagcagctcg agcaggggga caacccgtac ctcaagtaca accacgccga cgccgagttt | 540 |
| caggagcgtc ttcaagaaga tacgtctttt gggggcaacc tcgggcgagc agtcttccag | 600 |
| gccaagaagc gggttctcga acctctcggt ctggttgagg aaggcgctaa gacggctcct | 660 |
| ggaaagaaga gacccataga atcccccgac tcctccacgg gcatcggcaa gaaaggccag | 720 |
| cagcccgcta aaaagaagct caactttggg cagactggcg actcagagtc agtgcccgac | 780 |
| cctcaaccaa tcggagaacc ccccgcaggc ccctctggtc tgggatctgg tacaatggct | 840 |
| gcaggcggtg gcgctccaat ggcagacaat aacgaaggcg ccgacggagt gggtaatgcc | 900 |
| tccggaaatt ggcattgcga ttccacatgg ctgggcgaca gagtcatcac caccagcacc | 960 |
| cgcacctggg ccctgcccac ctacaacaac cacctctaca gcagatatc aagtcagagc | 1020 |
| ggggctacca cgacaacca cttcttcggc tacagcaccc cctggggcta ttttgacttc | 1080 |
| aacagattcc actgccactt ctcatcacgt gactggcagc gactcatcaa caacaactgg | 1140 |
| ggattccggc ccaagagact caacttcaag ctcttcaaca tccaggtcaa ggaggtcacg | 1200 |
| cagaatgaag caccaagac catcgccaat aaccttacca gcacgattca ggtctttacg | 1260 |
| gactcggaat accggctccc gtacgtcctc ggctctgcgc accagggctg cctgcctccg | 1320 |
| ttcccggcgg acgtcttcat gattcctcag tacgggtacc tgactctgaa caacggcagt | 1380 |
| caggccgtgg gccgttcctc cttctactgc ctggagtact tccttctca aatgctgaga | 1440 |
| acgggcaaca actttgagtt cagctaccag tttgaggacg tgccttttca cagcagctac | 1500 |

```
gcgcacagcc aaagcctgga ccggctgatg aaccccctca tcgaccagta cctgtactac    1560
ctgtctcgga ctcagtccac gggaggtacc gcaggaactc agcagttgct attttctcag    1620
gccgggccta ataacatgtc ggctcaggcc aaaaactggc tacccgggcc ctgctaccgg    1680
cagcaacgcg tctccacgac actgtcgcaa ataacaaca gcaactttgc ttggaccggt    1740
gccaccaagt atcatctgaa tggcagagac tctctggtaa atcccggtgt cgctatggca    1800
acgcacaagg acgacgaaga gcgattttt ccatccagcg gagtcttgat gtttgggaaa    1860
cagggagctg aaaagacaa cgtggactat agcagcgtta tgctaaccag tgaggaagaa    1920
atcaaaacca ccaacccagt ggccacagaa cagtacggcg tggtggccga taacctgcaa    1980
cagcaaaacg ccgctcctat tgtaggggcc gtcaacagtc aaggagcctt acctggcatg    2040
gtctggcaga accgggacgt gtacctgcag ggtcctatct gggccaagat tcctcacacg    2100
gacggcaact tcatccttc gccgctgatg ggaggctttg gactgaaaca cccgcctcct    2160
cagatcctga ttaagaatac acctgttccc gcggatcctc caactacctt cagtcaagcc    2220
aagccggcgt cgttcatcac gcagtacagc accggacagg tcagcgtgga aattgaatgg    2280
gagctgcaga aagagaacag caagcgctgg aacccagaga ttcagtatac ttccaactac    2340
tacaaatcta caaatgtgga ctttgctgtc aatactgagg gtacttattc agagcctcgc    2400
cccattggca cccgttacct cacccgtaac ctgtaattgc ctgttaatca ataaaccggt    2460
taattcgttt cagttgaact ttggtctctg cgaagggcga attc                      2504
```

<210> SEQ ID NO 34
<211> LENGTH: 3106
<212> TYPE: DNA
<213> ORGANISM: Unknown
<220> FEATURE:
<223> OTHER INFORMATION: AAV serotype, clone 42.5a

<400> SEQUENCE: 34

```
gaattcgccc ttctacggct gcgtcaactg gaccaatgag aactttccct tcaacgattg      60
cgtcgacaag atggtgatct ggtgggagga gggcaagatg acggccaagg tcgtggagtc     120
cgccaaggcc attctcggcg gcagcaaggt gcgcgtggac caaaagtgca agtcgtccgc    180
ccagatcgac cccaccccg tgatcgtcac ctccaacacc aacatgtgcg ccgtgattga     240
cgggaacagc accaccttcg agcaccagca gccgttgcag gaccggatgt tcaaatttga    300
actcacccgc cgtctggagc atgactttgg caaggcgaca agcaggaag tcaaagagtt     360 cttccgctgg gcgcaggatc acgtgaccga ggtggcgcat gagttctacg tcagaaaggg    420
tggagccaac aagagacccg ccccgatga cgcggataaa agcgagccca gcgggcccg     480 cccctcagtc gcggatccat cgacgtcaga gcggaagga gctccggtgg actttgccga    540
caggtaccaa aacaaatgtt ctcgtcacgc gggcatgctt cagatgctgt tccctgcaa     600 acatgcgag agaatgaatc agaatttcaa catttgcttc acgcacggga ccagagactg    660
ttcagaatgt ttccccggcg tgtcagaatc tcaaccggtc gtcagaaaga ggacgtatcg    720
gaaactctgt gccattcatc atctgctggg gcgggctccc gagattgctt gctcggcctg    780
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacggccg gggtctggtg cttcctggct acaagtacct cggacccttc aacggactcg    1020
```

```
acaagggaga gccggtcaac gaggcagacg ccgcggccct cgagcacgac aaggcctacg    1080
acaagcagct cgagcagggg gacaacccgt acctcaagta caaccacgcc gacgccgagt    1140
ttcaggagcg tcttcaagaa gatacgtctt ttgggggcaa cctcgggcga gcagtcttcc    1200
gggccaagaa gcgggttctc gaacctctcg gtctggttga ggaaggcgct aagacggctc    1260
ctggaaagaa gagacccata gaatcccccg actcctccac gggcatcggc aagaaaggcc    1320
agcagcccgc taaaaagaag ctcaactttg gcagactgg cgactcagag tcagtgcccg    1380 accccaacc tctcggagaa cctcccgccg cgccctcagg tctgggatct ggtacaatgg    1440
ctgcaggcgg tggcgcacca atggcagaca ataacgaagg cgccgacgga gtgggtaatg    1500
cctccggaaa ttggcattgc gattccacat ggctgggcga cagagtcatc accaccagca    1560
cccgcacctg ggccctgccc acctacaaca accacctcta caagcagata tcaagtcaga    1620
gcggggctac caacgacaac cacttcttcg gctacagcac ccctgggc tattttgact    1680 tcaacagatt ccactgccac ttctcaccac gtgactggca gcgactcatc aacaacaacc    1740
ggggattccg gcccagaaag ctgcggttca gttgttcaa catccaggtc aaggaggtca    1800
cgacgaacga cggcgttacg accatcgcta ataaccttac cagcacgatt caggtcttct    1860
cggactcgga gtaccaactg ccgtacgtcc tcggctctgc gcaccaggc tgcctccctc    1920 cgttccctgc ggacgtgttc atgattcctc agtacggata tctgactcta aacaacggca    1980
gtcagtctgt gggacgttcc tccttctact gcctggagta cttccttct cagatgctga    2040 gaacgggcaa taactttgaa ttcagctacc agtttgagga cgtgccctt cacagcagct    2100 acgcgcacac ccaaagcctg gaccggctga tgaaccccct catcgaccag tacctgtact    2160
acctgtctcg gactcagtcc acgggaggta ccgcaggaac tcagcagttg ctattttctc    2220
aggccgggcc taataacatg tcggctcagg ccaaaaactg gctacccggg ccctgctacc    2280
ggcagcaacg cgtctccacg acactgtcgc aaaataacaa cagcaacttt gcttggaccg    2340
gtgccaccaa gtatcatctg aatggcagag actctctggt aaatcccggt gtcgctatgg    2400
caacgcacaa ggacgacgaa gagcgatttt tccatccag cggagtcttg atgtttggga    2460
aacagggagc tggaaaagac aacgtggact atagcagcgt tatgctaacc agtgaggaag    2520
aaatcaaaac caccaaccca gtggccacag aacagtacgg cgtgtggcc gataacctgc    2580 aacagcaaaa cgccgctcct attgtagggg ccgtcaacag tcaaggagcc ttacctggca    2640
tggcctggca gaaccgggac gtgtacctgc agggtcctat ctgggccaag attcctcaca    2700
cggacggcaa cttcatcct cgccgctga tgggaggctt tggactgaaa cacccgcctc    2760
ctcagatcct gattaagaat acacctgttc ccgcggatcc tccaactacc ttcagtcaag    2820
ccaagctggc gtcgttcatc acgcagtaca gcaccggaca ggtcagcgtg gaaattgaat    2880
gggagctgca gaaagagaac agcaagcgct ggaacccaga gattcagtat acttccaact    2940
actacaaatc tacaaatgtg gactttgctg tcaatactga gggtacttat tcagagcctc    3000
gccccattgg caccgttac ctcacccgta acctgtaatt gcctgttaat caataaaccg    3060
gttaattcgt ttcagttgaa ctttggtctc tgcgaagggc gaattc                   3106
```

<210> SEQ ID NO 35
<211> LENGTH: 2489
<212> TYPE: DNA
<213> ORGANISM: Unknown
<220> FEATURE:
<223> OTHER INFORMATION: AAV serotype, clone 42.10

<400> SEQUENCE: 35

-continued

```
gaattcgccc tttctacggc tgcgtcaact ggaccaatga gaactttccc ttcaacgatt      60
gcgtcgacaa gatggtgatc tggtgggagg agggcaagat gacggccaag gtcgtgaagt     120
ccgccaaggc cattcatcat ctgctggggc gggctcccga gattgcttgc tcggcctgcg     180
atctggtcaa cgtggacctg gatgactgtg tttctgagca taaaatgact taaaccaggt     240
atggctgccg atggttatct tccagattgg ctcgaggaca acctctctga gggcattcgc     300
gagtggtggg acttgaaacc tggagccccg aaacccaaag ccaaccagca aaagcaggac     360
gacggccggg gtctggtgct tcctggctac aagtacctcg gacccttcaa cggactcgac     420
aagggagagc cggtcaacga ggcagacgcc gcggccctcg agcacgacaa ggcctacgac     480
aagcagctcg agcaggggga caacccgtac ctcaagtaca ccacgccga cgccgagttt     540
caggagcgtc ttcaagaaga tacgtctttt gggggcaacc tcgggcgagc agtcttccag     600
gccaagaagc gggttctcga acctctcggt ctggttgagg aaggcgctaa gacggctcct     660
ggaaagaaga gacccataga atcccccgac tcctccacgg gcatcggcag gaaaggccag     720
cagcccgcta aaagaagct caactttggg cagactggcg actcagagtc agtgcccgac     780
cctcaaccaa tcggagaacc ccccgcaggc ccctctggtc tgggatctgg tacaatggct     840
gcaggcggtg gcgctccaat ggcagacaat aacgaaggcg ccgacggagt gggtaatgcc     900
tccggaaatt ggcattgcga ttccacatgg ctgggcgaca gagtcatcac caccagcacc     960
cgcacctggg ccctgcccac ctacaacaac cacctctaca gcagatatc aagtcagagc    1020
ggggctacca cgacaaccac cttcttcggc tacagcaccc cctggggcta ttttgacttc    1080
aacagattcc actgccactt ctcaccacgt gactggcagc gactcatcaa caacaactgg    1140
ggattccggc cagaaagct gcggttcaag ttgttcaaca tccaggtcaa ggaggtcacg    1200
acgaacgacg gcgttacgac catcgccaat aaccttacca gcacgattca ggtcttctcg    1260
gactcggagt accaactgcc gtacgtcctc ggctctgcgc accagggctg cctccctccg    1320
ttccctgcgg acgtgttcat gattcctcag tacgatatc tgactctaaa caacggcagt    1380
cagtctgtgg acgttcctc cttctactgc ctggagtact ttccttctca gatgctgaga    1440
acgggcaata actttgaatt cagctacacc tttgaggaag tgcctttcca cagcagctat    1500
gcgcacagcc agagcctgga ccggctgatg aatcccctca tcgaccagta cctgtactac    1560
ctggcccgga cccagagcac tacgggtcc acaaggagc tgcagttcca tcaggctggg    1620
cccaacacca tggccgagca atcaaagaac tggctgcccg accctgtta tcggcagcag    1680
agactgtcaa aaacataga cagcaacaac aacagtaact ttgcctggac cggggccact    1740
aaataccatc tgaatggtag aaattcatta accaacccgg gcgtagccat ggccaccaac    1800
aaggacgacg aggaccagtt ctttcccatc aacggagtgc tggttttgg caaaacgggg    1860
gctgccaaca gacaacgct ggaaaacgtg ctaatgacca gcgaggagga gatcaaaacc    1920
accaatcccg tggctacaga agaatacggt gtggtctcca gcaacctgca atcgtctacg    1980
gccggacccc agacacagac tgtcaacagc cagggggctc tgcccggcat ggtctggcag    2040
aaccgggacg tgtacctgca gggtcccatc tgggccaaaa ttcctcacac ggacggcaac    2100
tttcacccgt ctcccctgat gggcggattt ggactcaaac accgcctcc tcaaattctc    2160
atcaaaaaca ccccggtacc tgctaatcct ccagaggtgt ttactcctgc caagtttgcc    2220
tcatttatca cgcagtacag caccggccag gtcagcgtgg agatcgagtg gaactgcag     2280
aaagaaaaca gcaaacgctg gaatccagag attcagtaca cctcaaatta tgccaagtct    2340
```

```
aataatgtgg aatttgctgt caacaacgaa ggggtttata ctgagcctcg ccccattggc    2400
acccgttacc tcacccgtaa cctgtaattg cctgttaatc aataaaccgg ttaattcgtt    2460
tcagttgaac tttggtcaag ggcgaattc                                      2489
```

<210> SEQ ID NO 36
<211> LENGTH: 2495
<212> TYPE: DNA
<213> ORGANISM: Unknown
<220> FEATURE:
<223> OTHER INFORMATION: AAV serotype, clone 42.3b

<400> SEQUENCE: 36

```
gaattcgccc tttctacggc tgcgtcaact agaccaatga gaactttccc ttcaacgatt     60
gcgtcgacaa gatggtgatc tggtgggagg agggcaagat gacggccaag gtcgtggagt    120
ccgccaaggc cattcatcat ctgctggggc gggctcccga gattgcttgc tcggcctgcg    180
atctggtcaa cgtggacctg gatgactgtg tttctgagca ataaatgact taaaccaggt    240
atggctgccg atggttatct tccagattgg ctcgaggaca acctctctga gggcattcgc    300
gagtggtggg acttgaaacc tggagccccg aaacccaaag ccaaccagca aaagcaggac    360
gacggccggg gtctggtgct tcctggctac aagtacctcg gacccttcaa cggactcgac    420
aagggagagc cggtcaacga ggcagacgcc gcggccctcg agcacgacaa ggcctacgac    480
aagcagctcg agcaggggga caacccgtac ctcaagtaca accacgccga cgccgagttt    540
caggagcgtc ttcaagaaga tacgtctttt ggggggcaacc tcgggcgagc agtcttccag    600
gccaagaagc gggttctcga acctctcggt ctggttgagg aaggcgctaa gacggctcct    660
ggaaagaaga gacccataga atcccccgac tcctccacgg gcatcggcaa gaaaggccag    720
cagcccgcta aaaagaagct caactttggg cagactggcg actcagagtc agtgcccgac    780
cctcaaccaa tcggagaacc ccccgcaggc ccctctggtc tgggatctgg tacaatggct    840
gcaggcggtg cgctccaat ggcagacaat aacgaaggcg ccgacggagt gggtaatgcc    900
tccggaaatt ggcattgcga ttccacatgg ctgggcgaca gagtcatcac caccagcacc    960
cgcacctggg ccctgcccac ctacaacaac cacctctaca agcagatatc aagtcagagc   1020
ggggctacca acgacaacca cttcttcggc tacagcaccc cctggggcta ttttgacttc   1080
aacagattcc actgccactt ctccaccgt gactggcagc gactcatcaa caacaactgg   1140
ggattccggc cagaaaagct gcggttcaag ttgttcaaca tccaggtcaa ggaggtcacg   1200
acgaacgacg gcgttacgac catcgctaat aaccttacca gcacgattca ggtcttctcg   1260
gactcggagt accaactgcc gtacgtcctc ggctctgcgc accagggctg cctccctccg   1320
ttccctgcgg acgtgttcat gattcctcag tacggatatc tgactctaaa caacggcagt   1380
cagtctgtgg acgttcctc cttctactgc ctggagtact tccttctca gatgctgaga   1440 acgggcaata actttgaatt cagctacacc tttgaggaag tgcctttcca cagcagctat   1500
gcgcacagcc agagcctgga ccggctgatg aatcccctca tcgaccagta cctgtactac   1560
ctggcccgga cccagagcac tacggggtcc acaagggagc tgcagttcca tcaggctggg   1620
cccaacacca tggccgagca atcaaagaac tggctgccga ccctgtta tcggcagcag   1680 agactgtcaa aaacatagaa cagcaacaac accagtaact ttgcctggac cggggccact   1740
aaataccatc tgaatggtag aaattcatta accaacccgg cgtagccat ggccaccaac   1800 aaggacgacg aggaccagtt ctttcccatc aacgagtgc tggttttgg caaacgggg   1860 gctgccaaca agacaacgct ggaaaacgtg ctaatgacca gcgaggagga gatcaaaacc   1920
```

-continued

| | |
|---|---|
| accaatcccg tggctacaga acagtacggt gtggtctcca gcaacctgca atcgtctacg | 1980 |
| gccggacccc agacacagac tgtcaacagc caggggctc tgcccggcat ggtctggcag | 2040 |
| aaccgggacg tgtacctgca gggtcccatc tgggccaaaa ttcctcacac ggacggcaac | 2100 |
| tttcacccgt ctcccctgat gggcggattt ggactcaaac acccgcctcc tcaaattctc | 2160 |
| atcaaaaaca ccccggtacc tgctaatcct ccagaggtgt ttactcctgc caagtttgcc | 2220 |
| tcatttatca cgcagtacag caccggccag gtcagcgtgg agatcgagtg ggaactgcag | 2280 |
| aaagaaaaca gcaaacgctg gaatccagag attcagtaca cctcaaatta tgccaagtct | 2340 |
| aataatgtgg aatttgctgt caacaacgaa ggggtttata ctgagcctcg ccccattggc | 2400 |
| acccgttacc tcacccgtaa cctgtaattg cctgttaatc aataaaccgg ttaattcgtt | 2460 |
| tcagttgaac tttggtctct gcgaagggcg aattc | 2495 |

<210> SEQ ID NO 37
<211> LENGTH: 3098
<212> TYPE: DNA
<213> ORGANISM: Unknown
<220> FEATURE:
<223> OTHER INFORMATION: AAV serotype, clone 42.11

<400> SEQUENCE: 37

| | |
|---|---|
| gaattcgccc tttctacggc tgcgtcaact ggaccaatga aactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgcgtgga ccaaaagtgc aagtcttccg | 180 |
| cccagatcga tcccaccccc gtgatcgtca cttccaacac caacatgtgc gccgtgattg | 240 |
| acgggaacag caccaccttc gagcaccagc agccgttaca agaccggatg ttcaaatttg | 300 |
| aactcacccg ccgtctggag cacgactttg gcaaggtgac aaagcaggaa gtcaaagagt | 360 |
| tcttccgctg gcgcaggat cacgtgaccg aggtggcgca tgagttctac gtcagaaagg | 420 |
| gtggagccaa caagagaccc gccccgatg acgcggataa aagcgagccc aagcgggcct | 480 |
| gcccctcagt cgcggatcca tcgacgtcag acgcggaagg agctccggtg gactttgccg | 540 |
| acaggtacca aaacaaatgt tctcgtcacg cgggcatgct tcagatgctg tttcccgca | 600 |
| agacatgcga gagaatgaat cagaatttca catttgctt cacgcacggg accggagact | 660 |
| gttcagaatg tttccccggc gtgtcagaat ctcaaccgt cgtcagaaag aggacgtatc | 720 |
| ggaaactctg tgccattcat catctgctgg ggcgggctcc cgagattgct tgctcggcct | 780 |
| gcgatctggt caacgtggac ctggatgact gtgtttctga gcaataaatg acttaaacca | 840 |
| ggtatggctg ccgatggtta tcttccagat tggctcgagg acaacctctc tgagggcatt | 900 |
| cgcgagtggt gggacttgaa acctggagcc ccgaaaccca agccaaccca gcaaaagcag | 960 |
| gacgacggcc ggggtctggt gcttcctggc tacaagtacc tcggacccctt caacggactc | 1020 |
| gacaagggag agccggtcaa cgcggcggac gcagcggccc tcgagcacga caaggcctac | 1080 |
| gaccagcagc tcaaagcggg tgacaatccg tacctgcggt ataaccacgc cgacgccgag | 1140 |
| tttcaggagc gtcttcaaga agatacgtct tttgggggca acctcgggcg agcagtcttc | 1200 |
| caggccaaga gcgggttct cgaacctctc ggtctggttg aggaaggcgc taagacggct | 1260 |
| cctggaaaga agagacccat agaatccccc gactcctcca cgggcatcgg caagaaaggc | 1320 |
| cagcagcccg ctaaaaagaa gctcaacttt gggcagactg gcgactcaga gtcagtgccc | 1380 |
| gaccctcaac caatcggaga accccccgca ggccctctg gtctgggatc tggtacaatg | 1440 |

| | |
|---|---|
| gctgcaggcg gtggcgctcc aatggcagac aataacgaag gcgccgacgg agtgggtaat | 1500 |
| gcctccggaa attggcattg cgattccaca tggctgggcg acagagtcat caccaccagc | 1560 |
| acccgcacct gggccctgcc cacctacaac aaccacctct acaagcagat atcaagtcag | 1620 |
| agcggggcta ccaacgacaa ccacttcttc ggctacagca ccccctgggg ctattttgac | 1680 |
| ttcaacagat tccactgcca cttctcacca cgtgactggc agcgactcat caacaacaac | 1740 |
| tggggattcc ggcccagaaa gctgcggttc aagttgttca acatccaggt caaggaggtc | 1800 |
| acgacgaacg acggcgttac gaccatcgct aataaccttac cagcacgat tcaggtcttc | 1860 |
| tcggactcgg agtaccaact gccgtacgtc ctcggctctg cgcaccaggg ctgcctccct | 1920 |
| ccgttccctg cggacgtgtt catgattcct cagtacggat atctgactct aaacaacggc | 1980 |
| agtcagtctg tgggacgttc ctccttctac tgcctggagt actttccttc tcagatgctg | 2040 |
| agaacgggca ataactttga attcagctac acctttgagg aagtgccttt ccacagcagc | 2100 |
| tatgcgcaca gccagagcct ggaccggctg atgaatcccc tcatcgacca gtacctgtac | 2160 |
| tacctggccc ggacccagag cactacgggg tccacaaggg agctgcagtt ccatcaggct | 2220 |
| gggcccaaca ccatggccga gcaatcaaag aactggctgc ccggaccctg ttatcggcgg | 2280 |
| cagagactgt caaaagacat agacagcaac aacaacagta actttgcctg gaccggggcc | 2340 |
| actaaatacc atctgaatgg tagaaattca ttaaccaacc cgggcgtagc catggccacc | 2400 |
| aacaaggacg acgaggacca gttctttccc atcaacggag tgctggtttt tggcaaaacg | 2460 |
| ggggctgcca acaagacaac gctggaaaac gtgctaatga ccagcgagga ggagatcaaa | 2520 |
| accaccaatc ccgtggctac agaagaatac ggtgtggtct ccagcaacct gcaatcgtct | 2580 |
| acggccggac cccagacaca gactgtcaac agccagggg ctctgcccgg catggtctgg | 2640 |
| cagaaccggg acgtgtacct gcagggtccc atctgggcca aaattcctca cacggacggc | 2700 |
| aactttcacc cgtctccccc tgatgggcgga tttggactca acacccgcc tcctcaaatt | 2760 |
| ctcatcaaaa acaccccggt acctgctaat cctccagagg tgtttactcc tgccaagttt | 2820 |
| gcctcattta tcacgcagta cagcaccggc caggtcagcg tggagatcga gtgggaactg | 2880 |
| cagaaagaga acagcaaacg ctggaatcca gagattcagt acacctcaaa ttatgccaag | 2940 |
| tctaataatg tggaatttgc tgtcaacaac gaagggggttt atactgagcc tcgccccatt | 3000 |
| ggcacccgtt acctcacccg taacctgtaa ttacttgtta atcaataaac cggttgattc | 3060 |
| gtttcagttg aactttggtc tctgcgaagg gcgaattc | 3098 |

<210> SEQ ID NO 38
<211> LENGTH: 3276
<212> TYPE: DNA
<213> ORGANISM: Unknown
<220> FEATURE:
<223> OTHER INFORMATION: AAV serotype, clone 42.6a

<400> SEQUENCE: 38

| | |
|---|---|
| gaattcgccc ttcgcagaga ccaaagttca actgaaacga attaaccggt ttattgatta | 60 |
| acaggcaatt acaggttacg ggtgaggtaa cgggtgccaa tggggcgagg ctcagtataa | 120 |
| accccttcgt tgttgacagc aaattccaca ttattagact tggcataatt tgaggtgtac | 180 |
| tgaatctctg gattccagcg tttgctgttt tctttctgca gttcccactc gatctccacg | 240 |
| ctgacctggc cggtgctgta ctgcgtgata aatgaggcaa acttggcagg agtaaacacc | 300 |
| tctggaggat tagcaggtac cggggtgttt ttgatgagaa tttgaggagg cgggtgtttg | 360 |
| agtccaaatc cgtccatcag gggagacggg tgaaagttgc cgtccgtgtg aggaattttg | 420 |

```
gcccagatgg gaccctgcag gtacacgtcc cggttctgcc agaccatgcc gggcagagcc      480
ccctggctgt tgacagtctg tgtctggggt ccggccgtag acgattgcag gttgctggag      540
accacaccgt attcttctgt agccacggga ttggtggttt tgatctcctc ctcgctggtc      600
attagcacgt tttccagcgt tgtcttgttg cagcccccg ttttgccaaa aaccagcact       660
ccgttgatgg gaaagaactg gtcctcgtcg tccttgttgg tggccatggc tacgcccggg      720
ttggttaatg aatttctacc attcagatgg tatttagtgg ccccggtcca ggcaaagtta     780
ctgttgttgt tgctgtctat gttttttgac agtctctgct gccgataaca gggtccgggc     840
agccagttct ttgattgctc ggccatggtg ttgggcccag cctgatgaa ctgcagctcc      900 cttgtggacc ccgtagtgct ctgggtccgg gccaggtagt acaggtactg gtcgatgagg    960
ggattcatca gccggtccag gctctggcta tgcgcatagc tgctgtggaa aggcacttcc    1020
tcaaaggtgt agctgaattc aaagttattg cccgttctca gcatctgaga aggaaagtac    1080
tccaggcagt agaaggagga acgtcccaca gactgactgc cgttgtttag agtcagatat    1140
ccgtactgag gaatcatgaa cacgtccgca gggaacggag ggaggcagcc ctggtgcgca    1200
gagccgagga cgtacggcag ttggtactcc gagtccgaga agacctgaat cgtgctggta    1260
aggttattag cgatggtcgt aacgccgtcg tccgtcgtga cctccttgac ctggatgttg    1320
aacaacttga accgcagctt tctgggccgg aatccccagt tgttgttgat gagtcgctgc    1380
cagtcacgtg gtgagaagtg gcagtggaat ctgttaaagt caaaataccc ccaggggggtg   1440 ctgtagccga agtaggtgtt gtcgttggtg cttcctcccg atgtcccgtt ggagatttgc    1500
ttgtagaggt ggttgttgta ggtggggagg gcccaggttc gggtgctggt ggtgatgact    1560
ctgtcgccca gccatgtgga atcgcaatgc caatttcctg aggaactacc cactccgtcg    1620
gcgccttcgt tattgtctgc cattggagcg ccaccgcctg cagccattgt accagatccc    1680
agaccagagg ggcctgcggg gggttctccg attggttgag ggtcgggcac tgactctgag    1740
tcgccagtct gcccaaagtt gagtctcttt ttcgcgggct gctggcctgt cttgccgatg    1800
cccgtagagg agtctggaga acgctggggt gatggctcta ccggtctctt ctttccagga    1860
gccgtcttag cgccttcctc aaccagaccg agaggttcga gaacccgctt cttggcctgg    1920
aagactgctc gcccgaggtt gcccccaaaa gacgtatctt cttgaagacg ctcctgaaac    1980
tcggcgtcgg cgtggttgta cttgaggtac gggttgtccc cctgctcgag ctgcttgtcg    2040
taggccttgt cgtgctcgag ggccgcggcg tctgcctcgt tgaccggctc tcccttgtcg    2100
agtccgttga agggtccgag gtacttgtag ccaggaagca ccagacccg gccgtcgtcc     2160 tgcttttgct ggttggcttt gggtttcggg gctccaggtt tcaagtccca ccactcgcga    2220
atgccctcag agaggttgtc ctcgagccaa tctggaagat aaccatcggc agccatacct    2280
ggtttaagtc atttattgct cagaaacaca gtcatccagg tccacgttga ccagatcgca    2340
ggccgagcaa gcaatctcgg gagcccgccc cagcagatga tgaatggcac agagtttccg    2400
atacgtcctc tttctgacga ccggttgaga ttctgacacg ccggggaaac attctgaaca    2460
gtctctggtc ccgtgcgtga agcaaatgtt gaaattctga ttcattctct cgcatgtctt    2520
gcagggaaac agcatctgaa gcatgcccgc gtgacgagaa cacttgtttt ggtacctgtc    2580
ggcaaagtcc accggagctc cttccgcgtc tgacgtcgat ggatgcaaaa tgtcgcaaaa    2640
gcactcacgt gacagctaat acaggaccac tccctatga cgtgatttac gtcagcgcta     2700
tgcccgcgtg acgagaacat ttgttttggt acctgtcggc aaagtccacc ggagctcctt    2760
```

```
ccgcgtctga cgtcgatgga tccgcgactg aggggcaggc ccgcttgggc tcgcttttat    2820
ccgcgtcatc gggggcgggt ctcttgttgg ctccacccct tctgacgtag aactcatgcg    2880
ccacctcggt cacgtgatcc tgcgcccagc ggaagaactc tttgacttcc tgctttgtca    2940
ccttgccaaa gtcatgctcc agacggcggg tgagttcaaa tttgaacatc cggtcctgca    3000
acggctgctg gtgctcgaag gtggtgctgt tcccgtcaat cacggcgcac atgttggtgt    3060
tggaagtgac gatcacgggg gtgggatcga tctgggcgga agacttgcac ttttggtcca    3120
cgcgcacctt gctgccgccg agaatggcct tggcggactc cacgaccttg gccgtcatct    3180
tgccctcctc ccaccagatc accatcttgt cgacgcaatc gttgaaggga aagttctcat    3240
tggtccagtt gacgcagccg tagaaagggc gaattc                              3276

<210> SEQ ID NO 39
<211> LENGTH: 3084
<212> TYPE: DNA
<213> ORGANISM: Unknown
<220> FEATURE:
<223> OTHER INFORMATION: AAV serotype, clone 43.1

<400> SEQUENCE: 39
gaattcgccc tttctacggc tgcatcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttgca ggaccggatg ttcaagttcg     300
aactcacccg ccgtctggag cacgactttg gcaaggtgac caagcaggaa gtcaaagagt     360
tcttccgctg ggcgcaggat cacgtgaccg aggtggcgca tgagttctac gtcagaaagg     420
gcggagccag caaaagaccc gcccccgatg acgcggatat aagcgagccc aagcgggcct     480
gccccctcag tcgcggatcca tcgacgtcag acgcggaagg agctccggtg gactttgccg     540
acaggtacca aaacaaatgt tctcgtcacg cgggcatgct tcagatgctg tttccctgca     600
aaacgtgcga gaaaatgaat cagaatttca acatttgctt cacgcacggg gtcagagact     660
gctcagaatg tttccccggt gcatcagaat ctcaaccggt cgtcagaaaa aaacgtatc      720 agaaactgtg tgccattcat catctgctgg ggcgggcacc cgagattgct tgctcggcct     780
gcgatctggt caacgtggac ctggacgact gtgtttctga gcaataaatg acttaaacca     840
ggtatggctg ccgatggtta tcttccagat tggcttgagg acaacctctc tgagggcatt     900
cgcgagtggt gggacctgaa acctggagcc ccgaaaccca agccaacca gcaaaagcag     960 gacgacggcc ggggtctggt gcttcctggc tacaagtacc tcggacccttt caacggactc    1020 gacaaggggg agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga agagaccggt agagccatca cctcagcgtt ccccgactc ctccacgggc    1320 atcggcaaga aggccacca gcccgcgaga aagagactga actttgggca gactggcgac    1380
tcggagtcag tccccgaccc tcaaccaatc ggagaaccac cagcaggccc ctctggtctg    1440
ggatctggta caatgctgc aggcggtggc gctccaatgg cagacaataa cgaaggcgcc    1500
gacggagtgg gtagttcctc aggaaattgg cattgcgatt ccacatggct gggcgacaga    1560
```

```
gtcatcacca ccagcacccg aacctgggcc ctgcccacct acaacaacca tctctacaag    1620
caaatctcca acgggacatc gggaggaagc actaacgaca acacctactt tggctacagc    1680
accccctggg ggtattttga cttcaacaga ttccactgcc acttctcacc acgtgactgg    1740
cagcgactca tcaacaataa ctggggattc cggcccaaga gactcaactt caagctcttc    1800
aacatccagg tcaaggaggt cacgcagaat gaaggcacca agaccatcgc caataacctt    1860
accagcacga ttcaggtgtt tacgactcg gaataccagc tcccgtacgt ccccggctct    1920
gcgcaccagg gctgcctccc tccgttcccg gcggacgtct tcatgattcc tcagtacggg    1980
tatctgaccc taaacaatgg cagtcaggct gtgggccgtt cctccttcta ctgcctggaa    2040
tacttcccct tctcaaatgc tgaggacggg caacaacttt gaattcagct acaccttcgag    2100 gacgtgcctt ccacagcag ctacgcgcac agccagagcc tggaccggct gatgaaccct    2160
ctcatcgacc agtacctgta ttacttatcc agaactcagt ccacaggagg aactcaaggt    2220
actcagcaat tgttattttc tcaagccggg cccgcaaaca tgtcggctca ggccaagaac    2280
tggctacctg gaccgtgtta ccgtcagcaa cgagtttcca cgacactgtc gcaaaacaac    2340
aacagcaatt ttgcttggac cggtgccacc aagtatcacc tgaatggcag agactccctg    2400
gttaatcccg gcgttgccat ggctacccac aaggacgacg aggagcgctt cttcccgtca    2460
agcggagttc taatgtttgg caagcagggg gctggaaaag acaatgtgga ctacagcagc    2520
gtgatgctca ccagcgaaga gaaaattaaa actactaacc cagtggctac agagcagtat    2580
ggtgtggtgg cagacaacct gcagcagacc aacggagctc ccattgtggg aactgtcaac    2640
agccaggggg ccttacctgg tatggtctgg caaaaccggg acgtgtacct gcagggcccc    2700
atctgggcca aaattcctca cacggacggc aactttcatc cttcgccgct gatgggaggc    2760
tttggactga aacacccgcc tcctcagatc ctggtgaaaa acactcctgt tcctgcggat    2820
cctccgacca ccttcagcca ggccaagctg gcttcttta tcacgcagta cagcaccgga    2880
caggtcagcg tggaaatcga atgggagctg cagaaagaaa acagcaagcg ctggaaccca    2940
gagattcagt atacttccaa ctactacaaa tctacaaatg tggactttgc tgtcaatact    3000
gagggtactt attcagagcc tcgccccatt ggcactcgtt atctcacccg taatctgtaa    3060
ttgcttgtta atcaataaac cggt                                          3084
```

<210> SEQ ID NO 40
<211> LENGTH: 2370
<212> TYPE: DNA
<213> ORGANISM: Unknown
<220> FEATURE:
<223> OTHER INFORMATION: AAV serotype, clone 43.5

<400> SEQUENCE: 40

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga ccccacccc gtgatcgtca cctccaacac caacatgtgc gccgtgattg    240
acgggaacag caccacctc gagcaccagc agccgttgca ggaccggatg ttcaagttcg    300
aactcacccg ccgtctggag cacgactttg gcaaggtgac caagcaggaa gtcaaagagt    360
tcttccgctg ggcgcaggat cacgtgaccg aggtggcgca tgagttctac gtcagaaagg    420
gcggagccag caaaagaccc gcccccgatg acgcggatat aagcgagccc aagcgggcct    480
```

```
gcccctcagt cgcggatcca tcgacgtcag acgcggaagg agctccggtg gactttgccg      540
acaggtacca aaacaaatgt tctcgtcacg cgggcatgct tcagacgctg tttccctgca      600
aaacgtgcga gagaatgaat cagaatttca acatttgctt cacgcacggg gtcagagact      660
gctcagaatg tttccccggt gcatcagaat ctcaaccgt cgtcagaaaa aaacgtatc       720 agaaactgtg tgccattcat catctgctgg ggcgggcacc cgagattgct tgctcggcct      780
gcgatctggt caacgtggac ctggacgact gtgtttctga gcaataaatg acttaaacca      840
ggtatggctg ccgatggtta tcttccagat tggcttgagg acaacctctc tgagggcatt      900
cgcgagtggt gggacctgaa acctggagcc ccgaaaccca agccaaccag caaaagcag      960 gacgacggcc ggggtctggt gcttcctggc tacaagtacc tcggacccytt caacggactc     1020 gacaaggggg agcccgtcaa cgcggcggac gcagcggccc tcgagcacga caaggcctac     1080
gaccagcagc tcaaagcggg tgacaatccg tacctgcggt ataaccacgc cgacgccgag     1140
tttcaggagc gtctgcaaga agatacgtct tttgggggca acctcgggcg agcagtcttc     1200
caggccaaga agcgggttct cgaacctctc ggtctggttg aggaaggcgc taagacggct     1260
cctggaaaga gagaccggt agagccatca cctcagcgtt ccccgactc ctccacgggc      1320 atcggcaaga aaggccacca gcccgcgaga aagagactga actttgggca gactggcgac     1380
tcggagtcag tccccgaccc tcaaccaatc ggagaaccac cagcaggccc ctctggtctg     1440
ggatctggta caatggctgc aggcggtggc gctccaatgg cagacaataa cgaaggcgcc     1500
gacggagtgg gtagttcctc aggaaattgg cattgcgatt ccacatggct gggcgacaga     1560
gtcatcacca ccagcacccg aacctgggcc ctgcccacct acaacaacca tctctacaag     1620
caaatctcca acgggacatc gggaggaagc actaacgaca cacctactt tggctacagc     1680 accccctggg ggtattttga cttcaacaga ttccactgcc acttctcacc acgtgactgg     1740
cagcgactca tcaacaataa ctggggattc cggcccaaga gactcaactt caagctcttc     1800
aacatccagg tcaaggaggt cacgcagaat gaaggcacca gaccatcgc caataacctt     1860 accagcacga ttcaggtgtt tacggactcg gaataccagc tcccgtacgt cctcggctct     1920
gcgcaccagg gctgcctccc tccgttcccg cggacgtct tcatgattcc tcagtacggg     1980
tatctgaccc taaacaatgg cagtcaggct gtgggccgtt cctccttcta ctgcctggaa     2040
tacttccctt ctcaaatgct gaggacgggc aacaactttg aattcagcta caccttcgag     2100
gacgtgcctt tccacagcag ctacgcgcac agccagagcc tggaccggct gatgaaccct     2160
ctcatcgacc agtacctgta ttacttatcc agaactcagt ccacaggagg aactcaaggt     2220
actcagcaat tgttattttc tcaagccggg cccgcaaaca tgtyggctca ggccaagaac     2280
tggctacctg gaccgtgtta ccgtcagcaa cgagtttcca cgacactgtc gcaaaacaac     2340
aacagcaatt tgctggacc ggtgccacca                                      2370
```

<210> SEQ ID NO 41
<211> LENGTH: 3123
<212> TYPE: DNA
<213> ORGANISM: Unknown
<220> FEATURE:
<223> OTHER INFORMATION: AAV serotype, clone 43.12

<400> SEQUENCE: 41

```
gaattcgccc ttggctgcgt caactggacc aatgagaact ttcccttcaa cgattgcgtc       60
gacaagatgt tgatctggtg ggaggagggc aagatgacgg ccaaggtcgt ggagtccgcc      120
aaggccattc tcggcggcag caaggtgcgc gtggaccaaa agtgcaagtc gtccgcccag      180
```

```
atcgacccca cccccgtgat cgtcacctcc aacaccaaca tgtgcgccgt gattgacggg    240
aacagcacca ccttcgagca ccagcagccg ttgcaggacc ggatgttcaa gttcgaactc    300
acccgccgtc tggagcacga ctttggcaag gtgaccaagc aggaagtcaa agagttcttc    360
cgctgggcgc aggatcacgt gaccgaggtg gcgcatgagt tctacgtcag aaagggcgga    420
gccagcaaaa gacccgcccc cgatgacgcg gatataagcg agcccaagcg ggcctgcccc    480
tcagtcgcgg atccatcgac gtcagacgcg aaggagctc cggtggactt tgccgacagg    540
taccaaaaca aatgttctcg tcacgcgggc atgctccaga tgctgtttcc ctgcaaaacg    600
tgcgagagaa tgaatcagaa tttcaacatt tgcttcacgc acggggtcag agactgctca    660
gaatgtttcc ccggtgcatc agaatctcaa ccggtcgtca gaaaaaaaac gtatcagaaa    720
ctgtgtgcca ttcatcatct gctggggcgg gcacccgaga ttgcttgctc ggcctgcgat    780
ctggtcaacg tggacctgga cgactgtgtt tctgagcaat aaatgactta aaccaggtat    840
ggctgccgat ggttatcttc cagattggct tgaggacaac ctctctgagg gcattcgcga    900
gtggtgggac ctgaaacctg agcccccgaa acccaaagcc aaccagcaaa agcaggacga    960
cggccggggt ctggtgcttc ctggctacaa gtacctcgga cccttcaacg gactcgacaa   1020
gggggagccc gtcaacgcgg cggacgcagc ggccctcgag cacgacaagg cctacgacca   1080
gcagctcaaa gcgggtgaca atccgtacct gcggtataac cacgccgacg ccgagtttca   1140
ggagcgtctg caagaagata cgtcttttgg gggcaacctc gggcgagcag tcttccaggc   1200
caagaagcgg gttctcgaac ctctcggtct ggttgaggaa ggcgctaaga cggctcctgg   1260
aaagaagaga ccggtagagc catcacctca gcgttccccc gactcctcca cgggcatcgg   1320
caagaaaggc caccagcccg cgagaaagag actgaacttt gggcagactg gcgactcgga   1380
gtcagtcccc gaccctcaac caatcggaga accaccagca ggccctctg gtctgggatc   1440 tggtacaatg gctgcaggcg gtggcgctcc aatggcagac aataacgaag gcgccgacgg   1500
agtgggtagt tcctcaggaa attggcattg cgattccaca tggctgggcg acagagtcat   1560
caccaccagc acccgaacct gggccctgcc cacctacaac aaccatctct acaagcaaat   1620
ctccaacggg acatcgggag gaagcactaa cgacaacacc tactttggct acagcacccc   1680 ctggggtat tttgacttca acagattcca ctgccacttc tcaccacgtg actggcagcg   1740
actcatcaac aataactggg gattccggcc caagagactc aacttcaagc tcttcaacat   1800
ccaggtcaag gaggtcacgc agaatgaagg caccaagacc atcgccaata accttaccag   1860
cacgattcag gtgtttacgg actcggaata ccagctcccg tacgtcctcg gctctgcgca   1920
ccagggctgc ctcccctccgt tcccggcgga cgtcttcatg attcctcagt acgggtatct   1980
gaccctaaac aatggcagtc aggctgtggg ccgttcctcc ttctactgcc tggaatactt   2040
cccttctcaa atgctgagga cgggcaacaa ctttgaattc agctacacct tcgaggacgt   2100
gcctttccac agcagctacg cgcacagcca gagcctggac cggctgatga ccctctcat   2160 cgaccagtac ctgtattact tatccagaac tcagtccaca ggaggaactc aaggtactca   2220
gcaattgtta ttttctcaag ccgggcccgc aaacatgtcg gctcaggcca gaactggct   2280 acctggaccg tgttaccgtc agcaacgagt ttccacgaca ctgtcgcaaa acaacaacag   2340
caattttgct tggaccggtg ccaccaagta tcacctgaat ggcagagact ccctggttaa   2400
tcccggcgtt gccatggcta cccacaagga cgacgaggag cgcttcttcc cgtcaagcgg   2460
agttctaatg tttggcaagc aggggggctgg aaaagacaat gtggactaca gcagcgtgat   2520
```

-continued

```
gctcaccagc gaagaagaaa ttaaaactac taacccagtg gctacagagc agtatggtgt    2580
ggtggcagac aacctgcagc agaccaacgg agctcccatt gtgggaactg tcaacagcca    2640
gggggcctta cctggtatgg tctggcaaaa ccgggacgtg tacctgcagg gccccatctg    2700
ggccaaaatt cctcacacgg acggcaactt tcatccttcg ccgctgatgg gaggcttttgg   2760 actgaaacac ccgcctcctc agatcctggt gaaaaacact cctgttcctg cggatcctcc    2820
gaccaccttc agccaggcca agctggcttc ttttatcacg cagtacagca ccggacaggt    2880
cagcgtggaa atcgaatggg agctgcagaa agaaaacagc aagcgctgga acccagagat    2940
tcagtatact tccaactact acaaatctac aaatgtggac tttgctgtca atactgaggg    3000
tacttattca gagcctcgcc ccattggcac tcgttatctc acccgtaatc tgtaattgct    3060
tgttaatcaa taaaccggtt aattcgtttc agttgaactt tggtctctgc gaagggcgaa    3120
ttc                                                                   3123
```

<210> SEQ ID NO 42
<211> LENGTH: 3122
<212> TYPE: DNA
<213> ORGANISM: Unknown
<220> FEATURE:
<223> OTHER INFORMATION: AAV serotype, clone 43.20

<400> SEQUENCE: 42

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgtgtgga ccaaaagtgc aagtcttccg     180
cccagatcga tcccaccccc gtgatcgtca cctccaacac caacatgtgc gccgtgattg     240
acgggaacag cgccaccttc gagcaccagc agccgttgca ggaccggatg ttcaaatttg     300
aactcacccg ccgtctggag catgactttg gcaaggtgac gaagcaggaa gtcaaagagt     360
tcttccgctg ggcgcaggat cacgtgaccg aggtggcgca tgagttccac gtcagaaagg     420
gtggagccaa caagagaccc gcccccgatg acgcggatat aagcgagccc aagcgggcct     480
gcccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg tttccccggc gtgtcagaat ctcaaccggt cgtcagaaag aggacgtatc     720
ggaaactctg tgcgattcat catctgctgg ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatt    900
cgcgagtggt gggacttgaa acctggagcc ccgaaaccca agccaaccca gcaaaagcag     960
gacgacggcc ggggtctggt gcttcctggc tacaagtacc tcggaccctt caacggactc    1020
gacaaggggg agcccgtcaa cgcggcggac gcagcggccc tcgagcacga caaagcctac    1080
gaccagcagc tcaaagcggg tgacaatccg tacctgcggt ataatcacgc cgacgccgag    1140
tttcaggagc gtctgcaaga agatacgtct tttgggggca acctcggacg agcagtcttc    1200
caggccaaga agcgggttct cgaacctctc ggtctggttg aggaaggcgc taagacggct    1260
cctggaaaga agagactggt agagcagtcg ccacaagagc cagactcctc ctcgggcatc    1320
ggcaagacag gccagcagcc cgctaaaaag agactcaatt ttggtcagac tggcgactca    1380
gagtcagtcc ccgacccaca acctctcgga gaacctccag cagcccctc aggtctggga    1440
```

```
cctaatacaa tggcttcagg cggtggcgct ccaatggcag acaataacga aggcgccgac    1500
ggagtgggta attcctcggg aaattggcat tgcgattcca catggctggg ggacagagtc    1560
atcaccacca gcacccgaac ctgggccctg cccacctaca acaaccacct ctacaagcaa    1620
atctccaacg gcacctcggg aggaagcacc aacgacaaca cctatttgg ctacagcacc     1680 ccctgggggt attttgactt caacagattc cactgtcact tttcaccacg tgactggcaa    1740
cgactcatca caacaattg gggattccgg cccaaaagac tcaacttcaa gctgttcaac     1800
atccaggtca aggaagtcac gacgaacgaa ggcaccaaga ccatcgccaa taatctcacc    1860
agcaccgtgc aggtctttac ggactcggag taccagttac cgtacgtgct aggatccgct    1920
caccagggat gtctgcctcc gttcccggcg gacgtcttca cggttcctca gtacggctat    1980
ttaactttaa acaatggaag ccaagccctg gacgttcct ccttctactg tctggagtat     2040
ttcccatcgc agatgctgag aaccggcaac aactttcagt tcagctacac cttcgaggac    2100
gtgcctttcc acagcagcta cgcgcacagc cagagcctgg acaggctgat gaatcccctc    2160
atcgaccagt acctgtacta cctggtcaga acgcaaacga ctggaactgg agggacgcag    2220
actctggcat tcagccaagc gggtcctagc tcaatggcca accaggctag aaattgggtg    2280 cccggaccttt gctaccggca gcagcgcgtc tccacgacaa ccaaccagaa caacaacagc    2340
aactttgcct ggacgggagc tgccaagttt aagctgaacg gccgagactc tctaatgaat    2400
ccgggcgtgg caatggcttc ccacaaggat gacgacgacc gcttcttccc ttcgagcggg    2460
gtcctgattt ttggcaagca aggagccggg aacgatggag tggattacag ccaagtgctg    2520
attacagatg aggaagaaat caaggctacc aaccccgtgg ccacagaaga atatgggagca   2580 gtggccatca caaccaggc cgccaatacg caggcgcaga ccggactcgt gcacaaccag     2640
ggggtgattc ccggcatggt gtggcagaat agagacgtgt acctgcaggg tcccatctgg    2700
gccaaaattc ctcacacgga cggcaacttt caccccgtct ccctgatggg cggctttgga    2760
ctgaagcacc cgcctcctca aattctcatc aagaacacac cggttccagc ggacccgccg    2820
cttaccttca accaggccaa gctgaactct ttcatcacgc agtacagcac cggacaggtc    2880
agcgtggaaa tcgagtggga gctgcagaaa gaaaacagca acgctggaa tccagagatt    2940 caatacactt ccaactacta caaatctaca aatgtggact tgctgtcaa cacggaagga    3000 gtttatagcg agcctcgccc cattggcacc cgttacctca cccgcaacct gtaattacat    3060
gttaatcaat aaaccggtta attcgtttca gttgaacttt ggtctctgcg aagggcgaat    3120
tc                                                                   3122
```

<210> SEQ ID NO 43
<211> LENGTH: 3117
<212> TYPE: DNA
<213> ORGANISM: Unknown
<220> FEATURE:
<223> OTHER INFORMATION: AAV serotype, clone 43.21

<400> SEQUENCE: 43

```
gaattcgccc ttggctgcgt caactggacc aatgagaact ttcccttcaa cgattgcgtc     60
gacaagatgg tgatctggtg ggaggagggc aagatgacgg ccaaggtcgt ggagtccgcc    120
aaggccattc tcggcggcag caaggtgcgt gtggaccaaa agtgcaagtc ttccgcccag    180
atcgatccca ccccgtgat cgtcacctcc aacaccaaca tgtgcgccgt gattgacggg      240
aacagcacca ccttcgagca ccagcagccg ttgcaggacc ggatgttcaa atttgaactc    300
```

-continued

```
acccgccgtc tggagcatga ctttggcaag gtgacgaagc aggaagtcaa agagttcttc      360
cgctgggcgc aggatcacgt gaccgaggtg gcgcatgagt tccacgtcag aaagggtgga      420
gccaacaaga gacccgcccc cgatgacgcg gatataagcg agcccaagcg ggcctgcccc      480
tcagtcgcgg atccatcgac gtcagacgcg aaggagctc cggtggactt tgccgacagg       540
taccaaaaca aatgttctcg tcacgcgggc atgcttcaga tgctgtttcc ctgcaagaca      600
tgcgagagaa tgaatcagaa tttcaacatt tgcttcacgc acgggaccag agactgttca      660
gaatgtttcc ccggcgtgtc agaatctcaa ccggtcgtca gaaagaggac gtatcggaaa      720
ctctgtgcga ttcatcatct gctggggcgg gctcccgaga ttgcttgctc ggcctgcgat      780
ctggtcaacg tggacctgga tgactgtgtt tctgagcaat aaatgactta aaccaggtat      840
ggctgccgat ggttatcttc cagattggct cgaggacaac ctctctgagg gcattcgcga      900
gtggtgggac ttgaaacctg agccccgaa acccaaagcc aaccagcaaa agcaggacga      960
cggccgggt ctggtgcttc ctggctacaa gtacctcgga cccttcaacg gactcgacaa      1020
gggggagccc gtcaacgcgg cggacgcagc ggccctcgag cacgacaaag cctacgacca     1080
gcagctcaaa gcgggtgaca atccgtacct gcggtataat cacgccgacg ccgagtttca     1140
ggagcgtctg caagaagata cgtcttttgg gggcaacctc gggcgagcag tcttccaggc     1200
caagaagcgg gttctcgaac ctctcggtct ggttgaggaa ggcgctaaga cggctcctgg     1260
aaagaagaga ccggtagagc agtcgccaca agagccagac tcctcctcgg gcatcggcaa    1320
gacaggccag cagcccgcta aaaagagact caattttggt cagactggcg actcagagtc     1380
agtccccgac ccacaacctc tcggagaacc tccagcagcc ccctcaggtc tgggacctaa     1440
tacaatggct tcaggcggtg gcgctccaat ggcagacaat aacgaaggcg ccgacggagt     1500
gggtaattcc tcgggaaatt ggcattgcga ttccacatgg ctgggggaca gagtcatcac     1560
caccagcacc cgaacctggg ccctgcccac ctacaacaac cacctctaca gcaaatctc    1620
caacggcacc tcgggaggaa gcaccaacga caacacctat ttttggctaca gcacccctg    1680
ggggtatttt gacttcaaca gattccactg tcactttca ccacgtgact ggcaacgact     1740
catcaacaac aattggggat ccggcccaa aagactcaac ttcaagctgt tcaacatcca     1800
ggtcaaggaa gtcacgacga acgaaggcac caagaccatc gccaataatc tcaccagcac     1860
cgtgcgggtc tttacggact cggagtacca gttaccgtac gtgctaggat ccgctcacca     1920
gggatgtctg cctccgttcc cggcggacgt cttcatggtt cctcagtacg ctatttaac     1980
tttaaacaat ggaagccaag ccctgggacg ttcctccttc tactgtctgg agtatttccc     2040
atcgcagatg ctgagaaccg gcaacaactt tcagttcagc tacaccttcg aggacgtgcc     2100
tttccacagc agctacgcgc acagccagag cctggacagg ctgatgaatc ccctcatcga     2160
ccagtacctg tactacctgg tcagaacgca acgactggga actggaggga cgcagactct     2220
ggcattcagc caagcgggtc ctagctcaat ggccaaccag gctagaaatt gggtgcccgg     2280
accttgctac cggcagcagc gcgtctccac gacaaccaac cagagcaaca acagcaactt     2340
tgcctggacg ggagctgcca gtttaagct gaacggccga gactctctaa tgaatccggg     2400
cgtggcaatg gcttcccaca aggatgacga cgaccgcttc ttcccttcga gcggggtcct     2460
gatttttggc aagcaaggag ccgggaacga tggagtggat tacagccaag tgctgattac     2520
agatgaggaa gaaatcaagg ctaccaaccc cgtggccaca aagaatatg agcagtggc      2580
catcaacaac caggccgcca atcgcaggc gcagaccgga ctcgtgcaca accaggggggt    2640
gattcccggc atggtgtggc agaatagaga cgtgtacctg cagggtccca tctgggccaa    2700
```

```
aattcctcac acggacggca actttcaccc gtctcccctg atgggcggct ttggactgaa    2760
gcacccgcct cctcaaattc tcatcaagaa cacaccggtt ccagcggacc cgccgcttac    2820
cttcaaccag gccaagctga actctttcat cacgcagtac agcaccggac aggtcagcgt    2880
ggaaatcgag tgggagctgc agaaagaaaa cagcaaacgc tggaatccag agattcaata    2940
cacttccaac tactacaaat ctacaaatgt ggactttgct gtcaacacgg aaggagttta    3000
tagcgagcct cgccccattg gcacccgtta cctcacccgc aacctgtaat tacatgttaa    3060
tcaataaacc ggttaattcg tttcagttga actttggtct ctgcgaaggg cgaattc      3117
```

<210> SEQ ID NO 44
<211> LENGTH: 3121
<212> TYPE: DNA
<213> ORGANISM: Unknown
<220> FEATURE:
<223> OTHER INFORMATION: AAV serotype, clone 43.23

<400> SEQUENCE: 44

```
gaattcgccc ttctacggct gcgtcaactg gaccaatgag aactttccct tcaacgattg     60
cgtcgacaag atggtgatct ggtgggagga gggcaagatg acggccaagg tcgtggagtc    120
cgccaaggcc attctcggcg gcagcaaggt gcgtgtggac caaaagtgca agtcttccgc    180
ccagatcgat cccaccccg tgatcgtcac ctccaacacc aacatgtgcg ccgtgattga    240
cgggaacagc accaccttcg agcaccagca gccgttgcag gaccggatgt tcaaatttga    300
actcacccgc cgtctggagc atgactttgg caaggtgacg aagcaggaag tcaaagagtt    360
cttccgctgg gcgcaggatc acgtgaccga ggtggcgcat gagttccacg tcagaaaggg    420
tggcgccaac aagagacccg cccccgatga cgcggatata gcgagcccca gcgggcctg    480
cccctcagtc gcggatccat cgacgtcaga cgcggaagga gctccggtgg actttgccga    540
caggtaccaa aacaaatgtt ctcgtcacgc gggcatgctt cagatgctgt ttccctgcaa    600
gacatgcgag agaatgaatc agaatttcaa catttgcttc acgcacggga ccagagactg    660
ttcagaatgt ttccccggcg tgtcagaatc tcaaccggtc gtcagaaaga ggacgtatcg    720
gaaactctgt gcgattcatc atctgctggg gcgggctccc gagattgctt gctcggcctg    780
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacgccg gggtctggtg cttcctggct acaagtacct cggaccttc aacgactcg      1020
acaaggggga gcccgtcaac gcggcggacg cagcggccct cgagcacgac aaagcctacg    1080
accagcagct caaagcgggt gacaatccgt acctgcggta taatcacgcc gacgccgagt    1140
ttcaggagcg tctgcaagaa gatacgtcct ttgggggcaa cctcgggcga gcagtcttcc    1200
aggccaagaa gcgggttctc gaacctctcg gtctggttga ggaaggcgct aagacggctc    1260
ctggaaagaa gagaccggta gagcagtcgc acaagagcc agactcctcc tcgggcatcg    1320
gcaagacagg ccagcagccc gctaaaaaga gactcaattt tggtcagact ggcgactcag    1380
agtcagtccc cgacccacaa cctctcggag aacctccagc agcccctca ggtctgggac    1440
ctaatacaat ggcttcaggc ggtggcgctc aatggcaga caataacgaa ggcgccgacg    1500
gagtgggtaa ttcctcggga aattggcatt gcgattccac atggctgggg gacagagtca    1560
tcaccaccag cacccgaacc tgggccctgc ccacctacaa caaccactc tacaagcaaa    1620
```

-continued

| | |
|---|---|
| tctccaacgg cacctcggga ggaagcacca acgacaacac ctattttggc tacagcaccc | 1680 |
| cctgggggta ttttgacttc aacagattcc actgtcactt ttcaccacgt gactggcaac | 1740 |
| gactcatcaa caacaattgg ggattccggc ccaaaagact caacttcaag ctgttcaaca | 1800 |
| tccaggtcaa ggaagtcacg acgaacgaag gcaccaagac catcgccaat aatctcacca | 1860 |
| gcaccgtgca ggtctttacg gacttggagt accagttacc gtacgtgcta ggatccgctc | 1920 |
| accagggatg tctgcctccg ttcccggcgg acgtcttcat ggttcctcag tacggctatt | 1980 |
| taactttaaa caatggaagc caagccctgg gacgttcctc cttctactgt ctggagtatt | 2040 |
| tcccatcgca gatgccgaga accggcaaca actttcagtt cagctacacc ttcgaggacg | 2100 |
| tgcctttcca cagcagctac gcgcacagcc agagcctgga caggctgatg aatcccctca | 2160 |
| tcgaccagta cctgtactac ctggtcagaa cgcaaacgac tggaactgga gggacgcaga | 2220 |
| ctctggcatt cagccaagcg ggtcctagct caatggccaa ccaggctaga aattgggtgc | 2280 |
| ccggaccttg ctaccggcag cagcgcgtct ccacgacaac caaccagaac aacaacagca | 2340 |
| actttgcctg gacgggagct gccaagttta gctgaacgg ccgagactct ctaatgaatc | 2400 |
| cgggcgtggc aatggcttcc cacaaggatg acgacgaccg cttcttccct tcgagcgggg | 2460 |
| tcctgatttt tggcaagcaa ggagccggga acgatggagt ggattacagc caagtgctga | 2520 |
| ttacagatga ggaagaaatc aaggctacca ccccgtggc cacagaagaa tatggagcag | 2580 |
| tggccatcaa caaccaggcc gccaatacgc aggcgcagac cggactcgtg cacaaccagg | 2640 |
| gggtgattcc cggcatggtg tggcagaata gagacgtgta cctgcagggt cccatctggg | 2700 |
| ccaaaattcc tcacacggac ggcaacttc acccgtctcc cctgatgggc ggctttggac | 2760 |
| tgaagcaccc gcctcctcaa attctcatca gaacacacc ggttccagcg acccgccgc | 2820 |
| ttaccttcaa ccaggccaag ctgaactctt tcatcacgca gtacagcacc ggacaggtca | 2880 |
| gcgtggaaat cgagtgggag ctgcagaaag aaaacagcaa acgctggaat ccagagattc | 2940 |
| aatacacttc caactactac aaatctcaaa atgtggactt tgctgtcaac acggaaggag | 3000 |
| tttatagcga gcctcgcccc attggcaccc gttacctcac ccgcaacctg taattacatg | 3060 |
| ttaatcaata aaccggttaa ttcgtttcag ttgaactttg gtctctgcga agggcgaatt | 3120 |
| c | 3121 |

<210> SEQ ID NO 45
<211> LENGTH: 3122
<212> TYPE: DNA
<213> ORGANISM: Unknown
<220> FEATURE:
<223> OTHER INFORMATION: AAV serotype, clone 43.25

<400> SEQUENCE: 45

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgtgtgga ccaaaagtgc aagtcttccg | 180 |
| cccagatcga tcccacccc gtgatcgtca cctccaacac caacatgtgc gccgtgattg | 240 |
| acgggaacag caccacctc gagcaccagc agccgttgca ggaccggatg ttcaaatttg | 300 |
| aactcacccg ccgtctggag catgactttg gcaaggtgac gaagcaggaa gtcaaagggt | 360 |
| tcttccgctg ggcgcaggat cacgtgaccg aggtggcgca tgagttccac gtgcgagccc | 420 |
| aagcgggcct gccctcagt cgcggatcca tcgacgtcag accagaaagg gtggagccaa | 480 |
| caagagaccc gccccgatg acgcggatat aagcggaagg agctccggtg gactttgccg | 540 |

```
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgcgattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaacca gcaaaagcag     960 gacgacggcc ggggtctggt gcttcctggc tacaagtacc tcggacccctt caacggactc   1020 gacaagggg agcccgtcaa cgcggcggac gcagcggccc tcgagcacga caaagcctac    1080
gaccagcagc tcaaagcggg tgacaatccg tacctgcgt ataatcacgc cgacgccgag    1140
tttcaggagc gtctgcaaga agatacgtct ttgggggca acctcgggcg agcagtcttc    1200
caggccaaga agcgggttct cgaacctctc ggtctggttg aggaaggcgc taagacggct    1260
cctggaaaga agagaccggt agagcagtcg ccacaagagc cagactcctc ctcgggcatc    1320
ggcaagacag gccagcagcc cgctaaaaag agactcaatt ttggtcagac tggcgactca    1380
gagtcagtcc ccgacccaca acctctcgga gaacctccag cagcccctc aggtctggga     1440 cctaatacaa tggcttcagg cggtggcgct ccaatggcag acaataacga aggcgccgac    1500
ggagtgggta attcctcggg aaattggcat tgcgattcca catggctggg ggacagagtc    1560
atcaccacca gcacccgaac ctgggccctg cccacctaca caaccaccct ctacaagcaa    1620
atctccaacg gcacctcggg aggaagcacc aacgacaaca cctattttgg ctacagcacc    1680
ccctgggggt attttgactt caacagattc cactgtcact tttcaccacg tgactggcaa    1740
cgactcatca acaacaattg gggattccgg cccaaaagac tcaacttcaa gctgttcaac    1800
atccaggtca aggaagtcac gacgaacgaa ggcaccaaga ccatcgccaa taatctcacc    1860
agcaccgtgc aggtctttac ggactcggag taccagttac cgtacgtgct aggatccgct    1920
caccagggat gtctgcctcc gttcccggcg gacgtcttca tggttcctca gtacggctat    1980
ttaactttaa acaatggaag ccaagccctg ggacgttcct ccttctactg tctggagtat    2040
ttcccatcgc agatgctgag aaccggcaac aactttcagt tcagctacac cttcgaggac    2100 gtgccttttcc acagcagcta cgcgcacagc cagagcctgg acaggctgat gaatcccctc    2160
atcgaccagt acctgtacta cctggtcaga acgcaaacga ctggaactgg agggacgcag    2220
actctggcat tcagccaagc gggtcctagc tcaatggcca accaggctag aaattgggtg    2280
cccggacctt gctaccggca gcagcgcgtc tccacgacaa ccaaccagaa caacaacagc    2340
aactttgcct ggacgggagc tgccaagttt aagctgaacg gccgagactc tctaatgaat    2400
ccgggcgtgg caatggcttc ccacaaggat gacgacgacc gcttcttccc ttcgagcggg    2460
gtcctgattt ttggcaagca aggagccggg aacgatggag tggattacag ccaagtgctg    2520
attacagatg aggaagaaat caaggctacc aaccccgtgg ccacagaaga atatggagca    2580
gtggccatca caaccaggc cgccaatacg caggcgcaga ccggactcgt gcacaaccag    2640
ggggtgattc ccgcatggt gtggcagaat agagacgtgt acctgcaggg tcccatctgg    2700
gccaaaattc ctcacacgga cggcaacttt caccccgtctc ccctgatggg cggctttgga    2760
ctgaagcacc cgcctcctca aattctcatc aagaacacac cggttccagc ggacccgccg    2820
cttaccttca accaggccaa gctgaactct ttcatcacgc agtacagcac cggacaggtc    2880
```

```
agcgtggaaa tcgagtggga gctgcagaaa gaaaacagca aacgctggaa tccagagatt    2940
caatacactt ccaactacta caaatctaca aatgtggact ttgctgtcaa cacggagggg    3000
gtttatagcg agcctcgccc cattggcacc cgttacctca cccgcaacct gtaattacat    3060
gttaatcaat aaaccggtta attcgtttca gttgaacttt ggtctctgcg aagggcgaat    3120
tc                                                                   3122

<210> SEQ ID NO 46
<211> LENGTH: 3128
<212> TYPE: DNA
<213> ORGANISM: Unknown
<220> FEATURE:
<223> OTHER INFORMATION: AAV serotype, clone 44.1

<400> SEQUENCE: 46
gaattcgccc tttctacggc tgcgtcaact ggaccaatga gaactttccc ttcaacgatt      60
gcgtcgacaa gatgttgatc tggtgggagg agggcaagat gacggccaag gtcgtggagt     120
ccgccaaggc cattctcggc ggcagcaaag tgcgcgtgga ccaaaagtgc aagccgtccg     180
cccagatcga ccccaccccc gtgatcgtca cctccaacac caacatgtgc gccgtgattg     240
acgggaacag caccaccttc gagcaccagc agccgttgcg ggaccggatg ttcaagtttg     300
aactcacccg ccgtctggag cacgactttg gcaaggtgac aaagcaggaa gtcagagagt     360
tcttccgctg ggcgcaggat cacgtgaccg aggtggcgca cgagttctac gtcagaaagg     420
gtggagccaa caagagaccc gcccccgatg acgcggataa aagcgagccc aagcgggcct     480
gcccctcagt cgcggatcca tcgacgtcag acgcggaagg agctccggtg gactttgccg     540
acaggtacca aaacaaatgt tctcgtcacg cgggcatgct tcagatgctg tttcccctgca    600 aaacatgcga gagaatgaat cagaatttca acatttgctt cacgcacggg accagagact    660
gttcagaatg tttccccggc gtgtcagaat ctcaaccggt cgtcagaaaa aagacgtatc    720
ggaaactctg tgcgattcat catctgctgg ggcgggcacc cgagattgct tgctcggcct    780
gcgatctggt caacgtggac ctagatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc cgaaacccaa agccaacca gcaaaagcag    960 gacgacggcc ggggtctggt gcttcctggc tacaagtacc tcggacccct caacggactc   1020 gacaagggg agcccgtcaa cgcggcggac gcagcggccc tcgagcacga caaggcctac   1080
gaccagcagc tcaaagcggg tgacaatccg tacctgcgt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctggaaaga gagaccgggt agagccatca ccccagcgtt ctccagactc tctacgggc    1320 atcggcaaga aggccagca gcccgcgaaa aagagactca actttgggca gactggcgac   1380
tcagagtcag tgcccgaccc tcaaccaatc ggagaaccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca cgggacttc gggaggaagc accaacgaca cacctactt cggctacagc   1680 accccctggg ggtattttga ctttaacaga ttccactgcc acttctcacc acgtgactgg   1740
cagcgactca tcaacaacaa ctggggattc cggcccaaga gactcaactt caagctcttc   1800
```

```
aacatccagg tcaaggaggt cacgcagaat gaaggcacca agaccatcgc caataacctt    1860
accagcacga ttcaggtctt tacggactcg gaataccagc tcccgtacgt cctcggctct    1920
gcgcaccagg gctgcctgcc tccgttcccg gcggacgtct tcatgattcc tcagtacggg    1980
tacctgactc tgaacaatgg cagtcaggcc gtgggccgtt cctccttcta ctgcctggag    2040
tactttcctt ctcaaatgct gagaacgggc aacaactttg agttcagcta ccagtttgag    2100
gacgtgcctt tcacagcag ctacgcgcac agccaaagcc tggaccggct gatgaacccc    2160
ctcatcgacc agtacctgta ctacctgtct cggactcagt ccacgggagg taccgcagga    2220
actcagcagt tgctatttc tcaggccggg cctaataaca tgtcggctca ggccaaaaac    2280
tggctacccg ggccctgcta ccggcagcaa cgcgtctcca cgacactgtc gcaaaataac    2340
aacagcaact gtaaatcccg tgtcgctat ggcaacccac aaggacgacg aagagcgatt    2400
ttgcctggac cggtgccacc aagtatcatc tgaatggcag agactctctg ttttccgtcc    2460
agcggagtct taatgtttgg gaaacaggga gctggaaaag acaacgtgga ctatagcagc    2520
gttatgctaa ccagtgagga agaaattaaa accaccaacc cagtggccac ggaacagtac    2580
ggcgtggtgg ccgataaccct gcaacagcaa acgccgctc ctattgtagg ggccgtcaac    2640
agtcaaggag ccttacctgg catggtctgg cagaaccggg acgtgtacct gcagggtcct    2700
atctgggcca agattcctca cacggacgga aactttcatc cctcgccgct gatgggaggc    2760
tttggactga acacccgcc tcctcagatc ctgattaaga atacacctgt tcccgcggat    2820
cctccaacta ccttcagtca agctaagctg cgtcgttca tcacgcagta cagcaccgga    2880
caggtcagcg tggaaattga atgggagctg cagaaagaaa acagcaaacg ctggaaccca    2940
gagattcaat acacttccaa ctactacaaa tctacaaatg tggacttcgc tgttaacaca    3000
gatggcactt attctgagcc tcgccccatt ggcacccgtt acctcacccg taatctgtaa    3060
ttgctcgtta atcaataaac cggttgattc gtttcagttg aactttggtc tctgcgaagg    3120
gcgaattc                                                             3128
```

<210> SEQ ID NO 47
<211> LENGTH: 3128
<212> TYPE: DNA
<213> ORGANISM: Unknown
<220> FEATURE:
<223> OTHER INFORMATION: AAV serotype, clone 44.5

<400> SEQUENCE: 47

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaaag tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttgca ggaccggatg ttcaagtttg     300
aactcacccg ccgtctggag cacgactttg gcaaggtgac aaagcaggaa gtcagagagt     360
tcttccgctg ggcgcaggat cacgtgaccg aggtggcgca cgagttctac gtcagaaagg     420
gtggagccaa caagagaccc gcccccgatg acgcggataa agcgagccc aagcgggcct     480 gcccctcagt cgcggatcca tcgacgtcag acgcggaagg agctccggtg gactttgccg     540 acagtacca aaacaaatgt tctcgtcacg cgggcatgct tcagatgctg tttccctgca     600
aaacatgcga gagaatgaat cagaatttca acatttgctt cacgcacggg accagagact     660
```

```
gttcagaatg tttccccggc gtgtcagaat ctcaaccggt tgtcagaaaa aagacgtatc    720
ggaaactctg tgcgattcat catctgctgg ggcgggcacc cgagattgct tgctcggcct    780
gcgatctggt caacgtggac ctagatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca aagccaacca gcaaaagcag    960
gacgacggcc ggggtctggt gcttcctggc tacaagtacc tcggacccct caacggactc   1020
gacaagggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagccatca ccccagcgtt ctccagactc ctctacgggc   1320
atcggcaaga aaggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacttc gggaggaagc accaacgaca cacctactt cggctacagc   1680
acccccgggg gtatttttga ctttaacaga ttccactgcc acttctcacc acgtgactgg   1740
cagcgactca tcaacaacaa ctggggattc cggcccaaga gacccaactt caagctcttc   1800
aacatccagg tcaaggaggt cacgcagaat gaaggcacca agaccatcgc caataacctt   1860
accagcacga ttcaggtctt tacggactcg gaataccagc tcccgtacgt cctcggctct   1920
gcgcaccagg gctgcctgcc tccgttcccg gcggacgtct tcatgattcc tcagtacggg   1980
tacctgactc tgaacaatgg cagtcaggcc gtgggccgtt cctccttcta ctgcctggag   2040
tactttcctt ctcaaatgct gagaacgggc aacaactttg agttcagcta ccagtttgag   2100
gacgtgcctt tcacagcag ctacgcgcac agccaaagcc tggaccggct gatgaacccc   2160
ctcatcgacc agtacctgta ctacctgtct cggactcagt ccacgggagg taccgcagga   2220
actcagcagt tgcctatttc tcaggccggg cctaataaca tgtcggctca ggccaaaaac   2280
tggctacccg ggcctgcta ccggcagcaa cgcgtctcca cgacactgtc gcaaaataac   2340
aacagcaact tgcctggac cggtgccacc aagtatcatc tgaatggcag agactctctg   2400
gtaaatcccg gtgtcgctat ggcaacccac aaggacgacg aagagcgatt ttttccgtcc   2460
agcggagtct taatgtttgg gaaacaggga gctggaaaag acaacgtgga ctatagcagc   2520
gttatgctaa ccagtgagga gaaaattaaa accaccaacc cagtggccac agaacagtac   2580
ggcgtggtgg ccgataacct gcaacagcaa acgccgctc ctattgtagg ggccgtcaac   2640
agtcaaggag ccttacctgg catggtctgg cagaaccggg acgtgtacct gcagggtcct   2700
atctgggcca agattcctca cacggacgga aactttcatc cctcgccgct gatgggaggc   2760
tttggactga aacacccgcc tcctcagatc ctgattaaga atacacctgt tcccgcggat   2820
cctccaacta ccttcagtca agctaagctg gcgtcgttca tcacgcagta cagcaccgga   2880
caggtcagcg tggaaattga atgggagctg cagaaagaaa acagcaaacg ctggaaccca   2940
gagattcaat acacttccaa ctactacaaa tctacaaatg tggactttgc tgttaacaca   3000
gatggcactt attctgagcc tcgcccccatt ggcacccgtt acctcacccg taatctgtaa   3060
```

-continued

```
ttgcttgtta atcaataaac cggttgattc gtttcagttg aactttggtc tctgcgaagg   3120
gcgaattc                                                             3128
```

<210> SEQ ID NO 48
<211> LENGTH: 1933
<212> TYPE: DNA
<213> ORGANISM: Unknown
<220> FEATURE:
<223> OTHER INFORMATION: AAV serotype, clone 223.10
<220> FEATURE:
<221> NAME/KEY: misc_feature
<222> LOCATION: (1302)..(1302)
<223> OTHER INFORMATION: can be a, c, g or t

<400> SEQUENCE: 48

```
caaggcctac gaccagcagc tcaaagcggg tgacaatccg tacctgcggt ataaccacgc     60
cgacgccgag tttcaggagc gtcttcaaga agatacgtct tttggggca acctcgggcg    120 agcagtcttc caggccaaaa agcgggttct cgaacctctt ggtctggttg agacgccagc    180
taagacggca cctggaaaga agcgaccggt agactcgcca gactccacct cgggcatcgg    240
caagaaaggc cagcagcccg cgaaaaagag actcaacttt gggcagactg gcgactcaga    300
gtcagtcccc gaccctcaac caatcggaga accaccagca ggcccctctg gtctgggatc    360
tggtacaatg gctgcaggcg gtggcgcacc aatggctgac aataacgagg gcgccgacgg    420
agtgggtaat gcctcaggaa attggcattg cgattccaca tggctgggcg acagagtcat    480
caccaccagc acccgaacct gggcctgcc cacctacaac aaccacctct acaagcaaat    540
ctccagtcag tcagcaggga gcaccaacga taacgtctat ttcggctaca gcaccccctg    600
ggggtatttt gacttcaaca gattccattg ccacttctca ccacgtgact ggcagcgact    660
tatcaacaac aactggggat ccggcccaa gaagctcaac ttcaagctct caacatcca    720 ggtcaaggag gtcacgacga atgacggtgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
ttctcagatg ctgagaacgg gcaacaactt cacctttagc tacaccttcg aggacgtgcc   1020
tttccacagc agctacgcgc acagccgag tctggaccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat gnaagaaatt cattggttaa   1320 tccccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acgggattgt   1500
aagcagcaac ttgcaggcgg ctagcaccgc agcccagaca caagttgtta acaaccaggg   1560
agccttacct ggcatggtct ggcagaaccg ggacgtgtac ctgcaaggtc ccatttgggc   1620
caagattcct cacacggacg gcaactttca cccgtctcct ctaatgggtg gctttggact   1680
gaaacacccg cctccccaga tcctgatcaa aaacacaccg gtacctgcta atcctccaga   1740
agtgtttact cctgccaagt ttgcttcctt catcacgcag tacagcaccg ggcaagtcag   1800
```

```
cgttgagatc gagtgggagc tgcagaaaga gaacagcaag cgctggaacc cagagattca    1860
gtacacctcc aactttgaca aacagactgg agtggacttt gctgttgaca gccagggtgt    1920
ttactctgag cct                                                       1933

<210> SEQ ID NO 49
<211> LENGTH: 1933
<212> TYPE: DNA
<213> ORGANISM: Unknown
<220> FEATURE:
<223> OTHER INFORMATION: AAV serotype, clone 223.2

<400> SEQUENCE: 49
caaggcctac gaccagcagc tcaaagcggg tgacaatccg tacctgcggt ataaccacgc      60
cgacgccgag tttcaggagt gtcttcaaga agatacgtct tttgggggca acctcgggcg     120
agcagtcttc caggccaaaa agcgggttct cgaacctctt ggtctggttg agacgccagc     180
taagacggca cctggaaaga agcgaccggt agactcgcca gactccacct cgggcatcgg     240
caagaaaggc cagcagcccg cgaaaaagag actcaacttt gggcagactg gcgactcaga     300
gtcagtcccc gaccctcaac caatcggaga accaccagca ggcccctctg gtctgggatc     360
tggtacaatg gttgcaggcg gtggcgcacc aatggctgac aataacgagg cgccgacgg      420 agtgggtaat gcctcaggaa attggcattg cgattccaca tggctgggcg acagagtcat     480
caccaccagc acccgaacct gggcctgcc cacctacaac aaccacctct acaagcaaat      540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat tccggcccaa gaagctcaac ttcaagctct tcaacatcca     720
ggtcaaggag gtcacgacga atgacggtgt cacaaccatc gctaataacc ttaccagcac     780
ggttcaggtc ttttcggact cggaatatca actgccgtac gtcctcggct ccgcgcacca     840
gggctgcctg cctccgttcc cggcagacgt gttcatgatt ccgcagtacg gatacctgac     900
tctgaacaat ggcagccaat cggtaggccg ttcctccttc tactgcctgg agtactttcc     960
ttctcagatg ctgagaacgg gcaacaactt cacctttagc tacaccttcg aggacgtgcc    1020
tttccacagc agctacgcgc acagccagag tctggaccgg ctgatgaatc ccctcatcga    1080
ccagtacctg tactacttgg ccagaacaca gagcaacgca ggaggtactg ctggcaatcg    1140
ggaactgcag ttttatcagg gcggacctac caccatggcc gaacaagcaa agaactggct    1200
gcccggacct tgcttccggc aacagagagt atccaagacg ctggatcaaa ataacaacag    1260
caactttgcc tggactggtg ccacaaaata ccatttaaat ggaagaaatt cattggttaa    1320
tcccggtgtc gccatggcaa cccacaagga cgacgaggaa cgcttctccc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acggggattgt    1500 aagcagcaac ttgcaggcgg ctagcaccgc agcccagaca caagttgtta acaaccaggg    1560
agccttacct ggcatggtct ggcagaaccg ggacgtgtac ctgcaaggtc ccatttgggc    1620
caagattcct cacacggacg gcaactttca cccgtctcct ctaatgggtg ctttggact     1680 gaaacacccg cctccccaga tcctgatcaa aaacacgccg gtacctgcta atcctccaga    1740
agtgtttact cctgccaagt ttgcttcctt catcacgcag tacagcaccg gcaagtcag     1800 cgttgagatc gagtgggagc tgcagaaaga gaacagcaag cgctggaacc cagagattca    1860
gtacacctcc aactttgaca aacagactgg agtggacttt gctgttgaca gccagggtgt    1920
```
ttactctgag cct                                                          1933

<210> SEQ ID NO 50
<211> LENGTH: 1933
<212> TYPE: DNA
<213> ORGANISM: Unknown
<220> FEATURE:
<223> OTHER INFORMATION: AAV serotype, clone 223.4

<400> SEQUENCE: 50
caaggcctac gaccagcagc tcaaagcggg tgacaatccg tacctgcggt ataaccacgc        60
cgacgccgag tttcaggagc gtcttcaaga agatacgtct tttgggggca acctcgggcg       120
agcagtcttc caggccaaaa agcgggttct cgaacctctt ggtctggttg agacgccagc       180
taagacggca cctggaaaga agcgaccggt agactcgcca gactccacct cgggcatcgg       240
caagaaaggc cagcagcccg cgaaaaagag actcaacttt gggcagactg gcgactcaga       300
gccagtcccc gaccctcaac caatcggaga accaccagca ggcccctctg gtctgggatc       360
tggtacaatg gctgcaggcg gtggcgcacc aatggctgac aataacgagg cgccgacgg        420
agtgggtaat gcctcaggaa attggcattg cgattccaca cggctgggcg acagagtcat       480
caccaccagc acccgaacct gggccctgcc cacctacaac aaccacctct acaagcaaat       540
ctccagtcag tcagcaggga gcaccaacga taacgtctat ttcggctaca gcacccctg       600
ggggtattt gacttcaaca gattccattg ccacttctca ccacgtgact ggcagcgact       660
tatcaacaac aactgggat ccggcccaa gaagctcaac ttcaagctct caacatcca       720
ggtcaaggag gtcacgacga tgacggcgt cacaaccatc gctaataacc ttaccagcac       780
ggttcaggtc ttttcggact cggaatatca actgccgtac gtcctcggct ccgcgcacca       840
gggctgcctg cctccgttcc cggcagacgt gttcatgatt ccgcagtacg atacctgac       900
tctgaacaat ggcagccaat cggtaggccg ttcctccttc tactgcctgg agtactttcc       960
ttctcagatg ctgagaacgg gcaacaactt cacctttagc tacaccttcg aggacgtgcc      1020
tttccacagc agctacgcgc acagccagag tctgggccgg ctgatgaatc ccctcatcga      1080
ccagtacctg tactacttgg ccagaacaca gagcaacgca ggaggtactg ctggcaatcg      1140
ggaactgcag ttttatcagg cggacctac accatggcc gaacaagcaa agaactggct       1200
gccccggacct tgcttccggc aacagagagt atccaagacg ctggatcaaa ataacaacag      1260
caactttgcc tggactggtg ccacaaaata ccatttaaat ggaagaaatt cattggttaa      1320
tcccggtgtc gccatggcaa cccacaagga cgacgaggaa cgcttcttcc cttcgagcgg      1380
agttctaatt tttggcaaaa ctggagcagc taataaaact acattagaaa acgtgctcat      1440
gacaaatgaa gaagaaattc gtcctaccaa cccggtagct accgaggaat acgggattgt      1500
aagcagcaac ttgcaggcgg ctagcaccgc agcccagaca caagttgtta caaccagg       1560
agccttacct ggcatggtct ggcagaaccg ggacgtgtac ctgcaaggtc ccatttgggc      1620
caagattcct cacacggacg gcaactttca cccgtctcct ctaatgggtg ctttggact       1680
gaaacacccg cctcccagae tcctgatcaa aaacacaccg gtacctgcta atcctccaga      1740
agtgtttact cctgccaagt tgcttccctt catcacgcag tacagcaccg ggcaagtcag      1800
cgttgagatc gaatgggagc tgcagaaaga aaacagcaag cgctggaacc cagagattca      1860
gtacaccctcc aactttgaca aacagactgg agtggacttt gctgttgaca gccagggtgt      1920
ttactctgag cct                                                         1933

<210> SEQ ID NO 51
<211> LENGTH: 1933
<212> TYPE: DNA
<213> ORGANISM: Unknown
<220> FEATURE:
<223> OTHER INFORMATION: AAV serotype, clone 223.5

<400> SEQUENCE: 51

```
caaggcctac gaccagcagc tcaaagcggg tgacaatccg tacctgcggt ataaccacgc      60
cgacgccgag tttcaggagc gtcttcaaga agatacgtct tttggggca  acctcgggcg     120
agcagtcttc caggccaaaa agcgggttct cgaacctctt ggtctggttg agacgccagc     180
taagacggca cctggaaaga agcgaccggt agactcgcca gactccacct cgggcatcgg     240
caagaaaggc cagcagcccg cgaaaaagag actcaacttt gggcagactg gcgactcaga     300
gccagtcccc gaccctcaac caatcggaga accaccagca ggcccctctg gtctgggatc     360
tggtacaatg gctgcaggcg gtggcgcacc aatggctgac aataacgagg cgccgacgg      420
agtgggtaat gcctcaggaa attggcattg cgattccaca cggctgggcg acagagtcat     480
caccaccagc acccgaacct gggccctgcc cacctacaac aaccacctct acaagcaaat     540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat ccggcccaa gaagctcaac ttcaagctct caacatcca      720
ggtcaaggag gtcacgacga tgacggcgt cacaaccatc gctaataacc ttaccagcac     780
ggttcaggtc ttttcggact cggaatatca actgccgtac gtcctcggct ccgcgcacca     840
gggctgcctg cctccgttcc cggcagacgt gttcatgatt ccgcagtacg atacctgac     900
tctgaacaat ggcagccaat cggtaggccg ttcctccttc tactgcctgg agtactttcc     960
ttctcagatg ctgagaacgg caacaacttt caccttttagc tacaccttcg aggacgtgcc    1020
tttccacagc agctacgcgc acagccgag  tctgggccgg ctgatgaatc ccctcatcga    1080
ccagtacctg tactacttgg ccagaacaca gagcaacgca ggaggtactg ctggcaatcg    1140
ggaactgcag ttttatcagg gcggacctac caccatggcc gaacaagcaa agaactggct    1200
gcccggacct tgcttccggc aacagagagt atccaagacg ctggatcaaa ataacaacag    1260
caactttgcc tggactggtg ccacaaaata ccatttaaat ggaagaaatt cattggttaa    1320
tcccggtgtc gccatggcaa cccacaagga cgacgaggaa cgcttcttcc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acgggattgt    1500
aagcagcaac ttgcaggcgg ctagcaccgc agcccagaca caagttgtta acaaccaggg    1560
agccttacct ggcatggtct ggcagaaccg ggacgtgtac ctgcaaggtc ccatttgggc    1620
caagattcct cacacggacg gcaactttca cccgtctcct ctaatgggtg gctttggact    1680
gaaacacccg cctccccaga tcctgatcaa aaacacaccg gtacctgcta atcctccaga    1740
agtgtttact cctgccaagt ttgcttcctt catcacgcag tacagcaccg gcaagtcag     1800
cgttgagatc gaatgggagc tgcagaaaga aacagcaag  cgctggaacc cagagattca    1860
gtacacctcc aactttgaca acagactgg  agtggacttt gctgttgaca gccagggtgt    1920
ttactctgag cct                                                        1933
```

<210> SEQ ID NO 52
<211> LENGTH: 1933

<212> TYPE: DNA
<213> ORGANISM: Unknown
<220> FEATURE:
<223> OTHER INFORMATION: AAV serotype, clone 223.6

<400> SEQUENCE: 52

```
caaggcctac gaccagcagc tcaaagcggg tgacaatccg tacctgcggt ataaccacgc      60
cgacgccgag tttcaggagc gtcttcaaga agatacgtct tttgggggca acctcgggcg     120
agcagtcttc caggccaaaa agcgggttct cgaacctctt ggtctggttg agacgccagc     180
taagacggca cctggaaaga agcgaccggt agactcgcca gactccacct cgggcatcgg     240
caagaaaggc cagcagcccg cgaaaaagag actcaacttt gggcagactg gcgactcaga     300
gtcagtcccc gaccctcaac caatcggaga accaccagca ggcccctctg gtctgggatc     360
tggtacaatg gctgcaggcg gtggcgcacc aatggctgac aatagcgagg gcgccgacgg     420
agtgggtaat gcctcaggaa attggcattg cgattccaca tggctgggcg acagagtcat     480
caccaccagc acccgaacct gggccctgcc cacctacaac aaccacctct acaagcaaat     540
ctccagtcag tcagcaggga gcaccaacga taacgtctat ttcggctaca gcaccccctg     600
ggggtatttt gacttcaaca gattccattg ccacttctca ccacgtgact ggcagcgact     660
tatcaacaac aactggggat tccggcccaa gaagctcaac ttcaagctct caacatcca     720
ggtcaaggag gtcacgacga atgacggtgt cacaaccatc gctaataacc ttaccagcac     780
ggttcaggtc ttttcggact cggaatatca actgccgtac gtcctcggct ccgcgcacca     840
gggctgcctg cctccgttcc cggcagacgt gttcatgatt ccgcagtacg gatacctgac     900
tctgaacaat ggcagccaat cggtaggccg ttcctccttc tactgcctgg agtactttcc     960
ttctcagatg ctgagaacgg gcaacaactt cacctttagc tacaccttcg aggacgtgcc    1020
tttccacagc agctacgcgc acagccagag tctggaccgg ctgatgaatc ccctcatcga    1080
ccagtacctg tactacttgg ccagaacaca gagcaacgca ggaggtactg ctggcaatcg    1140
ggaactgcag ttttatcagg gcggacctac caccatggcc gaacaagcaa agaactggct    1200
gcccggacct tgcttccggc aacagagagt atccaagacg ctggatcaaa ataacaacag    1260
caactttgcc tggactggtg ccacaaaata ccatttaaat ggaagaaatt cattggttaa    1320
tcccggtgtc gccatggcaa cccacaagga cgacgaggaa cgcttcttcc cttcgagcgg    1380
agttctaatt tttggcaaaa ctggagcagc taataaaact acattagaaa acgtgctcat    1440
gacaaatgaa gaagaaattc gtcctaccaa cccggtagct accgaggaat acgggattgt    1500
aagcagcaac ttgcaggcgg ctagcaccgc agcccagaca caagttgtta acaaccaggg    1560
agccttacct ggcatggtct ggcagaaccg ggacgtgtac ctgcaaggtc ccatttgggc    1620
caagattcct cacacggacg gcaactttca cccgtctcct ctaatgggtg ctttggact    1680
gaaacacccg cctccccaga tcctgatcaa aaacacaccg gtacctgcta atcctccaga    1740
agtgtttact cctgccaagc ttgcttcctt catcacgcag tacagcaccg ggcaagtcag    1800
cgttgagatc gagtgggagc tgcagaaaga aaacagcaag cgctggaacc cagagattca    1860
gtacacctcc aactttgaca aacagactgg agtggacttt gctgttgaca gccagggtgt    1920
ttactctgag cct                                                       1933
```

<210> SEQ ID NO 53
<211> LENGTH: 1933
<212> TYPE: DNA
<213> ORGANISM: Unknown
<220> FEATURE:

<223> OTHER INFORMATION: AAV serotype, clone 223.7

<400> SEQUENCE: 53

```
caaggcctac gaccagcagc tcaaagcggg tgacaatccg tacctgcggt ataaccacgc    60
cgacgccgag tttcaggagc gtcttcaaga agatacgtct tttggggggca acctcgggcg   120
agcagtcttc caggccaaaa agcgggttct cgaacctctt ggtctggttg agacgccagc   180
taagacggca cctggaaaga agcgaccggt agactcgcca gactccacct cgggcatcgg   240
caagaaaggc cagcagcccg cgaaaaagag actcaacttt gggcagactg gcgactcaga   300
gtcagtcccc gaccctcaac caatcggaga accaccagca ggcccctctg gtctgggatc   360
tggtacaatg gctgcaggcg gtggcgcacc aatggctgac aataacgagg gcgccgacgg   420
agtgggtaat gcctcaggaa attggcattg cgattccaca tggctgggcg acagagtcat   480
caccaccagc acccgaacct gggccctgcc cacctacaac aaccacctct acaagcaaat   540
ctccagtcag tcagcaggga gcaccaacga taacgtctat ttcggctaca gcaccccctg   600
ggggtatttt gacttcaaca gattccattg ccacttctca ccacgtgact ggcagcgact   660
tatcaacaac aactggggat tccggcccaa gaagctcaac ttcaagctct tcaacatcca   720
ggtcaaggag gtcacgacga atgacggcgt cacaaccatc gctaataacc ttaccagcac   780
ggttcaggtc tttttcggacc cggaatatca actgccgtac gtcctcggct ccgcgcacca   840
gggctgcctg cctccgttcc cggcagacgt gttcatgatt ccgcagtacg gatacctgac   900
tctgaacaat ggcagccaat cggtaggccg ttcctccttc tactgcctgg agtactttcc   960
ttctcagatg ctgagaacgg gcaacaactt cacctttagc tacaccttcg aggacgtgcc  1020
tttccacagc agctacgcgc acagccagag tctggaccgg ctgatgaatc ccctcatcga  1080
ccagtacctg tactacttgg ccagaacaca gagcaacgca ggaggtactg ctggcaatcg  1140
ggaactgcag ttttatcagg gcggacctac caccatggcc gaacaagcaa agaactggct  1200
gcccggacct tgcttccggc aacagagagt atccaagacg ctggatcaaa ataacaacag  1260
caactttgcc tggactggtg ccacaaaata ccatttaaat ggaagaaatt cattggttaa  1320
tcccggtgtc gccatggcaa cccacaagga cgacgaggaa cgcttcttcc cttcgagcgg  1380
agttctaatt tttggcaaaa ctggagcagc taataaaact acattagaaa acgtgctcat  1440
gacaaatgaa gaagaaattc gtcctaccaa cccggtagct accgaggaat acgggattgt  1500
aagcagcaac ttgcaggcgg ctagcaccgc agcccagaca caagttgtta acaaccaggg  1560
agccttacct ggcatggtct ggcagaaccg ggacgtgtac ctgcaaggtc ccatttgggc  1620
caagattcct cacacggacg gcaactttca cccgtctcct ctaatgggtg gctttggact  1680
gaaacacccg cctccccaga tcctgatcaa aaacacaccg gtacctgcta atcctccaga  1740
agtgtttact cctgccaaga ttgcttcctt catcacgcag tacagcaccg gcaagtcag   1800
cgttgagatc gagtgggagc tgcagaaaga gaacagcaag cgctggaacc cagagattca  1860
gtacacctcc aactttgaca aacagactgg agtggacttt gctgttgaca gccagggtgt  1920
ttactctgag cct                                                     1933
```

<210> SEQ ID NO 54
<211> LENGTH: 3123
<212> TYPE: DNA
<213> ORGANISM: Unknown
<220> FEATURE:
<223> OTHER INFORMATION: AAV serotype, clone A3.4

<400> SEQUENCE: 54

-continued

```
gaattcgccc tttctacggc tgcgtcaact ggaccaatga aaactttccc ttcaacgatt        60
gcgtcgacaa gatggtgatc tggtgggagg agggaaagat gaccgccaag gtcgtggaat       120
ctgccaaagc cattctgggt ggaagcaagg ttcgtgtgga ccagaaatgc aagtcttcgg       180
cccagatcga cccgactccg gtgattgtca cctctaacac caacatgtgc gccgtgattg       240
acggaaactc gaccaccttc gagcaccagc agccgttgca agaccggatg ttcaaatttg       300
aacttacccg ccgtttggat catgactttg gaaggtcac caagcaggaa gtcaaagact        360
ttttccggtg ggctcaagat cacgtgactg aggtggagca tgagttctac gtcaaaaagg       420
gtggagccaa gaaaaggccc gcccccgatg atgtatatat aaatgagccc aagcgggcgc       480
gcgagtcagt tgcgcagcca tcgacgtcag acgcggaagc ttcgataaac tacgcgggca       540
ggtaccaaaa caaatgttct cgtcacgtgg gcatgaatct gatgctgttt ccctgtcgac       600
aatgcgaaag aatgaatcag aattcaaata tctgcttcac acacgggcaa aaagactgtt       660
tggaatgctt tcccgtgtca gaatctcaac ccgtttctgt cgtcagaaaa acgtatcaga       720
aactttgtta cattcatcat atcatgggaa aagaaccaga cgcctgcact gcctgcgacc       780
tggtaaatgt ggacttggat gactgtattt ctgagcaata aatgacttaa atcaggtatg       840
gctgctgacg gttatcttcc agattggctc gaggacactc tctctgaagg aatcagacag       900
tggtggaagc tcaaacctgg cccaccaccg ccgaaaccta ccaacaaca ccgggacgac         960
agtaggggtc ttgtgcttcc tgggtacaag tacctcggac ccttcaacgg actcgacaaa      1020
ggagagccgg tcaacgaggc agacgccgcg gccctcgagc acgacaaagc ctacgaccac      1080
cagctcaagc aaggggacaa cccgtacctc aaatacaacc acgcggacgc tgaatttcag      1140
gagcgtcttc aagaagatac gtctttcggg ggcaacctcg ggcgagcagt cttccaggcc      1200
aaaaagaggg tactcgagcc tcttggtctg gttgaggaag ctgttaagac ggctcctgga      1260
aaaagagac ctatagagca gtctcctgca gaaccggact cttcctcggg catcggcgaa       1320
tcaggccagc agcccgctaa gaaaagactc aattttggtc agactggcga cacagagtca      1380
gtcccagacc ctcaaccaat cggagaaccc ccgcagcccc cctctggtgt gggatctaat      1440
acaatggctt caggcggtgg ggcaccaatg gcagacgata acgaaggcgc cgacggagtg      1500
ggtaattcct cgggaaattg gcattgcgat tccacatgga tgggcgacag agttatcacc      1560
accagcacaa gaacctgggc cctccccacc tacaataatc acctctacaa gcaaatctcc      1620
agcgaatcgg gagccaccaa cgacaaccac tacttcggct acagcacccc ctgggggtat      1680
tttgacttta acagattcca ctgtcacttc tcaccacgtg actggcagcg actcatcaac      1740
aacaactggg gatttagacc caagaaactc aatttcaagc tcttcaacat ccaagtcaag      1800
gaggtcacgc agaatgatgg aaccacgacc atcgccaata accttaccag cacggtgcag      1860
gtcttcacag actctgagta ccagctgccc tacgtcctcg gttcggctca ccagggctgc      1920
cttccgccgt tccagcaga cgtcttcatg attcctcagt acggctactt gactctgaac       1980
aatggcagcc aagcggtagg acgttcttca ttctactgtc tagagtattt tcccctctcag     2040
atgctgagga cggaaacaa cttcaccttc agctacactt ttgaagacgt gcctttccac       2100
agcagctacg cgcacagcca gagtctggat cggctgatga atcctctcat tgaccagtac      2160
ctgtattacc tgagcaaaac tcagggtaca agtggaacaa cgcagcaatc gagactgcag      2220
ttcagccaag ctgggcctag ctccatggct cagcaggcca aaaactggct accgggaccc      2280
agctaccgac agcagcgaat gtctaagacg gctaatgaca acaacaacag tgaatttgct      2340
```

```
tggactgcag ccaccaaata ttacctgaat ggaagaaatt ctctggtcaa tcccgggccc    2400
ccaatggcca gtcacaagga cgatgaggaa aagtatttcc ccatgcacgg aaatctcatc    2460
tttggaaaac aaggcacagg aactaccaat gtggacattg aatcagtgct tattacagac    2520
gaagaagaaa tcagaacaac taatcctgtg gctacagaac aatacggaca ggttgccacc    2580
aaccatcaga gtcaggacac cacagcttcc tatggaagtg tggacagcca gggaatctta    2640
cctggaatgg tgtggcagga ccgcgatgtc tatcttcaag gtcccatttg gccaaaaact    2700
cctcacacgg acggacactt tcatccttct ccgctcatgg gaggctttgg actgaaacac    2760
cctcctcccc agatcctgat caaaaacaca cctgtgccag cgaatcccgc gaccactttc    2820
actcctggaa agtttgcttc gttcattacc cagtattcca ccggacaggt cagcgtggaa    2880
atagagtggg agctgcagaa agaaaacagc aaacgctgga acccagaaat tcagtacacc    2940
tccaactaca acaagtcggt gaatgtggag tttaccgtgg acgcaaacgg tgtttattct    3000
gaacccccgc ctattggcac tcgttacctt acccggaact tgtaatttcc tgttaatgaa    3060
taaaccgatt tatgcgtttc agttgaactt tggtctctgc gaagggcgaa ttcgcggccg    3120
cta                                                                 3123

<210> SEQ ID NO 55
<211> LENGTH: 3113
<212> TYPE: DNA
<213> ORGANISM: Unknown
<220> FEATURE:
<223> OTHER INFORMATION: AAV serotype, clone A3.5

<400> SEQUENCE: 55
gaattcgccc tttctacggc tgcgtcaact ggaccaatga aaactttccc ttcaacgatt      60
gcgtcgacaa gatggtgatc tggtgggagg agggaaagat gaccgccaag gtcgtggaat     120
ctgccaaagc cattctgggt ggaagcaagg ttcgtgtgga ccagaaatgc aagtcttcgg     180
cccagatcga cccgactccg gtgattgtca cctctaacac caacatgtgc gccgtgattg     240
acggaaactc gaccaccttc gagcaccagc agccgttgca agaccggatg ttcaaatttg     300
aacttacccg ccgtttggat catgactttg gaaggtcac caagcaggaa gtcaaagact     360
ttttccggtg ggctcaagat cacgtgactg aggtggagca tgagttctac gtcaaaaagg     420
gtggagccaa gaaaaggccc gcccccgatg atgtatatat aaatgagccc aagcgggcgc     480
gcgagtcagt tgcgcagcca tcgacgtcag acgcggaagc ttcgataaac tacgcggaca     540
ggtaccaaaa caaatgttct cgtcacgtgg gcatgaatct gatgctgttt ccctgtcgac     600
aatgcgaaag aatgaatcag aattcaaata tctgcttcac acacgggcaa aaagactgtt     660
tggaatgctt tcccgtgtca gaatctcaac ccgttcctgt cgtcagaaaa acgtatcaga     720
aactttgtta cattcatcat atcatgggaa aagtaccaga cgcctgcact gcctgcgacc     780
tggtaaatgt ggacttggat gactgtattt ctgagcaata aatgacttaa atcaggtatg     840
gctgctgacg gttatcttcc agattggctc gaggacactc tctctgaagg aatcagacag     900
tggtggaagc tcaaacctgg cccaccaccg ccgaaaccta accaacaaca ccgggacgac     960
agtaggggtc ttgtgcttcc tgggtacaag tacctcggac ccttcaacgg actcgacaaa    1020
ggagagccgg tcaacgaggc agacgccgcg gccctcgagc acgacaaagc ctacgaccac    1080
cagctcaagc aagggacaa cccgtacctc aaatacaacc acgcggacgc tgaatttcag    1140
gagcgtcttc aagaagatac gtctttcggg ggcaacctcg gcgcagcagt cttccaggcc    1200
aaaaagaggg tactcgagcc tcttggtctg gttgaggaag ctgttaagac ggctcctgga    1260
```

```
aaaaagagac ctatagagca gtctcctgca gaaccggact cttcctcggg catcggcaaa    1320
tcaggccagc agcccgctaa gaaaagactc aatttggtc agactggcga cacagagtca     1380
gtcccagacc ctcaaccaat cggagaaccc cccgcagccc cctctggtgt gggatctaat    1440
acaatggctt caggcggtgg ggcaccaatg gcagacaata cgaaggcgc cgacggagtg     1500 ggtaattcct cgggaaattg gcattgcgat ccacatggga tgggcgacag agttatcacc    1560
accagcacaa gaacctgggc cctccccacc tacaataatc acctctacaa gcaaatctcc    1620
agcgaatcgg gagccaccaa cgacaaccac tacttcggct acagcacccc ctgggggtat    1680
tttgacttta acagattcca ctgtcacttc tcaccacgtg actggcagcg actcatcaat    1740
aacaactggg gatttagacc caagaaactc aatttcaagc tcttcaacat ccaagtcaag    1800
gaggtcacgc agaatgatgg aaccacgacc atcgccaata accttaccag cacggtgcag    1860
gtcttcacag actctgagta ccagctgccc tacgtcctcg gttcggctca ccagggctgc    1920
cttccgccgt tcccagcaga cgtcttcatg attcctcagt acggctactt gactctgaac    1980
aatggcagcc aagcggtagg acgttcttca ttctactgtc tagagtattt tccctctcag    2040
atgctgagga cgggaaacaa cttcaccttc agctacactt ttgaagacgt gccttttcac    2100
agcagctacg cgcacagcca gagtctggat cggctgatga atcctctcat tgaccagtac    2160
ctgtattacc tgagcaaaac tcagggtaca agtggaacaa cgcagcaatc gagactgcag    2220
ttcaaccaag ctgggcctag ctccatggct cagcaggcca aaaactggct accgggaccc    2280
agctaccgac agcagcgaat gtctaagacg gctaatgaca caacaacag tgaatttgct     2340 tggactgcag ccaccaaata ttacccgaat ggaagaaatt ctctggtcaa tcccgggccc    2400
ccaatggcca gtcacaagga cgatgaggaa agtatttcc ccatgcacgg aaatctcatc     2460
tttgaaaaac aaggcacagg aactaccaat gtggacattg aatcagtgct tattacagac    2520
gaagaagaaa tcagaacgac taatcctgtg gctacagaac aatacggaca ggttgccacc    2580
aaccgtcaga gtcagaacac cacagcttcc tatggaagtg tggacagcca gggaatctta    2640
cctggaatgg tgtggcagga ccgcgatgtc tatcttcaag gtcccatttg gccaaaaact    2700
cctcacacgg acggacactt tcatccttct ccgctcatgg gaggctttgg actgaaacac    2760
cctcctcccc agatcctgat caaaaacaca cctgtgccag cgaatcccgc gaccactttc    2820
actcctggaa gtttgcttc gttcattacc cagtattcca ccgacaggt cagcgtggaa      2880 atagagtggg agctgcagaa agaaaacagc aaacgctgga acccggaaat tcagtacacc    2940
tccaactaca acaagtcggt gaatgtggag tttaccgtgg acgcaaacgg tgtttattct    3000
gaaccccgcc ctattggcac tcgttacctt acccggaact tgtaatttcc tgttaatgaa    3060
taaaccgatt tatgcgtttc agttgaactt tggtctctgc aagggcgaa ttc             3113
```

<210> SEQ ID NO 56
<211> LENGTH: 3122
<212> TYPE: DNA
<213> ORGANISM: Unknown
<220> FEATURE:
<223> OTHER INFORMATION: AAV serotype, clone A3.7

<400> SEQUENCE: 56

```
agcggccgcg aattcgccct ttctacggct gcgtcaactg gaccaatgaa aactttccct     60
tcaacgattg cgtcgacaag atggtgatct ggtgggagga gggaaagatg accgccaagg    120
tcgtggaatc tgccaaagcc attctgggtg gaagcaaggt tcgtgtggac cagaaatgca    180
```

```
ggtcttcggc ccagatcgac ccgactccgg tgattgtcac ctctaacacc aacatgtgcg      240
ccgtgattga cggaaactcg accaccttcg agcaccagca gccgttgcaa gaccggatgt      300
tcaaatttga acttacccgc cgtttggatc atgactttgg aaggtcacc aagcaggaag       360 tcaaagactt tttccggtgg gctcaagatc acgtgactga ggtggagcat gagttctacg      420
tcaaaagggg tggagccaag aaaaggcccg cccccgatga tgtatatata aatgagccca      480
agcgggcgcg cgagtcagtt gcgcagccat cgacgtcaga cgcggaagct tcgataaact      540
acgcggacag gtaccaaaac aaatgttctc gtcacgtggg catgaatctg atgctgtttc      600
cctgtcgaca atgcgaaaga atgaatcaga attcaaatat ctgcttcaca cacgggcaaa      660
aagactgttt ggaatgcttt cccgtgtcag aatctcaacc cgtttctgtc gtcagaaaaa      720
cgtatcagaa actttgttac attcatcata tcatgggaaa agtaccagac gcctgcactg      780
cctgcgacct ggtaaatgtg gacttggatg actgtatttc tgagcaataa atgacttaaa      840
tcaggtatgg ctgctgacgg ttatcttcca gattggctcg aggacactct ctctgaagga      900
atcagacagt ggtggaagct caaacctggc ccaccaccgc cgaaacctaa ccaacaacac      960
cgggacgaca gtaggggtct tgtgcttcct gggtacaagt acctcggacc cttcaacgga     1020
ctcgacaaag agagccggt caacgaggca gacgccgcgg ccctcgagca cgacaaagcc     1080
tacgaccacc agctcaagca aggggacaac ccgtacctca aatacaacca cgcggacgct     1140
gaatttcagg agcgtcttca agaagatacg tctttcgggg caacctcgg gcagcagtc      1200 ttccaggcca aaagagggt actcgagcct cttggtctgg ttgaggaagc tgttaagacg      1260
gctcctggaa aaagagacc tatagagcag tctcctgcag aaccggactc ttcctcgggc     1320
atcggcaaat caggccagca gcccgctaag aaaagactca attttggtca gactggcgac      1380
acagagtcag tccagacccc tcaaccaatc ggagaacccc ccgcagcccc ctctggtgtg      1440
ggatctaata caatggcttc aggcggtggg gcaccaatgg cagacaataa cgaaggcgcc      1500 gacgagtgg gtaattcctc gggaaattgg cattgcgatt ccacatggat gggcgacaga      1560
gttatcacca ccagcacaag aacctgggcc ctccccacct acaataatcg cctctacaag     1620
caaatctcca gcgaatcggg agccaccaac gacaaccact acttcggcta cagcaccccc     1680
tgggggtatt ttgactttaa cagattccac tgtcacttct caccacgtga ctggcagcga      1740
ctcatcaaca caactggggg atttagaccc aagaaactca attttcaagct cttcaacatc      1800 caagtcaagg aggtcacgca gaatgatgga accacgacca tcgccaataa ccttaccagc      1860
acggtgcagg tcttcacaga ctctgagtac cagctgccct acgtcctcgg ttcggctcac      1920
cagggctgcc ttccgccgtt cccagcagac gtcttcatga ttcctcagta cggctacttg     1980
actctgaaca atggcagcca gcggtagga cgttcttcat tctactgtct agagtatttt      2040
ccctctcaga tgctgaggac gggaaacaac ttcaccttca gctacacttt tgaagacgtg      2100
cctttccaca gcagctacgc gcacagccag agtctggatc ggctgatgaa tcctctcatt     2160
gaccagtacc tgtattacct gagcaaaact cagggtacaa gtggaacaac gcagcaatcg      2220
agactgcagt tcagccaagc tgggcctagc tccatggctc agcaggccaa aaactggcta      2280
ccgggaccca gctaccgaca gcagcgaatg tctaagacgg ctaatgacaa caacaacagt      2340
gaatttgctt ggactgcagc caccaaatat tacctgaatg gaagaaattc tctggtcaat      2400
cccgggcccc caatggccag tcacaaggac gatgaggaaa agtatttccc catgcacgga      2460
aatctcatct ttggaaaaca aggcacagga actaccaatg tggacattga atcagtgctt      2520
attacagacg aagaagaaat cagaacaact aatcctgtgg ctacagaaca atacggacag      2580
```

-continued

```
gttgccacca accatcagag tcagaacacc acagcttcct atggaagtgt ggacagccag    2640
ggaatcttac ctggaatggt gtggcaggac cgcgatgtct atcttcaagg tcccatttgg    2700
gccaaaactc ctcacacgga cggacacttt catccttctc cgctcatggg aggctttgga    2760
ctgaaacacc ctcctcccca gatcctgatc aaaaacacac ctgtgccagc gaatcccgcg    2820
accactttca ctcctggaaa gtttgcttcg ttcattaccc agtattccac cggacaggtc    2880
agcgtggaaa tagagtggga gctgcagaaa gaaaacagca aacgctggaa cccagaaatt    2940
cagtacacct ccaactacaa caagtcggtg aatgtggagt ttaccgtgga cgcaaacggt    3000
gtttattctg aaccccgccc tattggcact cgttacctta cccggaactt gtaatttcct    3060
gttaatgaat aaaccgattt atgcgtttca gttgaacttt ggtctctgcg aagggcgaat    3120
tc                                                                   3122
```

<210> SEQ ID NO 57
<211> LENGTH: 3123
<212> TYPE: DNA
<213> ORGANISM: Unknown
<220> FEATURE:
<223> OTHER INFORMATION: AAV serotype, clone A3.3

<400> SEQUENCE: 57

```
gaattcgccc tttctacggc tgcgtcaact ggaccaatga aaactttccc ttcaacgatt      60
gcgtcgacaa gatggtgatc tggtgggagg agggaaagat gaccgccaag gtcgtggaat     120
ctgccaaagc cattctgggt ggaggcaagg ttcgtgtgga ccagaaatgc aagtcttcgg     180
cccagatcga cccgactccg gtgattgtca cctctaacac caacatgtgc gccgtgattg     240
acggaaactc gaccaccttc gagcaccagc agccgttgca agaccggatg ttcaaatttg     300
aacttacccg ccgtttggat catgactttg gaaggtcac caagcaggaa gtcaaagact     360 tttccggtg ggctcaagat cacgtgactg aggtggagca tgagttctac gtcaaaaagg     420
gtggagccaa gaaaaggccc gcccccgatg atgtatatat aaatgagccc aagcgggcgc     480
gcgagtcagt tgcgcagcca tcgacgtcag acgcggaagc ttcgataaac tacgcggaca     540
ggtaccaaaa caaatgttct cgtcacgtgg gcatgaatct gatgctgttt ccctgtcgac     600
aatgcgaaag aatgaatcag aattcaaata tctgcttcac acacgggcaa aaagactgtt     660
tggaatgctt tcccgtgtca gaatctcaac ccgtttctgt cgtcagaaaa acgtatcaga     720
aactttgtta cattcatcat atcatgggaa aagtaccaga cgcctgcact gcctgcgacc     780
tggtaaatgt ggacttggat gactgtattt ctgagcaata aatgacttaa atcaggtatg     840
gctgctgacg gttatcttcc agattggctc gaggacactc tctctgaagg aatcagacag     900
tggtggaagc tcaaacctgg cccaccaccg ccgaaaccta accaacaaca ccgggacgac     960
agtaggggtc ttgtgcttcc tgggtacaag tacctcggac ccttcaacgg actcgacaaa    1020
ggagagccgg tcaacgaggc agacgccgcg ccctcgagc acgacaaagc ctacgaccac    1080
cagctcaagc aaggggacaa cccgtacctc aaatacaacc acgcggacgc tgaatttcag    1140
gagcgtcttc aagaagatac gtctttcggg ggcaacctcg gcgagcagt cttccaggcc    1200 aaaaagaggg tactcgagcc tcttggtctg gttgaggaag ctgttaagac ggctcctgga    1260
aaaaagagac ctatagagca gtctcctgca gaaccggact cttcctcggg catcggcaaa    1320
tcaggccagc agcccgctaa gaaaagactc aattttggtc agactggcga cacagagtca    1380
gtcccaggcc ctcaaccaat cggagaaccc cccgcagccc cctctggtgt gggatctaat    1440
```

```
acaatggctt caggcggtgg ggcaccaatg gcagacaata cgaaggcgc cgacggagtg      1500 ggtaattcct cgggaaattg gcattgcgat tccacatgga tgggcgacag agttatcacc      1560
accagcacaa gaacctgggc cctccccacc tacaataatc acctctacaa gcaaatctcc      1620
agcgaatcgg gagccaccaa cgacaaccac tacttcggct acagcacccc ctgggggtat      1680 tttgactta acagattcca ctgtcacttc tcaccacgtg actggcagcg actcatcaac      1740
aacaactggg gatttagacc caagaaactc aatttcaagc tcttcaacat ccaagtcaag      1800
gaggtcacgc agaatgatgg aaccacgacc atcgccaata accttaccag cgcggtgcag      1860
gtcttcacag actctgagta ccagctgccc tacgtcctcg gttcggctca ccagggctgc      1920
cttccgccgt tcccagcaga cgtcttcatg attcctcagt acggctactt gactctgaac      1980
aatggcagcc aagcgtagg acgttcttca ttctactgtc tagagtattt tccctctcag      2040
atgctgagga cggaaacaa cttcaccttc agctacactt ttgaagacgt gccttttccac      2100 agcagctacg cgcacagcca gagtctggat cggctgatga atcctctcat tgaccagtac      2160
ctgtattacc tgagcaaaac tcagggtaca agtggaacaa cgcagcaatc gagactgcag      2220
ttcagccaag ctgggcctag ctccatggct cagcaggcca aaaactggct accgggaccc      2280
agctaccgac agcagcgaat gtctaagacg gctaatgaca caacaacag tgaatttgct      2340 tggactgcag ccaccaaata ttacctgaat ggaagaaatt ctctggtcaa tcccgggccc      2400
ccagtggcca gtcacaagga cgatgaggaa aagtatttcc ccatgcacgg aaatctcatc      2460
tttggaaaac aaggcacagg aactaccaat gtggacattg aatcagtgct tattacagac      2520
gaagaagaaa tcagaacaac taatcctgtg gctacagaac aatacggaca ggttgccacc      2580
aaccatcaga gtcagaacac cacagcttcc tatggaagtg tggacagcca gggaatctta      2640
cctggaatgg tgtggcagga ccgcgatgtc tatcttcaag gtcccattg ggccaaaact      2700 cctcacacgg acggacactt tcatccttct ccgctcatgg gaggctttgg actgaaacac      2760
cctcctcccc agatcctgat caaaaacaca cctgtgccag cgaatcccgc gaccactttc      2820
actcctggaa agtttgcttc gttcattacc cagtattcca cctgacaggt cagcgtggaa      2880
atagagtggg agctgcagaa agaaaacagc aaacgctgga acccagaaat tcagtacacc      2940
tccaactaca acaagtcggt gaatgtggag tttaccgtgg acgcaaacgg tgtttattct      3000
gaaccccgcc ctattggcac tcgttacctt acccggaact tgtaatttcc tgttaatgaa      3060
taagccgatt tatgcgtttc agttgaactt tggtctctgc gaagggcgaa ttcgtttaaa      3120
cct                                                                    3123
```

<210> SEQ ID NO 58
<211> LENGTH: 2969
<212> TYPE: DNA
<213> ORGANISM: Unknown
<220> FEATURE:
<223> OTHER INFORMATION: AAV serotype, clone 42.12

<400> SEQUENCE: 58

```
gaattcgccc tttctacggc tgcgtcaact ggaccaatga gaactttccc ttcaacgatt       60
gcgtcgacaa gatggtgatc tggtgggagg agggcaagat gacggccaag gtcgtggagt      120
ccgccaaggc cattctcggc ggcagcaagg tgcgcgtgga ccaaaagtgc aagtcgtccg      180
cccagatcga ccccacccc gtgatcgtca cctccaacac caacatgtgc gccgtgattg      240
acgggaacag caccaccttc gagcaccagc agccgttaca agaccggatg ttcaaatttg      300
aactcacccg ccgtctggag cacgactttg gcaaggtgac aaagcaggaa gtcaaagagt      360
```

```
tcttccgctg ggcgcaggat cacgtgaccg aggtggcgca tgagttctac gtcagaaagg    420
gtggagccaa caagagaccc gcccccgatg acgcgggataa aagcgagccc aagcgggcct    480
gcccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatc    900
cgcgagtggg gggacttgaa acctggagcc ccgaaaccca agccaaccca gcaaaagcag    960
gacgacggcc ggggtctggt gcttcctggc tacaagtacc tcggacccctt caacggactc   1020 gacaagggag agccggtcaa cgaggcagac gccgcgcccc tcgagcacga caaggcctac   1080
gacaagcagc tcgagcaggg ggacaacccg tacctcaagt acaaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagccatca ccccagcgtt ctccagactc ctctacgggc   1320
atcggcaaga caggccagca gcccgcgaaa aagagactca actttgggca gactggcgac   1380
tcagagtcag tgcccgaccc tcaaccaatc ggagaacccc cgcaggccc ctctggtctg   1440 ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacatc gggaggaagc accaacgaca cacctacttt cggctacagc   1680
accccctggg ggtattttga ctttaacaga ttccactgcc acttctcacc acgtgactgg   1740
cagcgactca tcaacaacaa ctggggattc cgcccaagaga gactcaactt caagctcttc   1800
aacatccagg tcaaggaggt cacgcagaat gaaggcacca gaccatcgc caataacctt   1860 accagcacga ttcaggtctt tacgactcg gaataccagc tcccgtacgt cctcggctct   1920
gcgcaccagg gctgcctgcc tccgttcccg gcggacgtct tcatgattcc tcagtacggg   1980
tacctgactc tgaacaacgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gacgaacccc   2160
ctcatcgacc agtacctgta ctacctgccc cggacccaga gcactacggg gtccacaagg   2220
gggctgcagt tccatcaggc tgggcccaac accatggccg agcaatcaaa gaactggctg   2280 cccgaccct gttatcggca gcagagactg tcaaaaaaca tagacagcaa caacaacagt   2340
aactttgcct ggaccggggc cactaaatac catctgaatg gtagaaattc attaaccaac   2400
ccgggcgtag ccatgccac caacaaggac gacgaggacc agttcttcc catcaacgga   2460 gtgctggttt ttggcaaaac ggggggctgcc aacaagacaa cgctggaaaa cgtgctaatg   2520
accagcgagg aggagatcaa aaccaccaat cccgtggcta cagaagaata cggtgtggtc   2580
tccagcaacc tgcaatcgtc tacggccgga ccccagacac agactgtcaa cagccagggg   2640
gctctgcccg gcatggtctg gcagaaccgg gacgtgtacc tgcagggtcc catctgggcc   2700
```

-continued

| | |
|---|---|
| aaaattcctc acacggacgg caactttcac ccgtctcccc tgatgggcgg atttggactc | 2760 |
| aaacacccgc ctcctcaaat tctcatcaag tatacttcca actactacaa atctacaaat | 2820 |
| gtggactttg ctgtcaatac tgagggtact tattcagagc ctcgcccat tggcacccgt | 2880 |
| tacctcaccc gtaacctgta attgcctgtt aatcaataaa ccggttaatt cgtttcagtt | 2940 |
| gaactttggt ctctgcgaag ggcgaattc | 2969 |

<210> SEQ ID NO 59
<211> LENGTH: 3129
<212> TYPE: DNA
<213> ORGANISM: Unknown
<220> FEATURE:
<223> OTHER INFORMATION: AAV serotype, clone 44.2

<400> SEQUENCE: 59

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaaag tgcgcgtgga ccaaaagtgc aagtcgtccg | 180 |
| cccagatcga ccccaccccc gtgatcgtca cctccaacac caacatgtgc gccgtgattg | 240 |
| acgggaacag caccaccttc gagcaccagc agccgttgca ggaccggatg ttcaagtttg | 300 |
| aactcacccg ccgtctggag cacgactttg gcaaggtgac aaagcaggaa gtcagagagt | 360 |
| tcttccgctg ggcgcaggat cacgtgaccg aggtggcgca cgagttctac gtcagaaagg | 420 |
| gtggagccaa caagagaccc gcccccgatg acgcggataa aagcgagccc aagcgggcct | 480 |
| gccccctcagt cgcggatcca tcgacgtcag acgcggaagg agctccggtg gactttgccg | 540 |
| acaggtacca aaacaaatgt tctcgtcacg cgggcatgct tcagatgctg tttcctgca | 600 |
| aaacatgcga gagaatgaat cagaatttca acatttgctt cacgcacggg accagagact | 660 |
| gttcagaatg tttccccggc gtgtcagaat ctcaaccggt cgtcagaaaa aagacgtatc | 720 |
| ggaaactctg tgcgattcat catctgctgg ggcgggcac ccgagattgc ttgctcggcc | 780 |
| tgcgatctgg tcaacgtgga cctagatgac tgtgtttctg agcaataaat gacttaaacc | 840 |
| aggtatggct gccgatggtt atcttccaga ttggctcgag acaacctct ctgagggcat | 900 |
| tcgcgagtgg tgggacttga aacctggagc cccgaaaccc aaagccaacc agcaaaagca | 960 |
| ggacgacggc cggggtctgg tgcttcctgg ctacaagtac ctcggaccct tcaacgtact | 1020 |
| cgacaagggg gagcccgtca acgcggcgga cgcagcggcc ctcgagcacg acaaggccta | 1080 |
| cgaccagcag ctcaaagcgg gtgacaatcc gtacctgcgg tataaccacg ccgacgccga | 1140 |
| gtttcaggag cgtctgcaag aagatacgtc ttttgggggc aacctcgggc gagcagtctt | 1200 |
| ccaggccaag aagcgggttc tcgaacctct cggtctggtt gaggaaggcg ctaagacggc | 1260 |
| tcctggaaag aagagaccgg tagagccatc accccagcgt tctccagact cctctacggg | 1320 |
| catcggcaag aaaggccagc agccccgcgaa aaagagactc aactttgggc agactggcga | 1380 |
| ctcagagtca gtgcccgacc ctcaaccaat cggagaaccc cccgcaggcc cctctggtct | 1440 |
| gggatctggt acaatggctg caggcggtgg cgctccaatg gcagacaata cgaaggcgc | 1500 |
| cgacggagtg ggtagttcct caggaaattg gcattgcgat tccacatggc tgggcgacag | 1560 |
| agtcatcacc accagcaccc gaacctgggc cctccccacc tacaacaacc acctctacaa | 1620 |
| gcaaatctcc aacgggactt cgggaggaag caccaacgac aacacctact cggctacag | 1680 |
| cacccctgg gggtatttg actttaacag attccactgc cacttctcac cacgtgactg | 1740 |
| gcagcgactc atcaacaaca actgggggat ccggcccaag agactcaact tcaagctctt | 1800 |

```
caacatccag gtcaaggagg tcacgcagaa tgaaggcacc aagaccatcg ccaataacct   1860
taccagcacg attcaggtct ttacggactc ggaataccag ctcccgtacg tcctcggctc   1920
tgcgcaccag ggctgcctgc ctccgttccc ggcggacgtc ttcatgattc ctcagtacgg   1980
gtacctgact ctgaacaatg cagtcaggc cgtgggccgt tcctccttct actgcctgga    2040
gtactttcct tctcaaatgc tgagaacggg caacaacttt gagttcagct accagtttga   2100
ggacgtgcct tttcacagca gctacgcgca gcccaaagc ctggaccggc tgatgaaccc    2160
cctcatcgac cagtacctgt actacctgtc tcggactcag tccacgggag gtaccgcagg   2220
aactcagcag ttgctatttt ctcaggccgg gcctaataac atgtcggctc aggccaaaaa   2280
ctggctaccc gggccctgct accggcagca acgcgtctcc acgacactgt cgcaaaataa   2340
caacagcaac tttgcctgga ccggtgccac caagtatcat ctgaatggca gagactctct   2400
ggtaaatccc ggtgtcgcta tgcaacccca aggacgac gaagagcgat ttttccgtc     2460 cagcggagtc ttaatgtttg gaaacaggg agctggaaaa acaacgtgg actatagcag    2520 cgttatgcta accagtgagg aagaaattaa aaccaccaac ccagtggcca gaacagta    2580 cggcgtggtg gccgataacc tgcaacagca aaacgccgct cctattgtag gggccgtcaa   2640
cagtcaagga gccttacctg gcatggtctg gcagaaccgg gacgtgtacc tgcagggtcc   2700
tatctgggcc aagattcctc acacggacgg aaacttcat ccctcgccgc tgatgggagg   2760 cttggactg aaacacccgc tcctcagat cctgattaag aatacacctg ttcccgcgga    2820
tcctccaact accttcagtc aagctaagct ggcgtcgttc atcacgcagt acagcaccgg   2880
acaggtcagc gtggaaattg aatgggagct gcagaaagaa acagcaaac gctggaaccc    2940 agagattcaa tacacttcca actactacaa atctacaaat gtggactttg ctgttaacac   3000
agatggcact tattctgagc ctcgccccat cggcacccgt tacctcaccc gtaatctgta   3060
attgcttgtt aatcaataaa ccggttgatt cgtttcagtt gaactttggt ctctgcgaag   3120
ggcgaattc                                                           3129
```

<210> SEQ ID NO 60
<211> LENGTH: 733
<212> TYPE: PRT
<213> ORGANISM: Unknown
<220> FEATURE:
<223> OTHER INFORMATION: capsid protein of AAV serotype, clone C1VP1

<400> SEQUENCE: 60

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro

```
            115                 120                 125
Leu Gly Leu Val Glu Glu Gly Ala Lys Thr Ala Pro Gly Lys Lys Arg
        130                 135                 140
Pro Leu Glu Ser Pro Gln Glu Pro Asp Ser Ser Gly Ile Gly Lys
145                 150                 155                 160
Lys Gly Lys Gln Pro Ala Lys Lys Arg Leu Asn Phe Glu Glu Asp Thr
                165                 170                 175
Gly Ala Gly Asp Gly Pro Pro Glu Gly Ser Asp Thr Ser Ala Met Ser
            180                 185                 190
Ser Asp Ile Glu Met Arg Ala Ala Pro Gly Gly Asn Ala Val Asp Ala
                195                 200                 205
Gly Gln Gly Ser Asp Gly Val Gly Asn Ala Ser Gly Asp Trp His Cys
        210                 215                 220
Asp Ser Thr Trp Ser Glu Gly Lys Val Thr Thr Thr Ser Thr Arg Thr
225                 230                 235                 240
Trp Val Leu Pro Thr Tyr Asn Asn His Leu Tyr Leu Arg Leu Gly Thr
                245                 250                 255
Thr Ser Asn Ser Asn Thr Tyr Asn Gly Phe Ser Thr Pro Trp Gly Tyr
            260                 265                 270
Phe Asp Phe Asn Arg Phe His Cys His Phe Ser Pro Arg Asp Trp Gln
        275                 280                 285
Arg Leu Ile Asn Asn Asn Trp Gly Leu Arg Pro Lys Ala Met Arg Val
        290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
            340                 345                 350
Leu Ser Pro Phe Pro Asn Asp Val Phe Met Val Pro Gln Tyr Gly Tyr
            355                 360                 365
Cys Gly Ile Val Thr Gly Glu Asn Gln Asn Gln Thr Asp Arg Asn Ala
        370                 375                 380
Phe Tyr Cys Leu Glu Tyr Phe Pro Ser Gln Met Leu Arg Thr Gly Asn
385                 390                 395                 400
Asn Phe Glu Met Ala Tyr Asn Phe Gly Lys Val Pro Phe His Ser Met
                405                 410                 415
Tyr Ala Tyr Ser Gln Ser Pro Asp Arg Leu Met Asn Pro Leu Leu Asp
                420                 425                 430
Gln Tyr Leu Trp His Leu Gln Ser Thr Thr Ser Gly Glu Thr Leu Asn
            435                 440                 445
Gln Gly Asn Ala Ala Thr Thr Phe Gly Lys Ile Arg Ser Gly Asp Phe
            450                 455                 460
Ala Phe Tyr Arg Lys Asn Trp Leu Pro Gly Pro Cys Val Lys Gln Gln
465                 470                 475                 480
Arg Leu Ser Lys Thr Ala Ser Gln Asn Tyr Lys Ile Pro Ala Ser Gly
                485                 490                 495
Gly Asn Ala Leu Leu Lys Tyr Asp Thr His Tyr Thr Leu Asn Asn Arg
            500                 505                 510
Trp Ser Asn Ile Ala Pro Gly Pro Pro Met Ala Thr Ala Gly Pro Ser
            515                 520                 525
Asp Gly Asp Phe Ser Asn Ala Gln Leu Ile Phe Pro Gly Pro Ser Val
            530                 535                 540
```

-continued

```
Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 61
<211> LENGTH: 733
<212> TYPE: PRT
<213> ORGANISM: Unknown
<220> FEATURE:
<223> OTHER INFORMATION: capsid protein of AAV serotype, clone C2VP1

<400> SEQUENCE: 61

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Leu
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe His Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175
```

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
            195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Ser Thr Arg Thr
225                 230                 235                 240

Trp Val Leu Pro Thr Tyr Asn His Leu Tyr Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Leu Arg Pro Lys Ala Met Arg Val
            290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Ile Val Thr Gly Glu Asn Gln Asn Gln Thr Asp Arg Asn Ala
370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
            405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
            515                 520                 525

Asp Gly Asp Phe Ser Asn Ala Gln Leu Ile Phe Pro Gly Pro Ser Val
            530                 535                 540

Thr Gly Asn Thr Thr Ser Ala Asn Asn Leu Leu Phe Thr Ser Glu
545                 550                 555                 560

Gly Glu Ile Ala Ala Thr Asn Pro Arg Asp Thr Asp Met Phe Gly Gln
            565                 570                 575

Ile Ala Asp Asn Asn Gln Asn Ala Thr Thr Ala Pro Ile Thr Gly Asn
            580                 585                 590

```
Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
                675                 680                 685

Ser Lys Arg Arg Asn Pro Glu Val Gln Phe Thr Ser Asn Tyr Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 62
<211> LENGTH: 733
<212> TYPE: PRT
<213> ORGANISM: Unknown
<220> FEATURE:
<223> OTHER INFORMATION: capsid protein of AAV serotype, clone C5VP1[@0002]

<400> SEQUENCE: 62

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Glu Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
210                 215                 220
```

```
Asp Ser Thr Trp Ser Glu Gly Lys Val Thr Thr Ser Thr Arg Thr
225                 230                 235                 240

Trp Val Leu Pro Thr Tyr Asn Asn His Leu Tyr Leu Arg Leu Gly Thr
            245                 250                 255

Thr Ser Asn Ser Asn Thr Tyr Asn Gly Phe Ser Thr Pro Trp Gly Tyr
        260                 265                 270

Phe Asp Phe Asn Arg Phe His Cys His Phe Ser Pro Arg Asp Trp Gln
    275                 280                 285

Arg Leu Ile Asn Asn Asn Trp Gly Leu Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
            325                 330                 335

Ser Ser Tyr Glu Leu Pro Tyr Val Met Asp Ala Gly Gln Glu Gly Ser
        340                 345                 350

Leu Pro Pro Phe Pro Asn Asp Val Phe Met Val Pro Gln Tyr Gly Tyr
    355                 360                 365

Cys Gly Ile Val Thr Gly Glu Asn Gln Asn Gln Thr Asp Arg Asn Ala
370                 375                 380

Phe Tyr Cys Leu Glu Tyr Phe Pro Ser Gln Met Leu Arg Thr Gly Asn
385                 390                 395                 400

Asn Phe Glu Thr Ala Tyr Asn Phe Glu Lys Val Pro Phe His Ser Met
            405                 410                 415

Tyr Ala His Ser Gln Ser Leu Asp Gly Leu Met Asn Pro Leu Leu Asp
        420                 425                 430

Gln Tyr Leu Trp His Leu Gln Ser Thr Thr Ser Gly Glu Thr Leu Asn
    435                 440                 445

Gln Gly Asn Ala Ala Thr Thr Phe Gly Lys Ile Arg Ser Gly Asp Phe
450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
            485                 490                 495

Gly Asn Ala Leu Leu Lys Tyr Asp Thr His Tyr Thr Leu Asn Asn Arg
        500                 505                 510

Trp Ser Asn Ile Ala Pro Gly Pro Pro Met Ala Thr Ala Gly Pro Ser
    515                 520                 525

Asp Gly Asp Phe Ser Asn Ala Gln Leu Ile Phe Pro Gly Pro Ser Val
530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
            565                 570                 575

Ile Ala Asp Asn Asn Gln Asn Ala Thr Thr Ala Pro Ile Thr Gly Asn
        580                 585                 590

Val Thr Ala Met Gly Val Leu Pro Gly Met Val Trp Gln Asn Arg Asp
    595                 600                 605

Ile Tyr Tyr Gln Gly Pro Ile Trp Ala Lys Ile Pro His Ala Asp Gly
610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Tyr Pro Ala
```

```
                        645                 650                 655
Thr Thr Phe Thr Ala Arg Val Asp Ser Phe Ile Thr Gln Tyr Ser
                660                 665                 670
Thr Gly Gln Val Ala Val Gln Ile Glu Trp Glu Ile Glu Lys Glu Arg
            675                 680                 685
Ser Lys Arg Trp Asn Pro Glu Val Gln Phe Thr Ser Asn Cys Gly Asn
        690                 695                 700
Gln Ser Ser Met Leu Trp Ala Pro Asp Thr Thr Gly Lys Tyr Thr Glu
705                 710                 715                 720
Pro Arg Val Ile Gly Ser Arg Tyr Leu Thr Asn His Leu
                725                 730

<210> SEQ ID NO 63
<211> LENGTH: 734
<212> TYPE: PRT
<213> ORGANISM: Unknown
<220> FEATURE:
<223> OTHER INFORMATION: capsid protein of AAV serotype, clone AAV4VP1

<400> SEQUENCE: 63

Met Thr Asp Gly Tyr Leu Pro Asp Trp Leu Glu Asp Asn Leu Ser Glu
1               5                   10                  15
Gly Val Arg Glu Trp Trp Ala Leu Gln Pro Gly Ala Pro Lys Pro Lys
            20                  25                  30
Ala Asn Gln Gln His Gln Asp Asn Ala Arg Gly Leu Val Leu Pro Gly
        35                  40                  45
Tyr Lys Tyr Leu Gly Pro Gly Asn Gly Leu Asp Lys Gly Glu Pro Val
    50                  55                  60
Asn Ala Ala Asp Ala Ala Ala Leu Glu His Asp Lys Ala Tyr Asp Gln
65                  70                  75                  80
Gln Leu Lys Ala Gly Asp Asn Pro Tyr Leu Lys Tyr Asn His Ala Asp
                85                  90                  95
Ala Glu Phe Gln Gln Arg Leu Gln Gly Asp Thr Ser Phe Gly Gly Asn
            100                 105                 110
Leu Gly Arg Ala Val Phe Gln Ala Lys Lys Arg Val Leu Glu Pro Leu
        115                 120                 125
Gly Leu Val Glu Gln Ala Gly Glu Thr Ala Pro Gly Lys Lys Arg Pro
    130                 135                 140
Leu Ile Glu Ser Pro Gln Gln Pro Asp Ser Ser Thr Gly Ile Gly Lys
145                 150                 155                 160
Lys Gly Lys Gln Pro Ala Lys Lys Lys Leu Val Phe Glu Asp Glu Thr
                165                 170                 175
Gly Ala Gly Asp Gly Pro Pro Glu Gly Ser Thr Ser Gly Ala Met Ser
            180                 185                 190
Asp Asp Ser Glu Met Arg Ala Ala Ala Gly Gly Ala Ala Val Glu Gly
        195                 200                 205
Gly Gln Gly Ala Asp Gly Val Gly Asn Ala Ser Gly Asp Trp His Cys
    210                 215                 220
Asp Ser Thr Trp Ser Glu Gly His Val Thr Thr Thr Ser Thr Arg Thr
225                 230                 235                 240
Trp Val Leu Pro Thr Tyr Asn Asn His Leu Tyr Lys Arg Leu Gly Glu
                245                 250                 255
Ser Leu Gln Ser Asn Thr Tyr Asn Gly Phe Ser Thr Pro Trp Gly Tyr
            260                 265                 270
Phe Asp Phe Asn Arg Phe His Cys His Phe Ser Pro Arg Asp Trp Gln
```

-continued

```
             275                 280                 285
Arg Leu Ile Asn Asn Trp Gly Met Arg Pro Lys Ala Met Arg Val
    290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
            340                 345                 350
Leu Pro Pro Phe Pro Asn Asp Val Phe Met Val Pro Gln Tyr Gly Tyr
            355                 360                 365
Cys Gly Leu Val Thr Gly Asn Thr Ser Gln Gln Gln Thr Asp Arg Asn
370                 375                 380
Ala Phe Tyr Cys Leu Glu Tyr Phe Pro Ser Gln Met Leu Arg Thr Gly
385                 390                 395                 400
Asn Asn Phe Glu Ile Thr Tyr Ser Phe Glu Lys Val Pro Phe His Ser
                405                 410                 415
Met Tyr Ala His Ser Gln Ser Leu Asp Arg Leu Met Asn Pro Leu Ile
                420                 425                 430
Asp Gln Tyr Leu Trp Gly Leu Gln Ser Thr Thr Thr Gly Thr Thr Leu
            435                 440                 445
Asn Ala Gly Thr Ala Thr Thr Asn Phe Thr Lys Leu Arg Pro Thr Asn
450                 455                 460
Phe Ser Asn Phe Lys Lys Asn Trp Leu Pro Gly Pro Ser Ile Lys Gln
465                 470                 475                 480
Gln Gly Phe Ser Lys Thr Ala Asn Gln Asn Tyr Lys Ile Pro Ala Thr
                485                 490                 495
Gly Ser Asp Ser Leu Ile Lys Tyr Glu Thr His Ser Thr Leu Asp Gly
            500                 505                 510
Arg Trp Ser Ala Leu Thr Pro Gly Pro Pro Met Ala Thr Ala Gly Pro
            515                 520                 525
Ala Asp Ser Lys Phe Ser Asn Ser Gln Leu Ile Phe Ala Gly Pro Lys
530                 535                 540
Gln Asn Gly Asn Thr Ala Thr Val Pro Gly Thr Leu Ile Phe Thr Ser
545                 550                 555                 560
Glu Glu Glu Leu Ala Ala Thr Asn Ala Thr Asp Thr Asp Met Trp Gly
                565                 570                 575
Asn Leu Pro Gly Gly Asp Gln Ser Asn Ser Asn Leu Pro Thr Val Asp
            580                 585                 590
Arg Leu Thr Ala Leu Gly Ala Val Pro Gly Met Val Trp Gln Asn Arg
            595                 600                 605
Asp Ile Tyr Tyr Gln Gly Pro Ile Trp Ala Lys Ile Pro His Thr Asp
            610                 615                 620
Gly His Phe His Pro Ser Pro Leu Ile Gly Gly Phe Gly Leu Lys His
625                 630                 635                 640
Pro Pro Pro Gln Ile Phe Ile Lys Asn Thr Pro Val Pro Ala Asn Pro
                645                 650                 655
Ala Thr Thr Phe Ser Ser Thr Pro Val Asn Ser Phe Ile Thr Gln Tyr
                660                 665                 670
Ser Thr Gly Gln Val Ser Val Gln Ile Asp Trp Glu Ile Gln Lys Glu
            675                 680                 685
Arg Ser Lys Arg Trp Asn Pro Glu Val Gln Phe Thr Ser Asn Tyr Gly
            690                 695                 700
```

-continued

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
            725                 730

<210> SEQ ID NO 64
<211> LENGTH: 736
<212> TYPE: PRT
<213> ORGANISM: Unknown
<220> FEATURE:
<223> OTHER INFORMATION: capsid protein of AAV serotype, clone AAV1

<400> SEQUENCE: 64

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

```
Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 65
<211> LENGTH: 736
```

```
<212> TYPE: PRT
<213> ORGANISM: Unknown
<220> FEATURE:
<223> OTHER INFORMATION: capsid protein of AAV serotype, clone AAV6VP1

<400> SEQUENCE: 65

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380
```

```
Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Asn Arg
    435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 66
<211> LENGTH: 735
<212> TYPE: PRT
<213> ORGANISM: Unknown
<220> FEATURE:
<223> OTHER INFORMATION: capsid protein of AAV serotype, clone A3.3

<400> SEQUENCE: 66

Met Ala Ala Asp Gly Tyr Leu Pro Asp Trp Leu Glu Asp Thr Leu Ser
1               5                   10                  15
```

-continued

```
Glu Gly Ile Arg Gln Trp Trp Lys Leu Lys Pro Gly Pro Pro Pro
            20                  25                  30
Lys Pro Asn Gln Gln His Arg Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
His Gln Leu Lys Gln Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Ala Val Lys Thr Ala Pro Gly Lys Lys Arg
    130                 135                 140
Pro Ile Glu Gln Ser Pro Ala Glu Pro Asp Ser Ser Gly Ile Gly
145                 150                 155                 160
Lys Ser Gly Gln Gln Pro Ala Lys Lys Arg Leu Asn Phe Gly Gln Thr
                165                 170                 175
Gly Asp Thr Glu Ser Val Pro Gly Pro Gln Pro Ile Gly Glu Pro Pro
            180                 185                 190
Ala Ala Pro Ser Gly Val Gly Ser Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Glu Ser Gly Ala Thr Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Lys Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Ala Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Ile Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Lys Thr
```

```
                435                 440                 445
Gln Gly Thr Ser Gly Thr Thr Gln Gln Ser Arg Leu Gln Phe Ser Gln
            450                 455                 460
Ala Gly Pro Ser Ser Met Ala Gln Gln Ala Lys Asn Trp Leu Pro Gly
465                 470                 475                 480
Pro Ser Tyr Arg Gln Gln Arg Met Ser Lys Thr Ala Asn Asp Asn Asn
                485                 490                 495
Asn Ser Glu Phe Ala Trp Thr Ala Ala Thr Lys Tyr Tyr Leu Asn Gly
            500                 505                 510
Arg Asn Ser Leu Val Asn Pro Gly Pro Val Ala Ser His Lys Asp
        515                 520                 525
Asp Glu Glu Lys Tyr Phe Pro Met His Gly Asn Leu Ile Phe Gly Lys
        530                 535                 540
Gln Gly Thr Gly Thr Thr Asn Val Asp Ile Glu Ser Val Leu Ile Thr
545                 550                 555                 560
Asp Glu Glu Ile Arg Thr Thr Asn Pro Val Ala Thr Glu Gln Tyr
                565                 570                 575
Gly Gln Val Ala Thr Asn His Gln Ser Gln Asn Thr Thr Ala Ser Tyr
            580                 585                 590
Gly Ser Val Asp Ser Gln Gly Ile Leu Pro Gly Met Val Trp Gln Asp
        595                 600                 605
Arg Asp Val Tyr Leu Gln Gly Pro Ile Trp Ala Lys Thr Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ala Thr Thr Phe Thr Pro Gly Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
        690                 695                 700
Asn Lys Ser Val Asn Val Glu Phe Thr Val Asp Ala Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 67
<211> LENGTH: 735
<212> TYPE: PRT
<213> ORGANISM: Unknown
<220> FEATURE:
<223> OTHER INFORMATION: capsid protein of AAV serotype, clone A3.7

<400> SEQUENCE: 67

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Asn Gln Gln His Arg Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
```

-continued

```
                65                  70                  75                  80
His Gln Leu Lys Gln Gly Asp Asn Pro Tyr Leu Lys Tyr Asn His Ala
                    85                  90                  95

Asp Ala Glu Phe Gln Glu Arg Leu Gln Glu Asp Thr Ser Phe Gly Gly
                    100                 105                 110

Asn Leu Gly Arg Ala Val Phe Gln Ala Lys Lys Arg Val Leu Glu Pro
                    115                 120                 125

Leu Gly Leu Val Glu Glu Ala Val Lys Thr Ala Pro Gly Lys Lys Arg
                    130                 135                 140

Pro Ile Glu Gln Ser Pro Ala Glu Pro Asp Ser Ser Gly Ile Gly
145                 150                 155                 160

Lys Ser Gly Gln Gln Pro Ala Lys Lys Arg Leu Asn Phe Gly Gln Thr
                    165                 170                 175

Gly Asp Thr Glu Ser Val Pro Asp Pro Gln Pro Ile Gly Glu Pro Pro
                    180                 185                 190

Ala Ala Pro Ser Gly Val Gly Ser Asn Thr Met Ala Ser Gly Gly Gly
                    195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn Arg Leu
                    245                 250                 255

Tyr Lys Gln Ile Ser Ser Glu Ser Gly Ala Thr Asn Asp Asn His Tyr
                    260                 265                 270

Phe Gly Tyr Ser Thr Pro Trp Gly Tyr Phe Asp Phe Asn Arg Phe His
                    275                 280                 285

Cys His Phe Ser Pro Arg Asp Trp Gln Arg Leu Ile Asn Asn Asn Trp
                    290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                    325                 330                 335

Thr Ser Thr Val Gln Val Phe Thr Asp Ser Glu Tyr Gln Leu Pro Tyr
                    340                 345                 350

Val Leu Gly Ser Ala His Gln Gly Cys Leu Pro Pro Phe Pro Ala Asp
                    355                 360                 365

Val Phe Met Ile Pro Gln Tyr Gly Tyr Leu Thr Leu Asn Asn Gly Ser
                    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                    405                 410                 415

Asp Val Pro Phe His Ser Ser Tyr Ala His Ser Gln Ser Leu Asp Arg
                    420                 425                 430

Leu Met Asn Pro Leu Ile Asp Gln Tyr Leu Tyr Tyr Leu Ser Lys Thr
                    435                 440                 445

Gln Gly Thr Ser Gly Thr Thr Gln Gln Ser Arg Leu Gln Phe Ser Gln
                    450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                    485                 490                 495
```

```
Asn Ser Glu Phe Ala Trp Thr Ala Thr Lys Tyr Tyr Leu Asn Gly
            500                 505                 510

Arg Asn Ser Leu Val Asn Pro Gly Pro Met Ala Ser His Lys Asp
            515                 520                 525

Asp Glu Glu Lys Tyr Phe Pro Met His Gly Asn Leu Ile Phe Gly Lys
            530                 535                 540

Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
                    565                 570                 575

Gly Gln Val Ala Thr Asn His Gln Ser Gln Asn Thr Thr Ala Ser Tyr
                580                 585                 590

Gly Ser Val Asp Ser Gln Gly Ile Leu Pro Gly Met Val Trp Gln Asp
            595                 600                 605

Arg Asp Val Tyr Leu Gln Gly Pro Ile Trp Ala Lys Thr Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                    645                 650                 655

Pro Ala Thr Thr Phe Thr Pro Gly Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                    725                 730                 735

<210> SEQ ID NO 68
<211> LENGTH: 735
<212> TYPE: PRT
<213> ORGANISM: Unknown
<220> FEATURE:
<223> OTHER INFORMATION: capsid protein of AAV serotype, clone A3.4

<400> SEQUENCE: 68

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Asn Gln Gln His Arg Asp Asp Ser Arg Gly Leu Val Leu Pro
            35                  40                  45

Gly Tyr Lys Tyr Leu Gly Pro Phe Asn Gly Leu Asp Lys Gly Glu Pro
            50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125
```

```
Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Glu Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asp Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Lys Thr
        435                 440                 445

Gln Gly Thr Ser Gly Thr Thr Gln Gln Ser Arg Leu Gln Phe Ser Gln
450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Ala Thr Lys Tyr Tyr Leu Asn Gly
            500                 505                 510

Arg Asn Ser Leu Val Asn Pro Gly Pro Pro Met Ala Ser His Lys Asp
        515                 520                 525

Asp Glu Glu Lys Tyr Phe Pro Met His Gly Asn Leu Ile Phe Gly Lys
530                 535                 540
```

```
Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
                565                 570                 575

Gly Gln Val Ala Thr Asn His Gln Ser Gln Asp Thr Thr Ala Ser Tyr
            580                 585                 590

Gly Ser Val Asp Ser Gln Gly Ile Leu Pro Gly Met Val Trp Gln Asp
        595                 600                 605

Arg Asp Val Tyr Leu Gln Gly Pro Ile Trp Ala Lys Thr Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ala Thr Thr Phe Thr Pro Gly Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 69
<211> LENGTH: 735
<212> TYPE: PRT
<213> ORGANISM: Unknown
<220> FEATURE:
<223> OTHER INFORMATION: capsid protein of AAV serotype, clone A3.5

<400> SEQUENCE: 69

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175
```

```
Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Lys Thr
        435                 440                 445

Gln Gly Thr Ser Gly Thr Thr Gln Gln Ser Arg Leu Gln Phe Asn Gln
    450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Ala Thr Lys Tyr Tyr Pro Asn Gly
            500                 505                 510

Arg Asn Ser Leu Val Asn Pro Gly Pro Pro Met Ala Ser His Lys Asp
        515                 520                 525

Asp Glu Glu Lys Tyr Phe Pro Met His Gly Asn Leu Ile Phe Gly Lys
    530                 535                 540

Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
                565                 570                 575

Gly Gln Val Ala Thr Asn Arg Gln Ser Gln Asn Thr Thr Ala Ser Tyr
            580                 585                 590

Gly Ser Val Asp Ser Gln Gly Ile Leu Pro Gly Met Val Trp Gln Asp
```

```
                    595                 600                 605
Arg Asp Val Tyr Leu Gln Gly Pro Ile Trp Ala Lys Thr Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                    645                 650                 655

Pro Ala Thr Thr Phe Thr Pro Gly Lys Phe Ala Ser Phe Ile Thr Gln
                    660                 665                 670

Tyr Ser Thr Gly Gln Val Ser Val Glu Ile Glu Trp Glu Leu Gln Lys
                    675                 680                 685

Glu Asn Ser Lys Arg Trp Asn Pro Glu Ile Gln Tyr Thr Ser Asn Tyr
690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                    725                 730                 735

<210> SEQ ID NO 70
<211> LENGTH: 735
<212> TYPE: PRT
<213> ORGANISM: Unknown
<220> FEATURE:
<223> OTHER INFORMATION: capsid protein of AAV serotype, clone AAV2

<400> SEQUENCE: 70

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
```

```
            225                 230                 235                 240

Thr Thr Ser Thr Arg Thr Trp Ala Leu Pro Thr Tyr Asn Asn His Leu
                        245                 250                 255

Tyr Lys Gln Ile Ser Ser Gln Ser Gly Ala Ser Asn Asp Asn His Tyr
                        260                 265                 270

Phe Gly Tyr Ser Thr Pro Trp Gly Tyr Phe Asp Phe Asn Arg Phe His
                        275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
        305                 310                 315                 320

Lys Glu Val Thr Gln Asn Asp Gly Thr Thr Thr Ile Ala Asn Asn Leu
                        325                 330                 335

Thr Ser Thr Val Gln Val Phe Thr Asp Ser Glu Tyr Gln Leu Pro Tyr
                        340                 345                 350

Val Leu Gly Ser Ala His Gln Gly Cys Leu Pro Pro Phe Pro Ala Asp
                        355                 360                 365

Val Phe Met Val Pro Gln Tyr Gly Tyr Leu Thr Leu Asn Asn Gly Ser
                        370                 375                 380

Gln Ala Val Gly Arg Ser Ser Phe Tyr Cys Leu Glu Tyr Phe Pro Ser
        385                 390                 395                 400

Gln Met Leu Arg Thr Gly Asn Asn Phe Thr Phe Ser Tyr Thr Phe Glu
                        405                 410                 415

Asp Val Pro Phe His Ser Ser Tyr Ala His Ser Gln Ser Leu Asp Arg
                        420                 425                 430

Leu Met Asn Pro Leu Ile Asp Gln Tyr Leu Tyr Tyr Leu Ser Arg Thr
                        435                 440                 445

Asn Thr Pro Ser Gly Thr Thr Thr Gln Ser Arg Leu Gln Phe Ser Gln
                        450                 455                 460

Ala Gly Ala Ser Asp Ile Arg Asp Gln Ser Arg Asn Trp Leu Pro Gly
        465                 470                 475                 480

Pro Cys Tyr Arg Gln Gln Arg Val Ser Lys Thr Ser Ala Asp Asn Asn
                        485                 490                 495

Asn Ser Glu Tyr Ser Trp Thr Gly Ala Thr Lys Tyr His Leu Asn Gly
                        500                 505                 510

Arg Asp Ser Leu Val Asn Pro Gly Pro Ala Met Ala Ser His Lys Asp
                        515                 520                 525

Asp Glu Glu Lys Phe Phe Pro Gln Ser Gly Val Leu Ile Phe Gly Lys
                        530                 535                 540

Gln Gly Ser Glu Lys Thr Asn Val Asp Ile Glu Lys Val Met Ile Thr
        545                 550                 555                 560

Asp Glu Glu Glu Ile Arg Thr Thr Asn Pro Val Ala Thr Glu Gln Tyr
                        565                 570                 575

Gly Ser Val Ser Thr Asn Leu Gln Arg Gly Asn Arg Gln Ala Ala Thr
                        580                 585                 590

Ala Asp Val Asn Thr Gln Gly Val Leu Pro Gly Met Val Trp Gln Asp
                        595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
        625                 630                 635                 640

His Pro Pro Pro Gln Ile Leu Ile Lys Asn Thr Pro Val Pro Ala Asn
                        645                 650                 655
```

```
Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 71
<211> LENGTH: 736
<212> TYPE: PRT
<213> ORGANISM: Unknown
<220> FEATURE:
<223> OTHER INFORMATION: capsid protein of AAV serotype, clone AAV3

<400> SEQUENCE: 71

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Gly Thr Val Asn His Gln Gly Ala Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700
```

```
Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 72
<211> LENGTH: 737
<212> TYPE: PRT
<213> ORGANISM: Unknown
<220> FEATURE:
<223> OTHER INFORMATION: capsid protein of AAV serotype, clone 3.3bVP1

<400> SEQUENCE: 72

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Asn Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Ser Val Gly Ser Gly Thr Val Ala Ala Gly Gly
    195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Glu Gln Ile Ser Ser Glu Thr Ala Gly Ser Thr Asn Asp Asn
        260                 265                 270

Thr Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
            325                 330                 335
```

```
Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asp Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asp Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 73
```

<211> LENGTH: 644
<212> TYPE: PRT
<213> ORGANISM: Unknown
<220> FEATURE:
<223> OTHER INFORMATION: capsid protein of AAV serotype, clone 223-4

<400> SEQUENCE: 73

```
Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Pro Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Gly
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
370                 375                 380
```

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
            405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
            435                 440                 445

Lys Asp Asp Glu Glu Arg Phe Phe Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
            485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
            515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
            565                 570                 575

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
            610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 74
<211> LENGTH: 644
<212> TYPE: PRT
<213> ORGANISM: Unknown
<220> FEATURE:
<223> OTHER INFORMATION: capsid protein of AAV serotype, clone 223-5

<400> SEQUENCE: 74

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
            85                  90                  95

```
Gly Asp Ser Glu Pro Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Gly
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
```

```
                515                 520                 525
Asn Arg Asp Val Tyr Leu Gln Gly Pro Ile Trp Ala Lys Ile Pro His
        530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
        565                 570                 575

Asn Pro Pro Glu Val Phe Thr Pro Ala Lys Phe Ala Ser Phe Ile Thr
        580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
        610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 75
<211> LENGTH: 644
<212> TYPE: PRT
<213> ORGANISM: Unknown
<220> FEATURE:
<223> OTHER INFORMATION: capsid protein of AAV serotype, clone 223-10
<220> FEATURE:
<221> NAME/KEY: MISC_FEATURE
<222> LOCATION: (434)..(434)
<223> OTHER INFORMATION: can be any amino acid

<400> SEQUENCE: 75

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
```

-continued

```
            210                 215                 220
Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Xaa Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
    530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
    610                 615                 620

Phe Asp Lys Gln Thr Gly Val Asp Phe Ala Val Asp Ser Gln Gly Val
625                 630                 635                 640
```

Tyr Ser Glu Pro

<210> SEQ ID NO 76
<211> LENGTH: 644
<212> TYPE: PRT
<213> ORGANISM: Unknown
<220> FEATURE:
<223> OTHER INFORMATION: capsid protein of AAV serotype, clone 223-2

<400> SEQUENCE: 76

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Cys Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Val Ala Gly Gly Gly
        115                 120                 125

Ala Pro Met Ala Asp Asn Asn Glu Gly Ala Asp Gly Val Gly Asn Ala
130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
            340                 345                 350

-continued

Arg Leu Met Asn Pro Leu Ile Asp Gln Tyr Leu Tyr Leu Ala Arg
            355                 360                 365

Thr Gln Ser Asn Ala Gly Gly Thr Ala Gly Asn Arg Glu Leu Gln Phe
370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Gly Ala Thr Lys Tyr His Leu
            420                 425                 430

Asn Gly Arg Asn Ser Leu Val Asn Pro Gly Val Ala Met Ala Thr His
            435                 440                 445

Lys Asp Asp Glu Glu Arg Phe Ser Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
            515                 520                 525

Asn Arg Asp Val Tyr Leu Gln Gly Pro Ile Trp Ala Lys Ile Pro His
            530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 77
<211> LENGTH: 644
<212> TYPE: PRT
<213> ORGANISM: Unknown
<220> FEATURE:
<223> OTHER INFORMATION: capsid protein of AAV serotype, clone 223-7

<400> SEQUENCE: 77

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
                20                  25                  30

Ser Phe Gly Gly Asn Leu Gly Arg Ala Val Phe Gln Ala Lys Lys Arg
            35                  40                  45

Val Leu Glu Pro Leu Gly Leu Val Glu Thr Pro Ala Lys Thr Ala Pro
50                  55                  60

Gly Lys Lys Arg Pro Val Asp Ser Pro Asp Ser Thr Ser Gly Ile Gly

-continued

```
                65                  70                  75                  80
Lys Lys Gly Gln Gln Pro Ala Lys Lys Arg Leu Asn Phe Gly Gln Thr
                        85                  90                  95
Gly Asp Ser Glu Ser Val Pro Asp Pro Gln Pro Ile Gly Glu Pro Pro
                100                 105                 110
Ala Gly Pro Ser Gly Leu Gly Ser Gly Thr Met Ala Ala Gly Gly Gly
                115                 120                 125
Ala Pro Met Ala Asp Asn Asn Glu Gly Ala Asp Gly Val Gly Asn Ala
                130                 135                 140
Ser Gly Asn Trp His Cys Asp Ser Thr Trp Leu Gly Asp Arg Val Ile
145                 150                 155                 160
Thr Thr Ser Thr Arg Thr Trp Ala Leu Pro Thr Tyr Asn Asn His Leu
                        165                 170                 175
Tyr Lys Gln Ile Ser Ser Gln Ser Ala Gly Ser Thr Asn Asp Asn Val
                180                 185                 190
Tyr Phe Gly Tyr Ser Thr Pro Trp Gly Tyr Phe Asp Phe Asn Arg Phe
                195                 200                 205
His Cys His Phe Ser Pro Arg Asp Trp Gln Arg Leu Ile Asn Asn Asn
                210                 215                 220
Trp Gly Phe Arg Pro Lys Lys Leu Asn Phe Lys Leu Phe Asn Ile Gln
225                 230                 235                 240
Val Lys Glu Val Thr Thr Asn Asp Gly Val Thr Thr Ile Ala Asn Asn
                        245                 250                 255
Leu Thr Ser Thr Val Gln Val Phe Ser Asp Pro Glu Tyr Gln Leu Pro
                260                 265                 270
Tyr Val Leu Gly Ser Ala His Gln Gly Cys Leu Pro Pro Phe Pro Ala
                275                 280                 285
Asp Val Phe Met Ile Pro Gln Tyr Gly Tyr Leu Thr Leu Asn Asn Gly
                290                 295                 300
Ser Gln Ser Val Gly Arg Ser Ser Phe Tyr Cys Leu Glu Tyr Phe Pro
305                 310                 315                 320
Ser Gln Met Leu Arg Thr Gly Asn Asn Phe Thr Phe Ser Tyr Thr Phe
                        325                 330                 335
Glu Asp Val Pro Phe His Ser Ser Tyr Ala His Ser Gln Ser Leu Asp
                340                 345                 350
Arg Leu Met Asn Pro Leu Ile Asp Gln Tyr Leu Tyr Tyr Leu Ala Arg
                355                 360                 365
Thr Gln Ser Asn Ala Gly Gly Thr Ala Gly Asn Arg Glu Leu Gln Phe
                370                 375                 380
Tyr Gln Gly Gly Pro Thr Thr Met Ala Glu Gln Ala Lys Asn Trp Leu
385                 390                 395                 400
Pro Gly Pro Cys Phe Arg Gln Gln Arg Val Ser Lys Thr Leu Asp Gln
                        405                 410                 415
Asn Asn Asn Ser Asn Phe Ala Trp Thr Gly Ala Thr Lys Tyr His Leu
                420                 425                 430
Asn Gly Arg Asn Ser Leu Val Asn Pro Gly Val Ala Met Ala Thr His
                435                 440                 445
Lys Asp Asp Glu Glu Arg Phe Phe Pro Ser Ser Gly Val Leu Ile Phe
                450                 455                 460
Gly Lys Thr Gly Ala Ala Asn Lys Thr Thr Leu Glu Asn Val Leu Met
465                 470                 475                 480
Thr Asn Glu Glu Glu Ile Arg Pro Thr Asn Pro Val Ala Thr Glu Glu
                        485                 490                 495
```

```
Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
                565                 570                 575

Asn Pro Pro Glu Val Phe Thr Pro Ala Lys Ile Ala Ser Phe Ile Thr
            580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 78
<211> LENGTH: 644
<212> TYPE: PRT
<213> ORGANISM: Unknown
<220> FEATURE:
<223> OTHER INFORMATION: capsid protein of AAV serotype, clone 223-6

<400> SEQUENCE: 78

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Ser Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205
```

```
His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
                260                 265                 270

Tyr Val Leu Gly Ser Ala His Gln Gly Cys Leu Pro Pro Phe Pro Ala
            275                 280                 285

Asp Val Phe Met Ile Pro Gln Tyr Gly Tyr Leu Thr Leu Asn Asn Gly
290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
                340                 345                 350

Arg Leu Met Asn Pro Leu Ile Asp Gln Tyr Leu Tyr Tyr Leu Ala Arg
                355                 360                 365

Thr Gln Ser Asn Ala Gly Gly Thr Ala Gly Asn Arg Glu Leu Gln Phe
                370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
                420                 425                 430

Asn Gly Arg Asn Ser Leu Val Asn Pro Gly Val Ala Met Ala Thr His
                435                 440                 445

Lys Asp Asp Glu Glu Arg Phe Phe Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
                500                 505                 510

Thr Gln Val Val Asn Asn Gln Gly Ala Leu Pro Gly Met Val Trp Gln
                515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Leu Ala Ser Phe Ile Thr
                580                 585                 590

Gln Tyr Ser Thr Gly Gln Val Ser Val Glu Ile Glu Trp Glu Leu Gln
                595                 600                 605

Lys Glu Asn Ser Lys Arg Trp Asn Pro Glu Ile Gln Tyr Thr Ser Asn
                610                 615                 620

Phe Asp Lys Gln Thr Gly Val Asp Phe Ala Val Asp Ser Gln Gly Val
```

```
                625                 630                 635                 640

Tyr Ser Glu Pro

<210> SEQ ID NO 79
<211> LENGTH: 738
<212> TYPE: PRT
<213> ORGANISM: Unknown
<220> FEATURE:
<223> OTHER INFORMATION: capsid protein of AAV serotype, clone 44.1

<400> SEQUENCE: 79

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350
```

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 80
<211> LENGTH: 738
<212> TYPE: PRT

<213> ORGANISM: Unknown
<220> FEATURE:
<223> OTHER INFORMATION: capsid protein of AAV serotype, clone 44.5

<400> SEQUENCE: 80

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Pro Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr

```
                385                 390                 395                 400
        Phe Pro Ser Gln Met Leu Arg Thr Gly Asn Asn Phe Glu Phe Ser Tyr
                        405                 410                 415
        Gln Phe Glu Asp Val Pro Phe His Ser Ser Tyr Ala His Ser Gln Ser
                        420                 425                 430
        Leu Asp Arg Leu Met Asn Pro Leu Ile Asp Gln Tyr Leu Tyr Tyr Leu
                        435                 440                 445
        Ser Arg Thr Gln Ser Thr Gly Gly Thr Ala Gly Thr Gln Gln Leu Leu
                        450                 455                 460
        Phe Ser Gln Ala Gly Pro Asn Asn Met Ser Ala Gln Ala Lys Asn Trp
        465                 470                 475                 480
        Leu Pro Gly Pro Cys Tyr Arg Gln Gln Arg Val Ser Thr Thr Leu Ser
                        485                 490                 495
        Gln Asn Asn Asn Ser Asn Phe Ala Trp Thr Gly Ala Thr Lys Tyr His
                        500                 505                 510
        Leu Asn Gly Arg Asp Ser Leu Val Asn Pro Gly Val Ala Met Ala Thr
                        515                 520                 525
        His Lys Asp Asp Glu Glu Arg Phe Phe Pro Ser Ser Gly Val Leu Met
                        530                 535                 540
        Phe Gly Lys Gln Gly Ala Gly Lys Asp Asn Val Asp Tyr Ser Ser Val
        545                 550                 555                 560
        Met Leu Thr Ser Glu Glu Glu Ile Lys Thr Thr Asn Pro Val Ala Thr
                        565                 570                 575
        Glu Gln Tyr Gly Val Val Ala Asp Asn Leu Gln Gln Gln Asn Ala Ala
                        580                 585                 590
        Pro Ile Val Gly Ala Val Asn Ser Gln Gly Ala Leu Pro Gly Met Val
                        595                 600                 605
        Trp Gln Asn Arg Asp Val Tyr Leu Gln Gly Pro Ile Trp Ala Lys Ile
                        610                 615                 620
        Pro His Thr Asp Gly Asn Phe His Pro Ser Pro Leu Met Gly Gly Phe
        625                 630                 635                 640
        Gly Leu Lys His Pro Pro Pro Gln Ile Leu Ile Lys Asn Thr Pro Val
                        645                 650                 655
        Pro Ala Asp Pro Pro Thr Thr Phe Ser Gln Ala Lys Leu Ala Ser Phe
                        660                 665                 670
        Ile Thr Gln Tyr Ser Thr Gly Gln Val Ser Val Glu Ile Glu Trp Glu
                        675                 680                 685
        Leu Gln Lys Glu Asn Ser Lys Arg Trp Asn Pro Glu Ile Gln Tyr Thr
                        690                 695                 700
        Ser Asn Tyr Tyr Lys Ser Thr Asn Val Asp Phe Ala Val Asn Thr Asp
        705                 710                 715                 720
        Gly Thr Tyr Ser Glu Pro Arg Pro Ile Gly Thr Arg Tyr Leu Thr Arg
                        725                 730                 735
        Asn Leu

<210> SEQ ID NO 81
<211> LENGTH: 738
<212> TYPE: PRT
<213> ORGANISM: Unknown
<220> FEATURE:
<223> OTHER INFORMATION: capsid protein of AAV serotype, clone 44.2

<400> SEQUENCE: 81

Met Ala Ala Asp Gly Tyr Leu Pro Asp Trp Leu Glu Asp Asn Leu Ser
        1               5                   10                  15
```

Glu Gly Ile Arg Glu Trp Trp Asp Leu Lys Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
         115                 120                 125

Leu Gly Leu Val Glu Glu Gly Ala Lys Thr Ala Pro Gly Lys Lys Arg
     130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                 165                 170                 175

Thr Gly Asp Ser Glu Ser Val Pro Asp Pro Gln Pro Ile Gly Glu Pro
             180                 185                 190

Pro Ala Gly Pro Ser Gly Leu Gly Ser Gly Thr Met Ala Ala Gly Gly
         195                 200                 205

Gly Ala Pro Met Ala Asp Asn Asn Glu Gly Ala Asp Gly Val Gly Ser
     210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                 245                 250                 255

Leu Tyr Lys Gln Ile Ser Asn Gly Thr Ser Gly Gly Ser Thr Asn Asp
             260                 265                 270

Asn Thr Tyr Phe Gly Tyr Ser Thr Pro Trp Gly Tyr Phe Asp Phe Asn
         275                 280                 285

Arg Phe His Cys His Phe Ser Pro Arg Asp Trp Gln Arg Leu Ile Asn
     290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                 325                 330                 335

Asn Asn Leu Thr Ser Thr Ile Gln Val Phe Thr Asp Ser Glu Tyr Gln
             340                 345                 350

Leu Pro Tyr Val Leu Gly Ser Ala His Gln Gly Cys Leu Pro Pro Phe
         355                 360                 365

Pro Ala Asp Val Phe Met Ile Pro Gln Tyr Gly Tyr Leu Thr Leu Asn
     370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                 405                 410                 415

Gln Phe Glu Asp Val Pro Phe His Ser Ser Tyr Ala His Ser Gln Ser
             420                 425                 430

```
Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 82
<211> LENGTH: 738
<212> TYPE: PRT
<213> ORGANISM: Unknown
<220> FEATURE:
<223> OTHER INFORMATION: capsid protein of AAV serotype, clone 29.3VP1

<400> SEQUENCE: 82

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
```

```
            50                  55                  60
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                     85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Thr Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
                195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala Arg Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
            450                 455                 460

Phe Ser Gln Ala Gly Pro Asn Asn Met Ser Ala Gln Ala Lys Asn Trp
465                 470                 475                 480
```

Leu Pro Gly Pro Cys Tyr Arg Gln Gln Arg Val Ser Thr Thr Leu Ser
              485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Gly Asn Val Asp Tyr Ser Ser Val
545                 550                 555                 560

Met Leu Thr Ser Glu Glu Glu Ile Lys Thr Thr Asn Pro Val Ala Thr
              565                 570                 575

Glu Gln Tyr Gly Val Val Ala Asp Asn Leu Gln Gln Gln Asn Ala Ala
          580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
              645                 650                 655

Pro Ala Asp Pro Pro Thr Thr Phe Ser Gln Ala Lys Leu Ala Ser Phe
          660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
              725                 730                 735

Asn Leu

<210> SEQ ID NO 83
<211> LENGTH: 738
<212> TYPE: PRT
<213> ORGANISM: Unknown
<220> FEATURE:
<223> OTHER INFORMATION: capsid protein of AAV serotype, clone 29.5VP1

<400> SEQUENCE: 83

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

```
Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Gly Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Ser Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asp Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
```

```
                515                 520                 525
His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 84
<211> LENGTH: 738
<212> TYPE: PRT
<213> ORGANISM: Unknown
<220> FEATURE:
<223> OTHER INFORMATION: capsid protein of AAV serotype, clone 42.15

<400> SEQUENCE: 84

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140
```

-continued

```
Pro Val Glu Pro Ser Pro Gln Arg Ser Pro Asp Ser Thr Gly Ile
145                 150                 155                 160

Gly Lys Thr Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Pro Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Arg Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560
```

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
        660                 665                 670

Ile Thr Gln Tyr Ser Thr Gly Gln Val Ser Val Glu Ile Glu Trp Glu
    675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 85
<211> LENGTH: 738
<212> TYPE: PRT
<213> ORGANISM: Unknown
<220> FEATURE:
<223> OTHER INFORMATION: capsid protein of AAV serotype, clone 42.8

<400> SEQUENCE: 85

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro

-continued

```
            180                 185                 190
Pro Ala Gly Pro Ser Gly Leu Gly Ser Gly Thr Met Ala Ala Gly Gly
            195                 200                 205
Gly Ala Pro Met Ala Asp Asn Asn Glu Gly Ala Asp Gly Val Gly Ser
            210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                    245                 250                 255
Leu Tyr Lys Gln Ile Ser Asn Gly Thr Ser Gly Gly Ser Thr Asn Asp
                    260                 265                 270
Asn Thr Tyr Phe Gly Tyr Ser Thr Pro Trp Gly Tyr Phe Asp Phe Asn
                    275                 280                 285
Arg Phe His Cys His Phe Ser Pro Arg Asp Trp Gln Arg Leu Ile Asn
                    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                    325                 330                 335
Asn Asn Leu Thr Ser Thr Ile Gln Val Phe Thr Asp Ser Glu Tyr Gln
                    340                 345                 350
Leu Pro Tyr Val Leu Gly Ser Ala His Gln Gly Cys Leu Pro Pro Phe
                    355                 360                 365
Pro Ala Asp Val Phe Met Ile Pro Gln Tyr Gly Tyr Leu Thr Leu Asn
                    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                    405                 410                 415
Gln Phe Glu Asp Val Pro Phe His Ser Ser Tyr Ala His Ser Gln Ser
                    420                 425                 430
Leu Asp Arg Leu Met Asn Pro Leu Ile Asp Gln Tyr Leu Tyr Tyr Leu
                    435                 440                 445
Ser Arg Thr Gln Ser Thr Gly Gly Thr Ala Gly Thr Gln Gln Leu Leu
                    450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                    485                 490                 495
Gln Asn Asn Asn Ser Asn Phe Ala Trp Thr Gly Ala Thr Lys Tyr His
                    500                 505                 510
Leu Asn Gly Arg Asp Ser Leu Val Asn Pro Gly Val Ala Met Ala Thr
                    515                 520                 525
His Lys Asp Asp Glu Glu Arg Phe Phe Pro Ser Ser Gly Val Leu Met
                    530                 535                 540
Phe Gly Lys Gln Gly Ala Gly Lys Asp Asn Val Asp Tyr Ser Ser Val
545                 550                 555                 560
Met Leu Thr Ser Glu Glu Ile Lys Thr Thr Asn Pro Val Ala Thr
                    565                 570                 575
Glu Gln Tyr Gly Val Val Ala Asp Asn Leu Gln Gln Gln Asn Ala Ala
                    580                 585                 590
Pro Ile Val Gly Ala Val Asn Ser Gln Gly Ala Leu Pro Gly Met Val
                    595                 600                 605
```

```
Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 86
<211> LENGTH: 733
<212> TYPE: PRT
<213> ORGANISM: Unknown
<220> FEATURE:
<223> OTHER INFORMATION: capsid protein of AAV serotype, clone 42.13

<400> SEQUENCE: 86

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Ser Ser Ser Gly Asn Trp
    210                 215                 220
```

```
His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Arg Leu Ile Asn Asn Asn Trp Gly Phe
    290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
                340                 345                 350

Gly Ser Ala His Gln Gly Cys Leu Pro Pro Phe Pro Ala Asp Val Phe
            355                 360                 365

Met Ile Pro Gln Tyr Gly Tyr Leu Thr Leu Asn Asn Gly Ser Gln Ala
370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
            435                 440                 445

Thr Gly Gly Thr Ala Gly Thr Gln Gln Leu Leu Phe Ser Gln Ala Gly
    450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Val Ser Gln Asn Asn Asn Ser
                485                 490                 495

Asn Phe Ala Trp Thr Gly Ala Thr Lys Tyr His Leu Asn Gly Arg Asp
            500                 505                 510

Ser Leu Val Asn Pro Gly Val Ala Met Ala Thr His Lys Gly Asp Glu
    515                 520                 525

Glu Arg Phe Phe Pro Ser Ser Gly Val Leu Met Phe Gly Lys Gln Gly
530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575

Val Ala Asp Asn Leu Gln Gln Asn Ala Ala Pro Ile Val Gly Ala
            580                 585                 590

Val Asn Ser Gln Gly Ala Leu Pro Gly Met Val Trp Gln Asn Arg Asp
    595                 600                 605

Val Tyr Leu Gln Gly Pro Ile Trp Ala Lys Ile Pro His Thr Asp Gly
    610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
```

645                 650                 655
Thr Thr Phe Ser Gln Ala Lys Leu Ala Ser Phe Ile Thr Gln Tyr Ser
                660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Tyr Lys
        690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Ser Leu
                725                 730

<210> SEQ ID NO 87
<211> LENGTH: 733
<212> TYPE: PRT
<213> ORGANISM: Unknown
<220> FEATURE:
<223> OTHER INFORMATION: capsid protein of AAV serotype, clone 42.3A

<400> SEQUENCE: 87

Met Ala Ala Asp Gly His Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Ser Ser Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
            260                 265                 270

Tyr Ser Thr Pro Trp Gly Tyr Phe Asp Phe Asn Arg Phe His Cys His

```
            275                 280                 285
Phe Ser Pro Arg Asp Trp Gln Arg Leu Ile Asn Asn Ser Trp Gly Phe
290                 295                 300
Arg Pro Lys Arg Leu Asn Phe Lys Leu Phe Asn Ile Gln Val Lys Glu
305                 310                 315                 320
Val Thr Gln Asn Glu Gly Thr Lys Thr Ile Ala Asn Asn Leu Thr Ser
                325                 330                 335
Thr Ile Gln Val Phe Thr Asp Ser Glu Tyr Gln Leu Pro Tyr Val Leu
            340                 345                 350
Gly Ser Ala His Gln Gly Cys Leu Pro Pro Phe Pro Ala Asp Val Phe
            355                 360                 365
Met Ile Pro Gln Tyr Gly Tyr Leu Thr Leu Asn Asn Gly Ser Gln Ala
370                 375                 380
Val Gly Arg Ser Ser Phe Tyr Cys Leu Glu Tyr Phe Pro Ser Gln Met
385                 390                 395                 400
Leu Arg Thr Gly Asn Asn Phe Glu Phe Ser Tyr Gln Phe Glu Asp Val
                405                 410                 415
Pro Phe His Ser Ser Tyr Ala His Ser Gln Ser Leu Asp Arg Leu Met
            420                 425                 430
Asn Pro Leu Ile Asp Gln Tyr Leu Tyr Tyr Leu Ser Arg Thr Gln Ser
            435                 440                 445
Thr Gly Gly Thr Ala Gly Thr Gln Gln Leu Leu Phe Ser Gln Ala Gly
            450                 455                 460
Pro Asn Asn Met Ser Ala Gln Ala Lys Asn Trp Leu Pro Gly Pro Cys
465                 470                 475                 480
Tyr Arg Gln Gln Arg Val Ser Thr Thr Leu Ser Gln Asn Asn Asn Ser
                485                 490                 495
Asn Phe Ala Trp Thr Gly Ala Thr Lys Tyr His Leu Asn Gly Arg Asp
            500                 505                 510
Ser Leu Val Asn Pro Gly Val Ala Met Ala Thr His Lys Asp Asp Glu
            515                 520                 525
Glu Arg Phe Phe Pro Ser Ser Gly Val Leu Met Phe Gly Lys Gln Gly
            530                 535                 540
Ala Gly Lys Asp Asn Val Asp Tyr Ser Ser Val Met Leu Thr Ser Glu
545                 550                 555                 560
Glu Glu Ile Lys Thr Thr Asn Pro Val Ala Thr Glu Gln Tyr Gly Val
                565                 570                 575
Val Ala Asp Asn Leu Gln Gln Gln Asn Ala Ala Pro Ile Val Gly Ala
            580                 585                 590
Val Asn Ser Gln Gly Ala Leu Pro Gly Met Val Trp Gln Asn Arg Asp
            595                 600                 605
Val Tyr Leu Gln Gly Pro Ile Trp Ala Lys Ile Pro His Thr Asp Gly
            610                 615                 620
Asn Phe His Pro Ser Pro Leu Met Gly Gly Phe Gly Leu Lys His Pro
625                 630                 635                 640
Pro Pro Gln Ile Leu Ile Lys Asn Thr Pro Val Pro Ala Asp Pro Pro
                645                 650                 655
Thr Thr Phe Ser Gln Ala Lys Leu Ala Ser Phe Ile Thr Gln Tyr Ser
            660                 665                 670
Thr Gly Gln Val Ser Val Glu Ile Glu Trp Glu Leu Gln Lys Glu Asn
            675                 680                 685
Ser Lys Arg Trp Asn Pro Glu Ile Gln Tyr Thr Ser Asn Tyr Tyr Lys
            690                 695                 700
```

-continued

```
Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
            725                 730

<210> SEQ ID NO 88
<211> LENGTH: 731
<212> TYPE: PRT
<213> ORGANISM: Unknown
<220> FEATURE:
<223> OTHER INFORMATION: capsid protein of AAV serotype, clone 42.4

<400> SEQUENCE: 88

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Ser Arg Asp Trp Gln Arg Leu Ile Asn Asn Trp Gly Phe Arg Pro
    290                 295                 300

Lys Arg Leu Asn Phe Lys Leu Phe Asn Ile Gln Val Lys Glu Val Thr
305                 310                 315                 320

Gln Asn Glu Gly Thr Lys Thr Ile Ala Asn Asn Leu Thr Ser Thr Ile
                325                 330                 335
```

-continued

```
Gln Val Phe Thr Asp Ser Glu Tyr Arg Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ala Val Gly
            370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Gln Phe Glu Asp Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ser Arg Thr Gln Ser Thr Gly
            435                 440                 445

Gly Thr Ala Gly Thr Gln Gln Leu Leu Phe Ser Gln Ala Gly Pro Asn
            450                 455                 460

Asn Met Ser Ala Gln Ala Lys Asn Trp Leu Pro Gly Pro Cys Tyr Arg
465                 470                 475                 480

Gln Gln Arg Val Ser Thr Thr Leu Ser Gln Asn Asn Asn Ser Asn Phe
                485                 490                 495

Ala Trp Thr Gly Ala Thr Lys Tyr His Leu Asn Gly Arg Asp Ser Leu
            500                 505                 510

Val Asn Pro Gly Val Ala Met Ala Thr His Lys Asp Asp Glu Glu Arg
            515                 520                 525

Phe Phe Pro Ser Ser Gly Val Leu Met Phe Gly Lys Gln Gly Ala Gly
            530                 535                 540

Lys Asp Asn Val Asp Tyr Ser Ser Val Met Leu Thr Ser Glu Glu Glu
545                 550                 555                 560

Ile Lys Thr Thr Asn Pro Val Ala Thr Glu Gln Tyr Gly Val Val Ala
                565                 570                 575

Asp Asn Leu Gln Gln Gln Asn Ala Ala Pro Ile Val Gly Ala Val Asn
            580                 585                 590

Ser Gln Gly Ala Leu Pro Gly Met Val Trp Gln Asn Arg Asp Val Tyr
            595                 600                 605

Leu Gln Gly Pro Ile Trp Ala Lys Ile Pro His Thr Asp Gly Asn Phe
            610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
                645                 650                 655

Phe Ser Gln Ala Lys Pro Ala Ser Phe Ile Thr Gln Tyr Ser Thr Gly
            660                 665                 670

Gln Val Ser Val Glu Ile Glu Trp Glu Leu Gln Lys Glu Asn Ser Lys
            675                 680                 685

Arg Trp Asn Pro Glu Ile Gln Tyr Thr Ser Asn Tyr Lys Ser Thr
690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
                725                 730
```

<210> SEQ ID NO 89
<211> LENGTH: 731

<212> TYPE: PRT
<213> ORGANISM: Unknown
<220> FEATURE:
<223> OTHER INFORMATION: capsid protein of AAV serotype, clone 42.5A

<400> SEQUENCE: 89

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Arg Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Arg Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Gln Phe Glu Asp Val Pro Phe
            405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ser Arg Thr Gln Ser Thr Gly
        435                 440                 445

Gly Thr Ala Gly Thr Gln Gln Leu Leu Phe Ser Gln Ala Gly Pro Asn
    450                 455                 460

Asn Met Ser Ala Gln Ala Lys Asn Trp Leu Pro Gly Pro Cys Tyr Arg
465                 470                 475                 480

Gln Gln Arg Val Ser Thr Thr Leu Ser Gln Asn Asn Asn Ser Asn Phe
            485                 490                 495

Ala Trp Thr Gly Ala Thr Lys Tyr His Leu Asn Gly Arg Asp Ser Leu
        500                 505                 510

Val Asn Pro Gly Val Ala Met Ala Thr His Lys Asp Asp Glu Glu Arg
    515                 520                 525

Phe Phe Pro Ser Ser Gly Val Leu Met Phe Gly Lys Gln Gly Ala Gly
530                 535                 540

Lys Asp Asn Val Asp Tyr Ser Ser Val Met Leu Thr Ser Glu Glu Glu
545                 550                 555                 560

Ile Lys Thr Thr Asn Pro Val Ala Thr Glu Gln Tyr Gly Val Val Ala
            565                 570                 575

Asp Asn Leu Gln Gln Gln Asn Ala Ala Pro Ile Val Gly Ala Val Asn
        580                 585                 590

Ser Gln Gly Ala Leu Pro Gly Met Ala Trp Gln Asn Arg Asp Val Tyr
    595                 600                 605

Leu Gln Gly Pro Ile Trp Ala Lys Ile Pro His Thr Asp Gly Asn Phe
610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
            645                 650                 655

Phe Ser Gln Ala Lys Leu Ala Ser Phe Ile Thr Gln Tyr Ser Thr Gly
        660                 665                 670

Gln Val Ser Val Glu Ile Glu Trp Glu Leu Gln Lys Glu Asn Ser Lys
    675                 680                 685

Arg Trp Asn Pro Glu Ile Gln Tyr Thr Ser Asn Tyr Tyr Lys Ser Thr
690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
            725                 730

<210> SEQ ID NO 90
<211> LENGTH: 733
<212> TYPE: PRT
<213> ORGANISM: Unknown
<220> FEATURE:
<223> OTHER INFORMATION: capsid protein of AAV serotype, clone 42.1B

<400> SEQUENCE: 90

Met Ala Ala Asp Gly Tyr Leu Pro Asp Trp Leu Glu Asp Asn Leu Ser
1               5                   10                  15

-continued

Glu Gly Ile Arg Glu Trp Trp Asp Leu Arg Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
         115                 120                 125

Leu Gly Leu Val Glu Glu Gly Ala Lys Thr Ala Pro Gly Lys Lys Arg
     130                 135                 140

Pro Ile Glu Ser Pro Asp Ser Ser Thr Gly Ile Gly Lys Lys Gly Gln
145                 150                 155                 160

Gln Pro Ala Lys Lys Arg Leu Asn Phe Gly Gln Thr Gly Asp Ser Glu
                 165                 170                 175

Ser Val Pro Asp Pro Gln Pro Ile Gly Glu Pro Pro Ala Gly Pro Ser
             180                 185                 190

Gly Leu Gly Ser Gly Thr Met Ala Ala Gly Gly Gly Ala Pro Met Ala
         195                 200                 205

Asp Asn Asn Glu Gly Ala Asp Gly Val Gly Ser Ser Ser Gly Asn Trp
     210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                 245                 250                 255

Ser Asn Gly Thr Ser Gly Gly Ser Thr Asn Asp Asn Thr Tyr Phe Gly
             260                 265                 270

Tyr Ser Thr Pro Trp Gly Tyr Phe Asp Phe Asn Arg Phe His Cys His
         275                 280                 285

Phe Ser Pro Arg Asp Trp Gln Arg Leu Ile Asn Asn Asn Trp Gly Phe
     290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                 325                 330                 335

Thr Ile Gln Val Phe Thr Asp Ser Glu Tyr Gln Leu Pro Tyr Val Leu
             340                 345                 350

Gly Ser Ala His Gln Gly Cys Leu Pro Pro Phe Pro Ala Asp Val Phe
         355                 360                 365

Met Ile Pro Gln Tyr Gly Tyr Leu Thr Leu Asn Asn Gly Ser Gln Ala
     370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                 405                 410                 415

Pro Phe His Ser Ser Tyr Ala His Ser Gln Ser Leu Asp Arg Leu Met
             420                 425                 430

Asn Pro Leu Ile Asp Gln Tyr Leu Tyr Tyr Leu Ser Arg Thr Gln Ser 435                 440                 445
Thr Gly Gly Thr Ala Gly Thr Gln Gln Leu Leu Phe Ser Gln Ala Gly
            450                 455                 460
Pro Asn Asn Met Ser Ala Gln Ala Lys Asn Trp Leu Pro Gly Pro Cys
465                 470                 475                 480
Tyr Arg Gln Gln Arg Val Ser Thr Thr Val Ser Gln Asn Asn Asn Ser
                485                 490                 495
Asn Phe Ala Trp Thr Gly Ala Thr Lys Tyr His Leu Asn Gly Arg Asp
            500                 505                 510
Ser Leu Val Asn Pro Gly Val Ala Met Ala Thr His Lys Gly Asp Glu
            515                 520                 525
Glu Arg Phe Phe Pro Ser Ser Gly Val Leu Met Phe Gly Lys Gln Gly
            530                 535                 540
Ala Gly Lys Asp Asn Val Asp Tyr Ser Ser Val Met Leu Thr Ser Glu
545                 550                 555                 560
Glu Glu Ile Lys Thr Thr Asn Pro Val Ala Thr Glu Gln Tyr Gly Val
                565                 570                 575
Val Ala Asp Asn Leu Gln Gln Gln Asn Ala Ala Pro Ile Val Gly Ala
            580                 585                 590
Val Asn Ser Gln Gly Ala Leu Pro Gly Met Val Trp Gln Asn Arg Asp
            595                 600                 605
Val Tyr Leu Gln Gly Pro Ile Trp Ala Lys Ile Pro His Thr Asp Gly
            610                 615                 620
Asn Phe His Pro Ser Pro Leu Met Gly Gly Phe Gly Leu Lys His Pro
625                 630                 635                 640
Pro Pro Gln Ile Leu Ile Lys Asn Thr Pro Val Pro Ala Asp Pro Pro
                645                 650                 655
Thr Thr Phe Ser Gln Ala Lys Leu Ala Ser Phe Ile Thr Gln Tyr Ser
            660                 665                 670
Thr Gly Gln Val Ser Val Glu Ile Glu Trp Glu Leu Gln Lys Glu Asn
            675                 680                 685
Ser Lys Arg Trp Asn Pro Glu Ile Gln Tyr Thr Ser Asn Tyr Tyr Lys
            690                 695                 700
Ser Thr Asn Val Asp Phe Ala Val Asn Thr Glu Gly Thr Tyr Ser Glu
705                 710                 715                 720
Pro Arg Pro Ile Gly Thr Arg Tyr Leu Thr Arg Asn Leu
                725                 730

<210> SEQ ID NO 91
<211> LENGTH: 738
<212> TYPE: PRT
<213> ORGANISM: Unknown
<220> FEATURE:
<223> OTHER INFORMATION: capsid protein of AAV serotype, clone 42.5B

<400> SEQUENCE: 91

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Glu Ala Asp Ala Ala Ala Leu Glu His Asp Lys Ala Tyr Asp

```
                65                  70                  75                  80
Lys Gln Leu Glu Gln Gly Asp Asn Pro Tyr Leu Lys Tyr Asn His Ala
                    85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
                195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495
```

-continued

Gln Asn Asn Asn Ser Asn Phe Ala Trp Thr Gly Ala Thr Lys Tyr His
              500                 505                 510

Leu Asn Gly Arg Asp Ser Leu Val Asn Pro Gly Val Ala Met Ala Thr
              515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
              565                 570                 575

Glu Gln Tyr Gly Val Val Ala Asp Asn Leu Gln Gln Gln Asn Ala Ala
              580                 585                 590

Pro Ile Val Gly Ala Val Asn Ser Gln Gly Ala Leu Pro Gly Met Val
              595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
              645                 650                 655

Pro Ala Asp Pro Pro Thr Thr Phe Ser Gln Ala Lys Leu Ala Ser Phe
              660                 665                 670

Ile Thr Gln Tyr Ser Thr Gly Gln Val Ser Val Glu Ile Glu Trp Glu
              675                 680                 685

Leu Gln Lys Glu Asn Ser Lys Arg Trp Asn Pro Glu Ile Gln Tyr Thr
              690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                  725                 730                 735

Asn Leu

<210> SEQ ID NO 92
<211> LENGTH: 738
<212> TYPE: PRT
<213> ORGANISM: Unknown
<220> FEATURE:
<223> OTHER INFORMATION: capsid protein of AAV serotype, clone 43.1

<400> SEQUENCE: 92

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
              20                  25                  30

Lys Ala Asn Gln Gln Lys Gln Asp Asp Gly Arg Gly Leu Val Leu Pro
              35                  40                  45

Gly Tyr Lys Tyr Leu Gly Pro Phe Asn Gly Leu Asp Lys Gly Glu Pro
          50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                  85                  90                  95

Asp Ala Glu Phe Gln Glu Arg Leu Gln Glu Asp Thr Ser Phe Gly Gly
              100                 105                 110

-continued

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
    195                 200                 205

Gly Ala Pro Met Ala Asp Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Pro Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
    435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
    515                 520                 525

His Lys Asp Asp Glu Glu Arg Phe Phe Pro Ser Ser Gly Val Leu Met

```
            530                 535                 540
Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
                580                 585                 590

Pro Ile Val Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 93
<211> LENGTH: 738
<212> TYPE: PRT
<213> ORGANISM: Unknown
<220> FEATURE:
<223> OTHER INFORMATION: capsid protein of AAV serotype, clone 43.12

<400> SEQUENCE: 93

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160
```

```
Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575
```

```
Glu Gln Tyr Gly Val Val Ala Asp Asn Leu Gln Gln Thr Asn Gly Ala
                580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 94
<211> LENGTH: 738
<212> TYPE: PRT
<213> ORGANISM: Unknown
<220> FEATURE:
<223> OTHER INFORMATION: capsid protein of AAV serotype, clone 43.5

<400> SEQUENCE: 94

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
```

```
            195                 200                 205
Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
                530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Thr Asn Gly Ala
                580                 585                 590

Pro Ile Val Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620
```

```
Pro His Thr Asp Gly Asn Phe His Pro Ser Pro Leu Met Gly Gly Phe
625                 630                 635                 640

Gly Leu Lys His Pro Pro Gln Ile Leu Val Lys Asn Thr Pro Val
            645                 650                 655

Pro Ala Asp Pro Pro Thr Thr Phe Ser Gln Ala Lys Leu Ala Ser Phe
        660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 95
<211> LENGTH: 738
<212> TYPE: PRT
<213> ORGANISM: Unknown
<220> FEATURE:
<223> OTHER INFORMATION: capsid protein of AAV serotype, clone AAV8

<400> SEQUENCE: 95

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240
```

```
Ile Thr Thr Ser Thr Arg Thr Trp Ala Leu Pro Thr Tyr Asn Asn His
            245             250             255

Leu Tyr Lys Gln Ile Ser Asn Gly Thr Ser Gly Gly Ala Thr Asn Asp
        260             265             270

Asn Thr Tyr Phe Gly Tyr Ser Thr Pro Trp Gly Tyr Phe Asp Phe Asn
        275             280             285

Arg Phe His Cys His Phe Ser Pro Arg Asp Trp Gln Arg Leu Ile Asn
        290             295             300

Asn Asn Trp Gly Phe Arg Pro Lys Arg Leu Ser Phe Lys Leu Phe Asn
305             310             315             320

Ile Gln Val Lys Glu Val Thr Gln Asn Glu Gly Thr Lys Thr Ile Ala
            325             330             335

Asn Asn Leu Thr Ser Thr Ile Gln Val Phe Thr Asp Ser Glu Tyr Gln
            340             345             350

Leu Pro Tyr Val Leu Gly Ser Ala His Gln Gly Cys Leu Pro Pro Phe
            355             360             365

Pro Ala Asp Val Phe Met Ile Pro Gln Tyr Gly Tyr Leu Thr Leu Asn
            370             375             380

Asn Gly Ser Gln Ala Val Gly Arg Ser Ser Phe Tyr Cys Leu Glu Tyr
385             390             395             400

Phe Pro Ser Gln Met Leu Arg Thr Gly Asn Asn Phe Gln Phe Thr Tyr
            405             410             415

Thr Phe Glu Asp Val Pro Phe His Ser Ser Tyr Ala His Ser Gln Ser
            420             425             430

Leu Asp Arg Leu Met Asn Pro Leu Ile Asp Gln Tyr Leu Tyr Tyr Leu
            435             440             445

Ser Arg Thr Gln Thr Thr Gly Gly Thr Ala Asn Thr Gln Thr Leu Gly
        450             455             460

Phe Ser Gln Gly Gly Pro Asn Thr Met Ala Asn Gln Ala Lys Asn Trp
465             470             475             480

Leu Pro Gly Pro Cys Tyr Arg Gln Gln Arg Val Ser Thr Thr Thr Gly
            485             490             495

Gln Asn Asn Asn Ser Asn Phe Ala Trp Thr Ala Gly Thr Lys Tyr His
        500             505             510

Leu Asn Gly Arg Asn Ser Leu Ala Asn Pro Gly Ile Ala Met Ala Thr
        515             520             525

His Lys Asp Asp Glu Glu Arg Phe Phe Pro Ser Asn Gly Ile Leu Ile
        530             535             540

Phe Gly Lys Gln Asn Ala Ala Arg Asp Asn Ala Asp Tyr Ser Asp Val
545             550             555             560

Met Leu Thr Ser Glu Glu Glu Ile Lys Thr Thr Asn Pro Val Ala Thr
            565             570             575

Glu Glu Tyr Gly Ile Val Ala Asp Asn Leu Gln Gln Gln Asn Thr Ala
            580             585             590

Pro Gln Ile Gly Thr Val Asn Ser Gln Gly Ala Leu Pro Gly Met Val
            595             600             605

Trp Gln Asn Arg Asp Val Tyr Leu Gln Gly Pro Ile Trp Ala Lys Ile
            610             615             620

Pro His Thr Asp Gly Asn Phe His Pro Ser Pro Leu Met Gly Gly Phe
625             630             635             640

Gly Leu Lys His Pro Pro Pro Gln Ile Leu Ile Lys Asn Thr Pro Val
            645             650             655

Pro Ala Asp Pro Pro Thr Thr Phe Asn Gln Ser Lys Leu Asn Ser Phe
```

```
            660                 665                 670
Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 96
<211> LENGTH: 736
<212> TYPE: PRT
<213> ORGANISM: Unknown
<220> FEATURE:
<223> OTHER INFORMATION: capsid protein of AAV serotype, clone 43.21

<400> SEQUENCE: 96

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285
```

-continued

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Arg Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Ser
                485                 490                 495

Asn Asn Ser Asn Phe Ala Trp Thr Gly Ala Ala Lys Phe Lys Leu Asn
                500                 505                 510

Gly Arg Asp Ser Leu Met Asn Pro Gly Val Ala Met Ala Ser His Lys
            515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
                580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700
```

```
Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 97
<211> LENGTH: 736
<212> TYPE: PRT
<213> ORGANISM: Unknown
<220> FEATURE:
<223> OTHER INFORMATION: capsid protein of AAV serotype, clone 43.25

<400> SEQUENCE: 97

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335
```

-continued

Asn Leu Thr Ser Thr Val Gln Val Phe Thr Asp Ser Glu Tyr Gln Leu
             340                 345                 350

Pro Tyr Val Leu Gly Ser Ala His Gln Gly Cys Leu Pro Pro Phe Pro
         355                 360                 365

Ala Asp Val Phe Met Val Pro Gln Tyr Gly Tyr Leu Thr Leu Asn Asn
     370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                 405                 410                 415

Phe Glu Asp Val Pro Phe His Ser Ser Tyr Ala His Ser Gln Ser Leu
             420                 425                 430

Asp Arg Leu Met Asn Pro Leu Ile Asp Gln Tyr Leu Tyr Tyr Leu Val
         435                 440                 445

Arg Thr Gln Thr Thr Gly Thr Gly Thr Gln Thr Leu Ala Phe Ser
     450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                 485                 490                 495

Asn Asn Ser Asn Phe Ala Trp Thr Gly Ala Ala Lys Phe Lys Leu Asn
             500                 505                 510

Gly Arg Asp Ser Leu Met Asn Pro Gly Val Ala Met Ala Ser His Lys
         515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                 565                 570                 575

Tyr Gly Ala Val Ala Ile Asn Asn Gln Ala Ala Asn Thr Gln Ala Gln
             580                 585                 590

Thr Gly Leu Val His Asn Gln Gly Val Ile Pro Gly Met Val Trp Gln
         595                 600                 605

Asn Arg Asp Val Tyr Leu Gln Gly Pro Ile Trp Ala Lys Ile Pro His
     610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                 645                 650                 655

Asp Pro Pro Leu Thr Phe Asn Gln Ala Lys Leu Asn Ser Phe Ile Thr
             660                 665                 670

Gln Tyr Ser Thr Gly Gln Val Ser Val Glu Ile Glu Trp Glu Leu Gln
         675                 680                 685

Lys Glu Asn Ser Lys Arg Trp Asn Pro Glu Ile Gln Tyr Thr Ser Asn
     690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                 725                 730                 735

<210> SEQ ID NO 98
<211> LENGTH: 736
<212> TYPE: PRT

<213> ORGANISM: Unknown
<220> FEATURE:
<223> OTHER INFORMATION: capsid protein of AAV serotype, clone 43.23

<400> SEQUENCE: 98

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Leu Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe

```
            385                 390                 395                 400
Pro Ser Gln Met Pro Arg Thr Gly Asn Asn Phe Gln Phe Ser Tyr Thr
                    405                 410                 415

Phe Glu Asp Val Pro Phe His Ser Ser Tyr Ala His Ser Gln Ser Leu
                    420                 425                 430

Asp Arg Leu Met Asn Pro Leu Ile Asp Gln Tyr Leu Tyr Tyr Leu Val
                    435                 440                 445

Arg Thr Gln Thr Thr Gly Thr Gly Gly Thr Gln Thr Leu Ala Phe Ser
        450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                    485                 490                 495

Asn Asn Ser Asn Phe Ala Trp Thr Gly Ala Ala Lys Phe Lys Leu Asn
                    500                 505                 510

Gly Arg Asp Ser Leu Met Asn Pro Gly Val Ala Met Ala Ser His Lys
                    515                 520                 525

Asp Asp Asp Arg Phe Phe Pro Ser Ser Gly Val Leu Ile Phe Gly
        530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                    565                 570                 575

Tyr Gly Ala Val Ala Ile Asn Asn Gln Ala Ala Asn Thr Gln Ala Gln
                    580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                    645                 650                 655

Asp Pro Pro Leu Thr Phe Asn Gln Ala Lys Leu Asn Ser Phe Ile Thr
                    660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735
```

<210> SEQ ID NO 99
<211> LENGTH: 736
<212> TYPE: PRT
<213> ORGANISM: Unknown
<220> FEATURE:
<223> OTHER INFORMATION: capsid protein of AAV serotype, clone 43.20

<400> SEQUENCE: 99

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
```

-continued

```
               20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Leu Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Ser Gly Leu Gly Pro Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Gly Thr Ser Gly Gly Ser Thr Asn Asp Asn
            260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Glu Gly Thr Lys Thr Ile Ala Asn
                325                 330                 335
Asn Leu Thr Ser Thr Val Gln Val Phe Thr Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Thr Val Pro Gln Tyr Gly Tyr Leu Thr Leu Asn Asn
    370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Val
        435                 440                 445
```

```
Arg Thr Gln Thr Thr Gly Thr Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 100
<211> LENGTH: 736
<212> TYPE: PRT
<213> ORGANISM: Unknown
<220> FEATURE:
<223> OTHER INFORMATION: capsid protein of AAV serotype, clone AAV9

<400> SEQUENCE: 100

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Glu Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                485                 490                 495
```

-continued

```
Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Glu Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 101
<211> LENGTH: 728
<212> TYPE: PRT
<213> ORGANISM: Unknown
<220> FEATURE:
<223> OTHER INFORMATION: capsid protein of AAV serotype, clone 24.1

<400> SEQUENCE: 101

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Arg Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Val Ala Lys Thr Ala Pro Gly Lys Lys Arg
    130                 135                 140
Pro Ile Glu Ser Pro Asp Ser Ser Thr Gly Ile Gly Lys Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Leu Gly Glu Pro Pro Ala Ala Pro Ser
            180                 185                 190
Gly Leu Gly Ser Gly Thr Met Ala Ala Gly Gly Ala Pro Met Ala
        195                 200                 205
Asp Asn Asn Glu Gly Ala Asp Gly Val Gly Asn Ala Ser Gly Asn Trp
    210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Ser Tyr Ser
            260                 265                 270
Thr Pro Trp Gly Tyr Phe Asp Phe Asn Arg Phe His Cys His Phe Ser
        275                 280                 285
Pro Arg Asp Trp Gln Arg Leu Ile Asn Asn Asn Trp Gly Phe Arg Pro
    290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ser Val Gly
    370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Val His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
Gly Ser Thr Arg Glu Leu Gln Phe His Gln Ala Gly Pro Asn Thr Met
    450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Ser Asn Phe Ala Trp
                485                 490                 495
Thr Gly Ala Thr Lys Tyr His Leu Asn Gly Arg Asn Ser Leu Thr Asn
            500                 505                 510
Pro Gly Val Ala Met Ala Thr Asn Lys Asp Asp Glu Asp Gln Phe Phe
        515                 520                 525
Pro Ile Asn Gly Val Leu Val Phe Gly Lys Thr Gly Ala Ala Asn Lys
    530                 535                 540
Thr Thr Leu Glu Asn Val Leu Met Thr Ser Glu Glu Glu Ile Lys Thr
```

```
                    545                 550                 555                 560
Thr Asn Pro Val Ala Thr Glu Glu Tyr Gly Val Val Ser Ser Asn Leu
                        565                 570                 575
Gln Ser Ser Thr Ala Gly Pro Gln Thr Gln Thr Val Asn Ser Gln Gly
                580                 585                 590
Ala Leu Pro Gly Met Val Trp Gln Asn Arg Asp Val Cys Leu Gln Gly
            595                 600                 605
Pro Ile Trp Ala Lys Ile Pro His Thr Asp Gly Asn Phe His Pro Ser
        610                 615                 620
Pro Leu Met Gly Gly Phe Gly Leu Lys His Pro Pro Gln Ile Leu
625                 630                 635                 640
Ile Lys Asn Thr Pro Val Pro Ala Asn Pro Pro Glu Val Phe Thr Pro
                    645                 650                 655
Ala Lys Phe Ala Ser Phe Ile Thr Gln Tyr Ser Thr Gly Gln Val Ser
                660                 665                 670
Val Glu Ile Glu Trp Glu Leu Gln Lys Glu Asn Ser Lys Arg Trp Asn
            675                 680                 685
Pro Glu Ile Gln Tyr Thr Ser Asn Tyr Ala Lys Ser Asn Asn Val Glu
        690                 695                 700
Phe Ala Val Asn Asn Glu Gly Val Tyr Thr Glu Pro Arg Pro Ile Gly
705                 710                 715                 720
Thr Arg Tyr Leu Thr Arg Asn Leu
                    725

<210> SEQ ID NO 102
<211> LENGTH: 728
<212> TYPE: PRT
<213> ORGANISM: Unknown
<220> FEATURE:
<223> OTHER INFORMATION: capsid protein of AAV serotype, clone 42.2REAL

<400> SEQUENCE: 102

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Glu Ala Asp Ala Ala Leu Glu His Asp Lys Ala Tyr Asp
65                  70                  75                  80
Lys Gln Leu Glu Gln Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Ile Glu Ser Pro Asp Ser Ser Thr Gly Ile Gly Lys Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Leu Gly Glu Pro Pro Ala Ala Pro Ser
```

-continued

```
            180                 185                 190
Gly Leu Gly Ser Gly Thr Met Ala Gly Gly Ala Pro Met Ala
        195                 200                 205
Asp Asn Asn Glu Gly Ala Asp Gly Val Gly Asn Ala Ser Gly Asn Trp
210                 215                 220
His Cys Asp Ser Thr Trp Leu Gly Asp Arg Val Ile Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
            260                 265                 270
Thr Pro Trp Gly Tyr Phe Asp Phe Asn Arg Phe His Cys His Phe Ser
        275                 280                 285
Pro Arg Asp Trp Gln Arg Leu Ile Asn Asn Asn Trp Gly Phe Arg Pro
    290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ser Val Gly
    370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
Gly Ser Thr Arg Glu Leu Gln Phe His Gln Ala Gly Pro Asn Thr Met
    450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Ser Asn Phe Ala Trp
                485                 490                 495
Thr Gly Ala Thr Lys Tyr His Leu Asn Gly Arg Asn Ser Leu Thr Asn
            500                 505                 510
Pro Gly Val Ala Met Ala Thr Asn Lys Asp Asp Glu Asp Gln Phe Phe
        515                 520                 525
Pro Ile Asn Gly Val Leu Val Phe Gly Glu Thr Gly Ala Ala Asn Lys
    530                 535                 540
Thr Thr Leu Glu Asn Val Leu Met Thr Ser Glu Glu Ile Lys Thr
545                 550                 555                 560
Thr Asn Pro Val Ala Thr Glu Glu Tyr Gly Val Val Ser Ser Asn Leu
                565                 570                 575
Gln Ser Ser Thr Ala Gly Pro Gln Thr Gln Thr Val Asn Ser Gln Gly
            580                 585                 590
Ala Leu Pro Gly Met Val Trp Gln Asn Arg Asp Val Tyr Leu Gln Gly
        595                 600                 605
```

```
Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
        690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 103
<211> LENGTH: 728
<212> TYPE: PRT
<213> ORGANISM: Unknown
<220> FEATURE:
<223> OTHER INFORMATION: capsid protein of AAV serotype, clone 7.2VP1

<400> SEQUENCE: 103

Met Ala Ala Asp Gly Tyr Leu Pro Asp Trp Leu Glu Gly Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Arg Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Asn Gly Gln
145                 150                 155                 160

Pro Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240
```

-continued

```
Arg Thr Trp Ala Leu Pro Thr Tyr Asn Asn His Leu Tyr Lys Gln Ile
            245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Trp Gly Phe Arg Pro
        290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                    325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
            370                 375                 380

Arg Ser Ser Phe Tyr Cys Leu Glu Tyr Phe Pro Ser Gln Met Leu Arg
385                 390                 395                 400

Thr Gly Asp Asn Phe Glu Phe Ser Tyr Thr Phe Glu Glu Val Pro Phe
                    405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Asn Ser Asn Phe Ala Trp
                485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
        610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655
```

```
Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
        690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 104
<211> LENGTH: 728
<212> TYPE: PRT
<213> ORGANISM: Unknown
<220> FEATURE:
<223> OTHER INFORMATION: capsid protein of AAV serotype, clone 27.3VP1

<400> SEQUENCE: 104

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Ser Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Gly Tyr Ser
            260                 265                 270

Thr Pro Trp Gly Tyr Phe Asp Phe Asn Arg Phe His Cys His Phe Ser
        275                 280                 285
```

```
Pro Arg Asp Trp Gln Arg Leu Ile Asn Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
370                 375                 380

Arg Ser Ser Phe Cys Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Val
450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Leu
                515                 520                 525

Pro Ile Asn Gly Val Leu Val Phe Gly Lys Thr Gly Ala Ala Asn Lys
530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Arg Thr Gln Thr Val Asn Ser Gln Gly
                580                 585                 590

Ala Leu Pro Gly Met Val Trp Gln Asn Arg Asp Val Tyr Leu Gln Gly
                595                 600                 605

Pro Ile Trp Ala Glu Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Glu Val Phe Thr Pro
                645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
                675                 680                 685

Pro Glu Ile Gln Tyr Thr Ser Asn Tyr Ala Lys Ser Asn Asn Val Glu
690                 695                 700

Phe Ala Val Asn Asn Glu Gly Val Tyr Thr Glu Pro Arg Pro Ile Gly
```

Thr Arg Tyr Leu Thr Arg Asn Leu
            725

<210> SEQ ID NO 105
<211> LENGTH: 728
<212> TYPE: PRT
<213> ORGANISM: Unknown
<220> FEATURE:
<223> OTHER INFORMATION: capsid protein of AAV serotype, clone 16.3VP1

<400> SEQUENCE: 105

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser

```
                    340             345             350
Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Met Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
        420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Gly Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Gly Val Phe Thr Pro
                645                 650                 655

Ala Leu Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
        675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 106
<211> LENGTH: 728
<212> TYPE: PRT
<213> ORGANISM: Unknown
```

<220> FEATURE:
<223> OTHER INFORMATION: capsid protein of AAV serotype, clone 42.10

<400> SEQUENCE: 106

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Arg Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
370                 375                 380

Arg Ser Ser Phe Tyr Cys Leu Glu Tyr Phe Pro Ser Gln Met Leu Arg
385                 390                 395                 400
```

```
Thr Gly Asn Asn Phe Glu Phe Ser Tyr Thr Phe Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
            485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
            565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
            645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 107
<211> LENGTH: 728
<212> TYPE: PRT
<213> ORGANISM: Unknown
<220> FEATURE:
<223> OTHER INFORMATION: capsid protein of AAV serotype, clone 42.3B

<400> SEQUENCE: 107

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
 50                  55                  60
Val Asn Glu Ala Asp Ala Ala Leu Glu His Asp Lys Ala Tyr Asp
 65              70                  75                  80
Lys Gln Leu Glu Gln Gly Asp Asn Pro Tyr Leu Lys Tyr Asn His Ala
                 85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Ile Glu Ser Pro Asp Ser Ser Thr Gly Ile Gly Lys Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Ile Gly Glu Pro Pro Ala Gly Pro Ser
                180                 185                 190
Gly Leu Gly Ser Gly Thr Met Ala Ala Gly Gly Ala Pro Met Ala
            195                 200                 205
Asp Asn Asn Glu Gly Ala Asp Gly Val Gly Asn Ala Ser Gly Asn Trp
210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
                260                 265                 270
Thr Pro Trp Gly Tyr Phe Asp Phe Asn Arg Phe His Cys His Phe Ser
            275                 280                 285
Pro Arg Asp Trp Gln Arg Leu Ile Asn Asn Asn Trp Gly Phe Arg Pro
        290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ser Val Gly
370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
```

```
Gly Ser Thr Arg Glu Leu Gln Phe His Gln Ala Gly Pro Asn Thr Met
            450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Thr Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
                515                 520                 525

Pro Ile Asn Gly Val Leu Val Phe Gly Lys Thr Gly Ala Ala Asn Lys
530                 535                 540

Thr Thr Leu Glu Asn Val Leu Met Thr Ser Glu Glu Ile Lys Thr
545                 550                 555                 560

Thr Asn Pro Val Ala Thr Glu Gln Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
                595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
                675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 108
<211> LENGTH: 728
<212> TYPE: PRT
<213> ORGANISM: Unknown
<220> FEATURE:
<223> OTHER INFORMATION: capsid protein of AAV serotype, clone 42.11

<400> SEQUENCE: 108

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80
```

-continued

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Arg Gln
465                 470                 475                 480

Arg Leu Ser Lys Asp Ile Asp Ser Asn Asn Asn Ser Asn Phe Ala Trp
                485                 490                 495

Thr Gly Ala Thr Lys Tyr His Leu Asn Gly Arg Asn Ser Leu Thr Asn

```
                500             505             510
Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
            610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 109
<211> LENGTH: 729
<212> TYPE: PRT
<213> ORGANISM: Unknown
<220> FEATURE:
<223> OTHER INFORMATION: capsid protein of AAV serotype, clone F1VP1

<400> SEQUENCE: 109

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
```

```
            130                 135                 140
Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
            180                 185                 190

Ser Val Gly Ser Gly Thr Met Ala Ala Gly Gly Ala Pro Met Ala
                195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
                260                 265                 270

Ser Thr Pro Trp Gly Tyr Phe Asp Phe Asn Arg Phe His Cys His Phe
                275                 280                 285

Ser Pro Arg Asp Trp Gln Arg Leu Ile Asn Asn Asn Trp Gly Phe Arg
                290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
                340                 345                 350

Ser Ala His Gln Gly Cys Leu Pro Pro Phe Pro Ala Asp Val Phe Met
                355                 360                 365

Ile Pro Gln Tyr Gly Tyr Leu Thr Leu Asn Asn Gly Ser Gln Ser Val
                370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
                420                 425                 430

Pro Leu Ile Asp Gln Tyr Leu Tyr Tyr Leu Ala Arg Thr Gln Ser Thr
                435                 440                 445

Thr Gly Ser Thr Arg Glu Leu Gln Phe His Gln Ala Gly Pro Asn Thr
                450                 455                 460

Met Ala Glu Gln Ser Lys Asn Trp Leu Pro Gly Pro Cys Tyr Arg Gln
465                 470                 475                 480

Gln Gly Leu Ser Lys Asn Leu Asp Phe Asn Asn Ser Asn Phe Ala
                485                 490                 495

Trp Thr Ala Ala Thr Lys Tyr His Leu Asn Gly Arg Asn Ser Leu Thr
                500                 505                 510

Asn Pro Gly Ile Pro Met Ala Thr Asn Lys Asp Asp Glu Asp Gln Phe
                515                 520                 525

Phe Pro Ile Asn Gly Val Leu Val Phe Gly Lys Thr Gly Ala Ala Asn
                530                 535                 540

Lys Thr Thr Leu Glu Asn Val Leu Met Thr Ser Glu Glu Glu Ile Lys
545                 550                 555                 560
```

-continued

```
Thr Thr Asn Pro Val Ala Thr Glu Glu Tyr Gly Val Ser Ser Asn
            565                 570                 575

Leu Gln Pro Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
            610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Pro Glu Val Phe Thr
            645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
            675                 680                 685

Asn Pro Glu Ile Gln Tyr Thr Ser Asn Tyr Ala Lys Ser Asn Asn Val
            690                 695                 700

Glu Phe Ala Val Asn Pro Asp Gly Val Tyr Thr Glu Pro Arg Pro Ile
705                 710                 715                 720

Gly Thr Arg Tyr Leu Pro Arg Asn Leu
            725

<210> SEQ ID NO 110
<211> LENGTH: 729
<212> TYPE: PRT
<213> ORGANISM: Unknown
<220> FEATURE:
<223> OTHER INFORMATION: capsid protein of AAV serotype, clone F5VP1[@0003]

<400> SEQUENCE: 110

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
            165                 170                 175

Ser Val Pro Asp Pro Gln Pro Leu Gly Glu Pro Pro Ala Ala Pro Ser
            180                 185                 190
```

-continued

Ser Val Gly Ser Gly Thr Met Ala Ala Gly Gly Ala Pro Thr Ala
    195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
            245                 250                 255

Ser Ser Ser Ser Ser Gly Ala Thr Asn Asp Asn His Tyr Phe Gly Tyr
        260                 265                 270

Ser Thr Pro Trp Gly Tyr Phe Asp Phe Asn Arg Phe His Cys His Phe
    275                 280                 285

Ser Pro Arg Asp Trp Gln Arg Leu Ile Asn Asn Trp Gly Phe Arg
290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365

Ile Pro Gln Tyr Gly Tyr Leu Thr Leu Asn Asn Gly Ser Gln Ser Val
    370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
            405                 410                 415

Phe His Ser Ser Tyr Ala His Ser Gln Ser Leu Asp Arg Leu Met Asn
        420                 425                 430

Pro Leu Ile Asp Gln Tyr Leu Tyr Tyr Leu Ala Arg Thr Gln Ser Thr
    435                 440                 445

Thr Gly Ser Thr Arg Glu Leu Gln Phe His Gln Ala Gly Pro Asn Thr
450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Asn Ser Asn Phe Ala
            485                 490                 495

Trp Thr Ala Ala Thr Lys Tyr His Leu Asn Gly Arg Asn Ser Leu Thr
        500                 505                 510

Asn Pro Gly Ile Pro Met Ala Thr Asn Lys Asp Asp Glu Asp Gln Phe
    515                 520                 525

Phe Pro Ile Asn Gly Val Leu Val Phe Gly Lys Thr Gly Ala Ala Asn
530                 535                 540

Lys Thr Thr Leu Glu Asn Val Leu Met Thr Ser Glu Glu Glu Ile Lys
545                 550                 555                 560

Thr Thr Asn Pro Val Ala Thr Glu Glu Tyr Gly Val Val Ser Ser Asn
            565                 570                 575

Leu Gln Ser Ser Thr Ala Gly Pro Gln Ser Gln Thr Ile Asn Ser Gln
        580                 585                 590

Gly Ala Leu Pro Gly Met Val Trp Gln Asn Arg Asp Val Tyr Leu Gln
    595                 600                 605

```
Gly Pro Ile Trp Ala Lys Ile Pro His Thr Asp Gly Asn Phe His Pro
            610                 615                 620
Ser Pro Leu Met Gly Gly Phe Gly Leu Glu His Pro Pro Gln Ile
625                 630                 635                 640
Leu Ile Lys Asn Thr Pro Val Pro Ala Asn Pro Pro Glu Val Phe Thr
                        645                 650                 655
Pro Ala Lys Phe Ala Ser Phe Ile Thr Gln Tyr Ser Thr Gly Gln Val
                660                 665                 670
Ser Val Glu Ile Glu Trp Glu Leu Gln Lys Glu Asn Ser Lys Arg Trp
            675                 680                 685
Asn Pro Glu Ile Gln Tyr Thr Ser Asn Tyr Ala Lys Ser Asn Asn Val
690                 695                 700
Glu Phe Ala Val Asn Pro Asp Gly Val Tyr Thr Glu Pro Arg Pro Ile
705                 710                 715                 720
Gly Thr Arg Tyr Leu Thr Arg Asn Leu
                725

<210> SEQ ID NO 111
<211> LENGTH: 729
<212> TYPE: PRT
<213> ORGANISM: Unknown
<220> FEATURE:
<223> OTHER INFORMATION: capsid protein of AAV serotype, clone F3VP1

<400> SEQUENCE: 111

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Ile Gly Ser Pro Asp Ser Ser Thr Gly Ile Gly Lys Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Leu Gly Glu Pro Ala Ala Pro Ser
            180                 185                 190
Ser Val Gly Ser Gly Thr Met Ala Ala Gly Gly Ala Pro Met Ala
        195                 200                 205
Asp Asn Asn Glu Gly Ala Asp Gly Val Gly Asn Ala Ser Gly Asn Trp
    210                 215                 220
His Cys Asp Ser Thr Trp Leu Gly Asp Arg Val Ile Thr Thr Ser Thr
225                 230                 235                 240
```

```
Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Asn Trp Gly Phe Arg
    290                 295                 300

Pro Lys Lys Leu Arg Phe Lys Leu Leu Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365

Ile Pro Gln Tyr Gly Tyr Leu Thr Leu Asp Asn Gly Ser Gln Ser Val
    370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Thr
        435                 440                 445

Thr Gly Ser Thr Arg Glu Leu Gln Phe His Gln Ala Gly Pro Asn Thr
    450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
                485                 490                 495

Trp Thr Ala Ala Thr Lys Tyr His Leu Asn Gly Arg Asn Ser Leu Thr
            500                 505                 510

Asn Pro Gly Ile Pro Met Ala Thr Asn Lys Asp Asp Glu Asp Gln Phe
        515                 520                 525

Phe Pro Ile Asn Gly Val Leu Val Phe Gly Lys Thr Gly Ala Ala Asn
    530                 535                 540

Lys Thr Thr Leu Glu Asn Val Leu Met Thr Ser Glu Glu Glu Ile Lys
545                 550                 555                 560

Thr Thr Asn Pro Val Ala Thr Glu Glu Tyr Gly Val Val Ser Ser Asn
                565                 570                 575

Leu Gln Ser Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
        595                 600                 605

Gly Pro Ile Trp Ala Lys Ile Pro His Thr Asp Gly Asn Phe His Pro
    610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Pro Glu Val Phe Thr
                645                 650                 655

Pro Ala Lys Phe Ala Ser Phe Ile Thr Gln Tyr Ser Thr Gly Gln Val
```

```
                660             665                 670
Ser Val Glu Ile Glu Trp Glu Leu Gln Lys Glu Asn Ser Lys Arg Trp
                675                 680                 685

Asn Pro Glu Ile Gln Tyr Thr Ser Asn Tyr Ala Lys Ser Asn Asn Val
            690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
                725

<210> SEQ ID NO 112
<211> LENGTH: 735
<212> TYPE: PRT
<213> ORGANISM: Unknown
<220> FEATURE:
<223> OTHER INFORMATION: capsid protein of AAV serotype, clone 42.6B

<400> SEQUENCE: 112

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
```

```
            290                 295                 300
Asn Asn Trp Gly Phe Arg Pro Arg Lys Leu Arg Phe Lys Leu Phe Asn
305                 310                 315                 320

Ile Gln Val Lys Glu Val Thr Thr Asp Asp Gly Val Thr Thr Ile Ala
                325                 330                 335

Asn Asn Leu Thr Ser Thr Ile Gln Val Phe Ser Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Glu Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ala Arg Thr Gln Ser Thr Thr Gly Ser Thr Arg Glu Leu Gln Phe His
450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
                485                 490                 495

Asn Asn Ser Asn Phe Ala Trp Thr Gly Ala Thr Lys Tyr His Leu Asn
                500                 505                 510

Gly Arg Asn Ser Leu Thr Asn Pro Gly Val Ala Met Ala Thr Asn Lys
                515                 520                 525

Asp Asp Glu Asp Gln Phe Phe Pro Ile Asn Gly Val Leu Val Phe Gly
530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Glu Tyr
                565                 570                 575

Gly Val Val Ser Ser Asn Leu Gln Ser Ser Thr Ala Gly Pro Gln Thr
                580                 585                 590

Gln Thr Val Asn Ser Gln Gly Ala Leu Pro Gly Met Val Trp Gln Asn
                595                 600                 605

Arg Asp Val Tyr Leu Gln Gly Pro Ile Trp Ala Lys Ile Pro His Thr
610                 615                 620

Asp Gly Asn Phe His Pro Ser Pro Leu Met Asp Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Ala Lys Ser Asn Asn Val Glu Phe Ala Val Asn Asn Glu Gly Val Tyr
705                 710                 715                 720
```

Thr Glu Pro Arg Pro Ile Gly Thr Arg Tyr Leu Thr Arg Asn Leu
                725                 730                 735

<210> SEQ ID NO 113
<211> LENGTH: 685
<212> TYPE: PRT
<213> ORGANISM: Unknown
<220> FEATURE:
<223> OTHER INFORMATION: capsid protein of AAV serotype, clone 42.12

<400> SEQUENCE: 113

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Thr Asn Pro Leu Ile Asp Gln Tyr Leu Tyr Tyr Leu
        435                 440                 445

Ala Arg Thr Gln Ser Thr Thr Gly Ser Thr Arg Gly Leu Gln Phe His
    450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
                485                 490                 495

Asn Asn Ser Asn Phe Ala Trp Thr Gly Ala Thr Lys Tyr His Leu Asn
            500                 505                 510

Gly Arg Asn Ser Leu Thr Asn Pro Gly Val Ala Met Ala Thr Asn Lys
        515                 520                 525

Asp Asp Glu Asp Gln Phe Phe Pro Ile Asn Gly Val Leu Val Phe Gly
    530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Glu Tyr
                565                 570                 575

Gly Val Val Ser Ser Asn Leu Gln Ser Ser Thr Ala Gly Pro Gln Thr
            580                 585                 590

Gln Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Tyr Thr Ser Asn Tyr Tyr Lys
                645                 650                 655

Ser Thr Asn Val Asp Phe Ala Val Asn Thr Glu Gly Thr Tyr Ser Glu
            660                 665                 670

Pro Arg Pro Ile Gly Thr Arg Tyr Leu Thr Arg Asn Leu
        675                 680                 685

<210> SEQ ID NO 114
<211> LENGTH: 724
<212> TYPE: PRT
<213> ORGANISM: Unknown
<220> FEATURE:
<223> OTHER INFORMATION: capsid protein of AAV serotype, clone AAV5CAP

<400> SEQUENCE: 114

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
            130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
            195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
            290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
            370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
            435                 440                 445

```
Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
                515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
                580                 585                 590

Gly Ser Val Trp Met Glu Arg Asp Val Tyr Leu Gln Gly Pro Ile Trp
                595                 600                 605

Ala Lys Ile Pro Glu Thr Gly Ala His Phe His Pro Ser Pro Ala Met
610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
                675                 680                 685

Tyr Thr Asn Asn Tyr Asn Asp Pro Gln Phe Val Asp Phe Ala Pro Asp
                690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 115
<211> LENGTH: 9
<212> TYPE: DNA
<213> ORGANISM: Artificial Sequence
<220> FEATURE:
<223> OTHER INFORMATION: DraIII restriction enzyme site

<400> SEQUENCE: 115 caccacgtc                                                                9

<210> SEQ ID NO 116
<211> LENGTH: 28
<212> TYPE: DNA
<213> ORGANISM: Unknown
<220> FEATURE:
<223> OTHER INFORMATION: AV2cas

<400> SEQUENCE: 116
cgcagagacc aaagttcaac tgaaacga                                           28

<210> SEQ ID NO 117
```

```
<211> LENGTH: 255
<212> TYPE: DNA
<213> ORGANISM: Unknown
<220> FEATURE:
<223> OTHER INFORMATION: adeno-associated virus serotype 10

<400> SEQUENCE: 117
ggtaattcct ccggaaattg gcattgcgat tccacatggc tgggcgacag agtcatcacc      60
accagcaccc gaacctgggt cctgcccacc tacaacaacc acatctacaa gcaaatctcc    120
agcgagacag gagccaccaa cgacaaccac tacttcggct acagcacccc ctgggggtat    180
tttgacttta acagattcca ctgccacttt tcaccacgtg actggcagcg actcatcaac    240
aacaactggg gattc                                                     255

<210> SEQ ID NO 118
<211> LENGTH: 258
<212> TYPE: DNA
<213> ORGANISM: Unknown
<220> FEATURE:
<223> OTHER INFORMATION: adeno-associated virus serotype 11

<400> SEQUENCE: 118
ggtaattcct ccggaaattg gcattgcgat tccacatggc tgggcgacag agtcatcacc      60
accagcaccc gaacctgggc cctgccaacc tacaacaacc acctctacaa acaaatctcc    120
agcgcttcaa cggggggccag caacgacaac cactactttg gctacagcac ccctgggggg    180
tattttgact ttaacagatt ccactgccac ttctcaccac gtgactggca gcgactcatc    240
aacaacaact ggggattc                                                  258

<210> SEQ ID NO 119
<211> LENGTH: 255
<212> TYPE: DNA
<213> ORGANISM: Unknown
<220> FEATURE:
<223> OTHER INFORMATION: adeno-associated virus serotype 12

<400> SEQUENCE: 119
ggtaattcct ccggaaattg gcattgcgat tccacatggc tgggcgaccg agtcattacc      60
accagcaccc ggacttgggc cctgcccacc tacaacaacc acctctacaa gcaaatctcc    120
agccaatcgg gtgccaccaa cgacaaccac tacttcggct acagcacccc ttgggggtat    180
tttgatttca acagattcca ctgccatttc tcaccacgtg actggcagcg actcatcaac    240
aacaactggg gattc                                                     255

<210> SEQ ID NO 120
<211> LENGTH: 2205
<212> TYPE: DNA
<213> ORGANISM: Unknown
<220> FEATURE:
<223> OTHER INFORMATION: adeno-associated virus serotype, clone A3.1vp1

<400> SEQUENCE: 120
atggctgccg atggttatct tccagattgg ctcgaggaca ctctctctga aggaatcaga      60
cagtggtgga gctcaaaacc tggcccacca ccgccgaaac ctaaccaaca caccgggac     120 gacagtaggg gtcttgtgct tcctgggtac aagtacctcg gacccttcaa cggactcgac    180
aaaggagagc cggtcaacga ggcagacgcc gcggccctcg agcacgacaa agcctacgac    240
caccagctca gcaagggga caacccgtac ctcaaatca accacgcgga cgctgaattt    300
caggagcgtc ttcaagaaga tacgtctttc gggggcaacc tcgggcgagc agtcttccag    360
```

```
gccaaaaaga gggtactcga gcctcttggt ctggttgagg aagctgttaa gacggctcct    420
ggaaaaaaga gacctataga gcagtctcct gcagaaccgg actcttcctc gggcatcggc    480
aaatcaggcc agcagcccgc taagaaaaga ctcaattttg gtcagactgg cgacacagag    540
tcagtcccag accctcaacc aatcggagaa ccccccgcag cccctctgg tgtgggatct     600 aatacaatgg cttcaggcgg tggggcacca atggcagaca ataacgaagg cgccgacgga    660
gtgggtaatt cctcgggaaa ttggcattgc gattccacat ggatgggcga cagagttatc    720
accaccagca caagaacctg ggccctcccc acctacaata atcacctcta caagcaaatc    780
tccagcgaat cgggagccac caacgacaac cactacttcg gctacagcac ccctggggg    840 tattttgact ttaacagatt ccactgtcac ttctcaccac gtgactggca gcgactcatc    900
aacaacaact ggggatttag acccaagaaa ctcaatttca agctcttcaa catccaagtc    960
aaggaggtca cgcagaatga tggaaccacg accatcgcca ataaccttac cagcacggtg   1020
caggtcttca cagactctga gtaccagctg ccctacgtcc tcggttcggc tcaccagggc   1080
tgccttccgc cgttcccagc agacgtcttc atgattcctc agtacggcta cttgactctg   1140
aacaatggca gccaagcggt aggacgttct tcattctact gtctagagta ttttccctct   1200
cagatgctga ggacgggaaa caacttcacc ttcagctaca cttttgaaga cgtgcctttc   1260
cacagcagct acgcgcacag ccagagtctg gatcggctga tgaatcctct cattgaccag   1320
tacctgtatt acctgagcaa aactcagggt acaagtggaa caacgcagca atcgagactg   1380
cagttcagcc aagctgggcc tagctccatg gctcagcagg ccaaaaactg gctaccggga   1440
cccagctacc gacagcagcg aatgtctaag acggctaatg acaacaacaa cagtgaattt   1500
gcttggactg cagccaccaa atattacctg aatggaagaa attctctggt caatcccggg   1560
cccccaatgg ccagtcacaa ggacgatgag gaaaagtatt tccccatgca cggaaatctc   1620
atctttggaa acaaggcac aggaactacc aatgtggaca ttgaatcagt gcttattaca   1680
gacgaagaag aaatcagaac aactaatcct gtggctacag aacaatacgg acaggttgcc   1740
accaaccatc agagtcagaa caccacagct tcctatgaa gtgtggacag ccagggaatc   1800
ttacctggaa tggtgtggca ggaccgcgat gtctatcttc aaggtccat ttgggccaaa    1860 actcctcaca cggacggaca ctttcatcct tctccgctca tgggaggctt tggactgaaa   1920
caccctcctc cccagatcct gatcaaaaac acacctgtgc cagcgaatcc cgcgaccact   1980
ttcactcctg gaaagtttgc ttcgttcatt acccagtatt ccaccggaca ggtcagcgtg   2040
gaaatagagt gggagctgca gaaagaaaac agcaaacgct ggaacccaga aattcagtac   2100
acctccaact acaacaagtc ggtgaatgtg gagtttaccg tggacgcaaa cggtgtttat   2160 tctgaaccc gccctattgg cactcgttac cttacccgga acttg                    2205
```

The invention claimed is:

1. A recombinant adeno-associated virus (AAV) comprising an AAV capsid comprising vp1 proteins having the sequence of amino acids 1 to 738 of SEQ ID NO: 85 or a sequence at least 95% identical to the full length of amino acids 1 to 738 of SEQ ID NO: 85, AAV vp2 proteins, and AAV vp3 proteins, wherein the recombinant AAV further comprises, packaged within the capsid, a nucleic acid molecule comprising at least one AAV inverted terminal repeat (ITR), and a non-AAV nucleic acid sequence encoding a gene product operably linked to sequences which direct expression of the gene product in a host cell, wherein the gene product is a dystrophin protein.

2. The recombinant AAV according to claim 1, wherein the sequence of the vp1 proteins is at least 97% identical to the full length of amino acids 1 to 738 of SEQ ID NO: 85.

3. The recombinant AAV according to claim 1, wherein the sequence of the vp1 proteins is at least 99% identical to the full-length of amino acids 1 to 738 of SEQ ID NO: 85.

4. The recombinant AAV according to claim 1, wherein the sequence of the vp1 proteins is the full-length of amino acids 1 to 738 of SEQ ID NO: 85.

5. A recombinant adeno-associated virus (AAV) having an AAV capsid comprising AAV vp1 proteins, AAV vp2 proteins having a sequence of amino acids 138 to 738 of SEQ ID NO:85 or a sequence at least 95% identical to the full-length of amino acids 138 to 738 of SEQ ID NO: 85, and AAV vp3 proteins, wherein the recombinant AAV further comprises, packaged within the capsid, a nucleic acid molecule comprising at least one AAV inverted terminal repeat (ITR) and a non-AAV nucleic acid sequence encoding a gene product operably linked to sequences which direct expression of the gene product in a host cell, wherein the gene product is a dystrophin protein.

6. The recombinant AAV according to claim 5, wherein the sequence of the vp2 proteins is at least 97% identical to the full length of amino acids 138 to 738 of SEQ ID NO: 85.

7. The recombinant AAV according to claim 5, wherein the sequence of the vp2 proteins is at least 99% identical to the full-length of amino acids 138 to 738 of SEQ ID NO: 85.

8. The recombinant AAV according to claim 5, wherein the sequence of the vp2 proteins is the full-length of amino acids 138 to 738 of SEQ ID NO: 85.

9. A recombinant adeno-associated virus (AAV) having an AAV capsid comprising AAV vp1 proteins, AAV vp2 proteins, and AAV vp3 proteins having a sequence of amino acids 204 to 738 of SEQ ID NO:85 or a sequence at least 95% identical to the full-length of amino acids 204 to 738 of SEQ ID NO: 85, wherein the recombinant AAV further comprises, packaged within the capsid, a nucleic acid molecule comprising at least one AAV inverted terminal repeat (ITR) and a non-AAV nucleic acid sequence encoding a gene product operably linked to sequences which direct expression of the gene product in a host cell, wherein the gene product is a dystrophin protein.

10. The recombinant AAV according to claim 9, wherein the sequence of the vp3 proteins is at least 97% identical to the full length of amino acids 204 to 738 of SEQ ID NO: 85.

11. The recombinant AAV according to claim 9, wherein the sequence of the vp3 proteins is at least 99% identical to the full-length of amino acids 204 to 738 of SEQ ID NO: 85.

12. The recombinant AAV according to claim 9, wherein the sequence of the vp3 proteins is the full-length of amino acids 204 to 738 of SEQ ID NO: 85.

13. The recombinant AAV according to claim 1, wherein the AAV ITR is from AAV2.

14. The recombinant AAV according to claim 5, wherein the AAV ITR is from AAV2.

15. The recombinant AAV according to claim 9, wherein the AAV ITR is from AAV2.

16. A composition comprising a pharmaceutically compatible carrier and at least the recombinant AAV according to claim 1.

17. A composition comprising a pharmaceutically compatible carrier and at least the recombinant AAV according to claim 5.

18. A composition comprising a pharmaceutically compatible carrier and at least the recombinant AAV according to claim 9.

19. A method for delivering a transgene product to a subject, said method comprising administering the recombinant AAV according to claim 1.

20. A method for delivering a transgene product to a subject, said method comprising administering the recombinant AAV according to claim 5.

21. A method for delivering a transgene product to a subject, said method comprising administering the recombinant AAV according to claim 9.

\* \* \* \* \*